(12) United States Patent
Yurkovetskiy et al.

(10) Patent No.: US 11,964,025 B2
(45) Date of Patent: *Apr. 23, 2024

(54) PEPTIDE-CONTAINING LINKERS FOR ANTIBODY-DRUG CONJUGATES

(71) Applicant: Mersana Therapeutics, Inc., Cambridge, MA (US)

(72) Inventors: Aleksandr V. Yurkovetskiy, Littleton, MA (US); Natalya D. Bodyak, Boston, MA (US); Bingfan Du, Cambridge, MA (US); Dmitry R. Gumerov, Waltham, MA (US); Mariya Kozytska, Brookline, MA (US); Timothy B. Lowinger, Carlisle, MA (US); Cheri A. Stevenson, Haverhill, MA (US); Mao Yin, Needham, MA (US)

(73) Assignee: Mersana Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/400,387

(22) Filed: Aug. 12, 2021

(65) Prior Publication Data

US 2023/0043447 A1 Feb. 9, 2023

Related U.S. Application Data

(63) Continuation of application No. 15/819,650, filed on Nov. 21, 2017, now Pat. No. 11,135,307.

(60) Provisional application No. 62/572,010, filed on Oct. 13, 2017, provisional application No. 62/425,895, filed on Nov. 23, 2016.

(51) Int. Cl.
| | |
|---|---|
| *A61K 47/65* | (2017.01) |
| *A61K 38/07* | (2006.01) |
| *A61K 47/68* | (2017.01) |
| *A61P 35/00* | (2006.01) |
| *A61K 47/54* | (2017.01) |
| *A61K 47/60* | (2017.01) |

(52) U.S. Cl.
CPC .......... *A61K 47/6889* (2017.08); *A61K 38/07* (2013.01); *A61K 47/65* (2017.08); *A61K 47/6803* (2017.08); *A61K 47/6849* (2017.08); *A61K 47/6851* (2017.08); *A61K 47/6855* (2017.08); *A61K 47/6883* (2017.08); *A61K 47/6885* (2017.08); *A61P 35/00* (2018.01); *A61K 47/549* (2017.08); *A61K 47/60* (2017.08)

(58) Field of Classification Search
CPC .......... A61K 47/6889; A61K 47/6885; A61K 47/6883; A61K 47/6855; A61K 47/65; A61K 38/07; A61K 47/6849; A61K 47/6803; A61K 47/6851; A61K 47/549; A61K 47/60; A61P 35/00

See application file for complete search history.

(56) References Cited

U.S. PATENT DOCUMENTS

| | | | |
|---|---|---|---|
| 5,208,020 | A | 5/1993 | Chari et al. |
| 5,416,064 | A | 5/1995 | Chari et al. |
| 5,475,092 | A | 12/1995 | Chari et al. |
| 5,585,499 | A | 12/1996 | Chari et al. |
| 5,643,575 | A | 7/1997 | Martinez et al. |
| 5,846,545 | A | 12/1998 | Chari et al. |
| 5,919,455 | A | 7/1999 | Greenwald et al. |
| 6,113,906 | A | 9/2000 | Greenwald et al. |
| 6,153,655 | A | 11/2000 | Martinez et al. |
| 6,333,410 | B1 | 12/2001 | Chari et al. |
| 6,340,701 | B1 | 1/2002 | Chari et al. |
| 6,372,738 | B2 | 4/2002 | Chari et al. |
| 6,395,266 | B1 | 5/2002 | Martinez et al. |
| 6,436,931 | B1 | 8/2002 | Chari et al. |
| 6,441,163 | B1 | 8/2002 | Chari et al. |
| 6,534,660 | B1 | 3/2003 | Yongxin et al. |
| 6,596,757 | B1 | 7/2003 | Chari et al. |
| 6,602,498 | B2 | 8/2003 | Shen |
| 6,630,579 | B2 | 10/2003 | Chari et al. |
| 6,638,499 | B2 | 10/2003 | Martinez et al. |
| 6,756,397 | B2 | 6/2004 | Zhao et al. |
| 6,777,387 | B2 | 8/2004 | Greenwald et al. |
| 7,026,440 | B2 | 4/2006 | Bentley et al. |
| 7,276,497 | B2 | 10/2007 | Chari et al. |
| 7,632,504 | B2 | 12/2009 | Whitlow et al. |
| 7,872,072 | B2 | 1/2011 | Bentley et al. |
| 7,888,536 | B2 | 2/2011 | Davis et al. |

(Continued)

FOREIGN PATENT DOCUMENTS

| | | |
|---|---|---|
| WO | WO 2008/034124 | 3/2008 |
| WO | WO 2008/112873 | 9/2008 |

(Continued)

OTHER PUBLICATIONS

Doronina et al. "Novel Peptide Linkers for Highly Potent Antibidy-Auristatin Conjugate", Bioconjugate Chem., 2008, vol. 19, No. 10, p. 1960-1963.

(Continued)

*Primary Examiner* — Sudhakar Katakam

(74) *Attorney, Agent, or Firm* — COOLEY LLP; Heidi A. Erlacher; Christine E. Dunne

(57) ABSTRACT

The present disclosure relates generally to antibody-drug conjugates comprising peptide-containing linkers and to methods of using these conjugates as therapeutics and/or diagnostics. Also disclosed herein are peptide-containing scaffolds useful to conjugate with a targeting moiety (e.g., an antibody), a drug, or both to produce the antibody-drug conjugates.

16 Claims, 5 Drawing Sheets

Specification includes a Sequence Listing.

(56) References Cited

U.S. PATENT DOCUMENTS

| | | | |
|---|---|---|---|
| 8,012,488 | B2 | 9/2011 | Sakanoue et al. |
| 8,273,833 | B2 | 9/2012 | Bentley et al. |
| 8,367,065 | B2 | 2/2013 | Zhao et al. |
| 8,440,816 | B2 | 5/2013 | Bentley et al. |
| 8,524,696 | B2 | 9/2013 | Borowy-Borowski et al. |
| 9,731,030 | B2 | 8/2017 | Jeffrey |
| 11,135,307 | B2 * | 10/2021 | Yurkovetskiy ..... A61K 47/6885 |
| 2009/0202573 | A1 | 8/2009 | Zhao et al. |
| 2016/0279260 | A1 | 9/2016 | Flygare et al. |
| 2016/0279261 | A1 | 9/2016 | Lee et al. |
| 2016/0310612 | A1 | 10/2016 | Lyon et al. |

FOREIGN PATENT DOCUMENTS

| | | |
|---|---|---|
| WO | WO 2009/035347 | 3/2009 |
| WO | WO 2012/088461 | 6/2012 |
| WO | WO 2014/062697 | 4/2014 |
| WO | WO-2015057699 A2 | 4/2015 |
| WO | WO 2016/085967 | 6/2016 |
| WO | WO 2016/148674 | 9/2016 |
| WO | WO 2016/183359 | 11/2016 |
| WO | WO-2018098269 A2 | 5/2018 |

OTHER PUBLICATIONS

Leamon, C. et al. "Reducing Undesirable Hepatic Clearance of a Tumor-Targeted Vinca Alkaloid via Novel Saccharopeptidic Modifications", The Journal of Pharmacology and Experimental Therapeutics, 2011, vol. 336, No. 2, p. 336-343.

Lu et al. "Linkers Having a Crucial Role in Antibody-Drug Conjugates", International Journal of Molecular Sciences, 2016, vol. 17, No. 561, p. 1-22.

Lyon R et al. "Reducing hydrophobicity of homogeneous antibody-drug conjugates improves pharmacokinetics and therapeutic index", Nature Biotechnology, 2015, vol. 33, No. 7, p. 733-735.

Nolting "Linker Technology for Antibody-Drug Conjugates", Antibody-Drug Conjugates, Methods in Molecular Biology, 2013, vol. 1045, Chapter 5, p. 71-100.

Vlahov, I. et al. "Carbohydrate-Based Synthetic Approach to Control Toxicity Profiles of Folate-Drug Conjugates", J. Org. Chem., vol. 75, p. 3685-3691, 2010.

Chen, X. "Fusion Protein Linkers: Property, Design and Functionality", Advanced Drug Delivery Reviews, Oct. 2013, 65(10), p. 1357-1369.

Bowie et al., "Deciphering the message in protein sequences: tolerance to amino acid substitutions", Science. (Mar. 16, 1990); 247(4948): 1306-10.

Burgess et al., "Possible dissociation of the heparin-binding and mitogenic activities of heparin-binding (acidic fibroblast) growth factor-1 from its receptor-binding activities by site-directed mutagenesis of a single lysine residue" The Journal of Cell Biology. (Nov. 1, 1990); 111(5): 2129-38.

Krop et al., "Phase I Study of Trastuzumab-DM1, an HER2 Antibody-Drug Conjugate, Given Every 3 Weeks to Patients With HER2-Positive Metastatic Breast Cancer", Journal of Clinical Oncology, 2010, vol. 28, No. 16, p. 2698-2704.

Lazar et al., "Transforming Growth Factor Alpha: Mutation of Aspartic Acid 47 and Leucine 48 Results in Different Biological Activities," Molecular and Cellular Biology, Mar. 1988, vol. 8 (3), pp. 1247-1252.

Ricart et al., "Technology insight: cytotoxic drug immunoconjugates for cancer therapy". Nature clinical practice Oncology. Apr. 2007; 4(4): 245-55.

* cited by examiner

Total antibody

Total AF-HPA

Conjugated AF-HPA

SEQUENCE LISTING

```
<160> NUMBER OF SEQ ID NOS: 29

<210> SEQ ID NO 1

<400> SEQUENCE: 1

000

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000

<210> SEQ ID NO 5
<211> LENGTH: 10
<212> TYPE: PRT
<213> ORGANISM: Homo Sapiens

<400> SEQUENCE: 5

Gly Tyr Thr Phe Thr Gly Tyr Asn Ile His
1               5                   10

<210> SEQ ID NO 6
<211> LENGTH: 17
<212> TYPE: PRT
<213> ORGANISM: Homo Sapiens

<400> SEQUENCE: 6

Ala Ile Tyr Pro Gly Asn Gly Asp Thr Ser Tyr Lys Gln Lys Phe Arg
1               5                   10                  15

Gly

<210> SEQ ID NO 7
<211> LENGTH: 10
<212> TYPE: PRT
<213> ORGANISM: Homo Sapiens

<400> SEQUENCE: 7

Gly Glu Thr Ala Arg Ala Thr Phe Ala Tyr
1               5                   10

<210> SEQ ID NO 8
<211> LENGTH: 11
<212> TYPE: PRT
<213> ORGANISM: Homo Sapiens

<400> SEQUENCE: 8

Ser Ala Ser Gln Asp Ile Gly Asn Phe Leu Asn
1               5                   10

<210> SEQ ID NO 9
<211> LENGTH: 7
```

```
<212> TYPE: PRT
<213> ORGANISM: Homo Sapiens

<400> SEQUENCE: 9

Tyr Thr Ser Ser Leu Tyr Ser
1               5

<210> SEQ ID NO 10
<211> LENGTH: 9
<212> TYPE: PRT
<213> ORGANISM: Homo Sapiens

<400> SEQUENCE: 10

Gln Gln Tyr Ser Lys Leu Pro Leu Thr
1               5

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19
```

000

<210> SEQ ID NO 20

<400> SEQUENCE: 20

000

<210> SEQ ID NO 21
<211> LENGTH: 7
<212> TYPE: PRT
<213> ORGANISM: Artificial Sequence
<220> FEATURE:
<223> OTHER INFORMATION: Synthetic Oligopeptide

<400> SEQUENCE: 21

Gly Ala Ser Ser Arg Ala Thr
1               5

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25
<211> LENGTH: 9
<212> TYPE: PRT
<213> ORGANISM: Artificial Sequence
<220> FEATURE:
<223> OTHER INFORMATION: Synthetic Oligopeptide

<400> SEQUENCE: 25

Phe Thr Phe Ser Ser Tyr Ser Met Asn
1               5

<210> SEQ ID NO 26
<211> LENGTH: 17
<212> TYPE: PRT
<213> ORGANISM: Artificial Sequence
<220> FEATURE:
<223> OTHER INFORMATION: Synthetic Oligopeptide

<400> SEQUENCE: 26

Tyr Ile Ser Ser Ser Ser Ser Thr Ile Tyr Tyr Ala Asp Ser Val Lys
1               5                   10                  15

Gly

<210> SEQ ID NO 27
<211> LENGTH: 8
<212> TYPE: PRT
<213> ORGANISM: Artificial Sequence
<220> FEATURE:
<223> OTHER INFORMATION: Synthetic Oligopeptide

```
<400> SEQUENCE: 27

Gly Gly His Gly Tyr Phe Asp Leu
1               5

<210> SEQ ID NO 28
<211> LENGTH: 12
<212> TYPE: PRT
<213> ORGANISM: Artificial Sequence
<220> FEATURE:
<223> OTHER INFORMATION: Synthetic Oligopeptide

<400> SEQUENCE: 28

Arg Ala Ser Gln Ser Val Ser Ser Ser Tyr Leu Ala
1               5                   10

<210> SEQ ID NO 29
<211> LENGTH: 9
<212> TYPE: PRT
<213> ORGANISM: Artificial Sequence
<220> FEATURE:
<223> OTHER INFORMATION: Synthetic Oligopeptide

<400> SEQUENCE: 29

Gln Gln Tyr His His Ser Pro Leu Thr
1               5
```

PEPTIDE-CONTAINING LINKERS FOR ANTIBODY-DRUG CONJUGATES

RELATED APPLICATIONS

This application is a continuation of U.S. application Ser. No. 15/819,650, filed Nov. 21, 2017, which claims priority to, and the benefit of, U.S. provisional application Nos. 62/425,895, filed Nov. 23, 2016 and 62/572,010, filed Oct. 13, 2017, under 35 USC § 119(e). The contents of each of these applications are hereby incorporated by reference in their entireties.

INCORPORATION-BY-REFERENCE OF SEQUENCE LISTING

The contents of the file named "MRSN-019_C01US_ST25.txt", which was created on Aug. 10, 2021, and is 3.2 KB in size are hereby incorporated by reference in their entirety.

BACKGROUND

Traditionally, pharmaceuticals have primarily consisted of small molecules that are dispensed orally (as solid pills and liquids) or as injectables. Over the past three decades, formulations (i.e., compositions that control the route and/or rate of drug delivery and allow delivery of the therapeutic agent at the site where it is needed) have become increasingly common and complex. Nevertheless, many questions and challenges regarding the development of new treatments as well as the mechanisms with which to administer them remain to be addressed. For example, many drugs exhibit limited or otherwise reduced potencies and therapeutic effects because they are either generally subject to partial degradation before they reach a desired target in the body, or accumulate in tissues other than the target, or both.

One objective in the field of drug delivery systems, therefore, is to deliver medications intact to specifically targeted areas of the body through a system that can stabilize the drug and control the in vivo transfer of the therapeutic agent utilizing either physiological or chemical mechanisms, or both.

Antibody-drug conjugates have been developed as target-specific therapeutic agents. Antibodies against various cancer cell-surface antigens have been conjugated with different cytotoxic agents that inhibit various essential cellular targets such as microtubules (such as maytansinoids, auristatins, and taxanes, see, e.g., U.S. Pat. Nos. 5,208,020; 5,416,064; 6,333,410; 6,441,163; 6,340,701; 6,372,738; 6,436,931; 6,596,757; and 7,276,497); DNA (such as calicheamicin, doxorubicin, and CC-1065 analogs; see, e.g., U.S. Pat. Nos. 5,475,092; 5,585,499; 5,846,545; 6,534,660; 6,756,397; and 6,630,579). Antibody conjugates with some of these cytotoxic drugs are actively being investigated in the clinic for cancer therapy (see, e.g., Ricart, A. D., and Tolcher, A. W., 2007, *Nature Clinical Practice*, 4, 245-255; Krop et al., 2010, *J. Clin. Oncol.*, 28, 2698-2704). However, existing antibody-drug conjugates have exhibited a few limitations. A major limitation is their inability to deliver a sufficient concentration of drug to the target site because of the limited number of targeted antigens and the relatively moderate cytotoxicity of cancer drugs like methotrexate, daunorubicin, maytansinoids, taxanes, and vincristine. One approach to achieving significant cytotoxicity is by linkage of a large number of drug molecules either directly or indirectly to the antibody. However such heavily modified antibodies often display impaired binding to the target antigen and/or fast in vivo clearance from the blood stream. Therefore, there is a need to improve the ability to deliver a sufficient concentration of a drug to the target such that maximum cytotoxicity for the drug is achieved.

SUMMARY

The present disclosure features a targeting moiety-drug conjugate that is biodegradable, biocompatible and exhibits high drug load as well as strong binding to target antigen. For example, the targeting moiety is a protein based recognition-molecule (PBRM). The present disclosure also features a peptide-containing scaffold useful to conjugate with a PBRM, a drug, or both, so as to obtain the targeting moiety-drug conjugate.

In one aspect, the disclosure relates to a conjugate comprising a targeting moiety and one or more Linker-Drug moieties covalently bonded to the targeting moiety, wherein each Linker-Drug moiety includes a Multifunctional Linker that connects the targeting moiety to one or more Drug Units through intermediacy of a Releasable Assembly Unit for each Drug Unit, and connects a hydrophilic group to the Drug Units of each Linker-Drug moiety, wherein the Releasable Assembly units are capable of releasing free drug in proximity to a target site targeted by the targeting moiety, and wherein the Multifunctional Linker comprises a peptide moiety between the targeting moiety and the hydrophilic group, wherein the peptide moiety includes at least two amino acids.

In another aspect, the disclosure relates to a conjugate comprising a targeting moiety and one or more Linker-Drug moieties covalently bonded to the targeting moiety, wherein
each Linker-Drug moiety includes a Multifunctional Linker that connects the targeting moiety to one or more Drug Units through intermediacy of a Releasable Assembly Unit for each Drug Unit, and connects a polyalcohol or a derivative thereof to the Drug Units of each Linker-Drug moiety, wherein the Releasable Assembly units are capable of releasing free drug in proximity to a target site targeted by the targeting moiety.

The disclosure also relates to a conjugate of Formula (I):

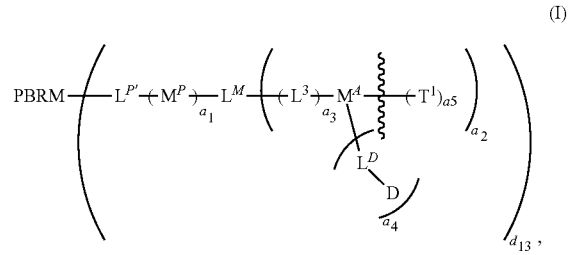

(I)

wherein
$a_1$ is an integer from 0 to 1;
$a_2$ is an integer from 1 to 3;
$a_3$ is an integer from 0 to 1;
$a_4$ is an integer from 1 to about 5;
$a_5$ is an integer from 1 to 3;
$d_{13}$ is an integer from 1 to about 14;
PBRM denotes a protein based recognition-molecule;

$L^{P'}$ is a divalent linker moiety connecting the PBRM to $M^P$; of which the corresponding monovalent moiety $L^P$ contains a functional group $W^P$ that is capable of forming a covalent bond with a functional group of the PBRM;

$M^P$ is a Stretcher unit;

$L^M$ is a bond, or a trivalent or tetravalent linker, and when $L^M$ is a bond, $a_2$ is 1, when $L^M$ is trivalent linker, $a_2$ is 2, or when $L^M$ is a tetravalent linker, $a_2$ is 3;

$L^3$ is a carbonyl-containing moiety;

$M^A$ comprises a peptide moiety that contains at least two amino acids;

$T^1$ is a hydrophilic group and the

between $T^1$ and $M^A$ denotes direct or indirect attachment of $T^1$ and $M^A$;

each occurrence of D is independently a therapeutic agent having a molecular weight≤about 5 kDa; and each occurrence of $L^D$ is independently a divalent linker moiety connecting D to $M^A$ and comprises at least one cleavable bond such that when the bond is broken, D is released in an active form for its intended therapeutic effect.

In yet another aspect, the disclosure relates to a peptide-containing scaffold, being any of Formulae (II)-(IX):

(II)
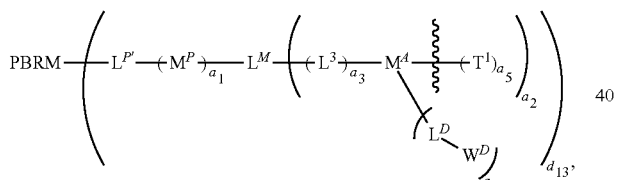

(III)
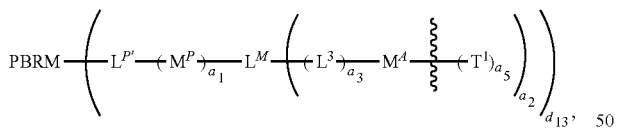

(IV)
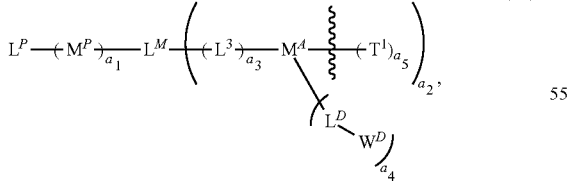

(V)
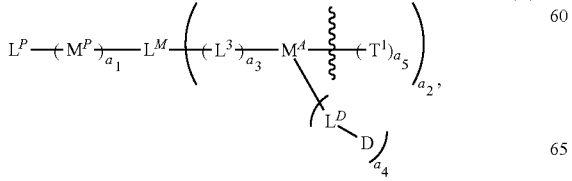

(VI)
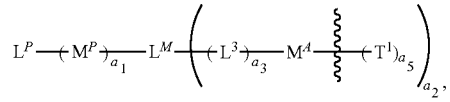

(VII)
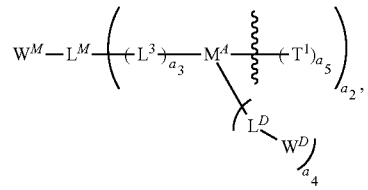

(VIII)
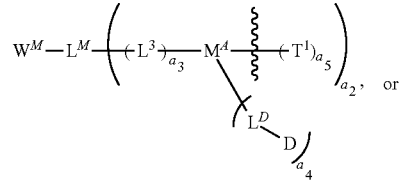

or (IX)
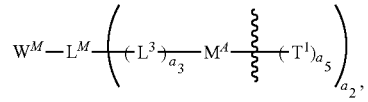

wherein
$a_1$ is an integer from 0 to 1;
$a_2$ is an integer from 1 to 3;
$a_3$ is an integer from 0 to 1;
$a_4$ is an integer from 1 to about 5;
$a_5$ is an integer from 1 to 3;
$d_{13}$ is an integer from 1 to about 14;
PBRM denotes a protein based recognition-molecule;
$L^{P'}$ is a divalent linker moiety connecting the PBRM to $M^P$; of which the corresponding monovalent moiety $L^P$ contains a functional group $W^P$ that is capable of forming a covalent bond with a functional group of the PBRM;
$M^P$ is a Stretcher unit;
$L^M$ is a bond, or a trivalent or tetravalent linker, and when $L^M$ is a bond, $a_1$ is 1, when $L^M$ is a trivalent linker, $a_2$ is 2, or when $L^M$ is a tetravalent linker, $a_2$ is 3;
$L^3$ is a carbonyl-containing moiety;
$M^A$ comprises a peptide moiety that contains at least two amino acids;
$T^1$ is a hydrophilic group and the

between $T^1$ and $M^A$ denotes direct or indirect attachment of $T^1$ and $M^A$;

each occurrence of $W^M$ is independently hydrogen, a protecting group, a leaving group, or a functional group that is capable of connecting $L^M$ to $M^P$ by forming a covalent bond;

each occurrence of $W^D$ is independently a functional group that is capable of forming a covalent bond with a functional group of a therapeutic agent ("D") having a molecular weight≤about 5 kDa; and each occurrence of $L^o$ is independently a divalent linker moiety connecting $W^D$ or D to $M^A$ and $L^D$ comprises at least one cleavable bond such that when the bond is broken, D is released in an active form for its intended therapeutic effect.

The conjugates and scaffolds of the disclosure can include one or more of the following features when applicable.

For example, each of the Drug Units and the hydrophilic group is connected to the Multifunctional Linker in parallel orientation.

For example, the targeting moiety is a protein based recognition-molecule (PBRM). For example, the PBRM is an antibody or antibody fragment.

For example, the peptide moiety in the Multifunctional Linker includes from three to about sixteen amino acids, e.g., about 4, 5, 6, 7, 8, 9, 10, 11, 12, 13, 14, 15 or 16 amino acids.

For example, the peptide moiety in the Multifunctional Linker includes from three to about ten amino acids, e.g., about 4, 5, 6, 7, 8, 9 or 10 amino acids.

For example, the peptide moiety contains from three to about ten amino acids selected from glycine, serine, glutamic acid, aspartic acid, lysine, cysteine, a stereoisomer thereof (e.g., isoglutamic acid or isoaspartic acid), and a combination thereof.

For example, the peptide moiety contains at least four glycines and at least one serine.

For example, the peptide moiety contains at least four glycines, at least one serine and at least one glutamic acid or isoglutamic acid.

For example, the hydrophilic group comprises a polyalcohol or a derivative thereof, a polyether or a derivative thereof, or a combination thereof.

For example, the hydrophilic group comprises an amino polyalcohol, e.g., glucamine or bis-glucamine.

For example, the hydrophilic group comprises:

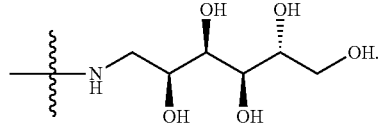 [SMILES: *NC[C@H](O)[C@@H](O)[C@H](O)[C@H](O)CO]

For example, the hydrophilic group comprises:

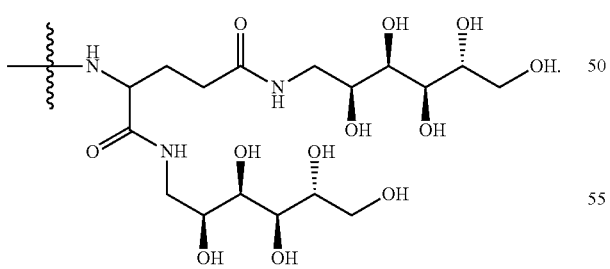

For example, the amino polyalcohol is

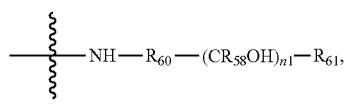

in which $n_1$ is an integer from 0 to about 6;

each $R_{58}$ is independently hydrogen or $C_{1-8}$ alkyl;

$R_{60}$ is a bond, a $C_{1-6}$ alkyl linker, or —$CHR_{59}$— in which $R_{59}$ is H, alkyl, cycloalkyl, or arylalkyl;

$R_{61}$ is $CH_2OR_{62}$, $COOR_{62}$, —$(CH_2)_{n2}COOR_{62}$, or a heterocycloalkyl substituted with one or more hydroxyl;

$R_{62}$ is H or $C_{1-8}$ alkyl; and $n_2$ is an integer from 1 to about 5.

For example, the hydrophilic group comprises

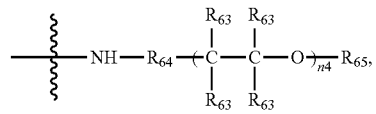

in which $n_4$ is an integer from 1 to about 25;

each $R_{63}$ is independently hydrogen or $C_{1-8}$ alkyl;

$R_{64}$ is a bond or a $C_{1-8}$ alkyl linker;

$R_{65}$ is H, $C_{1-8}$ alkyl or —$(CH_2)_{n2}COOR_{62}$;

$R_{62}$ is H or $C_{1-8}$ alkyl; and $n_2$ is an integer from 1 to about 5.

For example, the hydrophilic group comprises polyethylene glycol, e.g., polyethylene glycol with about 6 to about 24 PEG subunits, preferably about 6 to about 12 PEG subunits or about 8 to about 12 PEG subunits.

For example, $L^3$, when present, comprises —X—$C_{1-10}$ alkylene-C(O)—, with X directly connected to $L^M$, in which X is $CH_2$, O, or $NR_5$, and $R_5$ is hydrogen, $C_{1-6}$ alkyl, $C_{6-10}$ aryl, $C_{3-8}$ cycloalkyl, COOH, or COO—$C_{1-6}$ alkyl.

For example, $L^3$, when present, is —$NR_5$—$(CH_2)_v$—C(O)— or —$CF_2$—$(CH_2)_v$—C(O)—$NR_5$—$(CH_2)_v$—C(O)—, in which each v independently is an integer from 1 to 10 (e.g., each v independently being an integer from 1 to 6, or from 2 to 4, or 2). For example, $L^3$ is —NH—$(CH_2)_2$—C(O)— or —$(CH_2)_2$—C(O)—NH—$(CH_2)_2$—C(O)—.

For example, $a_4$ is 1, 2, or 3.

For example, $d_{13}$ is an integer from 1 to about 10, e.g., $d_{13}$ is 4 or 5.

For example, each $W^P$, when present, is independently:

(1)

(2)

(3)

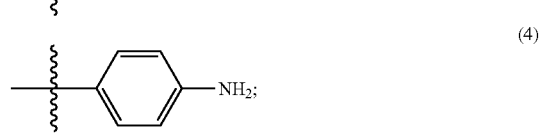

(4)

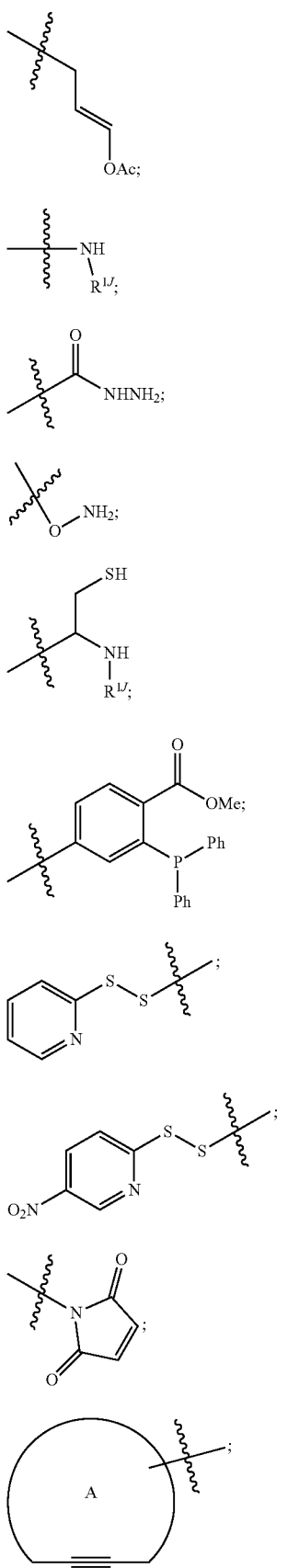
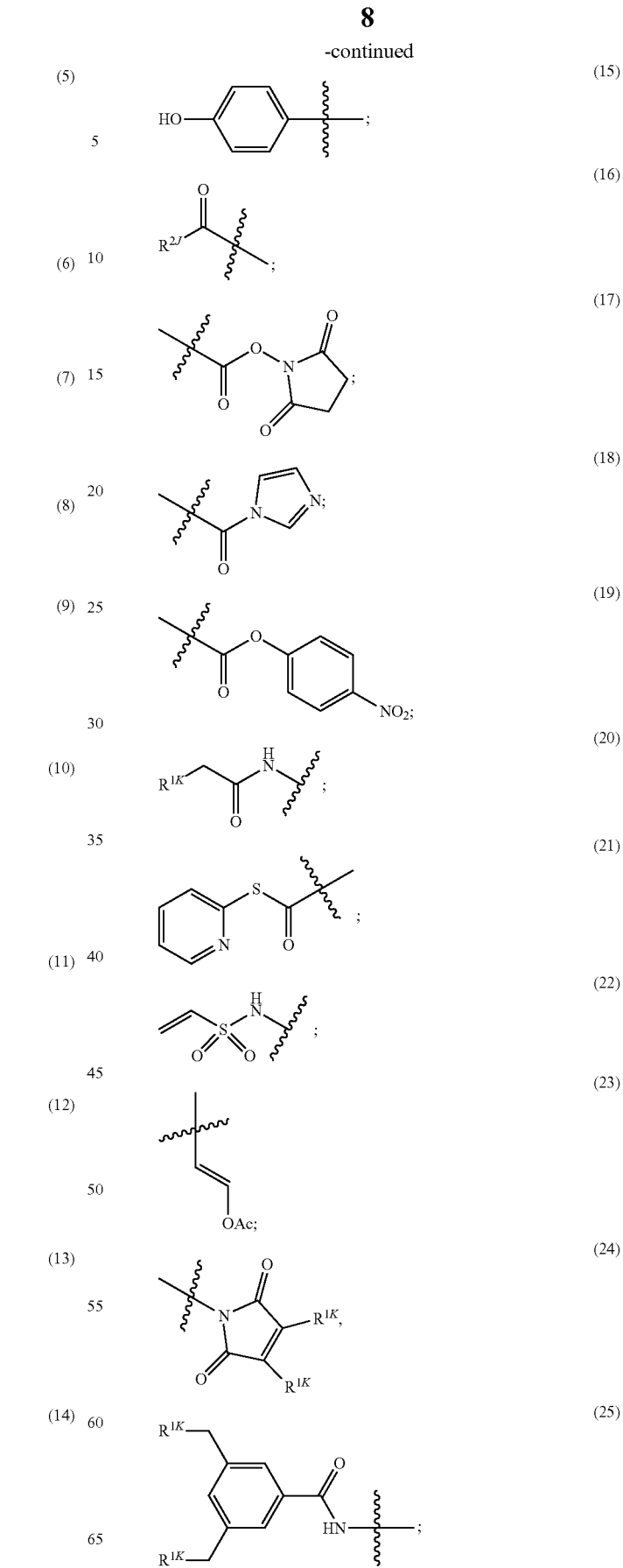

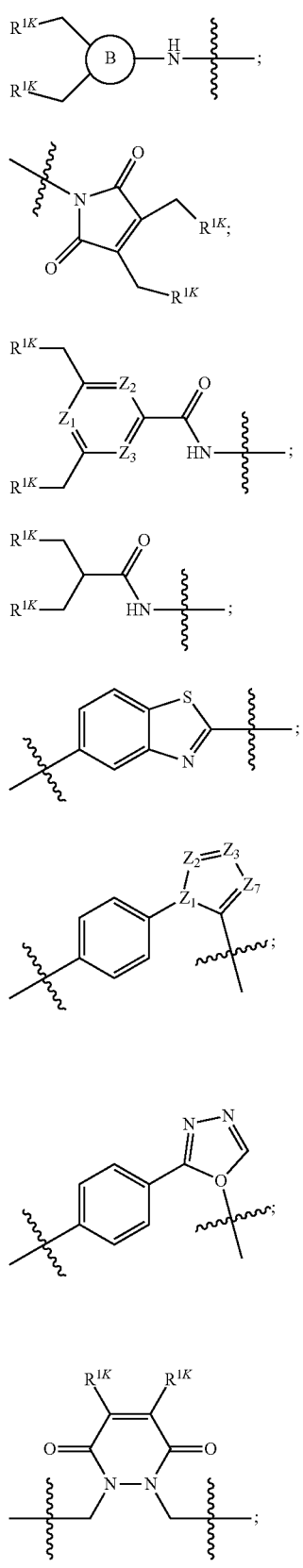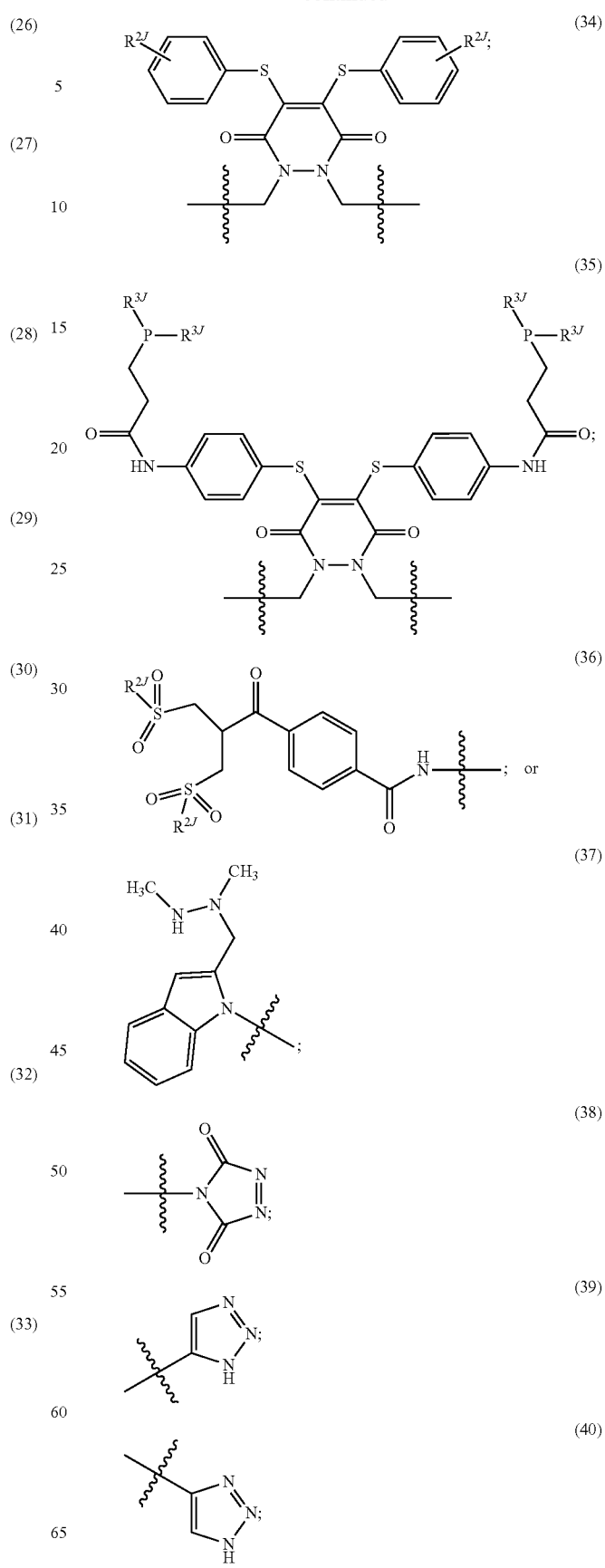

(41)
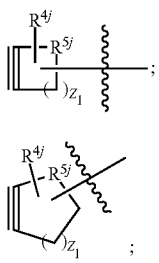

(43)

wherein
  ring A is cycloalkyl or heterocycloalkyl;
  ring B is cycloalkyl, heterocycloalkyl, aryl, or heteroaryl;
  $R^{1K}$ is a leaving group;
  $R^{1A}$ is a sulfur protecting group;
  $R^{1J}$ is hydrogen, an aliphatic, heteroaliphatic, carbocyclic, or heterocycloalkyl moiety;
  $R^{2J}$ is hydrogen, an aliphatic, aryl, heteroaliphatic, or carbocyclic moiety;
  $R^{3J}$ is $C_{1-6}$ alkyl and each of $Z_1$, $Z_2$, $Z_3$ and $Z_7$ is independently a carbon or nitrogen atom;
  $R^{4j}$ is hydrogen, halogen, OR, —$NO_2$, —CN, —$S(O)_2R$, $C_{1-24}$ alkyl (e.g., $C_{1-6}$ alkyl), or 6-24 membered aryl or heteroaryl, wherein the $C_{1-24}$ alkyl (e.g., $C_{1-6}$ alkyl), or 6-24 membered aryl or heteroaryl, is optionally substituted with one or more aryl or heteroaryl; or two $R^{4'}$ together form an annelated cycloalkyl, heterocycloalkyl, aryl, or heteroaryl; R is hydrogen, alkyl, heteroalkyl, cycloalkyl, or heterocycloalkyl;
  $R^{5j}$ is $C(R^{4j})_2$, O, S or NR; and
  $z_1$ is an integer 1, 2, 3, 4, 5, 6, 7, 8, 9 or 10.

For example, $R^{1K}$ is halo or RC(O)O— in which R is hydrogen, an aliphatic, heteroaliphatic, carbocyclic, or heterocycloalkyl moiety. For example, $R^{1A}$ is

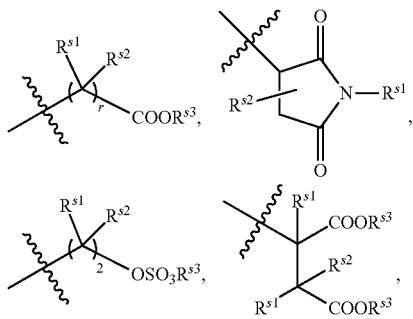

in which r is 1 or 2 and each of $R^{s1}$, $R^{s2}$, and $R^{s3}$ is hydrogen, an aliphatic, heteroaliphatic, carbocyclic, or heterocycloalkyl moiety.

For example, ring A can be

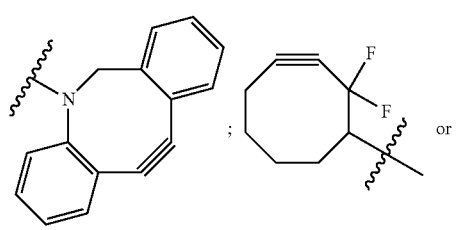

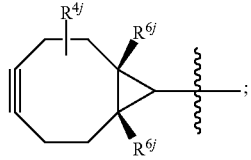

wherein $R^{6j}$ is hydrogen, halogen, $C_{1-24}$ alkyl (e.g., $C_{1-6}$ alkyl), or 6-24 membered aryl or heteroaryl, wherein the $C_{1-24}$ alkyl (e.g., $C_{1-6}$ alkyl), or 6-24 membered aryl or heteroaryl, is optionally substituted with one or more aryl or heteroaryl.

For example, ring A can be

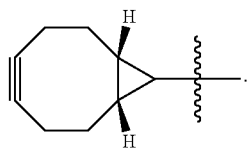 [SMILES: *C1[C@H]2CCC#CCC[C@@H]12]

For example, $M^P$, when present, is —$(Z_4)$—$[(Z_5)$—$(Z_6)]_z$—, with $Z_4$ connected to $L^{P'}$ or $L^P$ and $Z_6$ connected to $L^M$; in which
  z is 1, 2, or 3;

$Z_4$ is:

(1)
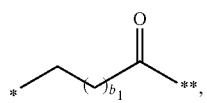

(2)
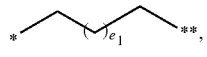

(3)
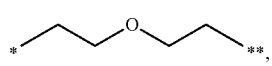

(4)
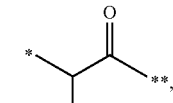

$R_{17}$, (5)

(6)
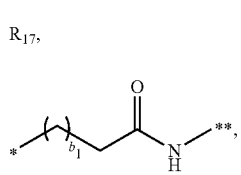

(7)
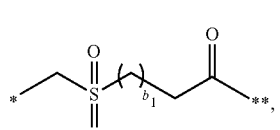

(8)
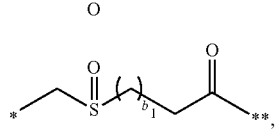

-continued (9)

*—CH₂—CF₂—(b₁)—C(O)—**

(10)

*—CH₂CH₂—S(=O)(CH₃)—CH—(b₁)—C(O)—**, or (11)

*—CH₂—C(O)—**, wherein * denotes attachment to $L^{P'}$ or $L^P$ and ** denotes attachment to $Z_5$ or $Z_6$ when present or to $L^M$ when $Z_5$ and $Z_6$ are both absent;

$b_1$ is an integer from 0 to 6;

$e_1$ is an integer from 0 to 8, $R_{17}$ is $C_{1-10}$ alkylene, $C_{1-10}$ heteroalkylene, $C_{3-8}$ cycloalkylene, O—($C_{1-8}$ alkylene, arylene, —$C_{1-10}$ alkylene-arylene-, -arylene-$C_{1-10}$ alkylene-, —$C_{1-10}$ alkylene-($C_{3-8}$ cycloalkylene)-, —($C_{3-8}$ cycloalkylene —$C_{1-10}$ alkylene-, 4 to 14-membered heterocycloalkylene, —$C_{1-10}$ alkylene-(4 to 14-membered heterocycloalkylene)-, -(4 to 14-membered heterocycloalkylene)-$C_{1-10}$ alkylene-, —$C_{1-10}$ alkylene-C(=O)—, —$C_{1-10}$ heteroalkylene-C(=O)—, —$C_{3-8}$ cycloalkylene-C(=O)—, —O—($C_{1-8}$ alkyl)-C(=O)—, -arylene-C(=O)—, —$C_{1-10}$ alkylene-arylene-C(=O)—, -arylene—$C_{1-10}$ alkylene-C(=O)—, —$C_{1-10}$ alkylene-($C_{3-8}$ cycloalkylene)-C(=O)—, —($C_{3-8}$ cycloalkylene)-$C_{1-10}$ alkylene-C(=O)—, -4 to 14-membered heterocycloalkylene-C(=O)—, —$C_{1-10}$ alkylene-(4 to 14-membered heterocycloalkylene)-C(=O)—, -(4 to 14-membered heterocycloalkylene)-$C_{1-10}$ alkylene-C(=O)—, —$C_{1-10}$ alkylene-NH—, —$C_{1-10}$ heteroalkylene-NH—, —$C_{3-8}$ cycloalkylene-NH—, —O—($C_{1-8}$ alkyl)-NH—, -arylene-NH—, —$C_{1-10}$ alkylene-arylene-NH—, -arylene-$C_{1-10}$ alkylene-NH—, —$C_{1-10}$ alkylene-($C_{3-8}$ cycloalkylene)-NH—, —($C_{3-8}$ cycloalkylene)-$C_{1-10}$ alkylene-NH—, -4 to 14-membered heterocycloalkylene-NH—, —$C_{1-10}$ alkylene-(4 to 14-membered heterocycloalkylene)-NH—, -(4 to 14-membered heterocycloalkylene)-$C_{1-10}$ alkylene-NH—, —$C_{1-10}$ alkylene-S—, —$C_{1-10}$ heteroalkylene-S—, —$C_{3-8}$ cycloalkylene-S—, —O—$C_{1-8}$ alkyl)-S—, -arylene-S—, —$C_{1-10}$ alkylene-arylene-S—, -arylene-$C_{1-10}$ alkylene-S—, —$C_{1-10}$ alkylene-($C_{3-8}$ cycloalkylene)-S—, —($C_{3-8}$ cycloalkylene)-$C_{1-10}$ alkylene-S—, -4 to 14-membered heterocycloalkylene-S—, —$C_{1-10}$ alkylene-(4 to 14-membered heterocycloalkylene)-S—, or -(4 to 14-membered heterocycloalkylene)-$C_1$-$C_{10}$ alkylene-S—;

each $Z_5$ independently is absent, $R_{57}$—$R_{17}$ or a polyether unit;

each $R_{57}$ independently is a bond, $NR_{23}$, S or O;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl; and each $Z_6$ independently is absent, —$C_{1-10}$ alkyl-$R_{3-}$, —$C_{1-10}$ alkyl-$NR_5$—, —$C_{1-10}$ alkyl-C(O)—, —$C_{1-10}$ alkyl-O—, —$C_{1-10}$ alkyl-S— or —($C_{1-10}$ alkyl-$R_3$)$_{g1}$—$C_{1-10}$ alkyl-C(O)—;

each $R_3$ independently is —C(O)—$NR_5$— or —$NR_5$—C(O)—;

each $R_5$ independently is hydrogen, $C_{1-6}$ alkyl, $C_{6-10}$ aryl, $C_{3-8}$ cycloalkyl, COOH, or COO—$C_{1-6}$ alkyl; and $g_1$ is an integer from 1 to 4.

For example, $M^P$, when present, is (1)

(1)

*—(b₁)—C(O)—**, (2)

*—(e₁)—**, (3)

*—CH₂CH₂—O—CH₂CH₂—**, (4)

*—CH₂—CH(CH₂NH₂)—C(O)—**, (5)

$R_{17}$, (6)

*—(b₁)—C(O)—NH—**, (7)

*—CH₂—C(O)—N(R₂₃)—R₁₇—**, (8)

*—(b₁)—C(O)—NH—CH₂CH₂—(O—CH₂CH₂)$_{f1}$—C(O)—**, (9)

*—(b₁)—C(O)—NH—CH₂CH₂—(O—CH₂CH₂)$_{f1}$—(R₃—(b₁)—C(O)—R₄)$_{g2}$—**, (10)

*—CH₂CH₂—S(=O)₂—(b₁)—C(O)—**, (11)

*—CH₂—S(=O)—(b₁)—C(O)—**, (12)

*—CH₂—CF₂—(b₁)—C(O)—**,

-continued

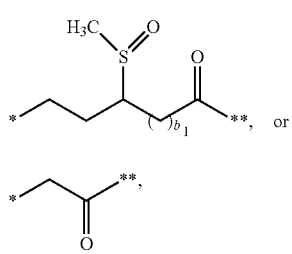

wherein * denotes attachment to $L^P$ or $L^P$ and ** denotes attachment to $L^M$;

$R_3$ is —C(O)—NR$_5$ or —NR$_5$—C(O)—;

$R_4$ is a bond or —NR$_5$—(CR$_{20}$R$_{21}$)—C(O)—;

$R_5$ is hydrogen, $C_{1-6}$ alkyl, $C_{6-10}$ aryl, $C_{3-8}$ cycloalkyl, —COOH, or —COO—$C_{1-6}$ alkyl;

$R_{17}$ is $C_{1-10}$ alkylene, $C_{1-10}$ heteroalkylene, $C_{3-8}$ cycloalkylene, 0-($C_{1-8}$ alkylene, arylene, —$C_{1-10}$ alkylene-arylene-, -arylene-$C_{1-10}$ alkylene-, —$C_{1-10}$ alkylene-($C_{3-8}$ cycloalkylene)-, —($C_{3-8}$ cycloalkylene —$C_{1-10}$ alkylene-, 4 to 14-membered heterocycloalkylene, —$C_{1-10}$ alkylene-(4 to 14-membered heterocycloalkylene)-, -(4 to 14-membered heterocycloalkylene)-$C_{1-10}$ alkylene-, —$C_{1-10}$ alkylene-C(=O)—, —$C_{1-10}$ heteroalkylene-C(=O)—, —$C_{3-8}$ cycloalkylene-C(=O)—, —O—($C_{1-8}$ alkyl)-C(=O)—, -arylene-C(=O)—, —$C_{1-10}$ alkylene-arylene-C(=O)—, -arylene —$C_{1-10}$ alkylene-C(=O)—, —$C_{1-10}$ alkylene-($C_{3-8}$ cycloalkylene)-C(=O)—, —($C_{3-8}$ cycloalkylene)-$C_{1-10}$ alkylene-C(=O)—, -4 to 14-membered heterocycloalkylene-C(=O)—, —$C_{1-10}$ alkylene-(4 to 14-membered heterocycloalkylene)-C(=O)—, -(4 to 14-membered heterocycloalkylene)-$C_{1-10}$ alkylene-C(=O)—, —$C_{1-10}$ alkylene-NH—, —$C_{1-10}$ heteroalkylene-NH—, —$C_{3-8}$ cycloalkylene-NH—, —O—($C_{1-8}$ alkyl)-NH—, -arylene-NH—, —$C_{1-10}$ alkylene-arylene-NH—, -arylene-$C_{1-10}$ alkylene-NH—, —$C_{1-10}$ alkylene-($C_{3-8}$ cycloalkylene)-NH—, —($C_{3-8}$ cycloalkylene)-$C_{1-10}$ alkylene-NH—, -4 to 14-membered heterocycloalkylene-NH—, —$C_{1-10}$ alkylene-(4 to 14-membered heterocycloalkylene)-NH—, -(4 to 14-membered heterocycloalkylene)-$C_{1-10}$ alkylene-NH—, —$C_{1-10}$ alkylene-S—, —$C_{1-10}$ heteroalkylene-S—, —$C_{3-8}$ cycloalkylene-S—, —O—$C_{1-8}$ alkyl)-S—, -arylene-S—, —$C_{1-10}$ alkylene-arylene-S—, -arylene-$C_{1-10}$ alkylene-S—, —$C_{1-10}$ alkylene-($C_{3-8}$ cycloalkylene)-S—, —($C_{3-8}$ cycloalkylene)-$C_{1-10}$ alkylene-S—, -4 to 14-membered heterocycloalkylene-S—, —$C_{1-10}$ alkylene-(4 to 14-membered heterocycloalkylene)-S—, or -(4 to 14-membered heterocycloalkylene)-$C_1$-$C_{10}$ alkylene-S—;

each $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

each $b_1$ independently is an integer from 0 to 6;

$e_1$ is an integer from 0 to 8, each $f_1$ independently is an integer from 1 to 6; and $g_2$ is an integer from 1 to 4.

For example, $M^P$, when present, is (1)

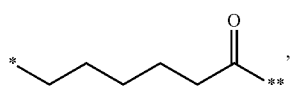

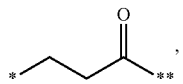

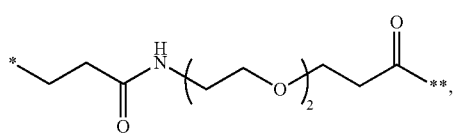

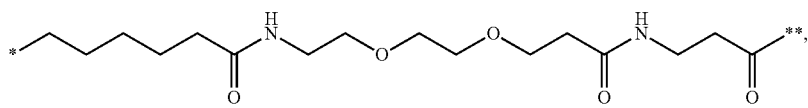

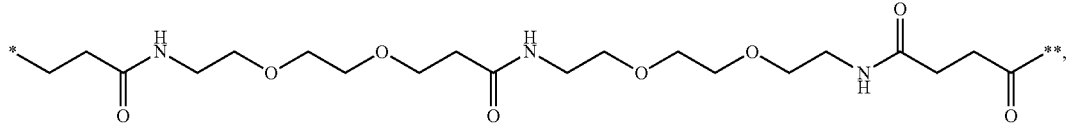

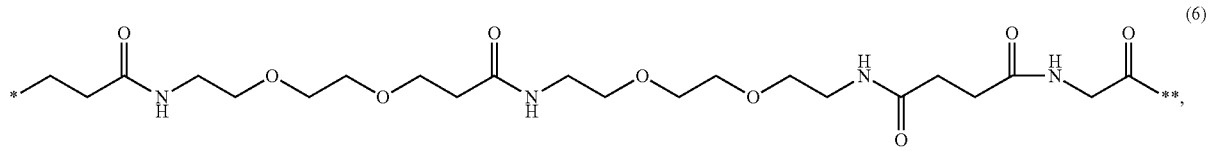

-continued

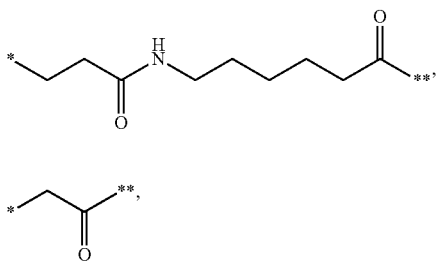
(7)

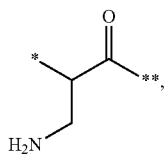
(8)

(9)

wherein * denotes attachment to $L^{P'}$ or $L^P$ and ** denotes attachment to $L^M$.

For example, $L^M$ is a bond and $a_2$ is 1.

For example, $a_2$ is 2 and $L^M$ is

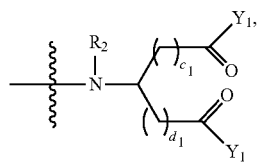
(1)

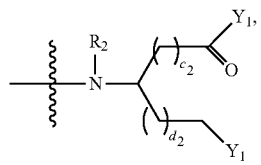
(2)

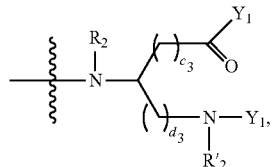
(3)

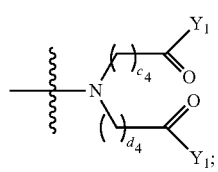
(4)

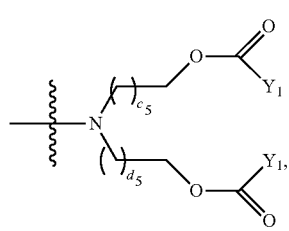
(5)

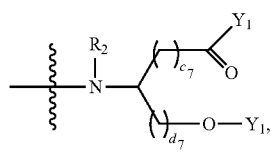
(6)

-continued

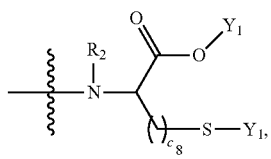
(7)

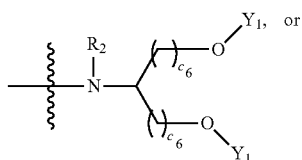
(8)

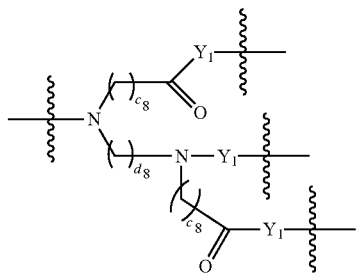
(9)

wherein $\{$ denotes attachment to $M^P$ when present or attachment to $L^P$ or $L^{P'}$ when $M^P$ is absent;

$Y_1$ denotes attachment to $L^3$ when present or attachment to $M^A$ when $L^3$ is absent;

$R_2$ and $R'_2$ are each independently hydrogen, an optionally substituted $C_{1-6}$ alkyl, an optionally substituted $C_{2-6}$ alkenyl, an optionally substituted $C_{2-6}$ alkynyl, an optionally substituted $C_{3-19}$ branched alkyl, an optionally substituted $C_{3-8}$ cycloalkyl, an optionally substituted $C_{6-10}$ aryl, an optionally substituted heteroaryl, an optionally substituted $C_{1-6}$ heteroalkyl, $C_{1-6}$alkoxy, aryloxy, $C_{1-6}$ heteroalkoxy, $C_{2-6}$ alkanoyl, an optionally substituted arylcarbonyl, $C_{2-6}$ alkoxycarbonyl, $C_{2-6}$ alkanoyloxy, arylcarbonyloxy, an optionally substituted $C_{2-6}$ alkanoyl, an optionally substituted $C_{2-6}$ alkanoyloxy, an optionally substituted $C_{2-6}$ substituted alkanoyloxy, —COOH, or —COO—$C_{1-6}$ alkyl;

each of $c_1$, $c_2$, $c_3$, $c_4$, $c_5$, $c_7$, and $c_8$ is an integer independently ranging between 0 and 10; and each of $d_1$, $d_2$, $d_3$, $d_4$, $d_5$, and $d_7$ is an integer independently ranging between 0 and 10.

For example, $a_2$ is 2 and $L^M$ is:
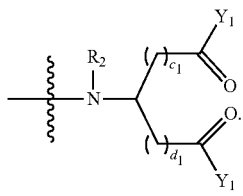
For example, $a_2$ is 3 and $L^M$ is:
(1)
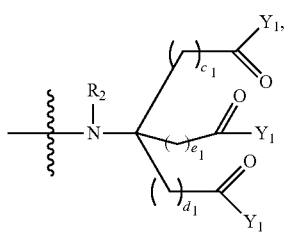
(2)
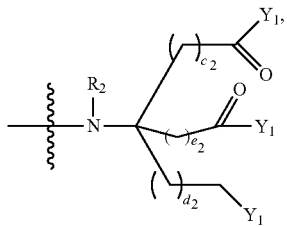
(3)
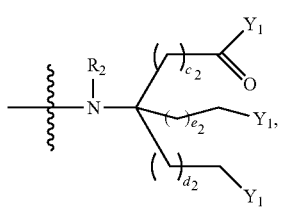
(4)
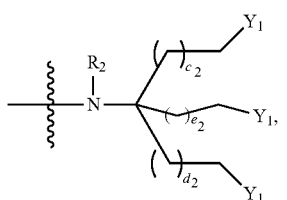
(5)
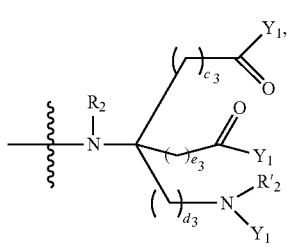
(6)
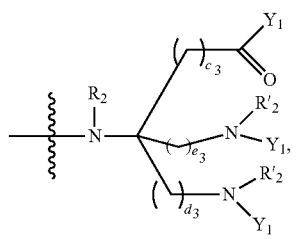
(7)
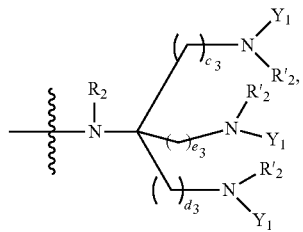
(8)
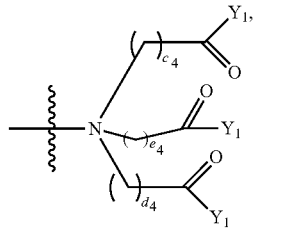
(9)
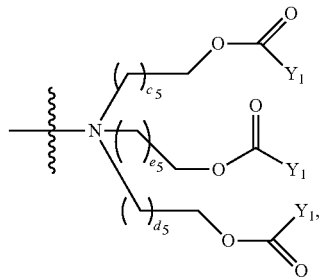
(10)
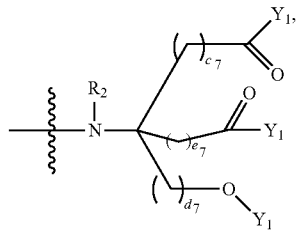
(11)
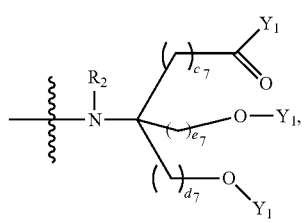

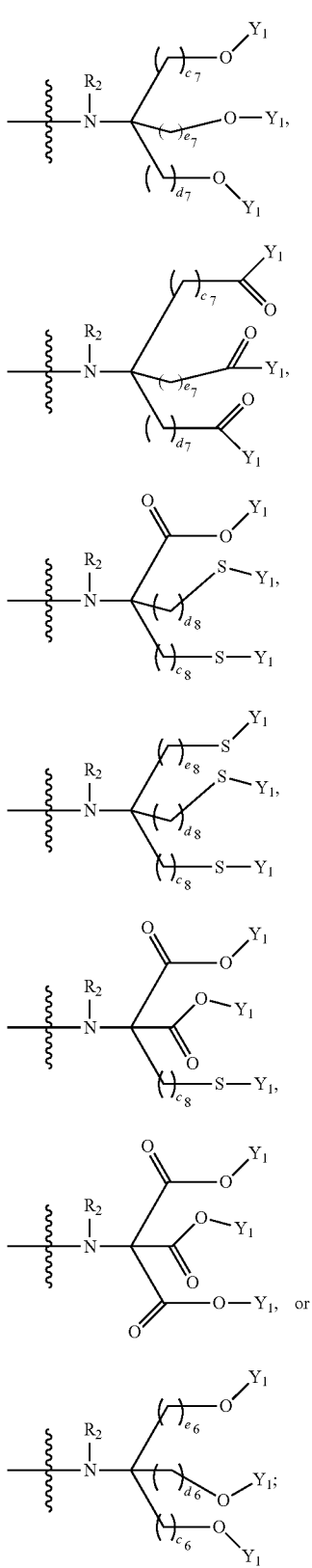

wherein:
⸹ denotes attachment to $M^P$ when present or attachment to $L^P$ or $L^{P'}$ when $M^P$ is absent;

$Y_1$ denotes attachment to $L^3$ when present or attachment to $M^4$ when $L^3$ is absent;

$R_2$ and $R'_2$ are each independently hydrogen, an optionally substituted $C_{1-6}$ alkyl, an optionally substituted $C_{2-6}$ alkenyl, an optionally substituted $C_{2-6}$ alkynyl, an optionally substituted $C_{3-19}$ branched alkyl, an optionally substituted $C_{3-8}$ cycloalkyl, an optionally substituted $C_{6-10}$ aryl, an optionally substituted heteroaryl, an optionally substituted $C_{1-6}$ heteroalkyl, $C_{1-6}$alkoxy, aryloxy, $C_{1-6}$ heteroalkoxy, $C_{2-6}$ alkanoyl, an optionally substituted arylcarbonyl, $C_{2-6}$ alkoxycarbonyl, $C_{2-6}$ alkanoyloxy, arylcarbonyloxy, an optionally substituted $C_{2-6}$ alkanoyl, an optionally substituted $C_{2-6}$ alkanoyloxy, an optionally substituted $C_{2-6}$ substituted alkanoyloxy, —COOH, or —COO—$C_{1-6}$ alkyl;

each of $c_1$, $c_2$, $c_3$, $c_4$, $c_5$, $c_6$, $c_7$, and $c_8$ is an integer independently ranging between 0 and 10;

each of $d_1$, $d_2$, $d_3$, $d_4$, $d_5$, $d_6$, $d_7$ and $d_8$ is an integer independently ranging between 0 and 10; and each of $e_1$, $e_2$, $e_3$, $e_4$, $e_5$, $e_6$, $e_7$, and $e_8$ is an integer independently ranging between 0 and 10.

For example, $a_2$ is 3 and $L^M$ is

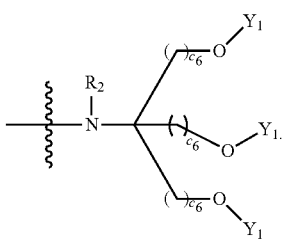

For example, $M^4$ comprises a peptide moiety that contains at least about five amino acids. For example, $M^4$ comprises a peptide moiety that contains at most about sixteen amino acids, e.g., about 4, 5, 6, 7, 8, 9, 10, 11, 12, 13, 14, 15 or 16 amino acids. For example, $M^4$ comprises a peptide moiety that contains at most about ten amino acids, e.g., about 4, 5, 6, 7, 8, 9, or 10 amino acids.

For example, $M^4$ comprises a peptide moiety that contains from three to about ten amino acids selected from glycine, serine, glutamic acid, aspartic acid, lysine, cysteine, a stereoisomer thereof (e.g., isoglutamic acid or isoaspartic acid), and a combination thereof.

For example, $M^4$ comprises a peptide moiety that contains at least four glycines and at least one serine.

For example, $M^4$ comprises a peptide moiety that contains at least four glycines and at least one glutamic acid.

For example, $M^4$ comprises a peptide moiety that contains at least four glycines, at least one serine and at least one glutamic acid.

For example, the ratio between D and PBRM or the ratio between Drug Units and the targeting moiety can be greater than 1:1, and up to 50:1, e.g., between 2:1 and 40:1; between 5:1 and 20:1; between 10:1 and 50:1, between 25:1 and 50:1, or between 30:1 and 50:1. Examples of PBRM include but are not limited to, full length antibodies such as IgG and IgM, antibody fragments such as Fabs, scFv, camelids, Fab2, and the like, small proteins, and peptides.

For example, the ratio between D and PBRM or the ratio between Drug Units and the targeting moiety is about 50:1, 40:1, 25:1, 20:1, 15:1, 10:1, 9:1, 8:1, 7:1, 6; 1, 5:1, 4:1, 3:1, or 2:1.

For example, the ratio between D and PBRM or the ratio between Drug Units and the targeting moiety can be about 25:1, 20:1, 15:1, 10:1, 5:1 or 2:1.

For example, the conjugate disclosed herein is used for the manufacture of a medicament useful for treating or lessening the severity of disorders, such as, characterized by abnormal growth of cells (e.g., cancer).

For example, the Drug Unit or D is locally delivered to a specific target cell, tissue, or organ.

The disclosure also provides compositions comprising the conjugates, methods for their preparation, and methods of use thereof in the treatment of various disorders, including, but not limited to cancer.

In one aspect, the disclosure further relates to a pharmaceutical composition comprising a scaffold or conjugate described herein and a pharmaceutically acceptable carrier.

In another aspect, the disclosure relates to a method of treating a disorder in a subject in need thereof, comprising administering to the subject an effective amount of a conjugate disclosed herein.

In yet another aspect, the disclosure relates to a method of diagnosing a disorder in a subject suspected of having the disorder. The method comprises administering an effective amount of the conjugate described herein to the subject suspected of having the disorder or performing an assay to detect a target antigen/receptor in a sample from the subject so as to determine whether the subject expresses target antigen or receptor.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Other features and advantages of the invention will be apparent from the following detailed description and claims.

DETAILED DESCRIPTION

Figure 1:
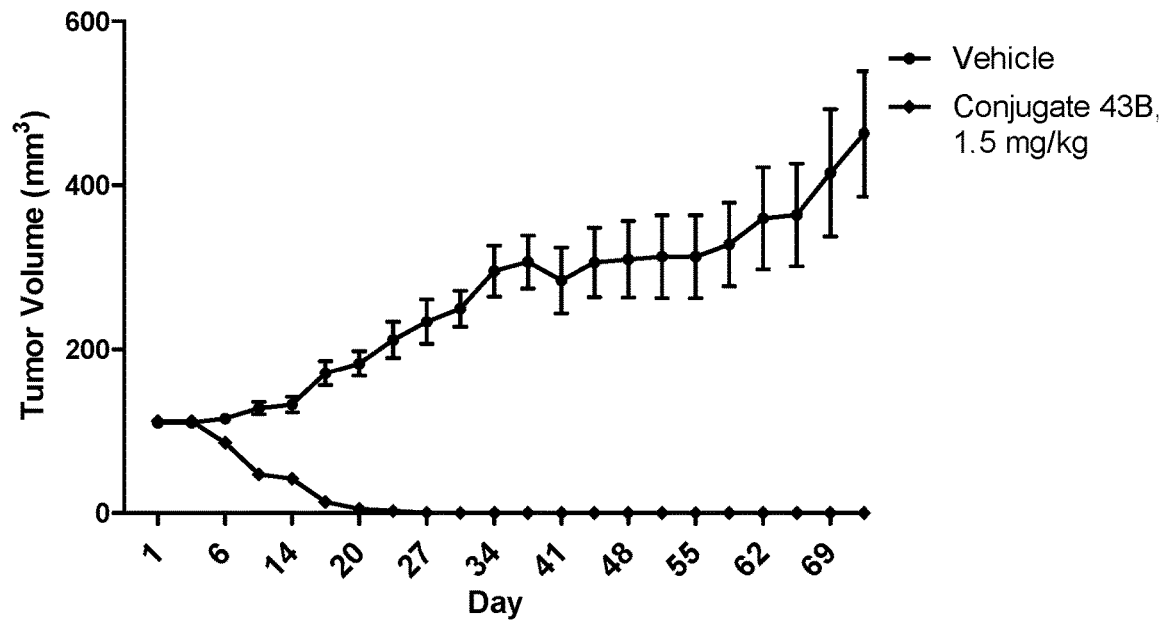
FIG. 1 illustrates the anti-tumor efficacy of the Trastuzumab-drug conjugate, Conjugate 43B (see Example 18), as measured in a N-87 mouse tumor xenograft model.

The present disclosure provides novel targeting moiety-drug conjugates, scaffolds for making the conjugates, synthetic methods for making the conjugates or scaffolds, pharmaceutical compositions containing them and various uses of the conjugates.

Certain compounds of the present disclosure and definitions of specific functional groups are also described in more detail herein. For purposes of this disclosure, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. Furthermore, it will be appreciated by one of ordinary skill in the art that the synthetic methods, as described herein, utilize a variety of protecting groups.

The use of the articles "a", "an", and "the" in both the following description and claims are to be construed to cover both the singular and the plural, unless otherwise indicated herein or clearly contradicted by context. The terms "comprising", "having", "being of" as in "being of a chemical formula", "including", and "containing" are to be construed as open terms (i.e., meaning "including but not limited to") unless otherwise noted, permits but does not require the inclusion of additional elements or steps. For example, a scaffold of a certain formula includes all components shown in the formula and may also include additional component not shown in the formula. Additionally whenever "comprising" or another open-ended term is used in an embodiment, it is to be understood that the same embodiment can be more narrowly claimed using the intermediate term "consisting essentially of" or the closed term "consisting of."

As used herein, the expressions "one or more of A, B, or C," "one or more A, B, or C," "one or more of A, B, and C," "one or more A, B, and C" and the like are used interchangeably and all refer to a selection from a group consisting of A, B, and/or C, i.e., one or more As, one or more Bs, one or more Cs, or any combination thereof.

The term "about", "approximately", or "approximate", when used in connection with a numerical value, means that a collection or range of values is included. For example, "about X" includes a range of values that are ±25%, ±20%, ±15%, ±10%, ±5%, ±2%, ±1%, ±0.5%, ±0.2%, or ±0.1% of X, where X is a numerical value. In one embodiment, the term "about" refers to a range of values which are 5% more or less than the specified value. In another embodiment, the term "about" refers to a range of values which are 2% more or less than the specified value. In another embodiment, the term "about" refers to a range of values which are 1% more or less than the specified value.

Recitation of ranges of values are merely intended to serve as a shorthand method of referring individually to each separate value falling within the range, unless otherwise indicated herein, and each separate value is incorporated into the specification as if it were individually recited herein. A range used herein, unless otherwise specified, includes the two limits of the range. For example, the expressions "x being an integer between 1 and 6" and "x being an integer of 1 to 6" both mean "x being 1, 2, 3, 4, 5, or 6", i.e., the terms "between X and Y" and "range from X to Y, are inclusive of X and Y and the integers there between.

"Protecting group": as used herein, the term protecting group means that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, certain exemplary oxygen protecting groups may be utilized. These oxygen protecting groups include, but are not limited to methyl ethers, substituted methyl ethers (e.g., MOM (methoxymethyl ether), MTM (methylthiomethyl ether), BOM (benzyloxymethyl ether), and PMBM (p-methoxybenzyloxymethyl ether)), substituted ethyl ethers, substituted benzyl ethers, silyl ethers (e.g., TMS (trimethylsilyl ether), TES (triethylsilyl ether), TIPS (triisopropylsilyl ether), TBDMS (t-butyldimethylsilyl ether), tribenzyl silyl ether, and TBDPS (t-butyldiphenyl silyl ether), esters (e.g., formate, acetate, benzoate (Bz), trifluoroacetate, and dichloroacetate), carbonates, cyclic acetals and ketals. In certain other exemplary embodiments, nitrogen protecting groups are utilized. Nitrogen protecting groups, as well as protection and deprotection methods are known in the art. Nitrogen protecting groups include, but are not limited to, carbamates (including methyl, ethyl and substituted ethyl carbamates (e.g., Troc), amides, cyclic imide derivatives, N-Alkyl and N-Aryl amines, imine derivatives, and enamine derivatives. In yet other embodiments, certain exemplary sulphur protecting groups may be utilized. The sulfur protecting groups include, but are not limited to those oxygen protecting group describe above as well as aliphatic carboxylic acid (e.g., acrylic acid), maleimide, vinyl sulfonyl, and optionally substituted maleic acid. Certain other exemplary protecting groups are detailed herein, however, it will be appreciated that the present disclosure is not intended to be limited to these protecting groups; rather, a variety of additional equivalent protecting groups can be readily identified using the above criteria and utilized in the present disclosure. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

"Leaving group" refers to a molecular fragment that departs with a pair of electrons in heterolytic bond cleavage. Leaving groups can be anions or neutral molecules. Leaving groups include, but are not limited to halides such as Cl⁻, Br⁻, and I⁻, sulfonate esters, such as para-toluenesulfonate ("tosylate", TsO⁻), and RC(O)O— in which R is hydrogen, an aliphatic, heteroaliphatic, carbocyclic, or heterocycloalkyl moiety.

"Antibody" refers to a full-length antibody or functional fragment of an antibody comprising an immunoglobulin. By a "functional fragment" it is meant a sufficient portion of the immunoglobulin or antibody is provided that the moiety effectively binds or complexes with the cell surface molecule for its target cell population, e.g., human oncofetal antigen.

An immunoglobulin may be purified, generated recombinantly, generated synthetically, or combinations thereof, using techniques known to those of skill in the art. While immunoglobulins within or derived from IgG antibodies are particularly well-suited for use in the conjugates or scaffolds of this disclosure, immunoglobulins from any of the classes or subclasses may be selected, e.g., IgG, IgA, IgM, IgD and IgE. Suitably, the immunoglobulin is of the class IgG including but not limited to IgG subclasses (IgG1, 2, 3 and 4) or class IgM which is able to specifically bind to a specific epitope on an antigen. Antibodies can be intact immunoglobulins derived from natural sources or from recombinant sources and can be immunoreactive portions of intact immunoglobulins. Antibodies may exist in a variety of forms including, for example, polyclonal antibodies, monoclonal antibodies, camelized single domain antibodies, intracellular antibodies ("intrabodies"), recombinant antibodies, anti-idiotypic antibodies, domain antibodies, linear antibody, multispecific antibody, antibody fragments, such as, Fv, Fab, F(ab)$_2$, F(ab)$_3$, Fab', Fab'-SH, F(ab')$_2$, single chain variable fragment antibodies (scFv), tandem/bis-scFv, Fc, pFc', scFvFc (or scFv-Fc), disulfide Fv (dsfv), bispecific antibodies (bc-scFv) such as BiTE antibodies; camelid antibodies, resurfaced antibodies, humanized antibodies, fully human antibodies, single-domain antibody (sdAb, also known as NANOBODY®), chimeric antibodies, chimeric antibodies comprising at least one human constant region, dual-affinity antibodies such as, dual-affinity retargeting proteins (DART™), divalent (or bivalent) single-chain variable fragments (di-scFvs, bi-scFvs) including but not limited to minibodies, diabodies, triabodies or tribodies, tetrabodies, and the like, and multivalent antibodies. "Antibody fragment" refers to at least a portion of the variable region of the immunoglobulin molecule that binds to its target, i.e., the antigen-binding region. As used herein, the term "antibody" refers to both the full-length antibody and antibody fragments unless otherwise specified.

"Protein based recognition-molecule" or "PBRM" refers to a molecule that recognizes and binds to a cell surface marker or receptor such as, a transmembrane protein, surface immobilized protein, or proteoglycan. Examples of PBRMs include but are not limited to, antibodies (e.g., Trastuzumab, Cetuximab, Rituximab, Bevacizumab, Epratuzumab, Veltuzumab, Labetuzumab, B7-H4, B7-H3, CA125, CD33, CXCR2, EGFR, FGFR1, FGFR2, FGFR3, FGFR4, HER2, NaPi2b, c-Met, NOTCH1, NOTCH2, NOTCH3, NOTCH4, PD-L1, c-Kit, MUC1, MUC13 and anti-5T4) or peptides (LHRH receptor targeting peptides, EC-1 peptide), lipocalins, such as, for example, anticalins, proteins such as, for example, interferons, lymphokines, growth factors, colony stimulating factors, and the like, peptides or peptide mimics, and the like. The protein based recognition molecule, in addition to targeting the conjugate to a specific cell, tissue or location, may also have certain therapeutic effect such as antiproliferative (cytostatic and/or cytotoxic) activity against a target cell or pathway. The protein based recognition molecule comprises or may be engineered to comprise at least one chemically reactive group such as, —COOH, primary amine, secondary amine —NHR, —SH, or a chemically reactive amino acid moiety or side chains such as, for example, tyrosine, histidine, cysteine, or lysine. In one embodiment, a PBRM may be a ligand (LG) or targeting moiety which specifically binds or complexes with a cell surface molecule, such as a cell surface receptor or antigen, for a given target cell population. Following specific binding or complexing of the ligand with its receptor, the cell is permissive for uptake of the ligand or ligand-drug-conjugate, which is then internalized into the cell. As used herein, a ligand that "specifically binds or complexes with" or "targets" a cell surface molecule preferentially associates with a cell surface molecule via intermolecular forces. For example, the ligand can preferentially associate with the cell surface molecule with a Kd of less than about 50 nM, less than about 5 nM, or less than 500 pM. Techniques for measuring binding affinity of a ligand to a cell surface molecule are well-known; for example, one suitable technique, is termed surface plasmon resonance (SPR). In one embodiment, the ligand is used for targeting and has no detectable therapeutic effect as separate from the drug which it delivers. In another embodiment, the ligand functions both as a targeting moiety and as a therapeutic or immunomodulatory agent (e.g., to enhance the activity of the active drug or prodrug).

"Biocompatible" as used herein is intended to describe compounds that exert minimal destructive or host response effects while in contact with body fluids or living cells or tissues. Thus a biocompatible group, as used herein, refers to an aliphatic, cycloalkyl, heteroaliphatic, heterocycloalkyl, aryl, or heteroaryl moiety, which falls within the definition of the term biocompatible, as defined above and herein. The term "Biocompatibility" as used herein, is also taken to mean that the compounds exhibit minimal interactions with recognition proteins, e.g., naturally occurring antibodies, cell proteins, cells and other components of biological systems, unless such interactions are specifically desirable. Thus, substances and functional groups specifically intended to cause the above minimal interactions, e.g., drugs and prodrugs, are considered to be biocompatible. Preferably (with exception of compounds intended to be cytotoxic, such as, e.g., antineoplastic agents), compounds are "biocompatible" if their addition to normal cells in vitro, at concentrations similar to the intended systemic in vivo concentrations, results in less than or equal to 1% cell death during the time equivalent to the half-life of the compound in vivo (e.g., the period of time required for 50% of the compound administered in vivo to be eliminated/cleared), and their administration in vivo induces minimal and medically acceptable inflammation, foreign body reaction, immunotoxicity, chemical toxicity and/or other such adverse effects. In the above sentence, the term "normal cells" refers to cells that are not intended to be destroyed or otherwise significantly affected by the compound being tested.

"Biodegradable": As used herein, "biodegradable" compounds or moieties are those that, when taken up by cells, can be broken down by the lysosomal or other chemical machinery or by hydrolysis into components that the cells can either reuse or dispose of without significant toxic effect on the cells. The term "biocleavable" as used herein has the same meaning of "biodegradable". The degradation fragments preferably induce little or no organ or cell overload or pathological processes caused by such overload or other adverse effects in vivo. Examples of biodegradation processes include enzymatic and non-enzymatic hydrolysis, oxidation and reduction. Suitable conditions for non-enzymatic hydrolysis of the biodegradable conjugates (or their components, e.g., the peptide-containing scaffolds and the linkers between the scaffolds and the antibody or the drug molecule) described herein, for example, include exposure of the biodegradable conjugates to water at a temperature and a pH of lysosomal intracellular compartment. Biodegradation of some conjugates (or their components, e.g., the peptide-containing scaffolds and the linkers between the scaffolds and the antibody or the drug molecule), can also be enhanced extracellularly, e.g., in low pH regions of the animal body, e.g., an inflamed area, in the close vicinity of activated macrophages or other cells releasing degradation facilitating factors. The integrity of the conjugates or scaffolds disclosed herein can be measured, for example, by size exclusion HPLC. Although faster degradation may be in some cases preferable, in general it may be more desirable that the conjugates or scaffolds disclosed herein degrade in cells with the rate that does not exceed the rate of metabolization or excretion of their fragments by the cells. In preferred embodiments, the biodegradation byproducts of conjugates or scaffolds disclosed herein are biocompatible.

"Bioavailability": The term "bioavailability" refers to the systemic availability (i.e., blood/plasma levels) of a given amount of drug or compound administered to a subject. Bioavailability is an absolute term that indicates measurement of both the time (rate) and total amount (extent) of drug or compound that reaches the general circulation from an administered dosage form.

"Hydrophilic": The term "hydrophilic" does not essentially differ from the common meaning of this term in the art, and denotes chemical moieties which contain ionizable, polar, or polarizable atoms, or which otherwise may be solvated by water molecules. Thus a hydrophilic moiety or group, as used herein, refers to an aliphatic, cycloalkyl, heteroaliphatic, heterocycloalkyl, aryl or heteroaryl moiety, which falls within the definition of the term hydrophilic, as defined above. Examples of particular hydrophilic organic moieties which are suitable include, without limitation, aliphatic or heteroaliphatic groups comprising a chain of atoms in a range of between about one and twelve atoms, hydroxyl, hydroxyalkyl, amine, carboxyl, amide, carboxylic ester, thioester, aldehyde, nitryl, isonitryl, nitroso, hydroxylamine, mercaptoalkyl, heterocycle, carbamates, carboxylic acids and their salts, sulfonic acids and their salts, sulfonic acid esters, phosphoric acids and their salts, phosphate esters, polyglycol ethers, polyamines, polycarboxylates, polyesters, polythioesters, polyalcohols and derivatives thereof. In certain embodiments, hydrophilic substituents comprise a carboxyl group (COOH), an aldehyde group (CHO), a ketone group ($COC_{1-4}$ alkyl), a methylol ($CH_2OH$) or a glycol (for example, $CHOH—CH_2OH$ or $CH—(CH_2OH)_2$), $NH_2$, F, cyano, $SO_3H$, $PO_3H$, and the like.

Hydrophilicity of the compounds (including drugs, conjugates and scaffolds) disclosed herein can be directly measured through determination of hydration energy, or determined through investigation between two liquid phases, or by chromatography on solid phases with known hydrophobicity, such as, for example, C4 or C18.

"Physiological conditions": The phrase "physiological conditions", as used herein, relates to the range of chemical (e.g., pH, ionic strength) and biochemical (e.g., enzyme concentrations) conditions likely to be encountered in the extracellular fluids of living tissues. For most normal tissues, the physiological pH ranges from about 7.0 to 7.4. Circulating blood plasma and normal interstitial liquid represent typical examples of normal physiological conditions.

"Polysaccharide", "carbohydrate" or "oligosaccharide": The terms "polysaccharide", "carbohydrate", or "oligosaccharide" are known in the art and refer, generally, to substances having chemical formula $(CH_2O)_n$, where generally n>2, and their derivatives. Carbohydrates are polyhydroxyaldehydes or polyhydroxyketones, or change to such substances on simple chemical transformations, such as hydrolysis, oxidation or reduction. Typically, carbohydrates are present in the form of cyclic acetals or ketals (such as, glucose or fructose). These cyclic units (monosaccharides) may be connected to each other to form molecules with few (oligosaccharides) or several (polysaccharides) monosaccharide units. Often, carbohydrates with well defined number, types and positioning of monosaccharide units are called oligosaccharides, whereas carbohydrates consisting of mixtures of molecules of variable numbers and/or positioning of monosaccharide units are called polysaccharides. The terms "polysaccharide", "carbohydrate", and "oligosaccharide", are used herein interchangeably. A polysaccharide may include natural sugars (e.g., glucose, fructose, galactose, mannose, arabinose, ribose, and xylose) and/or derivatives of naturally occurring sugars (e.g., 2'-fluororibose, 2'-deoxyribose, and hexose).

"Drug": As used herein, the term "drug" refers to a compound which is biologically active and provides a desired physiological effect following administration to a subject in need thereof (e.g., an active pharmaceutical ingredient).

"Prodrug": As used herein the term "prodrug" refers to a precursor of an active drug, that is, a compound that can be transformed to an active drug. Typically such a prodrug is subject to processing in vivo, which converts the drug to a physiologically active form. In some instances, a prodrug may itself have a desired physiologic effect. A desired physiologic effect may be, e.g., therapeutic, cytotoxic, immunomodulatory, or the like.

"Cytotoxic": As used herein the term "cytotoxic" means toxic to cells or a selected cell population (e.g., cancer cells). The toxic effect may result in cell death and/or lysis. In certain instances, the toxic effect may be a sublethal destructive effect on the cell, e.g., slowing or arresting cell growth. In order to achieve a cytotoxic effect, the drug or prodrug may be selected from a group consisting of a DNA damaging agent, a microtubule disrupting agent, or a cytotoxic protein or polypeptide, amongst others.

"Cytostatic": As used herein the term "cytostatic" refers to a drug or other compound which inhibits or stops cell growth and/or multiplication.

"Small molecule": As used herein, the term "small molecule" refers to molecules, whether naturally-occurring or artificially created (e.g., via chemical synthesis) that have a relatively low molecular weight. Preferred small molecules are biologically active in that they produce a local or systemic effect in animals, preferably mammals, more preferably humans. In certain preferred embodiments, the small molecule is a drug and the small molecule is referred to as "drug molecule" or "drug" or "therapeutic agent". In certain embodiments, the drug molecule has MW less than or equal to about 5 kDa. In other embodiments, the drug molecule has MW less than or equal to about 1.5 kDa. In embodiments, the drug molecule is selected from vinca alkaloids, auristatins, duocarmycins, kinase inhibitors, MEK inhibitors, KSP inhibitors, PI3 kinase inhibitors, calicheamicins, SN38, camptothecin, topoisomerase inhibitors, non-natural camptothecins, protein synthesis inhibitor, RNA polymerase inhibitor, pyrrolobenzodiazepines, maytansinoids, DNA-binding drugs, DNA intercalation drugs and analogs thereof. Preferably, though not necessarily, the drug is one that has already been deemed safe and effective for use by an appropriate governmental agency or body, e.g., the FDA. For example, drugs for human use listed by the FDA under 21 C.F.R. §§ 330.5, 331 through 361, and 440 through 460; drugs for veterinary use listed by the FDA under 21 C.F.R. §§ 500 through 589, incorporated herein by reference, are all considered suitable for the methods, conjugates, and scaffolds disclosed herein. Classes of drug molecules that can be used in the practice of the present invention include, but are not limited to, anti-cancer substances, radionuclides, vitamins, anti-AIDS substances, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or antithrombotic agents, local anesthetics, ophthalmics, prostaglandins, anti-depressants, anti-psychotic substances, anti-emetics, imaging agents. Many large molecules are also drugs and such large molecules may be used in the conjugates and other constructs described herein. Examples of suitable large molecules include, e.g., amino acid based molecules. Amino acid based molecules may encompass, e.g., peptides, polypeptides, enzymes, antibodies, immunoglobulins, or functional fragments thereof, among others.

A more complete, although not exhaustive, listing of classes and specific drugs suitable for use in the present disclosure may be found in "Pharmaceutical Substances: Syntheses, Patents, Applications" by Axel Kleemann and Jurgen Engel, Thieme Medical Publishing, 1999 and the "Merck Index: An Encyclopedia of Chemicals, Drugs, and Biologicals", Edited by Susan Budavari et al., CRC Press, 1996, both of which are incorporated herein by reference. In preferred embodiments, the drug used in this disclosure is a therapeutic agent that has antiproliferative (cytostatic and/or cytotoxic) activity against a target cell or pathway. The drug may have a chemically reactive group such as, for example, —COOH, primary amine, secondary amine —NHR, —OH, —SH, —C(O)H, —C(O)R, —C(O)NHR$^{2b}$, C(S)OH, —S(O)$_2$OR$^{2b}$, —P(O)$_2$OR$^{2b}$, —CN, —NC or —ONO, in which R is an aliphatic, heteroaliphatic, carbocyclic or heterocycloalkyl moiety and R$^{2b}$ is a hydrogen, an aliphatic, heteroaliphatic, carbocyclic, or heterocyclic moiety.

"Active form" as used herein refers to a form of a compound that exhibits intended pharmaceutical efficacy in vivo or in vitro. In particular, when a drug molecule intended to be delivered by the conjugate of the disclosure is released from the conjugate, the active form can be the drug itself or its derivatives, which exhibit the intended therapeutic properties. The release of the drug from the conjugate can be achieved by cleavage of a biodegradable bond of the linker which attaches the drug to the scaffold or conjugate of the disclosure. The active drug derivatives accordingly can comprise a portion of the linker.

"Diagnostic label": As used herein, the term diagnostic label refers to an atom, group of atoms, moiety or functional group, a nanocrystal, or other discrete element of a composition of matter, that can be detected in vivo or ex vivo using analytical methods known in the art. When associated with a conjugate of the present disclosure, such diagnostic labels permit the monitoring of the conjugate in vivo. Alternatively or additionally, constructs and compositions that include diagnostic labels can be used to monitor biological functions or structures. Examples of diagnostic labels include, without limitation, labels that can be used in medical diagnostic procedures, such as, radioactive isotopes (radionuclides) for gamma scintigraphy and Positron Emission Tomography (PET), contrast agents for Magnetic Resonance Imaging (MRI) (for example paramagnetic atoms and superparamagnetic nanocrystals), contrast agents for computed tomography and other X-ray-based imaging methods, agents for ultrasound-based diagnostic methods (sonography), agents for neutron activation (e.g., boron, gadolinium), fluorophores for various optical procedures, and, in general moieties which can emit, reflect, absorb, scatter or otherwise affect electromagnetic fields or waves (e.g., gamma-rays, X-rays, radiowaves, microwaves, light), particles (e.g., alpha particles, electrons, positrons, neutrons, protons) or other forms of radiation, e.g., ultrasound.

"Animal": The term animal, as used herein, refers to humans as well as non-human animals, at any stage of development, including, for example, mammals, birds, reptiles, amphibians, fish, worms and single cells. Cell cultures and live tissue samples are considered to be pluralities of animals. Preferably, the non-human animal is a mammal (e.g., a rodent, a mouse, a rat, a rabbit, a monkey, a dog, a cat, a primate, or a pig). An animal may be a transgenic animal or a human clone. The term "subject" encompasses animals.

"Efficient amount": In general, as it refers to an active agent or drug delivery device, the term "efficient amount" refers to the amount necessary to elicit the desired biological response. As will be appreciated by those of ordinary skill in this art, the efficient amount of an agent or device may vary depending on such factors as the desired biological endpoint, the agent to be delivered, the composition of the encapsulating matrix, the target tissue, etc. For example, the efficient amount of microparticles containing an antigen to be delivered to immunize an individual is the amount that results in an immune response sufficient to prevent infection with an organism having the administered antigen.

"Natural amino acid" as used herein refers to any one of the common, naturally occurring L-amino acids found in naturally occurring proteins, such as, glycine (Gly), alanine (Ala), valine (Val), leucine (Leu), isoleucine (Ile), lysine (Lys), arginine (Arg), histidine (His), proline (Pro), serine (Ser), threonine (Thr), phenylalanine (Phe), tyrosine (Tyr), tryptophan (Trp), aspartic acid (Asp), glutamic acid (Glu), asparagine (Asn), glutamine (Gln), cysteine (Cys), methionine (Met) or a stereoisomer thereof, e.g., isoglutamic acid (iGlu) or isoaspartic acid (iAsp). Unless specified otherwise, a reference to an amino acid includes the amino acid itself and its stereoisomers. For example, the term "glutamic acid" includes both Glu and iGlu while the term "aspartic acid" includes both Asp and iAsp.

"Unnatural amino acid" as used herein refers to any amino acid which is not a natural amino acid. This includes, for example, amino acids that comprise α-, β-, γ-, D-, L-amino acyl residues. More generally, the unnatural amino acid comprises a residue of the general formula

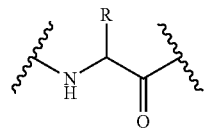

wherein the side chain R is other than the amino acid side chains occurring in nature. Exemplary unnatural amino acids, include, but are not limited to, sarcosine (N-methylglycine), citrulline (cit), homocitrulline, β-ureidoalanine, thiocitrulline, hydroxyproline, allothreonine, pipecolic acid (homoproline), α-aminoisobutyric acid, tert-butylglycine, tert-butylalanine, allo-isoleucine, norleucine, α-methylleucine, cyclohexylglycine, β-cyclohexylalanine, β-cyclopentylalanine, α-methylproline, phenylglycine, α-methylphenylalanine and homophenylalanine.

"Alkyl" by itself or as part of another term, as used herein, refers to a substituted or unsubstituted straight chain or branched, saturated or unsaturated hydrocarbon having the indicated number of carbon atoms (e.g., "—$C_{1-8}$ alkyl" or $C_{1-10}$ alkyl refer to an alkyl group having from 1 to 8 or 1 to 10 carbon atoms, respectively). When the number of carbon atoms is not indicated, the alkyl group has from 1 to 8 carbon atoms. Representative straight chain "—$C_{1-8}$ alkyl" groups include, but are not limited to, -methyl, -ethyl, -n-propyl, -n-butyl, -n-pentyl, -n-hexyl, -n-heptyl and -n-octyl; while branched —$C_{1-8}$ alkyls include, but are not limited to, -isopropyl, -sec-butyl, -isobutyl, -tert-butyl, -isopentyl, and -2-methylbutyl; unsaturated —$C_{2-8}$ alkyls include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexyl, 2-hexyl, -3-hexyl, -acetylenyl, -propynyl, -1-butynyl, -2-butynyl, -1-pentynyl, -2-pentynyl and -3-methyl-1 butynyl. In some embodiments, an alkyl group is unsubstituted. An alkyl group can be substituted with one or more groups. In other aspects, an alkyl group will be saturated.

"Alkylene" by itself of as part of another term, as used herein, refers to a substituted or unsubstituted saturated or unsaturated branched or straight chain or cyclic hydrocarbon radical of the stated number of carbon atoms, typically 1-10 carbon atoms, and having two monovalent radical centers derived by the removal of two hydrogen atoms from the same or two different carbon atoms of a parent alkane. Typical alkylene radicals include, but are not limited to: methylene (—$CH_2$—), 1,2-ethyl (—$CH_2CH_2$—), 1,3-propyl (—$CH_2CH_2CH_2$—), 1,4-butyl (—$CH_2CH_2CH_2CH_2$—), and the like. In some embodiments, an alkylene is a branched or straight chain hydrocarbon (i.e., it is not a cyclic hydrocarbon). In any of the embodiments provided herein, the alkylene can be a saturated alkylene.

"Aryl" by itself or as part of another term, as used herein, means a substituted or unsubstituted monovalent carbocyclic aromatic hydrocarbon radical of 6-20 carbon (preferably 6-14 carbon) atoms derived by the removal of one hydrogen atom from a single carbon atom of a parent aromatic ring system. Some aryl groups are represented in the exemplary structures as "Ar". Typical aryl groups include, but are not limited to, radicals derived from benzene, substituted benzene, naphthalene, anthracene, biphenyl, and the like. An exemplary aryl group is a phenyl group.

"Arylene" by itself or as part of another term, as used herein, is an aryl group as defined above wherein one of the aryl group's hydrogen atoms is replaced with a bond (i.e., it is divalent) and can be in the ortho, meta, or para orientations as shown in the following structures, with phenyl as the exemplary group:

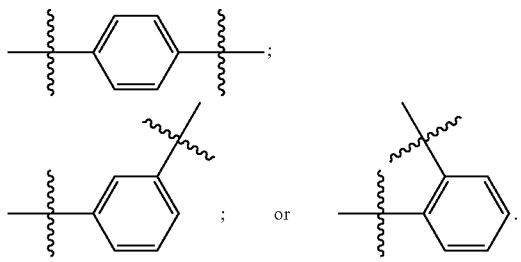

In some embodiments, e.g., when a Multifunctional Linker or Drug Unit, comprises an arylene, the arylene is an aryl group defined above wherein one or two of the aryl group's hydrogen atoms is replaced with a bond (i.e., the arylene can be divalent or trivalent).

"Heterocycle" by itself or as part of another term, as used herein, refers to a monovalent substituted or unsubstituted aromatic ("heteroaryl") or non-aromatic ("heterocycloalkyl") monocyclic, bicyclic, tricyclic, or tetracyclic ring system having a certain number of (e.g., from 3 to 8 or $C_{3-5}$) carbon atoms (also referred to as ring members) and one to four heteroatom ring members independently selected from N, O, P or S, and derived by removal of one hydrogen atom from a ring atom of a parent ring system. One or more N, C or S atoms in the heterocycle can be oxidized. The ring that includes the heteroatom can be aromatic or nonaromatic. Unless otherwise noted, the heterocycle is attached to its pendant group at any heteroatom or carbon atom that results in a stable structure. Representative examples of a heterocycle (e.g., $C_{3-8}$ heterocycle) include, but are not limited to, pyrrolidinyl, azetidinyl, piperidinyl, morpholinyl, tetrahydrofuranyl, tetrahydropyranyl, benzofuranyl, benzothiophene, indolyl, benzopyrazolyl, pyrrolyl, thiophenyl (thiophene), furanyl, thiazolyl, imidazolyl, pyrazolyl, pyrimidinyl, pyridinyl, pyrazinyl, pyridazinyl, isothiazolyl, and isoxazolyl.

"Heterocyclo" or "Heterocyclo-" when used herein, refers to a heterocycle group (e.g., $C_{3-8}$ heterocycle) defined above wherein one or more of additional hydrogen atoms of the heterocycle are replaced with a bond (i.e., it is multivalent, such as divalent or trivalent). In some embodiments, when a hydrophilic group, Multifunctional Linker or Linker-Drug moiety comprises a heterocyclo, the heterocyclo is a heterocycle group defined above wherein one or two of the heterocycle group's hydrogen atoms is replaced with a bond (i.e., the heterocyclo can be divalent or trivalent).

"Carbocycle" by itself or as part of another term, when used herein, is monovalent, substituted or unsubstituted, aromatic ("aryl") or saturated or unsaturated non-aromatic ("cycloalkyl"), monocyclic, bicyclic, tricyclic, or tetracyclic carbocyclic ring system having a certain number of (e.g., from 3 to 8 or $C_{3-8}$) carbon atoms (also referred to as ring members) derived by the removal of one hydrogen atom from a ring atom of a parent ring system. A carbocycle can be 3-, 4-, 5-, 6-, 7- or 8-membered. Representative $C_{3-8}$ carbocycles include, but are not limited to, cyclopropyl, cyclobutyl, cyclopentyl, cyclopentadienyl, cyclohexyl, cyclohexenyl, phenyl, 1,3-cyclohexadienyl, 1,4-cyclohexadienyl, cycloheptyl, 1,3-cycloheptadienyl, 1,3,5-cycloheptatrienyl, cyclooctyl, and cyclooctadienyl.

"Carbocyclo" or "Carbocyclo-" by itself or as part of another term, when used herein, refers to a $C_{3-8}$ carbocycle group defined above wherein another of the carbocycle groups' hydrogen atoms is replaced with a bond (i.e., it is divalent). In select embodiments, e.g., when a hydrophilic group, Multifunctional Linker or Linker-Drug moiety comprises a carbocyclo, the carbocyclo is a carbocycle group defined above wherein one or two of the carbocycle group's hydrogen atoms is replaced with a bond (i.e., the carbocyclo can be divalent or trivalent).

"Heteroalkyl" by itself or in combination with another term, when used herein, means, unless otherwise stated, a stable straight or branched chain hydrocarbon, or combinations thereof, fully saturated or containing from 1 to 3 degrees of unsaturation, consisting of the stated number of carbon atoms and from one to ten, preferably one to three, heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group or at the position at which the alkyl group is attached to the remainder of the molecule. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —NH—$CH_2$—$CH_2$—NH—C(O)—$CH_2$—$CH_3$, —$CH_2$—$CH_2$—S(O)$_2$—$CH_3$, —CH=CH—O—$CH_3$, —Si($CH_3$)$_3$, —$CH_2$—CH=NO—$CH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. In preferred embodiments, a $C_{1-4}$ heteroalkyl or heteroalkylene has 1 to 4 carbon atoms and 1 or 2 heteroatoms and a $C_{1-3}$ heteroalkyl or heteroalkylene has 1 to 3 carbon atoms and 1 or 2 heteroatoms. In some aspects, a heteroalkyl or heteroalkylene is saturated.

"Heteroalkylene" by itself or as part of another substituent, when used herein, means a divalent group derived from heteroalkyl (as discussed above), as exemplified by —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini. Still further, for alkylene and heteroalkylene linking groups, no orientation of the linking group is implied. In select embodiments, e.g., when a hydrophilic group, Multifunctional Linker or Linker-Drug moiety comprises a heteroalkylene, the heteroalkylene is a heteroalkyl group defined above wherein one or two of the heteroalkyl group's hydrogen atoms is replaced with a bond (i.e., the heteroalkylene can be divalent or trivalent).

"Optionally substituted" when used herein, means that a chemical moiety (such as alkyl, heteroalkyl, carbocycle, and heterocycle, etc.) is either substituted or unsubstituted. Unless otherwise specified, the chemical moieties disclosed herein are optionally substituted. When a chemical moiety is substituted, one or more hydrogen atoms are each independently replaced with a substituent. Typical substituents include, but are not limited to, —X', —R', —O, —OR', —SR', —S$^-$, —N(R')$_2$, —N(R')$_3$, =NR', —C(X')$_3$, —CN, —OCN, —SCN, —N=C=O, —NCS, —NO, —NO$_2$, =N$_2$, —N$_3$, —NR'C(=O)R', —C(=O)R', —C(=O)N(R')$_2$, —SO$_3^-$, —SO$_3$H, —S(=O)$_2$R', —OS(=O)$_2$OR', —S(=O)$_2$NR', —S(=O)R', —OP(=O)(OR')$_2$, —P(=O)(OR')$_2$, —PO$_3^-$, —PO$_3$H$_2$, —AsO$_2$H$_2$, —C(=O)R', —C(=O)X', —C(=S)R', —CO$_2$R', —CO$_2^-$, —C(=S)

OR', C(=O)SR', C(=S)SR', C(=O)N(R')$_2$, C(=S)N(R')$_2$, or C(=NR')N(R')$_2$, wherein each X' is independently a halogen: —F, —Cl, —Br, or —I; and each R' is independently —H, —C$_{1-20}$ alkyl, —C$_{6-20}$ aryl, —C$_3$-C$_{14}$ heterocycle, a protecting group or a prodrug moiety. Typical substituents also include oxo (=O).

"Linker-Drug moiety" as used herein, refers to the non-targeting moiety portion of a conjugate disclosed herein. The Linker component of the Linker-Drug moiety has the release mechanism, which is referred to as the Releasable Assembly Unit, interposed between a Multifunctional Linker and a Drug Unit.

"Multifunctional Linker" as used herein, refers to a linker that connects one or more hydrophilic groups, one or more Drug Units, and a targeting moiety (e.g., a PBRM) to form a conjugate or scaffold as disclosed herein. The connection of these components to the Multifunctional Linker can either be parallel or serial. In some embodiments, the Multifunctional Linker comprises a peptide moiety between the targeting moiety and the hydrophilic group, wherein the peptide moiety includes at least two amino acids. In other embodiments, the Multifunctional Linker does not have to comprise a peptide moiety of at least two amino acids when the hydrophilic group is a polyalcohol or a derivative thereof. In other embodiments, the Multifunctional Linker does not have to comprise a peptide moiety of at least two amino acids when the hydrophilic group is a glucosyl-amine, a di-glucosyl-amine, a tri-glucosyl-amine or a derivative thereof.

As used herein, the phrase "parallel orientation", "parallel placement", "parallel connection" or like terms refer to a configuration wherein the parallel-placed or parallel-oriented or parallel-connected components are attached to the Multifunctional Linker in such a manner that each has one end tethered to the Multifunctional Linker and one free end. The term "parallel" is used herein is not being used to denote that two components are side-by-side in space or have the same distance between them throughout some or their entire lengths. In instances where a parallel-oriented component is itself branched and thus has multiple ends, it still has only one tethered end. In some embodiments, only those hydrophilic groups, required to mask hydrophobicity for a given Linker-Drug moiety are in parallel orientation to the Drug Unit, which does not necessarily require all of the Drug Units and hydrophilic groups connected to the Multifunctional Linker be in parallel orientations to one another. In other embodiments, all of the Drug Units and hydrophilic groups connected to the Multifunctional Linker are in parallel orientations to one another.

The phrase "serial orientation" or "serial placement" or "serial connection" or like terms refer to a configuration of a component in a conjugate or scaffold of the disclosure wherein the serially-oriented component is attached in such a manner that it has two tethered ends with each end connected to a different component of the conjugate or scaffold of the disclosure. For example, one or more (OCH$_2$CH$_2$) subunits, which characterize a PEG unit or subunit, are interposed between the Drug Unit and the targeting moiety.

"Free drug" as used herein, refers to a biologically active form of a drug moiety that is not covalently attached either directly or indirectly to a hydrophilic group or to a degradant product of a Ligand Unit. Free drug can refer to the drug, as it exists immediately upon cleavage from the Multifunctional Linker via the release mechanism, which is provided by the Releasable Assembly Unit in the Linker-Drug moiety, or, to subsequent intracellular conversion or metabolism. In some aspects, the free drug will have the form H-D or may exist a as a charged moiety. The free drug is a pharmacologically active species which can exert the desired biological effect. In some aspects, the pharmacologically active species may not be the parent drug and may include a component of the linker through which the drug is connected to the targeting moiety, which has not undergone subsequent intracellular metabolism.

Hydrophobicity can be measured using S log P. S log P is defined as the log of the octanol/water partition coefficient (including implicit hydrogens) and can be calculated using the program MOE™ from the Chemical Computing group (S log P values calculated using Wildman, S. A., Crippen, G. M.; Prediction of Physiochemical Parameters by Atomic Contributions; J. Chem. Inf. Comput. Sci. 39 No. 5 (1999) 868-873).

In certain embodiments, the present disclosure provides a targeting moiety-drug conjugate composition comprising a population of targeting moiety-drug conjugates. The targeting moiety-drug conjugate comprises a targeting moiety unit and multiple Linker-Drug moieties attached thereto. Preferably, there is an average of from about 2 to about 14, about 3 to about 10, or about 3 to about 5 Linker-Drug moieties (e.g., d$_{13}$ of Formula (I)) per targeting moiety in the conjugate. Exemplary attachment to the targeting moiety is via thioether linkages. Exemplary conjugation sites on a targeting moiety are the thiol groups obtained from reduction of interchain disulfide residues and/or thiol-containing residues introduced into the targeting moiety such as introduced cysteines. Attachment can be, for example, via thiol residues derived from an interchain disulfide and from 0 to 8 introduced cysteine residues.

As used herein, "molecular weight" or "MW" of a polymer refers to the weight average molecular weight unless otherwise specified.

The present disclosure is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

The present disclosure is intended to include all isomers of the compound (e.g., the drug, conjugate, and scaffold disclosed herein), which refers to and includes, optical isomers, and tautomeric isomers, where optical isomers include enantiomers and diastereomers, chiral isomers and non-chiral isomers, and the optical isomers include isolated optical isomers as well as mixtures of optical isomers including racemic and non-racemic mixtures; where an isomer may be in isolated form or in a mixture with one or more other isomers.

Conjugates and Peptide-Containing Scaffolds

In one aspect, the disclosure relates to a conjugate of Formula (I) with a protein based recognition-molecule (PBRM):

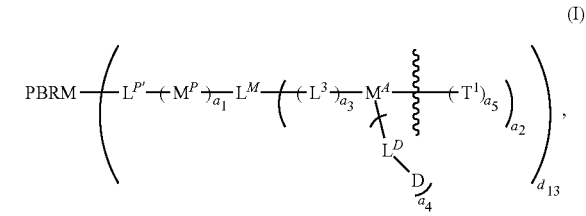

(I)

wherein
- $a_1$ is an integer from 0 to 1;
- $a_2$ is an integer from 1 to 3;
- $a_3$ is an integer from 0 to 1;
- $a_4$ is an integer from 1 to about 5;
- $a_5$ is an integer from 1 to 3;
- $d_{13}$ is an integer from 1 to about 14;
- PBRM denotes a protein based recognition-molecule;
- $L^{P'}$ is a divalent linker moiety connecting the PBRM to $M^P$; of which the corresponding monovalent moiety $L^P$ contains a functional group $W^P$ that is capable of forming a covalent bond with a functional group of the PBRM;
- $M^P$ is a Stretcher unit;
- $L^M$ is a bond, or a trivalent or tetravalent linker, and when $L^M$ is a bond, $a_2$ is 1, when $L^M$ is trivalent linker, $a_2$ is 2, or when $L^M$ is a tetravalent linker, $a_2$ is 3;
- $L^3$ is a carbonyl-containing moiety;
- $M^A$ comprises a peptide moiety that contains at least two amino acids;
- $T^1$ is a hydrophilic group and the

between $T^1$ and $M^A$ denotes direct or indirect attachment of $T^1$ and $M^A$;
- each occurrence of D is independently a therapeutic agent having a molecular weight≤about 5 kDa; and
- each occurrence of $L^D$ is independently a divalent linker moiety connecting D to $M^A$ and comprises at least one cleavable bond such that when the bond is broken, D is released in an active form for its intended therapeutic effect.

In another aspect, the disclosure relates to a peptide-containing scaffold of any one of Formulae (II)-(XIV):

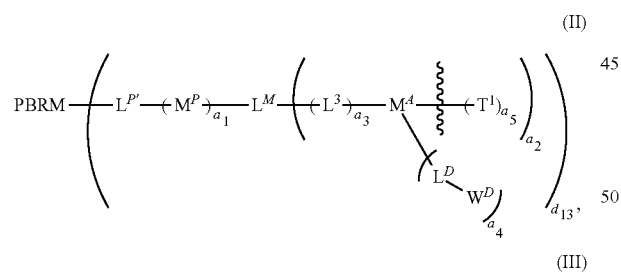
(II)

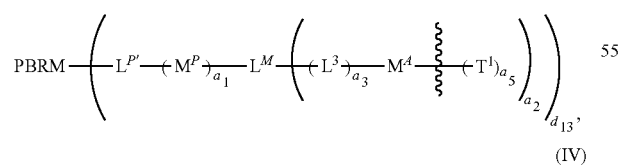
(III)

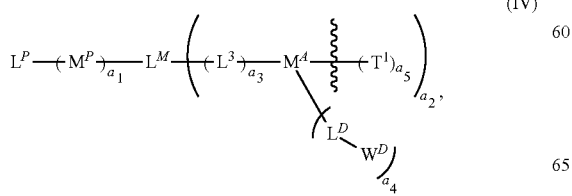
(IV)

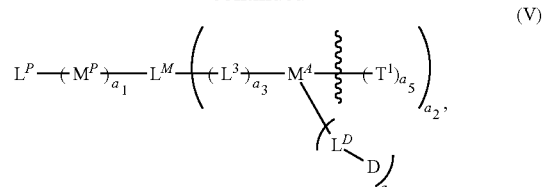
(V)

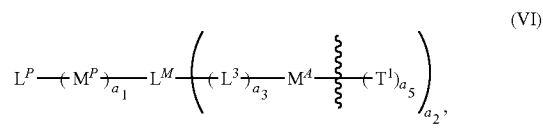
(VI)

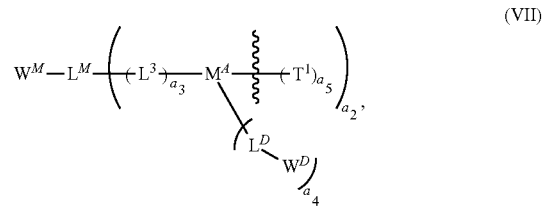
(VII)

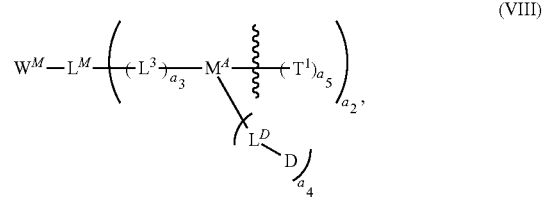
(VIII)

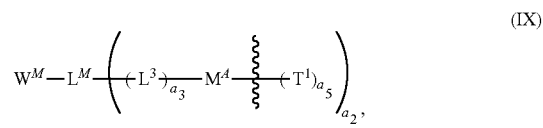
(IX)

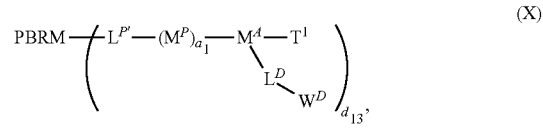
(X)

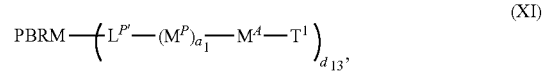
(XI)

(XII)

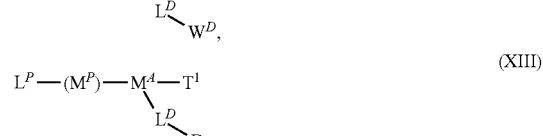
(XIII)

(XIV)

wherein
- $a_1$ is an integer from 0 to 1;
- $a_2$ is an integer from 1 to 3;
- $a_3$ is an integer from 0 to 1;
- $a_4$ is an integer from 1 to about 5;
- $a_5$ is an integer from 1 to 3;
- $d_{13}$ is an integer from 1 to about 10;
- PBRM denotes a protein based recognition-molecule;
- $L^{P'}$ is a divalent linker moiety connecting the PBRM to $M^P$; of which the corresponding monovalent moiety $L^P$ contains a functional group $W^P$ that is capable of forming a covalent bond with a functional group of the PBRM;

$M^P$ is a Stretcher unit;

$L^M$ is a bond, or a trivalent or tetravalent linker, and when $L^M$ is a bond, $a_2$ is 1, when $L^M$ is trivalent linker, $a_2$ is 2, or when $L^M$ is a tetravalent linker, $a_2$ is 3;

$L^3$ is a carbonyl-containing moiety;

$M^A$ comprises a peptide moiety that contains at least two amino acids;

$T^1$ is a hydrophilic group and the

between $T^1$ and $M^A$ denotes direct or indirect attachment of $T^1$ and $M^A$;

each occurrence of $W^M$ is independently hydrogen, a protecting group, a leaving group, or a functional group that is capable of connecting $L^M$ to $M^P$ by forming a covalent bond;

each occurrence of $W^D$ is independently a functional group that is capable of forming a covalent bond with a functional group of a therapeutic agent ("D") having a molecular weight ≤about 5 kDa; and each occurrence of $L^D$ is independently a divalent linker moiety connecting $W^D$ or D to $M^A$ and $L^D$ comprises at least one cleavable bond such that when the bond is broken, D is released in an active form for its intended therapeutic effect.

The conjugates and scaffolds of the disclosure can include one or more of the following features when applicable.

In one embodiment, $d_{13}$ is an integer from 2 to 14, from 2 to 12, from 2 to 10, from 2 to 8, from 2 to 6, from 2 to 4, from 4 to 10, from 4 to 8, from 4 to 6, from 6 to 14, from 6 to 12, from 6 to 10, from 6 to 8, from 8 to 14, from 8 to 12, or from 8 to 10.

In one embodiment, $d_{13}$ is an integer from 2 to 4 (e.g., $d_{13}$ is 2, 3, or 4).

In one embodiment, $d_{13}$ is an integer from 4 to 6 (e.g., $d_{13}$ is 4, 5, or 6).

In one embodiment, $d_{13}$ is an integer from 6 to 8 (e.g., $d_{13}$ is 6, 7, or 8).

In one embodiment, $d_{13}$ is an integer from 6 to 10 (e.g., $d_{13}$ is 6, 7, 8, 9, or 10).

In a specific embodiment, $d_{13}$ is 4 or 5.

In some embodiments, $L^3$, when present, comprises —X—$C_{1-10}$ alkylene-C(O)—, with X directly connected to $L^M$, in which X is $CH_2$, O, or $NR_5$, and $R_5$ is hydrogen, $C_{1-6}$ alkyl, $C_{6-10}$ aryl, $C_{3-8}$ cycloalkyl, COOH, or COO—$C_{1-6}$ alkyl.

In some embodiments, $L^3$ is —$NR_5$—$(CH_2)_v$—C(O)— or —$CH_2$—$(CH_2)_v$—C(O)—$NR_5$—$(CH_2)_v$—C(O)—, in which each v independently is an integer from 1 to 10. For example, $L^3$, when present, is —NH—$(CH_2)_2$—C(O)— or —$(CH_2)_2$—C(O)—NH—$(CH_2)_2$—C(O)—.

In one embodiment, each v independently is an integer from 1 to 6, or from 2 to 4, or v is 2.

In one embodiment, $a_4$ is 1.

In one embodiment, $a_4$ is 2.

In one embodiment, $a_4$ is 3.

$L^P$ and $L^{P'}$ $L^P$, when not connected to PBRM, comprises a terminal group $W^P$, in which each $W^P$ independently is:

 (1)

 (2)

 (3)

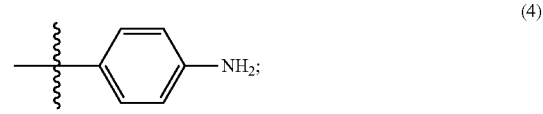 (4)

 (5)

 (6)

 (7)

 (8)

 (9)

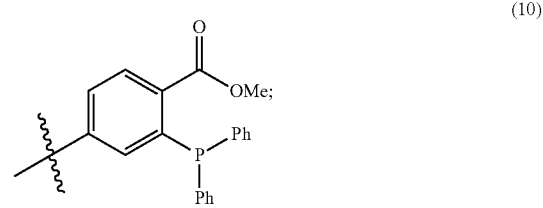 (10)

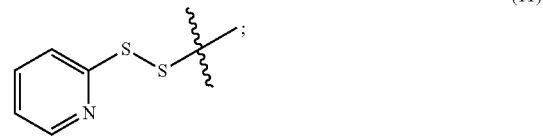 (11)

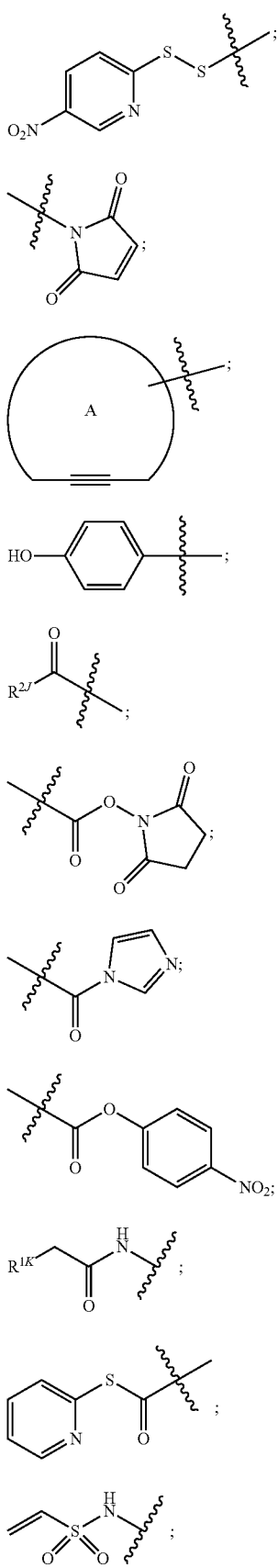
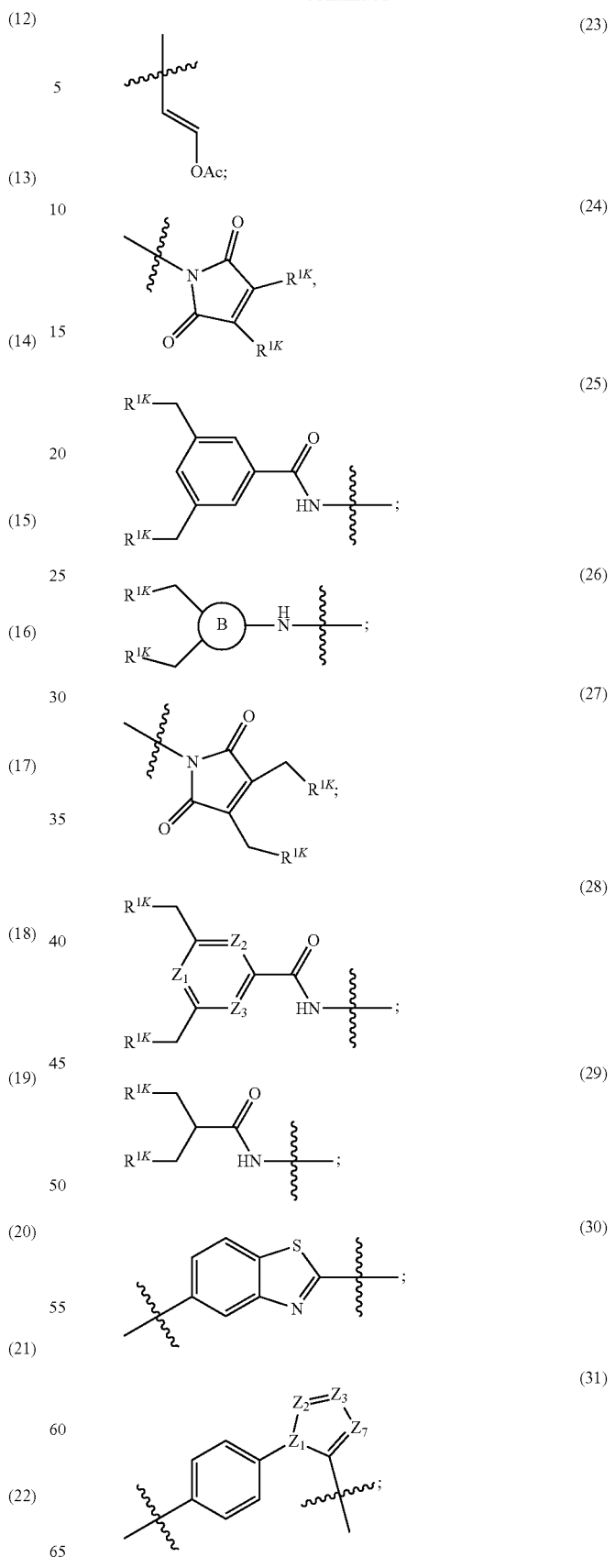

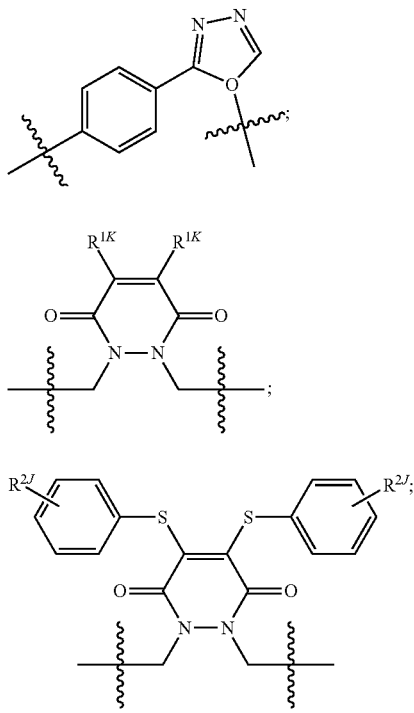
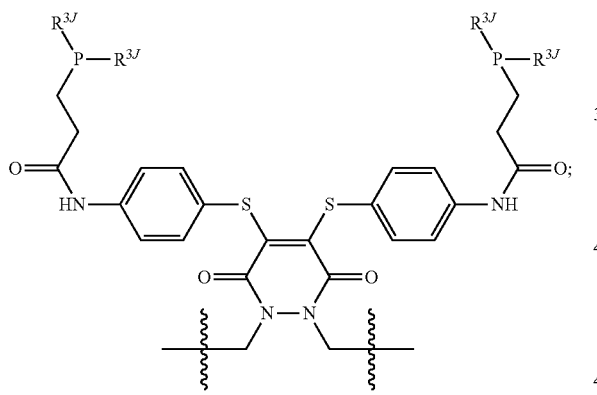
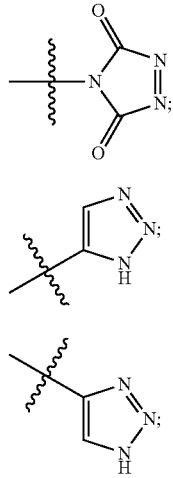
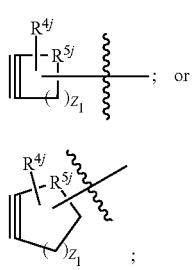

wherein
ring A is cycloalkyl or heterocycloalkyl;
ring B is cycloalkyl, heterocycloalkyl, aryl, or heteroaryl;
$R^{1K}$ is a leaving group;
$R^{1A}$ is a sulfur protecting group;
$R^{1J}$ is hydrogen, an aliphatic, heteroaliphatic, carbocyclic, or heterocycloalkyl moiety;
$R^{2J}$ is hydrogen, an aliphatic, aryl, heteroaliphatic, or carbocyclic moiety;
$R^{3J}$ is $C_{1-6}$ alkyl and each of $Z_1$, $Z_2$, $Z_3$ and $Z_7$ is independently a carbon or nitrogen atom;
$R^{4j}$ is hydrogen, halogen, OR, —$NO_2$, —CN, —$S(O)_2R$, $C_{1-24}$ alkyl (e.g., $C_{1-6}$ alkyl), or 6-24 membered aryl or heteroaryl, wherein the $C_{1-24}$ alkyl (e.g., $C_{1-6}$ alkyl), or 6-24 membered aryl or heteroaryl, is optionally substituted with one or more aryl or heteroaryl; or two $R^{4j}$ together form an annelated cycloalkyl, heterocycloalkyl, aryl, or heteroaryl; R is hydrogen, alkyl, heteroalkyl, cycloalkyl, or heterocycloalkyl;
$R^{5j}$ is $C(R^{4j})_2$, O, S or NR; and
$z_1$ is an integer 1, 2, 3, 4, 5, 6, 7, 8, 9 or 10.
$L^{P'}$ is a divalent linker moiety connecting the PBRM to $M^P$; of which the corresponding monovalent moiety is $L^P$.
For example, each $R^{1K}$ is halo or RC(O)O— in which R is hydrogen, an aliphatic, heteroaliphatic, carbocyclic, or heterocycloalkyl moiety.

For example, each $R^{1A}$ independently is

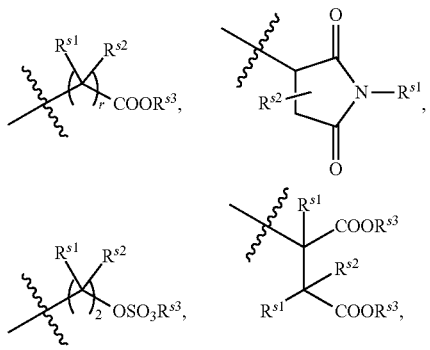

in which r is 1 or 2 and each of $R^{s1}$, $R^{s2}$, and $R^{s3}$ is hydrogen, an aliphatic, heteroaliphatic, carbocyclic, or heterocycloalkyl moiety.

For example, ring A can be $C_{3-8}$ cycloalkyl or 5-19 membered heterocycloalkyl.

For example, ring A can be

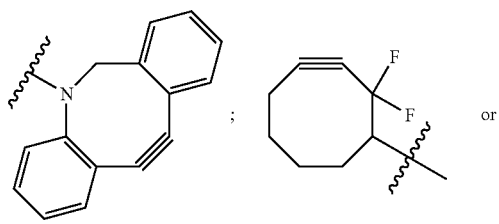

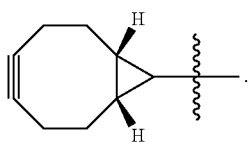

wherein $R^{6j}$ is hydrogen, halogen, $C_{1-24}$ alkyl (e.g., $C_{1-6}$ alkyl), or 6-24 membered aryl or heteroaryl, wherein the $C_{1-24}$ alkyl (e.g., $C_{1-6}$ alkyl), or 6-24 membered aryl or heteroaryl, is optionally substituted with one or more aryl or heteroaryl.

For example, ring A can be H

For example, ring A or B can be $C_{3-8}$ cycloalkyl or 3-12 membered heterocycloalkyl.

For example, ring A or B can be piperazinyl or piperidinyl.

For example, each of $R^{s1}$, $R^{s2}$, and $R^{s3}$ can be hydrogen or $C_{1-6}$ alkyl.

In some embodiments, $W^P$ is

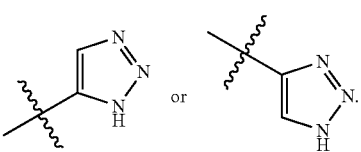 [SMILES: *c1cnn[nH]1 ; *c1c[nH]nn1]

In some embodiments, $W^P$ is

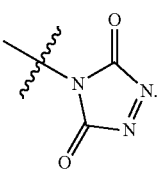

In some embodiments, when $W^P$ is

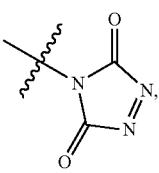 [SMILES: *N1C(=O)N=NC1=O]

$L^{P'}$ comprises

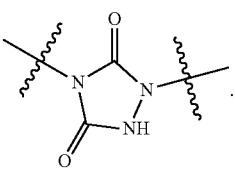 [SMILES: *n1[nH]c(=O)n(*)c1=O]

In some embodiments, when $W^P$ is

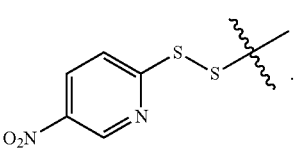 [SMILES: *SSc1ccc([N+](=O)[O-])cn1]

In some embodiments, when $W^P$ is

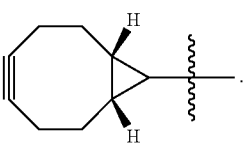

In some embodiments, when $W^P$ is

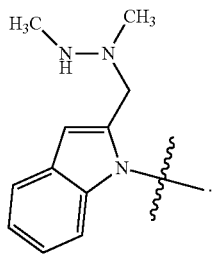 [SMILES: *n1c(CN(C)NC)cc2ccccc21]

In some embodiments, $W^P$ is

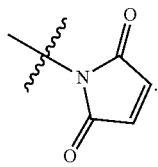 [SMILES: *N1C(=O)C=CC1=O]

In some embodiments, when $W^P$ is

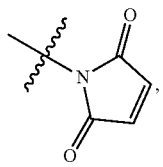 [SMILES: *N1C(=O)C=CC1=O]

$L^{P'}$ comprises

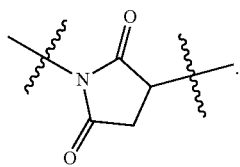 [SMILES: *C1CC(=O)N(*)C1=O]

In some embodiments, $W^P$ is

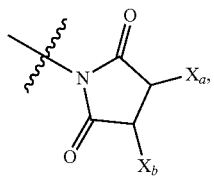

wherein one of $X_a$ and $X_b$ is H and the other is a maleimido blocking moiety. For example, a maleimido blocking compound (i.e., a compound that can react with maleimide to convert it to succinimide) may be used to quench the reaction between, e.g., the Linker-Drug moiety and PBRM, and a maleimido blocking moiety refers to the chemical moiety attached to the succinimide upon conversion. For example, the maleimido blocking moieties are moieties that can be covalently attached to one of the two olefin carbon atoms upon reaction of the maleimido group with a thiol-containing compound of Formula (II'):

$$R_{90}-(CH_2)_d-SH \quad \quad (II')$$

wherein:
$R_{90}$ is $NHR_{91}$, OH, $COOR_{93}$, $CH(NHR_{91})COOR_{93}$ or a substituted phenyl group;
$R_{93}$ is hydrogen or $C_{1-4}$ alkyl;
$R_{91}$ is hydrogen, $CH_3$ or $CH_3CO$ and
d is an integer from 1 to 3.

For example, the maleimido blocking compound can be cysteine, N-acetyl cysteine, cysteine methyl ester, N-methyl cysteine, 2-mercaptoethanol, 3-mercaptopropanoic acid, 2-mercaptoacetic acid, mercaptomethanol (i.e., $HOCH_2SH$), benzyl thiol in which phenyl is substituted with one or more hydrophilic substituents, or 3-aminopropane-1-thiol. The one or more hydrophilic substituents on phenyl comprise OH, SH, methoxy, ethoxy, COOH, CHO, $COC_{1-4}$ alkyl, $NH_2$, F, cyano, $SO_3H$, $PO_3H$, and the like.

For example, the maleimido blocking group is —S—$(CH_2)_d$—$R_{90}$, in which,
$R_{90}$ is OH, COOH, or $CH(NHR_{91})COOR_{93}$;
$R_{93}$ is hydrogen or $CH_3$;
$R_{91}$ is hydrogen or $CH_3CO$; and
d is 1 or 2.

For example, the maleimido blocking group is —S—$CH_2$—$CH(NH_2)COOH$.

Stretcher Unit $M^P$ $M^P$, when present, is —$(Z_4)$—$[(Z_5)$—$(Z_6)]_z$—, with $Z_4$ connected to $L^{P'}$ or $L^P$ and $Z_6$ connected to $L^M$; in which
z is 1, 2, or 3;
$Z_4$ is:

(1)

*\~\~$(\quad)_{b_1}$\~\~**;

(2)

*\~\~$(\quad)_{e_1}$\~\~**;

(3)

*\~\~O\~\~**;

(4)

*—CH(CH$_2$NH$_2$)—C(O)—**;

(5)

$R_{17}$;

(6)

*\~\~$(\quad)_{b_1}$—C(O)—NH—**, (7)

*\~\~S(O)$_2$—$(\quad)_{b_1}$—C(O)—**, (8)

*\~\~S(O)—$(\quad)_{b_1}$—C(O)—**,

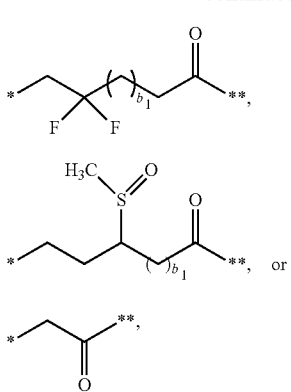

wherein * denotes attachment to $L^{P'}$ or $L^P$ and ** denotes attachment to $Z_5$ or $Z_6$ when present or to $L^M$ when $Z_5$ and $Z_6$ are both absent;

$b_1$ is an integer from 0 to 6;

$e_1$ is an integer from 0 to 8, $R_{17}$ is $C_{1-10}$ alkylene, $C_{1-10}$ heteroalkylene, $C_{3-8}$ cycloalkylene, O—($C_{1-8}$ alkylene, arylene, —$C_{1-10}$ alkylene-arylene-, -arylene-$C_{1-10}$ alkylene-, —$C_{1-10}$ alkylene-($C_{3-8}$ cycloalkylene)-, —($C_{3-8}$ cycloalkylene —$C_{1-10}$ alkylene-, 4 to 14-membered heterocycloalkylene, —$C_{1-10}$ alkylene-(4 to 14-membered heterocycloalkylene)-, -(4 to 14-membered heterocycloalkylene)-$C_{1-10}$ alkylene-, —$C_{1-10}$ alkylene-C(=O)—, —$C_{1-10}$ heteroalkylene-C(=O)—, —$C_{3-8}$ cycloalkylene-C(=O)—, —O—($C_{1-8}$ alkyl)-C(=O)—, -arylene-C(=O)—, —$C_{1-10}$ alkylene-arylene-C(=O)—, -arylene —$C_{1-10}$ alkylene-C(=O)—, —$C_{1-10}$ alkylene-($C_{3-8}$ cycloalkylene)-C(=O)—, —($C_{3-8}$ cycloalkylene)-$C_{1-10}$ alkylene-C(=O)—, -4 to 14-membered heterocycloalkylene-C(=O)—, —$C_{1-10}$ alkylene-(4 to 14-membered heterocycloalkylene)-C(=O)—, -(4 to 14-membered heterocycloalkylene)-$C_{1-10}$ alkylene-C(=O)—, —$C_{1-10}$ alkylene-NH—, —$C_{1-10}$ heteroalkylene-NH—, —$C_{3-8}$ cycloalkylene-NH—, —O—($C_{1-8}$ alkyl)-NH—, -arylene-NH—, —$C_{1-10}$ alkylene-arylene-NH—, -arylene-$C_{1-10}$ alkylene-NH—, —$C_{1-10}$ alkylene-($C_{3-8}$ cycloalkylene)-NH—, —($C_{3-8}$ cycloalkylene)-$C_{1-10}$ alkylene-NH—, -4 to 14-membered heterocycloalkylene-NH—, —$C_{1-10}$ alkylene-(4 to 14-membered heterocycloalkylene)-NH—, -(4 to 14-membered heterocycloalkylene)-$C_{1-10}$ alkylene-NH—, —$C_{1-10}$ alkylene-S—, —$C_{1-10}$ heteroalkylene-S—, —$C_{3-8}$ cycloalkylene-S—, —O—$C_{1-8}$ alkyl)-S—, -arylene-S—, —$C_{1-10}$ alkylene-arylene-S—, -arylene-$C_{1-10}$ alkylene-S—, —$C_{1-10}$ alkylene-($C_{3-8}$ cycloalkylene)-S—, —($C_{3-8}$ cycloalkylene)-$C_{1-10}$ alkylene-S—, -4 to 14-membered heterocycloalkylene-S—, —$C_{1-10}$ alkylene-(4 to 14-membered heterocycloalkylene)-S—, or -(4 to 14-membered heterocycloalkylene)-$C_1$-$C_{10}$ alkylene-S—;

each $Z_5$ independently is absent, $R_{57}$—$R_{17}$ or a polyether unit;

each $R_{57}$ independently is a bond, $NR_{23}$, S or O;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl; and each $Z_6$ independently is absent, —$C_{1-10}$ alkyl-$R_3$—, —$C_{1-10}$ alkyl-$NR_5$—, —$C_{1-10}$ alkyl-C(O)—, —$C_{1-10}$ alkyl-O—, —$C_{1-10}$ alkyl-S— or —($C_{1-10}$ alkyl-$R_3$)$_{g1}$—$C_{1-10}$ alkyl-C(O)—;

each $R_3$ independently is —C(O)—$NR_5$— or —$NR_5$—C(O)—;

each $R_5$ independently is hydrogen, $C_{1-6}$ alkyl, $C_{6-10}$ aryl, $C_{3-8}$ cycloalkyl, COOH, or COO—$C_{1-6}$ alkyl; and $g_1$ is an integer from 1 to 4.

In one embodiment, $Z_4$ is

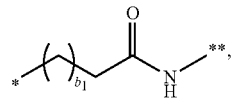

e.g., wherein $b_1$ is 1 or 4.

In another embodiment, $Z_4$ is

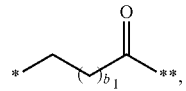

e.g., wherein bi is 4.

In another embodiment, $Z_4$ is

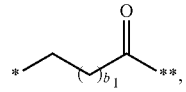

e.g., wherein $b_1$ is 0.

In another embodiments, Z4 is:

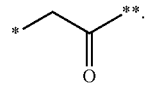

In some embodiments, each $Z_5$ independently is a polyalkylene glycol (PAO), including but are not limited to, polymers of lower alkylene oxides, in particular polymers of ethylene oxide, such as, for example, propylene oxide, polypropylene glycols, polyethylene glycol (PEG), polyoxyethylenated polyols, copolymers thereof and block copolymers thereof. In other embodiments, the polyalkylene glycol is a polyethylene glycol (PEG) including, but not limited to, polydisperse PEG, monodisperse PEG and discrete PEG. Polydisperse PEGs are a heterogeneous mixture of sizes and molecular weights whereas monodisperse PEGs are typically purified from heterogeneous mixtures and are therefore provide a single chain length and molecular weight. In another embodiment, the PEG units are discrete PEGs provide a single molecule with defined and specified chain length. In some embodiments, the polyethylene glycol is mPEG.

As used herein a subunit when referring to the PEG unit refers to a polyethylene glycol subunit having the formula

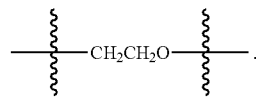

In some such embodiments, the PEG unit comprises multiple PEG subunits.

In some embodiments, when z is 2 or 3, at least one $Z_5$ is a polyalkylene glycol (PAO), e.g., a PEG unit.

In one embodiment, the PEG unit comprises 1 to 6 subunits.

In another embodiment, the PEG unit comprises 1 to 4 subunits.

In other embodiments, the PEG unit comprises 1 to 3 subunits.

In one embodiment, the PEG unit comprises 2 subunits.

In another embodiment, the PEG unit comprises 1 subunit.

In other embodiments, the PEG unit comprises one or multiple PEG subunits linked together by a PEG linking unit. The PEG linking unit that connects one or more chains of repeating $CH_2CH_2O$— subunits can be $Z_6$. For example, $Z_6$ is —$C_{1-10}$ alkyl-$R_3$—, —$C_{2-10}$ alkyl-NH—, —$C_{2-10}$ alkyl-C(O)—, —$C_{2-10}$ alkyl-O— or —$C_{1-10}$ alkyl-S—, wherein $R_3$ is —C(O)—$NR_5$— or —$NR_5$—C(O)—.

In some embodiments, the PEG linking unit is —$C_{1-10}$ alkyl-C(O)—NH— or —$C_{1-10}$ alkyl-NH—C(O)—. In one embodiment, the PEG linking unit is —$(CH_2)_2$—C(O)—NH—.

In some embodiments, each $Z_5$ is absent.

In some embodiments, when z is 2 or 3, at least one $Z_5$ is absent.

In some embodiments, each $Z_5$ is —$(CH_2$—$CH_2$—$O$—$)_2$—.

In some embodiments, when z is 2 or 3, at least one $Z_5$ is —$(CH_2$—$CH_2$—$O$—$)_2$—.

In some embodiments, each $Z_5$ independently is $R_{57}$—$R_{17}$. For example, each $Z_5$ independently is $R_{17}$, $NHR_{17}$, $OR_{17}$, or $SR_{17}$.

In some embodiments, when z is 2 or 3, at least one $Z_5$ is $R_{57}$—$R_{17}$, e.g., $R_{17}$, $NHR_{17}$, $OR_{17}$, or $SR_{17}$.

In some embodiments, each $Z_6$ is absent.

In some embodiments, when z is 2 or 3, at least one $Z_6$ is absent.

In some embodiments, at least one of $Z_5$ and $Z_6$ is not absent.

In some embodiments, each $Z_6$ independently is —$C_{1-10}$ alkyl-$R_3$-, —$C_{1-10}$ alkyl-NH—, —$C_{1-10}$ alkyl-C(O)—, —$C_{1-10}$ alkyl-O—, —$C_{1-10}$ alkyl-S— or —$(C_{1-10}$ alkyl-$R_3)_{g1}$—$C_{1-10}$ alkyl-C(O)—. For example, $g_1$ is an integer from 1 to 4.

In some embodiments, when z is 2 or 3, at least one $Z_6$ is —$C_{1-10}$ alkyl-$R_3$-, —$C_{1-10}$ alkyl-NH—, —$C_{1-10}$ alkyl-C(O)—, —$C_{1-10}$ alkyl-O—, —$C_{1-10}$ alkyl-S— or —$(C_{1-10}$ alkyl-$R_3)_{g1}$—$C_{1-10}$ alkyl-C(O)—. For example, $g_1$ is an integer from 1 to 4.

In some embodiments, each $Z_6$ independently or at least one $Z_6$ is —$(C_{2-10}$ alkyl-C(O)—, e.g., —$(CH_2)_2$—C(O)—.

In some embodiments, each $Z_6$ independently or at least one $Z_6$ is —$C_{2-10}$ alkyl-$R_3$—$C_{2-10}$ alkyl-C(O)—, e.g., —$(CH_2)_2$—C(O)NH—$(CH_2)_2$—C(O)—.

In some embodiments, each $Z_6$ independently or at least one $Z_6$ is —$(C_{2-10}$ alkyl-$R_3)_{g1}$—$C_{2-10}$ alkyl-C(O)—, e.g., —$(CH_2)_2$—C(O)NH—$(CH_2)_2$—NHC(O)—$(CH_2)$—C(O)—.

In one embodiment, —$[(Z_5)$—$(Z_6)]_z$— is not absent.

In one embodiment, —$[(Z_5)$—$(Z_6)]_z$— is a bond.

In one embodiment, —$[(Z_5)$—$(Z_6)]_z$— is —$(CH_2CH_2O)_2$—$(CH_2)_2$—C(O)—NH—$(CH_2CH_2O)_2$—.

In some embodiments, $M^P$, when present, is

(1)

(2)

(3)

(4)

$R_{17}$, (5)

(6)

$*$—$CH_2$—$C(O)$—$N$—$R_{17}$—$**$, with $R_{23}$ on N (7)

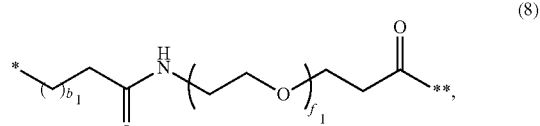

(8)

(9)

(10)

(11)

(12)

(13)

, or

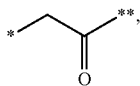
(14)

wherein * denotes attachment to $L^{P'}$ or $L^P$ and ** denotes attachment to $L^M$;

$R_3$, $R_5$, $R_{17}$, and $R_{23}$ are as defined herein;

$R_4$ is a bond or $-NR_5-(CR_{20}R_{21})-C(O)-$;

each $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

each $b_1$ independently is an integer from 0 to 6;

$e_1$ is an integer from 0 to 8, each $f_1$ independently is an integer from 1 to 6; and $g_2$ is an integer from 1 to 4.

In some embodiments, $b_1$ is 1.

In some embodiments, each $f_1$ independently is 1 or 2.

In some embodiments, $f_1$ is 2.

In some embodiments, $g_2$ is 1 or 2.

In some embodiments, $g_2$ is 2.

In some embodiments, $R_{17}$ is unsubstituted.

In some embodiments, $R_{17}$ is optionally substituted.

In some embodiments, $R_{17}$ is optionally substituted by a basic unit, e.g., $-(CH_2)_xNH_2$, $-(CH_2)_xNHR^a$, and $-(CH_2)_xN(R^a)_2$, wherein x is an integer from 1 to 4 and each $R^a$ is independently selected from $C_{1-6}$ alkyl and $C_{1-6}$ haloalkyl, or two $R^a$ groups are combined with the nitrogen to which they are attached to form an azetidinyl, pyrrolidinyl or piperidinyl group.

In some embodiments, $R^{17}$ is $-C_{2-5}$ alkylene-C(=O)— wherein the alkylene is optionally substituted by a basic unit, e.g., $-(CH_2)_xNH_2$, $-(CH_2)_xNHR^a$, and $-(CH_2)_xN(R^a)_2$, wherein x and $R^a$ are as defined herein.

In some embodiments, wherein $M^P$, when present, is:

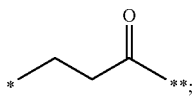
(1)

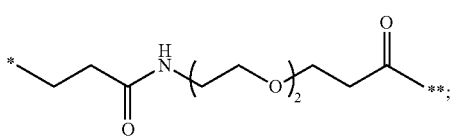
(2)

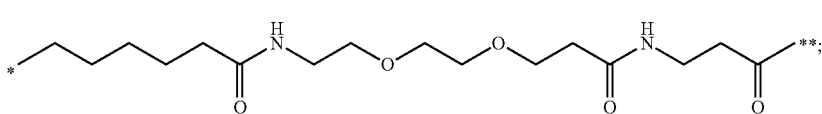
(3)

(4)

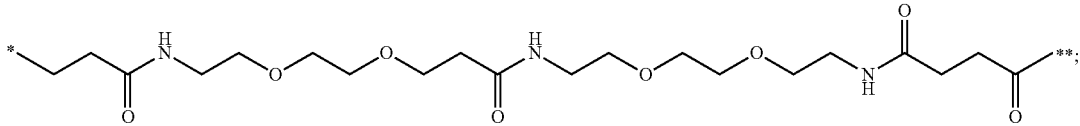
(5)

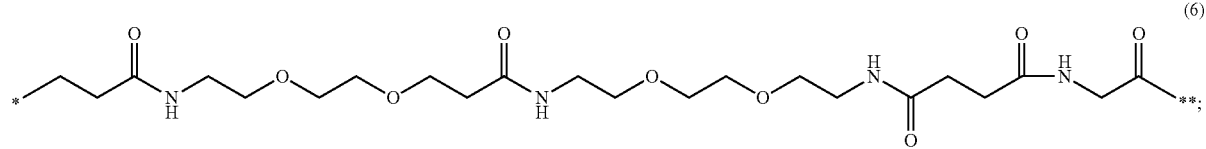
(6)

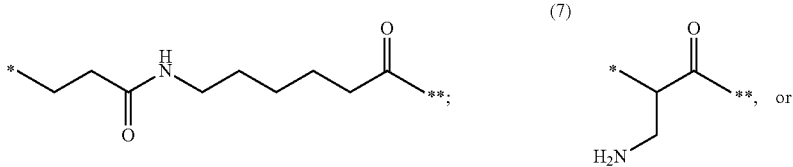
(7) (8)

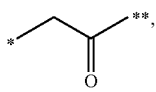
(9)

wherein * denotes attachment to $L^{P'}$ or $L^P$ and ** denotes attachment to $L^M$.

In some embodiments, wherein $M^P$, when present, is:

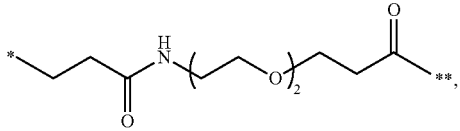

wherein * denotes attachment to $L^{P'}$ or $L^P$ and ** denotes attachment to $L^M$.

In some embodiments, wherein $M^P$, when present, is:

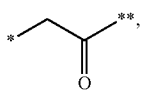

wherein * denotes attachment to $L^{P'}$ or $L^P$ and ** denotes attachment to $L^M$.

$L^M$ and $W^M$ $L^M$ is a bond, or a multi-armed linker (e.g., trivalent or tetravalent or having 3 or 4 arms), wherein each arm maybe the same or different.

In some embodiments, $a_2$ is 2 and $L^M$ is (1)
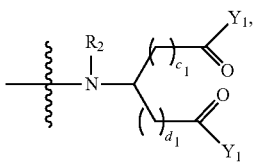

(2)
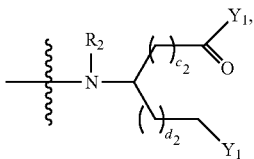

(3)
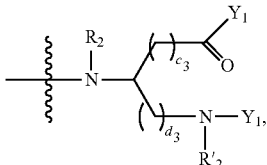

(4)
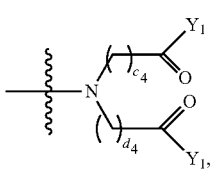

(5)
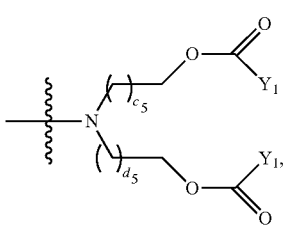

(6)
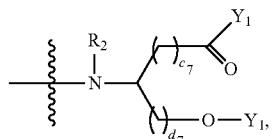

(7)
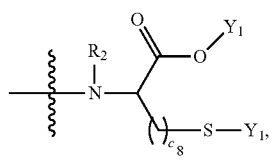

(8)
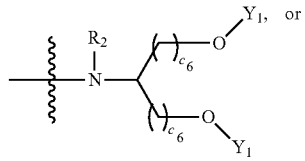

(9)
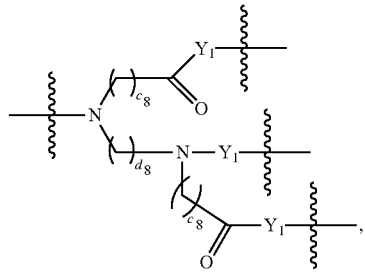

wherein:

⸹ denotes attachment to $M^P$ when present or attachment to $L^P$ or $L^{P'}$ when $M^P$ is absent;

$Y_1$ denotes attachment to $L^3$ when present or attachment to $M^A$ when $L^3$ is absent;

$R_2$ and $R'_2$ are each independently hydrogen, an optionally substituted $C_{1-6}$ alkyl, an optionally substituted $C_{2-6}$ alkenyl, an optionally substituted $C_{2-6}$ alkynyl, an optionally substituted $C_{3-19}$ branched alkyl, an optionally substituted $C_{3-8}$ cycloalkyl, an optionally substituted $C_{6-10}$ aryl, an optionally substituted heteroaryl, an optionally substituted $C_{1-6}$ heteroalkyl, $C_{1-6}$alkoxy, aryloxy, $C_{1-6}$ heteroalkoxy, $C_{2-6}$ alkanoyl, an optionally substituted arylcarbonyl, $C_{2-6}$ alkoxycarbonyl, $C_{2-6}$ alkanoyloxy, arylcarbonyloxy, an optionally substituted $C_{2-6}$ alkanoyl, an optionally substituted $C_{2-6}$ alkanoyloxy, an optionally substituted $C_{2-6}$ substituted alkanoyloxy, —COOH, or —COO—$C_{1-6}$ alkyl;

each of $c_1, c_2, c_3, c_4, c_5, c_7$, and $c_8$ is an integer independently ranging between 0 and 10; and each of $d_1, d_2, d_3, d_4, d_5$, and $d_7$ is an integer independently ranging between 0 and 10.

In some embodiments, $a_2$ is 2 and $L^M$ is

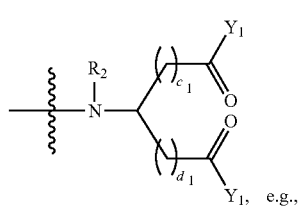

e.g.,

-continued

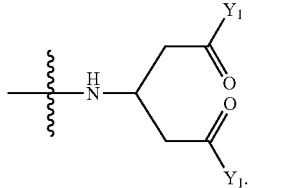

In some embodiments, $c_1$, $c_2$, $c_3$, $c_4$, $c_5$, $c_7$, and $c_8$ are each independently 0 or 1.

In some embodiments, $c_1$, $c_2$, $c_3$, $c_4$, $c_5$, $c_7$, and $c_8$ are each independently 1, 2, 3, 4, 5, 6, 7, 8, 9, or 10.

In some embodiments, $c_1$, $c_2$, $c_3$, $c_4$, $c_5$, $c_7$, and $c_8$ are each independently 0, 1 or 2.

In some embodiments, $d_1$, $d_2$, $d_3$, $d_4$, $d_5$, and $d_7$ are each independently 0 or 1.

In some embodiments, $d_1$, $d_2$, $d_3$, $d_4$, $d_5$, and $d_7$ are each independently 1, 2, 3, 4, 5, 6, 7, 8, 9, or 10.

In some embodiments, $d_1$, $d_2$, $d_3$, $d_4$, $d_5$, and $d_7$ are each independently 1, 2, 3 or 4.

In some embodiments, $R_2$ and $R'_2$ are each independently hydrogen, $C_{1-6}$ alkyl, $C_{6-10}$ aryl, $C_{3-8}$ cycloalkyl, —COOH, or —COO—$C_{1-6}$ alkyl;

In some embodiments, $R_2$ and $R'_2$ are each independently hydrogen or $C_{1-6}$ alkyl.

In some embodiments, $R_2$ and $R'_2$ are each independently hydrogen.

In some embodiments, $R_2$ and $R'_2$ are each independently $C_{1-6}$ alkyl.

In some embodiments, $L^M$ is:

(1)

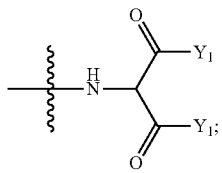

(2)

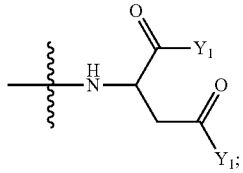

(3)

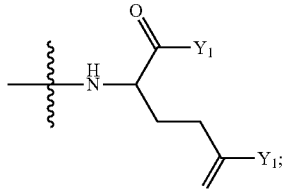

(4)

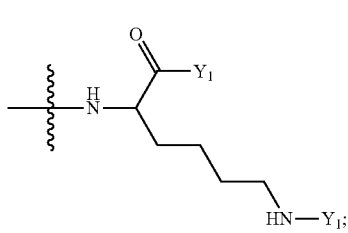

(5)

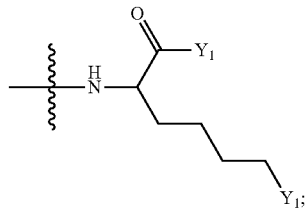

(6)

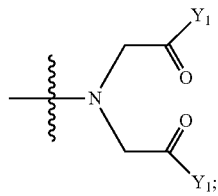

(7)

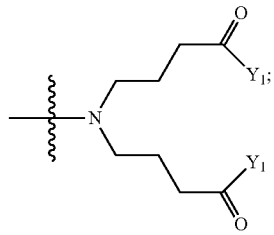

(8)

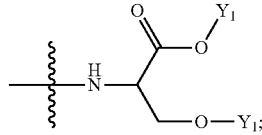

(9)

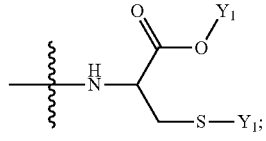

(10)

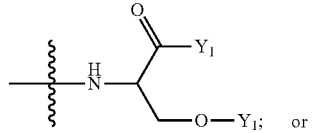

or (11)

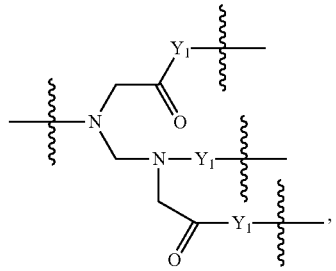

In some embodiments, $a_2$ is 3 and $L^M$ is
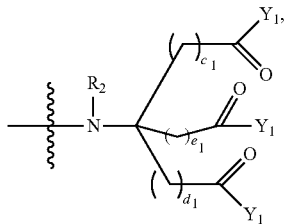 (1)
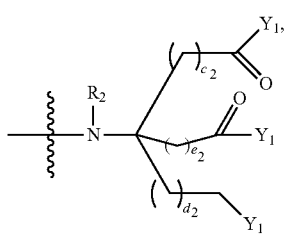 (2)
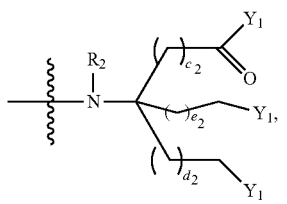 (3)
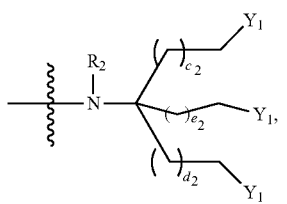 (4)
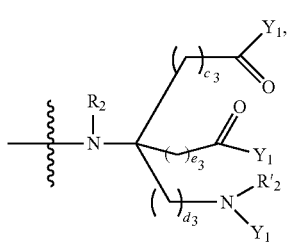 (5)
-continued
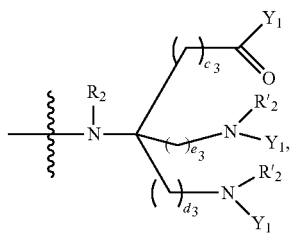 (6)
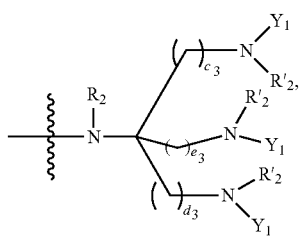 (7)
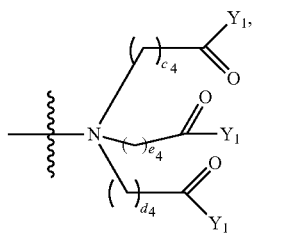 (8)
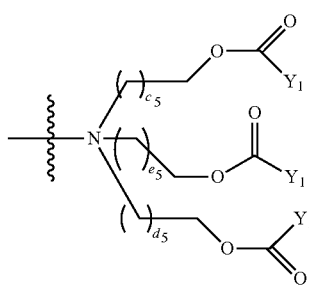 (9)
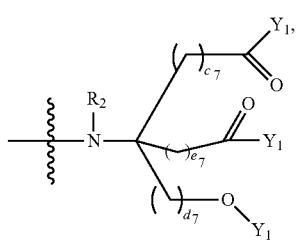 (10)
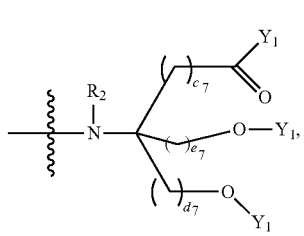 (11)

-continued

(12) 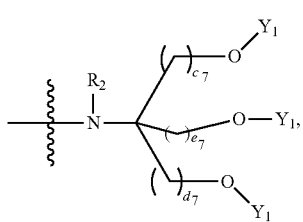

(13) 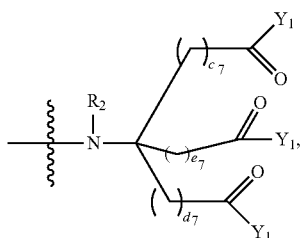

(14) 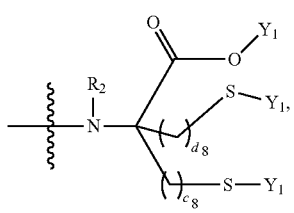

(15) 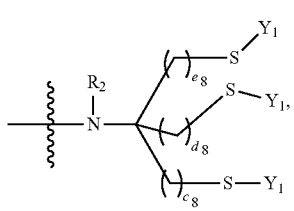

(16) 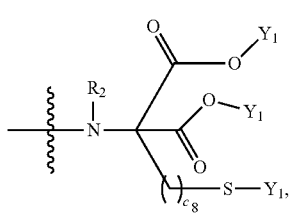

(17) 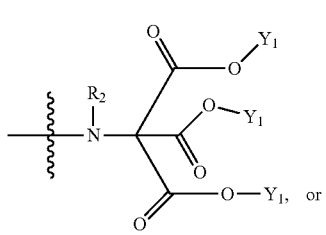

(18) 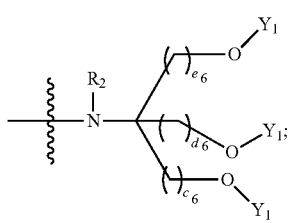

wherein:

⸹ denotes attachment to $M^P$ when present or attachment to $L^P$ or $L^{P'}$ when $M^P$ is absent;

$Y_1$ denotes attachment to $L^3$ when present or attachment to $M^A$ when $L^3$ is absent;

$R_2$ and $R'_2$ are each independently hydrogen, an optionally substituted $C_{1-6}$ alkyl, an optionally substituted $C_{2-6}$ alkenyl, an optionally substituted $C_{2-6}$ alkynyl, an optionally substituted $C_{3-19}$ branched alkyl, an optionally substituted $C_{3-8}$ cycloalkyl, an optionally substituted $C_{6-10}$ aryl, an optionally substituted heteroaryl, an optionally substituted $C_{1-6}$ heteroalkyl, $C_{1-6}$ alkoxy, aryloxy, $C_{1-6}$ heteroalkoxy, $C_{2-6}$ alkanoyl, an optionally substituted arylcarbonyl, $C_{2-6}$ alkoxycarbonyl, $C_{2-6}$ alkanoyloxy, arylcarbonyloxy, an optionally substituted $C_{2-6}$ alkanoyl, an optionally substituted $C_{2-6}$ alkanoyloxy, an optionally substituted $C_{2-6}$ substituted alkanoyloxy, —COOH, or —COO—$C_{1-6}$ alkyl;

each of $c_1$, $c_2$, $c_3$, $c_4$, $c_5$, $c_6$, $c_7$, and $c_8$ is an integer independently ranging between 0 and 10;

each of $d_1$, $d_2$, $d_3$, $d_4$, $d_5$, $d_6$, $d_7$ and $d_8$ is an integer independently ranging between 0 and 10; and each of $e_1$, $e_2$, $e_3$, $e_4$, $e_5$, $e_6$, $e_7$, and $e_8$ is an integer independently ranging between 0 and 10.

In some embodiments, $a_2$ is 3 and $L^M$ is

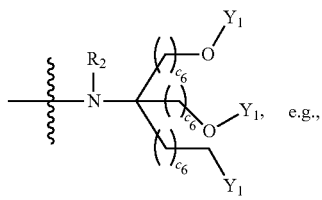

e.g.,

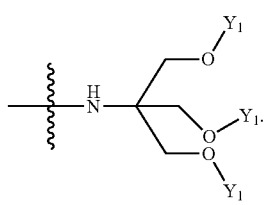

In some embodiments, $-L^M-(L^3)_{a2}-$ is:

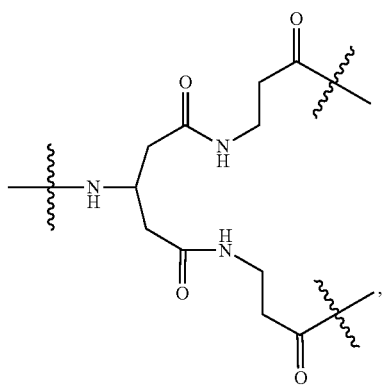

-continued
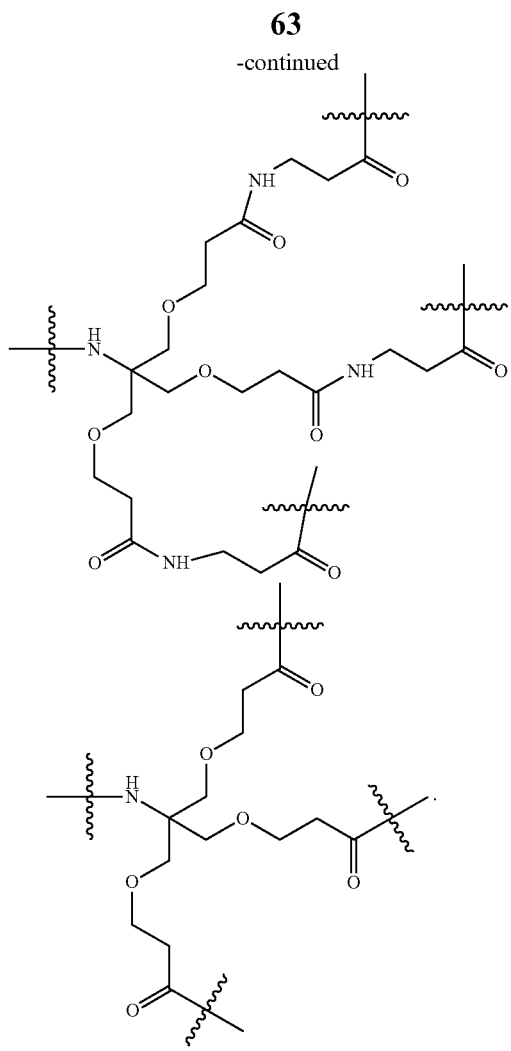
In certain embodiments, $a_2$ is 2 and $L^M$ is selected from
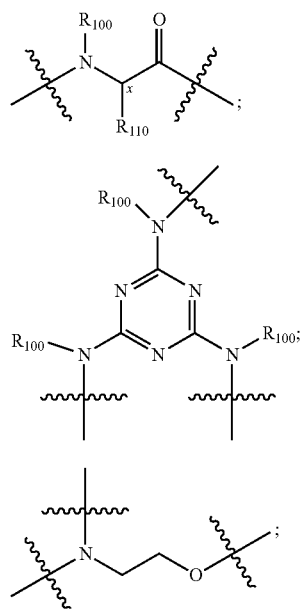
-continued
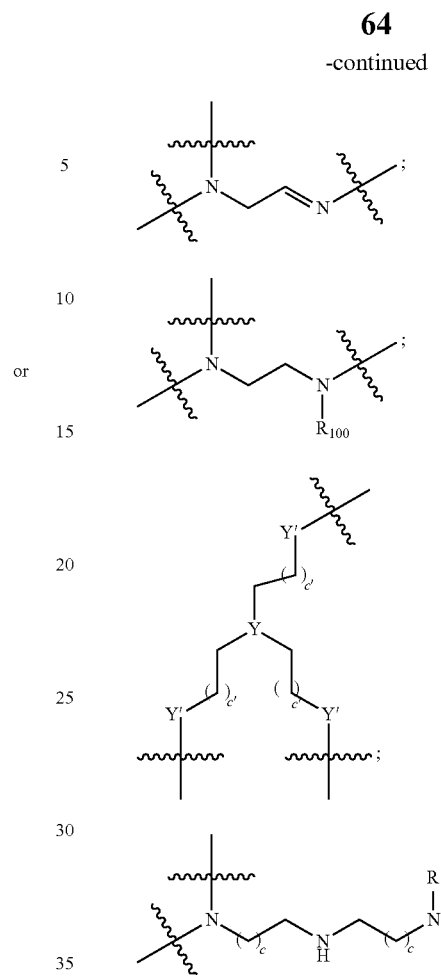
wherein:
the wavy line indicates attachment sites within the conjugate of the disclosure or intermediates thereof;
$R_{110}$ is:
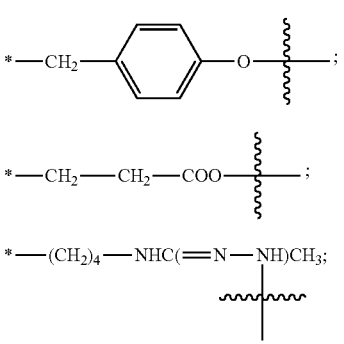

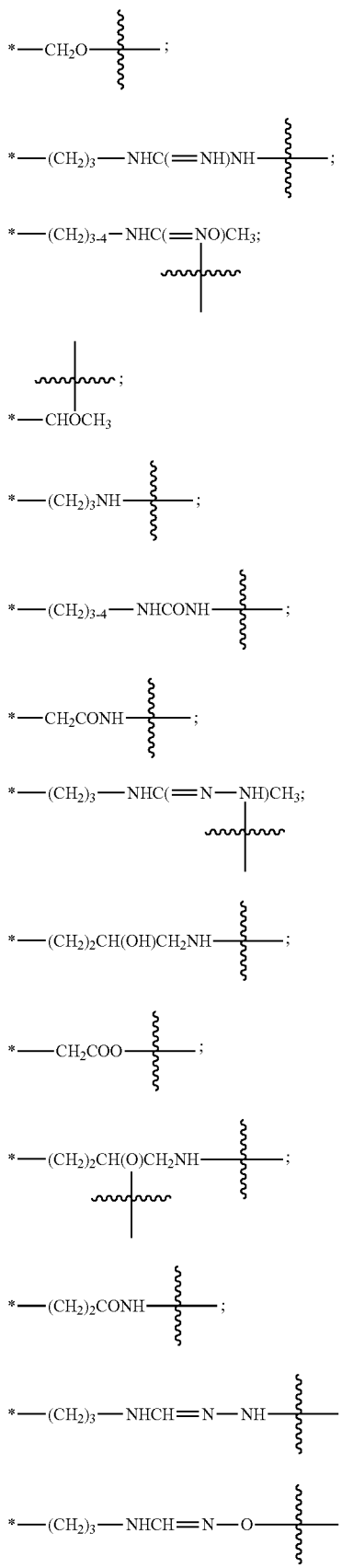

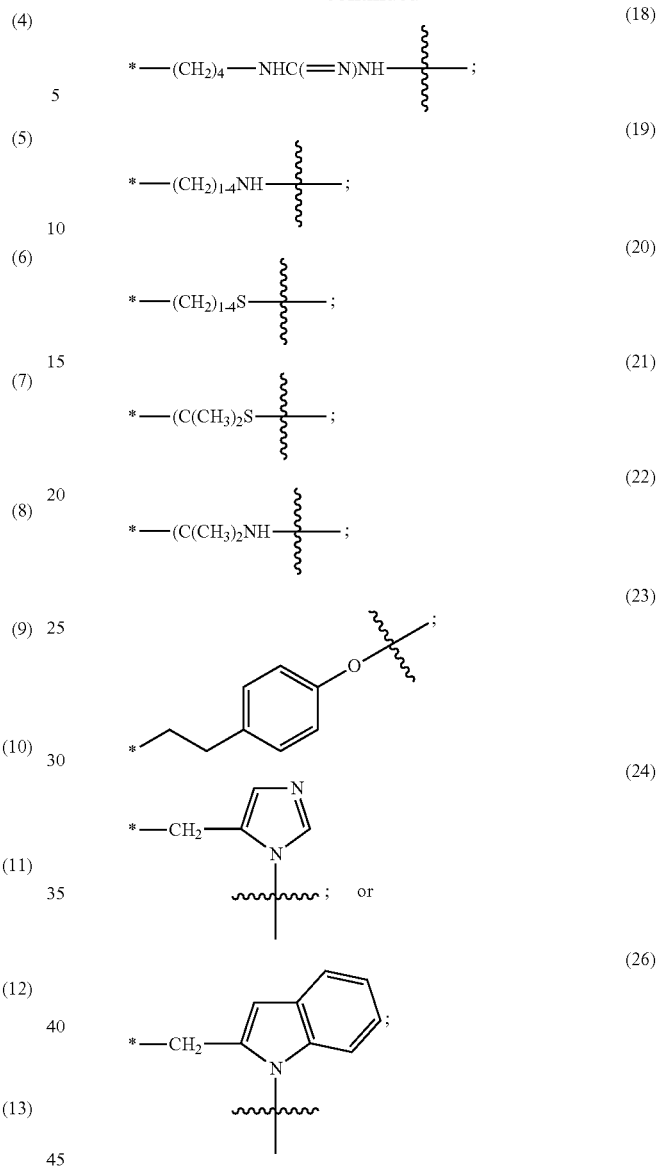

wherein the asterisk indicates attachment to the carbon labeled x and the wavy line indicates one of the three attachment sites;

$R_{100}$ is independently selected from hydrogen or $-C_{1-3}$ alkyl;

Y is N or CH;

each occurrence of Y' is independently selected from NH, O, or S, and each occurrence of c' is independently an integer from 1 to 10.

In some embodiments, $R_{100}$ is independently selected from hydrogen and $CH_3$.

In some embodiments, Y is N.

In some embodiments, Y is CH.

In some embodiments, $R_{100}$ is H or $CH_3$.

In some embodiments, each c' is independently an integer from 1 to 3.

In some embodiments, $R_{110}$ is not

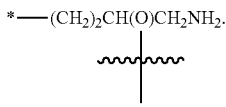

In some embodiments, where an AA unit has two attachment sites (i.e., a terminal drug unit) one of the attachment sites shown above can replaced, for example, by H, OH, or a $C_{1-3}$ unsubstituted alkyl group.

When $L^M$ is a multi-armed linker and not yet connected to the Stretcher unit $M^P$, $W^M$ is a terminus of $L^M$ and each occurrence of $W^M$ is independently hydrogen, a protecting group, a leaving group, or a functional group that is capable of connecting $L^M$ to $M^P$ by forming a covalent bond.

In some embodiments, $W^M$ is an amine protecting group, e.g., BOC. In some embodiments, $W^M$ is an amine protecting group, e.g., BOC, and $L^M$ is

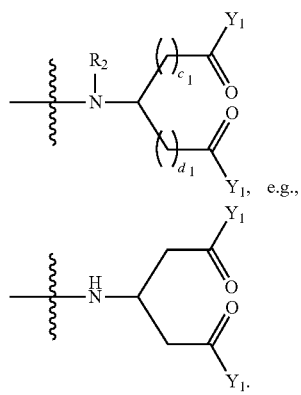

In some embodiments, $W^M$ comprises an amine group, e.g., —C(O)—(CH$_2$)$_w$—NH$_2$, in which w is an integer from 1 to 6.

In some embodiments, $W^M$ is —C(O)—CH$_2$—NH$_2$. In some embodiments, $W^M$ is —C(O)—CH$_2$—NH$_2$ and $L^M$ is

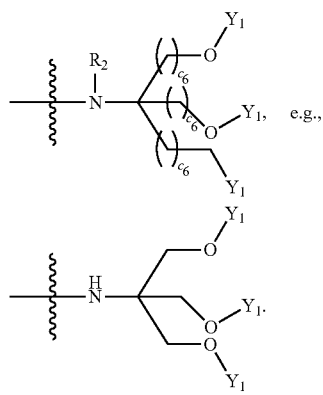

In some embodiments, $W^M$ is hydrogen.

$M^A$ $M^A$ is a linker moiety that is capable of connecting one or more drugs and one or more hydrophilic groups to $L^P$ or $L^{P'}$. In some embodiments, $M^A$ comprises a peptide moiety of at least two amino acids (AA's).

The peptide moiety is a moiety that is capable of forming a covalent bond with a -$L^D$-D unit and allows for the attachment of multiple drugs. In some embodiments, peptide moiety comprises a single AA unit or has two or more AA units (e.g., 2 to 10, preferably from 2 to 6, e.g., 2, 3, 4, 5 or 6) wherein the AA units are each independently a natural or non-natural amino acid, an amino alcohol, an amino aldehyde, a diamine, or a polyamine or combinations thereof. If necessary in order to have the requisite number of attachments, at least one of AA units will have a functionalized side chain to provide for attachment of the -$L^D$-D unit. Exemplary functionalized AA units (e.g., amino acids, amino alcohols, or amino aldehydes) include, for example, azido or alkyne functionalized AA units (e.g., amino acid, amino alcohol, or amino aldehyde modified to have an azide group or alkyne group for attachment using click chemistry).

In some embodiments, the peptide moiety has 2 to 12 AA units.

In some embodiments, the peptide moiety has 2 to 10 AA units.

In another embodiment, the peptide moiety has 2 to 6 AA units.

In yet another embodiment, the peptide moiety has 2, 3, 4, 5 or 6 AA units.

In some embodiments, an AA unit has three attachment sites, (e.g., for attachment to $L^M$, the hydrophilic group or another AA unit, and to the -$L^D$-D unit). For example, the AA unit has the formula below:

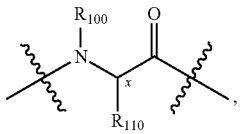

wherein the wavy line indicates attachment sites within the conjugate of the disclosure or intermediates thereof; and $R_{100}$ and $R_{110}$ are as defined herein.

In some embodiments, an AA unit has two attachment sites (i.e., a terminal unit) and one of the attachment sites shown above can replaced, for example, by H, OH, or an unsubstituted $C_{1-3}$ alkyl group.

In some embodiments, the peptide moiety comprises at least two AA units of the following formula:

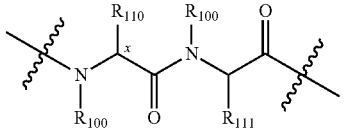

wherein:
each $R_{111}$ independently is H, p-hydroxybenzyl, methyl, isopropyl, isobutyl, sec-butyl, —CH$_2$OH, —CH(OH)CH$_3$, —CH$_2$CH$_2$SCH$_3$, —CH$_2$CONH$_2$, —CH$_2$COOH, —CH$_2$CH$_2$CONH$_2$, —CH$_2$CH$_2$COOH, —(CH$_2$)$_3$NHC(=NH)NH$_2$, —(CH$_2$)$_3$NH$_2$, —(CH$_2$)$_3$NHCOCH$_3$, —(CH$_2$)$_3$NHCHO, —(CH$_2$)$_4$NHC(=NH)NH$_2$, —(CH$_2$)$_4$NH$_2$, —(CH$_2$)$_4$NHCOCH$_3$, —(CH$_2$)$_4$NHCHO, —(CH$_2$)$_3$NHCONH$_2$, —(CH$_2$)$_4$NHCONH$_2$, —CH$_2$CH$_2$CH(OH)CH$_2$NH$_2$, 2-pyridylmethyl-, 3-pyridylmethyl-, 4-pyridylmethyl,

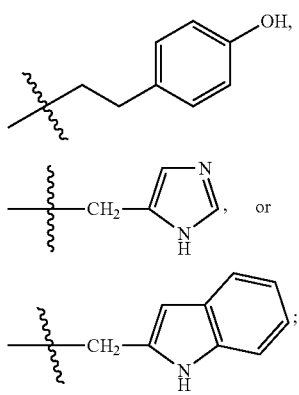

the wavy line indicates the attachment sites within the conjugate or intermediates thereof; and $R_{100}$ and $R_{110}$ are as defined herein.

In some embodiments, the peptide moiety comprises at least two AA units, e.g., cysteine-alanine as shown below:

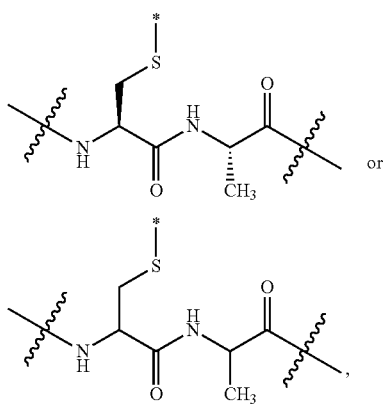

wherein the wavy lines and asterisk indicates attachment sites within the conjugate or intermediates thereof. For example, asterisk indicates attachment site of -L$^D$-D unit or a hydrophilic group. For example, the wavy line next to the carbonyl group indicates attachment site of -L$^D$-D unit or a hydrophilic group. For example, the wavy line next to the amine group indicates attachment site of -L$^D$-D unit or a hydrophilic group. For example, one or two of the wavy lines and asterisk indicate attachment site(s) of one or more -L$^D$-D units or one or more hydrophilic groups.

In some embodiments, the peptide moiety comprises at least two AA units, which provide two attachment sites, e.g., cysteine-alanine as shown below:

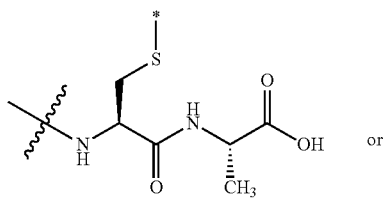

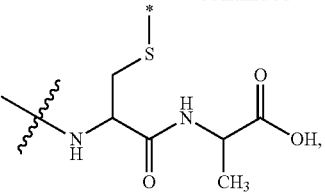

wherein the wavy line and asterisk indicates attachment sites within the conjugate or intermediates thereof. For example, asterisk indicates attachment site of -L$^D$-D unit or a hydrophilic group. For example, the wavy line indicates attachment site of -L$^D$-D unit or a hydrophilic group.

One or more AA units (e.g., an amino acid, amino alcohol, amino aldehyde or polyamine) of the peptide moiety can be replaced by an optionally substituted $C_{1-20}$ heteroalkylene (e.g., optionally substituted $C_{1-12}$ heteroalkylene), optionally substituted $C_{3-8}$ heterocyclo, optionally substituted $C_{6-14}$ arylene, or optionally substituted $C_{3-8}$ carbocyclo as described herein. The optionally substituted heteroalkylene, heterocycle, arylene or carbocyclo may have one or more functional groups for attachment within a conjugate or intermediates thereof. Suitable substituents include, but are not limited to (=O), —$R^{1C}$, —$R^{1B}$, —$OR^{1B}$, —$SR^{1B}$, —$N(R^{1B})_2$, —$N(R^{1B})_3$, =$NR^{1B}$, $C(R^{1C})_3$, CN, OCN, SCN, N=C=O, NCS, NO, $NO_2$, =$N_2$, $N_3$, $NR^{1B}C(=O)R^{1B}$, —$C(=O)R^{1B}$, —$C(=O)N(R^{1B})_2$, $SO_3^-$, $SO_3H$, $S(=O)_2R^{1B}$, —$OS(=O)_2OR^{1B}$, —$S(=O)_2NR^{1B}$, —$S(=O)R^{1B}$, —$OP(=O)(OR^{1B})_2$, —$P(=O)(OR^{1B})_2$, $PO_3^-$, $PO_3H_2$, $AsO_2H_2$, $C(=O)R^{1B}$, $C(=O)R^{1C}$, $C(=S)R^{1B}$, $CO_2R^{1B}$, $CO_2$—, $C(=S)OR^{1B}$, $C(=O)SR^{1b}$, $C(=S)SR^{1b}$, $C(=O)N(R^{1B})_2$, $C(=S)N(R^{1B})_2$, and $C(=NR^{1B})N(R^{1B})_2$, where each $R^{1C}$ is independently a halogen (e.g., —F, —Cl, —Br, or —I), and each $R^{1B}$ is independently —H, —$C_{1-20}$ alkyl, —$C_{6-20}$ aryl, —$C_{3-14}$ heterocycle, a protecting group or a prodrug moiety.

In some embodiments, the one or more substituents for the heteroalkylene, heterocycle, arylene or carbocyclo are selected from (=O), $R^{1C}$, $R^{1B}$, $OR^{1B}$, $SR^{1B}$, and $N(R^{1B})_2$.

In some embodiments, the peptide moiety can be a straight chain or branched moiety of having the Formula:

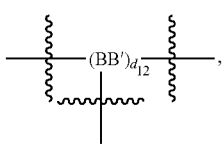

wherein:
  each BB' is independently an amino acid, optionally substituted $C_{1-20}$ heteroalkylene (e.g., optionally substituted $C_{1-12}$ heteroalkylene), optionally substituted $C_{3-8}$ heterocyclo, optionally substituted $C_{6-14}$ arylene, or optionally substituted $C_3$-$C_8$ carbocyclo;
  $d_{12}$ is an integer from 1 to 10; and
  the wavy line indicates the covalent attachment sites within the conjugate or intermediate thereof.
  In some embodiments, $d_{12}$ is an integer from 2 to 10.
  In some embodiments, $d_{12}$ is an integer from 2 to 6.
  In some embodiments, $d_{12}$ is an integer from 4, 5 or 6.
  In some embodiments, $d_{12}$ is an integer from 5 or 6.
  In some embodiments, the optionally substituted heteroalkylene, heterocycle, arylene or carbocyclo have functional groups for attachments between the BB' subunits and/or for attachments within a conjugate or intermediates thereof disclosed herein.

In some embodiments, the peptide moiety comprises no more than 2 optionally substituted $C_{1-20}$ heteroalkylenes, optionally substituted $C_{3-18}$ heterocyclos, optionally substituted $C_{6-14}$ arylenes, or optionally substituted $C_{3-8}$ carbocyclos.

In other embodiments, the peptide moiety comprises no more than 1 optionally substituted $C_{1-20}$ heteroalkylenes, optionally substituted $C_{3-ix}$ heterocyclos, optionally substituted $C_{6-14}$ arylenes, or optionally substituted $C_{3-8}$ carbocyclos. The optionally substituted heteroalkylene, heterocycle, arylene or carbocyclo will have functional groups for attachment between the BB' subunits and/or for attachments within a conjugate or intermediates thereof disclosed herein.

In some embodiments, at least one BB is an amino acid. For example, the amino acid can be an alpha, beta, or gamma amino acid, which can be natural or non-natural. The amino acid can be a D or L isomer.

In some embodiments, attachment within the peptide moiety or with the other components of the conjugate (or intermediate thereof, or scaffold) can be, for example, via amino, carboxy, or other functionalities.

In one embodiment, each amino acid of the peptide moiety can be independently D or L isomer of a thiol containing amino acid. The thiol containing amino acid can be, for example, cysteine, homocysteine, or penicillamine.

In another embodiment, each amino acid that comprises the peptide moiety can be independently the L- or D-isomers of the following amino acids: alanine (including β-alanine), arginine, aspartic acid, asparagine, cysteine, histidine, glycine, glutamic acid, glutamine, phenylalanine, lysine, leucine, methionine, serine, tyrosine, threonine, tryptophan, proline, ornithine, penicillamine, aminoalkynoic acid, aminoalkanedioic acid, heterocyclo-carboxylic acid, citrulline, statine, diaminoalkanoic acid, stereoisomers thereof (e.g., isoaspartic acid and isoglutamic acid), and derivatives thereof.

In one embodiment, each amino acid that comprises the peptide moiety is independently cysteine, homocysteine, penicillamine, ornithine, lysine, serine, threonine, glycine, glutamine, alanine, aspartic acid, glutamic acid, selenocysteine, proline, glycine, isoleucine, leucine, methionine, valine, alanine, or a stereoisomers thereof (e.g., isoaspartic acid and isoglutamic acid).

In some embodiments, the peptide moiety comprises a monopeptide, a dipeptide, tripeptide, tetrapeptide, or pentapeptide.

In some embodiments, the peptide moiety contains at least about five amino acids (e.g., 5, 6, 7, 8, 9, or 10 amino acids).

In some embodiments, the peptide moiety contains at most about ten amino acids.

In one embodiment, the peptide moiety comprises a pentapeptide.

In one embodiment, each amino acid that comprises the peptide moiety is independently glycine, serine, glutamic acid, lysine, aspartic acid and cysteine.

In another embodiment, the peptide moiety comprises at least four glycines and at least one serine, e.g., (glycine)$_4$ and serine wherein the serine is at any position along the peptide chain, such as, for example, (serine)-(glycine)$_4$; (glycine)-(serine)-(glycine)$_3$; (glycine)$_2$-(serine)-(glycine)$_2$; (glycine)$_3$-(serine)-(glycine); or (glycine)$_4$-(serine).

In another embodiment, the peptide moiety comprises (glycine)$_4$-(serine) or (serine)-(glycine)$_4$.

In another embodiment, the peptide moiety comprises at least four glycines and at least one glutamic acid e.g., (glycine)$_4$ and glutamic acid wherein the glutamic acid is at any position along the peptide chain, such as, for example, (glutamic acid)-(glycine)$_4$; (glycine)-(glutamic acid)-(glycine)$_3$; (glycine)$_2$-(glutamic acid)-(glycine)$_2$; (glycine)$_3$-(glutamic acid)-(glycine); or (glycine)$_4$-(glutamic acid).

In another embodiment, the peptide moiety comprises (glutamic acid)-(glycine)$_4$; or (glycine)$_4$-(glutamic acid).

In another embodiment, the peptide moiety comprises (β-alanine)-(glycine)$_4$-(serine) wherein the serine is at any position along the peptide chain, such as, for example, (β-alanine)-(serine)-(glycine)$_4$; (β-alanine)-(glycine)-(serine)-(glycine)$_3$; (β-alanine)-(glycine)$_2$-(serine)-(glycine)$_2$; (β-alanine)-(glycine)$_3$-(serine)-(glycine); or (β-alanine)-(glycine)$_4$-(serine).

In another embodiment, the peptide moiety comprises (glycine)$_4$-(serine)-(glutamic acid) wherein the serine is at any position along the peptide chain, such as, for example, (serine)-(glycine)$_4$-(glutamic acid); (glycine)-(serine)-(glycine)$_3$-(glutamic acid); (glycine)$_2$-(serine)-(glycine)$_2$-(glutamic acid); (glycine)$_3$-(serine)-(glycine)-(glutamic acid); or (glycine)$_4$-(serine)-(glutamic acid). In another embodiment, the peptide moiety comprises (β-alanine)-(glycine)$_4$-(serine)-(glutamic acid) wherein the serine is at any position along the peptide chain, such as, for example, (β-alanine)-(serine)-(glycine)$_4$-(glutamic acid); (β-alanine)-(glycine)-(serine)-(glycine)$_3$-(glutamic acid); (β-alanine)-(glycine)$_2$-(serine)-(glycine)$_2$-(glutamic acid); (β-alanine)-(glycine)$_3$-(serine)-(glycine)-(glutamic acid); or (β-alanine)-(glycine)$_4$-(serine)-(glutamic acid).

In other embodiments, when at least one of hydrophilic groups (or $T^1$) is a polyalcohol or derivative thereof (e.g., an amino polyalcohol) or a glucosyl-amine or a di-glucosyl-amine or a tri-glucosyl-amine, $M^A$ does not have to comprise a peptide moiety, e.g., $M^A$ comprising those multi-armed linkers as listed herein for $L^M$. For example, $M^A$ comprises one or more of the following:

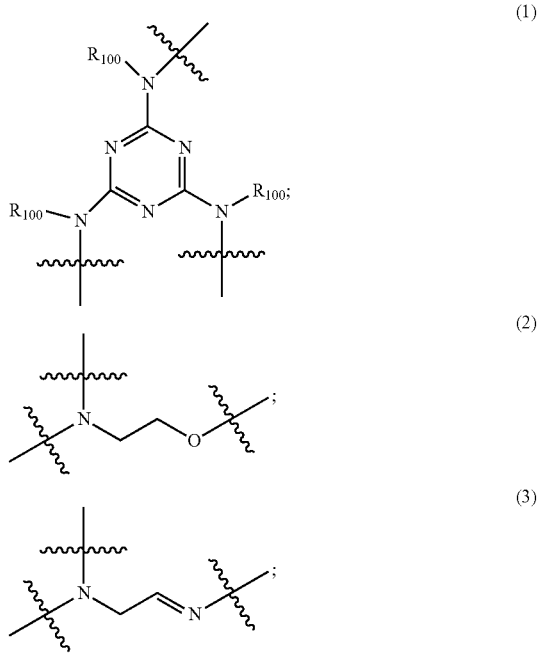

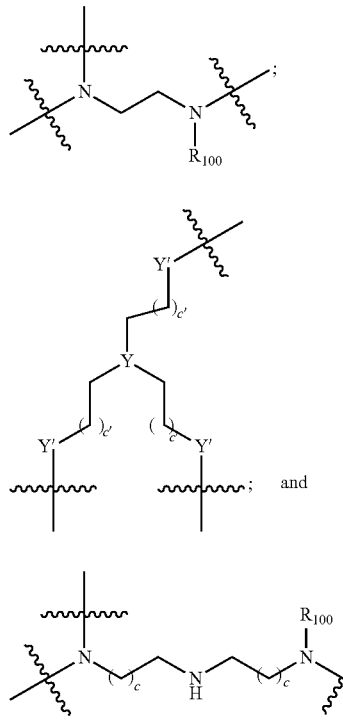
(4)
(5)
(6)
wherein:
the wavy line indicates attachment sites within the conjugate of the disclosure or intermediates thereof; and
$R_{100}$ and $R_{110}$ are as defined herein.
In some embodiments, $R_{110}$ is:
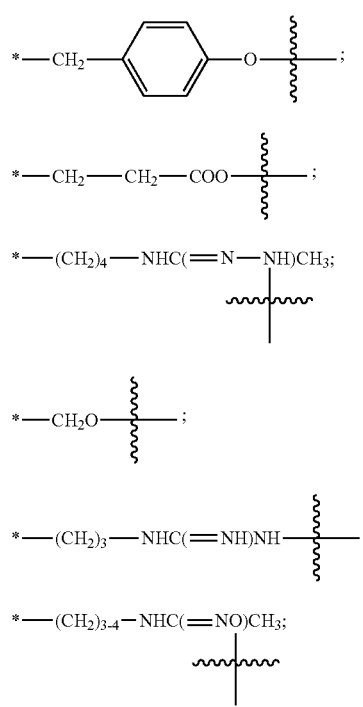
(1)
(2)
(3)
(4)
(5)
(6)
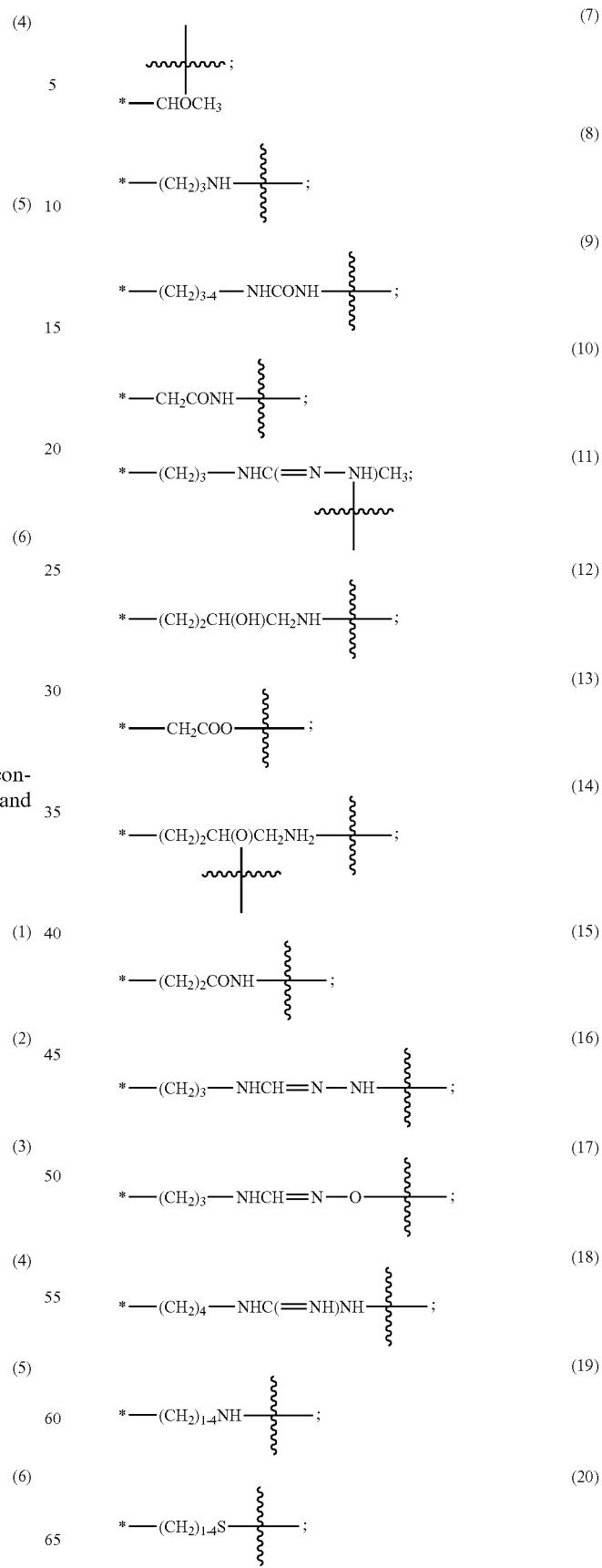

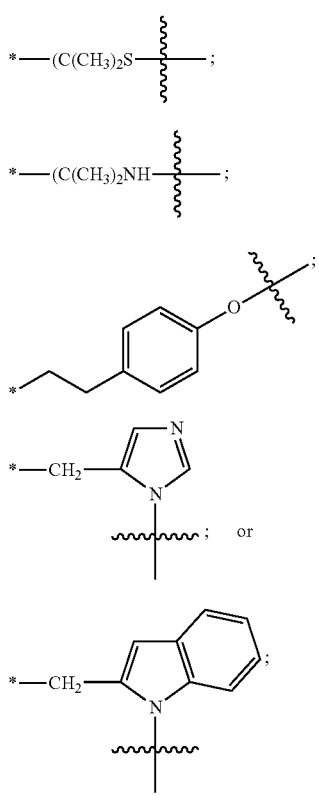

wherein the asterisk indicates attachment to the carbon labeled x and the wavy line indicates one of the three attachment sites.

In some embodiments, $R_{100}$ is independently selected from hydrogen and $CH_3$.

In some embodiments, Y is N.
In some embodiments, Y is CH.
In some embodiments, $R_{100}$ is H or $CH_3$.
In some embodiments, each c' is independently an integer from 1 to 3.
In some embodiments, $R_{110}$ is not

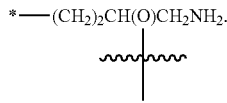

$L^D$ and $W^D$

Each occurrence of $L^D$ is independently a divalent linker moiety connecting D to $M^A$ and comprises at least one cleavable bond such that when the bond is broken, D is released in an active form for its intended therapeutic effect.

In some embodiments, $L^D$ is a component of the Releasable Assembly Unit. In other embodiments, $L^D$ is the Releasable Assembly Unit.

In some embodiments, $L^D$ comprises one cleavable bond.

In some embodiments, $L^D$ comprises multiple cleavage sites or bonds.

Functional groups for forming a cleavable bond can include, for example, sulfhydryl groups to form disulfide bonds, aldehyde, ketone, or hydrazine groups to form hydrazone bonds, hydroxylamine groups to form oxime bonds, carboxylic or amino groups to form peptide bonds, carboxylic or hydroxy groups to form ester bonds, and sugars to form glycosidic bonds. In some embodiments, $L^D$ comprises a disulfide bond that is cleavable through disulfide exchange, an acid-labile bond that is cleavable at acidic pH, and/or bonds that are cleavable by hydrolases (e.g., peptidases, esterases, and glucuronidases). In some embodiments, $L^D$ comprises a carbamate bond (i.e., —O—C(O)—NR—, in which R is H or alkyl or the like).

The structure and sequence of the cleavable bond(s) in $L^D$ can be such that the bond(s) is cleaved by the action of enzymes present at the target site. In other embodiments, the cleavable bond(s) can be cleavable by other mechanisms.

In some embodiments, the cleavable bond(s) can be enzymatically cleaved by one or more enzymes, including a tumor-associated protease, to liberate the Drug unit or D, which in one embodiment is protonated in vivo upon release to provide a Drug unit or D.

In certain embodiments, $L^D$ can comprise one or more amino acids. For example, each amino acid in $L^D$ can be natural or unnatural and/or a D- or L-isomer provided that there is a cleavable bond. In some embodiments, $L^D$ comprising an alpha, beta, or gamma amino acid that can be natural or non-natural. In some embodiments, $L^D$ comprises 1 to 12 (e.g., 1 to 6, or 1 to 4, or 1 to 3, or 1, 2, 3, 4, 5, 6, 7, 8, 9, 10, 11, or 12) amino acids in contiguous sequence.

In certain embodiments, $L^D$ can comprise only natural amino acids. In other embodiments, $L^D$ can comprise only non-natural amino acids. In some embodiments, $L^D$ can comprise a natural amino acid linked to a non-natural amino acid. In some embodiments, $L^D$ can comprise a natural amino acid linked to a D-isomer of a natural amino acid. An exemplary $L^D$ comprises a dipeptide such as -Val-Cit-, -Phe-Lys- or -Val-Ala-.

In some embodiments, $L^D$ comprises, a monopeptide, a dipeptide, a tripeptide, a tetrapeptide, a pentapeptide, a hexapeptide, a heptapeptide, an octapeptide, a nonapeptide, a decapeptide, an undecapeptide or a dodecapeptide unit.

In some embodiments, $L^D$ comprises a peptide (e.g., of 1 to 12 amino acids), which is conjugated directly to the drug unit. In some such embodiments, the peptide is a single amino acid or a dipeptide.

In some embodiments, each amino acid in $L^D$ is independently selected from alanine, β-alanine, arginine, aspartic acid, asparagine, histidine, glycine, glutamic acid, glutamine, phenylalanine, lysine, leucine, serine, tyrosine, threonine, isoleucine, proline, tryptophan, valine, cysteine, methionine, selenocysteine, ornithine, penicillamine, aminoalkanoic acid, aminoalkynoic acid, aminoalkanedioic acid, aminobenzoic acid, amino-heterocyclo-alkanoic acid, heterocyclo-carboxylic acid, citrulline, statine, diaminoalkanoic acid, and derivatives thereof.

In some embodiments, each amino acid is independently selected from alanine, β-alanine, arginine, aspartic acid, asparagine, histidine, glycine, glutamic acid, glutamine, phenylalanine, lysine, leucine, serine, tyrosine, threonine, isoleucine, proline, tryptophan, valine, cysteine, methionine, citrulline and selenocysteine.

In some embodiments, each amino acid is independently selected from the group consisting of alanine, β-alanine, arginine, aspartic acid, asparagine, histidine, glycine, glutamic acid, glutamine, phenylalanine, lysine, leucine, serine, tyrosine, threonine, isoleucine, proline, tryptophan, valine, citrulline and derivatives thereof.

In some embodiments, each amino acid is selected from the proteinogenic or the non-proteinogenic amino acids.

In some embodiments, each amino acid in $L^D$ can be independently selected from L- or D-isomers of the following amino acids: alanine, β-alanine, arginine, aspartic acid, asparagine, cysteine, histidine, glycine, glutamic acid, glutamine, phenylalanine, lysine, leucine, methionine, serine, tyrosine, threonine, tryptophan, proline, ornithine, penicillamine, aminoalkynoic acid, aminoalkanedioic acid, heterocyclo-carboxylic acid, citrulline, statine, diaminoalkanoic acid, valine, citrulline or derivatives thereof.

In some embodiments, each amino acid in $L^D$ is independently cysteine, homocysteine, penicillamine, ornithine, lysine, serine, threonine, glycine, glutamine, alanine, aspartic acid, glutamic acid, selenocysteine, proline, glycine, isoleucine, leucine, methionine, valine, citrulline or alanine.

In some embodiments, each amino acid in $L^D$ is independently selected from L-isomers of the following amino acids: alanine, β-alanine, arginine, aspartic acid, asparagine, histidine, glycine, glutamic acid, glutamine, phenylalanine, lysine, leucine, serine, tyrosine, threonine, isoleucine, tryptophan, citrulline or valine.

In some embodiments, each amino acid in $L^D$ is independently selected from D-isomers of the following amino acids: alanine, β-alanine, arginine, aspartic acid, asparagine, histidine, glycine, glutamic acid, glutamine, phenylalanine, lysine, leucine, serine, tyrosine, threonine, isoleucine, tryptophan, citrulline or valine.

In some embodiments, each amino acid in $L^D$ is alanine, β-alanine, glutamic acid, isoglutamic acid, isoaspartic acid, valine citrulline or aspartic acid.

In one embodiment, $L^D$ comprises β-alanine.

In another embodiment, $L^D$ comprises (β-alanine)-(alanine).

In another embodiment, $L^D$ comprises (β-alanine)-(glutamic acid).

In another embodiment, $L^D$ comprises (β-alanine)-(isoglutamic acid).

In another embodiment, $L^D$ comprises (β-alanine)-(aspartic acid).

In another embodiment, $L^D$ comprises (β-alanine)-(isoaspartic acid).

In another embodiment, $L^D$ comprises (β-alanine)-(valine).

In another embodiment, $L^D$ comprises (β-alanine)-(valine)-(alanine).

In another embodiment, $L^D$ comprises (β-alanine)-(alanine)-(alanine).

In another embodiment, $L^D$ comprises (β-alanine)-(valine)-(citruline).

In some embodiments, $L^D$ comprises a carbamate bond in addition to one or more amino acids.

In certain embodiments, $L^D$ can be designed and optimized in their selectivity for enzymatic cleavage by a particular enzyme, e.g., a tumor-associated protease.

In one embodiment, $L^D$ comprises a bond whose cleavage is catalyzed by cathepsin B, C and D, or a plasmin protease.

In another embodiment, $L^D$ comprises a sugar cleavage site. In some such embodiments, $L^D$ comprises a sugar moiety (Su) linked via an oxygen glycosidic bond to a self-immolative group. A "self-immolative group" can be a tri-functional chemical moiety that is capable of covalently linking together three spaced chemical moieties (i.e., the sugar moiety (via a glycosidic bond), a drug unit (directly or indirectly), and $M^A$ (directly or indirectly). The glycosidic bond will be one that can be cleaved at the target site to initiate a self-immolative reaction sequence that leads to a release of the drug.

For example, $L^D$ comprises a sugar moiety (Su) linked via a glycoside bond (—O'—) to a self-immolative group (K) of the formula:

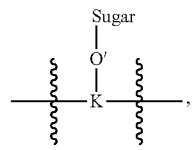

wherein the self-immolative group (K) forms a covalent bond with the drug unit (directly or indirectly) and also forms a covalent bond with $M^A$ (directly or indirectly). Examples of self-immolative groups are described in, e.g., WO 2015/057699, the contents of which are hereby incorporated by reference in its entirety.

When not connected to or prior to connecting to a drug, $L^D$ comprises a functional a functional group $W^D$. Each $W^D$ independently can be a functional group as listed for $W^P$. For example, each $W^D$ independently is

(1)

(2)

(3)

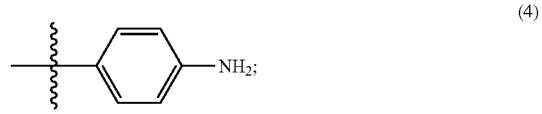

(4)

(5)

(6)

(7)

(8)

(9)

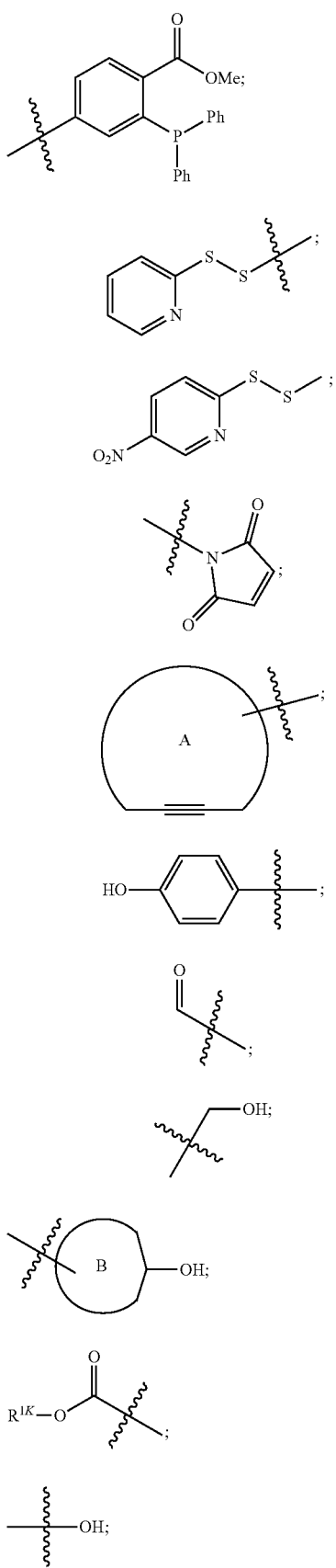
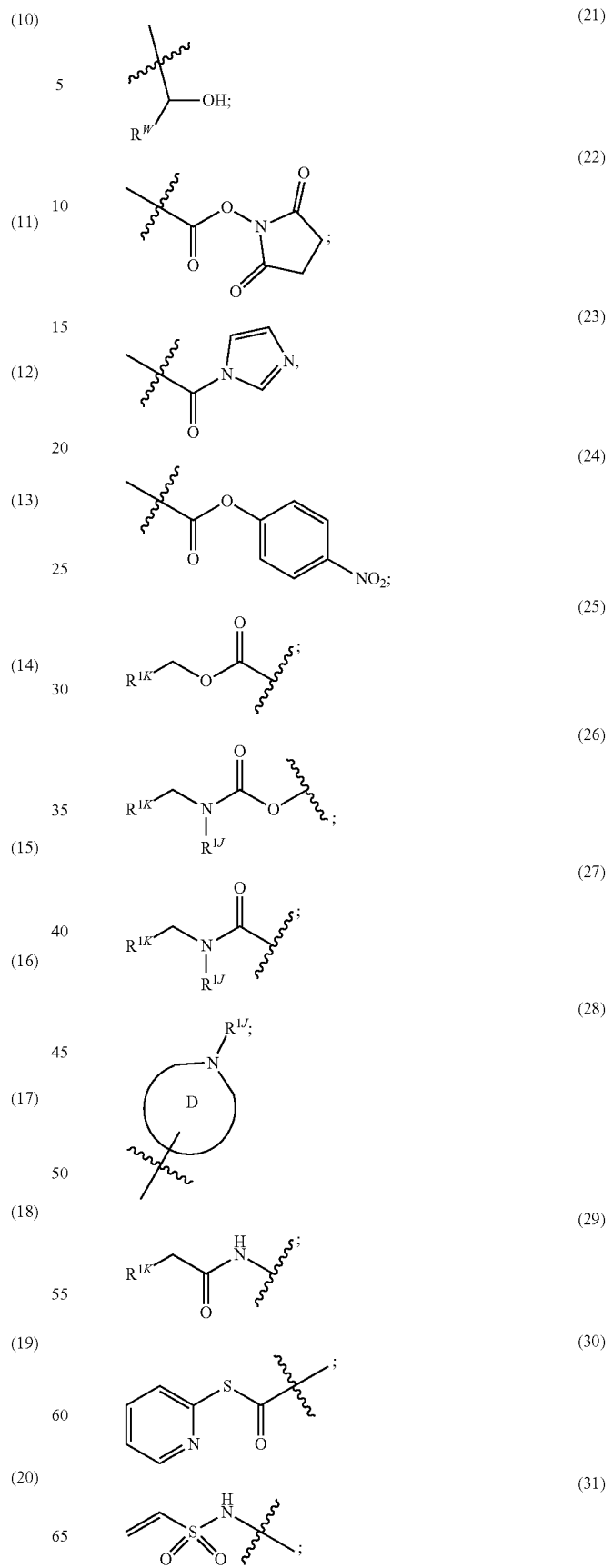

-continued

—COOH; (32)

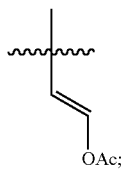
OAc; (33)

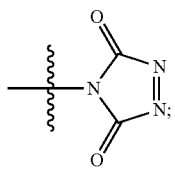 (34)

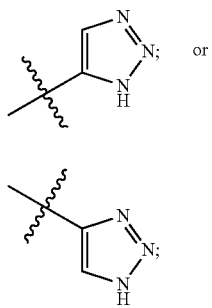 or (35)

(36)

in which $R^{1A}$ is a sulfur protecting group, each of ring A and B, independently, is cycloalkyl or heterocycloalkyl, $R^W$ is an aliphatic, heteroaliphatic, carbocyclic or heterocycloalkyl moiety; ring D is heterocycloalkyl; $R^{1J}$ is hydrogen, an aliphatic, heteroaliphatic, carbocyclic, or heterocycloalkyl moiety; and $R^{1K}$ is a leaving group (e.g., halide or RC(O)O— in which R is hydrogen, an aliphatic, heteroaliphatic, carbocyclic, or heterocycloalkyl moiety).

In some embodiments, $W^D$ is

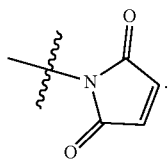 [SMILES: *N1C(=O)C=CC1=O]

In some embodiments, $W^D$ is

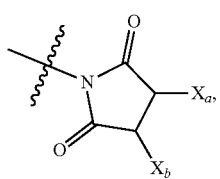

wherein one of $X_a$ and $X_b$ is H and the other is a maleimido blocking moiety.

In some embodiments, $W^D$ is

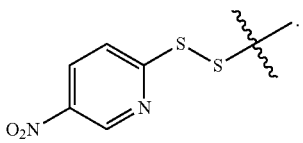 [SMILES: *SSc1ccc([N+](=O)[O-])cn1]

Therapeutic Agents, Drug Unit, or D

In certain embodiments, the therapeutic agent is a small molecule having a molecular weight preferably ≤about 5 kDa, more preferably ≤about 4 kDa, more preferably ≤about 3 kDa, most preferably ≤about 1.5 kDa or ≤about 1 kDa.

In certain embodiments, the therapeutic agent has an $IC_{50}$ of about less than 1 nM.

In another embodiment, the therapeutic agent has an $IC_{50}$ of about greater than 1 nM, for example, the therapeutic agent has an $IC_{50}$ of about 1 to 50 nM.

Some therapeutic agents having an $IC_{50}$ of greater than about 1 nM (e.g., "less potent drugs") are unsuitable for conjugation with an antibody using art-recognized conjugation techniques. Without wishing to be bound by theory, such therapeutic agents have a potency that is insufficient for use in targeted antibody-drug conjugates using conventional techniques as sufficient copies of the drug (i.e., more than 8) cannot be conjugated using art-recognized techniques without resulting in diminished pharmacokinetic and physiochemical properties of the conjugate. However sufficiently high loadings of these less potent drugs can be achieved using the conjugation strategies described herein thereby resulting in high loadings of the therapeutic agent while maintaining the desirable pharmacokinetic and physiochemical properties. Thus, the disclosure also relates to an antibody-drug conjugate which includes an antibody, a scaffold and at least eight therapeutic agent moieties, wherein the therapeutic agent has an $IC_{50}$ of greater than about 1 nM.

The small molecule therapeutic agents used in this disclosure (e.g., antiproliferative (cytotoxic and cytostatic) agents capable of being linked to a targeting moiety via the linker(s) of the disclosure) include cytotoxic compounds (e.g., broad spectrum), angiogenesis inhibitors, cell cycle progression inhibitors, PI3K/m-TOR/AKT pathway inhibitors, MAPK signaling pathway inhibitors, kinase inhibitors, protein chaperones inhibitors, HDAC inhibitors, PARP inhibitors, nicotinamide phosphoribosyl transferase (NAMPT) inhibitors, Wnt/Hedgehog signaling pathway inhibitors and RNA polymerase inhibitors.

Broad spectrum cytotoxins include, but are not limited to, DNA-binding, intercalating or alkylating drugs, microtubule stabilizing and destabilizing agents, platinum compounds, topoisomerase I inhibitors and protein synthesis inhibitors.

Exemplary DNA-binding, intercalation or alkylating drugs include, CC-1065 and its analogs, anthracyclines (doxorubicin, epirubicin, idarubicin, daunorubicin, nemorubicin and its derivatives, PNU-159682), bisnapththalimide compounds such as elinafide (LU79553). and its analogs, alkylating agents, such as calicheamicins, dactinomycins, mitomycins, pyrrolobenzodiazepines, and the like. Exemplary CC-1065 analogs include duocarmycin SA, duocarmycin A, duocarmycin C1, duocarmycin C2, duocarmycin B1, duocarmycin B2, duocarmycin D, DU-86, KW-2189, adozelesin, bizelesin, carzelesin, seco-adozelesin, and related analogs and prodrug forms, examples of which are described in U.S. Pat. Nos. 5,475,092; 5,595,499; 5,846,545; 6,534,660; 6,586,618; 6,756,397 and 7,049,316. Doxorubicin and its analogs include those described in U.S. Pat. No. 6,630,579. Calicheamicins include, e.g., enediynes, e.g., esperamicin, and those described in U.S. Pat. Nos. 5,714,586 and 5,739,116. Duocarmycins include those described in U.S. Pat. Nos. 5,070,092; 5,101,038; 5,187,186; 6,548,530; 6,660,742; and 7,553,816 B2; and Li et al., *Tet Letts.*, 50:2932-2935 (2009).

Pyrrolobenzodiazepines (PBD) and analogs thereof include those described in Denny, *Exp. Opin. Ther. Patents.*, 10(4):459-474 (2000) and Antonow and Thurston, Chem Rev., 2815-2864 (2010).

Exemplary microtubule stabilizing and destabilizing agents include taxane compounds, such as paclitaxel, docetaxel, tesetaxel and carbazitaxel; maytansinoids, auristatins and analogs thereof, vinca alkaloid derivatives, epothilones and cryptophycins.

Exemplary maytansinoids or maytansinoid analogs include maytansinol and maytansinol analogs, maytansine or DM-1 and DM-4 are those described in U.S. Pat. Nos. 5,208,020; 5,416,064; 6,333.410; 6,441,163; 6,716,821; RE39,151 and 7,276,497. In certain embodiments, the cytotoxic agent is a maytansinoid another group of anti-tubulin agents (ImmunoGen, Inc.; see also Chari et al., 1992, Cancer Res. 52:127-131), maytansinoids or maytansinoid analogs. Examples of suitable maytansinoids include maytansinol and maytansinol analogs. Suitable maytansinoids are disclosed in U.S. Pat. Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 6,333,410; 5,475,092; 5,585,499; and 5,846,545.

Exemplary auristatins include auristatin E (also known as a derivative of dolastatin-10), auristatin EB (AEB), auristatin EFP (AEFP), monomethyl auristatin E (MMAE), monomethyl auristatin F (MMAF), auristatin F, auristatin F phenylenediamine (AFP), auristatin F hydroxylpropylamide (AF HPA), monomethyl auristatin F hydroxylpropylamide (MMAF HP A), and dolastatin. Suitable auristatins are also described in U.S. Publication Nos. 2003/0083263, 2011/0020343, and 2011/0070248; PCT Application Publication Nos. WO 09/117531, WO 2005/081711, WO 04/010957; WO 02/088172 and WO 01/24763, and U.S. Pat. Nos. 7,498,298; 6,884,869; 6,323,315; 6,239,104; 6,124,431; 6,034,065; 5,780,588; 5,767,237; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414, the disclosures of which are incorporated herein by reference in their entirety.

Exemplary vinca alkaloids include vincristine, vinblastine, vindesine, and navelbine (vinorelbine). Suitable Vinca alkaloids that can be used in the present disclosure are also disclosed in U.S. Publication Nos. 2002/0103136 and 2010/0305149, and in U.S. Pat. No. 7,303,749 B1, the disclosures of which are incorporated herein by reference in their entirety.

Exemplary epothilone compounds include epothilone A, B, C, D, E and F, and derivatives thereof. Suitable epothilone compounds and derivatives thereof are described, for example, in U.S. Pat. Nos. 6,956,036; 6,989,450; 6,121,029; 6,117,659; 6,096,757; 6,043,372; 5,969,145; and 5,886,026; and WO 97/19086; WO 98/08849; WO 98/22461; WO 98/25929; WO 98/38192; WO 99/01124; WO 99/02514; WO 99/03848; WO 99/07692; WO 99/27890; and WO 99/28324; the disclosures of which are incorporated herein by reference in their entirety.

Exemplary cryptophycin compounds are described in U.S. Pat. Nos. 6,680,311 and 6,747,021.

Exemplary platinum compounds include cisplatin (PLATINOL®), carboplatin (PARAPLATIN®), oxaliplatin (ELOXATINE®), iproplatin, ormaplatin, and tetraplatin.

Still other classes of compounds or compounds with these or other cytotoxic modes of action may be selected, including, e.g., mitomycin C, mitomycin A, daunorubicin, doxorubicin, morpholino-doxorubicin, cyanomorpholino-doxorubicin, aminopterin, bleomycin, 1-(chloromethyl)-2,3-dihydro-1H-benzo[e]indol-5-ol, pyrrolobenzodiazepine (PBD) polyamide and dimers thereof. Other suitable cytotoxic agents include, for example, puromycins, topotecan, rhizoxin, echinomycin, combretastatin, netropsin, estramustine, cryptophysins, cemadotin, discodermolide, eleutherobin, and mitoxantrone.

Exemplary topoisomerase I inhibitors include camptothecin, camptothecin derivatives, camptothecin analogs and non-natural camptothecins, such as, for example, CPT-11 (irinotecan), SN-38, GI-147211C, topotecan, 9-aminocamptothecin, 7-hydroxymethyl camptothecin, 7-aminom ethyl camptothecin, 10-hydroxy camptothecin, (20S)-camptothecin, rubitecan, gimatecan, karenitecin, silatecan, lurtotecan, exatecan, diflomotecan, belotecan, lurtotecan and S39625. Other camptothecin compounds that can be used in the present disclosure include those described in, for example, J. Med. Chem., 29:2358-2363 (1986); J. Med. Chem., 23:554 (1980); J. Med. Chem., 30:1774 (1987).

Angiogenesis inhibitors include, but are not limited, MetAP2 inhibitors, VEGF inhibitors, PIGF inhibitors, VGFR inhibitors, PDGFR inhibitors, MetAP2 inhibitors. Exemplary VGFR and PDGFR inhibitors include sorafenib (Nexavar), sunitinib (Sutent) and vatalanib. Exemplary MetAP2 inhibitors include fumagillol analogs, meaning any compound that includes the fumagillin core structure, including fumagillamine, that inhibits the ability of MetAP-2 to remove $NH_2$-terminal methionines from proteins as described in Rodeschini et al., *J. Org. Chem.*, 69, 357-373, 2004 and Liu, et al., *Science* 282, 1324-1327, 1998. Non limiting examples of "fumagillol analogs" are disclosed in *J. Org. Chem.*, 69, 357, 2004; *J. Org. Chem.*, 70, 6870, 2005; European Patent Application 0 354 787; *J. Med. Chem.*, 49, 5645, 2006; *Bioorg. Med. Chem.*, 11, 5051, 2003; *Bioorg. Med. Chem.*, 14, 91, 2004; *Tet. Lett.* 40, 4797, 1999; WO99/61432; U.S. Pat. Nos. 6,603,812; 5,789,405; 5,767,293; 6,566,541; and 6,207,704.

Exemplary cell cycle progression inhibitors include CDK inhibitors such as, for example, BMS-387032 and PD0332991; Rho-kinase inhibitors such as, for example GSK429286; checkpoint kinase inhibitors such as, for example, AZD7762; aurora kinase inhibitors such as, for example, AZD1152, MLN8054 and MLN8237; PLK inhibitors such as, for example, BI 2536, BI6727 (Volasertib), GSK461364, ON-01910 (Estybon); and KSP inhibitors such as, for example, SB 743921, SB 715992 (ispinesib), MK-0731, AZD8477, AZ3146 and ARRY-520.

Exemplary PI3K/m-TOR/AKT signaling pathway inhibitors include phosphoinositide 3-kinase (PI3K) inhibitors, GSK-3 inhibitors, ATM inhibitors, DNA-PK inhibitors and PDK-1 inhibitors.

Exemplary PI3 kinase inhibitors are disclosed in U.S. Pat. No. 6,608,053, and include BEZ235, BGT226, BKM120, CAL101, CAL263, demethoxyviridin, GDC-0941, GSK615, IC87114, LY294002, Palomid 529, perifosine, PI-103, PF-04691502, PX-866, SAR245408, SAR245409, SF1126, Wortmannin, XL147 and XL765.

Exemplary AKT inhibitors include, but are not limited to AT7867.

Exemplary MAPK signaling pathway inhibitors include MEK, Ras, JNK, B-Raf and p38 MAPK inhibitors.

Exemplary MEK inhibitors are disclosed in U.S. Pat. No. 7,517,994 and include GDC-0973, GSK1120212, MSC1936369B, AS703026, RO5126766 and RO4987655, PD0325901, AZD6244, AZD 8330 and GDC-0973.

Exemplary B-raf inhibitors include CDC-0879, PLX-4032, and SB590885.

Exemplary B p38 MAPK inhibitors include BIRB 796, LY2228820 and SB 202190.

Receptor tyrosine kinases (RTK) are cell surface receptors which are often associated with signaling pathways stimulating uncontrolled proliferation of cancer cells and neoangiogenesis. Many RTKs, which over express or have mutations leading to constitutive activation of the receptor, have been identified, including, but not limited to, VEGFR, EGFR, FGFR, PDGFR, EphR and RET receptor family receptors. Exemplary specific RTK targets include ErbB2, FLT-3, c-Kit, and c-Met.

Exemplary inhibitors of ErbB2 receptor (EGFR family) include but not limited to AEE788 (NVP-AEE 788), BIBW2992, (Afatinib), Lapatinib, Erlotinib (Tarceva), and Gefitinib (Iressa).

Exemplary RTK inhibitors targeting more than one signaling pathway (multitargeted kinase inhibitors) include AP24534 (Ponatinib) that targets FGFR, FLT-3, VEGFR-PDGFR and Bcr-Abl receptors; ABT-869 (Linifanib) that targets FLT-3 and VEGFR-PDGFR receptors; AZD2171 that targets VEGFR-PDGFR, Flt-1 and VEGF receptors; CHR-258 (Dovitinib) that targets VEGFR-PDGFR, FGFR, Flt-3, and c-Kit receptors; Sunitinib (Sutent) that targets VEGFR, PDGFR, KIT, FLT-3 and CSF-IR; Sorafenib (Nexavar) and Vatalanib that target VEGFR, PDGFR as well as intracellular serine/threonine kinases in the Raf/Mek/Erk pathway.

Exemplary protein chaperon inhibitors include HSP90 inhibitors. Exemplary HSP90 inhibitors include 17AAG derivatives, BIIB021, BIIB028, SNX-5422, NVP-AUY-922 and KW-2478.

Exemplary HDAC inhibitors include Belinostat (PXD101), CUDC-101, Droxinostat, ITF2357 (Givinostat, Gavinostat), JNJ-26481585, LAQ824 (NVP-LAQ824, Dacinostat), LBH-589 (Panobinostat), MC1568, MGCD0103 (Mocetinostat), MS-275 (Entinostat), PCI-24781, Pyroxamide (NSC 696085), SB939, Trichostatin A and Vorinostat (SAHA).

Exemplary PARP inhibitors include iniparib (BSI 201), olaparib (AZD-2281), ABT-888 (Veliparib), AG014699, CEP 9722, MK 4827, KU-0059436 (AZD2281), LT-673, 3-aminobenzamide, A-966492, and AZD2461.

Exemplary NAMPT inhibitors include FK866 (AP0866) and CHS828, GPP78, GMX1778 (CHS828), STF-118804, STF-31, CB 300919, CB 30865, GNE-617, IS001, TP201565, Nampt-IN-1, P7C3, MPC-9528, CB30865, MPI0479883 and (E)-N-(5-((4-(((2-(1H-Indol-3-yl)ethyl) (isopropyl)amino)methyl)phenyl)amino)pentyl)-3-(pyridin-3-yl)acrylamide.

Exemplary Wnt/Hedgehog signaling pathway inhibitors include vismodegib (RG3616/GDC-0449), cyclopamine (11-deoxojervine) (Hedgehog pathway inhibitors) and XAV-939 (Wnt pathway inhibitor).

Exemplary RNA polymerase inhibitors include amatoxins. Exemplary amatoxins include α-amanitins, β-amanitins, γ-amanitins, ε-amanitins, amanullin, amanullic acid, amaninamide, amanin, and proamanullin.

Exemplary protein synthesis inhibitors include trichothecene compounds.

In one embodiment, the drug is a topoisomerase inhibitor (such as, for example, a non-natural camptothecin compound), vinca alkaloid, kinase inhibitor (e.g., PI3 kinase inhibitor (GDC-0941 and PI-103)), MEK inhibitor, KSP inhibitor, RNA polymerase inhibitor, protein synthesis inhibitor, PARP inhibitor, NAMPT inhibitor, docetaxel, paclitaxel, doxorubicin, duocarmycin, auristatin, dolastatin, calicheamicins, topotecan, SN38, camptothecin, exatecan, nemorubicin and its derivatives, PNU-159682, CC1065, elinafide, trichothecene, pyrrolobenzodiazepines, maytansinoids, DNA-binding drugs or a platinum compound, and analogs thereof. In specific embodiments, the drug is a derivative of SN-38, camptothecin, topotecan, exatecan, calicheamicin, nemorubicin, PNU-159682, anthracycline, maytansinoid, taxane, trichothecene, CC1065, elinafide, vindesine, vinblastine, PI-103, AZD 8330, dolastatin, auristatin E, auristatin F, a duocarmycin compound, ispinesib, pyrrolobenzodiazepine, ARRY-520 and stereoisomers, isosteres and analogs thereof.

In another embodiment, the drug used in the disclosure is a combination of two or more drugs, such as, for example, PI3 kinase inhibitors and MEK inhibitors; broad spectrum cytotoxic compounds and platinum compounds; PARP inhibitors, NAMPT inhibitors and platinum compounds; broad spectrum cytotoxic compounds and PARP inhibitors.

In yet another embodiment, the drug used in the disclosure is auristatin F-hydroxypropylamide-L-alanine.

In one embodiment, the Vinca alkaloid is a compound of Formula (VI),

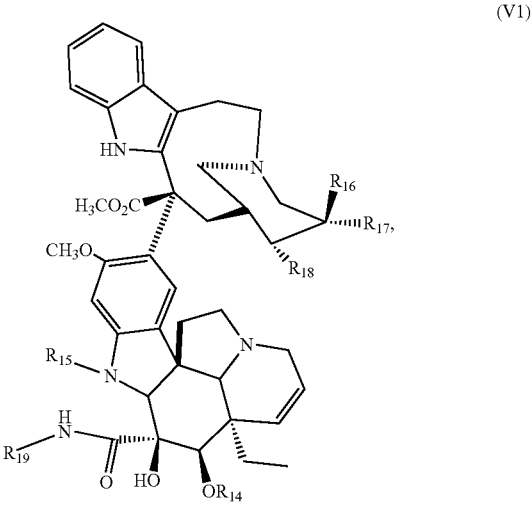

(VI)

wherein:
$R_{14}$ is hydrogen, —C(O)—$C_{1-3}$ alkyl or —C(O)-chloro substituted $C_{1-3}$ alkyl;
$R_{15}$ is hydrogen, —$CH_3$ or —CHO;
when $R_{17}$ and $R_{18}$ are taken independently, Rix is hydrogen, and either $R_{16}$ or $R_{17}$ is ethyl and the other is hydroxyl;
when $R_{17}$ and $R_{18}$ are taken together with the carbon to which they are attached to form an oxiran ring, $R_{16}$ is ethyl;
$R_{19}$ is hydrogen, OH, amino group, alkyl amino or —[C($R_{20}R_{21}$)]$_a$—$R_{22}$;
each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

$R_{22}$ is —OH, —$NH_2$, —COOH, —$R_{82}$—C(O)($CH_2$)$_c$—C(H)($R_{23}$)—N(H)($R_{23}$), —$R_{82}$—C(O)($CH_2$)$_d$—(O—$CH_2$—$CH_2$)$_f$—N(H)($R_{23}$) or —$R_{82}$—(C(O)—CH($X^2$)—NH)$_d$—$R_{77}$;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

$X^2$ is a side chain of a natural or unnatural amino acid;

$R_{77}$ is hydrogen or $X^2$ and $NR_{77}$ form a nitrogen containing heterocyclic moiety;

$R_{82}$ is —$NR_{23}$ or oxygen;

a is an integer from 1 to 6;

c is an integer from 0 to 3;

d is an integer from 1 to 3; and f is an integer from 1 to 12.

Further examples of Vinca alkaloids are described in U.S. Pat. No. 8,524,214B2 and US 2002/0103136.

In one embodiment the Vinca alkaloid of Formula (VI) is a compound of Formula (VII):

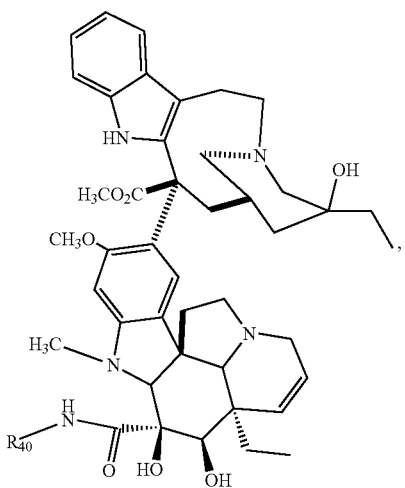

(VII)

wherein:

$R_{40}$ is hydrogen, —OH, —$NH_2$, or any of the following structures:

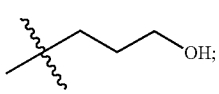

(1)

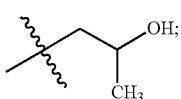

(2)

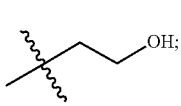

(3)

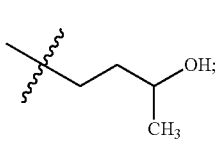

(4)

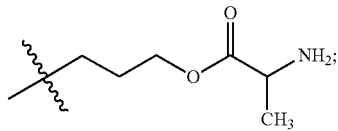

(5)

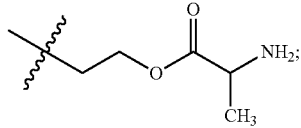

(6)

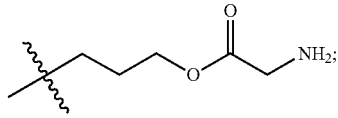

(7)

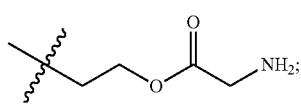

(8)

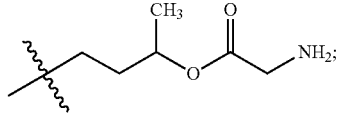

(9)

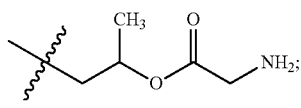

(10)

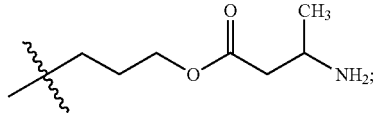

(11)

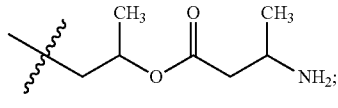

(12)

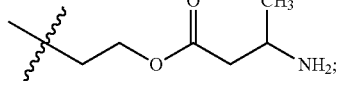

(13)

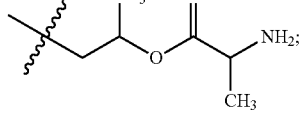

(14)

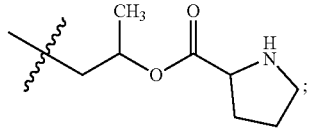

(15)

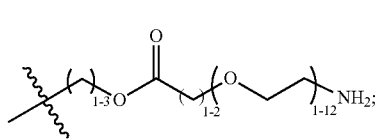

(16)

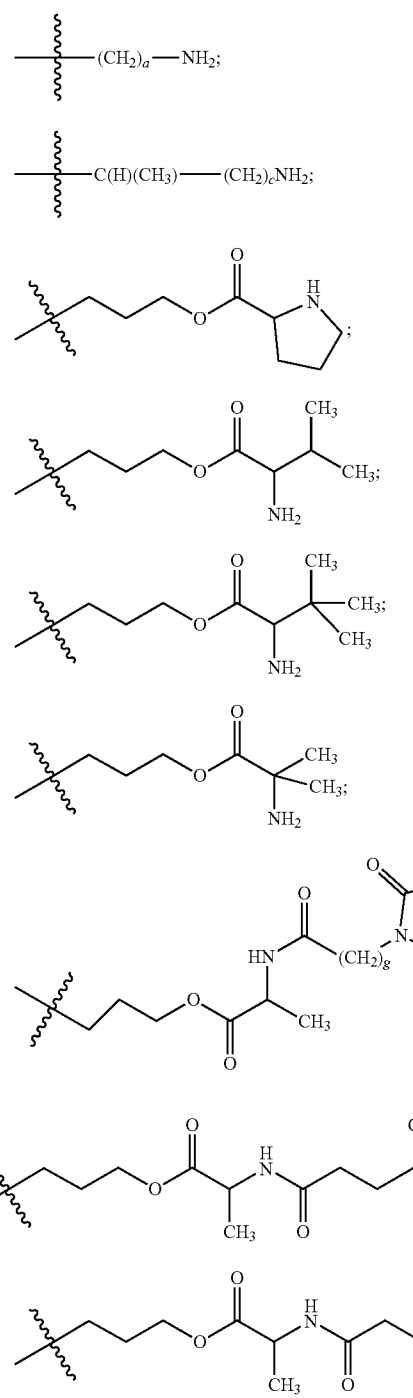
wherein:
a is an integer from 1 to 6;
g is an integer from 2 to 6; and
c is an integer from 0 to 3.
In one embodiment, in Formula (VII), R$_{40}$ is
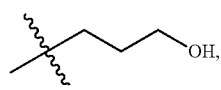
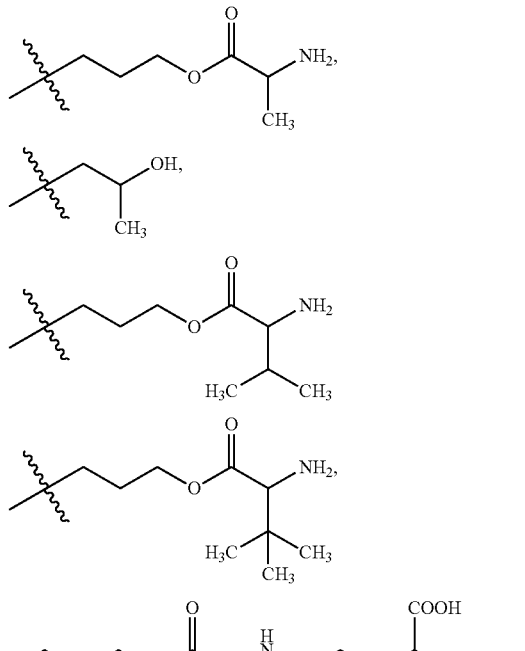
In another embodiment, R$_{40}$ is
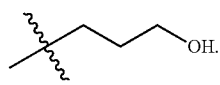 [SMILES: *CCCO]
In another embodiment, R$_{40}$ is
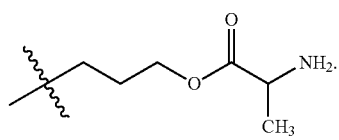 [SMILES: *CCCOC(=O)C(C)N]
In another embodiment, R$_{40}$ is
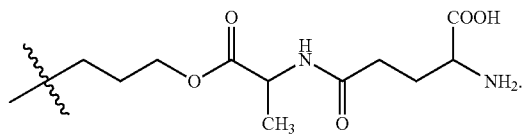 [SMILES: *CCCOC(=O)C(C)NC(=O)CCC(N)C(=O)O]

In another embodiment, R$_{40}$ is
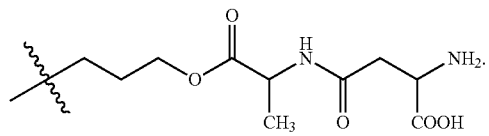 [SMILES: *CCCOC(=O)C(C)NC(=O)CC(N)C(=O)O]
In another embodiment, the compound of Formula (VII) is a compound of Formula (VIa), (VIb), (VIc), (VId), (VIe) or (VIf):
(VIa)
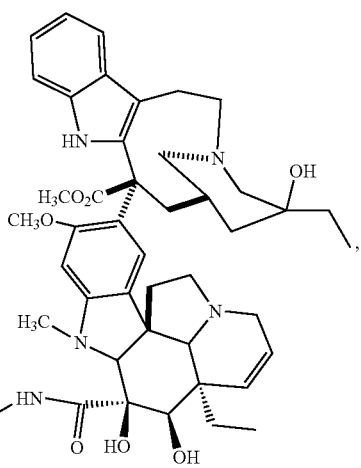
(VIb)
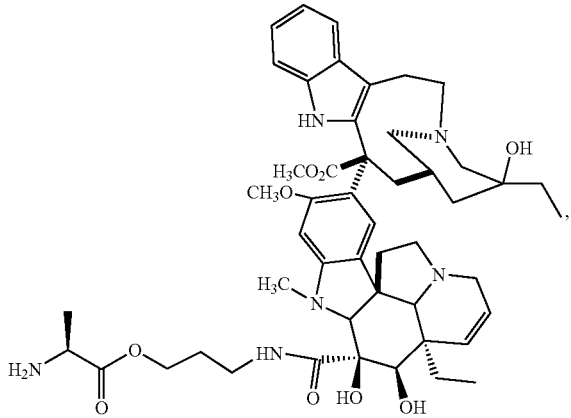
(VIc)
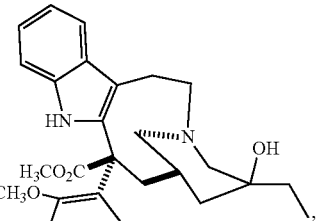
(VId)
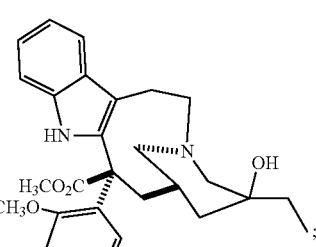
(VIe)
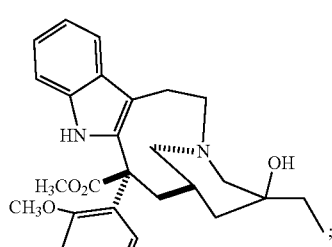
; or
(VIf)
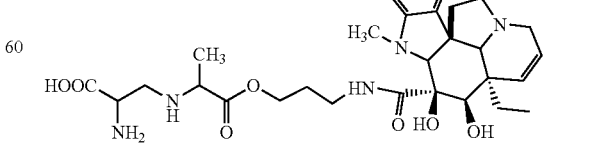
In another embodiment, the topoisomerase inhibitor is a camptothecin compound of Formula (VIII):

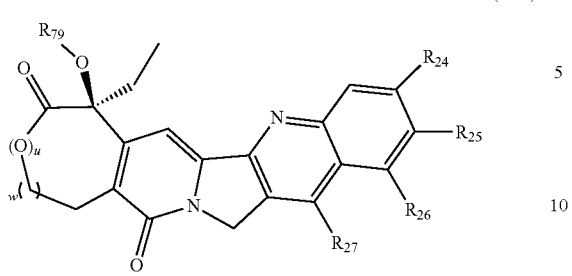

(VIII)

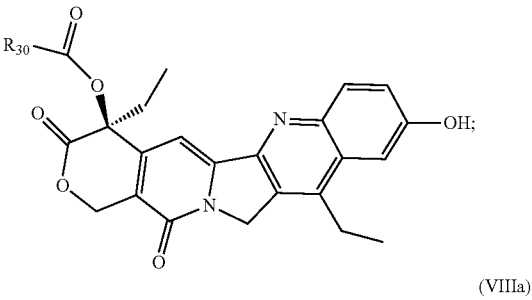

(VIII1)

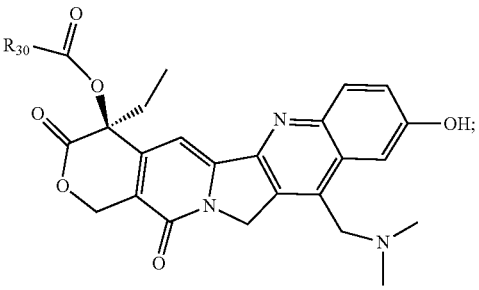

(VIIIa)

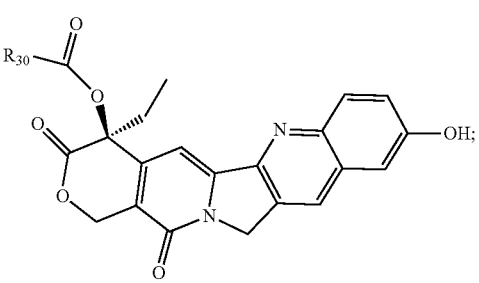

(VIIIb)

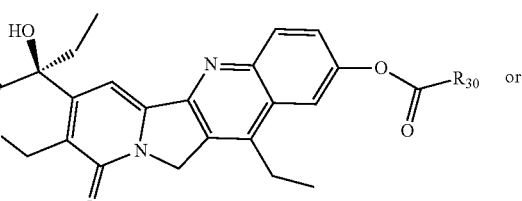

(XXV)

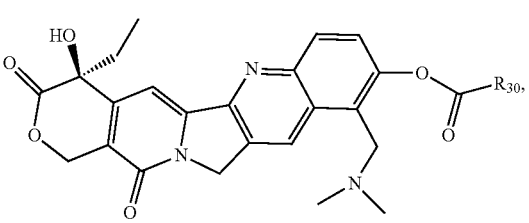

(XXVa)

wherein:

$R_{24}$ is —H, —Cl, —F, —OH or alkyl; or $R_{24}$ and $R_{25}$, may be taken together to form an optionally substituted five- or six-membered ring;

$R_{25}$ is —H, —F, —OH, —CH$_3$, —CH=N—O-t-Butyl, —CH$_2$CH$_2$Si(CH$_3$)$_3$, —Si((CH$_3$)$_2$)-t-butyl, —O—C(O)—R$_{29}$;

$R_{29}$ is —NH$_2$, —R$_{28}$—C$_{1-6}$ alkyl-R$_{22}$, 5 to 12-membered heterocycloalkyl, R$_{28}$—C$_{5-12}$ heterocycloalkyl-C$_{1-6}$ alkyl-R$_{22}$ or —R$_{28}$—C$_{1-6}$ alkyl-C$_{6-12}$ aryl-C$_{1-6}$ alkyl-R$_{22}$; or R$_{29}$ is R$_{47}$ as defined herein;

$R_{26}$ is —H, —CH$_2$—N(CH$_3$)$_2$, NH$_2$, or NO$_2$;

$R_{27}$ is —H, ethyl, N-methyl piperidine, cycloalkyl, —CH$_2$OH, —CH$_2$CH$_2$NHCH(CH$_3$)$_2$, or —N-4-methylcyclohexylamine;

$R_{79}$ is —H or —C(O)—R$_{28}$—[C(R$_{20}$R$_{21}$)]$_a$—R$_{22}$;

each of $R_{20}$ and $R_{21}$ independently is hydrogen, C$_{1-6}$ alkyl, C$_{6-10}$ aryl, hydroxylated C$_{6-10}$ aryl, polyhydroxylated C$_{6-10}$ aryl, 5 to 12-membered heterocycle, C$_{3-8}$ cycloalkyl, hydroxylated C$_{3-8}$ cycloalkyl, polyhydroxylated C$_{3-8}$ cycloalkyl or a side chain of a natural or unnatural amino acid;

$R_{22}$ is —OH, —NH$_2$, —COOH, —R$_{82}$—C(O)(CH$_2$)$_c$—C(H)(R$_{23}$)—N(H)(R$_{23}$), —R$_{82}$—C(O)(CH$_2$)$_d$—(OCH$_2$—CH$_2$)$_f$—N(H)(R$_{23}$), or —R$_{82}$—(C(O)—CH(X$^2$)—NH)$_d$—R$_{77}$;

each $R_{23}$ independently is hydrogen, C$_{1-6}$ alkyl, C$_{6-10}$ aryl, C$_{3-8}$ cycloalkyl, —COOH, or —COO—C$_{1-6}$ alkyl;

$X^2$ is a side chain of a natural or unnatural amino acid;

$R_{77}$ is a hydrogen or $X^2$ and NR$_{77}$ form a nitrogen containing cyclic compound;

$R_{82}$ is —NR$_{23}$ or oxygen;

or $R_{26}$ and $R_{27}$ when taken together with the two carbon atoms to which they attach and the third carbon atom connecting the two carbon atoms form an optionally substituted six-membered ring;

$R_{28}$ is absent, NR$_{23}$ or oxygen;

a is an integer from 1 to 6;

c is an integer from 0 to 3;

d is an integer from 1 to 3;

f is an integer from 1 to 12;

u is an integer 0 or 1;

w is an integer 0 or 1; and with the proviso that the compound of Formula (VIII) must contain at least one of $R_{29}$ and $R_{79}$.

In one embodiment the camptothecin compound of Formula (VIII) is a compound of Formula (VIII1), (VIIIa), or (VIIIb), or Formula (XXV) or (XXVa):

wherein:

$R_{30}$ is —NH$_2$, —R$_{28}$—[C(R$_{20}$R$_{21}$)]$_a$—R$_{22}$, —R$_{28}$—C$_{1-6}$ alkyl-R$_{22}$, 5 to 12-membered heterocycloalkyl, R$_{28}$—C$_{5-12}$ heterocycloalkyl-C$_{1-6}$ alkyl-R$_{22}$ or —R$_{28}$—C$_{1-6}$ alkyl-C$_{6-12}$ aryl-C$_{1-6}$ alkyl-R$_{22}$;

$R_{28}$ is absent, NR$_{23}$ or oxygen;

each of $R_{20}$ and $R_{21}$ independently is hydrogen, C$_{1-6}$ alkyl, C$_{6-10}$ aryl, hydroxylated C$_{6-10}$ aryl, polyhydroxylated C$_{6-10}$ aryl, 5 to 12-membered heterocycle, C$_{3-8}$ cycloalkyl, hydroxylated $C_{3-8}$ cycloalkyl, polyhydroxylated $C_{3-8}$ cycloalkyl or a side chain of a natural or unnatural amino acid;

$R_{22}$ is —OH, —NH$_2$, —COOH, —$R_{82}$—C(O)(CH$_2$)$_c$—C(H)(R$_{23}$)—N(H)(R$_{23}$), —$R_{82}$—C(O)(CH$_2$)$_d$—(OCH$_2$—CH$_2$)$_f$—N(H)(R$_{23}$) or —$R_{82}$—(C(O)—CH(X$^2$)—NR$_{23}$)$_d$—R$_{77}$;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

$X^2$ is a side chain of a natural or unnatural amino acid;

$R_{77}$ is a hydrogen or $X^2$ and NR$_{77}$ form a nitrogen containing cyclic compound;

$R_{82}$ is —NR$_{23}$ or oxygen;

a is an integer from 1 to 6;

c is an integer from 0 to 3;

d is an integer from 1 to 3; and f is an integer from 1 to 12.

In some embodiments, $R_{30}$ is any one of the following structures:

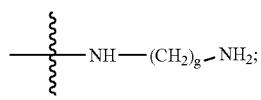
(1)

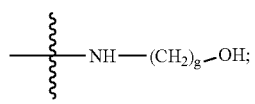
(2)

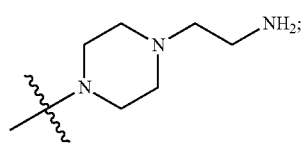
(3)

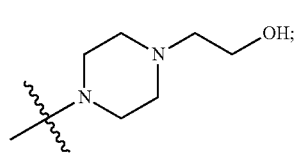
(4)

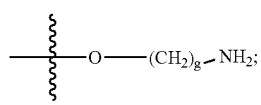
(5)

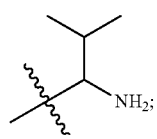
(6)

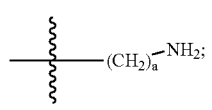
(7)

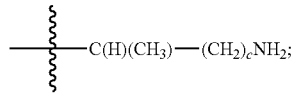
(8)

-continued

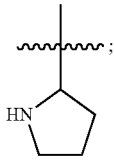
(9)

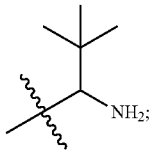
(10)

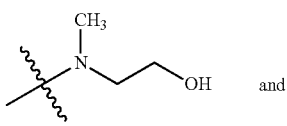
(11)

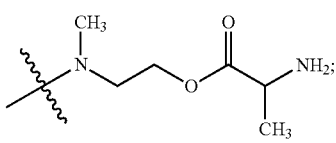
(12)

wherein:

a is an integer from 1 to 6;

c is an integer from 0 to 3; and g is an integer from 2 to 6.

In one embodiment, in Formula (VIII), $R_{30}$ is:

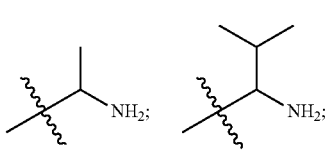

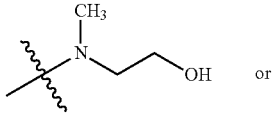

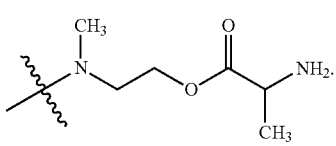

In another embodiment, the compound of Formula (VIII) is a compound of Formula (VIIa), (VIIb), (VIIc), (VIId), (VIIe), (VIIf), (VIIg), (VIIh), (VIIi), or (VIIj):

(VIIa)
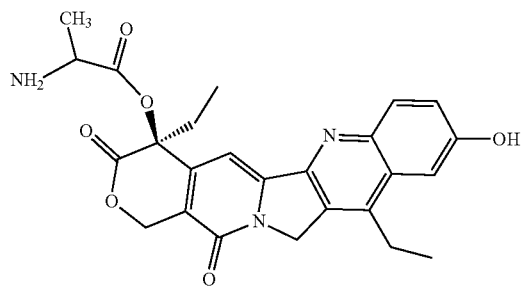
(VIIf)
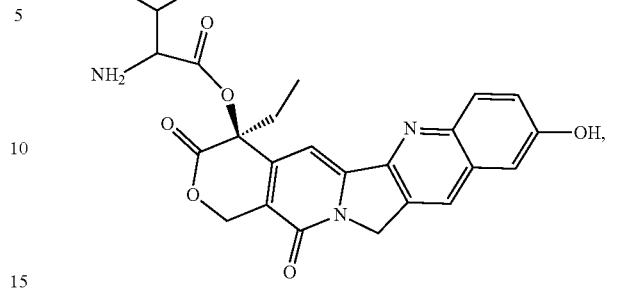
(VIIb)
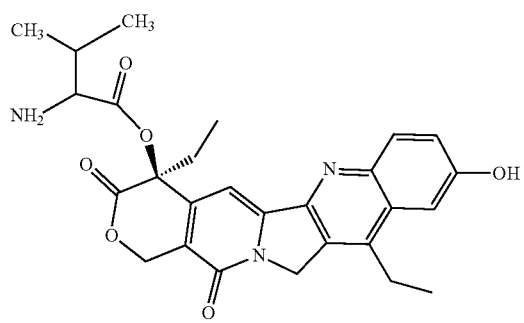
(VIIg)
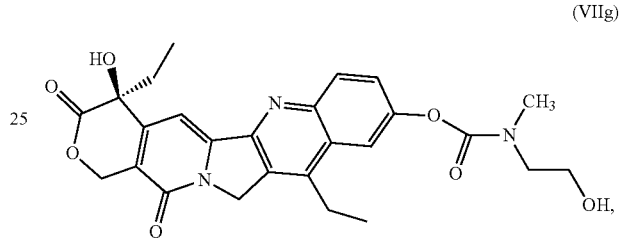
(VIIc)
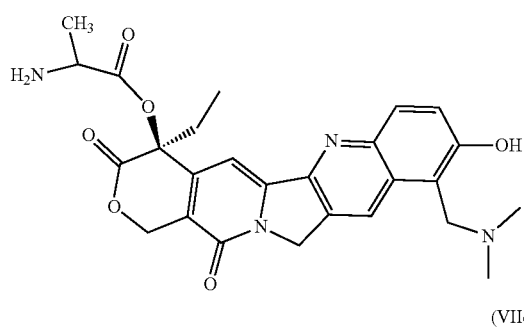
(VIIh)
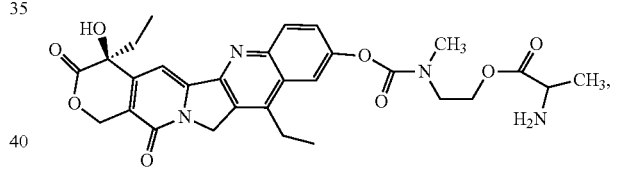
(VIId)
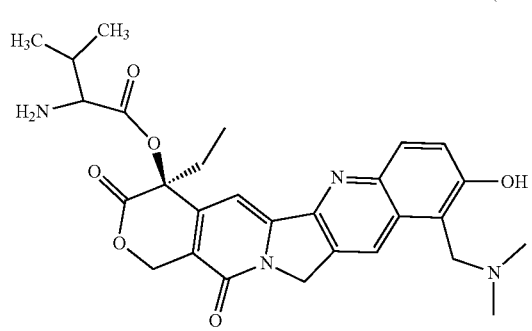
(VIIi)
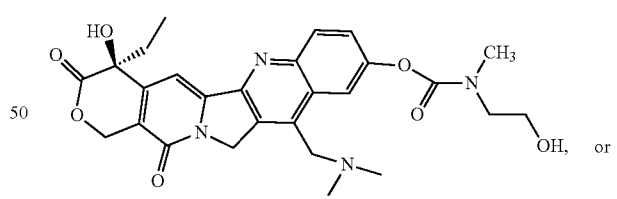
or
(VIIe)
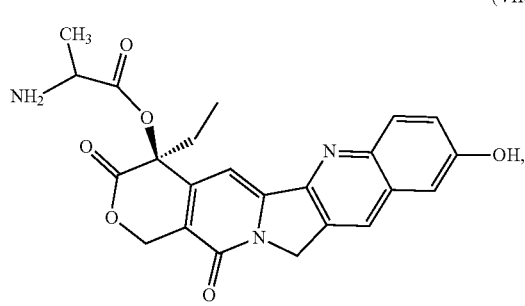
(VIIj)
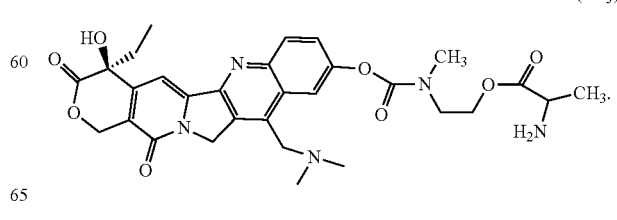

In another embodiment the PI3 kinase inhibitor is a compound of Formula (IX1):
wherein

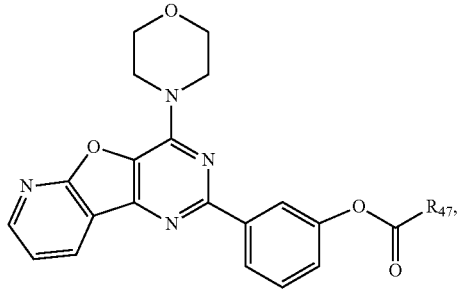

(IX1)

$R_{47}$ is an amino group, $-R_9-[C(R_{20}R_{21})]_a-R_{10}$, $-R_9-C_{5-12}$ heterocycloalkyl-$C_{1-6}$ alkyl-$R_{10}$, 5 to 12-membered heterocycloalkyl, or $-R_9-C_{6-10}$ aryl;

each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

$R_{10}$ is $-OH$, $-NHR_{83}$, $-N-(R_{83})R_{11}$, $-COOH$, $-R_{82}-C(O)(CH_2)_c-C(H)(R_{23})-N(H)(R_{23})$, $-R_{82}-C(O)(CH_2)_d-(OCH_2-CH_2)_f-N(H)(R_{23})$, $-R_{82}-(C(O)-CH(X^2)-NH)_d-R_{77}$ or $-R_{82}-C(O)-[C(R_{20}R_{21})]_a-R_{82}-R_{83}$;

each $R_{23}$ independently is hydrogen, $C_{1-6}$ alkyl, $C_{6-10}$ aryl, $C_{3-8}$ cycloalkyl, $-COOH$, or $-COO-C_{1-6}$ alkyl;

$X^2$ is a side chain of a natural or unnatural amino acid;

$R_{77}$ is a hydrogen or $X^2$ and $NR_{77}$ form a nitrogen containing cyclic compound;

$R_{82}$ is $-NR_{23}$ or oxygen;

$R_9$ is absent, $N-(R_{83})$ or oxygen;

$R_{83}$ is hydrogen or $CH_3$; or $R_{11}$:

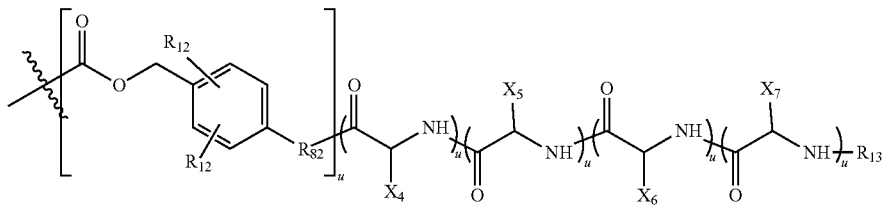

each $R_{12}$ independently is hydrogen, chloride, $-CH_3$ or $-OCH_3$;

$R_{13}$ is hydrogen or $-C(O)-(CH_2)_d-(O-CH_2-CH_2)_f-NH_2$;

$R_{82}$ is $-NR_{23}$ or oxygen $X_4$ is the side chain of lysine, arginine, citrulline, alanine or glycine;

$X_5$ is the side chain of phenylalanine, valine, leucine, isoleucine or tryptophan;

each of $X_6$ and $X_7$ is independently the side chain of glycine, alanine, serine, valine or proline;

a is an integer from 1 to 6;

c is an integer from 0 to 3;

d is an integer from 1 to 3;

f is an integer from 1 to 12; and each u independently is an integer 0 or 1;

or $R_{11}$ is $-Y_u-W_q-R_{88}$, wherein:

Y is any one of the following structures:

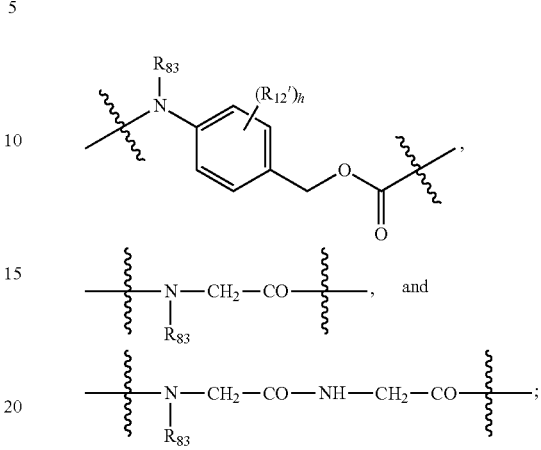

in each of which the terminal $NR_{83}$ group of Y is proximal to $R_{88}$;

$R_{83}$ is hydrogen or $CH_3$;

each W is an amino acid unit;

each $R_{12}'$ independently is halogen, $-C_{1-8}$ alkyl, $-O-C_{1-8}$ alkyl, nitro or cyano;

$R_{88}$ is hydrogen or $-C(O)-(CH_2)_{ff}-(NH-C(O))_{aa}-E_j-(CH_2)_{bb}-R_{85}$ $R_{85}$ is $NH_2$ or $OH$;

E is $-CH_2-$ or $-CH_2CH_2O-$;

u is an integer 0 or 1;

q is an integer from 0 to 12;

aa is an integer 0 or 1;

bb is an integer 0 or 2;

ff is an integer from 0 to 10;

h is an integer from 0 to 4;

j is an integer from 0 to 12; and when E is $-CH_2-$, bb is 0 and j is an integer from 0 to 10; and when E is $-CH_2CH_2-O-$, bb is 2 and j is an integer from 1 to 12;

or $R_{11}$ is:

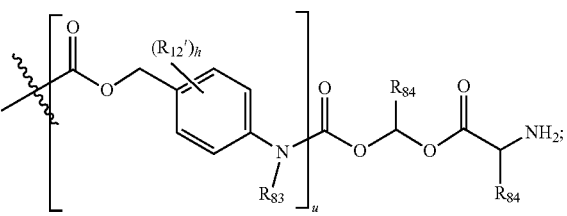

wherein:
R₈₃ is hydrogen or CH₃;
R₈₄ is C₁₋₆ alkyl or C₆₋₁₀ aryl;
each R₁₂' independently is halogen, —C₁₋₈ alkyl, —O—C₁₋₈ alkyl, nitro or cyano;
h is an integer from 0 to 4; and
u is an integer 0 or 1.

In some embodiments, $R_{11}$ is:

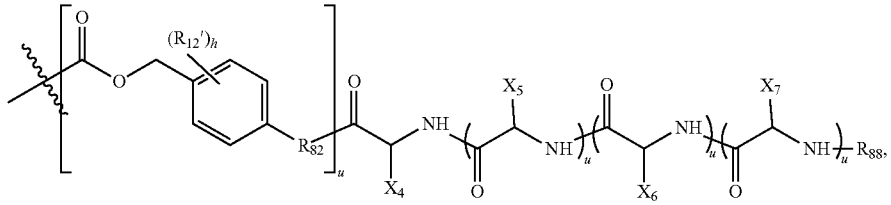

wherein:
each $R_{12}'$ independently is chloride, —CH₃ or —OCH₃;
$R_{88}$ is hydrogen or —C(O)—(CH₂)$_{ff}$—(CH₂—CH₂O)$_j$—CH₂—CH₂—NH₂;
$R_{82}$ is —NR₂₃ or oxygen
$X_4$ is the side chain of lysine, arginine, citrulline, alanine or glycine;
$X_5$ is the side chain of phenylalanine, valine, leucine, isoleucine or tryptophan;
each of $X_6$ and $X_7$ is independently the side chain of glycine, alanine, serine, valine or proline;
ff is an integer from 1 to 3;
j is an integer from 1 to 12
h is an integer from 0 to 4; and
each u independently is an integer 0 or 1.

In some embodiments,

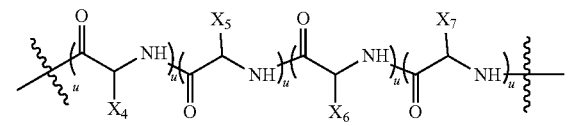

is citrulline-valine; lysine-phenylalanine; citrulline-phenylalanine; citrulline-leucine; citrulline-valine-glycine-glycine; glycine-phenylalanine-glycine-glycine; valine; proline; leucine or isoleucine.

In another embodiment, $R_{11}$ is any one of the following structures:

(1)

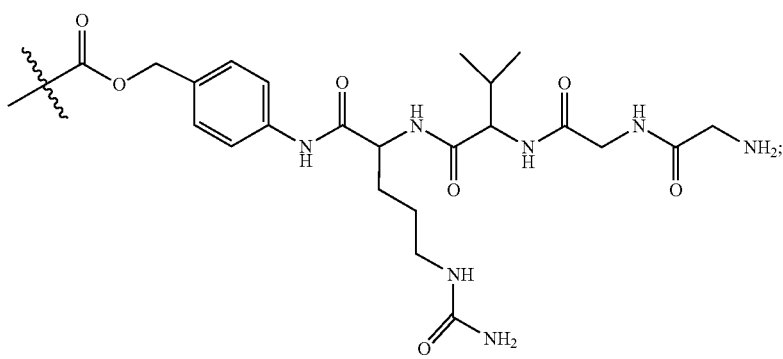

(2)

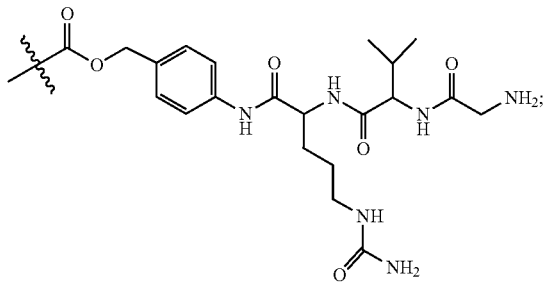

(3)

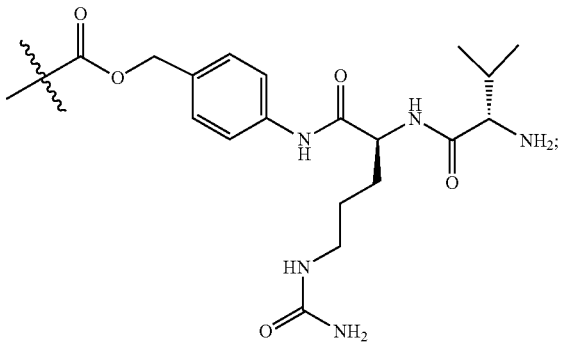

-continued
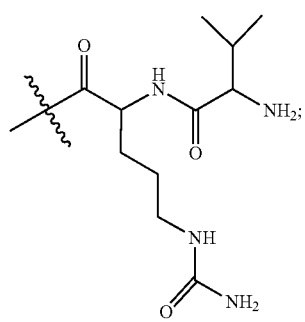
(4)
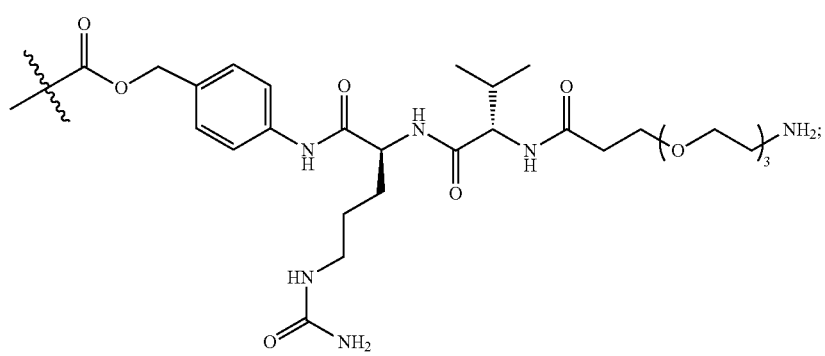
(5)
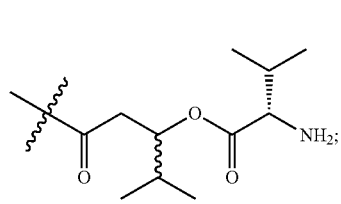
(6)
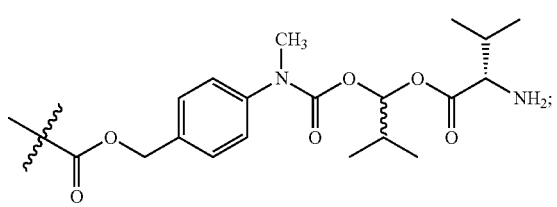
(7)
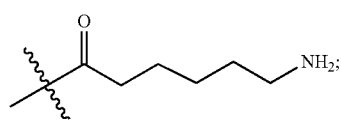
(8)
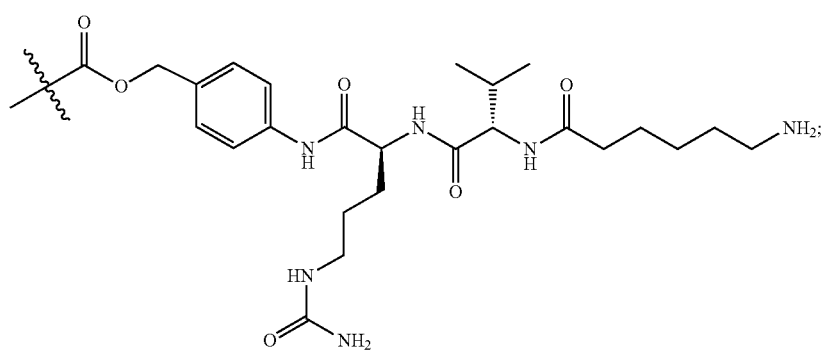
(9)

-continued
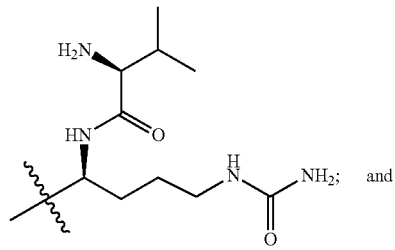 (10)
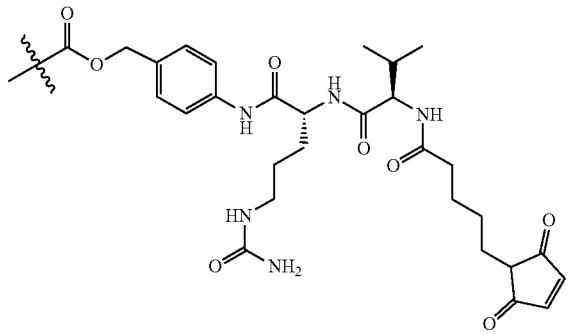 (11)
In some embodiments, $R_{47}$ is any one of the following structures:
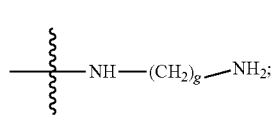 (1)
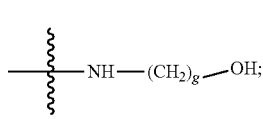 (2)
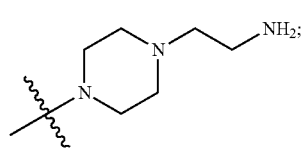 (3)
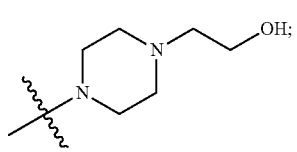 (4)
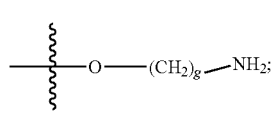 (5)
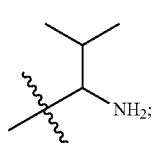 (6)
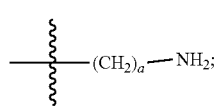 (7)
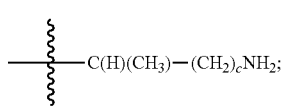 (8)
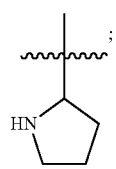 (9)
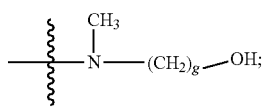 (10)
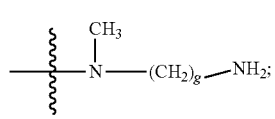 (11)
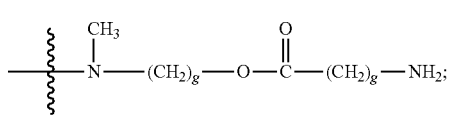 (12)
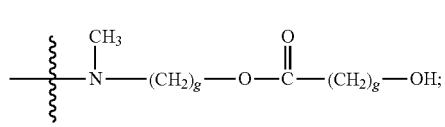 (13)
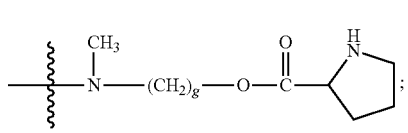 (14)

-continued
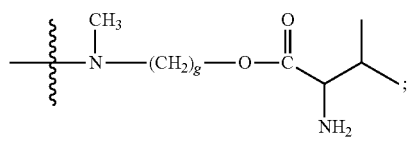
(15)
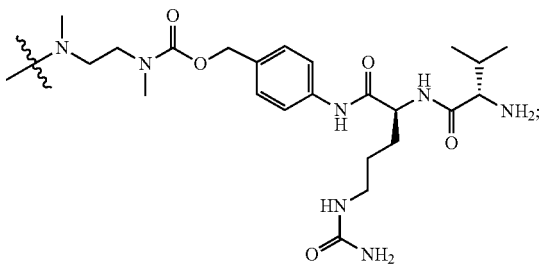
(16)
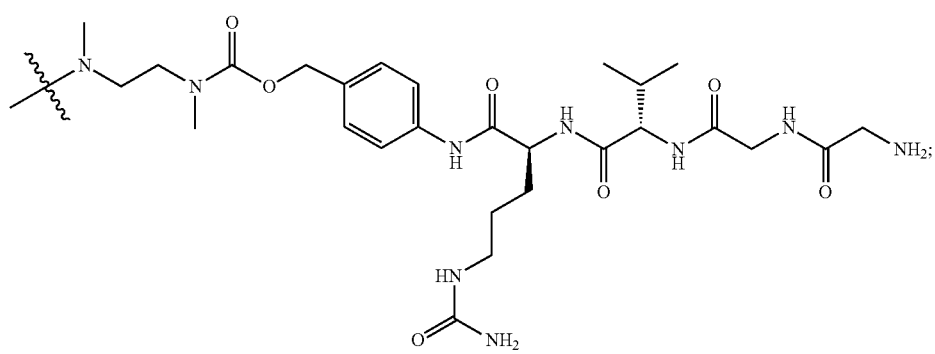
(17)
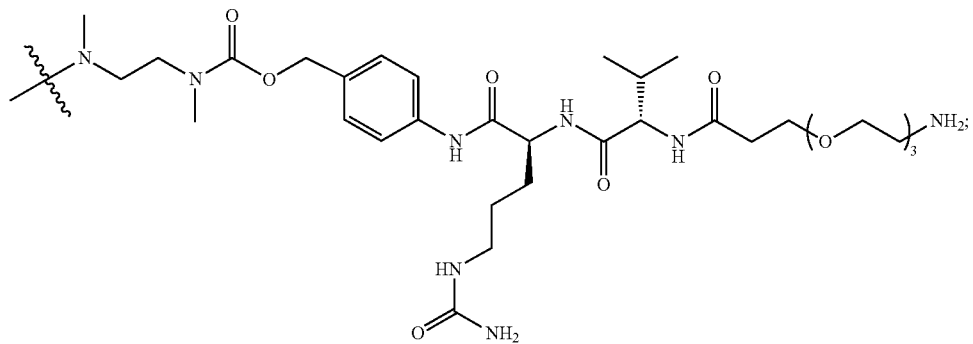
(18)
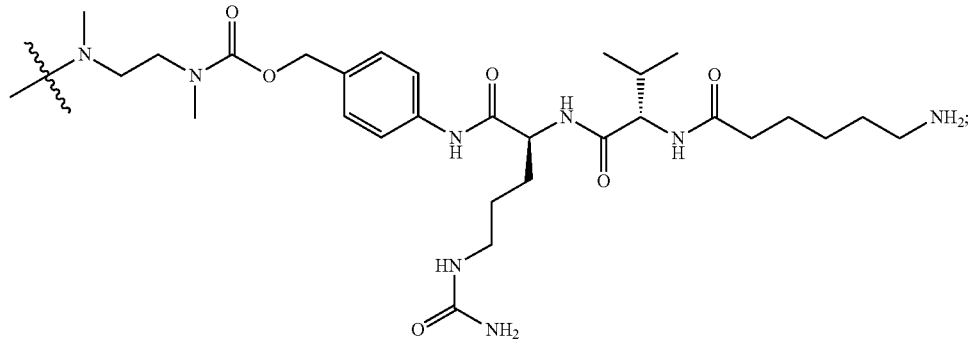
(19)
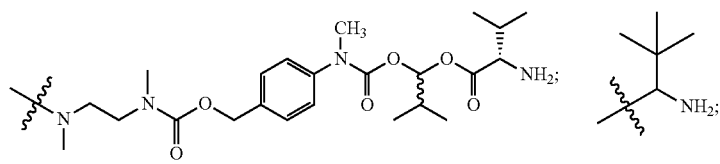
(20)                    (21)

-continued

(22)
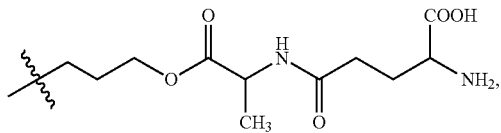
or

(23)
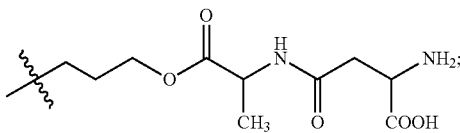

wherein:
 a is an integer from 1 to 6;
 c is an integer from 0 to 3; and
 g is an integer from 2 to 6.

In another embodiment the auristatin is a compound of Formula (X):

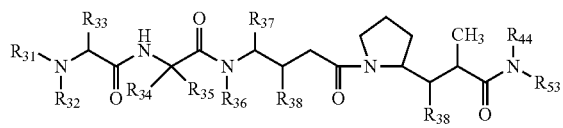

wherein:
 each of $R_{31}$ and $R_{32}$ independently is hydrogen or $C_{1-8}$ alkyl and at most one of $R_{31}$ and $R_{32}$ is hydrogen;
 $R_{33}$ is hydrogen, $C_{1-8}$ alkyl, $C_{3-8}$ carbocycle, $C_{6-10}$ aryl, $C_{1-8}$ alkyl-$C_{6-10}$ aryl, $X^1$—($C_{3-8}$ carbocycle), $C_{3-8}$ heterocycle or $X^1$—($C_{3-8}$ heterocycle);
 $R_{34}$ is hydrogen, $C_{1-8}$ alkyl, $C_{3-8}$ carbocycle, $C_{6-10}$ aryl, $X^1$—$C_{6-10}$ aryl, $X^1$—($C_{3-8}$ carbocycle), $C_{3-8}$ heterocycle or $X^1$—($C_{3-8}$ heterocycle);
 $R_{35}$ is hydrogen or methyl;
 or $R_{34}$ and $R_{35}$, together with the carbon atom to which they attach form a carbocyclic ring having the formula —$(CR_{55}R_{41})_b$— wherein each of $R_{55}$ and $R_{41}$ independently is hydrogen or $C_{1-8}$ alkyl and b is an integer from 3 to 7;
 $R_{36}$ is hydrogen or $C_{1-8}$ alkyl;
 $R_{37}$ is hydrogen, $C_{1-8}$ alkyl, $C_{3-8}$ carbocycle, $C_{6-10}$ aryl, —$X^1$—$C_{6-10}$ aryl, —$X^1$—($C_{3-8}$ carbocycle), $C_{3-8}$ heterocycle or —$X^1$—($C_{3-8}$ heterocycle);
 each $R_{38}$ independently is hydrogen, OH, $C_{1-8}$ alkyl, $C_{3-8}$ carbocycle or O—($C_{1-8}$ alkyl);
 $R_{53}$ is:

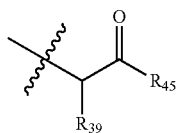

or $R_{54}$;
 $R_{39}$ is H, $C_{1-8}$ alkyl, $C_{6-10}$ aryl, —$X^1$—$C_{6-10}$ aryl, $C_{3-8}$ carbocycle, $C_{3-8}$ heterocycle, —$X^1$—$C_{3-8}$ heterocycle, —$C_{1-8}$ alkylene-$NH_2$, or $(CH_2)_2SCH_3$;
 each $X^1$ independently is $C_{1-10}$ alkylene or $C_{3-10}$ cycloalkylene;
 $R_{44}$ is hydrogen or $C_{1-8}$ alkyl;
 $R_{45}$ is $X^3$—$R_{42}$ or NH—$R_{19}$;
 $X^3$ is O or S;
 $R_{19}$ is hydrogen, OH, amino group, alkyl amino or —[C($R_{20}R_{21}$)]$_a$—$R_{22}$;

$R_{42}$ is an amino group, $C_{1-6}$ alkyl amino or —[C($R_{20}R_{21}$)]$_a$—$R_{22}$;
 each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;
 $R_{22}$ is —OH, —$NHR_{23}$, —COOH, —$R_{82}$—C(O)($CH_2$)$_c$—C(H)($R_{23}$)—N(H)($R_{23}$), —$R_{82}$—C(O)($CH_2$)$_d$—(OCH$_2$—CH$_2$)$_f$—N(H)($R_{23}$) or —$R_{82}$—(C(O)—CH($X^2$)—NH)$_d$—$R_{77}$;
 each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;
 $X^2$ is a side chain of a natural or unnatural amino acid;
 $R_{77}$ is a hydrogen or $X^2$ and $NR_{77}$ form a nitrogen containing cyclic compound;
 $R_{82}$ is —$NR_{23}$ or oxygen;
 $R_{54}$ is —C($R_{56}$)$_2$—C($R_{56}$)$_2$—$C_{6-10}$ aryl, —C($R_{56}$)$_2$—C($R_{56}$)$_2$—$C_{3-8}$ heterocycle or —C($R_{56}$)$_2$—C($R_{56}$)$_2$—$C_{3-8}$ carbocycle;
 $R_{56}$ is independently selected from H, OH, $C_{1-8}$ alkyl, $C_{3-8}$ carbocycle, —O—$C_{1-8}$ alkyl, —O—C(O)—$R_{29}$ and —O—$R_{23}$—O—$C_{1-6}$ alkyl-$NH_2$;
 $R_{29}$ is an amino group, 5 to 12-membered heterocycloalkyl, —$R_{28}$—$C_{1-6}$ alkyl-$R_{22}$, $R_{28}$—$C_{5-12}$ heterocycloalkyl-$C_{1-6}$ alkyl-$R_{22}$, —[C($R_{20}R_{21}$)]$_a$—$R_{22}$, or —$R_{28}$—$C_{1-6}$ alkyl-$C_{6-12}$ aryl-$C_{1-6}$ alkyl-$R_{22}$; or $R_{29}$ is $R_{47}$ as defined herein;
 $R_{28}$ is absent, $NR_{23}$ or oxygen;
 a is an integer from 1 to 6;
 c is an integer from 0 to 3;
 d is an integer from 1 to 3; and
 f is an integer from 1 to 12.

In some embodiments, in the auristatin compound of Formula (X):
 $R_{39}$ is benzyl or

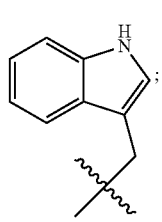 [SMILES: *Cc1c[nH]c2ccccc12]

and
 $R_{44}$ is hydrogen.

In another embodiment the auristatin is a compound of Formula (Xa):

(Xa)

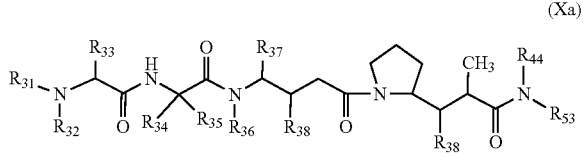

wherein:

R$_{33}$ through R$_{38}$, and R$_{44}$ are as defined herein, one of R$_{31}$ and R$_{32}$ is hydrogen or C$_{1-8}$ alkyl and the other is:

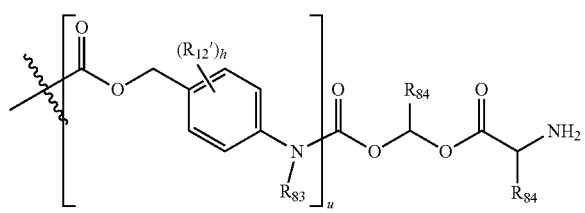

wherein:

R$_{83}$ is hydrogen or CH$_3$;

R$_{84}$ is C$_{1-6}$ alkyl or C$_{6-10}$ aryl;

each R$_{12}'$ independently is halogen, —C$_{1-8}$ alkyl, —O—C$_{1-8}$ alkyl, nitro or cyano;

h is an integer from 0 to 4; and u is an integer 0 or 1;

R$_{53}$ is:

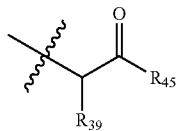

or R$_{54}$

R$_{39}$ is H, C$_{1-8}$ alkyl, C$_{6-10}$ aryl, —X$^1$—C$_{6-10}$ aryl, C$_{3-8}$ carbocycle, C$_{3-8}$ heterocycle, —X$^1$—C$_{3-8}$ heterocycle, —C$_{1-8}$ alkylene-NH$_2$, or (CH$_2$)$_2$SCH$_3$, each X$^1$ independently is C$_{1-10}$ alkylene or C$_{3-10}$ cycloalkylene;

R$_{45}$ is X$^3$—R$_{42}$ or NH—R$_{19}$;

X$^3$ is O or S;

R$_{19}$ is hydrogen, OH, amino group, alkyl amino or —[C(R$_{20}$R$_{21}$)]$_a$—R$_{22}$;

R$_{42}$ is H, an amino group, C$_{1-6}$ alkyl amino or —[C(R$_{20}$R$_{21}$)]$_a$—R$_{22}$;

each of R$_{20}$ and R$_{21}$ independently is hydrogen, C$_{1-6}$ alkyl, C$_{6-10}$ aryl, hydroxylated C$_{6-10}$ aryl, polyhydroxylated C$_{6-10}$ aryl, 5 to 12-membered heterocycle, C$_{3-8}$ cycloalkyl, hydroxylated C$_{3-8}$ cycloalkyl, polyhydroxylated C$_{3-8}$ cycloalkyl or a side chain of a natural or unnatural amino acid;

R$_{22}$ is —OH, —NHR$_{23}$, —COOH, —R$_{82}$—C(O)(CH$_2$)$_c$—C(H)(R$_{23}$)—N(H)(R$_{23}$), —R$_{82}$—C(O)(CH$_2$)$_d$—(O—CH$_2$—CH$_2$)$_f$—N(H)(R$_{23}$) or —R$_{82}$—(C(O)—CH(X$^2$)—NH)$_d$—R$_{77}$;

each R$_{23}$ independently is hydrogen, C$_{1-6}$ alkyl, C$_{6-10}$ aryl, C$_{3-8}$ cycloalkyl, —COOH, or —COO—C$_{1-6}$ alkyl;

X$^2$ is a side chain of a natural or unnatural amino acid;

R$_{77}$ is a hydrogen or X$^2$ and NR$_{77}$ form a nitrogen containing cyclic compound;

R$_{82}$ is —NR$_{23}$ or oxygen;

R$_{54}$ is —C(R$_{56}$)$_2$—C(R$_{56}$)$_2$—C$_{6-10}$ aryl, —C(R$_{56}$)$_2$—C(R$_{56}$)$_2$—C$_{3-8}$ heterocycle or —C(R$_{56}$)$_2$—C(R$_{56}$)$_2$—C$_{3-8}$ carbocycle;

R$_{56}$ is independently selected from H, OH, C$_{1-8}$ alkyl, C$_{3-8}$ carbocycle, —O—C$_{1-8}$ alkyl, —O—C(O)—R$_{29}$ and —O—R$_{23}$—O—C$_{1-6}$ alkyl-NH$_2$;

R$_{29}$ is an amino group, 5 to 12-membered heterocycloalkyl, —R$_{28}$—C$_{1-6}$ alkyl-R$_{22}$, R$_{28}$—C$_{5-12}$ heterocycloalkyl-C$_{1-6}$ alkyl-R$_{22}$, —[C(R$_{20}$R$_{21}$)]$_a$—R$_{22}$, or —R$_{28}$—C$_{1-6}$ alkyl-C$_{6-12}$ aryl-C$_{1-6}$ alkyl-R$_{22}$; or R$_{29}$ is R$_{47}$ as defined herein;

R$_{28}$ is absent, NR$_{23}$ or oxygen;

a is an integer from 1 to 6;

c is an integer from 0 to 3;

d is an integer from 1 to 3; and f is an integer from 1 to 12.

In one embodiment, the auristatin compound of Formula (Xa) is a compound of Formula (XIa) or Formula (XIb):

(XIa)

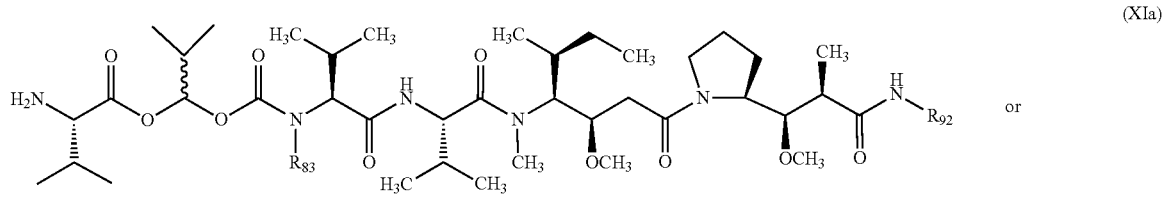

or (XIb)

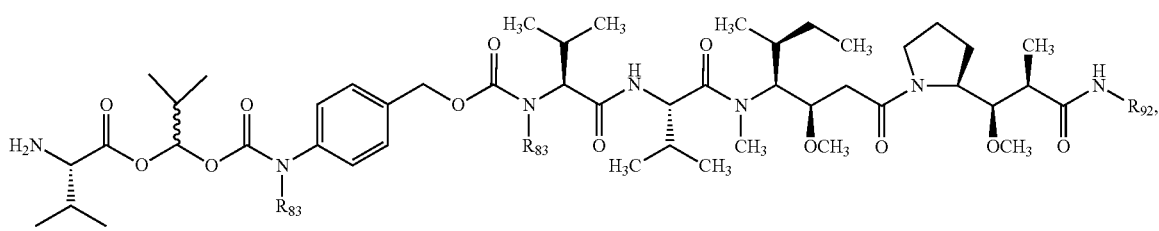

wherein:
R$_{92}$ is:
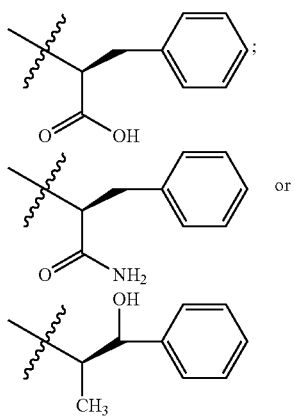
and
R$_{83}$ is hydrogen or CH$_3$.
In one embodiment the auristatin of Formula (X) is a compound of Formula (XI), Formula (XII) or Formula (XIII):
wherein the compound of Formula (XI) is:
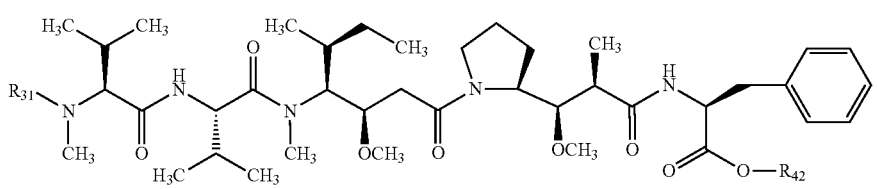
(XI)
wherein R$_{31}$ is H or CH$_3$ and R$_{42}$ is —CH$_3$ or any one of the following structures:
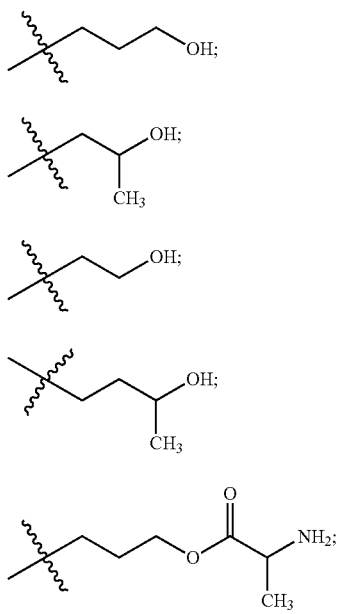
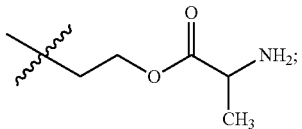
(6)
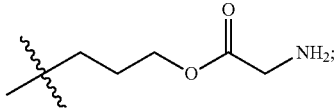
(7)
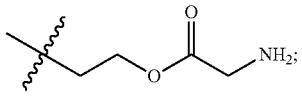
(8)
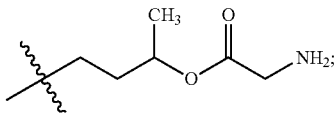
(9)
-continued
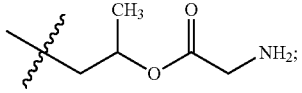
(10)
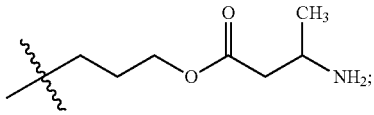
(11)
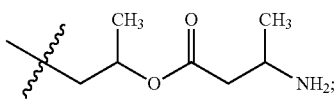
(12)
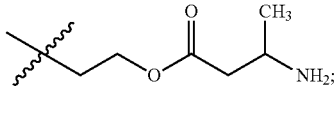
(13)
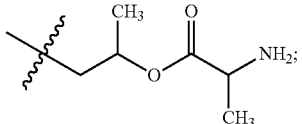
(14)

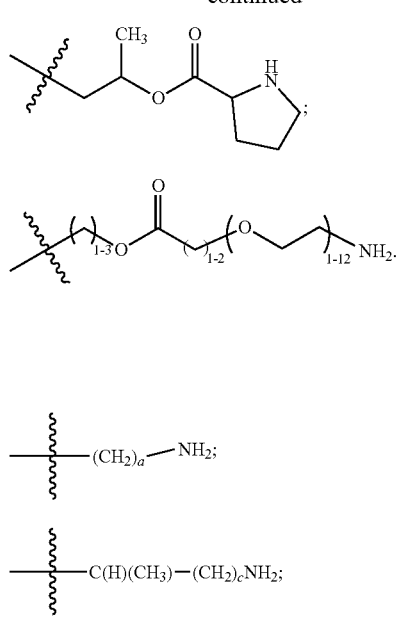
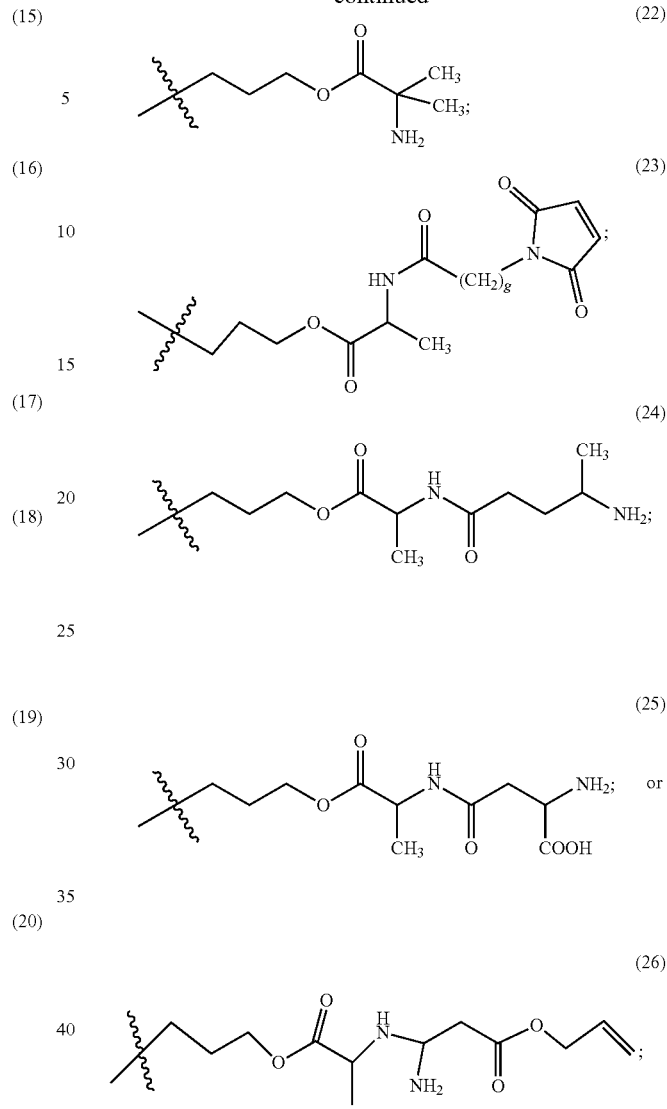
wherein:
a is an integer from 1 to 6;
c is an integer from 0 to 3; and
g is an integer from 2 to 6;
wherein the compound of Formula (XII) is:
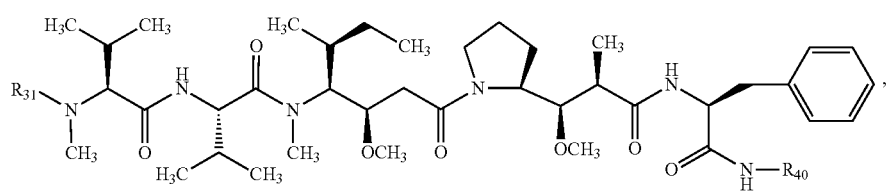
(XII)

wherein $R_{31}$ is H or $CH_3$ and $R_{40}$ is hydrogen, —OH, —$NH_2$, or any of the following structures:
(1)
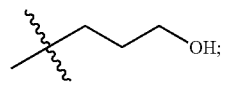
(2)
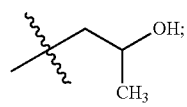
(3)
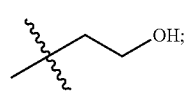
(4)
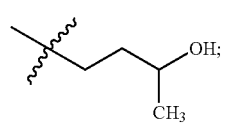
(5)
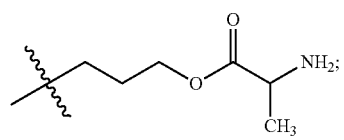
(6)
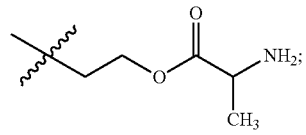
(7)
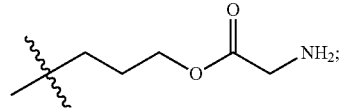
(8)
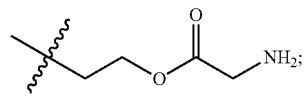
(9)
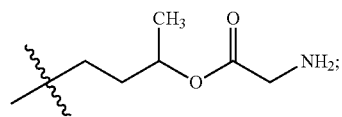
(10)
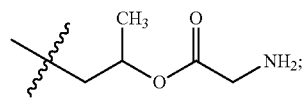
(11)
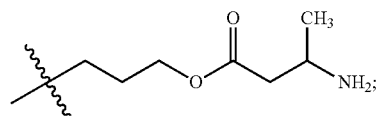
(12)
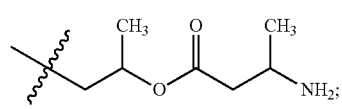
-continued
(13)
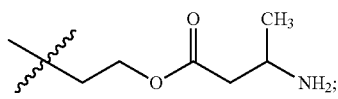
(14)
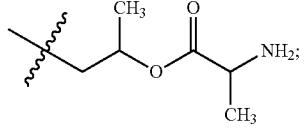
(15)
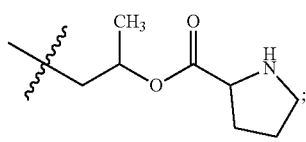
(16)
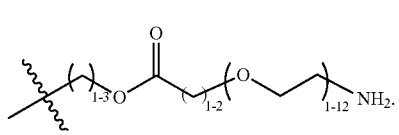
(17)
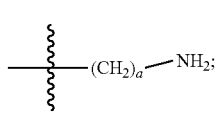
(18)
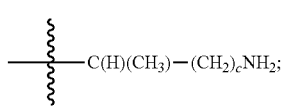
(19)
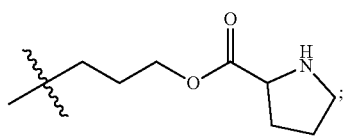
(20)
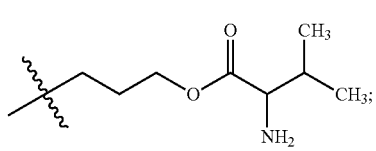
(21)
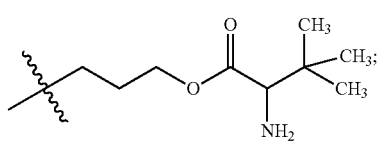
(22)
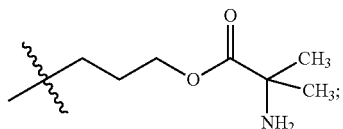
(23)
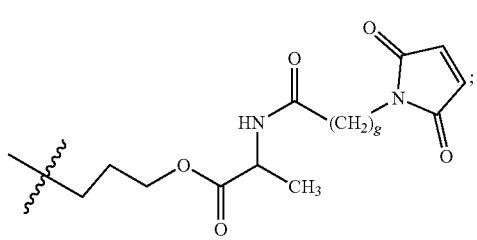

-continued

(24)
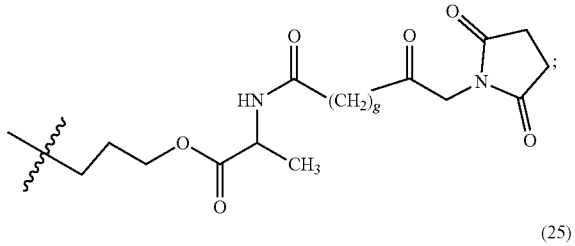

(25)
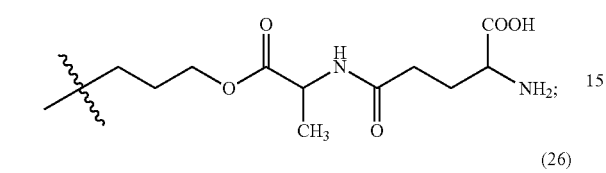

(26)
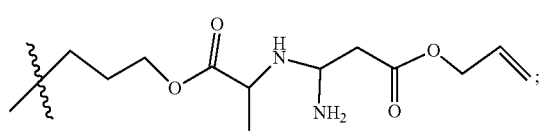

(27)
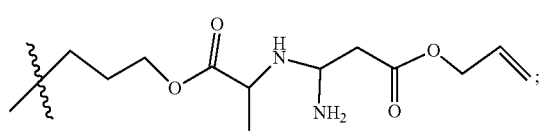

wherein:
a is an integer from 1 to 6;
g is an integer from 2 to 6; and
c is an integer from 0 to 3;
wherein the compound of Formula (XIII) is:

(XIII)
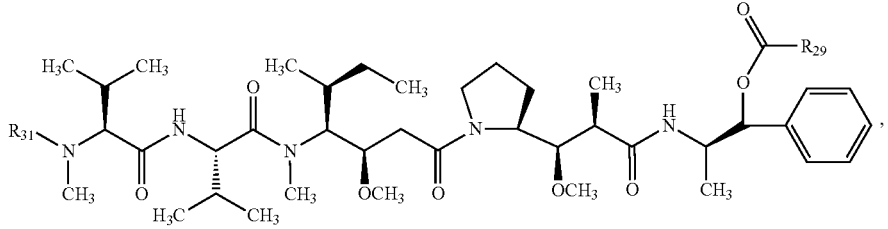

wherein:
$R_{31}$ is H or $CH_3$;
$R_{29}$ is an amino group, 5 to 12-membered heterocycloalkyl, $-R_{28}-C_{1-6}$ alkyl-$R_{22}$, $R_{28}-C_{5-12}$ heterocycloalkyl-$C_{1-6}$ alkyl-$R_{22}$, $-R_{28}-[C(R_{20}R_{21})]_a-R_{22}$, or $-R_{28}-C_{1-6}$ alkyl-$C_{6-12}$ aryl-$C_{1-6}$ alkyl-$R_{22}$; or $R_{29}$ is $R_{47}$ as defined herein;
each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;
$R_{22}$ is $-OH$, $-NHR_{23}$, $-COOH$, $-R_{82}-C(O)(CH_2)_c-C(H)(R_{23})-N(H)(R_{23})$, $-R_{82}-C(O)(CH_2)_d-(OCH_2-CH_2)_f-N(H)(R_{23})$ or $-R_{82}-(C(O)-CH(X^2)-NH)_d-R_{77}$;

each $R_{23}$ independently is hydrogen, $C_{1-6}$ alkyl, $C_{6-10}$ aryl, $C_{3-8}$ cycloalkyl, $-COOH$, or $-COO-C_{1-6}$ alkyl;
$X^2$ is a side chain of a natural or unnatural amino acid;
$R_{77}$ is a hydrogen or $X^2$ and $NR_{77}$ form a nitrogen containing cyclic compound;
$R_{82}$ is $-NR_{23}$ or oxygen;
$R_{28}$ is absent, $NR_{23}$ or oxygen;
a is an integer from 1 to 6;
c is an integer from 0 to 3;
d is an integer from 1 to 3; and
f is an integer from 1 to 12.

In one embodiment, in Formula (XII), $R_{40}$ is

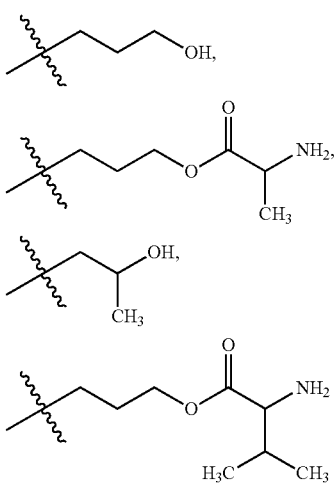

-continued

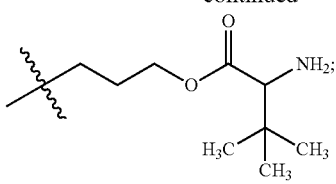

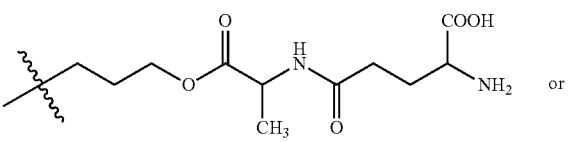 or

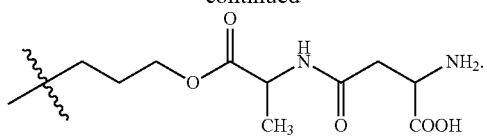
5
10
In another embodiment, the compound of Formula (XII) is a compound of Formula (XIIa), (XIIb), (XIIc), (XIId), (XIIe), (XIIf), (XIIg) or (XIIh):
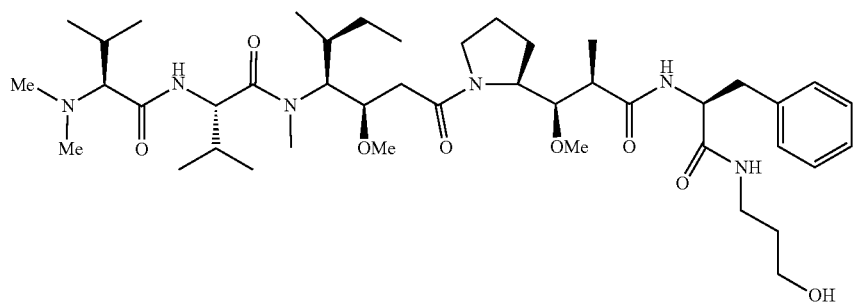
(XIIa)
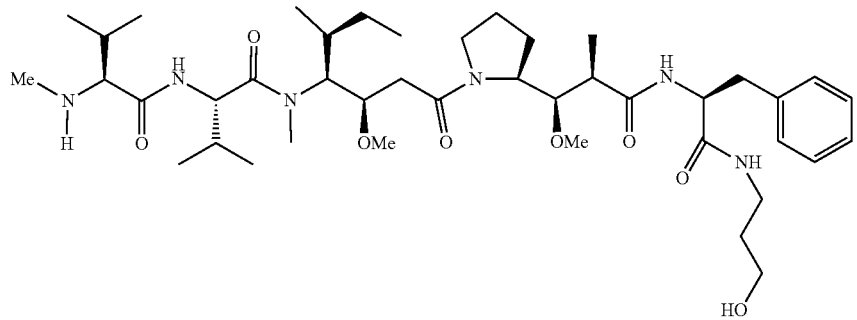
(XIIb)
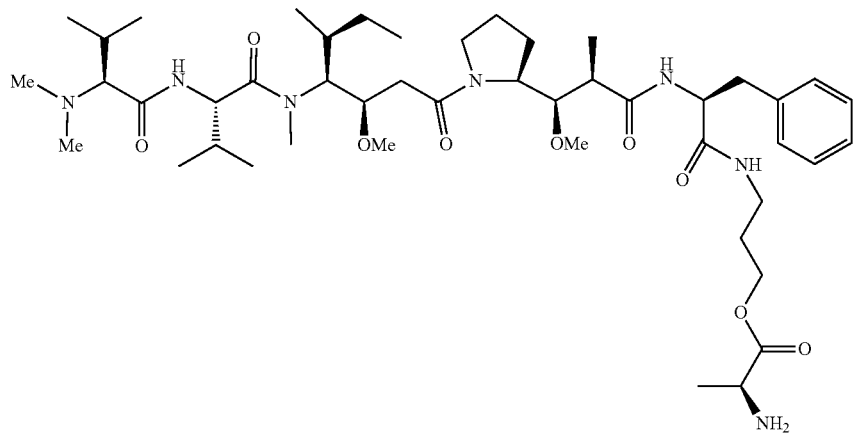
(XIIc)

-continued
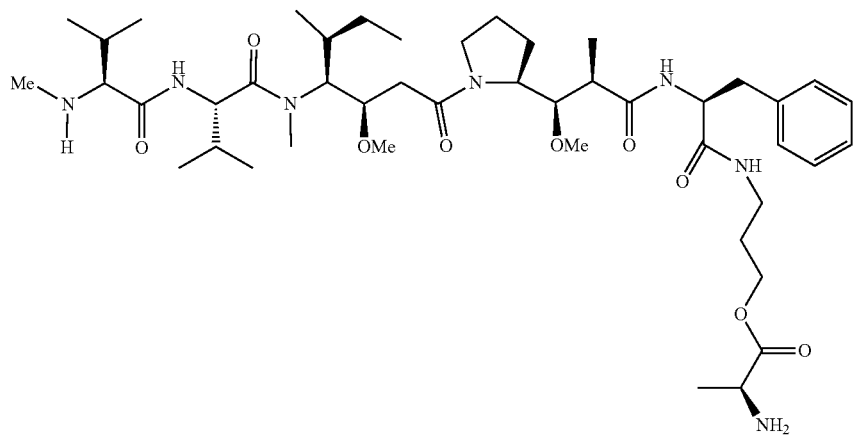
(XIId)
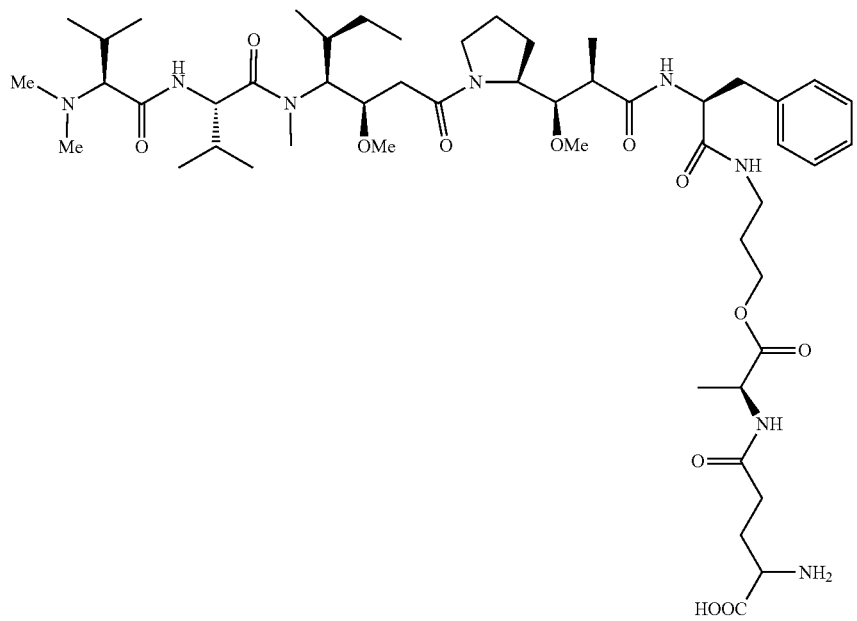
(XIIe)
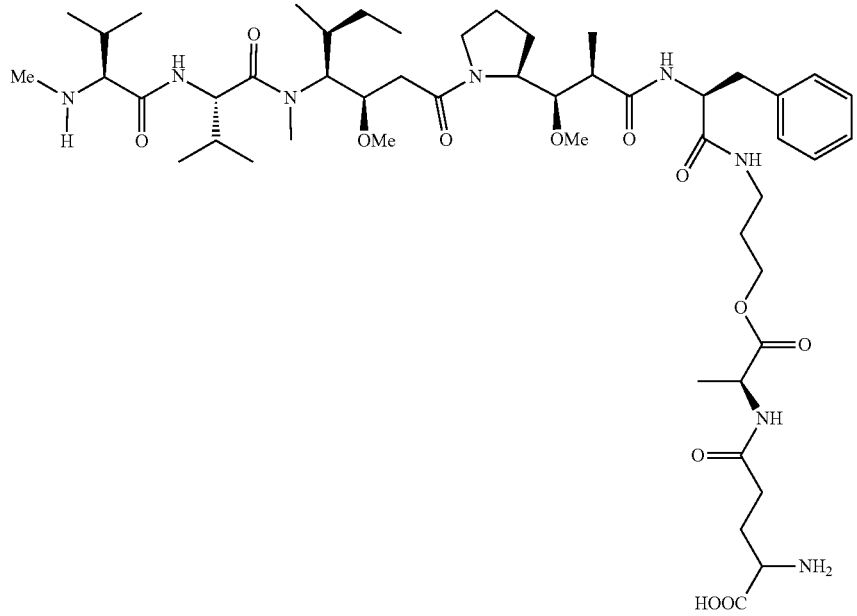
(XIIf)

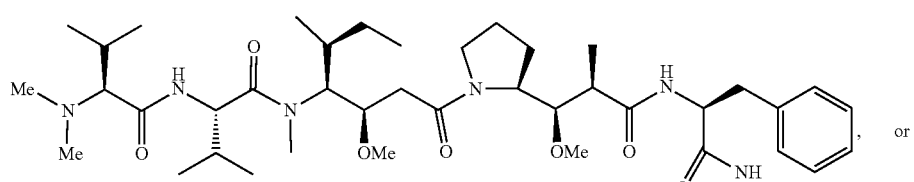 (XIIg)

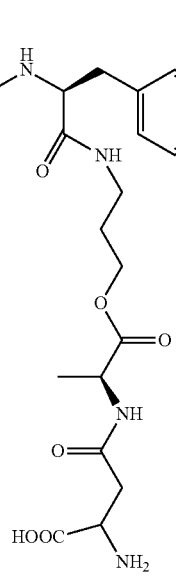

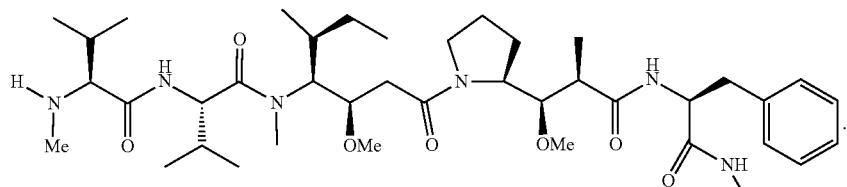 (XIIh)

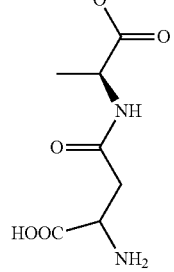

In one embodiment in the compound of Formula (XIII), $R_{29}$ is —$NH_2$, 5 membered heterocycloalkyl, —$R_{28}$—$C_{1-6}$ alkyl-$R_{22}$, $R_{28}$—$C_{5-12}$ heterocycloalkyl-$C_{1-6}$ alkyl-$R_{22}$ or —$R_{28}$—$C_{1-6}$ alkyl-$C_{6-12}$ aryl-$C_{1-6}$ alkyl-$R_{22}$; or $R_{29}$ is $R_{47}$ as defined herein;

$R_{28}$ is absent, $NR_{23}$ or oxygen;

$R_{22}$ is —OH, —$NHR_{23}$, —COOH, —$R_{82}$—C(O)($CH_2$)$_c$—C(H)($R_{23}$)—N(H)($R_{23}$), —$R_{82}$—C(O)($CH_2$)$_d$—(OCH$_2$—CH$_2$)$_f$—N(H)($R_{23}$) or —$R_{82}$—(C(O)—CH($X^2$)—NH)$_d$—$R_{77}$;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

$X^2$ is a side chain of a natural or unnatural amino acid;

$R_{77}$ is a hydrogen or $X^2$ and $NR_{77}$ form a nitrogen containing cyclic compound;

$R_{82}$ is —$NR_{23}$ or oxygen;

c is an integer from 0 to 3;

d is an integer from 1 to 3; and f is an integer from 1 to 12.

In yet another embodiment, $R_{29}$ is any one of the following structures:

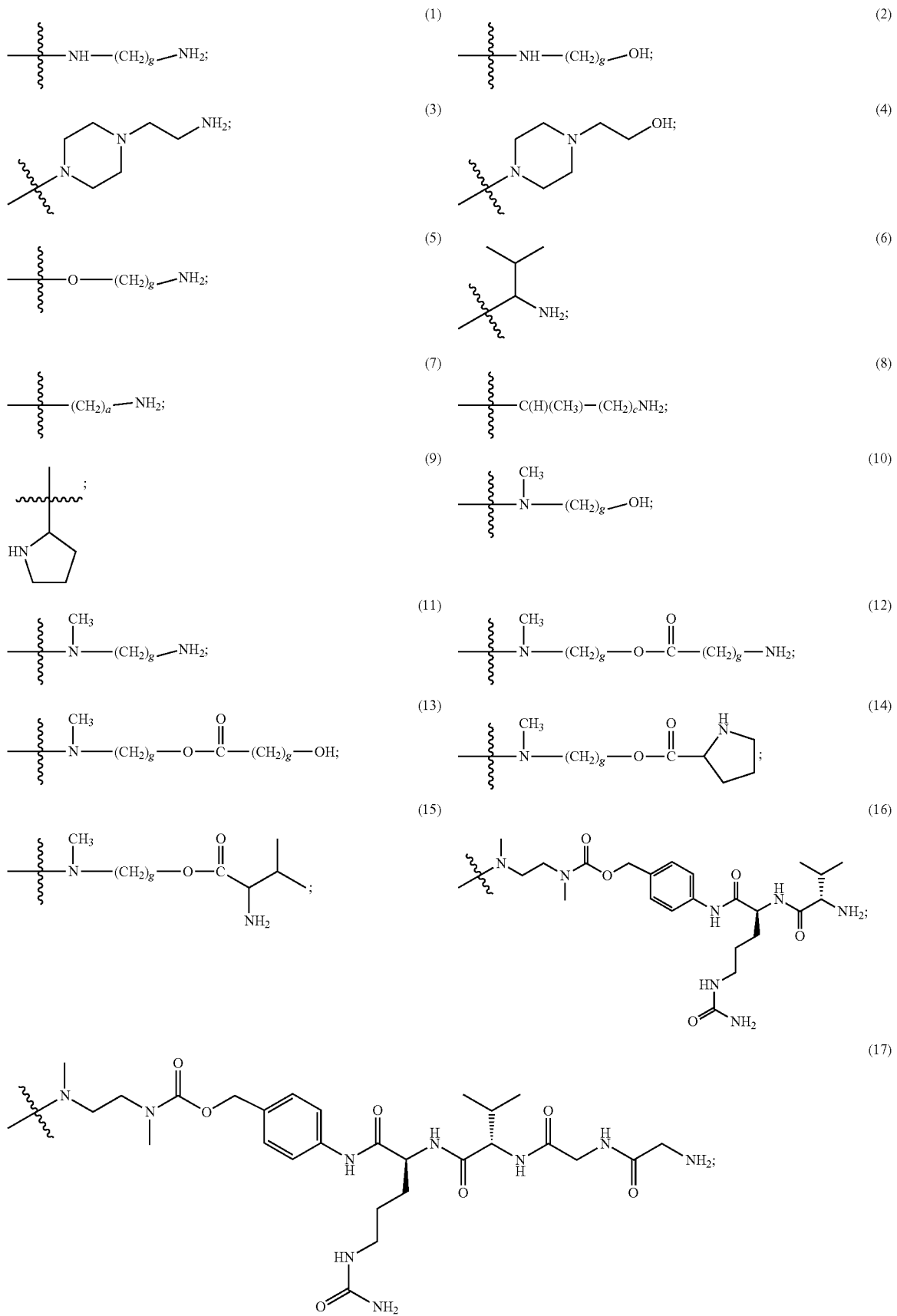

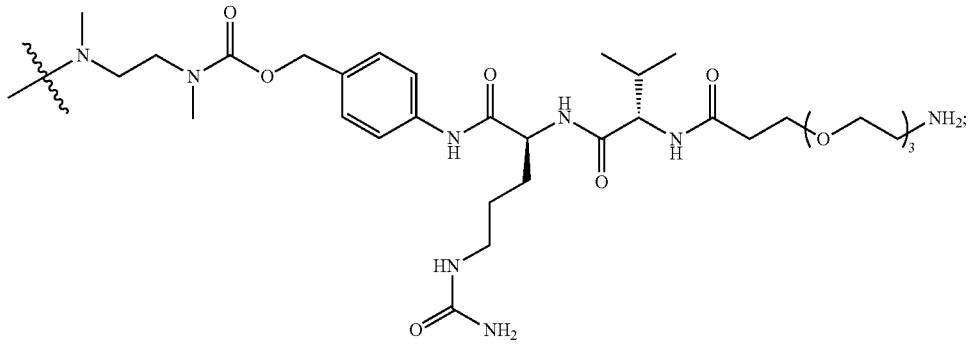

(18)

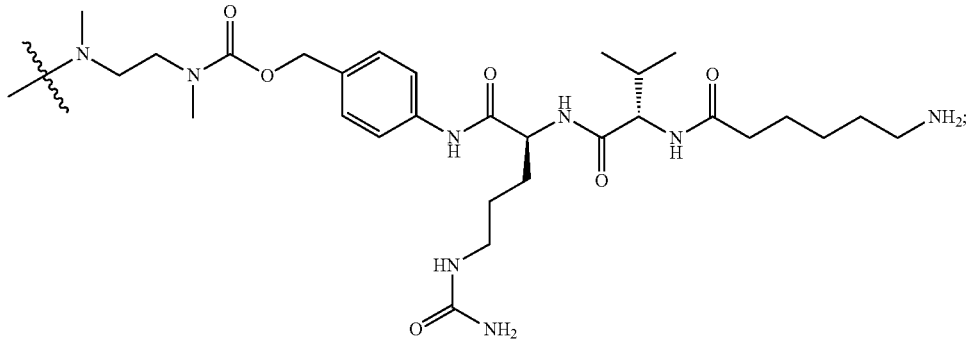

(19)

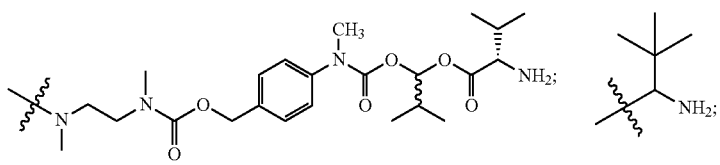

(20)

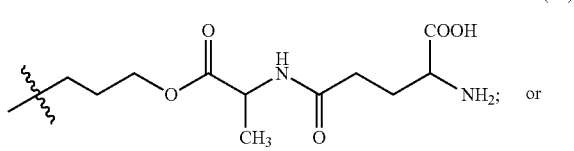

(21)

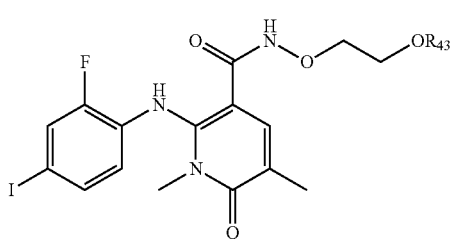

(22)

(23)

wherein:
a is an integer from 1 to 6;
c is an integer from 0 to 3; and
g is an integer from 2 to 6.

In one embodiment, the MEK inhibitor is a compound of Formula (XIV):

(XIV)

wherein:
$R_{43}$ is H or —$R_{46}$—$R_{47}$;
each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;
$R_{22}$ is —OH, —$NH_2$, —COOH, —$R_{82}$—$C(O)(CH_2)_c$—$C(H)(R_{23})$—$N(H)(R_{23})$, —$R_{82}$—$C(O)(CH_2)_d$—$(OCH_2$—$CH_2)_f$—$N(H)(R_{23})$ or —$R_{82}$—$(C(O)$—$CH(X^2)$—$NH)_d$—$R_{77}$;
each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;
$X^2$ is a side chain of a natural or unnatural amino acid;
$R_{77}$ is a hydrogen or $X^2$ and $NR_{77}$ form a nitrogen containing cyclic compound;
$R_{82}$ is —$NR_{23}$ or oxygen;
$R_{46}$ is —C(O)—; —C(O)—O—, —C(O)—NH—, or absent;
$R_{47}$ is as defined herein;
a is an integer from 1 to 6;
c is an integer from 0 to 3;
d is an integer from 1 to 3; and
f is an integer from 1 to 12.

Further examples of the MEK inhibitor are disclosed in U.S. Pat. No. 7,517,994 B2.

In some embodiments, $R_{43}$ is —C(O)—(CH$_2$)$_a$—NH$_2$, or —C(O)—C(H)(CH$_3$)—(CH$_2$)$_c$—NH$_2$; in which a is an integer from 1 to 6; and c is an integer from 0 to 3.

In another embodiment, the duocarmycin compound is a compound of Formula (XV):

(XV)

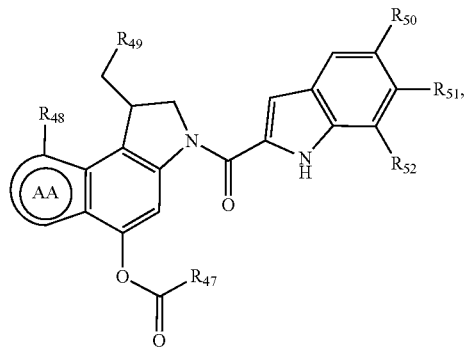

wherein:
$R_{47}$ is as defined herein;
$R_{48}$ is hydrogen, —COOC$_{1-6}$ alkyl, —COOH, —NH$_2$ or —CH$_3$;
$R_{49}$ is Cl, Br or —OH;

$R_{50}$ is hydrogen, —OCH$_3$,

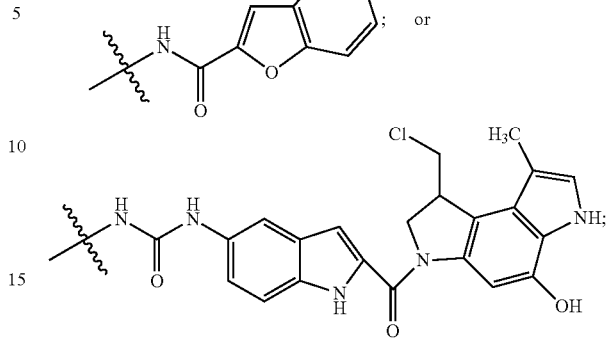

each of $R_{51}$ and $R_{52}$ independently is hydrogen or —OCH$_3$; and
ring AA is either a phenyl or pyrrolyl ring.

Further examples of duocarmycin compounds are disclosed in U.S. Pat. No. 7,553,816.

In one embodiment the duocarmycin compound of Formula (XV) is a compound of Formula (XVI), (XVII), (XVIII) or (XIX):

(XVI)

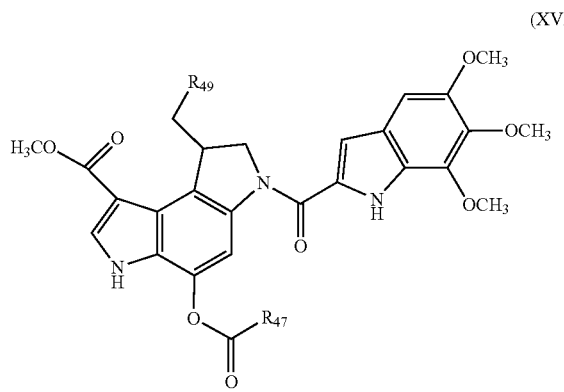

(XVII)

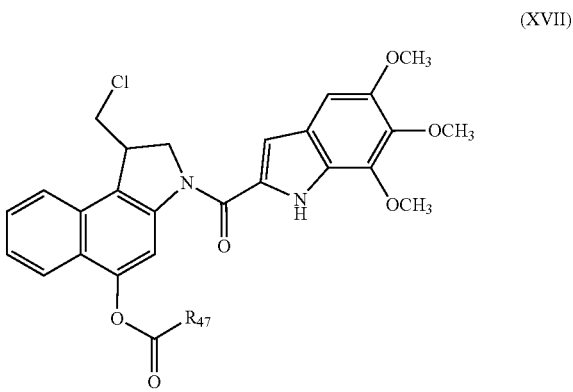

(XVIII)

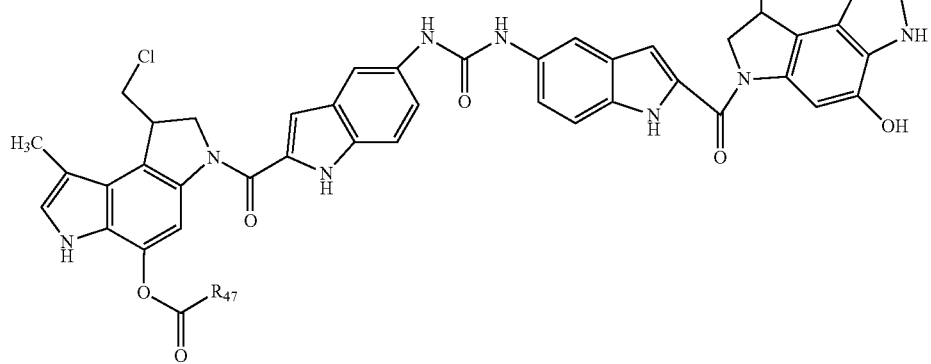

(XIX)

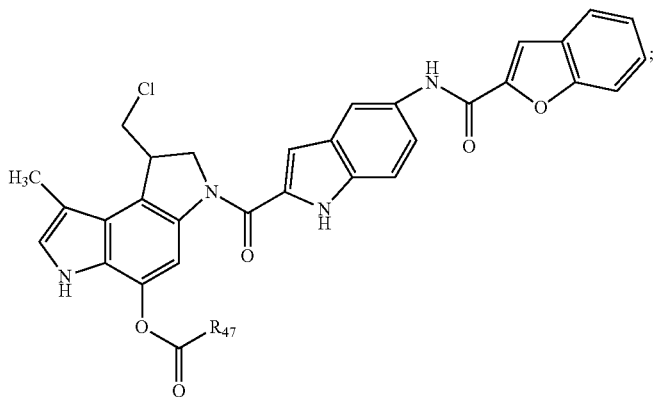

wherein:
R$_{49}$ is Cl, Br or —OH; and
R$_{47}$ is as defined herein.

In another embodiment, the duocarmycin compound is a duocarmycin SA compound of Formula (XX) or (XXI):

(XX)

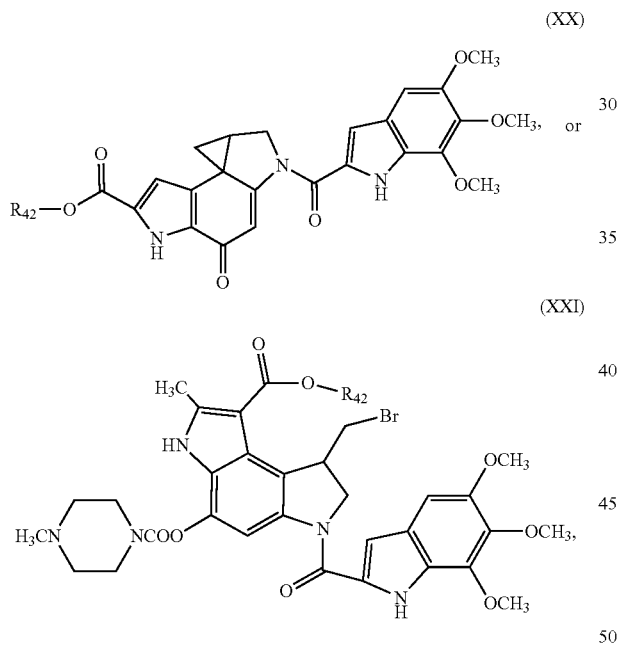

(XXI)

wherein:
R$_{42}$ is C$_{1-6}$ alkyl amino or —[C(R$_{20}$R$_{21}$)]$_a$—R$_{22}$;
each of R$_{20}$ and R$_{21}$ independently is hydrogen, C$_{1-6}$ alkyl, C$_{6-10}$ aryl, hydroxylated C$_{6-10}$ aryl, polyhydroxylated C$_{6-10}$ aryl, 5 to 12-membered heterocycle, C$_{3-8}$ cycloalkyl, hydroxylated C$_{3-8}$ cycloalkyl, polyhydroxylated C$_{3-8}$ cycloalkyl or a side chain of a natural or unnatural amino acid;
R$_{22}$ is —OH, —NH$_2$, —COOH, —R$_{82}$—C(O)(CH$_2$)$_c$—C(H)(R$_{23}$)—N(H)(R$_{23}$), —R$_{82}$—C(O)(CH$_2$)$_d$—(OCH$_2$—CH$_2$)$_f$—N(H)(R$_{23}$), or —R$_{82}$—(C(O)—CH(X$^2$)—NH)$_d$—R$_{77}$;
each R$_{23}$ independently is hydrogen, C$_{1-6}$ alkyl, C$_{6-10}$ aryl, C$_{3-8}$ cycloalkyl, —COOH, or —COO—C$_{1-6}$ alkyl;
X$^2$ is a side chain of a natural or unnatural amino acid;
R$_{77}$ is a hydrogen or X$^2$ and NR$_{77}$ form a nitrogen containing cyclic compound;
R$_{82}$ is —NR$_{23}$ or oxygen;
a is an integer from 1 to 6;
c is an integer from 0 to 3;
d is an integer from 1 to 3; and
f is an integer from 1 to 12.

In some embodiments, R$_{42}$ is any one of the following structures:

(1)
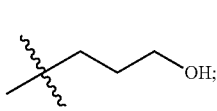

(2)
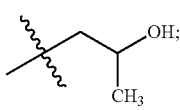

(3)
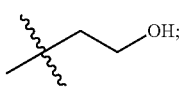

(4)
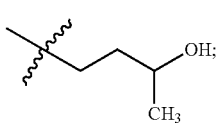

(5)
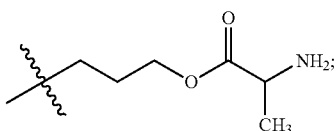

(6)
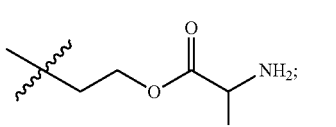

(7)
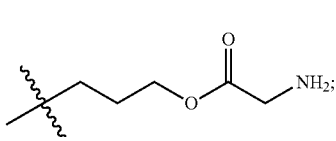

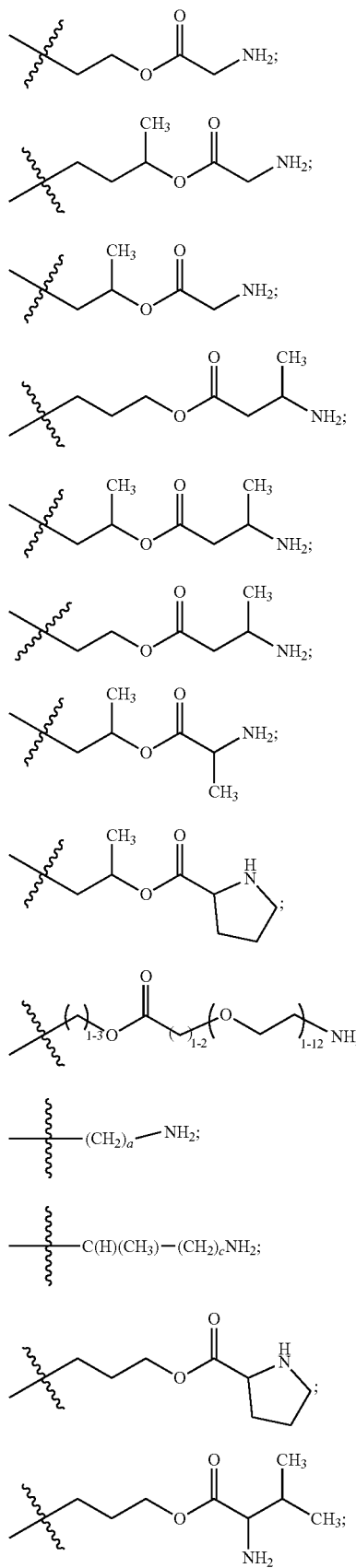
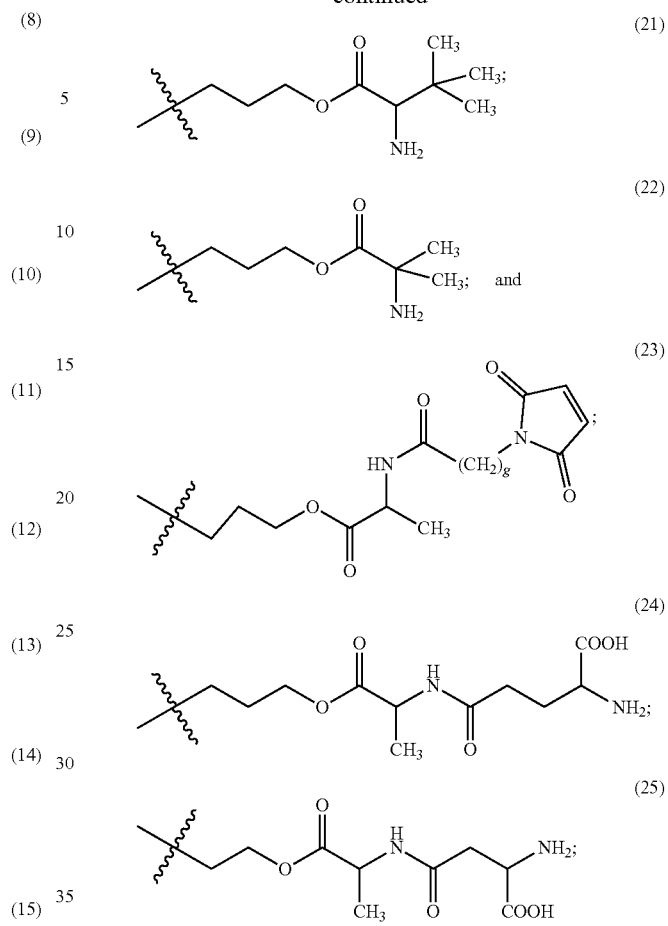
wherein:
a is an integer from 1 to 6;
g is an integer from 2 to 6; and
c is an integer from 0 to 3.
In another embodiment, the KSP inhibitor compound is a compound of Formula (XXVI):
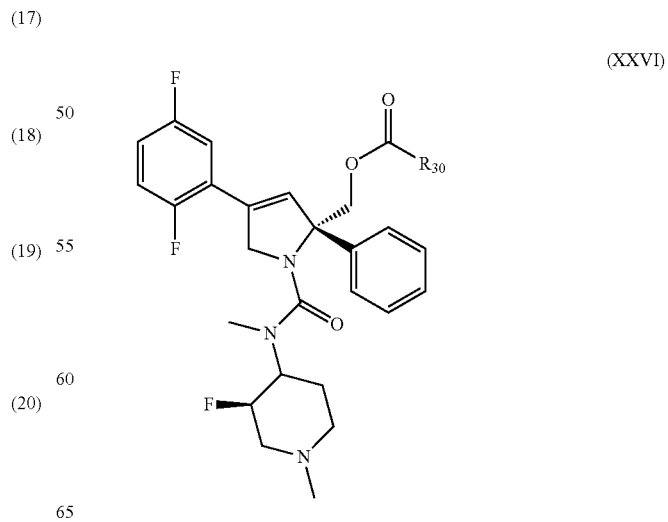
wherein $R_{30}$ is as defined herein.

In some embodiments, $R_{30}$ is:

(1) 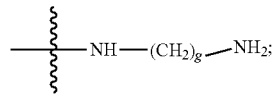

(2) 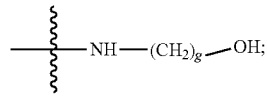

(3) 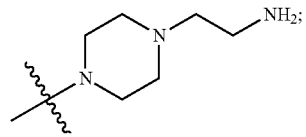

(4) 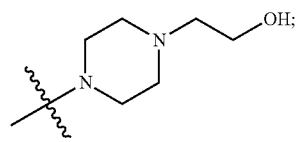

(5) 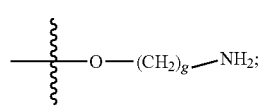

(6) 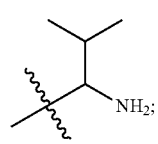

(7) 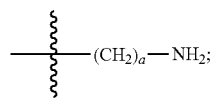

(8) 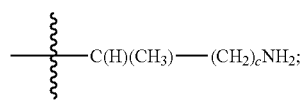

(9) 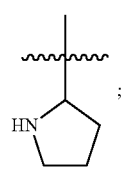

(10) 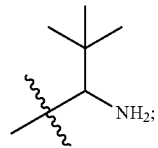

(11) 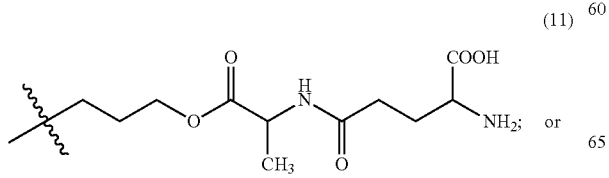 or

(12) 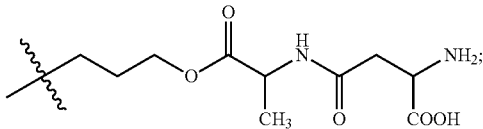

wherein:

a is an integer from 1 to 6;

c is an integer from 0 to 3; and g is an integer from 2 to 6.

In another embodiment, the duocarmycin compound is Duocarmycin A, Duocarmycin B1, Duocarmycin B2, Duocarmycin C1, Duocarmycin C2, Duocarmycin D, CC-1065, Adozelesin, Bizelesin or Carzelesin. Additional duocarmycin compounds suitable for the conjugates, scaffolds and methods of the disclosure are described in U.S. Pat. No. 5,101,038.

In another embodiment the KSP inhibitor compound is a compound of Formula (XXVII), (XXVIII) or (XXIX):

(XXVII)

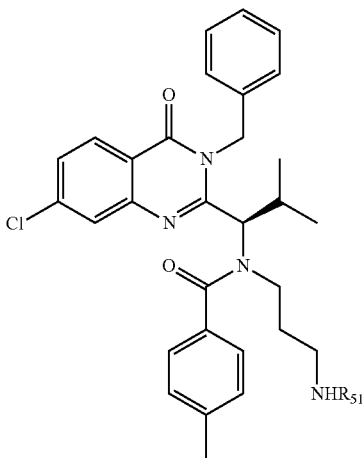

(XXVIII)

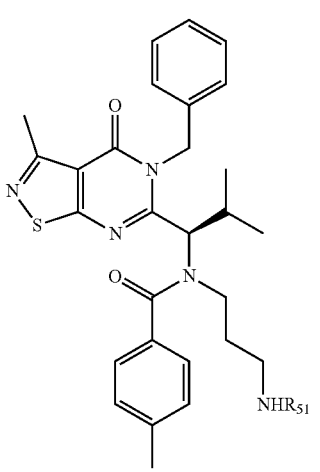

-continued (XXIX)

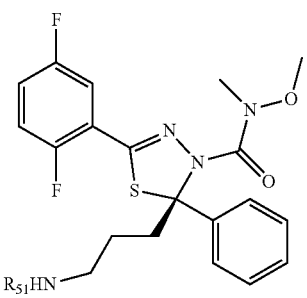

wherein:
R$_{51}$ is a bond, —C(O)—(CH$_2$)—C(O)NH—(CH$_2$)$_2$—NH—, —C(O)—(CH$_2$O—CH$_2$)—C(O)NH—(CH$_2$)$_2$—NH—, or R$_{11}$ is as defined herein.

One skilled in the art of therapeutic agents will readily understand that each of the therapeutic agents described herein can be modified in such a manner that the resulting compound still retains the specificity and/or activity of the original compound. The skilled artisan will also understand that many of these compounds can be used in place of the therapeutic agents described herein. Thus, the therapeutic agents disclosed herein include analogs and derivatives of the compounds described herein.

Table A below provides more examples of the therapeutic agents and derivatives thereof suitable for conjugation to form the antibody-drug conjugates or drug-carrying scaffolds of the disclosure. Spectral data of certain compounds are also provided (ND in the table means "not determined"). These examples may also be the active form of the drug when it is released from the conjugates in vitro or in vivo.

TABLE A (VI1)

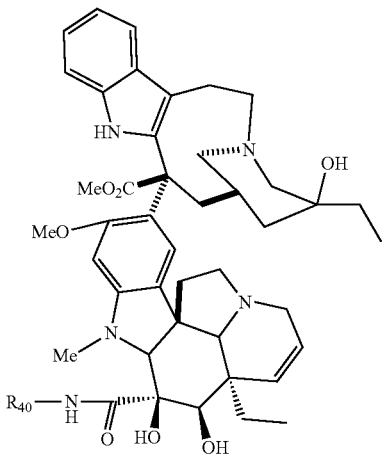

R$_{40}$

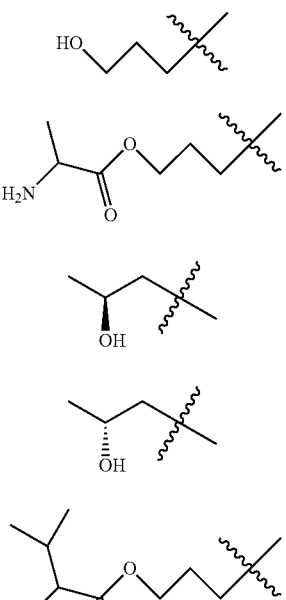

TABLE A-continued
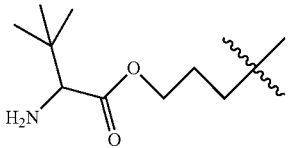 [SMILES: *CCCOC(=O)C(N)C(C)(C)C]
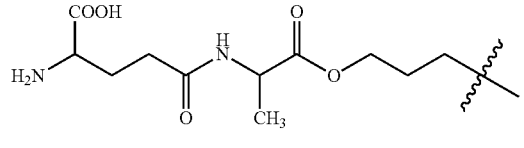 [SMILES: *CCCOC(=O)C(C)NC(=O)CCC(N)C(=O)O]
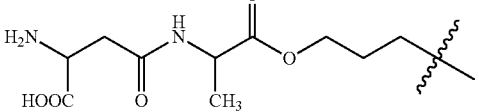
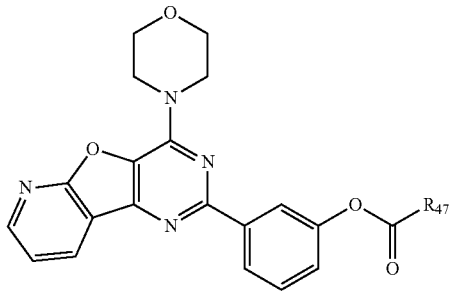 (IX1)
| $R_{47}$ | m/z |
|---|---|
| 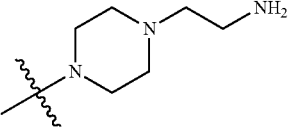 [SMILES: *N1CCN(CCN)CC1] | ND |
| 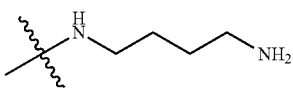 [SMILES: *NCCCCN] | ND |
| 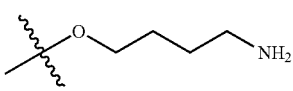 [SMILES: *OCCCCN] | ND |
| 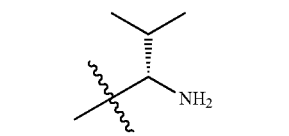 [SMILES: *[C@@H](N)C(C)C] | ND |
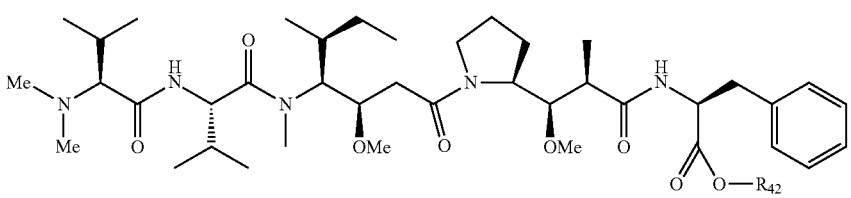 (XI)
| $R_{42}$ | m/z |
|---|---|
| —CH$_3$ (H) | 760 |

TABLE A-continued
| $R_{40}$ | m/z |
|---|---|
| 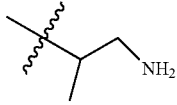 [SMILES: *C(C)CN] | 802.6 |
|  | 790 |
| 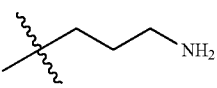 [SMILES: *CCCN] | 804 |
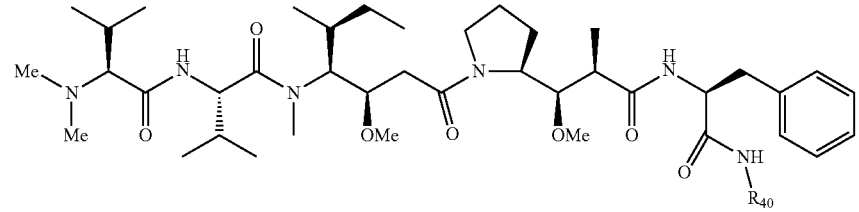
(XII)
| $R_{40}$ | m/z |
|---|---|
| —H | 803.5 |
| 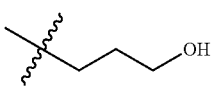 [SMILES: *CCCO] | 789.1 |
| 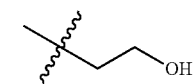 [SMILES: *CCO] | 974.2 |
| 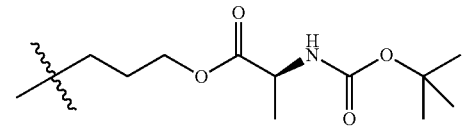 [SMILES: *CCCOC(=O)[C@H](C)NC(=O)OC(C)(C)C] | 874.5 |
| 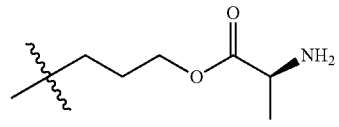 [SMILES: *CCCOC(=O)[C@H](C)N] | 902.2 |
| 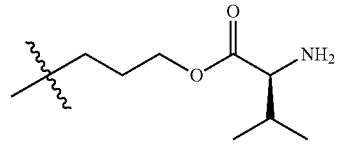 [SMILES: *CCCOC(=O)[C@@H](N)C(C)C] | ND |
| 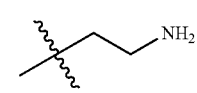 | ND |
| —OH | 788 |
| 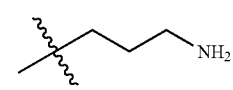 [SMILES: *CCCN] | 803.4 |

TABLE A-continued

| Structure | Value |
|---|---|
| (structure with CH₃ and OH) | 803.4 |
| (structure with CH₃ and isobutyrate ester) | 874.4 |
| (structure with CH₃ and isobutyrate ester) | 874.4 |
| (structure with CH₃ and alanine ester, NH₂) | 874.4 |
| (structure with CH₃ and alanine ester, NH₂) | 874.4 |
| (structure with CH₃ and proline ester) | 900.2 |
| (structure with CH₃ and proline ester) | 900.2 |
| (structure with proline ester on butyl chain) | 900.5 |
| (structure with valine ester on butyl chain) | 900.5 |
| (structure with tert-leucine ester on butyl chain) | 1016.6 |

TABLE A-continued

| Structure | Value |
|---|---|
| (structure with ester, alanine, glutamine: COOH, NH₂) | 989.5 |
| (structure with ester, alanine, aspartic acid: NH₂, COOH) | 975.5 |
| Structure (XIII): H₃C-N(CH₃)-Val-Val-N(CH₃)-CH(OCH₃)-CH₂-C(O)-Pro-CH(CH₃)-CH(OCH₃)-C(O)-NH-CH(CH₃)-CH(OC(O)R₂₉)-phenyl | (XIII) |
| —C(O)—R₂₉ | m/z |
| (Boc-protected alanine ester) | 903.2 |
| (alanine with NH₂) | 803.1 |
| (glycine amide with NH₂) | 790 |
| (ester-propylamine) | 832.6 |
| (proline amide) | 829.1 |
| (leucine with NH₂) | 802 |
| Structure (XIV): 2-fluoro-4-iodo-phenylamino pyridinone with N-methyl, methyl, and C(O)NH-O-CH₂CH₂-OR₄₃ | (XIV) |

TABLE A-continued

| $R_{43}$ | m/z |
|---|---|
| (structure: amino acid-like group with NH₂) | ND |
| (structure: glutaric acid amide derivative) | 644.9 |

(XVII) (structure shown with chloromethyl indoline linked via carbonyl to trimethoxy indole, with OC(O)R₄₇ substituent)

| $R_{47}$ | m/z |
|---|---|
| (ethylenediamine -NH-CH₂CH₂-NH₂) | 553.1 |
| (propylamine chain -NH₂) | 538.1 |
| (pyrrolidine) | 654.1 |
| (valine-like, H₂N with isopropyl) | 566.1 |
| (N-methyl-N-(2-hydroxyethyl)amino) | 568.1 |
| (N-methyl-N-(2-(β-alanyloxy)ethyl)amino) | ND |

TABLE A-continued
| Structure | Value |
|---|---|
| 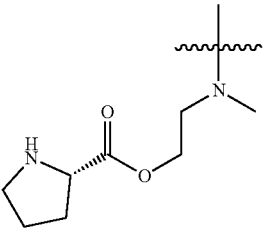 [SMILES: *N(C)CCOC(=O)[C@@H]1CCCN1] | ND |
| 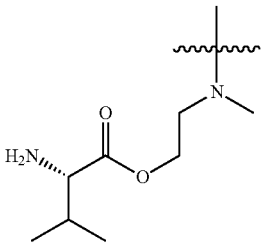 [SMILES: *N(C)CCOC(=O)[C@@H](N)C(C)C] | 667.2 |
| 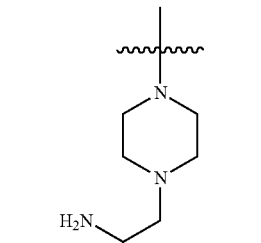 | 622.2 |
| 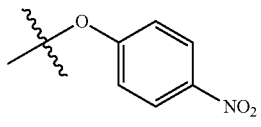 [SMILES: *Oc1ccc([N+](=O)[O-])cc1] | 632.02 |
| 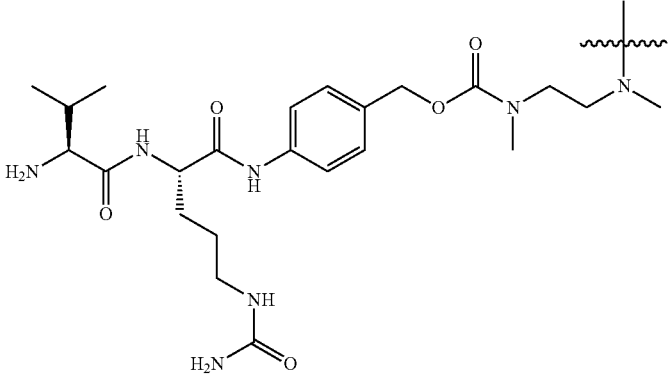 [SMILES: *N(C)CCN(C)C(=O)OCc1ccc(NC(=O)[C@H](CCCNC(N)=O)NC(=O)[C@@H](N)C(C)C)cc1] | 986.2 |
| 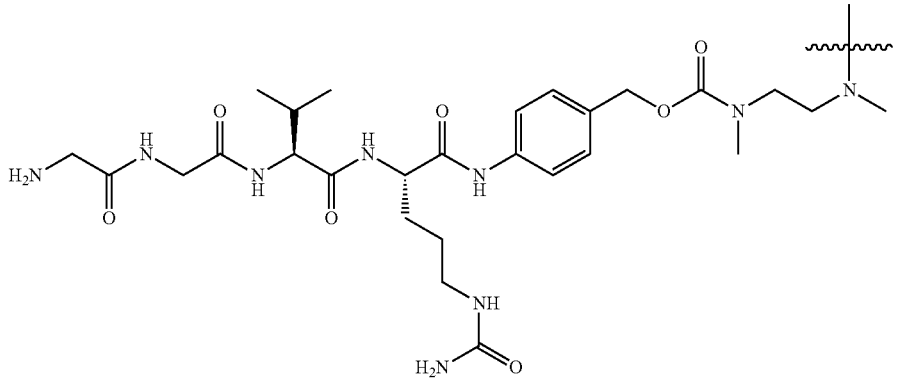 [SMILES: *N(C)CCN(C)C(=O)OCc1ccc(NC(=O)[C@H](CCCNC(N)=O)NC(=O)[C@@H](NC(=O)CNC(=O)CN)C(C)C)cc1] | ND |

TABLE A-continued
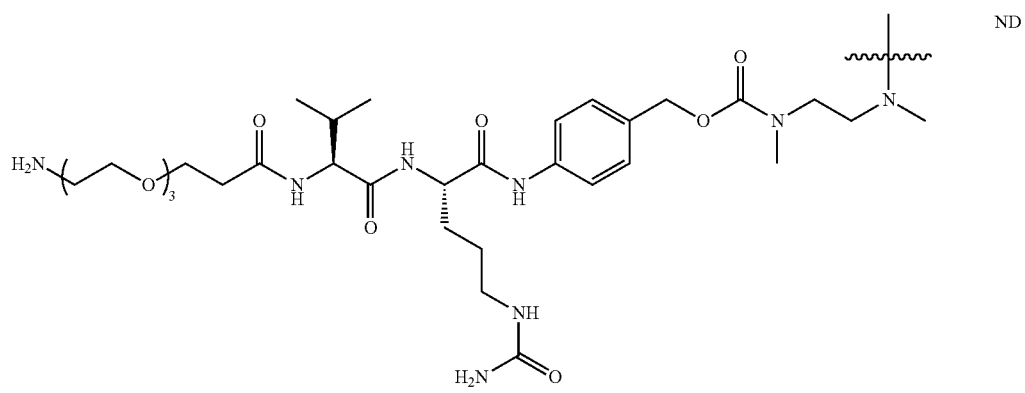
ND
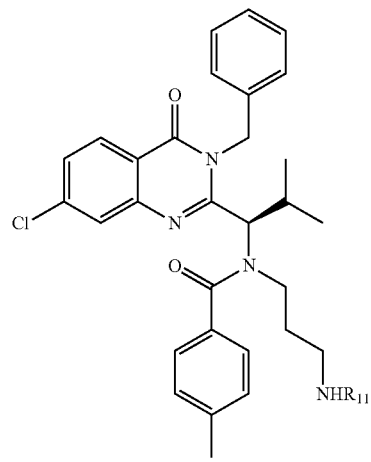
(XXVII)
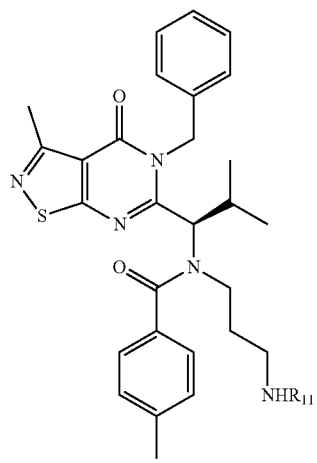
(XXVIII)
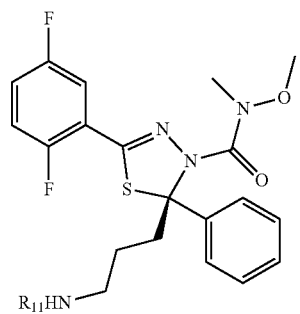
(XXIX)

TABLE A-continued
| $R_{11}$ | m/z (XXVII) |
|---|---|
| 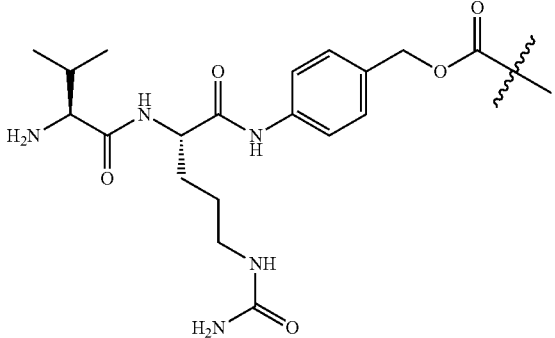 [SMILES: *C(=O)OCc1ccc(NC(=O)[C@H](CCCNC(N)=O)NC(=O)[C@@H](N)C(C)C)cc1] | 922.3 |
| 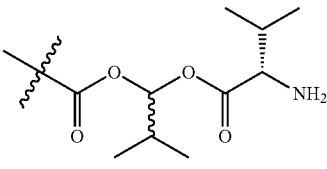 [SMILES: *C(=O)OC(OC(=O)[C@@H](N)C(C)C)C(C)C] | 732.2 |
| 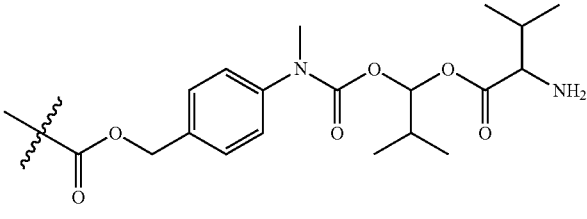 [SMILES: *C(=O)OCc1ccc(N(C)C(=O)OC(OC(=O)C(N)C(C)C)C(C)C)cc1] | ND |
| 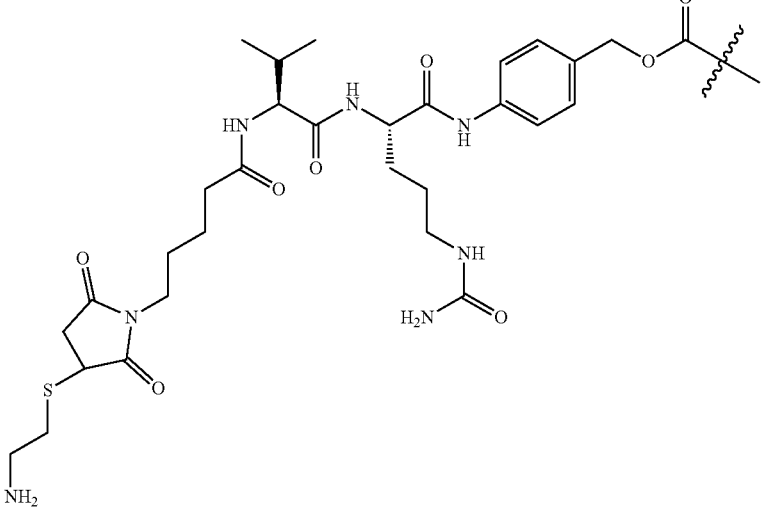 | ND |
| 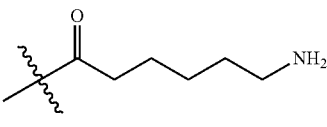 [SMILES: *C(=O)CCCCCN] | ND |

TABLE A-continued

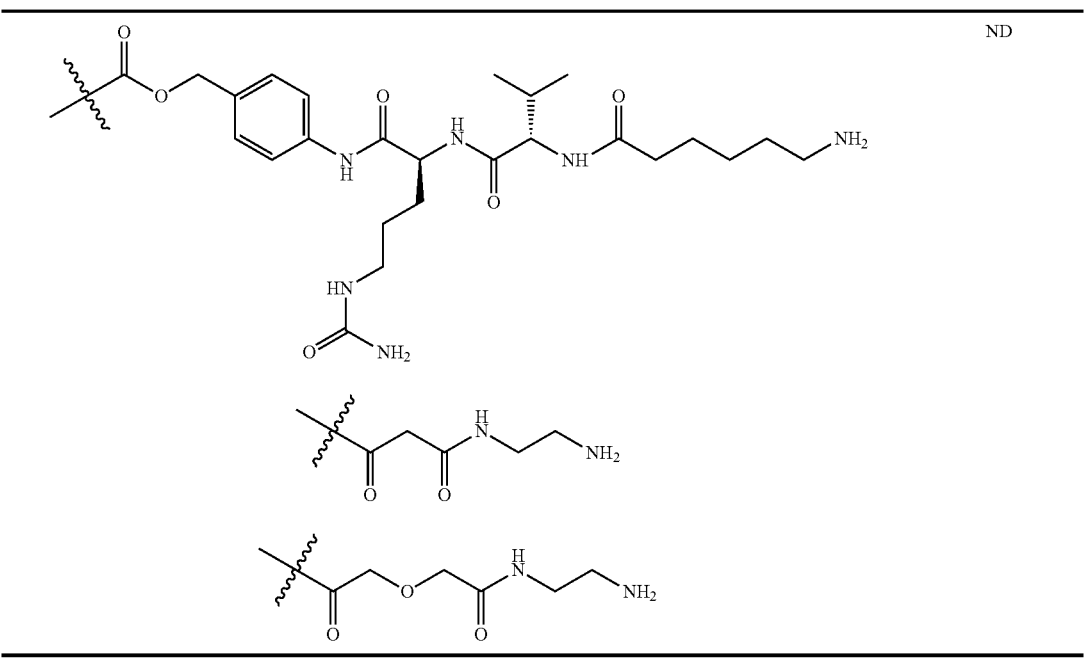

ND

Hydrophilic Group or T[1]

In one embodiment, the hydrophilic group included in the conjugates or scaffolds of the disclosure is a water-soluble and substantially non-antigenic polymer. Examples of the hydrophilic group, include, but are not limited to, polyalcohols, polyethers, polyanions, polycations, polyphosphoric acids, polyamines, polysaccharides, polyhydroxy compounds, polylysines, and derivatives thereof. One end of the hydrophilic group can be functionalized so that it can be covalently attached to the Multifunctional Linker or $M^A$ linker (e.g., to an amino acid in the $M^A$ linker) by means of a non-cleavable linkage or via a cleavable linkage. Functionalization can be, for example, via an amine, thiol, NHS ester, maleimide, alkyne, azide, carbonyl, or other functional group. The other terminus (or termini) of the hydrophilic group will be free and untethered. By "untethered", it is meant that the hydrophilic group will not be attached to another moiety, such as D or a Drug Unit, Releasable Assembly Unit, or other components of the conjugates or scaffolds of the disclosure. The free and untethered end of the hydrophilic group may include a methoxy, carboxylic acid, alcohol or other suitable functional group. The methoxy, carboxylic acid, alcohol or other suitable functional group acts as a cap for the terminus or termini of the hydrophilic group.

A cleavable linkage refers to a linkage that is not substantially sensitive to cleavage while circulating in the plasma but is sensitive to cleavage in an intracellular or intratumoral environment. A non-cleavable linkage is one that is not substantially sensitive to cleavage in any biological environment. Chemical hydrolysis of a hydrazone, reduction of a disulfide, and enzymatic cleavage of a peptide bond or glycosidic linkage are examples of cleavable linkages. Exemplary attachments of the hydrophilic group are via amide linkages, ether linkages, ester linkages, hydrazone linkages, oxime linkages, disulfide linkages, peptide linkages or triazole linkages. In some embodiments, the attachment of the hydrophilic group to the Multifunctional Linker or $M^A$ linker (e.g., to an amino acid in the $M^A$ linker) is via an amide linkage.

For those embodiments wherein the conjugate or scaffold of the disclosure comprises more than one hydrophilic groups, the multiple hydrophilic groups may be the same or different chemical moieties (e.g., hydrophilic groups of different molecular weight, number of subunits, or chemical structure). The multiple hydrophilic groups can be attached to the Multifunctional Linker or $M^A$ linker at a single attachment site or different sites.

The addition of the hydrophilic group may have two potential impacts upon the pharmacokinetics of the resulting conjugate. The desired impact is the decrease in clearance (and consequent in increase in exposure) that arises from the reduction in non-specific interactions induced by the exposed hydrophobic elements of the drug or drug-linker. The second impact is undesired impact and is the decrease in volume and rate of distribution that may arise from the increase in the molecular weight of the conjugate. Increasing the molecular weight of the hydrophilic group increases the hydrodynamic radius of a conjugate, resulting in decreased diffusivity that may diminish the ability of the conjugate to penetrate into a tumor. Because of these two competing pharmacokinetic effects, it is desirable to use a hydrophilic group that is sufficiently large to decrease the conjugate clearance thus increasing plasma exposure, but not so large as to greatly diminish its diffusivity, which may reduce the ability of the conjugate to reach the intended target cell population.

In some embodiments, the hydrophilic group, includes, but is not limited to, a sugar alcohol (also known as polyalcohol, polyhydric alcohol, alditol or glycitol, such as inositol, glycerol, erythritol, threitol, arabitol, xylitol, ribitol, galactitol, mannitol, sorbitol, and the like) or a derivative thereof (e.g., amino polyalcohol), carbohydrate (e.g., a saccharide), a polyvinyl alcohol, a carbohydrate-based polymer (e.g., dextrans), a hydroxypropylmethacrylamide (HPMA), a polyalkylene oxide, and/or a copolymer thereof.

In one embodiment, the hydrophilic group comprises a plurality of hydroxyl ("—OH") groups, such as moieties that incorporate monosaccharides, oligosaccharides, polysaccharides, and the like. In yet another embodiment the hydrophilic group comprises a plurality of —(CR$_{58}$OH)— groups, wherein R$_{58}$ is hydrogen or C$_{1-8}$ alkyl.

In some embodiments, the hydrophilic group comprises one or more of the following fragments of the formula:

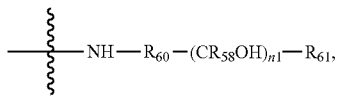
(5)

in which
- n$_1$ is an integer from 0 to about 6;
- each R$_{58}$ is independently hydrogen or C$_{1-8}$ alkyl;
- R$_{60}$ is a bond, a C$_{1-6}$ alkyl linker, or —CHR$_{59}$— in which R$_{59}$ is H, alkyl, cycloalkyl, or arylalkyl;
- R$_{61}$ is CH$_2$OR$_{62}$, COOR$_{62}$, —(CH$_2$)$_{n2}$COOR$_{62}$, or a heterocycloalkyl substituted with one or more hydroxyl;
- R$_{62}$ is H or C$_{1-8}$ alkyl; and
- n$_2$ is an integer from 1 to about 5.

For example, R$_{58}$ is hydrogen, R$_{60}$ is a bond or a C$_{1-6}$ alkyl linker, n 1 is an integer from 1 to about 6, and R$_{61}$ is CH$_2$OH or COOH. For example, R$_{58}$ is hydrogen, R$_{60}$ is —CHR$_{59}$—, n$_1$ is 0, and R$_{61}$ is a heterocycloalkyl substituted with one or more hydroxyl, e.g., a monosaccharide.

In some embodiments, the hydrophilic group comprises a glucosyl-amine, a diamine or a tri-amine.

In some embodiments, the hydrophilic group comprises one or more of the following fragments or a stereoisomer thereof:

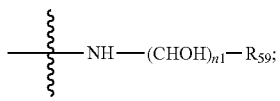
(1)

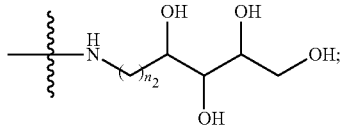
(2)

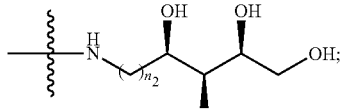
(3)

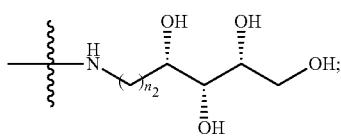
(4)

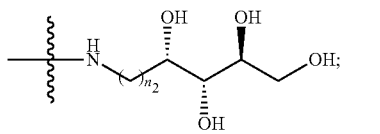
(5)

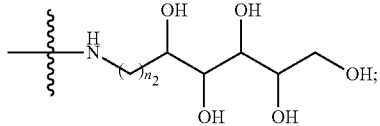
(6)

-continued

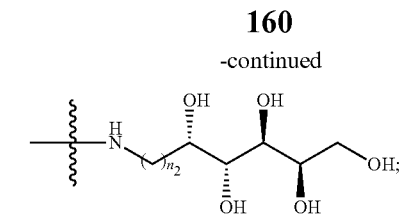
(7)

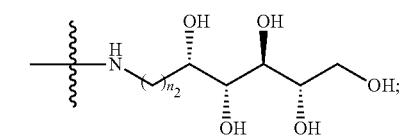
(8)

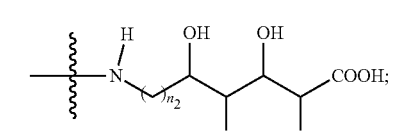
(9)

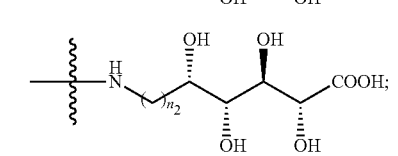
(10)

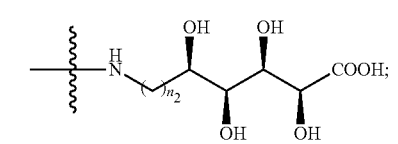
(11)

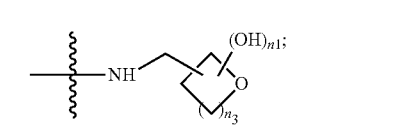
(12)

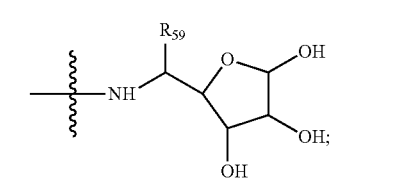
(13)

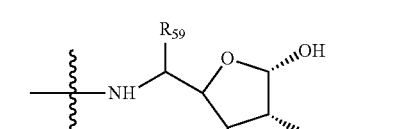
(14)

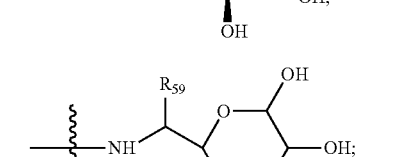
(15)

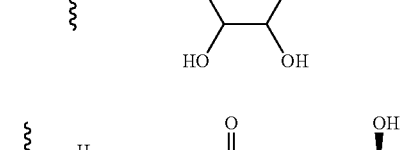
(16)

-continued

(17)
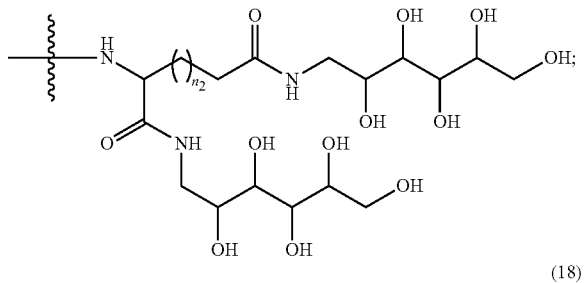

(18)
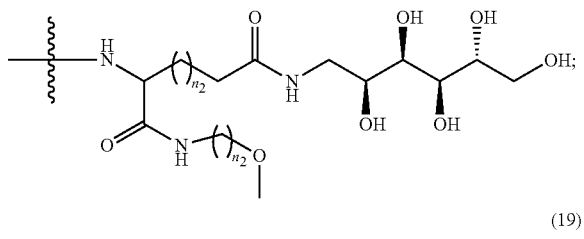

(19)
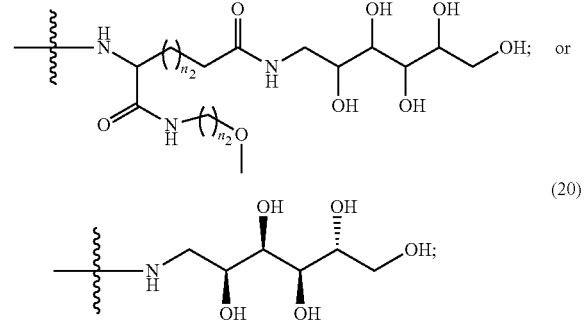

(20)
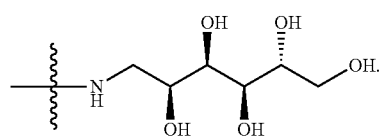

wherein:
$R_{59}$ is H, alkyl, cycloalkyl, or arylalkyl;
$n_1$ is an integer from 1 to about 6;
$n_2$ is an integer from 1 to about 5; and
$n_3$ is an integer from about 1 to about 3.

It is understood that all stereochemical forms of the hydrophilic groups are contemplated herein. For example, in the above formula, the hydrophilic group may be derived from ribose, xylose, glucose, mannose, galactose, or other sugar and retain the stereochemical arrangements of pendant hydroxyl and alkyl groups present on those molecules. In addition, it is to be understood that in the foregoing formulae, various deoxy compounds are also contemplated. Illustratively, one or more of the following features are contemplated for the hydrophilic groups when applicable:

For example, $n_3$ is 2 or 3.
For example, $n_1$ is 1, 2, or 3.
For example, $n_2$ is 1.
For example, $R_{59}$ is hydrogen.
For example, the hydrophilic group comprises:

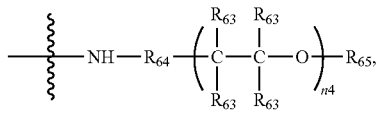

For example, the hydrophilic group comprises:

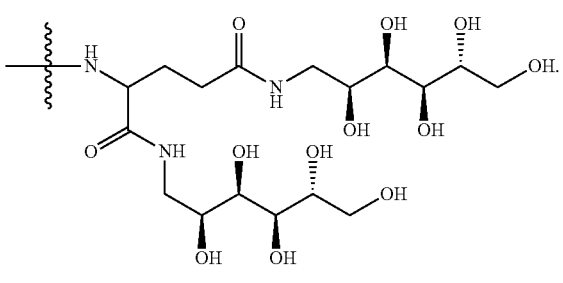 [SMILES: *NC(CCC(=O)NC[C@H](O)[C@@H](O)[C@H](O)[C@H](O)CO)C(=O)NC[C@H](O)[C@@H](O)[C@H](O)[C@H](O)CO]

For example, the hydrophilic group comprises:

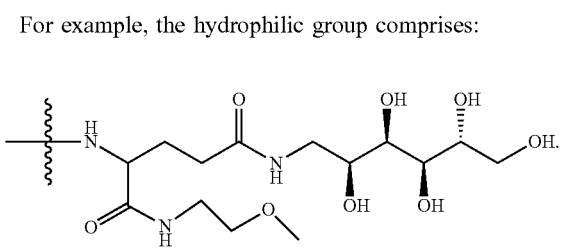

In some embodiments, the hydrophilic group comprises

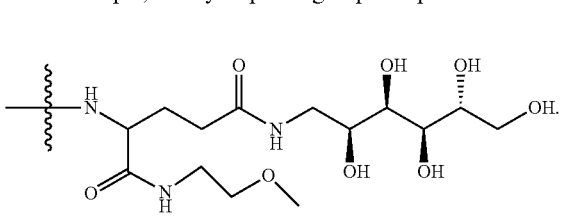

in which
$n_4$ is an integer from 1 to about 25;
each $R_{63}$ is independently hydrogen or $C_{1-8}$ alkyl;
$R_{64}$ is a bond or a $C_{1-8}$ alkyl linker;
$R_{65}$ is H, $C_{1-8}$ alkyl, or $-(CH_2)_{n2}COOR_{62}$;
$R_{62}$ is H or $C_{1-8}$ alkyl; and
$n_2$ is an integer from 1 to about 5.

In some embodiments, the hydrophilic group comprises:

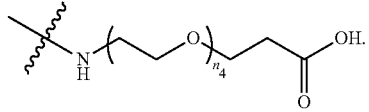

For example, $n_4$ is an integer from about 2 to about 20, from about 4 to about 16, from about 6 to about 12, from about 8 to about 12.

For example, $n_4$ is 6, 7, 8, 9, 10, 11, or 12.

In other embodiments, the hydrophilic group comprises a polyether, e.g., a polyalkylene glycol (PAO). PAO includes but is not limited to, polymers of lower alkylene oxides, in particular polymers of ethylene oxide, such as, for example, propylene oxide, polypropylene glycols, polyethylene glycol (PEG), polyoxyethylenated polyols, copolymers thereof and block copolymers thereof. In other embodiments the polyalkylene glycol is a polyethylene glycol (PEG) including, but not limited to, polydisperse PEG, monodisperse PEG and discrete PEG. Polydisperse PEGs are a heterogeneous mixture of sizes and molecular weights whereas monodisperse PEGs are typically purified from heterogeneous mixtures and are therefore provide a single chain length and molecular weight. In another embodiment, the PEG units are discrete PEGs provide a single molecule with defined and specified chain length. In some embodiments, the polyethylene glycol is mPEG.

In some embodiments, the hydrophilic group comprises a PEG unit which comprises one or multiple polyethylene glycol chains. The polyethylene glycol chains can be linked together, for example, in a linear, branched or star shaped configuration. The PEG unit, in addition to comprising repeating polyethylene glycol subunits, may also contain non-PEG material (e.g., to facilitate coupling of multiple PEG chains to each other or to facilitate coupling to the amino acid). Non-PEG material refers to the atoms in the PEG chain that are not part of the repeating —$CH_2CH_2O$— subunits. In one embodiment, the PEG chain can comprise two monomeric PEG chains linked to each other via non-PEG elements. In another embodiment, the PEG Unit can comprise two linear PEG chains attached to a central core that is attached to the amino acid (i.e., the PEG unit itself is branched).

The PEG unit may be covalently bound to the Multifunctional Linker or $M^A$ linker (e.g., to an amino acid in the $M^A$ linker) via a reactive group. Reactive groups are those to which an activated PEG molecule may be bound (e.g., a free amino or carboxyl group). For example, N-terminal amino acids and lysines (K) have a free amino group; and C-terminal amino acid residues have a free carboxyl group. Sulfhydryl groups (e.g., as found on cysteine residues) may also be used as a reactive group for attaching PEG.

In some embodiments, the PEG unit may be attached to the Multifunctional Linker or $M^A$ linker (e.g., to an amino acid in the $M^A$ linker) by using methoxylated PEG ("mPEG") having different reactive moieties, including, but not limited to, succinimidyl succinate (SS), succinimidyl carbonate (SC), mPEG-imidate, para-nitrophenylcarbonate (NPC), succinimidyl propionate (SPA), and cyanuric chloride. Examples of mPEGs include, but are not limited to, mPEG-succinimidyl succinate (mPEG-SS), mPEG$_2$-succinimidyl succinate (mPEG$_2$-SS), mPEG-succinimidyl carbonate (mPEG-SC), mPEG$_2$-succinimidyl carbonate (mPEG$_2$-SC), mPEG-imidate, mPEG-para-nitrophenylcarbonate (mPEG-NPC), mPEG-imidate, mPEG$_2$-para-nitrophenylcarbonate (mPEG$_2$-NPC), mPEG-succinimidyl propionate (mPEG-SPA), mPEG$_2$-succinimidyl propionate (mPEG$_2$-SPA), mPEG-N-hydroxy-succinimide (mPEG-NHS), mPEG$_2$-N-hydroxy-succinimide (mPEG$_2$-NHS), mPEG-cyanuric chloride, mPEG$_2$-cyanuric chloride, mPEG$_2$-Lysinol-NPC, and mPEG$_2$-Lys-NHS. A wide variety of PEG species can be used, and substantially any suitable reactive PEG reagent can be used. In some embodiments, the reactive PEG reagent will result in formation of a carbamate or amide bond upon attachment to the Multifunctional Linker or $M^A$ linker (e.g., to an amino acid in the $M^A$ linker). The reactive PEG reagents include, but are not limited to, mPEG$_2$-N-hydroxy-succinimide (mPEG$_2$-NHS), bifunctional PEG propionaldehyde (mPEG$_2$-ALD), multi-Arm PEG, maleimide-containing PEG (mPEG(MAL)$_2$, mPEG$_2$ (MAL)), mPEG-NH$_2$, mPEG-succinimidyl propionate (mPEG-SPA), succinimide of mPEG butanoate acid (mPEG-SB A), mPEG-thioesters, mPEG-Double Esters, mPEG-BTC, mPEG-ButyrALD, mPEG-acetaldehyde diethyl acetal (mPEG-ACET), heterofunctional PEGs (e.g., NH$_2$-PEG-COOH, Boc-PEG-NHS, Fmoc-PEG-NHS, NHS-PEG-vinylsulfone (NHS-PEG-VS), or NHS-PEG-MAL), PEG acrylates (ACRL-PEG-NHS), PEG-phospholipids (e.g., mPEG-DSPE), multi-armed PEGs of the SUN-BRITE™ series including the glycerine-based PEGs activated by a chemistry chosen by those skilled in the art, any SUNBRETE activated PEGs (including but not limited to carboxyl-PEGs, p-NP-PEGs, Tresyl-PEGs, aldehyde PEGs, acetal-PEGs, amino-PEGs, thiol-PEGs, maleimido-PEGs, hydroxyl-PEG-amine, amino-PEG-COOK hydroxyl-PEG-aldehyde, carboxylic anhydride type-PEG, functionalized PEG-phospholipid, and other similar and/or suitable reactive PEGs.

In some embodiments, the PEG unit comprises at least 6 subunits, at least 7 subunits, at least 8 subunits, at least 9 subunits, at least 10 subunits, at least 11 subunits, at least 12 subunits, at least 13 subunits, at least 14 subunits, at least 15 subunits, at least 16 subunits, at least 17 subunits, at least 18 subunits, at least 19 subunits, at least 20 subunits, at least 21 subunits, at least 22 subunits, at least 23 subunits, or at least 24 subunits. In some such embodiments, the PEG unit comprises no more than about 72 subunits.

In some embodiments, the PEG unit comprises at least 6 subunits, at least 7 subunits, at least 8 subunits, at least 9 subunits, at least 10 subunits, at least 11 subunits, at least 12 subunits, at least 13 subunits, at least 14 subunits, at least 15 subunits, at least 16 subunits, at least 17 subunits, at least 18 subunits, at least 19 subunits, at least 20 subunits, at least 21 subunits, at least 22 subunits, at least 23 subunits, or at least 24 subunits.

In some embodiments, the PEG unit comprises at least 6 subunits, at least 7 subunits, at least 8 subunits, at least 9 subunits, at least 10 subunits, at least 11 subunits, at least 12 subunits, at least 13 subunits, at least 14 subunits, at least 15 subunits, at least 16 subunits, at least 17 subunits, or at least 18 subunits.

In some embodiments, the PEG unit comprises at least 6 subunits, at least 7 subunits, at least 8 subunits, at least 9 subunits, at least 10 subunits, at least 11 subunits, or at least 12 subunits.

In some embodiments, the PEG unit comprises at least 8 subunits, at least 9 subunits, at least 10 subunits, at least 11 subunits, or at least 12 subunits.

In some embodiments, the PEG unit comprises at least 6 subunits, at least 7 subunits, or at least 8 subunits.

In some embodiments, the PEG unit comprises one or more linear PEG chains each having at least 2 subunits, at least 3 subunits, at least 4 subunits, at least 5 subunits, at least 6 subunits, at least 7 subunits, at least 8 subunits, at least 9 subunits, at least 10 subunits, at least 11 subunits, at least 12 subunits, at least 13 subunits, at least 14 subunits, at least 15 subunits, at least 16 subunits, at least 17 subunits, at least 18 subunits, at least 19 subunits, at least 20 subunits, at least 21 subunits, at least 22 subunits, at least 23 subunits, or at least 24 subunits. In another embodiment, the PEG unit comprises a combined total of at least 6 subunits, at least 8, at least 10 subunits, or at least 12 subunits. In some such embodiments, the PEG unit comprises no more than a combined total of about 72 subunits, preferably no more than a combined total of about 36 subunits.

In some embodiments, the PEG unit comprises a combined total of from 4 to 72, 4 to 60, 4 to 48, 4 to 36 or 4 to 24 subunits, from 5 to 72, 5 to 60, 5 to 48, 5 to 36 or 5 to 24 subunits, from 6 to 72, 6 to 60, 6 to 48, 6 to 36 or from 6 to 24 subunits, from 7 to 72, 7 to 60, 7 to 48, 7 to 36 or 7 to 24 subunits, from 8 to 72, 8 to 60, 8 to 48, 8 to 36 or 8 to 24 subunits, from 9 to 72, 9 to 60, 9 to 48, 9 to 36 or 9 to 24 subunits, from 10 to 72, 10 to 60, 10 to 48, 10 to 36 or 10 to 24 subunits, from 11 to 72, 11 to 60, 11 to 48, 11 to 36 or 11 to 24 subunits, from 12 to 72, 12 to 60, 12 to 48, 12 to 36 or 12 to 24 subunits, from 13 to 72, 13 to 60, 13 to 48, 13 to 36 or 13 to 24 subunits, from 14 to 72, 14 to 60, 14 to 48, 14 to 36 or 14 to 24 subunits, from 15 to 72, 15 to 60, 15 to 48, 15 to 36 or 15 to 24 subunits, from 16 to 72, 16 to 60, 16 to 48, 16 to 36 or 16 to 24 subunits, from 17 to 72, 17 to 60, 17 to 48, 17 to 36 or 17 to 24 subunits, from 18 to 72, 18 to 60, 18 to 48, 18 to 36 or 18 to 24 subunits, from 19 to 72, 19 to 60, 19 to 48, 19 to 36 or 19 to 24 subunits, from 20 to 72, 20 to 60, 20 to 48, 20 to 36 or 20 to 24 subunits, from 21 to 72, 21 to 60, 21 to 48, 21 to 36 or 21 to 24 subunits, from 22 to 72, 22 to 60, 22 to 48, 22 to 36 or 22 to 24 subunits, from 23 to 72, 23 to 60, 23 to 48, 23 to 36 or 23 to 24 subunits, or from 24 to 72, 24 to 60, 24 to 48, 24 to 36 or 24 subunits.

In some embodiments, the PEG unit comprises one or more linear PEG chains having a combined total of from 4 to 72, 4 to 60, 4 to 48, 4 to 36 or 4 to 24 subunits, from 5 to 72, 5 to 60, 5 to 48, 5 to 36 or 5 to 24 subunits, from 6 to 72, 6 to 60, 6 to 48, 6 to 36 or 6 to 24 subunits, from 7 to 72, 7 to 60, 7 to 48, 7 to 36 or 7 to 24 subunits, from 8 to 72, 8 to 60, 8 to 48, 8 to 36 or 8 to 24 subunits, from 9 to 72, 9 to 60, 9 to 48, 9 to 36 or 9 to 24 subunits, from 10 to 72, 10 to 60, 10 to 48, 10 to 36 or 10 to 24 subunits, from 11 to 72, 11 to 60, 11 to 48, 11 to 36 or 11 to 24 subunits, from 12 to 72, 12 to 60, 12 to 48, 12 to 36 or 12 to 24 subunits, from 13 to 72, 13 to 60, 13 to 48, 13 to 36 or 13 to 24 subunits, from 14 to 72, 14 to 60, 14 to 48, 14 to 36 or 14 to 24 subunits, from 15 to 72, 15 to 60, 15 to 48, 15 to 36 or 15 to 24 subunits, from 16 to 72, 16 to 60, 16 to 48, 16 to 36 or 16 to 24 subunits, from 17 to 72, 17 to 60, 17 to 48, 17 to 36 or 17 to 24 subunits, from 18 to 72, 18 to 60, 18 to 48, 18 to 36 or 18 to 24 subunits, from 19 to 72, 19 to 60, 19 to 48, 19 to 36 or 19 to 24 subunits, from 20 to 72, 20 to 60, 20 to 48, 20 to 36 or 20 to 24 subunits, from 21 to 72, 21 to 60, 21 to 48, 21 to 36 or 21 to 24 subunits, from 22 to 72, 22 to 60, 22 to 48, 22 to 36 or 22 to 24 subunits, from 23 to 72, 23 to 60, 23 to 48, 23 to 36 or 23 to 24 subunits, or from 24 to 72, 24 to 60, 24 to 48, 24 to 36 or 24 subunits.

In some embodiments, the PEG unit is a derivatized linear single PEG chain having at least 2 subunits, at least 3 subunits, at least 4 subunits, at least 5 subunits, at least 6 subunits, at least 7 subunits, at least 8 subunits, at least 9 subunits, at least 10 subunits, at least 11 subunits, at least 12 subunits, at least 13 subunits, at least 14 subunits, at least 15 subunits, at least 16 subunits, at least 17 subunits, at least 18 subunits, at least 19 subunits, at least 20 subunits, at least 21 subunits, at least 22 subunits, at least 23 subunits, or at least 24 subunits.

In some embodiments, the PEG unit is a derivatized linear single PEG chain having from 6 to 72, 6 to 60, 6 to 48, 6 to 36 or 6 to 24 subunits, from 7 to 72, 7 to 60, 7 to 48, 7 to 36 or 7 to 24 subunits, from 8 to 72, 8 to 60, 8 to 48, 8 to 36 or 8 to 24 subunits, from 9 to 72, 9 to 60, 9 to 48, 9 to 36 or 9 to 24 subunits, from 10 to 72, 10 to 60, 10 to 48, 10 to 36 or 10 to 24 subunits, from 11 to 72, 11 to 60, 11 to 48, 11 to 36 or 11 to 24 subunits, from 12 to 72, 12 to 60, 12 to 48, 12 to 36 or 12 to 24 subunits, from 13 to 72, 13 to 60, 13 to 48, 13 to 36 or 13 to 24 subunits, from 14 to 72, 14 to 60, 14 to 48, 14 to 36 or 14 to 24 subunits, from 15 to 72, 15 to 60, 15 to 48, 15 to 36 or 15 to 24 subunits, from 16 to 72, 16 to 60, 16 to 48, 16 to 36 or 16 to 24 subunits, from 17 to 72, 17 to 60, 17 to 48, 17 to 36 or 17 to 24 subunits, from 18 to 72, 18 to 60, 18 to 48, 18 to 36 or 18 to 24 subunits, from 19 to 72, 19 to 60, 19 to 48, 19 to 36 or 19 to 24 subunits, from 20 to 72, 20 to 60, 20 to 48, 20 to 36 or 20 to 24 subunits, from 21 to 72, 21 to 60, 21 to 48, 21 to 36 or 21 to 24 subunits, from 22 to 72, 22 to 60, 22 to 48, 22 to 36 or 22 to 24 subunits, from 23 to 72, 23 to 60, 23 to 48, 23 to 36 or 23 to 24 subunits, or from 24 to 72, 24 to 60, 24 to 48, 24 to 36 or 24 subunits.

In some embodiments, the PEG unit is a derivatized linear single PEG chain having from 2 to 72, 2 to 60, 2 to 48, 2 to 36 or 2 to 24 subunits, from 2 to 72, 2 to 60, 2 to 48, 2 to 36 or 2 to 24 subunits, from 3 to 72, 3 to 60, 3 to 48, 3 to 36 or 3 to 24 subunits, from 3 to 72, 3 to 60, 3 to 48, 3 to 36 or 3 to 24 subunits, from 4 to 72, 4 to 60, 4 to 48, 4 to 36 or 4 to 24 subunits, from 5 to 72, 5 to 60, 5 to 48, 5 to 36 or 5 to 24 subunits.

For example, a linear PEG unit is:

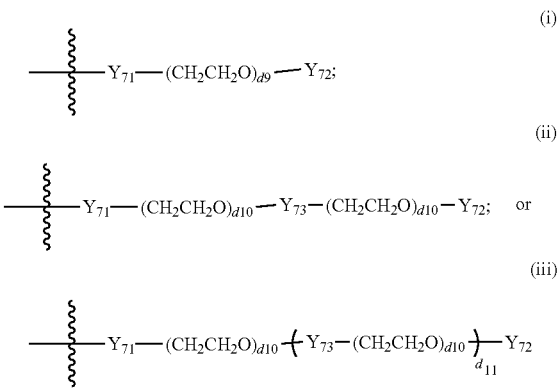

wherein;
the wavy line indicates site of attachment to the Multifunctional Linker or $M^A$ linker (e.g., to an amino acid in the $M^A$ linker);
$Y_{71}$ is a PEG attachment unit;
$Y_{72}$ is a PEG capping unit;
$Y_{73}$ is an PEG coupling unit (i.e., for coupling multiple PEG subunit chains together);
$d_9$ is an integer from 2 to 72, preferably from 4 to 72, more preferably from 6 to 72, from 8 to 72, from 10 to 72, from 12 to 72 or from 6 to 24;
each $d_{10}$ is independently an integer from 1 to 72.
$d_{11}$ is an integer from 2 to 5.

In some embodiments, there are at least 6, preferably at least 8, at least 10, or at least 12 PEG subunits in the PEG unit. In some embodiments, there are no more than 72 or 36 PEG subunits in the PEG unit.

In some embodiments, $d_9$ is 8 or about 8, 12 or about 12, 24 or about 24.

In some embodiments, each $Y_{72}$ is independently —$C_{1-10}$ alkyl, —$C_{2-10}$ alkyl-$CO_2H$, —$C_{2-10}$ alkyl-OH, —$C_{2-10}$ alkyl-$NH_2$, —$C_{2-10}$ alkyl-NH($C_{1-3}$ alkyl), or $C_{2-10}$ alkyl-N($C_{1-3}$ alkyl)$_2$.

In some embodiments, $Y_{72}$ is —$C_{1-10}$ alkyl, —$C_{2-10}$ alkyl-CO2H, —$C_{2-10}$ alkyl-OH, or —$C_{2-10}$ alkyl-$NH_2$.

The PEG coupling unit is part of the PEG unit and is non-PEG material that acts to connect two or more chains of repeating $CH_2CH_2O$— subunits. In some embodiments, the PEG coupling unit $Y_{73}$ is —$C_{2-10}$ alkyl-C(O)—NH—, —$C_{2-10}$ alkyl-NH—C(O)—, —$C_{2-10}$ alkyl-NH—, —$C_{2-10}$ alkyl-C(O)—, —$C_{2-10}$ alkyl-O— or —$C_{2-10}$ alkyl-S—.

In some embodiments, each $Y_{73}$ is independently —$C_{1-10}$ alkyl-C(O)—NH—, —$C_{1-10}$ alkyl-NH—C(O)—, —$C_{2-10}$ alkyl-NH—, —$C_{2-10}$ alkyl-O—, —$C_{1-10}$ alkyl-S—, or —$C_{1-10}$ alkyl-NH—.

The PEG attachment unit is part of the PEG unit and acts to link the PEG unit to the Multifunctional Linker or $M^A$ linker (e.g., to an amino acid in the $M^A$ linker). For example, the amino acid has a functional group that forms a bond with the PEG Unit. Functional groups for attachment of the PEG unit to the amino acid include sulfhydryl groups to form disulfide bonds or thioether bonds, aldehyde, ketone, or hydrazine groups to form hydrazone bonds, hydroxylamine to form oxime bonds, carboxylic or amino groups to form peptide bonds, carboxylic or hydroxy groups to form ester bonds, sulfonic acids to form sulfonamide bonds, alcohols to form carbamate bonds, and amines to form sulfonamide bonds or carbamate bonds or amide bonds. Accordingly, the PEG unit can be attached to the amino acid, for example, via a disulfide, thioether, hydrazone, oxime, peptide, ester, sulfonamide, carbamate, or amide bond. Typically, the reaction for attaching the PEG unit can be a cycloaddition, addition, addition/elimination or substitution reaction, or a combination thereof when applicable.

In some embodiments, the PEG attachment unit $Y_{71}$ is a bond, —C(O)—, —O—, —S—, —S(O)—, —S(O)$_2$—, —NR$_5$—, —C(O)O—, —C(O)—C$_{1-10}$ alkyl, —C(O)—C$_{1-10}$ alkyl-O—, —C(O)—C$_{1-10}$ alkyl-CO$_2$—, —C(O)—C$_{1-10}$ alkyl-NR$_5$—, —C(O)—C$_{1-10}$ alkyl-S—, —C(O)—C$_{1-10}$ alkyl-C(O)—NR$_5$—, —C(O)—C$_{1-10}$ alkyl-NR$_5$-C(O)—, —C$_{1-10}$ alkyl, —C$_{1-10}$ alkyl-O—, —C$_{1-10}$ alkyl-CO$_2$—, —C$_{1-10}$ alkyl-NR$_5$—, —C$_{1-10}$ alkyl-S—, —C$_{1-10}$ alkyl-C(O)—NR$_5$—, —C$_{1-10}$ alkyl-NR$_5$—C(O)—, —CH$_2$CH$_2$SO$_2$—C$_{1-10}$ alkyl-, —CH$_2$C(O)—C$_{1-10}$ alkyl-, =N—(O or N)—C$_{1-10}$ alkyl-O—, =N—(O or N)—C$_{1-10}$ alkyl-NR$_5$—, =N—(O or N)—C$_{1-10}$ alkyl-CO$_2$—, =N—(O or N)—C$_{1-10}$ alkyl-S—,

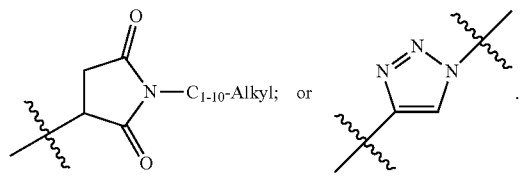

In some embodiments, $Y_{71}$ is —NH—, —C(O)—, a triazole group, —S—, or a maleimido-group such as

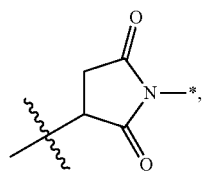

wherein the wavy line indicates attachment to the Multifunctional Linker or $M^A$ linker (e.g., to an amino acid in the $M^A$ linker) and the asterisk indicates the site of attachment within the PEG Unit.

Examples of linear PEG units include:

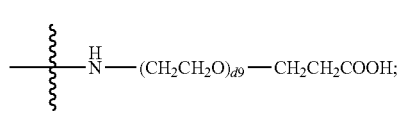

(i)

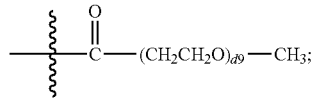

(ii)

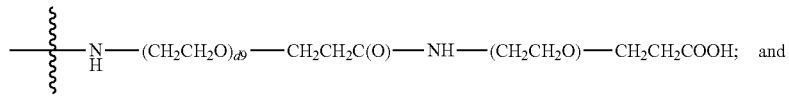

(iii)

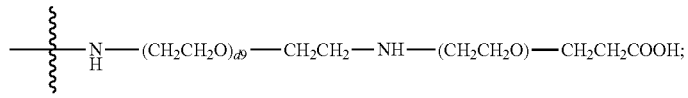

(iv)

(v)

wherein the wavy line indicates site of attachment to the Multifunctional Linker or $M^A$ linker (e.g., to an amino acid in the $M^A$ linker), and each $d_9$ is independently an integer from 4 to 24, 6 to 24, 8 to 24, 10 to 24, 12 to 24, 14 to 24, or 16 to 24.

In some embodiments, $d_9$ is about 8, about 12, or about 24.

In other embodiments, the PEG unit is from about 300 daltons to about 5 kilodaltons; from about 300 daltons, to about 4 kilodaltons; from about 300 daltons, to about 3 kilodaltons; from about 300 daltons, to about 2 kilodaltons; or from about 300 daltons, to about 1 kilodalton. In some such aspects, the PEG unit has at least 6 subunits or at least 8, 10 or 12 subunits. In some embodiments, the PEG unit has at least 6 subunits or at least 8, 10 or 12 subunits but no more than 72 subunits, preferably no more than 36 subunits.

Suitable polyethylene glycols may have a free hydroxy group at each end of the polymer molecule, or may have one hydroxy group etherified with a lower alkyl, e.g., a methyl group. Also suitable for the practice of the disclosure are derivatives of polyethylene glycols having esterifiable carboxy groups. Polyethylene glycols are commercially available under the trade name PEG, usually as mixtures of polymers characterized by an average molecular weight. Polyethylene glycols having an average molecular weight from about 300 to about 5000 are preferred, those having an average molecular weight from about 600 to about 1000 being particularly preferred.

Other examples of hydrophilic groups that are suitable for the conjugates, scaffolds, and methods disclosed herein can be found in e.g., U.S. Pat. No. 8,367,065 column 13; U.S. Pat. No. 8,524,696 column 6; WO2015/057699 and WO 2014/062697, the contents of each of which are hereby incorporated by reference in their entireties.

Protein-Based Recognition Molecules (PBRMs)

The protein-based recognition molecule directs the conjugates comprising a peptide linker to specific tissues, cells, or locations in a cell. The protein-based recognition molecule can direct the conjugate in culture or in a whole organism, or both. In each case, the protein-based recognition molecule has a ligand that is present on the cell surface of the targeted cell(s) to which it binds with an effective specificity, affinity and avidity. In some embodiments, the protein-based recognition molecule targets the conjugate to tissues other than the liver. In other embodiments the protein-based recognition molecule targets the conjugate to a specific tissue such as the liver, kidney, lung or pancreas. The protein-based recognition molecule can target the conjugate to a target cell such as a cancer cell, such as a receptor expressed on a cell such as a cancer cell, a matrix tissue, or a protein associated with cancer such as tumor antigen. Alternatively, cells comprising the tumor vasculature may be targeted. Protein-based recognition molecules can direct the conjugate to specific types of cells such as specific targeting to hepatocytes in the liver as opposed to Kupffer cells. In other cases, protein-based recognition molecules can direct the conjugate to cells of the reticular endothelial or lymphatic system, or to professional phagocytic cells such as macrophages or eosinophils. (In such cases the conjugate itself might also be an effective delivery system, without the need for specific targeting).

In still other embodiments, the protein based recognition molecule can target the conjugate to a location within the cell, such as the nucleus, the cytoplasm, or the endosome, for example. In specific embodiments, the protein based recognition molecule can enhance cellular binding to receptors, or cytoplasmic transport to the nucleus and nuclear entry or release from endosomes or other intracellular vesicles.

In specific embodiments the protein based recognition molecules include antibodies, proteins and peptides or peptide mimics.

In a preferred embodiment, the protein based recognition molecule comprises a sulfhydryl group and the protein based recognition molecule is conjugated to the Linker-Drug moiety by forming a covalent bond via the sulfhydryl group and a functional group of the Linker-Drug moiety.

Exemplary antibodies or antibodies derived from Fab, Fab2, scFv or camel antibody heavy-chain fragments specific to the cell surface markers, include, but are not limited to, 5T4, AOC3, ALK, AXL, C242, C4.4a, CA-125, CCL11, CCR 5, CD2, CD3, CD4, CD5, CD15, CA15-3, CD18, CD19, CA19-9, CDH6, CD20, CD22, CD23, CD25, CD28, CD30, CD31, CD33, CD37, CD38, CD40, CD41, CD44, CD44 v6, CD51, CD52, CD54, CD56, CD62E, CD62P, CD62L, CD70, CD74, CD79-B, CD80, CD125, CD138, CD141, CD147, CD152, CD154, CD326, CEA, CEACAM-5, clumping factor, CTLA-4, CXCR2, EGFR (HER1), ErbB2, ErbB3, EpCAM, EPHA2, EPHB2, EPHB4, FGFR (i.e. FGFR1, FGFR2, FGFR3, FGFR4), FLT3, folate receptor, FAP, GD2, GD3, GPNMB, GCC (GUCY2C), HGF, HER2, HER3, HMI.24, ICAM, ICOS-L, IGF-1 receptor, VEGFR1, EphA2, TRPV1, CFTR, gpNMB, CA9, Cripto, c-KIT, c-MET, ACE, APP, adrenergic receptor-beta2, Claudine 3, LIV1, LY6E, Mesothelin, MUC1, MUC13, NaPi2b, NOTCH1, NOTCH2, NOTCH3, NOTCH4, RON, ROR1, PD-L1, PD-L2, PTK7, B7-H3, B7-B4, IL-2 receptor, IL-4 receptor, IL-13 receptor, TROP-2, frizzled-7, integrins (including $\alpha_4$, $\alpha_v\beta_3$, $\alpha_v\beta_5$, $\alpha_v\beta_6$, $\alpha_1\beta_4$, $\alpha_4\beta_1$, $\alpha_4\beta_7$, $\alpha_5\beta_1$, $\alpha_6\beta_4$, $\alpha_{IIb}\beta_3$ intergins), IFN-α, IFN-γ, IgE, IgE, IGF-1 receptor, IL-1, IL-12, IL-23, IL-13, IL-22, IL-4, IL-5, IL-6, interferon receptor, ITGB2 (CD18), LFA-1 (CD11a), L-selectin (CD62L), mucin, myostatin, NCA-90, NGF, PDGFRα, phosphatidylserine, prostatic carcinoma cell, *Pseudomonas aeruginosa*, rabies, RANKL, respiratory syncytial virus, Rhesus factor, SLAMF7, sphingosine-1-phosphate, TAG-72, T-cell receptor, tenascin C, TGF-1, TGF-β2, TGF-β, TNF-α, TRAIL-R1, TRAIL-R2, tumor antigen CTAA16.88, VEGF-A, VEGFR2, vimentin, and the like.

In one embodiment the antibodies or antibody derived from Fab, Fab2, scFv or camel antibody heavy-chain fragments specific to the cell surface markers include CA-125, C242, CD3, CD19, CD22, CD25, CD30, CD31, CD33, CD37, CD40, CD44, CD51, CD54, CD56, CD62E, CD62P, CD62L, CD70, CD138, CD141, CD326, CEA, CTLA-4, EGFR (HER1), ErbB2, ErbB3, FAP, folate receptor, IGF-1 receptor, GD3, GPNMB, HGF, HER2, VEGF-A, VEGFR2, VEGFR1, EphA2, EpCAM, 5T4, TAG-72, tenascin C, TRPV1, CFTR, gpNMB, CA9, Cripto, ACE, APP, PDGFR α, phosphatidylserine, prostatic carcinoma cells, adrenergic receptor-beta2, Claudine 3, mucin, MUC1, NaPi2b, B7H3, B7H4, C4.4a, CEACAM-5, MUC13, TROP-2, frizzled-7, Mesothelin, IL-2 receptor, IL-4 receptor, IL-13 receptor and integrins (including $\alpha_v\beta_3$, $\alpha_v\beta_5$, $\alpha_v\beta_6$, $\alpha_1\beta_4$, $\alpha_4\beta_1$, $\alpha_5\beta_1$, $\alpha_6\beta_4$ intergins), tenascin C, TRAIL-R2 and vimentin.

Exemplary antibodies include 3F8, abagovomab, abciximab (REOPRO), adalimumab (HUMIRA), adecatumumab, afelimomab, afutuzumab, alacizumab, ALD518, alemtuzumab (CAMPATH), altumomab, amatuximab, anatumomab, anrukinzumab, apolizumab, arcitumomab (CEA-SCAN), aselizumab, atlizumab (tocilizumab, Actemra, RoActemra), atorolimumab, bapineuzumab, basiliximab (Simulect), bavituximab, bectumomab (LYMPHOSCAN), belimumab (BENLYSTA), benralizumab, bertilimumab, besilesomab (SCINITIMUN), bevacizumab (AVASTIN), biciromab (FIBRISCINT), bivatuzumab, blinatumomab, brentuximab, briakinumab, canakinumab (ILARIS), cantuzumab, capromab, catumaxomab (REMOVAB), CC49, cedelizumab, certolizumab, cetuximab (ERBITUX), citatuzumab, cixutumumab, clenoliximab, clivatuzumab, conatumumab, CR6261, dacetuzumab, daclizumab (ZENAPAX), daratumumab, denosumab (PROLIA), detumomab, dorlimomab, dorlixizumab, ecromeximab, eculizumab (SOLIRIS), edobacomab, edrecolomab (PANOREX), efalizumab (RAPTIVA), efungumab (MYCOGRAB), elotuzumab, elsilimomab, enlimomab, epitumomab, epratuzumab, erlizumab, ertumaxomab (REXOMUN), etaracizumab (ABEGRIN), exbivirumab, fanolesomab (NEUTROSPEC), faralimomab, farletuzumab, felvizumab, fezakinumab, flgitumumab, fontolizumab (HuZAF), foravirumab, fresolimumab, galiximab, gantenerumab, gavilimomab, gemtuzumab, girentuximab, glembatumumab, golimumab (SIMPONI), gomiliximab, ibalizumab, ibritumomab, igovomab (INDIMACIS-125), imciromab (MYOSCINT), infliximab (REMICADE), intetumumab, inolimomab, inotuzumab, ipilimumab, iratumumab, keliximab, labetuzumab (CEA-CIDE), lebrikizumab, lemalesomab, lerdelimumab, lexatumumab, libivirumab, lintuzumab, lucatumumab, lumiliximab, mapatumumab, maslimomab, matuzumab, mepolizumab (BOSATRIA), metelimumab, milatuzumab, minretumomab, mitumomab, morolimumab, motavizumab (NUMAX), muromonab-CD3 (ORTHOCLONE OKT3), nacolomab, naptumomab, natalizumab (TYSABRI), nebacumab, necitumumab, nerelimomab, nimotuzumab (THERACIM), nofetumomab, ocrelizumab, odulimomab, ofatumumab (ARZERRA), olaratumab, omalizumab (XOLAIR), ontecizumab, oportuzumab, oregovomab (OVAREX), otelixizumab, pagibaximab, palivizumab (SYNAGIS), panitumumab (VECTIBIX), panobacumab, pascolizumab, pemtumomab (THERAGYN), pertuzumab (OMNITARG), pexelizumab, pintumomab, priliximab, pritumumab, PRO 140, raflvirumab, ramucimmab, ranibizumab (LUCENTIS), raxibacumab, regavirumab, reslizumab, rilotumumab, rituximab (RITUXAN), robatumumab, rontalizumab, rovelizumab (LEUKARREST), ruplizumab (ANTOVA), satumomab pendetide, sevirumab, sibrotuzumab, sifalimumab, siltuximab, siplizumab, solanezumab, sonepcizumab, sontuzumab, stamulumab, sulesomab (LEUKOSCAN), tacatuzumab (AFP-CIDE), tetraxetan, tadocizumab, talizumab, tanezumab, taplitumomab paptox, teflbazumab (AUREXIS), telimomab, tenatumomab, teneliximab, teplizumab, TGN1412, ticilimumab (tremelimumab), tigatuzumab, TNX-650, tocilizumab (atlizumab, ACTEMRA), toralizumab, tositumomab (BEXXAR), trastuzumab (HERCEPTIN), tremelimumab, tucotuzumab, tuvirumab, urtoxazumab, ustekinumab (STELERA), vapaliximab, vedolizumab, veltuzumab, vepalimomab, visilizumab (NUVION), volociximab (HU-MASPECT), votumumab, zalutumumab (HuMEX-EGFr), zanolimumab (HuMAX-CD4), ziralimumab and zolimomab.

In some embodiments, the antibodies are directed to cell surface markers for 5T4, CA-125, CEA, CDH6, CD3, CD19, CD20, CD22, CD30, CD33, CD40, CD44, CD51, CTLA-4, CEACAM5, EpCAM, HER2, EGFR (HER1), FAP, folate receptor, GCC (GUCY2C), HGF, integrin $\alpha_v\beta_3$, integrin $\alpha_5\beta_1$, IGF-1 receptor, GD3, GPNMB, mucin, LIV1, LY6E, mesothelin, MUC1, MUC13, PTK7, phosphatidylserine, prostatic carcinoma cells, PDGFR α, TAG-72, tenascin C, TRAIL-R2, VEGF-A and VEGFR2. In this embodiment the antibodies are abagovomab, adecatumumab, alacizumab, altumomab, anatumomab, arcitumomab, bavituximab, bevacizumab (AVASTIN), bivatuzumab, blinatumomab, brentuximab, cantuzumab, catumaxomab, capromab, cetuximab, citatuzumab, clivatuzumab, conatumumab, dacetuzumab, edrecolomab, epratuzumab, ertumaxomab, etaracizumab, farletuzumab, figitumumab, gemtuzumab, glembatumumab, ibritumomab, igovomab, intetumumab, inotuzumab, labetuzumab, lexatumumab, lintuzumab, lucatumumab, matuzumab, mitumomab, naptumomab estafenatox, necitumumab, oportuzumab, oregovomab, panitumumab, pemtumomab, pertuzumab, pritumumab, rituximab (RITUXAN), rilotumumab, robatumumab, satumomab, sibrotuzumab, taplitumomab, tenatumomab, tenatumomab, ticilimumab (tremelimumab), tigatuzumab, trastuzumab (HERCEPTIN), tositumomab, tremelimumab, tucotuzumab celmoleukin, volociximab and zalutumumab.

In specific embodiments the antibodies directed to cell surface markers for HER2 are pertuzumab or trastuzumab and for EGFR (HER1) the antibody is cetuximab or panitumumab; and for CD20 the antibody is rituximab and for VEGF-A is bevacizumab and for CD-22 the antibody is epratuzumab or veltuzumab and for CEA the antibody is labetuzumab.

Exemplary peptides or peptide mimics include integrin targeting peptides (RGD peptides), LHRH receptor targeting peptides, ErbB2 (HER2) receptor targeting peptides, prostate specific membrane bound antigen (PSMA) targeting peptides, lipoprotein receptor LRP1 targeting, ApoE protein derived peptides, ApoA protein peptides, somatostatin receptor targeting peptides, chlorotoxin derived peptides, and bombesin.

In specific embodiments the peptides or peptide mimics are LHRH receptor targeting peptides and ErbB2 (HER2) receptor targeting peptides Exemplary proteins comprise insulin, transferrin, fibrinogen-gamma fragment, thrombospondin, claudin, apolipoprotein E, Affibody molecules such as, for example, ABY-025, Ankyrin repeat proteins, ankyrin-like repeats proteins and synthetic peptides.

In some embodiments, the protein-drug conjugates comprise broad spectrum cytotoxins in combination with cell surface markers for HER2 such as pertuzumab or trastuzumab; for EGFR such as cetuximab and panitumumab; for CEA such as labetuzumab; for CD20 such as rituximab; for VEGF-A such as bevacizumab; or for CD-22 such as epratuzumab or veltuzumab.

In other embodiments, the protein-drug conjugates or protein conjugates used in the disclosure comprise combinations of two or more protein based recognition molecules, such as, for example, combination of bispecific antibodies directed to the EGF receptor (EGFR) on tumor cells and to CD3 and CD28 on T cells; combination of antibodies or antibody derived from Fab, Fab2, scFv or camel antibody heavy-chain fragments and peptides or peptide mimetics; combination of antibodies or antibody derived from Fab, Fab2, scFv or camel antibody heavy-chain fragments and proteins; combination of two bispecific antibodies such as CD3×CD19 plus CD28×CD22 bispecific antibodies.

In other embodiments, the protein-drug conjugates or protein conjugates used in the disclosure comprise protein based recognition molecules are antibodies against antigens, such as, for example, Trastuzumab, Cetuximab, Rituximab, Bevacizumab, Epratuzumab, Veltuzumab, Labetuzumab, B7-H4, B7-H3, CA125, CDH6, CD33, CXCR2, CEACAM5, EGFR, FGFR1, FGFR2, FGFR3, FGFR4, GCC (GUCY2C), HER2, LIV1, LY6E, NaPi2b, c-Met, mesothelin, NOTCH1, NOTCH2, NOTCH3, NOTCH4, PD-L1, PTK7, c-Kit, MUC1, MUC13, and 5T4.

In a specific embodiment, the protein-drug conjugates or protein conjugates of the disclosure comprise protein based recognition molecules which are antibodies against 5T4, such as, for example a humanized anti-5T4 scFvFc antibody.

Examples of suitable 5T4 targeting ligands or immunoglobulins include those which are commercially available, or have been described in the patent or non-patent literature, e.g., U.S. Pat. Nos. 8,044,178, 8,309,094, 7,514,546, EP1036091 (commercially available as TroVax™, Oxford Biomedica), EP2368914A1, WO 2013041687 A1 (Amgen), US 2010/0173382, and P. Sapra, et al., Mol. Cancer Ther. 2013, 12:38-47. An anti-5T4 antibody is disclosed in U.S. Provisional Application No. 61/877,439, filed Sep. 13, 2013 and U.S. Provisional Application No. 61/835,858, filed Jun. 17, 2013. The contents of each of the patent documents and scientific publications are herein incorporated by reference in their entireties.

As used herein, the term "5T4 antigen-binding portion" refers to a polypeptide sequence capable of selectively binding to a 5T4 antigen. In exemplary conjugates, the 5T4 antigen-binding portion generally comprises a single chain scFv-Fc form engineered from an anti-5T4 antibody. A single-chain variable fragment (scFv-Fc) is a fusion protein of the variable regions of the heavy (VH) and light chains (VL) of an immunoglobulin, connected with a linker peptide, and further connected to an Fc region comprising a hinge region and $CH_2$ and $CH_3$ regions of an antibody (any such combinations of antibody portions with each other or with other peptide sequences is sometimes referred to herein as an "immunofusion" molecule). Within such a scFvFc molecule, the scFv section may be C-terminally linked to the N-terminus of the Fc section by a linker peptide.

In other specific embodiments, the protein-drug conjugates or protein conjugates of the disclosure comprise protein based recognition molecules which are Her-2 or NaPi2b antibodies.

For example the Her-2 antibody suitable for the conjugate or scaffold of the disclosure comprises a variable heavy chain complementarity determining region 1 (CDRH1) comprising the amino acid sequence FTFSSYSMN (SEQ ID NO: 25); a variable heavy chain complementarity determining region 2 (CDRH2) comprising the amino acid sequence YISSSSSTIYYADSVKG (SEQ ID NO: 26); a variable heavy chain complementarity determining region 3 (CDRH3) comprising the amino acid sequence GGHGYFDL (SEQ ID NO: 27); a variable light chain complementarity determining region 1 (CDRL1) comprising the amino acid sequence RASQSVSSSYLA (SEQ ID NO: 28); a variable light chain complementarity determining region 2 (CDRL2) comprising the amino acid sequence GASSRAT (SEQ ID NO: 21); and a variable light chain complementarity determining region 3 (CDRL3) comprising the amino acid sequence QQYHHSPLT (SEQ ID NO: 29) (see, e.g., US20150366987(A1) published Dec. 24, 2015).

For example, the NaPi2b antibody suitable for the conjugate or scaffold of the disclosure comprises a variable light chain complementarity determining region 1 (CDRL1) comprising the amino acid sequence SASQDIGNFLN (SEQ ID NO: 8); a variable light chain complementarity determining region 2 (CDRL2) comprising the amino acid sequence YTSSLYS (SEQ ID NO: 9); a variable light chain complementarity determining region 3 (CDRL3) comprising the amino acid sequence QQYSKLPLT (SEQ ID NO: 10); a variable heavy chain complementarity determining region 1 (CDRH1) comprising the amino acid sequence GYTFTGYNIH (SEQ ID NO: 5); a variable heavy chain complementarity determining region 2 (CDRH2) comprising the amino acid sequence AIYPGNGDTSYKQKFRG (SEQ ID NO: 6); and a variable heavy chain complementarity determining region 3 (CDRH3) comprising the amino acid sequence GETARATFAY (SEQ ID NO: 7) (see, e.g., co-pending application U.S. Ser. No. 15/457,574 filed Mar. 13, 2017).

PBRM-Drug Conjugates

Conjugates of the disclosure comprise one or more occurrences of D, where D is a therapeutic agent, e.g., a drug, wherein the one or more occurrences of D may be the same or different.

In certain other embodiments, one or more occurrences of PBRM is attached to the Linker-Drug moiety, wherein the one or more occurrences of PBRM may be the same or different. In certain other embodiments, one or more Linker-Drug moieties that contains one or more occurrences of D are connected to one PBRM (e.g., an antibody).

In one embodiment, D is a) an auristatin compound; (b) a calicheamicin compound; (c) a duocarmycin compound; (d) a topoisomerase inhibitor, (e) a pyrrolobenzodiazepine compound; (f) a vinca compound; (g) a protein synthesis inhibitor; (h) a RNA polymerase inhibitor; (i) a tubulin binding compound; (j) a NAMPT inhibitor or an analog thereof.

In certain embodiment, D is (a) an auristatin compound; (b) a calicheamicin compound; (c) a duocarmycin compound; (d) a camptothecin compound, (e) a pyrrolobenzodiazepine compound; (f) a vinca compound; or an analog thereof.

For example, the auristatin compound is auristatin, dolastatin, monomethylauristatin E (MMAE), monomethylauristatin F (MMAF), auristatin F, AF HPA, MMAF HPA, or phenylenediamine (AFP).

For example, the duocarmycin or an analog thereof is duocarmycin A, duocarmycin B1, duocarmycin B2, duocarmycin C1, duocarmycin C2, duocarmycin D, duocarmycin SA, CC-1065, adozelesin, bizelesin, or carzelesin.

For example, the camptothecin compound is camptothecin, CPT-11 (irinotecan), SN-38, ortopotecan.

For example, the pyrrolobenzodiazepine compound is a pyrrolobenzodiazepine monomer, a symmetrical pyrrolobenzodiazepine dimer or an unsymmetrical pyrrolobenzodiazepine dimer.

The PBRM-drug conjugate of the disclosure comprise a PBRM that has a molecular weight of about 40 kDa or greater (e.g., 60 kDa or greater; 80 kDa or greater; 100 kDa or greater; 120 kDa or greater; 140 kDa or greater; 160 kDa or greater; 180 kDa or greater; or 200 kDa or greater, or about 40-200 kDa, 40-180 kDa, 40-140 kDa, 60-200 kDa, 60-180 kDa, 60-140 kDa, 80-200 kDa, 80-180 kDa, 80-140 kDa, 100-200 kDa, 100-180 kDa, or 100-140 kDa).

For example, the PBRM has a molecular weight of about 40 kDa or greater (e.g., 60 kDa or greater; 80 kDa or greater; 100 kDa or greater; 120 kDa or greater; 140 kDa or greater; 160 kDa or greater; 180 kDa or greater; or 200 kDa or greater, or about 40-200 kDa, 40-180 kDa, 40-140 kDa, 60-200 kDa, 60-180 kDa, 60-140 kDa, 80-200 kDa, 80-180 kDa, 80-140 kDa, 100-200 kDa, 100-180 kDa, or 100-140 kDa) and has a sulfhydryl (i.e., —SH or thiol) group.

For example, the total number of sulfide bonds formed between the PHF and the PBRM (or total number of attachment points) is 10 or less.

For example, for conjugation with one or more Linker-Drug moieties, the PBRM has a molecular weight of 40 kDa or greater (e.g., 60 kDa or greater, 80 kDa or greater, 100 kDa or greater, 120 kDa or greater, 140 kDa or greater, 160 kDa or greater or 180 kDa or greater, or about 40-200 kDa, 40-180 kDa, 40-140 kDa, 60-200 kDa, 60-180 kDa, 60-140 kDa, 80-200 kDa, 80-180 kDa, 80-140 kDa, 100-200 kDa, 100-180 kDa, or 100-140 kDa For example, for conjugation with one or more Linker-Drug moieties, the PBRM has a molecular weight of 40 kDa to 200 kDa.

For example, for conjugation with one or more Linker-Drug moieties, the PBRM has a molecular weight of 40 kDa to 80 kDa.

PBRMs in this molecular weight range include, but are not limited to, for example, antibody fragments, such as, for example, Fabs.

For example, for conjugation with one or more Linker-Drug moieties, the PBRM has a molecular weight of 60 kDa to 120 kDa.

PBRMs in this molecular weight range include, but are not limited to, for example, camelids, Fab2, scFvFc, and the like.

For example, for conjugation with one or more Linker-Drug moieties, the PBRM has a molecular weight of 140 kDa to 180 kDa.

PBRMs in this molecular weight range include, but are not limited to, for example, full length antibodies, such as, IgG, IgM.

These targeting ligands, the linkers and the drug or prodrug fragments described herein can be assembled into the conjugate or scaffold of the disclosure, for example according to the disclosed techniques and methods. Therapeutic and targeting conjugates of the disclosure, and methods for producing them, are described below by way of non-limiting example.

For example, the total number of sulfide bonds formed between the Linker-Drug moiety and the PBRM (or total number of attachment points) is 14 or less.

For example, the ratio between the Linker-Drug moiety and the PBRM is greater than 1:1 and less than or equal to 14:1.

For example, the ratio between Linker-Drug moiety is about 14:1, 12:1, 13:1, 12:1, 11:1, 10;1, 9:1, 8:1, 7:1, 6:1, 5:1, 4:1, 3:1, or 2:1.

For example, the ratio between Linker-Drug moiety and the PBRM is between 2:1 and 10:1.

For example, the ratio between Linker-Drug moiety and the PBRM is about 10:1, 9:1, 8:1, 7:1, 6:1, 5:1, 4:1, 3:1, or 2:1.

For example, the ratio between Linker-Drug moiety and the PBRM is between 2:1 and 4:1.

For example, the ratio between Linker-Drug moiety and the PBRM is about 4:1, 3:1, or 2:1.

In some embodiments, the Linker-Drug moiety is conjugated with PBRMs by utilizing cysteine-based bioconjugation strategy. See, e.g., WO2010100430 and U.S. Pat. No. 7,595,292, the contents of which are hereby incorporated by reference in their entireties. In one embodiment, one or more Linker-Drug moieties conjugate with a PBRM (e.g., an antibody) via cysteines in the antibody hinge region. Without wishing to be bound by the theory, the resulting conjugate is stabilized through the formation of inter-chain bridge structures.

Accordingly, the disclosure also relates to a Linker-Drug moiety comprising at least two moieties, in which each moiety is capable of conjugation to a thiol group from an amino acid (e.g., cysteine) in a PBRM so as to form a protein-Linker-Drug conjugate.

In embodiments, one or more free thiol groups of a PBRM are produced by reducing a protein. The one or more free thiol groups of the PBRM then react with one or more Linker-Drug moieties that are capable of conjugation to a thiol group from an amino acid so as to conjugate the PBRM with the Linker-Drug moiety. In one embodiment, the at least two moieties connected to the PBRM are maleimide groups.

In embodiments, the free thiol groups of the PBRM that are used for the conjugation are derived from a disulfide bridge of a native protein or a disulfide bridge of a protein complex consisting of two or more protein chains connected by the disulfide bridge. A disulfide bridge may be intrachain or interchain bridge. Alternatively, the free thiol groups of the PBRM are cysteines or the unpaired thiol groups of the native protein that are not involved in inter or intra disulfide bridge formation.

Disulfide bonds can be reduced, for example, with dithiothreitol, mercaptoethanol, tris-carboxyethylphosphine, dehydroascorbic acid, copper sulfate, using conventional methods. A protein can contain one or more disulfide bridges. Reduction to give free thiol groups can be controlled to reduce one or more specific disulfide bridges in a protein. Depending on the extent of disulfide reduction and the stoichiometry of the moieties on the Linker-Drug moiety, it is possible to conjugate one or more Linker-Drug moieties to the protein. Immobilized reducing agents may be used if it is desired to reduce less than the total number of disulfides, as can partial reduction using different reaction conditions or the addition of denaturants.

For example, for conjugating of the Linker-Drug moiety, a PBRM has a molecular weight of 40 kDa or greater (e.g., 60 kDa or greater; 80 kDa or greater; or 100 kDa or greater; 120 kDa or greater; 140 kDa or greater; 160 kDa or greater or 180 kDa or greater). In this embodiment the ratio of PBRM per Linker-Drug moiety is between about 1:1 and about 1:10, between about 1:1 and about 1:9, between about 1:1 and about 1:8, between about 1:1 and about 1:7, between about 1:1 and about 1:6, between about 1:1 and about 1:5, between about 1:1 and about 1:4, between about 1:1 and about 1:3, between about 1:1 and about 1:2, between about 1:2 and about 1:6, between about 1:2 and about 1:5, between about 1:2 and about 1:4 or between about 1:2 and about 1:3.

PBRMs in this molecular weight range include, but are not limited to, for example, full length antibodies, such as, IgG, IgM.

For example, for conjugation with one or more Linker-Drug moieties a PBRM has a molecular weight of 60 kDa to 120 kDa. In this embodiment the ratio of PBRM per Linker-Drug moiety is between about 1:1 and about 1:10, between about 1:1 and about 1:9, between about 1:1 and about 1:8, between about 1:1 and about 1:7, between about 1:1 and about 1:6, between about 1:1 and about 1:5, between about 1:1 and about 1:4, between about 1:1 and about 1:3, between about 1:1 and about 1:2, between about 1:2 and about 1:6, between about 1:2 and about 1:5, between about 1:2 and about 1:4 or between about 1:2 and about 1:3.

PBRMs in this molecular weight range include, but are not limited to, for example, antibody fragments such as, for example Fab2, scFcFv and camelids.

For example, for conjugation with one or more Linker-Drug moieties a PBRM has a molecular weight of 40 kDa to 80 kDa. In this embodiment the ratio of PBRM per Linker-Drug moiety is between about 1:1 and about 1:10, between about 1:1 and about 1:9, between about 1:1 and about 1:8, between about 1:1 and about 1:7, between about 1:1 and about 1:6, between about 1:1 and about 1:5, between about 1:1 and about 1:4, between about 1:1 and about 1:3, between about 1:1 and about 1:2, between about 1:2 and about 1:6, between about 1:2 and about 1:5, between about 1:2 and about 1:4 or between about 1:2 and about 1:3.

PBRMs in this molecular weight range include, but are not limited to, for example, antibody fragments, such as, Fabs.

In another aspect, the disclosure features a scaffold useful to conjugate with either or both of a protein based recognition-molecule (PBRM) and a therapeutic agent (D), e.g., the scaffold of any of Formulae (II)-(IX) disclosed herein.

In some embodiments, the drug-carrying scaffolds (i.e., without linking to a PBRM), described herein each typically have a polydispersity index (PDI) of 1.

Conjugates and scaffolds disclosed herein can be purified (i.e., removal of any starting materials) by extensive diafiltration. If necessary, additional purification by size exclusion chromatography can be conducted to remove any aggregated conjugates. In general, the conjugates as purified typically contain less than 5% (e.g., <2% w/w) aggregated conjugates as determined by SEC; less than 0.5% (e.g., <0.1% w/w) free (unconjugated) drug as determined by RP-HPLC; less than 1% drug carrying-peptide-containing scaffolds as determined by SEC and less than 2% (e.g., <1% w/w) unconjugated PBRM as determined by HIC-HPLC.

Tables B and C below provide examples of the drug carrying-peptide-containing scaffolds and the conjugates of the disclosure respectively.

TABLE B

| Scaffold No. | Structure |
|---|---|
| Scaffold No. 7 Example 1 | (structure) |
| Scaffold No. 17 Example 2 | (structure) |
| Scaffold No. 24 Example 6 | (structure) |

TABLE B-continued
| Scaffold No. | Structure |
|---|---|
| | 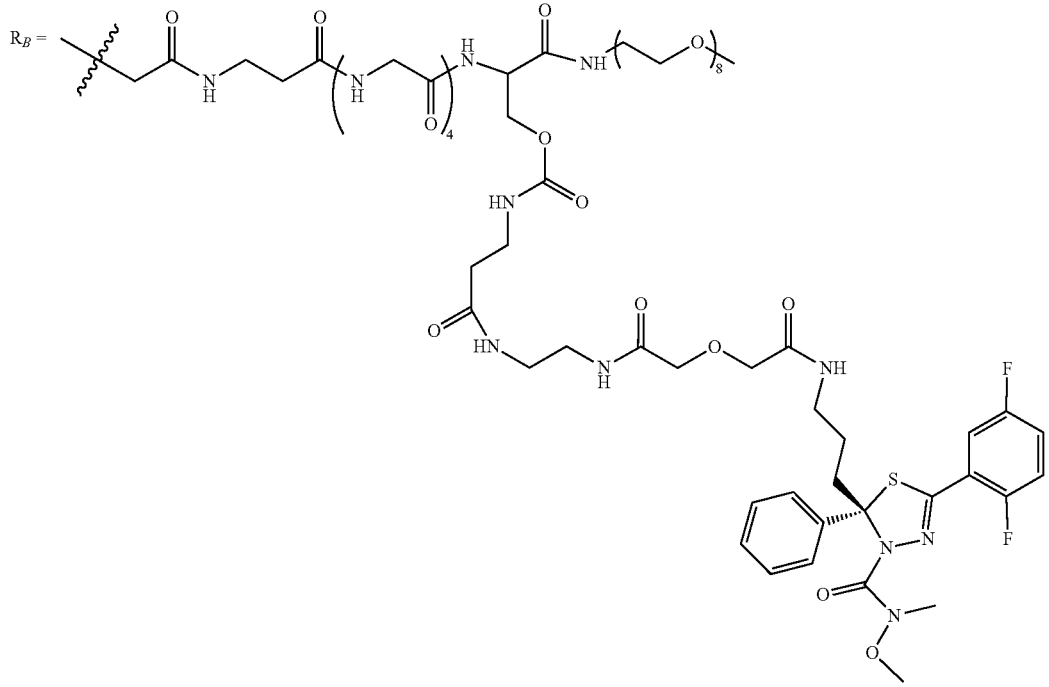 |
| Scaffold No. 27 Example 8 | 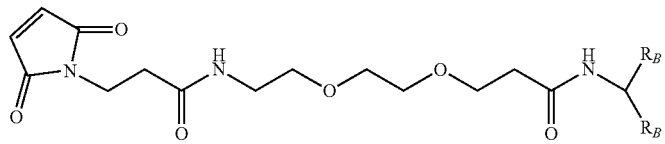<br>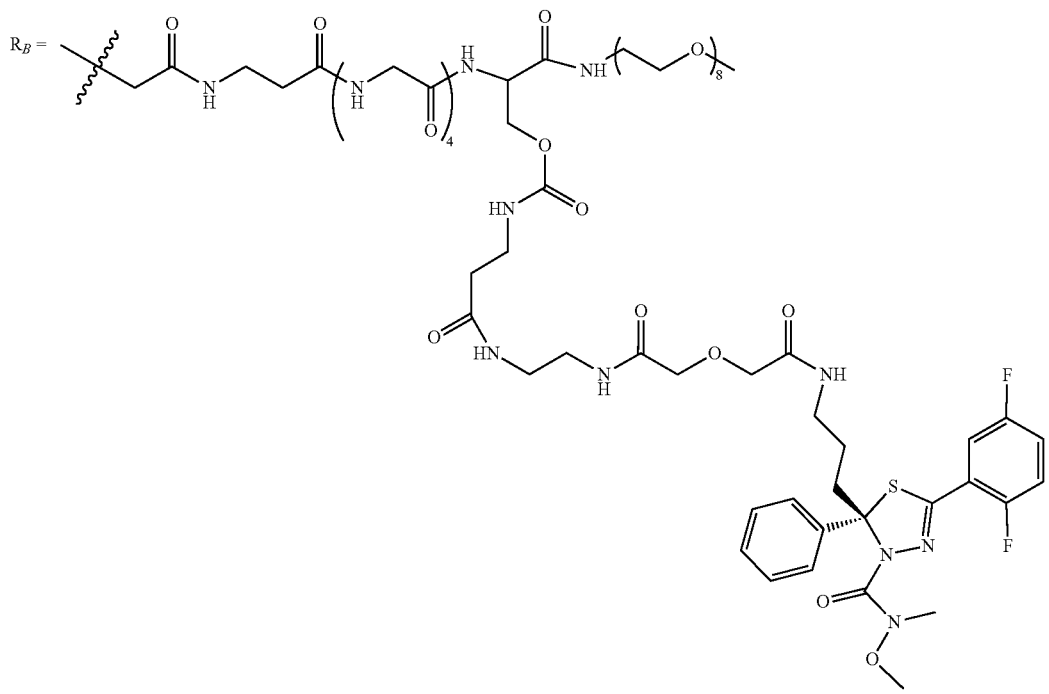 |

TABLE B-continued
| Scaffold No. | Structure |
|---|---|
| Scaffold No. 30 Example 10 | 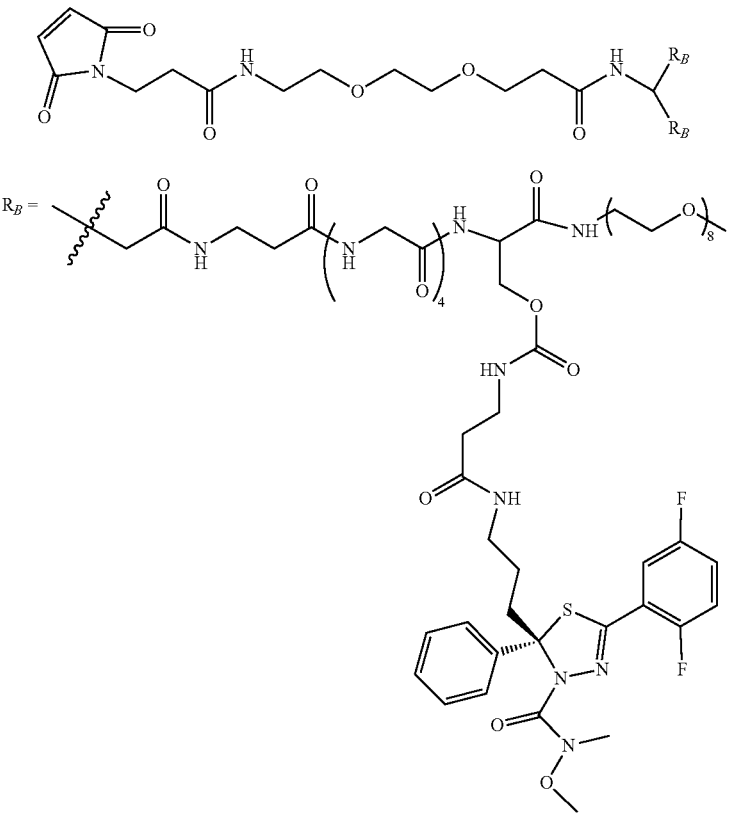 |
| Scaffold No. 33 Example 12 | 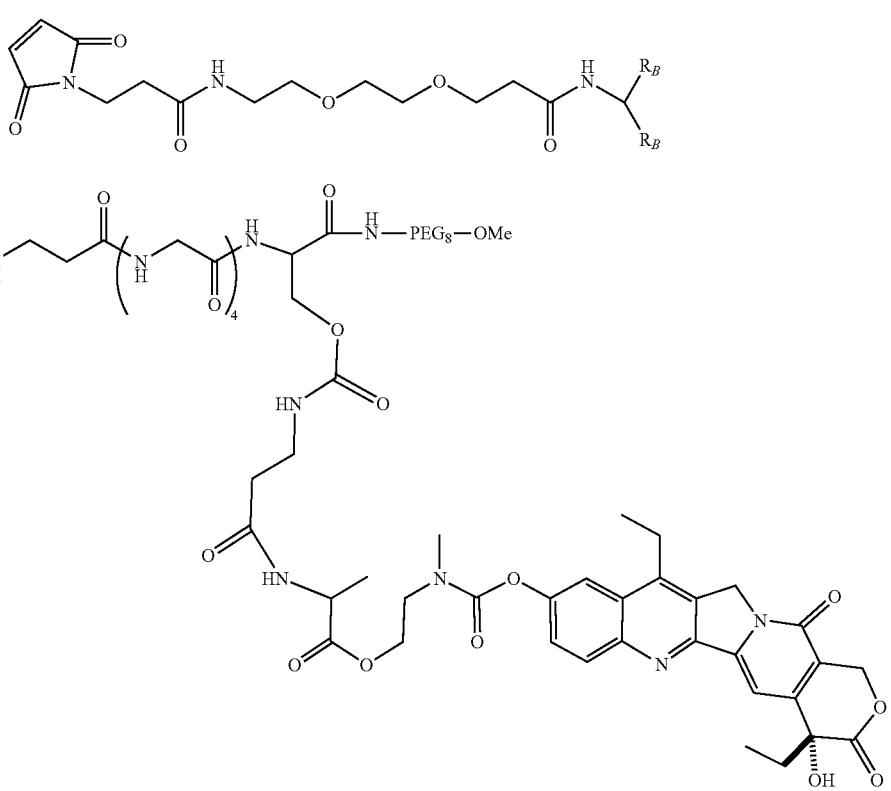 |

TABLE B-continued

| Scaffold No. | Structure |
|---|---|
| Scaffold No 42 Example 17 | (chemical structure) |
| Scaffold No 45 Example 19 | (chemical structure) |

TABLE B-continued

| Scaffold No. | Structure |
|---|---|
| Scaffold No. 47 Example 21 | (chemical structure) |
| Scaffold No. 49 Example 22 | (chemical structure) |

TABLE B-continued

| Scaffold No. | Structure |
|---|---|
| Scaffold No. 51 Example 23 | (chemical structure) |
| Scaffold No. 54 Example 25 | (chemical structure) |
| Scaffold No. 56 Example 26 | (chemical structure) |

TABLE B-continued

| Scaffold No. | Structure |
|---|---|
| | $R_A$ = [structure showing PEG-linked peptide with serine, β-alanine, aspartic acid with CO₂H, alanine ester linked to propyl carbamate, phenylalanine, N-methyl amino acid with OMe, proline, N-methyl amino acid with OMe, N-methyl valine, N,N-dimethyl valine — auristatin-type payload] |
| Scaffold No. 58 Example 27 | [Maleimide-(CH₂)₂-C(O)-NH-CH₂CH₂-(O-CH₂CH₂)₂-O-CH₂CH₂-NH-C(O)-CH₂CH₂-C(O)-NH-CH₂-C(O)-NH-CH(R_A)(R_A)] |
| | $R_A$ = [structure with -O-CH₂CH₂-C(O)-NH-β-Ala-[Gly]₄-Ser-NH-(CH₂CH₂O)₁₂- with serine side chain carbamate to β-Ala-Glu(CO₂H)-NH-C(O)-Ala ester linked to propyl carbamate-Phe-MeOAla-Pro-MeOAla-N-Me-Val-N,N-Me₂-Val (auristatin payload)] |
| Scaffold No. 60 Example 28 | [Maleimide-(CH₂)₂-C(O)-NH-CH₂CH₂-(O-CH₂CH₂)₂-O-CH₂CH₂-NH-C(O)-CH₂CH₂-C(O)-NH-CH₂-C(O)-NH-CH(R_A)(R_A)] |

TABLE B-continued
| Scaffold No. | Structure |
|---|---|
| | 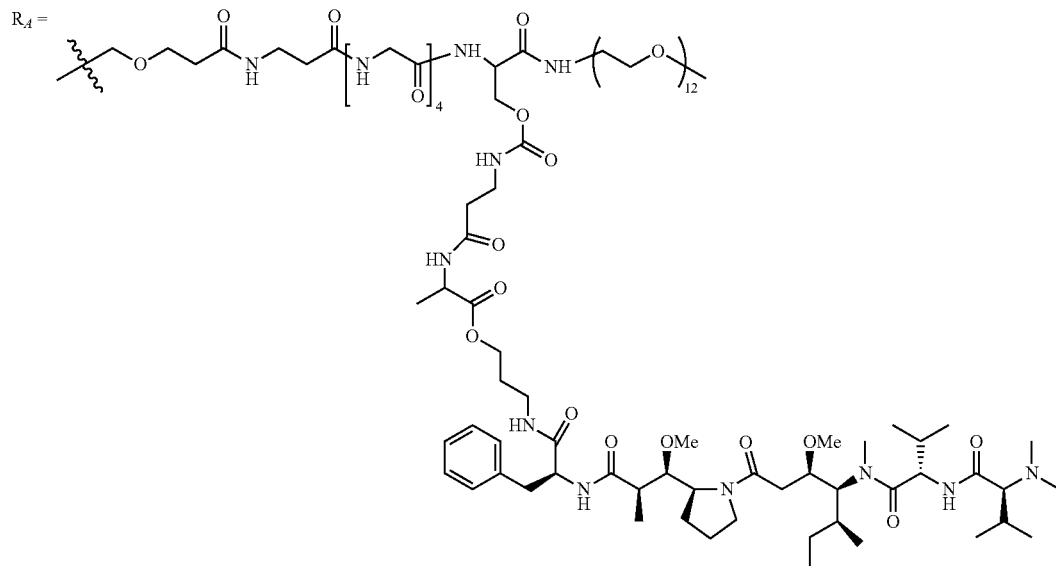 |
| Scaffold No. 65 Example 29 | 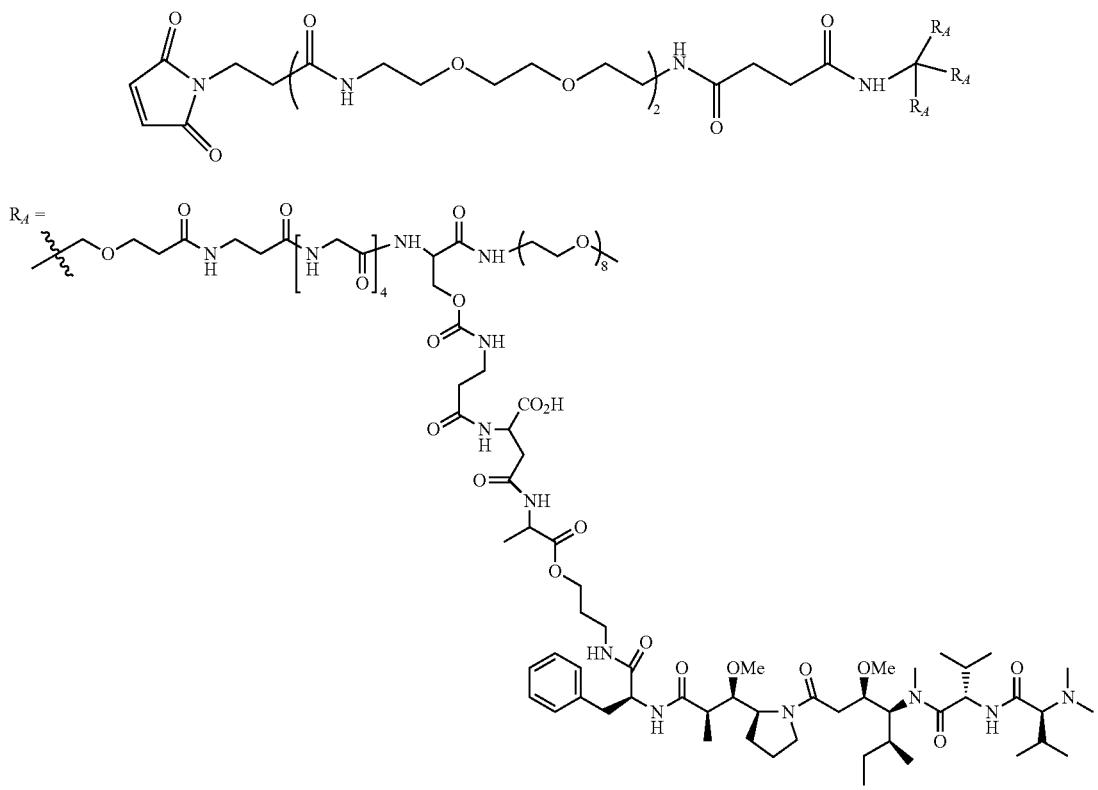 |
| | 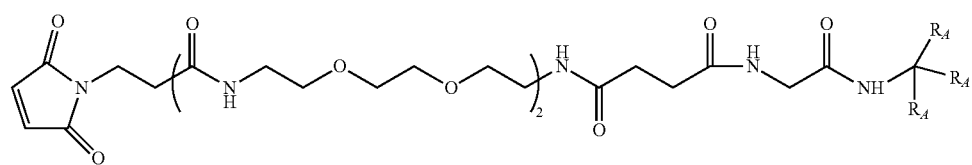 |

TABLE B-continued
| Scaffold No. | Structure |
|---|---|
| | $R_A =$ 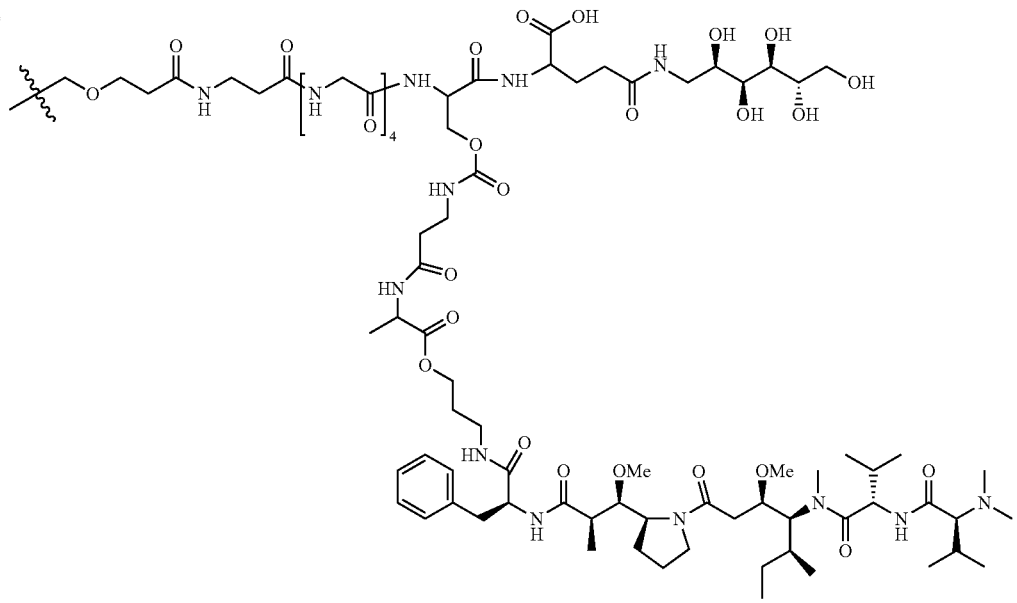 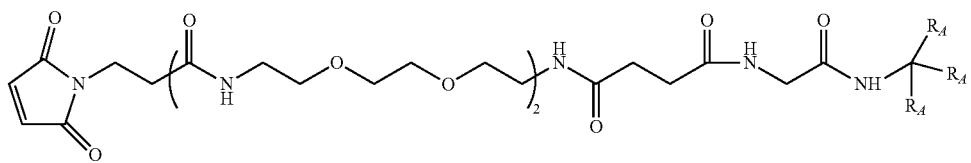 |
| | $R_A =$ 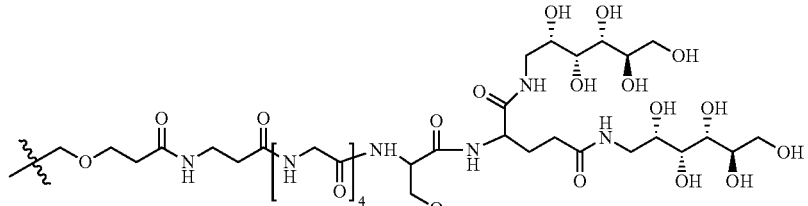 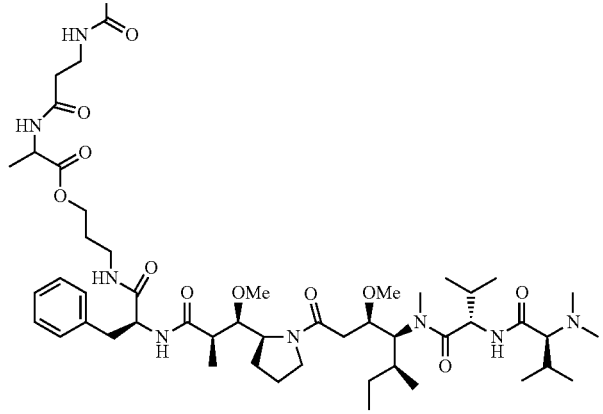 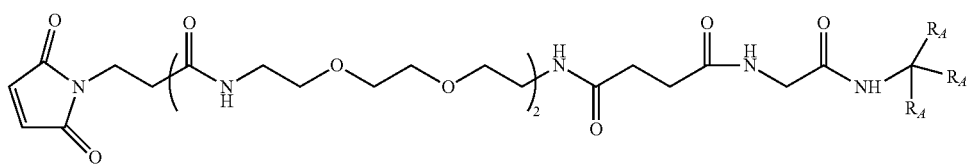 |

TABLE B-continued

| Scaffold No. | Structure |
|---|---|
| | |
| Scaffold No. 75 Example 32 Example 36 | 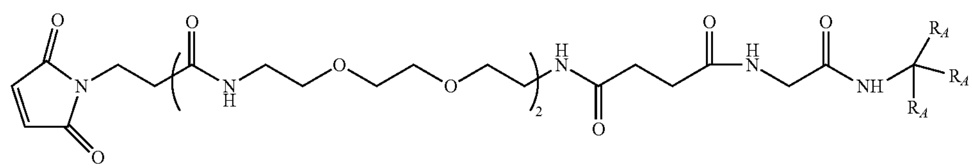 |
| Scaffold No. 77 Example 33 | 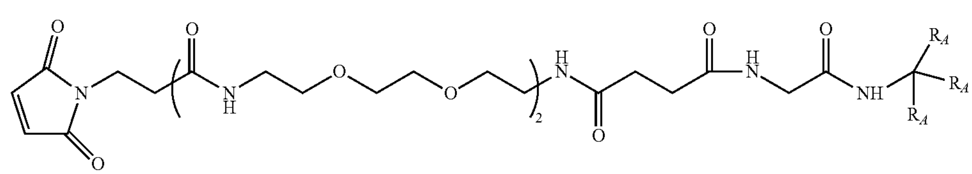 |

TABLE B-continued
| Scaffold No. | Structure |
|---|---|
| | $R_A =$ 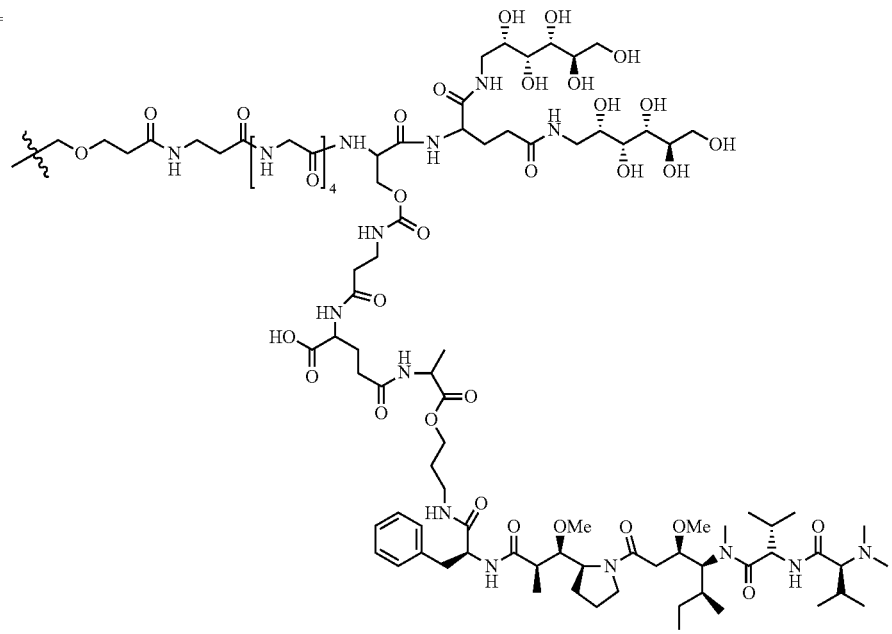 |
| Scaffold No. 84 Example 38 | 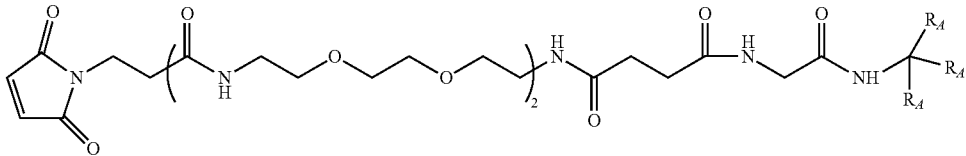 |
| | $R_A =$ 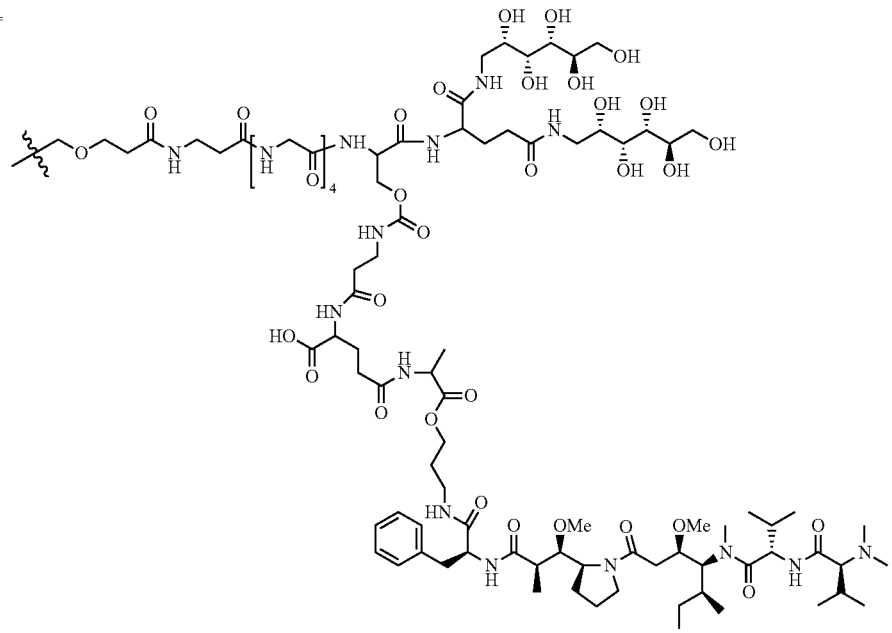 |

TABLE C

| Conjugate No. | Structure |
|---|---|
| Conjugate No. 25 Example 7 | Trastuzumab-S-[maleimide]-C(O)-NH-CH₂CH₂-O-CH₂CH₂-O-CH₂CH₂-C(O)-NH-CH(R_B)(R_B) |

$R_B$ = [structure showing peptide linker with β-alanine, (CH₂)₄, serine with carbamate branch, PEG₈, and a thiadiazole-containing payload bearing 2,5-difluorophenyl, phenyl, and N-methoxy-N-methylcarbamoyl groups]

| Conjugate No. 28 Example 9 | Trastuzumab-S-[maleimide]-C(O)-NH-CH₂CH₂-O-CH₂CH₂-O-CH₂CH₂-C(O)-NH-CH(R_B)(R_B) |

TABLE C-continued

| Conjugate No. | Structure |
|---|---|
| | $R_B$ = [structure showing linker with PEG8, serine carbamate, beta-alanine, ethylenediamine, oxyacetamide, and thiadiazole-containing drug with 2,5-difluorophenyl and N-methoxy-N-methylcarbamate groups] |
| Conjugate No. 31 Example 11 | Trastuzumab—S—[maleimide]—C(O)—NH—CH₂CH₂—O—CH₂CH₂—O—CH₂CH₂CH₂—NH—CH(R_B)(R_B) <br><br> $R_B$ = [structure showing linker with PEG8, serine carbamate, beta-alanine amide connected to propyl-thiadiazole bearing phenyl, 2,5-difluorophenyl, and N-methoxy-N-methylcarbamate] |

TABLE C-continued

| Conjugate No. | Structure |
|---|---|
| Conjugate No. 34 Example 13 | (structure image) |
| Conjugate No. 43 Example 18 | (structure image) |

TABLE C-continued
| Conjugate No. | Structure |
|---|---|
| Conjugate No. 46 Example 20 | 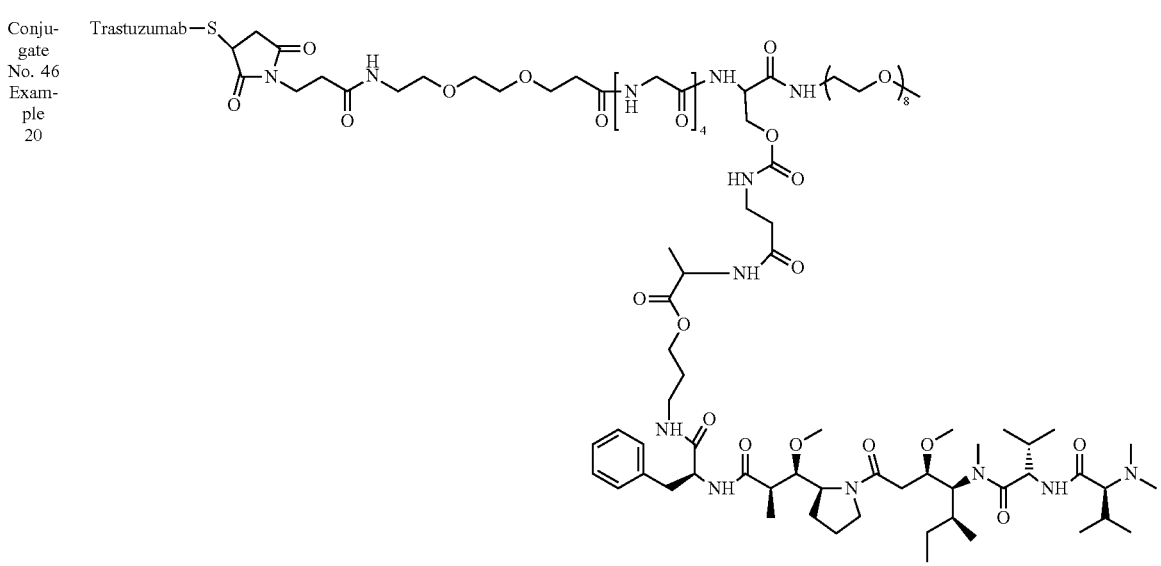 |
| Conjugate No. 48 Example 21 | 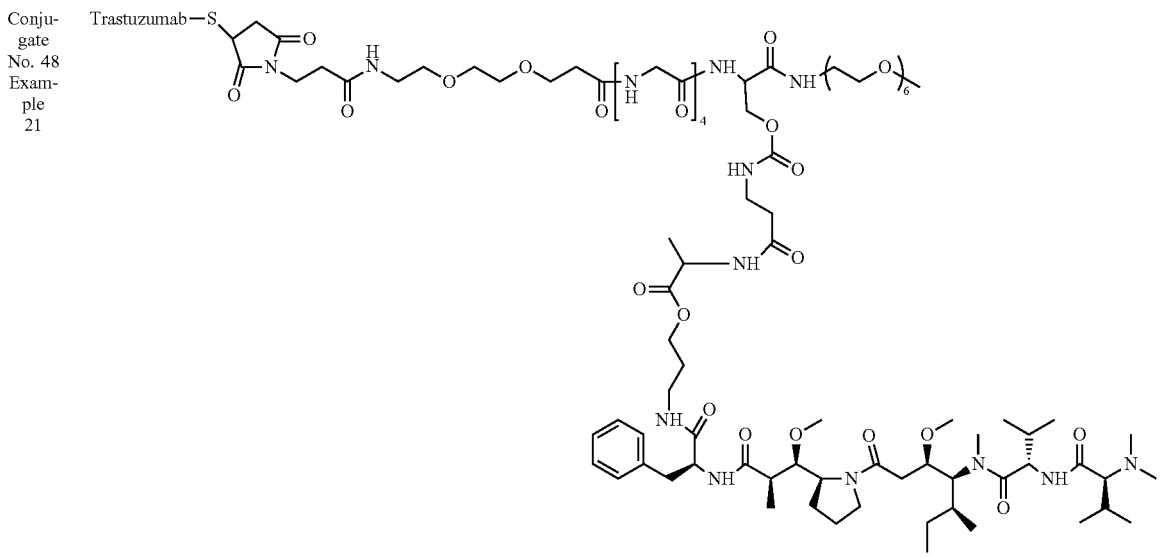 |

TABLE C-continued
| Conjugate No. | Structure |
|---|---|
| Conjugate No. 50 Example 22 | 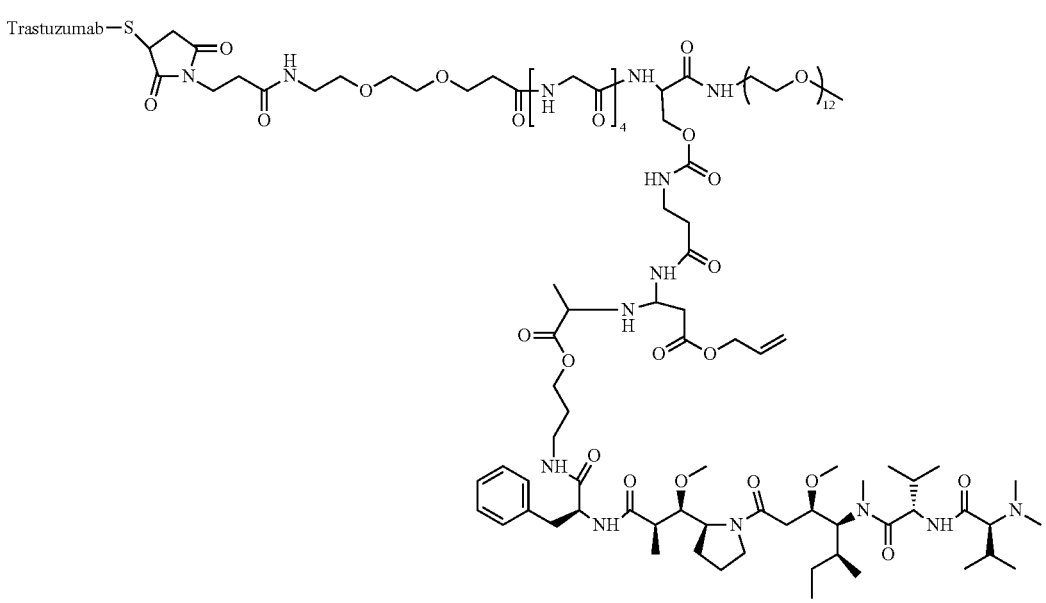 |
| Conjugate No. 52 Example 23 | 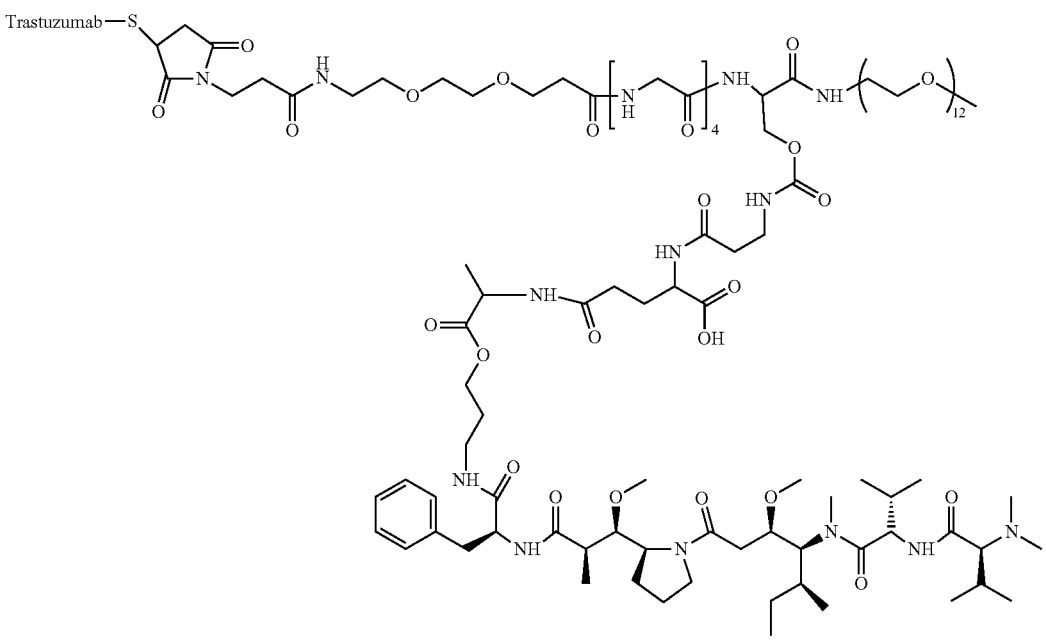 |
| Conjugate No. 53 Example 24 | 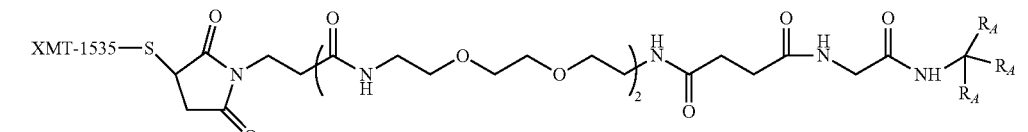 |

TABLE C-continued
| Conjugate No. | Structure |
|---|---|
| | $R_A =$ 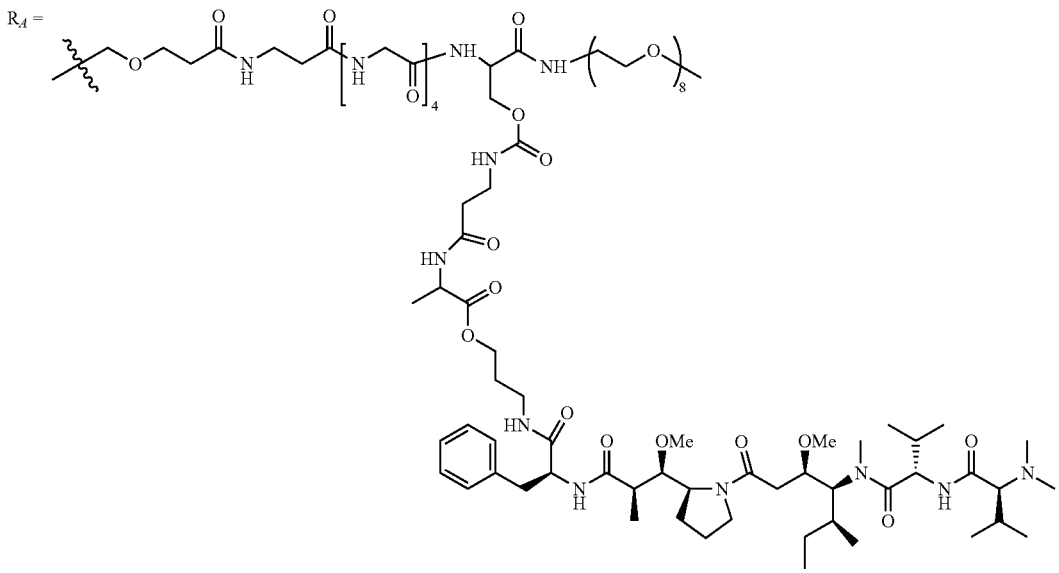 |
| Conjugate No. 55 Example 25 | 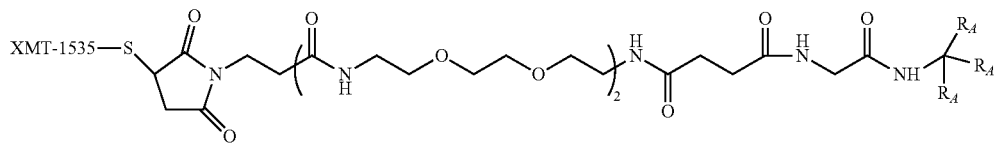 |
| | $R_A =$ 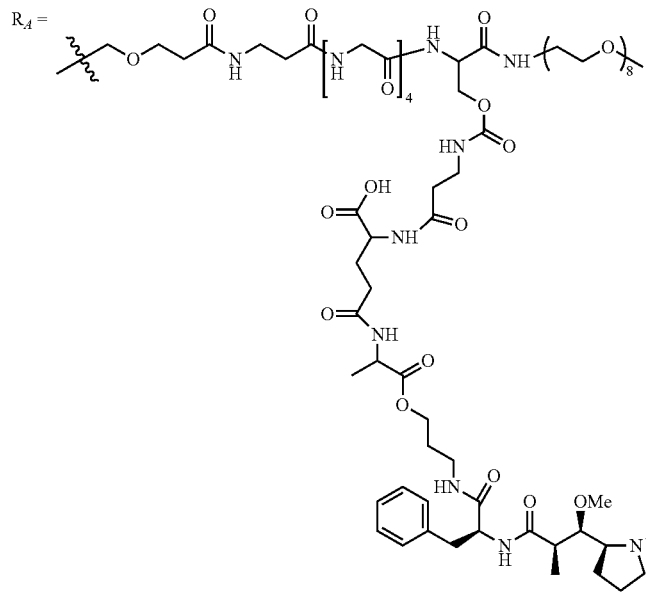 |
| Conjugate No. 57 Example 26 | 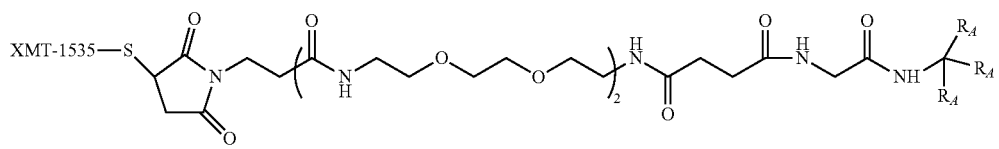 |

| Conjugate No. | Structure |
|---|---|
| | 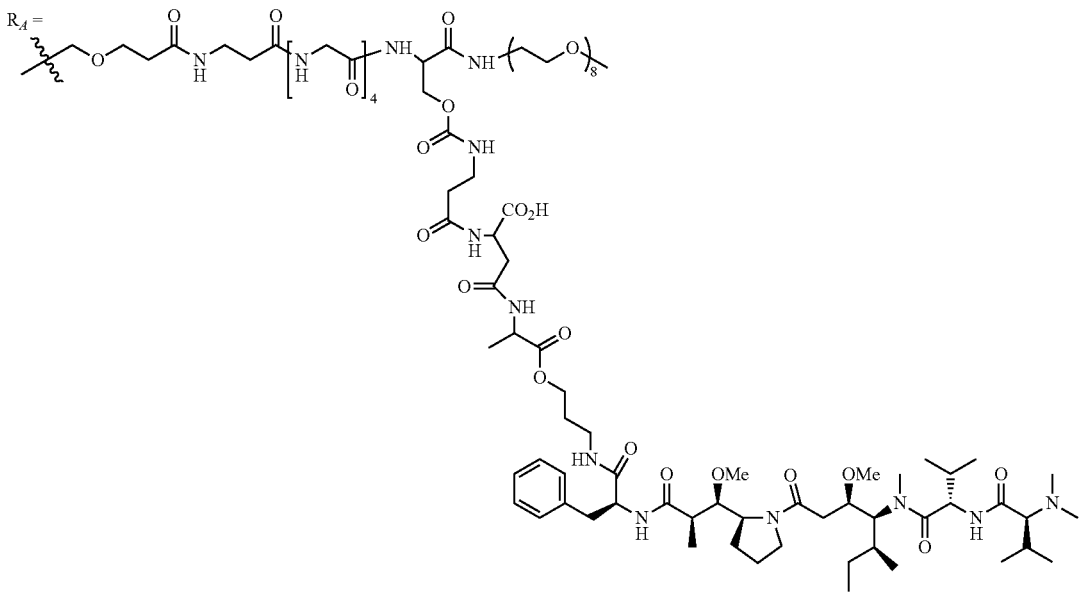 |
| Conjugate No. 59 Example 27 | 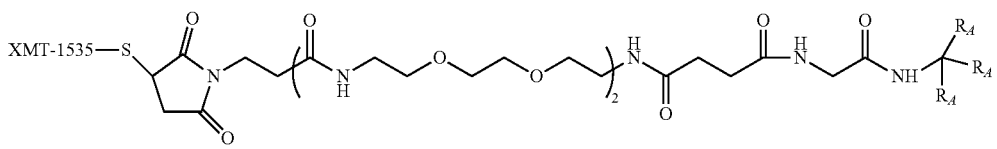 |
| | 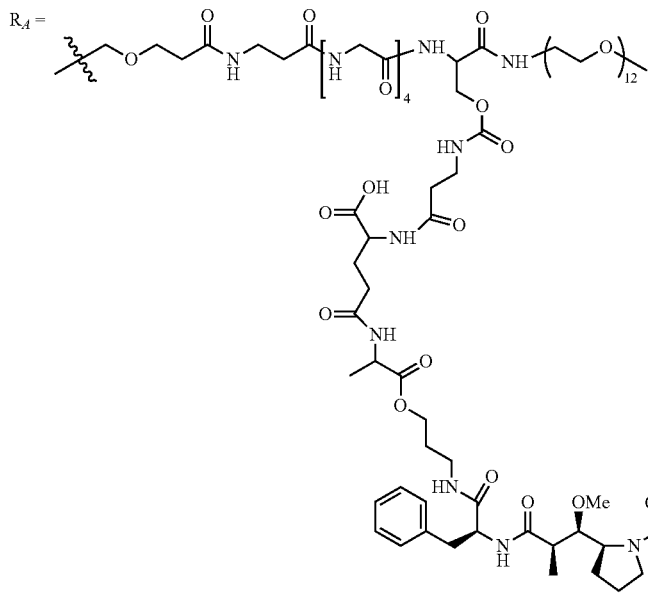 |
| Conjugate No. 61 Example 28 | 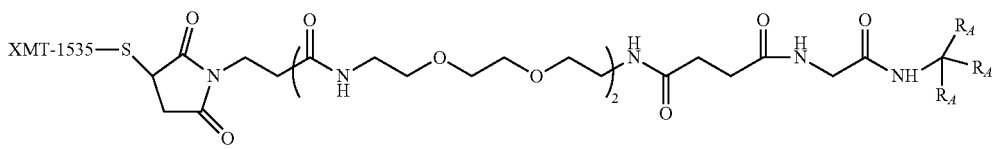 |

TABLE C-continued
| Conjugate No. | Structure |
|---|---|
| | $R_A =$ 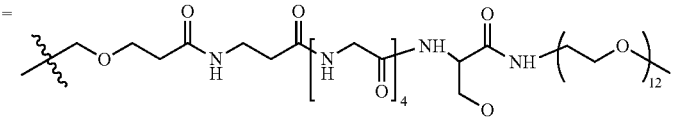 |
| Conjugate No. 66 Example 29 | 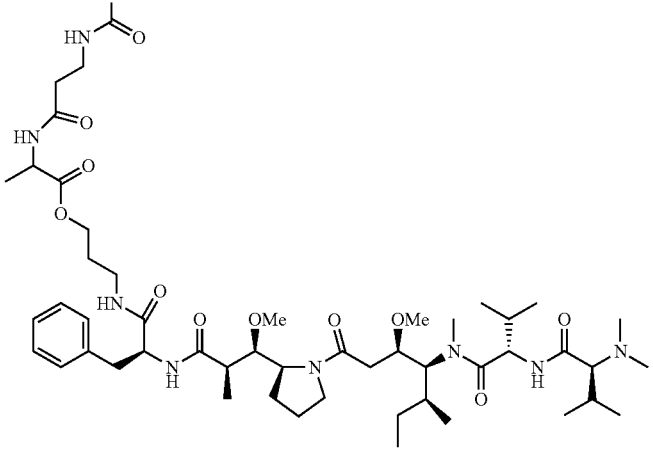 |
| Conjugate 79, Example 35 | $R_A =$ 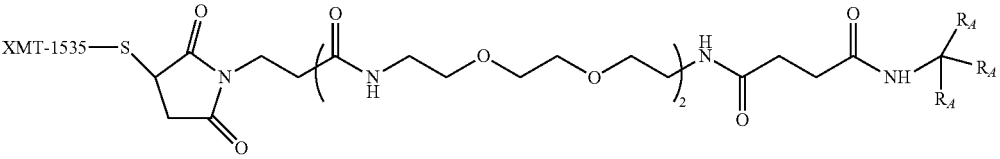 |
| Conjugate No. 67 Example 30 | 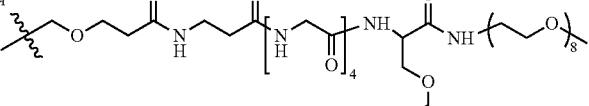 |

TABLE C-continued
| Conjugate No. | Structure |
|---|---|
| | $R_A =$ 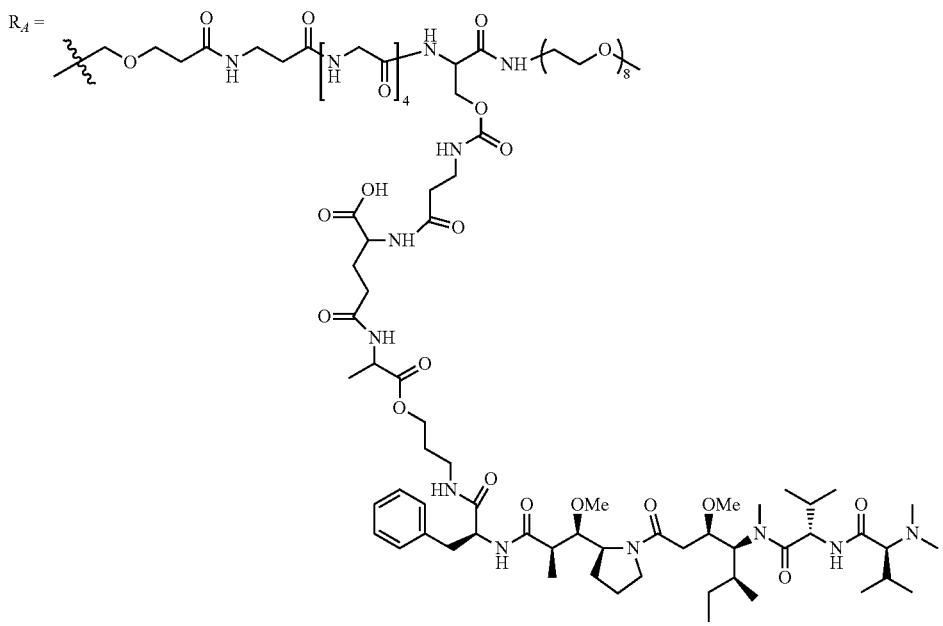 |
| Conjugate No. 68 Example 31 | 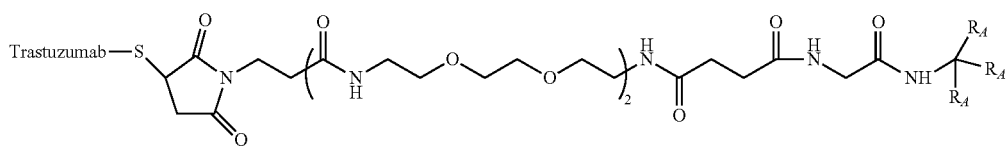 |
| | $R_A =$ 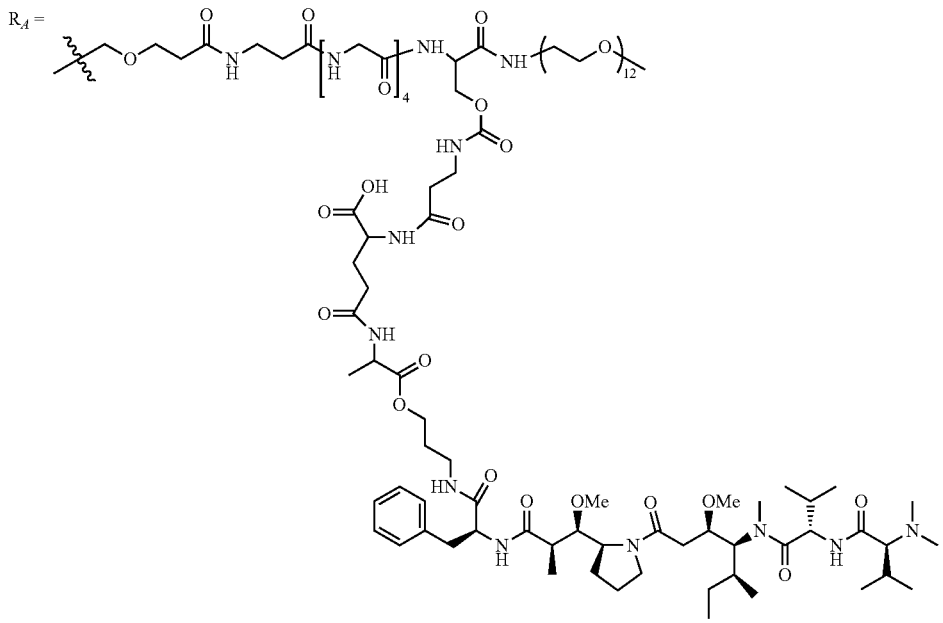 |
| | 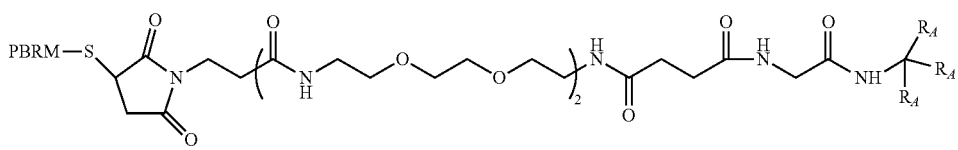 |

TABLE C-continued

| Conjugate No. | Structure |
|---|---|

(Chemical structures only)

TABLE C-continued
| Conjugate No. | Structure |
|---|---|
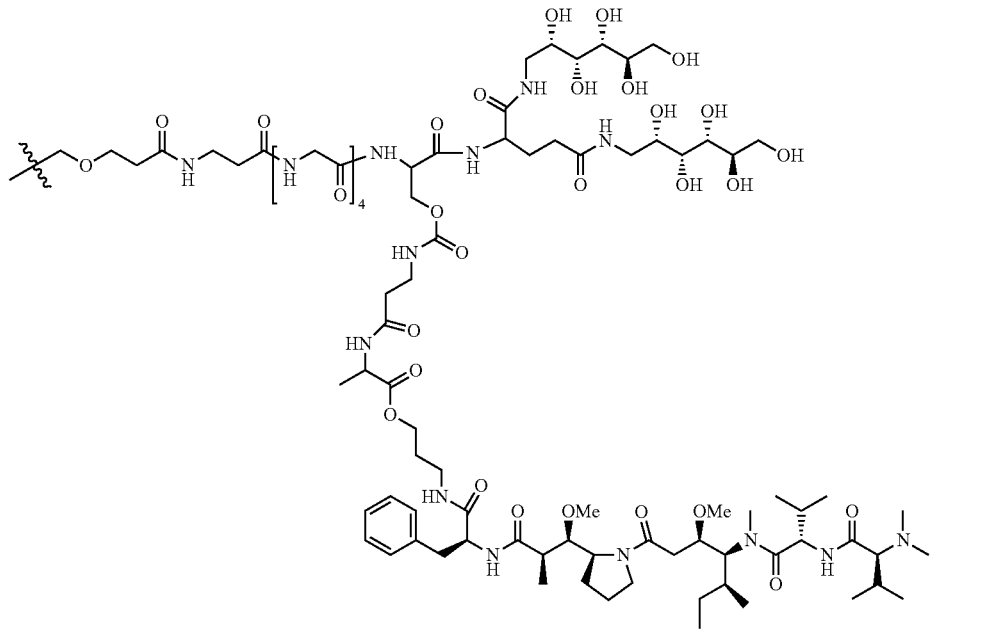
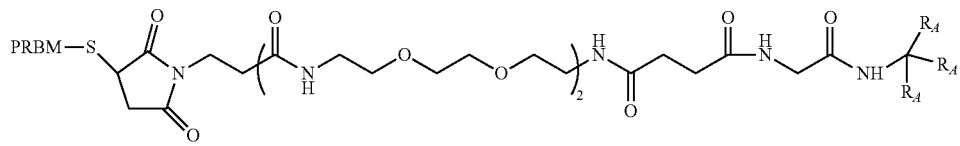
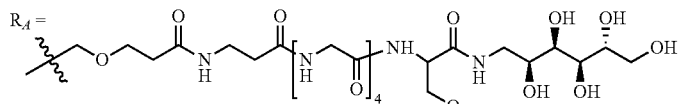
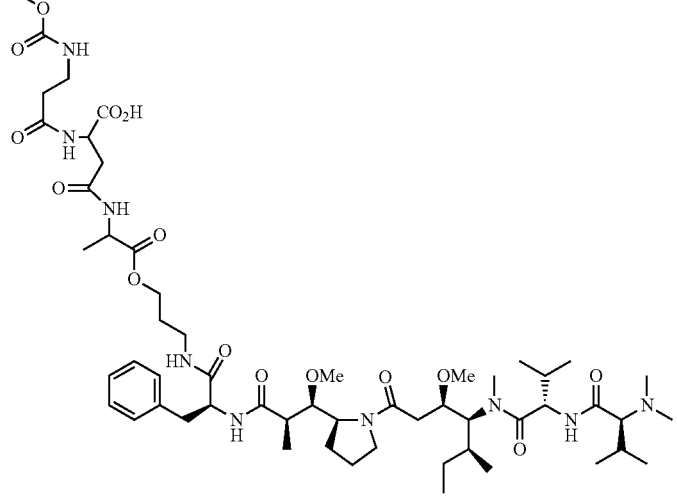
Conjugate No. 76 Example 33
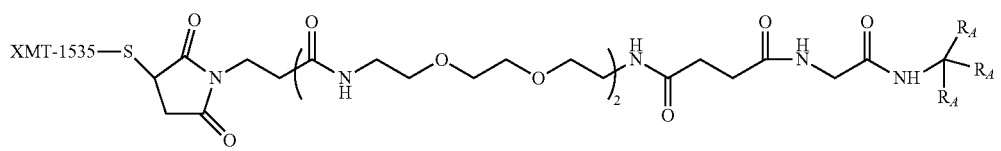

TABLE C-continued

| Conjugate No. | Structure |
|---|---|
| Conjugate No. 83 Example 37 | $R_A =$ [structure] |
| Conjugate No. 78 Example 34 | XMT-1535—S—[structure] |
| Conjugate No. 85 Example 38 | $R_A =$ [structure] |

In some embodiments, the protein-drug conjugates are conjugates of Formula (XXX):
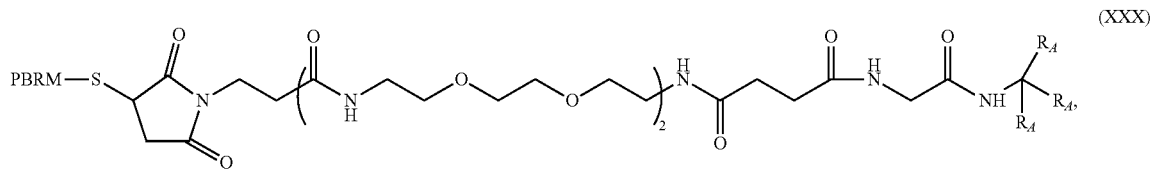
(XXX)
wherein each $R_A$ is
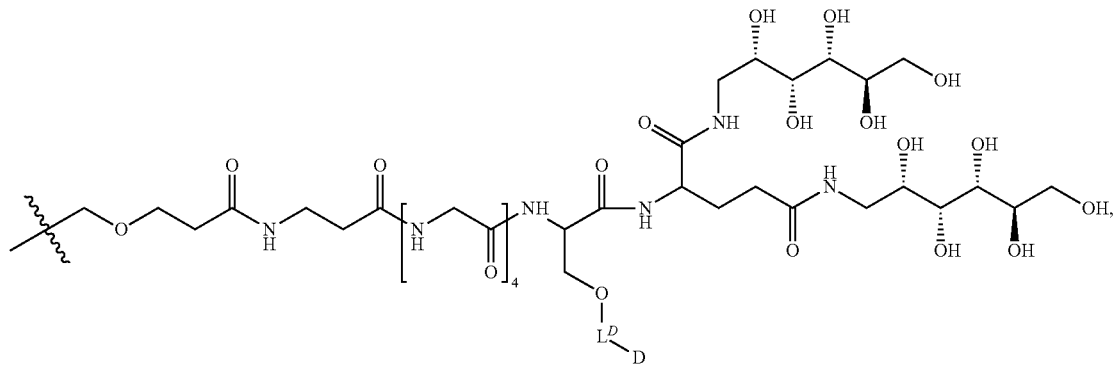
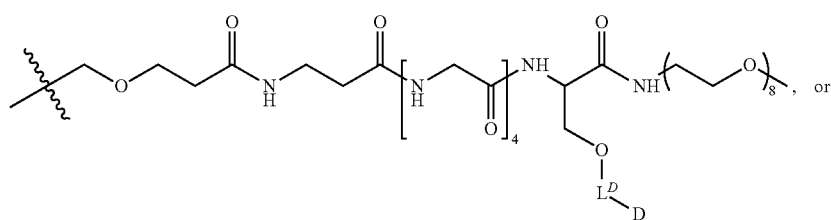, or
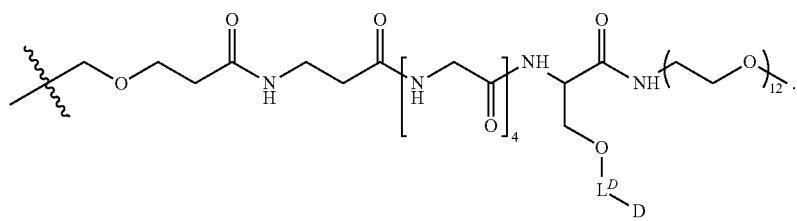.
In other embodiments, the protein-drug conjugates are conjugates of Formula (XXX):
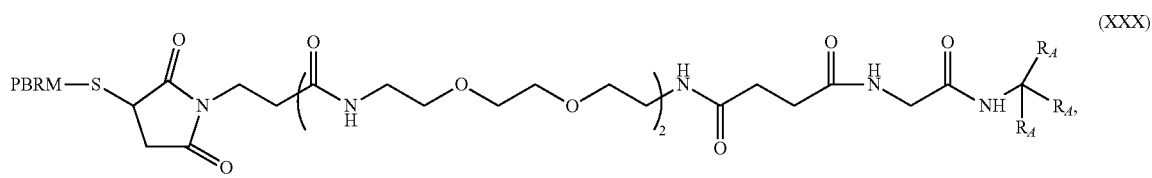
(XXX)

wherein each $R_A$ is
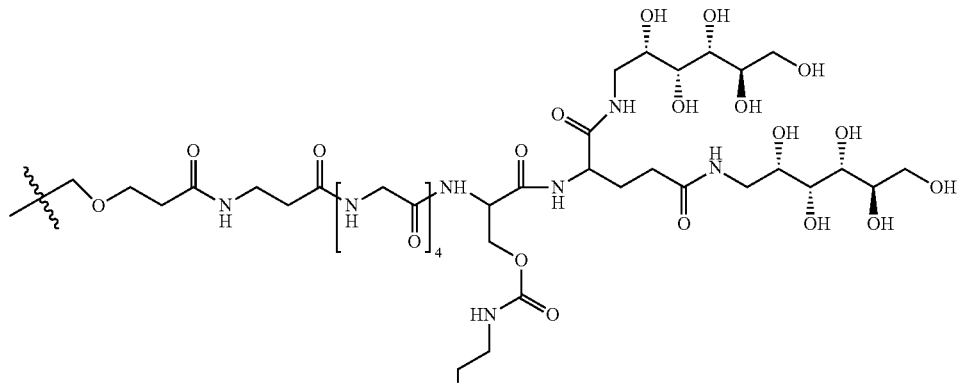
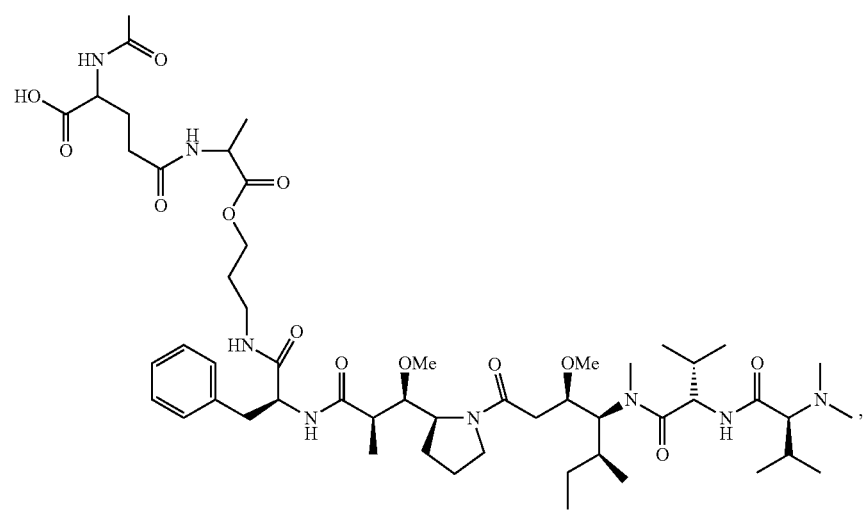
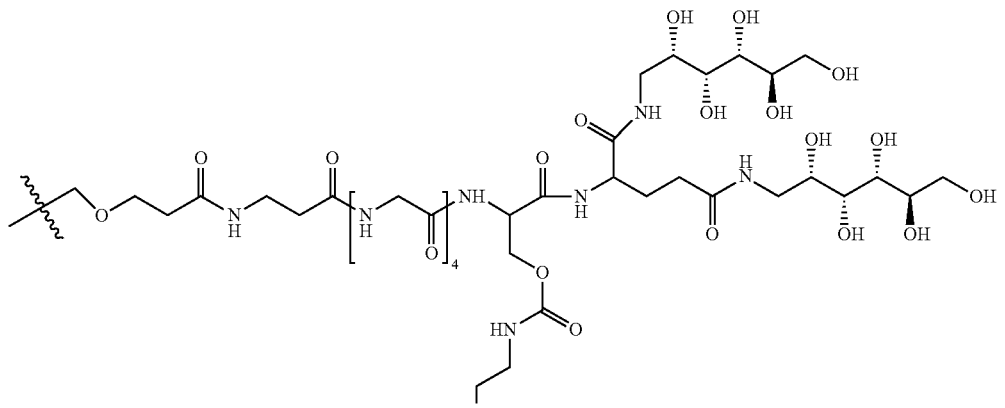

-continued
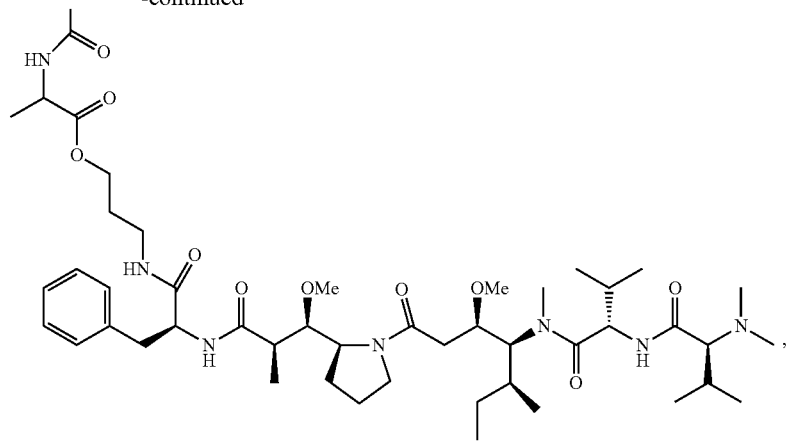
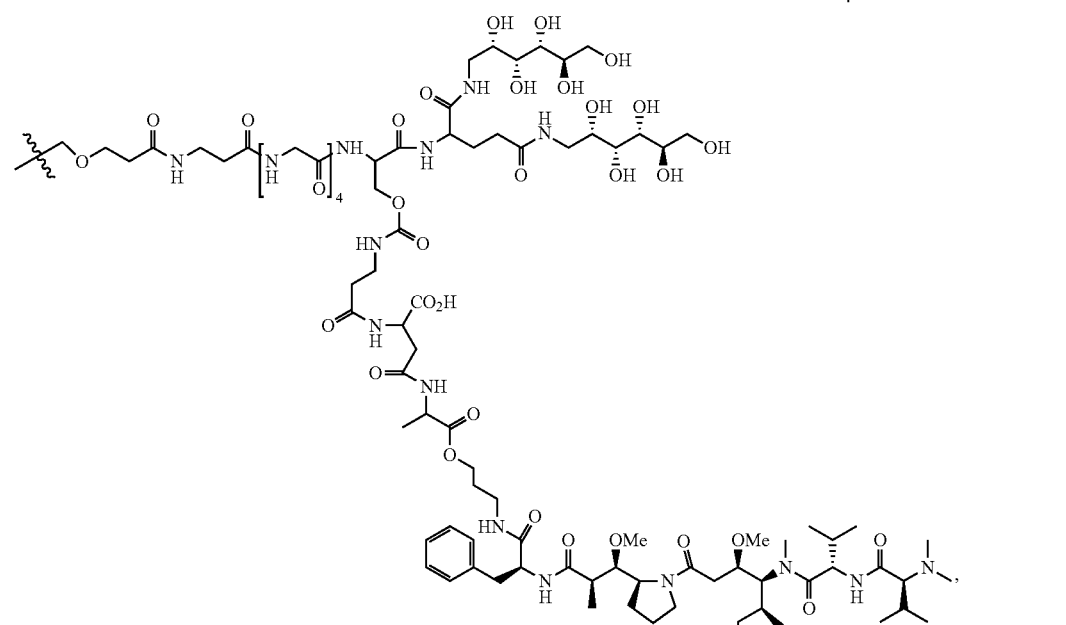
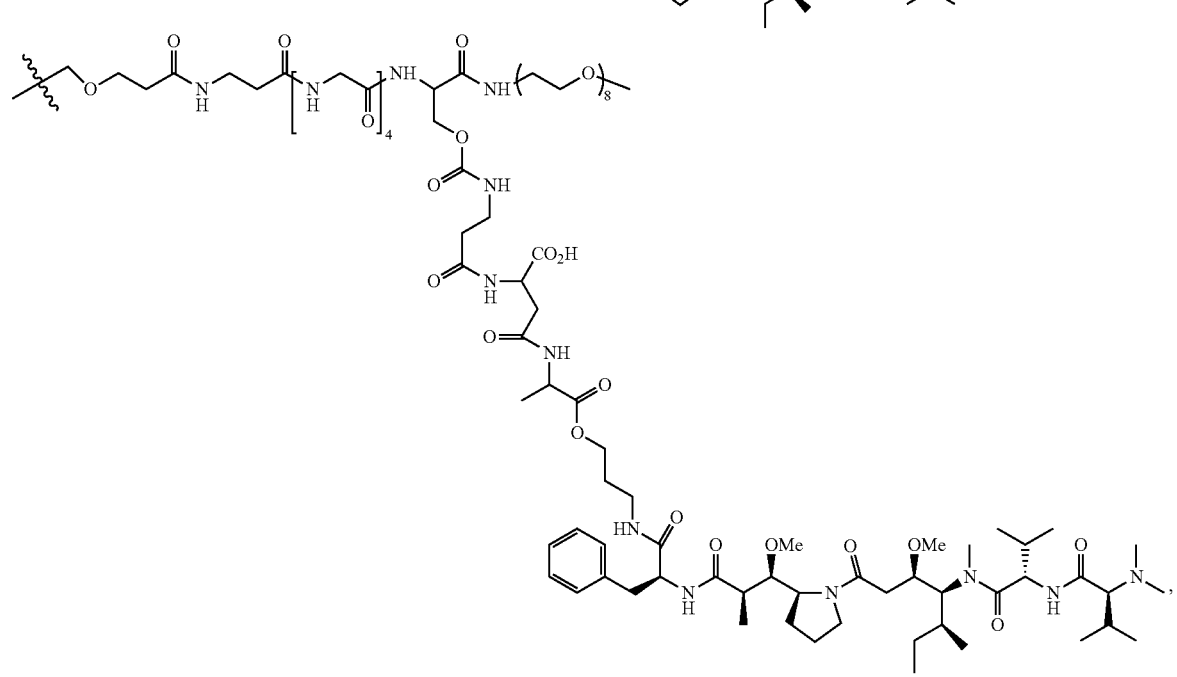

-continued
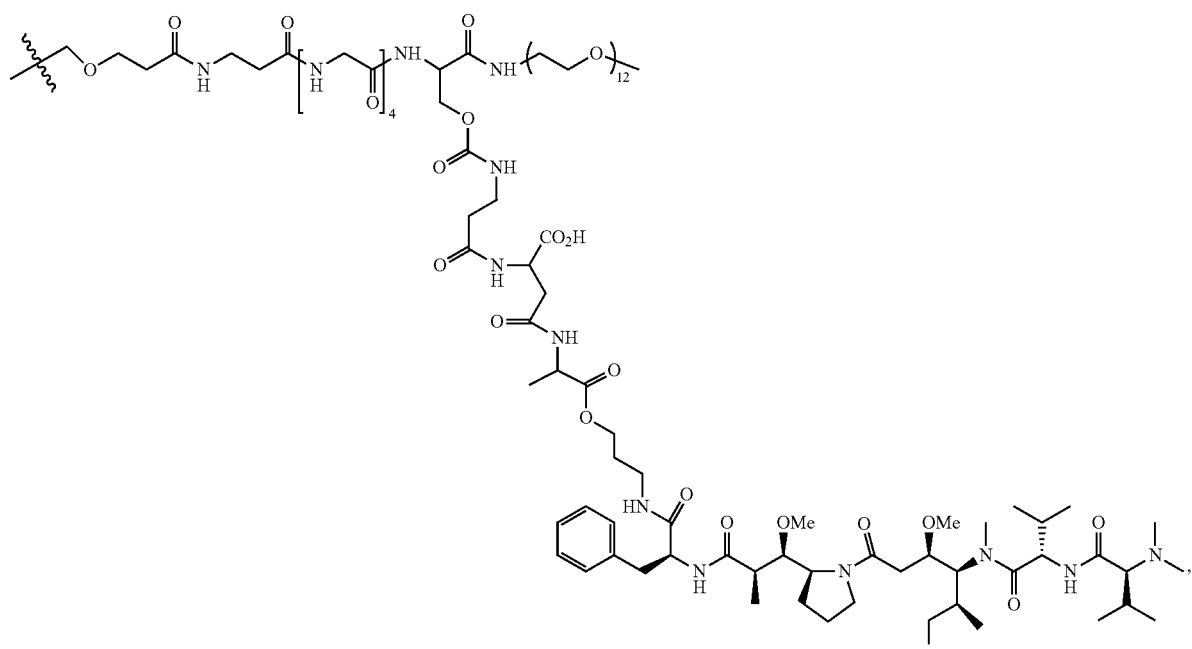
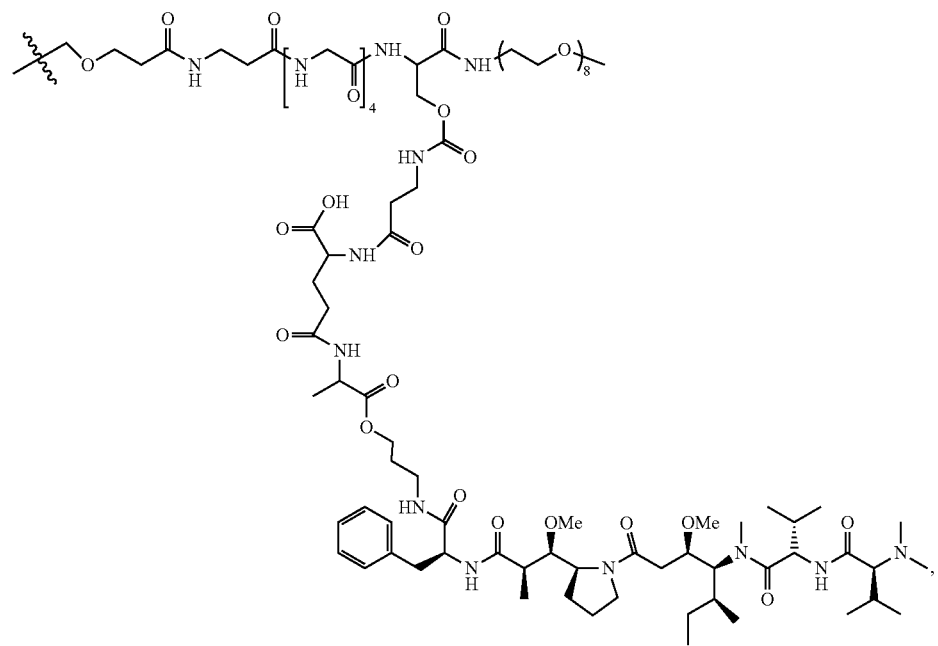

-continued
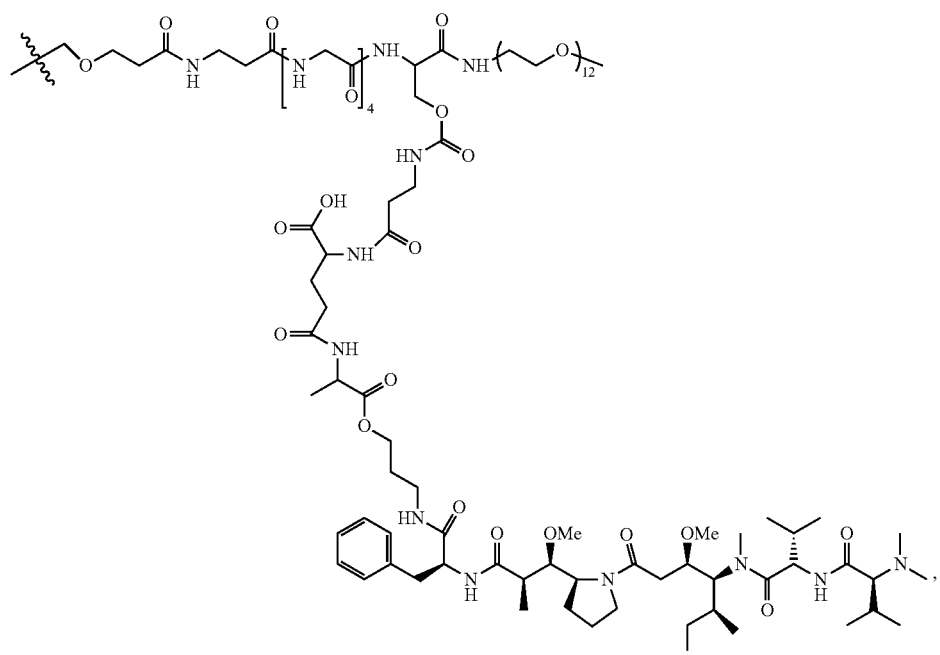
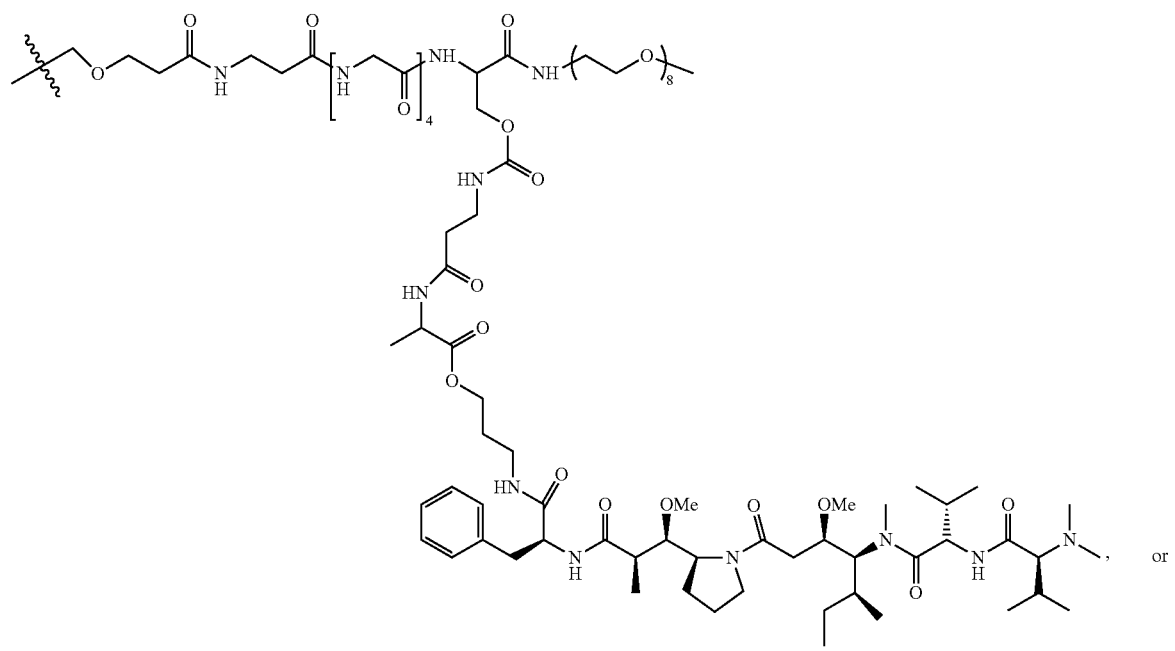

-continued
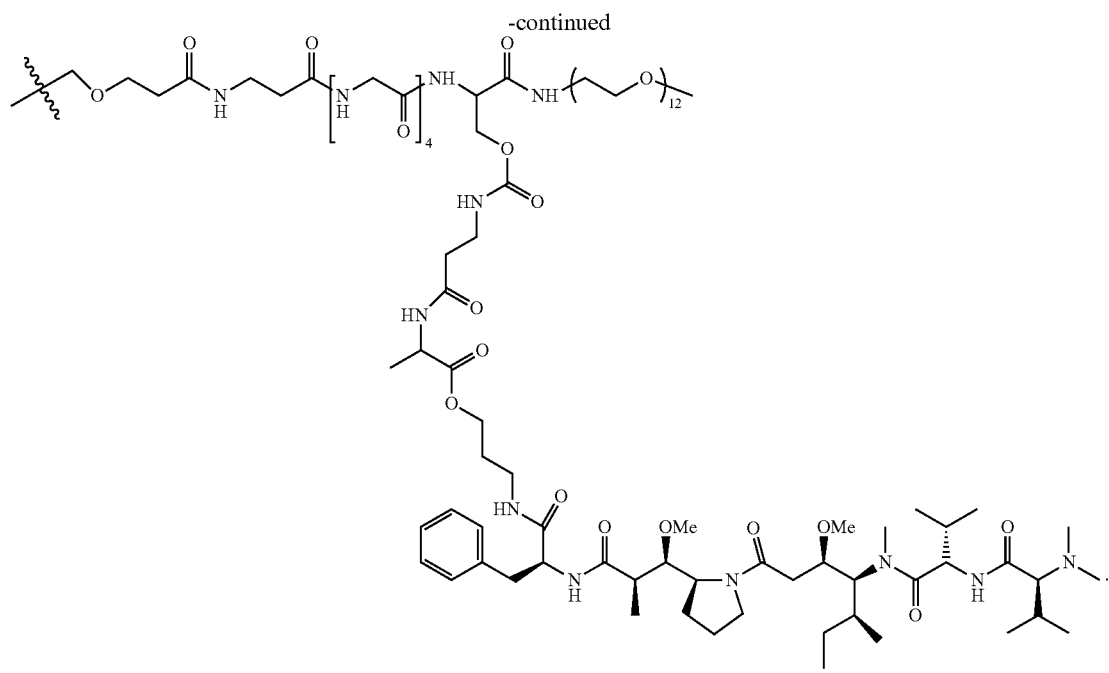
For example, the protein-drug conjugate is of Formula (XXX), wherein each $R_A$ is
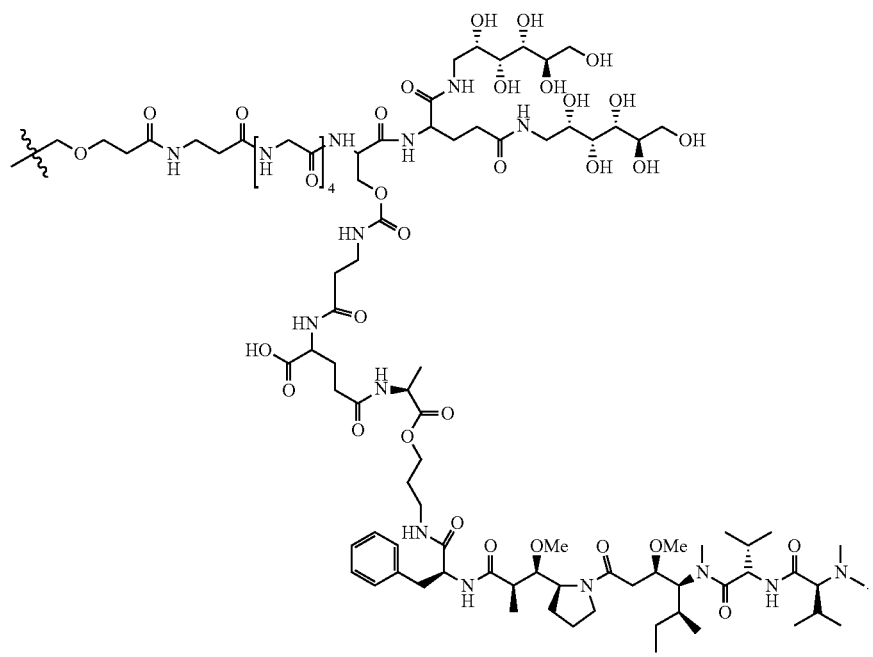
For example, the protein-drug conjugate is of Formula (XXX), wherein each $R_A$ is

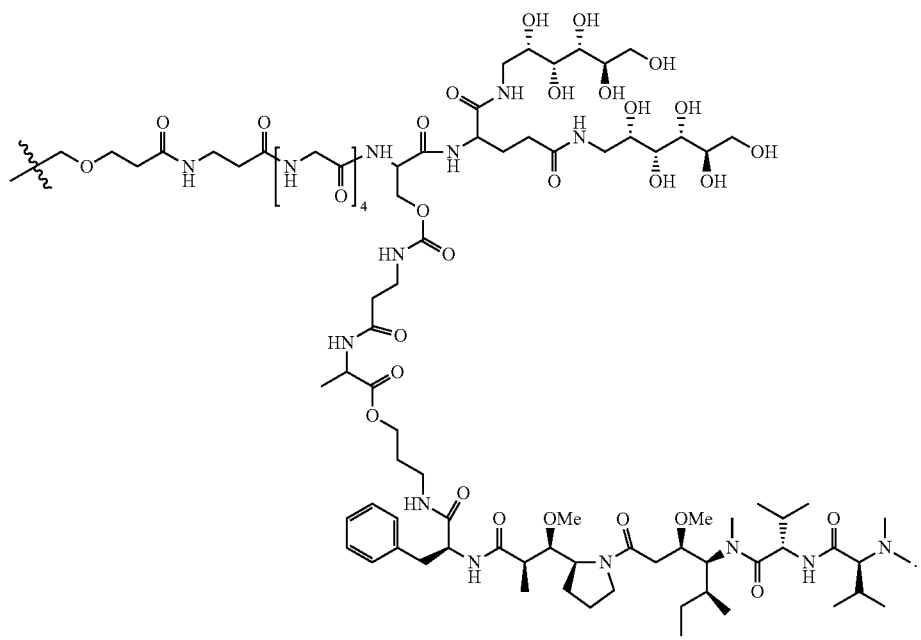
For example, the protein-drug conjugate is of Formula (XXX), wherein each $R_A$ is
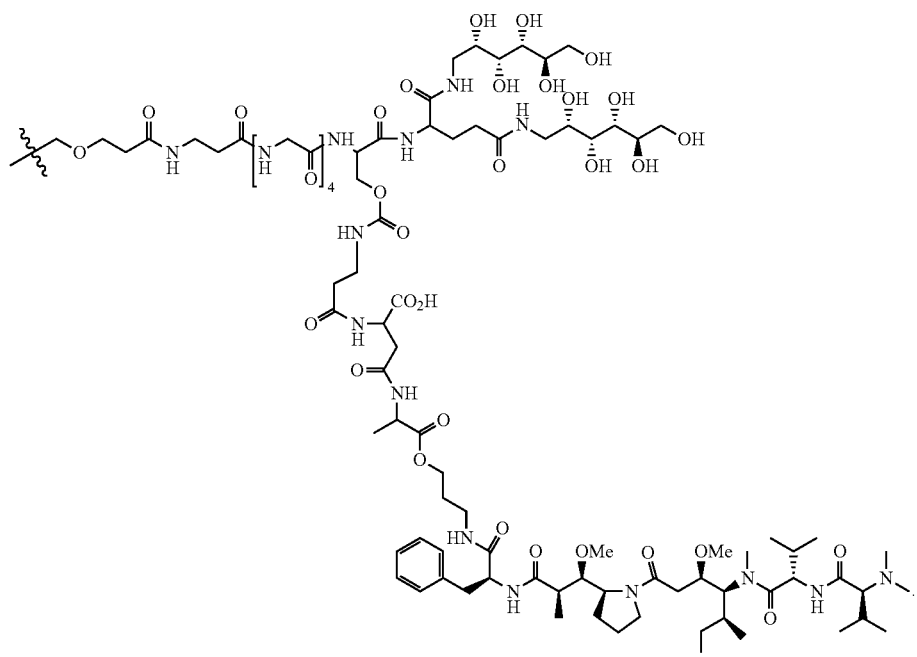
For example, the protein-drug conjugate is of Formula (XXX), wherein each $R_A$ is

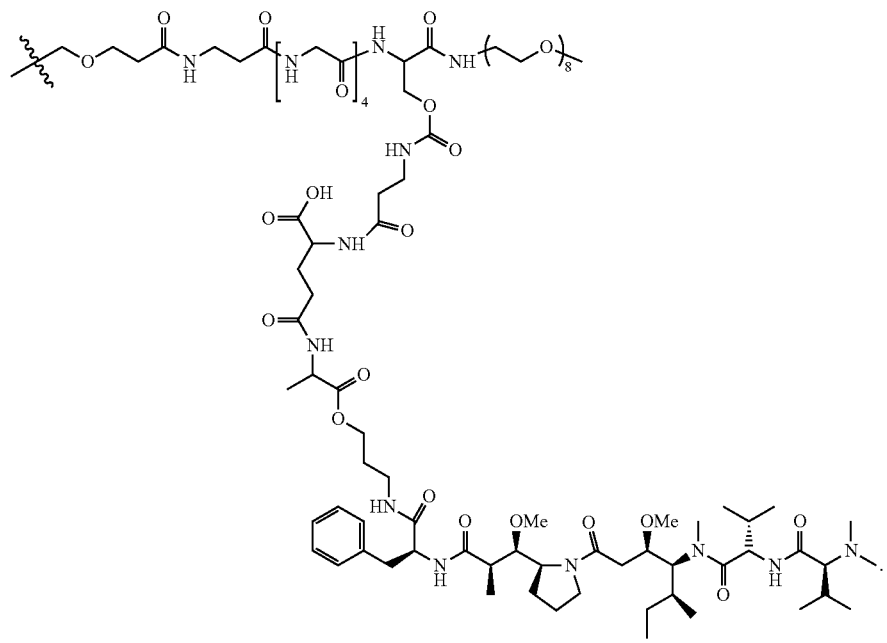
For example, the protein-drug conjugate is of Formula (XXX), wherein each $R_A$ is
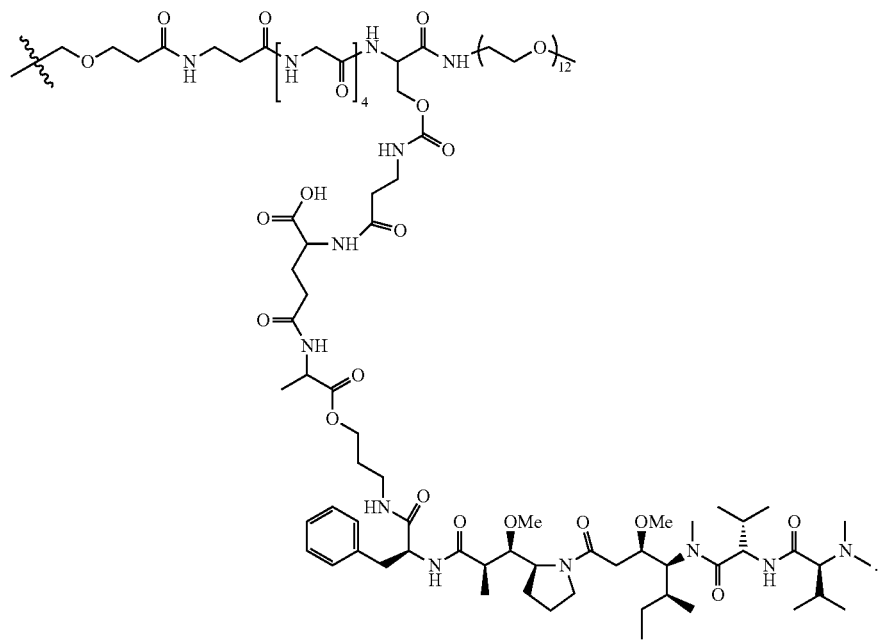
For example, the protein-drug conjugate is of Formula (XXX), wherein each $R_A$ is

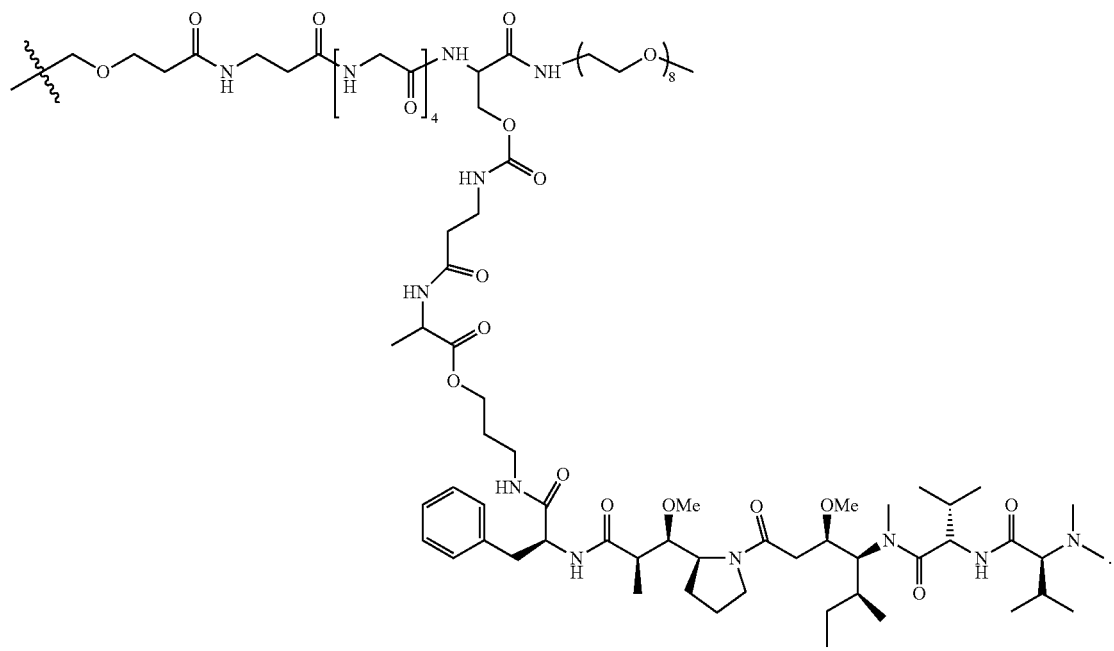
For example, the protein-drug conjugate is of Formula (XXX), wherein each $R_A$ is
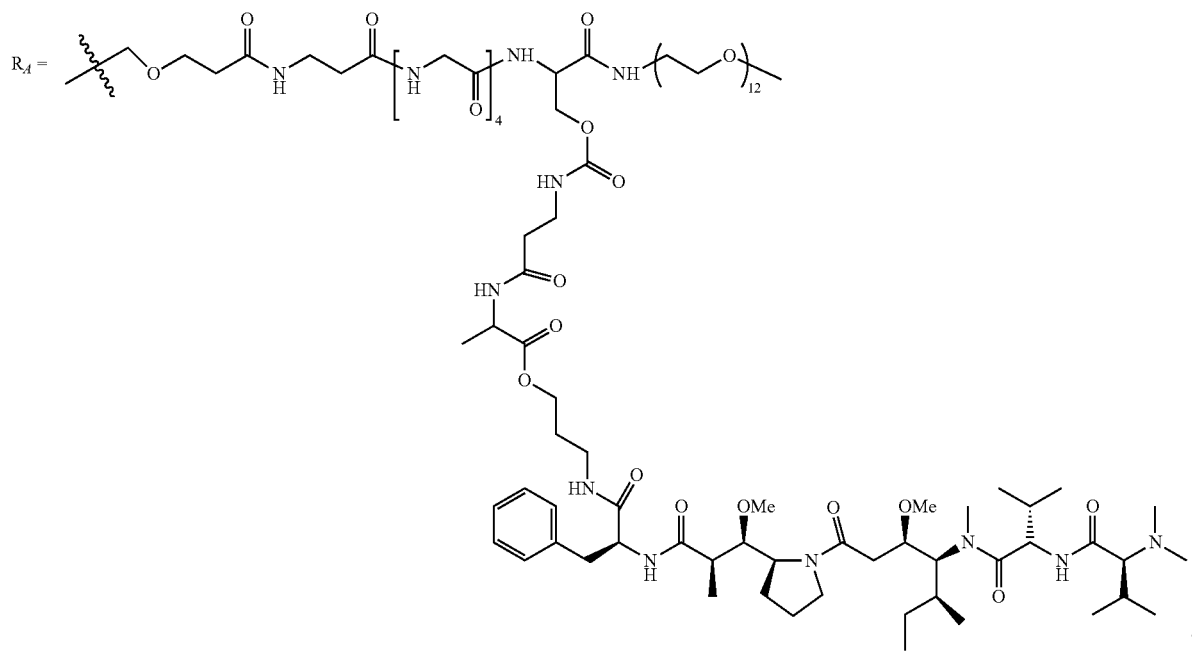
For example, the protein-drug conjugate is of Formula (XXX), wherein each $R_A$ is:

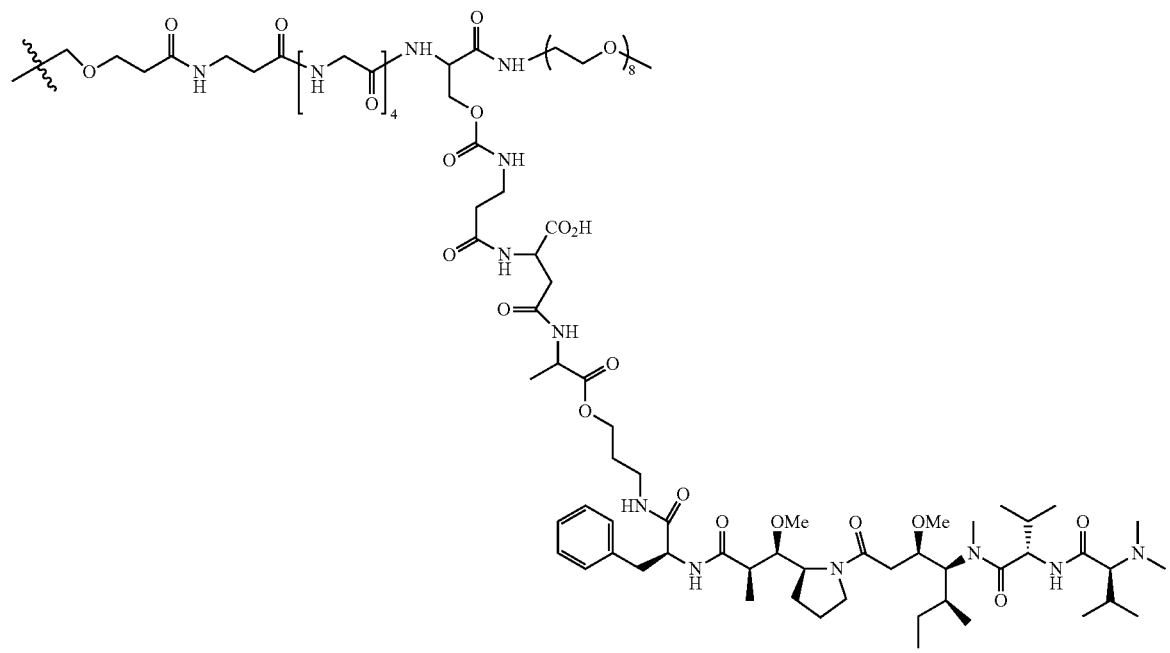
For example, the protein-drug conjugate is of Formula (XXX), wherein each $R_A$ is
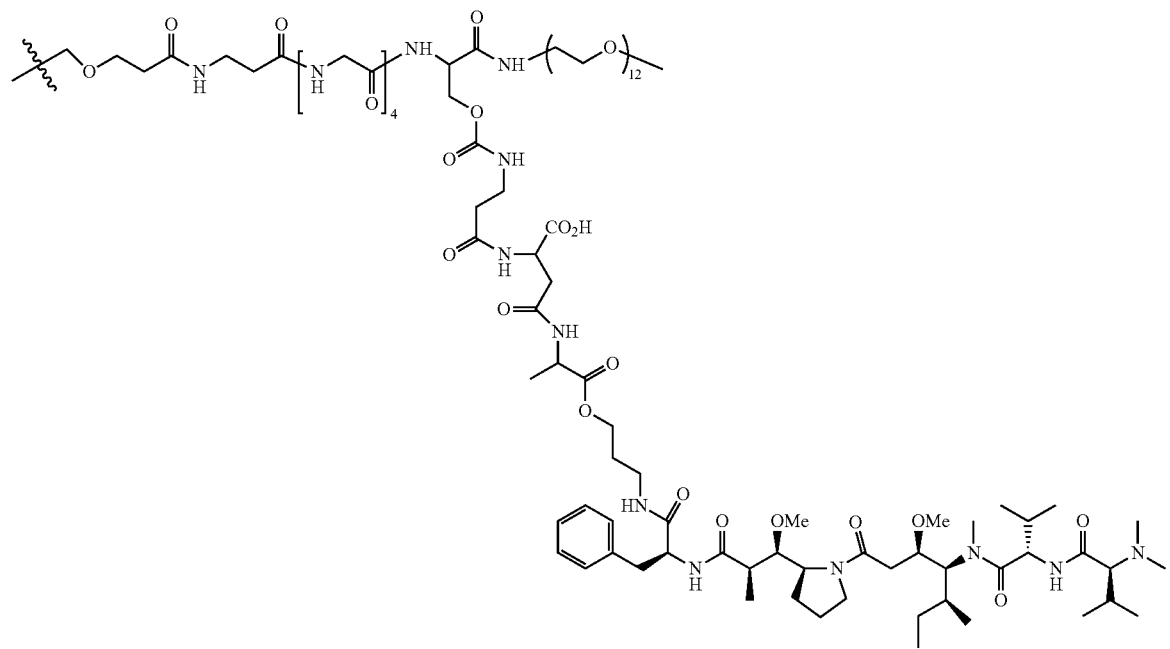
In some embodiments, the protein-drug conjugates are conjugates of Formula (XXXII-1), (XXXII-2), (XXXII-3) or (XXXII-4):

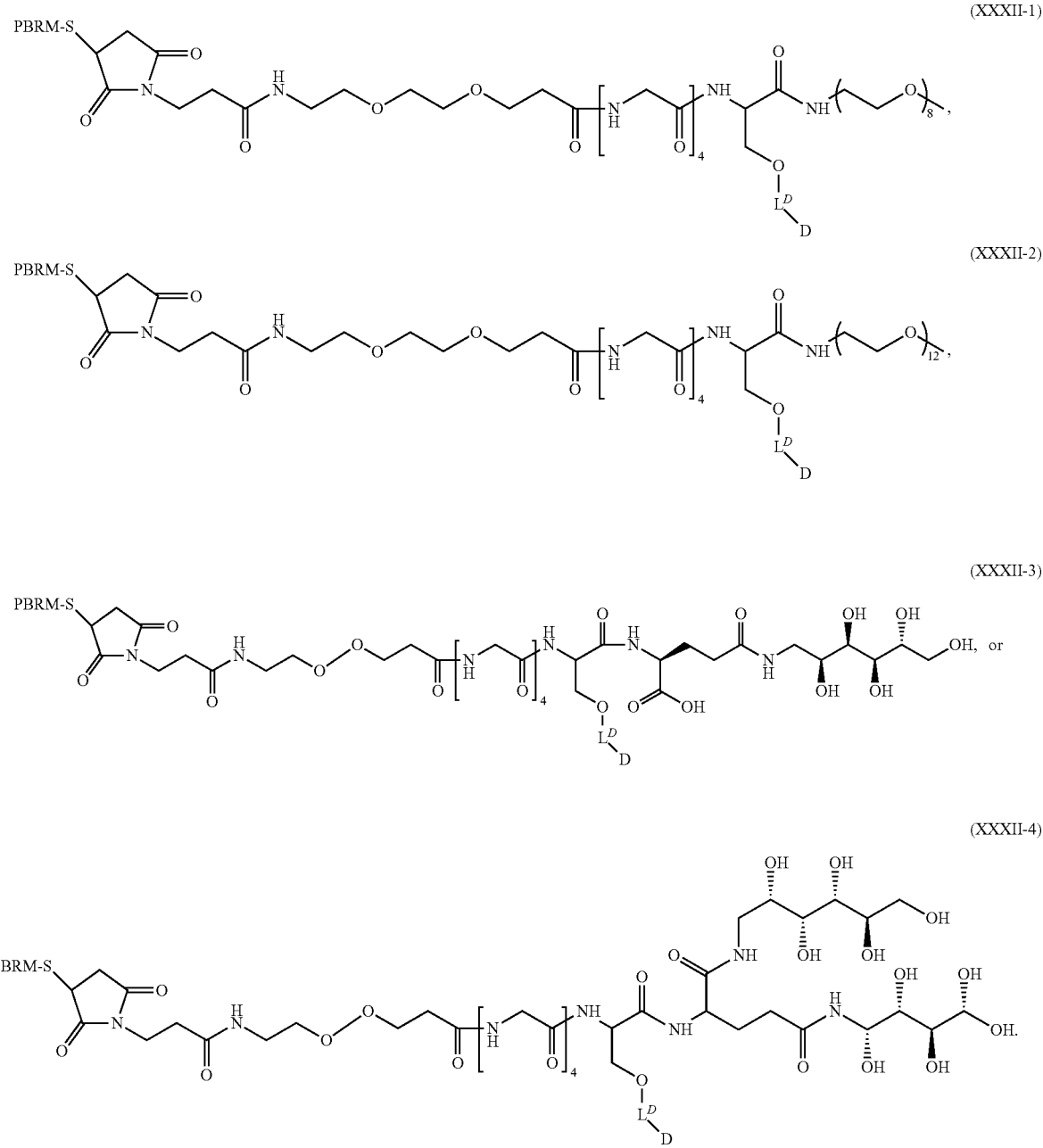
(XXXII-4).
In some embodiments, the protein-drug conjugates are conjugates of Formula (XXXIII):
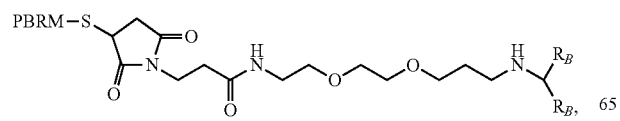

wherein each $R_B$ is:
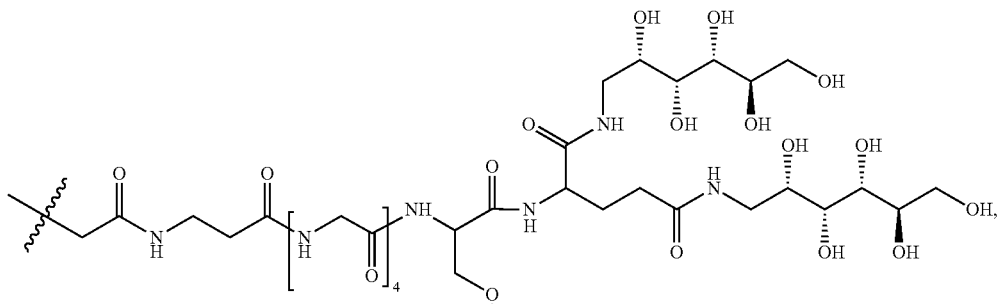
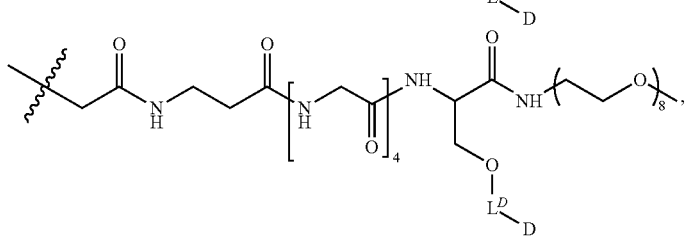
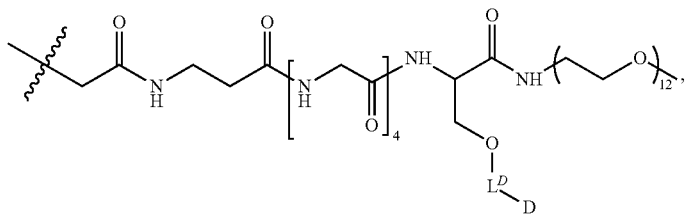
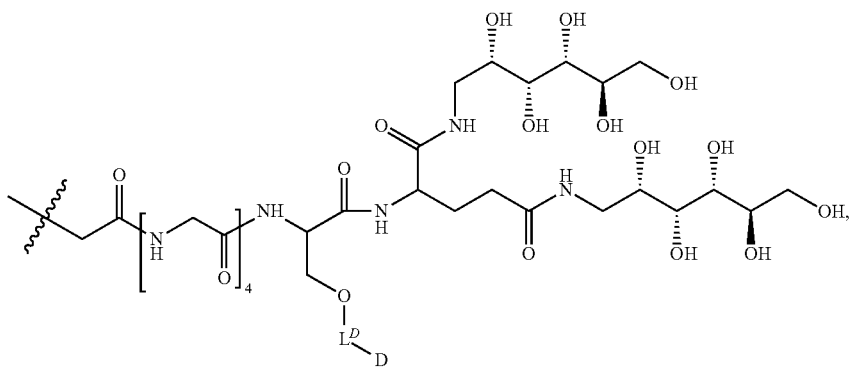
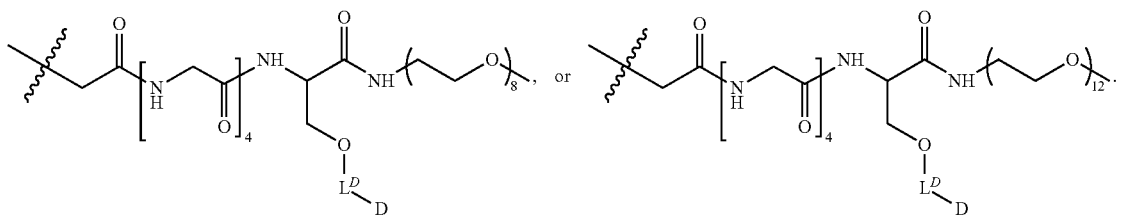
In some embodiments, in the protein-drug conjugates are conjugates of Formula (XXXII-1), (XXXII-2), (XXXII-3), (XXXII-4) or (XXXIII), the variable -$L^D$-D is:

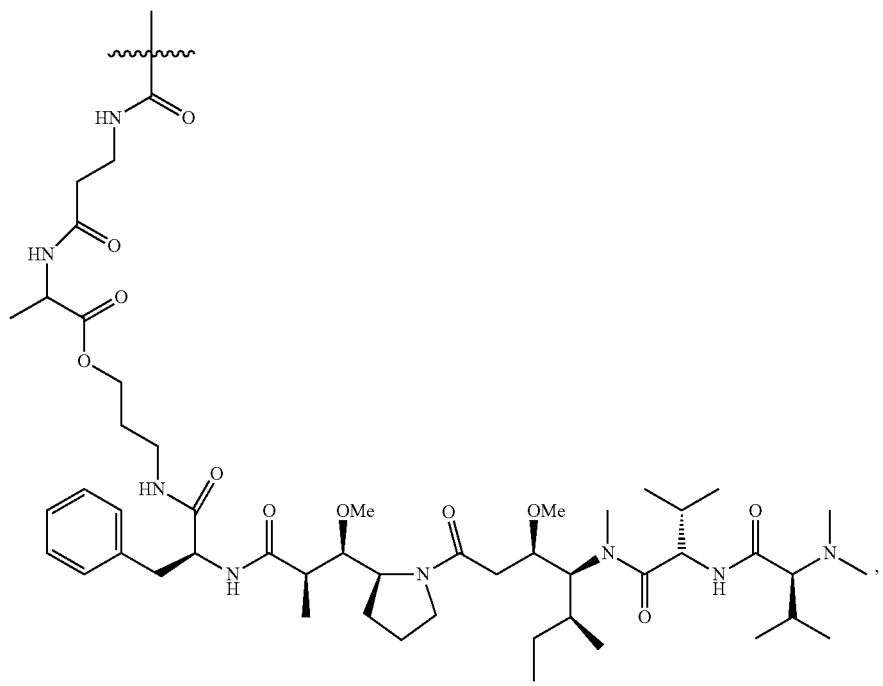
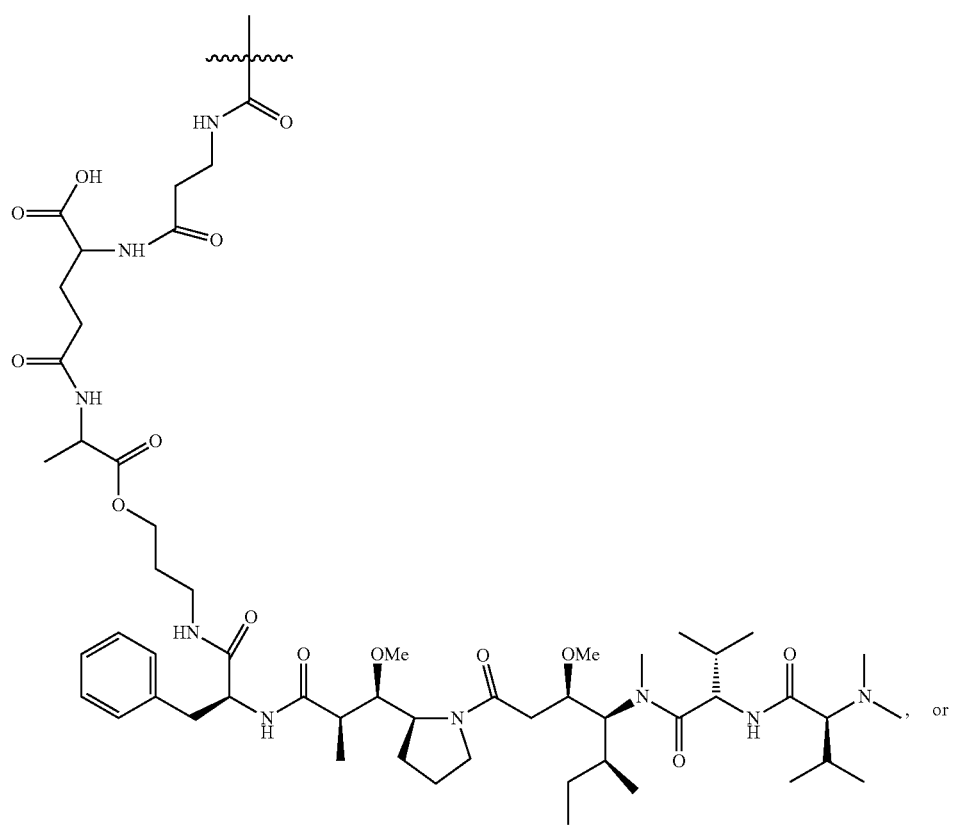

-continued
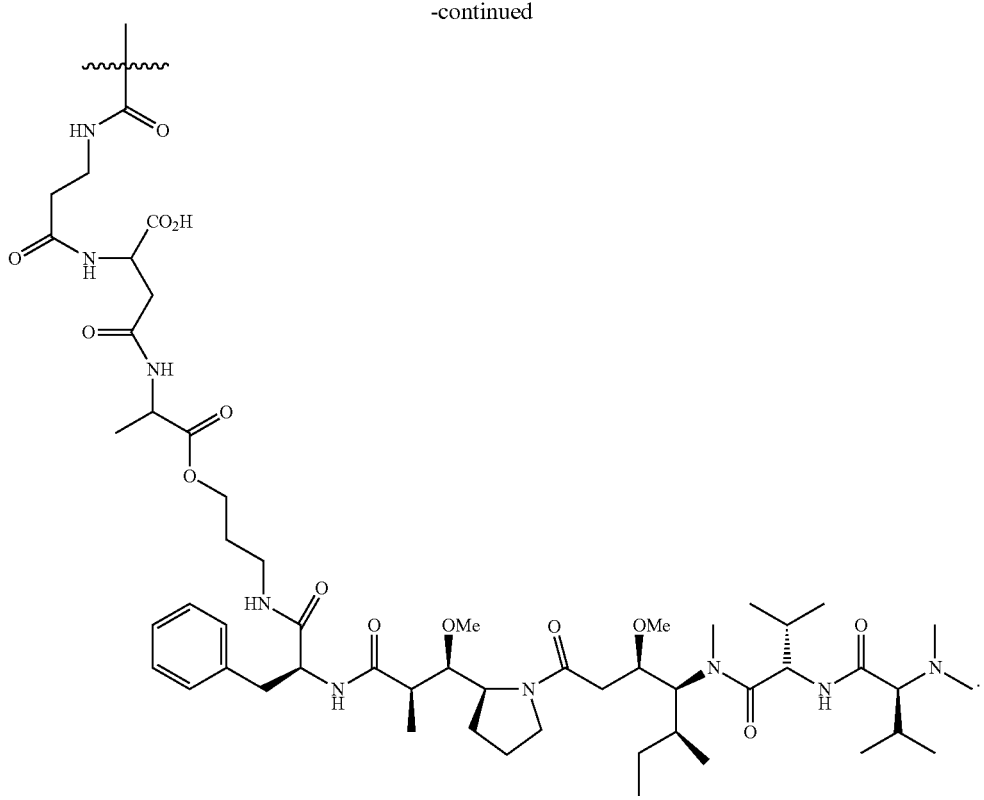
In other embodiments, the protein-drug conjugates are conjugates of Formula (XXXIV-1) (XXXIV-2), (XXXIV-3) or (XXXIV-4):
(XXXIV-1)
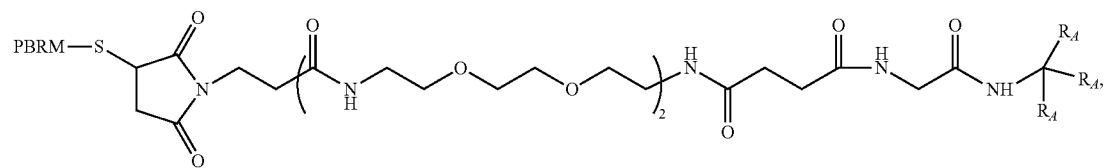

-continued
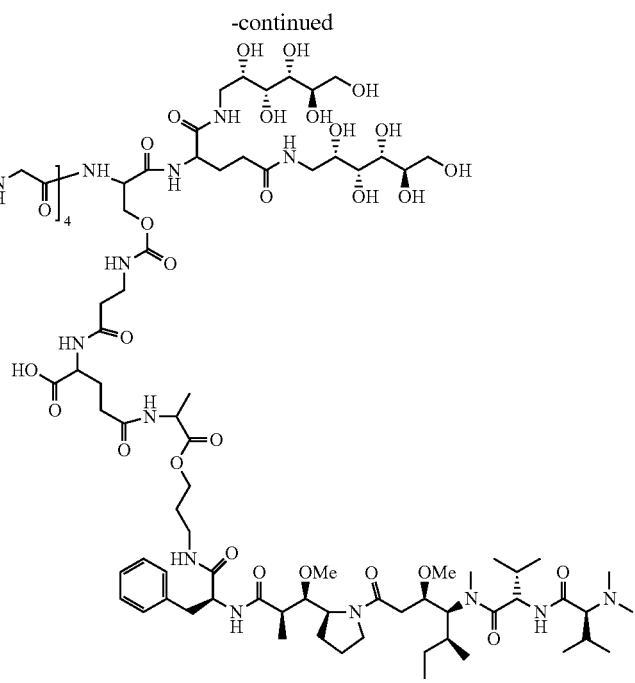
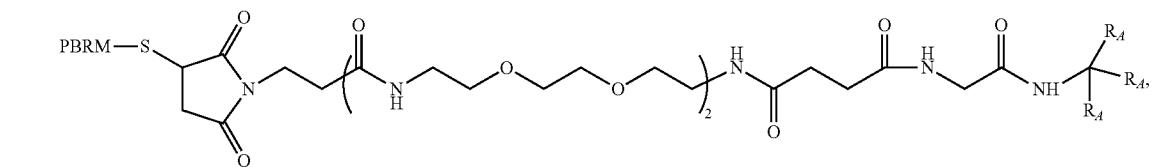
(XXXIV-2)
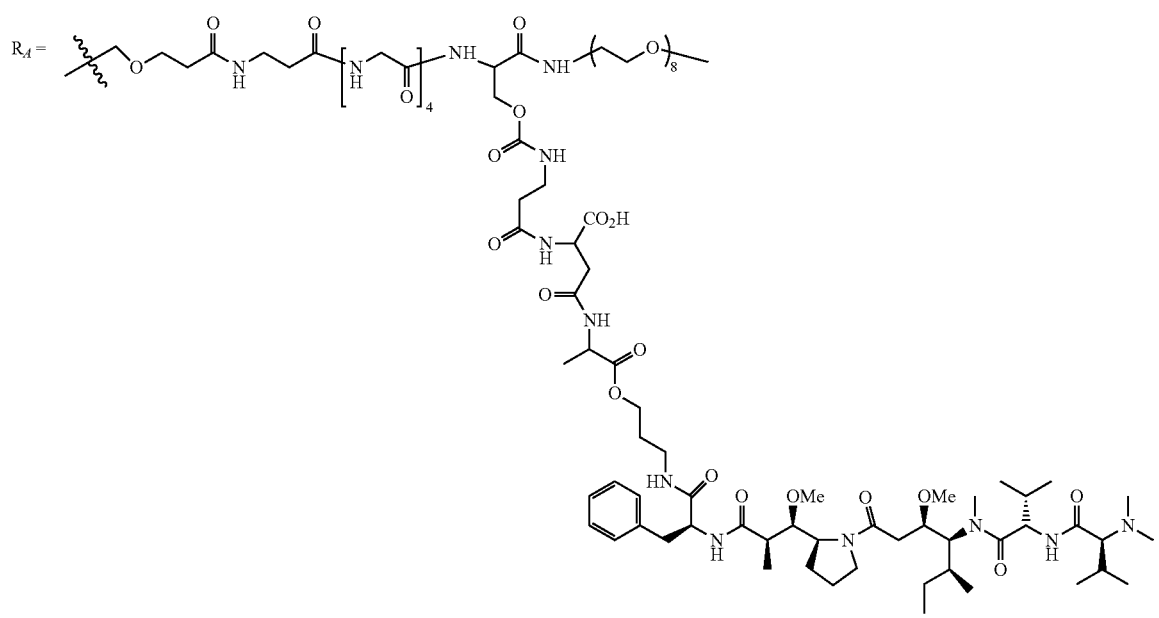
(XXXIV-3)
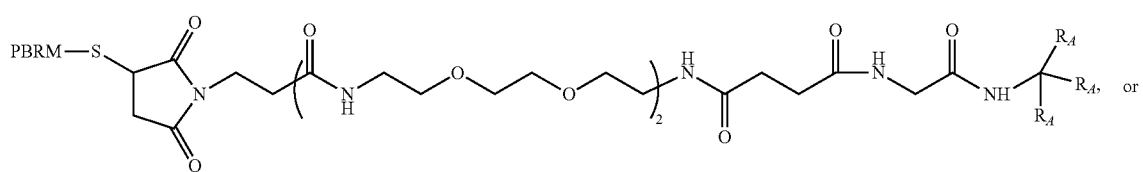

-continued

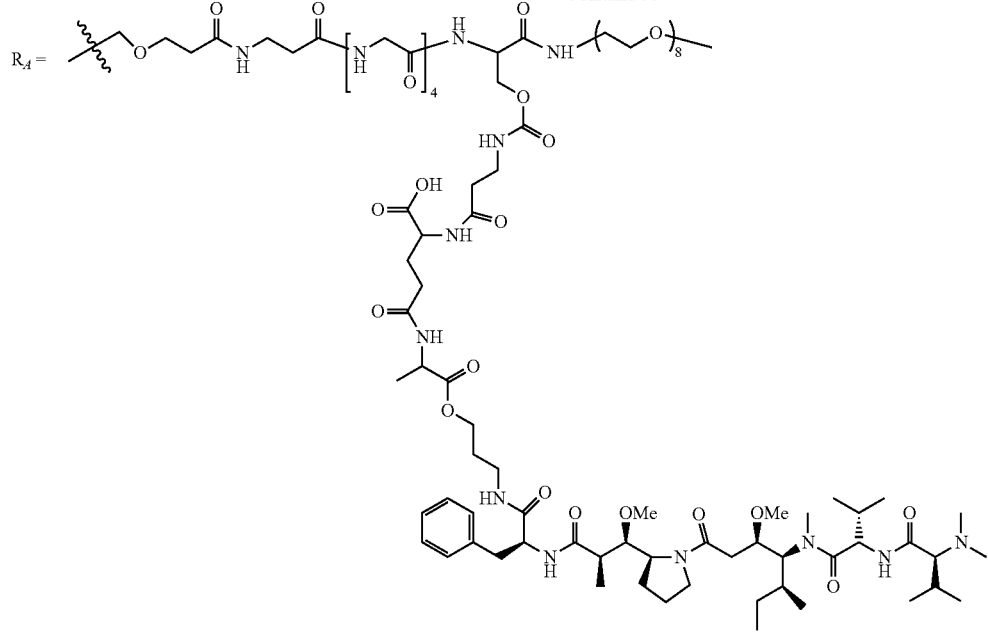

(XXXIV-4)

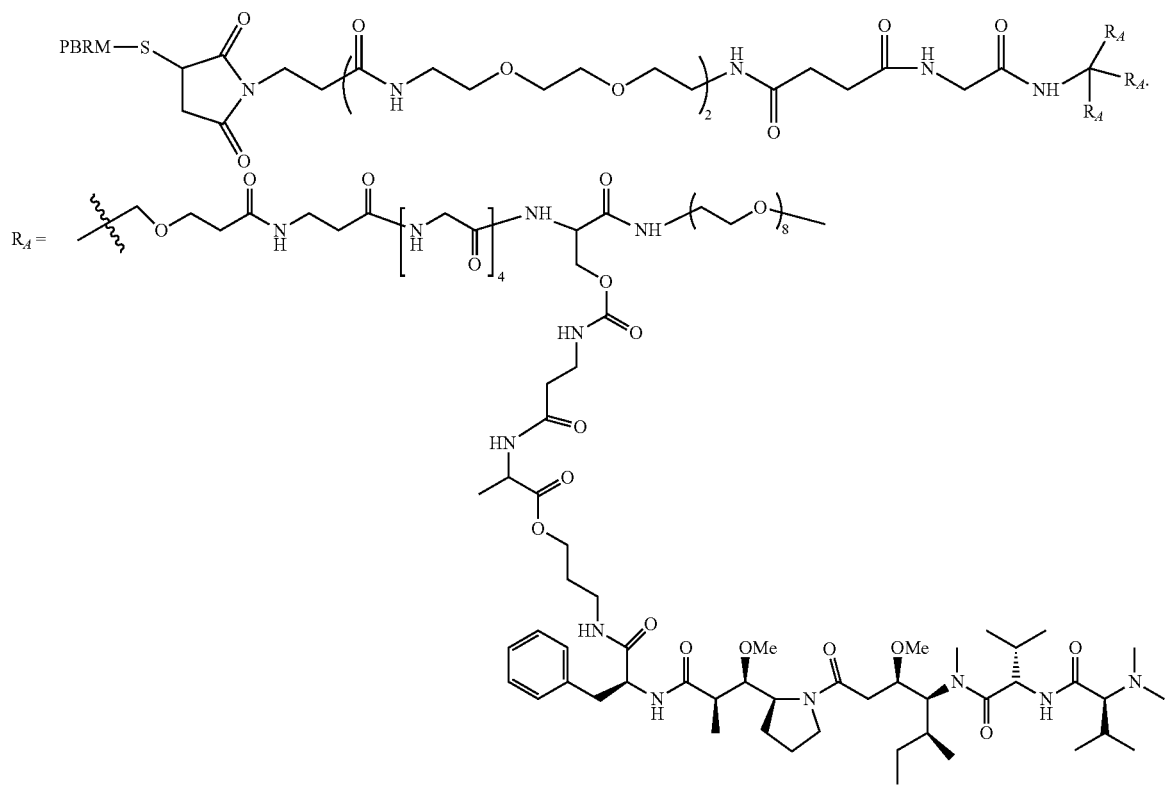

Pharmaceutical Compositions

Also included are pharmaceutical compositions comprising one or more conjugates as disclosed herein in an acceptable carrier, such as a stabilizer, buffer, and the like. The conjugates can be administered and introduced into a subject by standard means, with or without stabilizers, buffers, and the like, to form a pharmaceutical composition. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal, oral or parenteral administration including intravenous, intraarterial, subcutaneous, intraperitoneal or intramuscular injection or infusion or intracranial, e.g., intrathecal or intraventricular, administration. The conjugates can be formulated and used as sterile solutions and/or suspensions for injectable administration; lyophilized powders for reconstitution prior to injection/infusion; topical compositions; as tablets, capsules, or elixirs for oral administration; or suppositories for rectal administration, and the other compositions known in the art.

A pharmacological composition or formulation refers to a composition or formulation in a form suitable for administration, e.g., systemic administration, into a cell or subject, including for example a human. Suitable forms, in part, depend upon the use or the route of entry, for example oral, inhaled, transdermal, or by injection/infusion. Such forms should not prevent the composition or formulation from reaching a target cell (i.e., a cell to which the drug is desirable for delivery). For example, pharmacological compositions injected into the blood stream should be soluble. Other factors are known in the art, and include considerations such as toxicity and forms that prevent the composition or formulation from exerting its effect.

By "systemic administration" is meant in vivo systemic absorption or accumulation of the conjugate in the blood stream followed by distribution throughout the entire body. Administration routes that lead to systemic absorption include, without limitation: intravenous, subcutaneous, intraperitoneal, inhalation, oral, intrapulmonary, and intramuscular. Each of these administration routes exposes the conjugates to an accessible diseased tissue. The rate of entry of an active agent into the circulation has been shown to be a function of molecular weight or size. The use of a conjugate of this disclosure can localize the drug delivery in certain cells, such as cancer cells via the specificity of PBRMs.

A "pharmaceutically acceptable formulation" means a composition or formulation that allows for the effective distribution of the conjugates in the physical location most suitable for their desired activity. In one embodiment, effective delivery occurs before clearance by the reticuloendothelial system or the production of off-target binding which can result in reduced efficacy or toxicity. Non-limiting examples of agents suitable for formulation with the conjugates include: P-glycoprotein inhibitors (such as Pluronic P85), which can enhance entry of active agents into the CNS; biodegradable polymers, such as poly (DL-lactide-coglycolide) microspheres for sustained release delivery after intracerebral implantation; and loaded nanoparticles, such as those made of polybutylcyanoacrylate, which can deliver active agents across the blood brain barrier and can alter neuronal uptake mechanisms.

Also included herein are pharmaceutical compositions prepared for storage or administration, which include a pharmaceutically effective amount of the desired conjugates in a pharmaceutically acceptable carrier or diluent. Acceptable carriers, diluents, and/or excipients for therapeutic use are well known in the pharmaceutical art. For example, buffers, preservatives, bulking agents, dispersants, stabilizers, dyes, can be provided. In addition, antioxidants and suspending agents can be used Examples of suitable carriers, diluents and/or excipients include, but are not limited to: (1) Dulbecco's phosphate buffered saline, pH about 6.5, which would contain about 1 mg/ml to 25 mg/ml human serum albumin, (2) 0.9% saline (0.9% w/v NaCl), and (3) 5% (w/v) dextrose.

The term "pharmaceutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Pharmaceutically effective amounts for a given situation can be determined by routine experimentation that is within the skill and judgment of the clinician. In a preferred aspect, the disease or condition to can be treated via gene silencing.

For any conjugate, the pharmaceutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

For example, a drug or its derivatives, drug-conjugates or PBRM-drug conjugates can be evaluated for their ability to inhibit tumor growth in several cell lines using Cell titer Glo. Dose response curves can be generated using SoftMax Pro software and IC50 values can be determined from four-parameter curve fitting. Cell lines employed can include those which are the targets of the PBRM and a control cell line that is not the target of the PBRM contained in the test conjugates.

In one embodiment, the conjugates are formulated for parenteral administration by injection including using conventional catheterization techniques or infusion. Formulations for injection may be presented in unit dosage form, e.g., in ampules or in multi-dose containers, with an added preservative. The conjugates can be administered parenterally in a sterile medium. The conjugate, depending on the vehicle and concentration used, can either be suspended or dissolved in the vehicle. Advantageously, adjuvants such as local anesthetics, preservatives, and buffering agents can be dissolved in the vehicle. The term "parenteral" as used herein includes percutaneous, subcutaneous, intravascular (e.g., intravenous), intramuscular, or intrathecal injection or infusion techniques and the like. In addition, there is provided a pharmaceutical formulation comprising conjugates and a pharmaceutically acceptable carrier. One or more of the conjugates can be present in association with one or more non-toxic pharmaceutically acceptable carriers and/or diluents and/or adjuvants, and if desired other active ingredients.

The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose, a bland fixed oil can be employed including synthetic mono- or diglycerides. In addition, fatty acids such as oleic acid find use in the preparation of injectables.

The conjugates and compositions described herein may be administered in appropriate form, preferably parenterally, more preferably intravenously. For parenteral administration, the conjugates or compositions can be aqueous or nonaqueous sterile solutions, suspensions or emulsions. Propylene glycol, vegetable oils and injectable organic esters, such as ethyl oleate, can be used as the solvent or vehicle. The compositions can also contain adjuvants, emulsifiers or dispersants.

Dosage levels of the order of from between about 0.001 mg and about 140 mg per kilogram of body weight per day are useful in the treatment of the above-indicated conditions (between about 0.05 mg and about 7 g per subject per day). In some embodiments, the dosage administered to a patient is between about 0.001 mg/kg to about 100 mg/kg of the subject's body weight. In some embodiments, the dosage administered to a patient is between about 0.01 mg/kg to about 15 mg/kg of the subject's body weight. In some embodiments, the dosage administered to a patient is between about 0.1 mg/kg and about 15 mg/kg of the subject's body weight. In some embodiments, the dosage administered to a patient is between about 0.1 mg/kg and about 20 mg/kg of the subject's body weight. In some embodiments, the dosage administered is between about 0.1 mg/kg to about 5 mg/kg or about 0.1 mg/kg to about 10 mg/kg of the subject's body weight. In some embodiments, the dosage administered is between about 1 mg/kg to about 15 mg/kg of the subject's body weight. In some embodiments, the dosage administered is between about 1 mg/kg to about 10 mg/kg of the subject's body weight. The amount of conjugate that can be combined with the carrier materials to produce a single dosage form varies depending upon the host treated and the particular mode of administration. Dosage unit forms can generally contain from between about 0.001 mg and about 100 mg; between about 0.01 mg and about 75 mg; or between about 0.01 mg and about 50 mg; or between about 0.01 mg and about 25 mg; of a conjugate.

For intravenous administration, the dosage levels can comprise ranges described in the preceding paragraphs, or from about 0.01 to about 200 mg of a conjugate per kg of the animal's body weight. In one aspect, the composition can include from about 1 to about 100 mg of a conjugate per kg of the animal's body weight. In another aspect, the amount administered will be in the range from about 0.1 to about 25 mg/kg of body weight of a compound.

In some embodiments, the conjugates can be administered are as follows. The conjugates can be given daily for about 5 days either as an i.v., bolus each day for about 5 days, or as a continuous infusion for about 5 days.

Alternatively, the conjugates can be administered once a week for six weeks or longer. As another alternative, the conjugates can be administered once every two or three weeks. Bolus doses are given in about 50 to about 400 ml of normal saline to which about 5 to about 10 ml of human serum albumin can be added. Continuous infusions are given in about 250 to about 500 ml of normal saline, to which about 25 to about 50 ml of human serum albumin can be added, per 24 hour period.

In some embodiments, about one to about four weeks after treatment, the patient can receive a second course of treatment. Specific clinical protocols with regard to route of administration, excipients, diluents, dosages, and times can be determined by the skilled artisan as the clinical situation warrants.

In other embodiments, the therapeutically effective amount may be provided on another regular schedule, i.e., daily, weekly, monthly, or yearly basis or on an irregular schedule with varying administration days, weeks, months, etc. Alternatively, the therapeutically effective amount to be administered may vary. In one embodiment, the therapeutically effective amount for the first dose is higher than the therapeutically effective amount for one or more of the subsequent doses. In another embodiment, the therapeutically effective amount for the first dose is lower than the therapeutically effective amount for one or more of the subsequent doses. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The number and frequency of dosages corresponding to a completed course of therapy will be determined according to the recommendations of the relevant regulatory bodies and judgment of a health-care practitioner. The therapeutically effective amounts described herein refer to total amounts administered for a given time period; that is, if more than one different conjugate described herein is administered, the therapeutically effective amounts correspond to the total amount administered. It is understood that the specific dose level for a particular subject depends upon a variety of factors including the activity of the specific conjugate, the age, body weight, general health, sex, diet, time of administration, route of administration, and rate of excretion, combination with other active agents, and the severity of the particular disease undergoing therapy.

In some embodiments, a therapeutically effective amount of a conjugate disclosed herein relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. Common ranges for therapeutically effective dosing of conjugates disclosed herein may be, by way of nonlimiting example, from about 0.1 mg/kg body weight to about 50 mg/kg body weight, from about 0.1 mg/kg body weight to about 100 mg/kg body weight or from about 0.1 mg/kg body weight to about 150 mg/kg body weight. Common dosing frequencies may range, for example, from twice daily to once a month (e.g., once daily, once weekly; once every other week; once every 3 weeks or monthly). For example, conjugates disclosed herein can be administered (e.g., as a single dose weekly, every 2 weeks, every 3 weeks, or monthly) at about 0.1 mg/kg to about 20 mg/kg (e.g., 0.2 mg/kg, 0.5 mg/kg, 0.67 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, or 20 mg/kg). For example, conjugates disclosed herein can be administered (e.g., as a single dose weekly, every 2 weeks, every 3 weeks, or monthly) at about 0.1 mg/kg to about 20 mg/kg (e.g., 0.2 mg/kg, 0.5 mg/kg, 0.67 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 19 mg/kg, or 20 mg/kg) for treating cancer.

For administration to non-human animals, the conjugates can also be added to the animal feed or drinking water. It can be convenient to formulate the animal feed and drinking water so that the animal takes in a therapeutically appropriate quantity of the conjugates along with its diet. It can also be convenient to present the conjugates as a premix for addition to the feed or drinking water.

The conjugates can also be administered to a subject in combination with other therapeutic compounds to increase the overall therapeutic effect. The use of multiple compounds to treat an indication can increase the beneficial effects while reducing the presence of side effects. In some embodiments, the conjugates are used in combination with chemotherapeutic agents, such as those disclosed in U.S. Pat. No. 7,303,749. In other embodiments the chemotherapeutic agents, include, but are not limited to letrozole, oxaliplatin, docetaxel, 5-FU, lapatinib, capecitabine, leucovorin, erlotinib, pertuzumab, bevacizumab, and gemcitabine. The present disclosure also provides pharmaceutical kits comprising one or more containers filled with one or more of the conjugates and/or compositions of the present disclosure, including, one or more chemotherapeutic agents. Such kits can also include, for example, other compounds and/or compositions, a device(s) for administering the compounds and/or compositions, and written instructions in a form prescribed by a governmental agency regulating the manufacture, use or sale of pharmaceuticals or biological products. The compositions described herein can be packaged as a single dose or for continuous or periodic discontinuous administration. For continuous administration, a package or kit can include the conjugates in each dosage unit (e.g., solution or other unit described above or utilized in drug delivery), and optionally instructions for administering the doses daily, weekly, or monthly, for a predetermined length of time or as prescribed. If varying concentrations of a composition, of the components of the composition, or the relative ratios of the conjugates or agents within a composition over time is desired, a package or kit may contain a sequence of dosage units which provide the desired variability.

A number of packages or kits are known in the art for dispensing pharmaceutical agents for periodic oral use. In one embodiment, the package has indicators for each period. In another embodiment, the package is a labeled blister package, dial dispenser package, or bottle. The packaging means of a kit may itself be geared for administration, such as a syringe, pipette, eye dropper, or other such apparatus, from which the formulation may be applied to an affected area of the body, injected into a subject, or even applied to and mixed with the other components of the kit.

Methods of Use
Methods of Treating

In certain preferred embodiments, the protein-drug conjugate of the disclosure are used in methods of treating animals (preferably mammals, most preferably humans and includes males, females, infants, children and adults). In one embodiment, the conjugates of the present disclosure may be used in a method of treating animals which comprises administering to the animal a biodegradable biocompatible conjugate of the disclosure. For example, conjugates of the disclosure can be administered in the form of soluble linear polymers, copolymers, conjugates, colloids, particles, gels, solid items, fibers, films, etc. Biodegradable biocompatible conjugates disclosed herein can be used as drug carriers and drug carrier components, in systems of controlled drug release, preparations for low-invasive surgical procedures, etc. Pharmaceutical formulations can be injectable, implantable, etc.

In yet another aspect, the disclosure provides a method of treating a disease or disorder in a subject in need thereof, comprising administering to the subject an efficient amount of at least one conjugate of the disclosure; wherein said conjugate releases one or more therapeutic agents upon biodegradation.

In another embodiment the conjugates can be administered in vitro, in vivo and/or ex vivo to treat patients and/or to modulate the growth of selected cell populations including, for example, cancer. In some embodiments, the particular types of cancers that can be treated with the conjugates include, but are not limited to: (1) solid tumors, including but not limited to fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophogeal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma bile duct carcinoma, choriocarcinoma, seminoma, embryonal carcinoma, Wilms' tumor, cervical cancer, uterine cancer, testicular cancer, small cell lung carcinoma, non-small cell lung carcinoma, bladder carcinoma, lung cancer, epithelial carcinoma, glioma, glioblastoma, multiforme astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma; (2) blood-borne cancers, including but not limited to acute lymphoblastic leukemia "ALL", acute lymphoblastic B-cell leukemia, acute lymphoblastic T-cell leukemia, acute myeloblastic leukemia "AML", acute promyelocytic leukemia "APL", acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia "CML", chronic lymphocytic leukemia "CLL", hairy cell leukemia, multiple myeloma, acute and chronic leukemias, e.g., lymphoblastic myelogenous and lymphocytic myelocytic leukemias; and (3) lymphomas such as Hodgkin's disease, non-Hodgkin's Lymphoma, Multiple myeloma, Waldenstrom's macroglobulinemia, Heavy chain disease, and Polycythemia vera.

In another embodiment the conjugates can be administered in vitro, in vivo and/or ex vivo to treat patients and/or to modulate the growth of selected cell populations in patients having anal, astrocytoma, leukemia, lymphoma, head and neck, liver, testicular, cervical, sarcoma, hemangioma, esophageal, eye, laryngeal, mouth, mesothelioma, skin, myeloma, oral, rectal, throat, bladder, breast, uterus, ovary, prostate, lung, colon, pancreas, renal, or gastric cancer.

In another embodiment, the cancers are selected from the group consisting of breast cancer, gastric cancer, non-small cell lung cancer (NSCLC), prostate cancer and ovarian cancer.

In another embodiment, the conjugates can be administered in vitro, in vivo and/or ex vivo to treat, prevent, reduce the risk of developing and/or delay onset of certain pathologies or disorders, for example, a cancer. For example, the conjugates of the disclosure are useful in treating, preventing, delaying the progression of or otherwise ameliorating a symptom of a cancer selected from the group consisting of anal cancer, astrocytoma, leukemia, lymphoma, head and neck cancer, liver cancer, testicular cancer, cervical cancer, sarcoma, hemangioma, esophageal cancer, eye cancer, laryngeal cancer, mouth cancer, mesothelioma, skin cancer, myeloma, oral cancer, rectal cancer, throat cancer, bladder cancer, breast cancer, uterine cancer, ovarian cancer, prostate cancer, lung cancer, non-small cell lung cancer (NSCLC), colon cancer, pancreatic cancer, renal cancer, and gastric cancer.

In another embodiment the conjugates can be administered in vitro, in vivo and/or ex vivo to treat autoimmune diseases, such as systemic lupus, rheumatoid arthritis, psoriasis, and multiple sclerosis; graft rejections, such as renal transplant rejection, liver transplant rejection, lung transplant rejection, cardiac transplant rejection, and bone marrow transplant rejection; graft versus host disease; viral infections, such as CMV infection, HIV infection, and AIDS; and parasite infections, such as giardiasis, amoebiasis, schistosomiasis, and the like.

In certain embodiments the conjugates can also be used for the manufacture of a medicament useful for treating or lessening the severity of disorders, such as, characterized by abnormal growth of cells (e.g., cancer).

In certain embodiments, the therapeutic agent is locally delivered to a specific target cell, tissue, or organ.

In certain embodiments, in practicing the method of the disclosure, the conjugate further comprises or is associated with a diagnostic label. In certain exemplary embodiments, the diagnostic label is selected from the group consisting of: radiopharmaceutical or radioactive isotopes for gamma scintigraphy and PET, contrast agent for Magnetic Resonance Imaging (MRI), contrast agent for computed tomography, contrast agent for X-ray imaging method, agent for ultrasound diagnostic method, agent for neutron activation, moiety which can reflect, scatter or affect X-rays, ultrasounds, radiowaves and microwaves and fluorophores. In certain exemplary embodiments, the conjugate is further monitored in vivo.

Examples of diagnostic labels include, but are not limited to, diagnostic radiopharmaceutical or radioactive isotopes for gamma scintigraphy and PET, contrast agent for Magnetic Resonance Imaging (MRI) (for example paramagnetic atoms and superparamagnetic nanocrystals), contrast agent for computed tomography, contrast agent for X-ray imaging method, agent for ultrasound diagnostic method, agent for neutron activation, and moiety which can reflect, scatter or affect X-rays, ultrasounds, radiowaves and microwaves, fluorophores in various optical procedures, etc. Diagnostic radiopharmaceuticals include □-emitting radionuclides, e.g., indium-111, technetium-99m and iodine-131, etc. Contrast agents for MRI (Magnetic Resonance Imaging) include magnetic compounds, e.g., paramagnetic ions, iron, manganese, gadolinium, lanthanides, organic paramagnetic moieties and superparamagnetic, ferromagnetic and antiferromagnetic compounds, e.g., iron oxide colloids, ferrite colloids, etc. Contrast agents for computed tomography and other X-ray based imaging methods include compounds absorbing X-rays, e.g., iodine, barium, etc. Contrast agents for ultrasound based methods include compounds which can absorb, reflect and scatter ultrasound waves, e.g., emulsions, crystals, gas bubbles, etc. Still other examples include substances useful for neutron activation, such as boron and gadolinium. Further, labels can be employed which can reflect, refract, scatter, or otherwise affect X-rays, ultrasound, radiowaves, microwaves and other rays useful in diagnostic procedures. Fluorescent labels can be used for photoimaging. In certain embodiments a modifier comprises a paramagnetic ion or group.

In another aspect, the disclosure provides a method of treating a disease or disorder in a subject, comprising preparing an aqueous formulation of at least one conjugate of the disclosure and parenterally injecting said formulation in the subject.

In another aspect, the disclosure provides a method of treating a disease or disorder in a subject, comprising preparing an implant comprising at least one conjugate of the disclosure, and implanting said implant into the subject. In certain exemplary embodiments, the implant is a biodegradable gel matrix.

In another aspect, the disclosure provides a method for treating of an animal in need thereof, comprising administering a conjugate according to the methods described above.

In another aspect, the disclosure provides a method for eliciting an immune response in an animal, comprising administering a conjugate as in the methods described above.

In another aspect, the disclosure provides a method of diagnosing a disease in an animal, comprising steps of:

administering a conjugate as in the methods described above, wherein said conjugate comprises a detectable molecule; and detecting the detectable molecule.

In certain exemplary embodiments, the step of detecting the detectable molecule is performed non-invasively. In certain exemplary embodiments, the step of detecting the detectable molecule is performed using suitable imaging equipment.

In one embodiment, a method for treating an animal comprises administering to the animal a biodegradable biocompatible conjugate of the disclosure as a packing for a surgical wound from which a tumor or growth has been removed. The biodegradable biocompatible conjugate packing will replace the tumor site during recovery and degrade and dissipate as the wound heals.

In certain embodiments, the conjugate is associated with a diagnostic label for in vivo monitoring.

The conjugates described above can be used for therapeutic, preventative, and analytical (diagnostic) treatment of animals. The conjugates are intended, generally, for parenteral administration, but in some cases may be administered by other routes.

In one embodiment, soluble or colloidal conjugates are administered intravenously. In another embodiment, soluble or colloidal conjugates are administered via local (e.g., subcutaneous, intramuscular) injection. In another embodiment, solid conjugates (e.g., particles, implants, drug delivery systems) are administered via implantation or injection.

In another embodiment, conjugates comprising a detectable label are administered to study the patterns and dynamics of label distribution in animal body.

In certain embodiments, any one or more of the conjugates disclosed herein may be used in practicing any of the methods described herein.

The pharmaceutical compositions of the conjugates described herein can be included in a container, pack, or dispenser together with instructions for administration.

In certain embodiments, the compositions can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

In one embodiment, the active compounds (e.g., conjugates or drugs of the disclosure) are administered in combination therapy, i.e., combined with other agents, e.g., therapeutic agents, that are useful for treating pathological conditions or disorders, such as various forms of cancer, autoimmune disorders and inflammatory diseases. The term "in combination" in this context means that the agents are given substantially contemporaneously, either simultaneously or sequentially. If given sequentially, at the onset of administration of the second compound, the first of the two compounds is preferably still detectable at effective concentrations at the site of treatment.

For example, the combination therapy can include one or more conjugates disclosed herein coformulated with, and/or coadministered with, one or more additional antibodies, which can be the same as the antibody used to form the conjugate or a different antibody.

For example, the combination therapy can include one or more therapeutic agent and/or adjuvant. In certain embodiments, the additional therapeutic agent is a small molecule inhibitor, another antibody-based therapy, a polypeptide or peptide-based therapy, a nucleic acid-based therapy and/or other biologic.

In certain embodiments, the additional therapeutic agent is a cytotoxic agent, a chemotherapeutic agent, a growth inhibitory agent, an angiogenesis inhibitor, a PARP (poly (ADP)-ribose polymerase) inhibitor, an alkylating agent, an anti-metabolite, an anti-microtubule agent, a topoisomerase inhibitor, a cytotoxic antibiotic, any other nucleic acid damaging agent or an immune checkpoint inhibitor. In one embodiment, the therapeutic agent used in the treatment of cancer, includes but is not limited to, a platinum compound (e.g., cisplatin or carboplatin); a taxane (e.g., paclitaxel or docetaxel); a topoisomerase inhibitor (e.g., irinotecan or topotecan); an anthracycline (e.g., doxorubicin (ADRIAMYCIN®) or liposomal doxorubicin (DOXIL®)); an anti-metabolite (e.g., gemcitabine, pemetrexed); cyclophosphamide; vinorelbine (NAVELBINE®); hexamethylmelamine; ifosfamide; etoposide; an angiogenesis inhibitor (e.g., Bevacizumab (Avastin®)), thalidomide, TNP-470, platelet factor 4, interferon or endostatin); a PARP inhibitor (e.g., Olaparib (Lynparza™)); an immune checkpoint inhibitor, such as for example, a monoclonal antibody that targets either PD-1 or PD-L ((Pembrolizumab (Keytruda®), atezolizumab (MPDL3280A) or Nivolumab (Opdivo®)) or CTA-4 (Ipilimumab (Yervoy®), a kinase inhibitor (e.g., sorafenib or erlotinib), a proteasome inhibitor (e.g., bortezomib or carfilzomib), an immune modulating agent (e.g., lenalidomide or IL-2), a radiation agent, an ALK inhibitor (e.g. crizotinib (Xalkori), ceritinib (Zykadia), alectinib (Alecensa), dalantercept (ACE-041), brigatinib (AP26113), entrectinib (NMS-E628), PF-06463922 TSR-011, CEP-37440 and X-396) and/or a biosimilar thereof and/or combinations thereof. Other suitable agents include an agent considered standard of care by those skilled in the art and/or a chemotherapeutic agent well known to those skilled in the art.

In some embodiments, the immune checkpoint inhibitor is an inhibitor of CTLA-4. In some embodiments, the immune checkpoint inhibitor is an antibody against CTLA-4. In some embodiments, the immune checkpoint inhibitor is a monoclonal antibody against CTLA-4. In other embodiments, the immune checkpoint inhibitor is a human or humanized antibody against CTLA-4. In one embodiment, the anti-CTLA-4 antibody blocks the binding of CTLA-4 to CD80 (B7-1) and/or CD86 (B7-2) expressed on antigen presenting cells. Exemplary antibodies against CTLA-4 include, but are not limited to, Bristol Meyers Squibb's anti-CTLA-4 antibody ipilimumab (also known as Yervoy®, MDX-010, BMS-734016 and MDX-101); anti-CTLA4 Antibody, clone 9H10 from Millipore; Pfizer's tremelimumab (CP-675,206, ticilimumab); and anti-CTLA4 antibody clone BNI3 from Abeam.

In some embodiments, the anti-CTLA-4 antibody is an anti-CTLA-4 antibody disclosed in any of the following patent publications (herein incorporated by reference): WO 2001014424; WO 2004035607; US2005/0201994; EP 1212422 B1; WO2003086459; WO2012120125; WO2000037504; WO2009100140; WO200609649; WO2005092380; WO2007123737; WO2006029219; WO20100979597; WO200612168; and WO1997020574. Additional CTLA-4 antibodies are described in U.S. Pat. Nos. 5,811,097, 5,855,887, 6,051,227, and 6,984,720; in PCT Publication Nos. WO 01/14424 and WO 00/37504; and in U.S. Publication Nos. 2002/0039581 and 2002/086014; and/or U.S. Pat. Nos. 5,977,318, 6,682,736, 7,109,003, and 7,132,281, incorporated herein by reference). In some embodiments, the anti-CTLA-4 antibody is for example, those disclosed in: WO 98/42752; U.S. Pat. Nos. 6,682,736 and 6,207,156; Hurwitz et al, Proc. Natl. Acad. Sci. USA, 95(17): 10067-10071 (1998); Camacho et al, J. Clin. Oncol., 22(145): Abstract No. 2505 (2004) (antibody CP-675206); Mokyr et al, Cancer Res., 58:5301-5304 (1998) (incorporated herein by reference).

In some embodiments, the CTLA-4 inhibitor is a CTLA-4 ligand as disclosed in WO1996040915.

In some embodiments, the CTLA-4 inhibitor is a nucleic acid inhibitor of CTLA-4 expression. For example, anti-CTLA4 RNAi molecules may take the form of the molecules described by Mello and Fire in PCT Publication Nos. WO 1999/032619 and WO 2001/029058; U.S. Publication Nos. 2003/0051263, 2003/0055020, 2003/0056235, 2004/265839, 2005/0100913, 2006/0024798, 2008/0050342, 2008/0081373, 2008/0248576, and 2008/055443; and/or U.S. Pat. Nos. 6,506,559, 7,282,564, 7,538,095, and 7,560,438 (incorporated herein by reference). In some instances, the anti-CTLA4 RNAi molecules take the form of double stranded RNAi molecules described by Tuschl in European Patent No. EP 1309726 (incorporated herein by reference). In some instances, the anti-CTLA4 RNAi molecules take the form of double stranded RNAi molecules described by Tuschl in U.S. Pat. Nos. 7,056,704 and 7,078,196 (incorporated herein by reference). In some embodiments, the CTLA4 inhibitor is an aptamer described in PCT Publication No. WO2004081021.

Additionally, the anti-CTLA4 RNAi molecules of the present disclosure may take the form be RNA molecules described by Crooke in U.S. Pat. Nos. 5,898,031, 6,107,094, 7,432,249, and 7,432,250, and European Application No. EP 0928290 (incorporated herein by reference).

In some embodiments, the immune checkpoint inhibitor is an inhibitor of PD-L1. In some embodiments, the immune checkpoint inhibitor is an antibody against PD-L1. In some embodiments, the immune checkpoint inhibitor is a monoclonal antibody against PD-L1. In other or additional embodiments, the immune checkpoint inhibitor is a human or humanized antibody against PD-L1. In one embodiment, the immune checkpoint inhibitor reduces the expression or activity of one or more immune checkpoint proteins, such as PD-L1. In another embodiment, the immune checkpoint inhibitor reduces the interaction between PD-1 and PD-L1.

Exemplary immune checkpoint inhibitors include antibodies (e.g., an anti-PD-L1 antibody), RNAi molecules (e.g., anti-PD-L1 RNAi), antisense molecules (e.g., an anti-PD-L1 antisense RNA), dominant negative proteins (e.g., a dominant negative PD-L1 protein), and small molecule inhibitors. Antibodies include monoclonal antibodies, humanized antibodies, deimmunized antibodies, and Ig fusion proteins. An exemplary anti-PD-L1 antibody includes clone EH12. Exemplary antibodies against PD-L1 include: Genentech's MPDL3280A (RG7446); Anti-mouse PD-L1 antibody Clone 10F.9G2 (Cat #BE0101) from BioXcell; anti-PD-L1 monoclonal antibody MDX-1105 (BMS-936559) and BMS-935559 from Bristol-Meyer's Squibb; MSB0010718C; mouse anti-PD-L1 Clone 29E.2A3; and AstraZeneca's MEDI4736. In some embodiments, the anti-PD-L1 antibody is an anti-PD-L1 antibody disclosed in any of the following patent publications (herein incorporated by reference): WO2013079174; CN101104640; WO2010036959; WO2013056716; WO2007005874; WO2010089411; WO2010077634; WO2004004771; WO2006133396; WO201309906; US 20140294898; WO2013181634 or WO2012145493.

In some embodiments, the PD-L1 inhibitor is a nucleic acid inhibitor of PD-L1 expression. In some embodiments, the PD-L1 inhibitor is disclosed in one of the following patent publications (incorporated herein by reference): WO2011127180 or WO2011000841. In some embodiments, the PD-L1 inhibitor is rapamycin.

In some embodiments, the immune checkpoint inhibitor is an inhibitor of PD-L2. In some embodiments, the immune checkpoint inhibitor is an antibody against PD-L2. In some embodiments, the immune checkpoint inhibitor is a monoclonal antibody against PD-L2. In other or additional embodiments, the immune checkpoint inhibitor is a human or humanized antibody against PD-L2. In some embodiments, the immune checkpoint inhibitor reduces the expression or activity of one or more immune checkpoint proteins, such as PD-L2. In other embodiments, the immune checkpoint inhibitor reduces the interaction between PD-1 and PD-L2. Exemplary immune checkpoint inhibitors include antibodies (e.g., an anti-PD-L2 antibody), RNAi molecules (e.g., an anti-PD-L2 RNAi), antisense molecules (e.g., an anti-PD-L2 antisense RNA), dominant negative proteins (e.g., a dominant negative PD-L2 protein), and small molecule inhibitors. Antibodies include monoclonal antibodies, humanized antibodies, deimmunized antibodies, and Ig fusion proteins.

In some embodiments, the PD-L2 inhibitor is GlaxoSmithKline's AMP-224 (Amplimmune). In some embodiments, the PD-L2 inhibitor is rHIgM12B7.

In some embodiments, the immune checkpoint inhibitor is an inhibitor of PD-L1. In some embodiments, the immune checkpoint inhibitor is an antibody against PD-1. In some embodiments, the immune checkpoint inhibitor is a monoclonal antibody against PD-1. In other embodiments, the immune checkpoint inhibitor is a human or humanized antibody against PD-1. For example, the inhibitors of PD-1 biological activity (or its ligands) disclosed in U.S. Pat. Nos. 7,029,674; 6,808,710; or U.S. Patent Application Nos: 20050250106 and 20050159351 can be used in the combinations provided herein. Exemplary antibodies against PD-1 include: Anti-mouse PD-1 antibody Clone J43 (Cat #BE0033-2) from BioXcell; Anti-mouse PD-1 antibody Clone RMP1-14 (Cat #BE0146) from BioXcell; mouse anti-PD-1 antibody Clone EH12; Merck's MK-3475 anti-mouse PD-1 antibody (Keytruda®, pembrolizumab, lambrolizumab, h409A11); and AnaptysBio's anti-PD-1 antibody, known as ANB011; antibody MDX-1 106 (ONO-4538); Bristol-Myers Squibb's human IgG4 monoclonal antibody nivolumab (Opdivo®, BMS-936558, MDX1106); AstraZeneca's AMP-514, and AMP-224; and Pidilizumab (CT-011 or hBAT-1), CureTech Ltd.

Additional exemplary anti-PD-1 antibodies are described by Goldberg et al, Blood 1 10(1): 186-192 (2007), Thompson et al, Clin. Cancer Res. 13(6): 1757-1761 (2007), and Korman et al, International Application No. PCT/JP2006/309606 (publication no. WO 2006/121168 A1), each of which are expressly incorporated by reference herein. In some embodiments, the anti-PD-1 antibody is an anti-PD-1 antibody disclosed in any of the following patent publications (herein incorporated by reference): WO014557; WO2011110604; WO2008156712; US2012023752; WO2011110621; WO2004072286; WO2004056875; WO20100036959; WO2010029434; WO201213548; WO2002078731; WO2012145493; WO2010089411; WO2001014557; WO2013022091; WO2013019906; WO2003011911; US20140294898; and WO2010001617.

In some embodiments, the PD-1 inhibitor is a PD-1 binding protein as disclosed in WO200914335 (herein incorporated by reference).

In some embodiments, the PD-1 inhibitor is a peptidomimetic inhibitor of PD-1 as disclosed in WO2013132317 (herein incorporated by reference).

In some embodiments, the PD-1 inhibitor is an anti-mouse PD-1 mAb: clone J43, BioXCell (West Lebanon, N.H.).

In some embodiments, the PD-1 inhibitor is a PD-L1 protein, a PD-L2 protein, or fragments, as well as antibody MDX-1 106 (ONO-4538) tested in clinical studies for the treatment of certain malignancies (Brahmer et al., J Clin Oncol. 2010 28(19): 3167-75, Epub 2010 Jun. 1). Other blocking antibodies may be readily identified and prepared by the skilled person based on the known domain of interaction between PD-1 and PD-L1/PD-L2, as discussed above. For example, a peptide corresponding to the IgV region of PD-1 or PD-L1/PD-L2 (or to a portion of this region) could be used as an antigen to develop blocking antibodies using methods well known in the art.

In some embodiments, the immune checkpoint inhibitor is an inhibitor of IDO1. In some embodiments, the immune checkpoint inhibitor is a small molecule against IDOL Exemplary small molecules against IDO1 include: Incyte's INCB024360, NSC-721782 (also known as 1-methyl-D-tryptophan), and Bristol Meyers Squibb's F001287.

In some embodiments, the immune checkpoint inhibitor is an inhibitor of LAG3 (CD223). In some embodiments, the immune checkpoint inhibitor is an antibody against LAG3. In some embodiments, the immune checkpoint inhibitor is a monoclonal antibody against LAG3. In other or additional embodiments, the immune checkpoint inhibitor is a human or humanized antibody against LAG3. In additional embodiments, an antibody against LAG3 blocks the interaction of LAG3 with major histocompatibility complex (MHC) class II molecules. Exemplary antibodies against LAG3 include: anti-Lag-3 antibody clone eBioC9B7W (C9B7W) from eBioscience; anti-Lag3 antibody LS-B2237 from LifeSpan Biosciences; IMP321 (ImmuFact) from Immutep; anti-Lag3 antibody BMS-986016; and the LAG-3 chimeric antibody A9H12. In some embodiments, the anti-LAG3 antibody is an anti-LAG3 antibody disclosed in any of the following patent publications (herein incorporated by reference): WO2010019570; WO2008132601; or WO2004078928.

In some embodiments, the immune checkpoint inhibitor is an antibody against TIM3 (also known as HAVCR2). In some embodiments, the immune checkpoint inhibitor is a monoclonal antibody against TIM3. In other or additional embodiments, the immune checkpoint inhibitor is a human or humanized antibody against TIM3. In additional embodiments, an antibody against TIM3 blocks the interaction of TIM3 with galectin-9 (Gal9). In some embodiments, the anti-TIM3 antibody is an anti-TIM3 antibody disclosed in any of the following patent publications (herein incorporated by reference): WO2013006490; WO201155607; WO2011159877; or WO200117057. In another embodiment, a TIM3 inhibitor is a TIM3 inhibitor disclosed in WO2009052623.

In some embodiments, the immune checkpoint inhibitor is an antibody against B7-H3. In one embodiment, the immune checkpoint inhibitor is MGA271.

In some embodiments, the immune checkpoint inhibitor is an antibody against MR. In one embodiment, the immune checkpoint inhibitor is Lirilumab (IPH2101). In some embodiments, an antibody against MR blocks the interaction of KIR with HLA.

In some embodiments, the immune checkpoint inhibitor is an antibody against CD137 (also known as 4-1BB or TNFRSF9). In one embodiment, the immune checkpoint inhibitor is urelumab (BMS-663513, Bristol-Myers Squibb), PF-05082566 (anti-4-1BB, PF-2566, Pfizer), or XmAb-5592 (Xencor). In one embodiment, an anti-CD137 antibody is an antibody disclosed in U.S. Published Application No. US 2005/0095244; an antibody disclosed in issued U.S. Pat. No. 7,288,638 (such as 20H4.9-IgG4 [1007 or BMS-663513] or 20H4.9-IgG1 [BMS-663031]); an antibody disclosed in issued U.S. Pat. No. 6,887,673 [4E9 or BMS-554271]; an antibody disclosed in issued U.S. Pat. No. 7,214,493; an antibody disclosed in issued U.S. Pat. No. 6,303,121; an antibody disclosed in issued U.S. Pat. No. 6,569,997; an antibody disclosed in issued U.S. Pat. No. 6,905,685; an antibody disclosed in issued U.S. Pat. No. 6,355,476; an antibody disclosed in issued U.S. Pat. No. 6,362,325 [1D8 or BMS-469492; 3H3 or BMS-469497; or 3E1]; an antibody disclosed in issued U.S. Pat. No. 6,974,863 (such as 53A2); or an antibody disclosed in issued U.S. Pat. No. 6,210,669 (such as 1D8, 3B8, or 3E1). In a further embodiment, the immune checkpoint inhibitor is one disclosed in WO 2014036412. In another embodiment, an antibody against CD137 blocks the interaction of CD137 with CD137L.

In some embodiments, the immune checkpoint inhibitor is an antibody against PS. In one embodiment, the immune checkpoint inhibitor is Bavituximab.

In some embodiments, the immune checkpoint inhibitor is an antibody against CD52. In one embodiment, the immune checkpoint inhibitor is alemtuzumab.

In some embodiments, the immune checkpoint inhibitor is an antibody against CD30. In one embodiment, the immune checkpoint inhibitor is brentuximab vedotin. In another embodiment, an antibody against CD30 blocks the interaction of CD30 with CD30L.

In some embodiments, the immune checkpoint inhibitor is an antibody against CD33. In one embodiment, the immune checkpoint inhibitor is gemtuzumab ozogamicin.

In some embodiments, the immune checkpoint inhibitor is an antibody against CD20. In one embodiment, the immune checkpoint inhibitor is ibritumomab tiuxetan. In another embodiment, the immune checkpoint inhibitor is ofatumumab. In another embodiment, the immune checkpoint inhibitor is rituximab. In another embodiment, the immune checkpoint inhibitor is tositumomab.

In some embodiments, the immune checkpoint inhibitor is an antibody against CD27 (also known as TNFRSF7). In one embodiment, the immune checkpoint inhibitor is CDX-1127 (Celldex Therapeutics). In another embodiment, an antibody against CD27 blocks the interaction of CD27 with CD70.

In some embodiments, the immune checkpoint inhibitor is an antibody against OX40 (also known as TNFRSF4 or CD134). In one embodiment, the immune checkpoint inhibitor is anti-OX40 mouse IgG. In another embodiment, an antibody against 0×40 blocks the interaction of OX40 with OX40L.

In some embodiments, the immune checkpoint inhibitor is an antibody against glucocorticoid-induced tumor necrosis factor receptor (GITR). In one embodiment, the immune checkpoint inhibitor is TRX518 (GITR, Inc.). In another embodiment, an antibody against GITR blocks the interaction of GITR with GITRL.

In some embodiments, the immune checkpoint inhibitor is an antibody against inducible T-cell COStimulator (ICOS, also known as CD278). In one embodiment, the immune checkpoint inhibitor is MEDI570 (MedImmune, LLC) or AMG557 (Amgen). In another embodiment, an antibody against ICOS blocks the interaction of ICOS with ICOSL and/or B7-H2.

In some embodiments, the immune checkpoint inhibitor is an inhibitor against BTLA (CD272), CD160, 2B4, LAIR1, TIGHT, LIGHT, DR3, CD226, CD2, or SLAM. As described elsewhere herein, an immune checkpoint inhibitor can be one or more binding proteins, antibodies (or fragments or variants thereof) that bind to immune checkpoint molecules, nucleic acids that downregulate expression of the immune checkpoint molecules, or any other molecules that bind to immune checkpoint molecules (i.e. small organic molecules, peptidomimetics, aptamers, etc.). In some instances, an inhibitor of BTLA (CD272) is HVEM. In some instances, an inhibitor of CD160 is HVEM. In some cases, an inhibitor of 2B4 is CD48. In some instances, an inhibitor of LAIR1 is collagen. In some instances, an inhibitor of TIGHT is CD112, CD113, or CD155. In some instances, an inhibitor of CD28 is CD80 or CD86. In some instances, an inhibitor of LIGHT is HVEM. In some instances, an inhibitor of DR3 is TL1A. In some instances, an inhibitor of CD226 is CD155 or CD112. In some cases, an inhibitor of CD2 is CD48 or CD58. In some cases, SLAM is self inhibitory and an inhibitor of SLAM is SLAM.

In certain embodiments, the immune checkpoint inhibitor inhibits a checkpoint protein that include, but are not limited to CTLA4 (cytotoxic T-lymphocyte antigen 4, also known as CD152), PD-L1 (programmed cell death 1 ligand 1, also known as CD274), PDL2 programmed cell death protein 2), PD-1 (programmed cell death protein 1, also known as CD279), a B-7 family ligand (B7-H1, B7-H3, B7-H4) BTLA (B and T lymphocyte attenuator, also known as CD272), HVEM, TIM3 (T-cell membrane protein 3), GAL9, LAG-3 (lymphocyte activation gene-3; CD223), VISTA, KIR (killer immunoglobulin receptor), 2B4 (also known as CD244), CD160, CGEN-15049, CHK1 (Checkpoint kinase 1), CHK2 (Checkpoint kinase 2), A2aR (adenosine A2a receptor), CD2, CD27, CD28, CD30, CD40, CD70, CD80, CD86, CD137, CD226, CD276, DR3, GITR, HAVCR2, HVEM, IDO1 (indoleamine 2,3-dioxygenase 1), IDO2 (indoleamine 2,3-dioxygenase 2), ICOS (inducible T cell costimulator), LAIR1, LIGHT (also known as TNFSF14, a TNF family member), MARCO (macrophage receptor with collagenous structure), OX40 (also known as tumor necrosis factor receptor superfamily, member 4, TNFRSF4, and CD134) and its ligand OX40L (CD252), SLAM, TIGHT, VTCN1 or a combination thereof.

In certain embodiments, the immune checkpoint inhibitor interacts with a ligand of a checkpoint protein that comprises CTLA-4, PDL1, PDL2, PD1, BTLA, HVEM, TIM3, GAL9, LAG3, VISTA, KIR, 2B4, CD160, CGEN-15049, CHK1, CHK2, A2aR, a B-7 family ligand, CD2, CD27, CD28, CD30, CD40, CD70, CD80, CD86, CD137, CD226, CD276, DR3, GITR, HAVCR2, HVEM, IDO1, IDO2, ICOS (inducible T cell costimulator), LAIR1, LIGHT, MARCO (macrophage receptor with collagenous structure), OX-40, SLAM, TIGHT, VTCN1 or a combination thereof.

In certain embodiments, the immune checkpoint inhibitor inhibits a checkpoint protein that comprises CTLA-4, PDL1, PD1 or a combination thereof.

In certain embodiments, the immune checkpoint inhibitor inhibits a checkpoint protein that comprises CTLA-4 and PD1 or a combination thereof.

In certain embodiments, the immune checkpoint inhibitor comprises pembrolizumab (MK-3475), nivolumab (BMS-936558), pidilizumab (CT-011), AMP-224, MDX-1 105, durvalumab (MEDI4736), MPDL3280A, BMS-936559, IPH2101, TSR-042, TSR-022, ipilimumab, lirilumab, atezolizumab, avelumab, tremelimumab, or a combination thereof.

In certain embodiments, the immune checkpoint inhibitor is nivolumab (BMS-936558), ipilimumab, pembrolizumab, atezolizumab, tremelimumab, durvalumab, avelumab, or a combination thereof.

In certain embodiments, the immune checkpoint inhibitor is pembrolizumab.

Throughout the description, where compounds, scaffolds, and compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

All methods described herein can be performed in any suitable order unless otherwise indicated herein or otherwise clearly contradicted by context. The use of any and all examples, or exemplary language (e.g., "such as") provided herein, is intended merely to better illustrate the invention and is not to be construed as a limitation on the scope of the claims unless explicitly otherwise claimed. No language in the specification is to be construed as indicating that any non-claimed element is essential to what is claimed.

Synthetic Methods

Any available techniques can be used to make the conjugates or compositions thereof, and intermediates and components (e.g., scaffolds) useful for making them. For example, semi-synthetic and fully synthetic methods may be used.

The general methods of producing the conjugates or scaffolds disclosed herein are illustrated in Schemes 1 and 2 below. More specific methods of syntheses are described in the Examples. The variables (e.g., $M^P$, $M^A$, $L^3$, $W^D$, $W^M$, $L^D$, and $L^P$, etc.) in these schemes have the same definitions as described herein unless otherwise specified.

Scheme 1

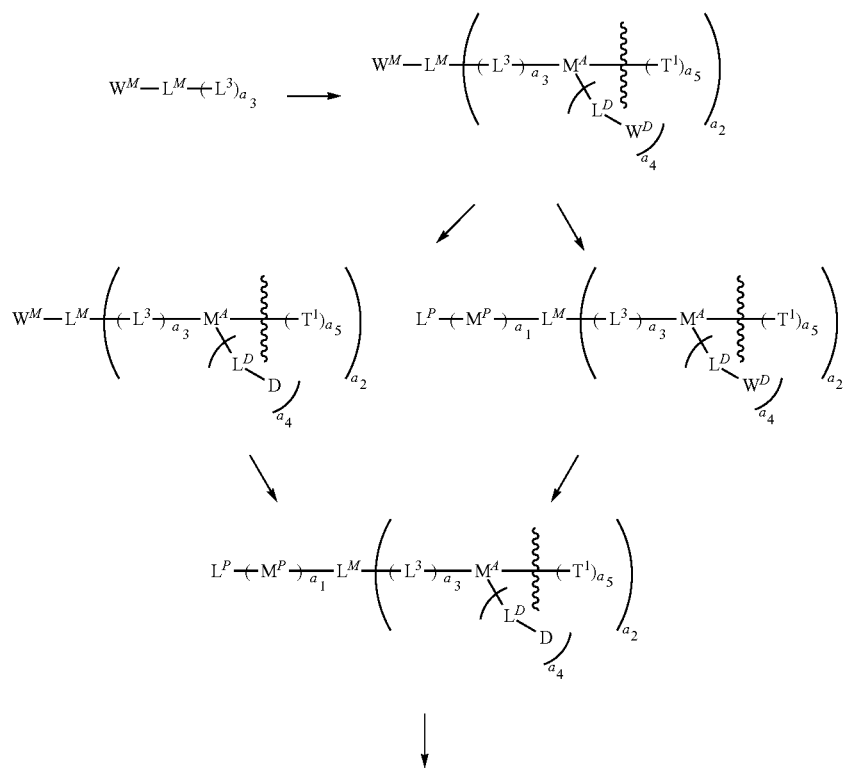

-continued

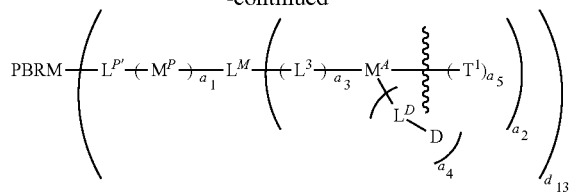

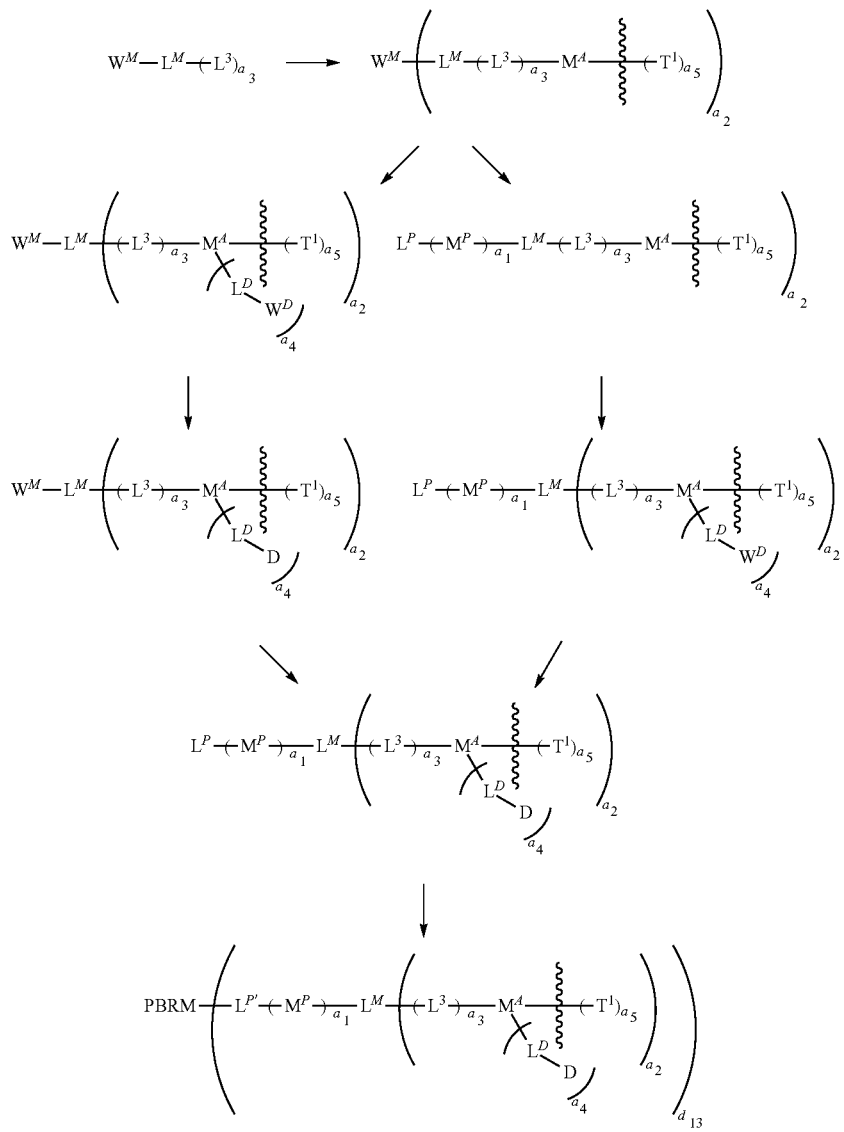

Scheme 2

The synthetic processes of the disclosure can tolerate a wide variety of functional groups; therefore various substituted starting materials can be used. The processes generally provide the desired final compound at or near the end of the overall process, although it may be desirable in certain instances to further convert the compound to a pharmaceutically acceptable salt, ester or prodrug thereof.

Drug compounds used for the conjugates of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry; Reactions, Mechanisms, and Structure*, 5$^{th}$ edition, John Wiley & Sons: New York, 2001; and Greene, T. W., Wuts, P. G. M., *Protective Groups in Organic Synthesis*, 3$^{rd}$ edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present disclosure.

Conjugates of the present disclosure and the drug compounds included therein can be conveniently prepared by a variety of methods familiar to those skilled in the art. The conjugates or compounds of the disclosure with each of the formulae described herein may be prepared according to the following procedures from commercially available starting materials or starting materials which can be prepared using literature procedures. These procedures show the preparation of representative conjugates of this disclosure.

Conjugates designed, selected and/or optimized by methods described above, once produced, can be characterized using a variety of assays known to those skilled in the art to determine whether the conjugates have biological activity. For example, the conjugates can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the conjugate molecules described herein for activity, using techniques known in the art. General methodologies for performing high-throughput screening are described, for example, in Devlin (1998) High Throughput Screening, Marcel Dekker; and U.S. Pat. No. 5,763,263. High-throughput assays can use one or more different assay techniques including, but not limited to, those described below.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

The following working examples are illustrative of the linkers, drug molecules and antibodies or antibody fragments, and methods for preparing same. These are not intended to be limiting and it will be readily understood by one of skill in the art that other reagents or methods may be utilized.

Abbreviations

The following abbreviations are used in the reaction schemes and synthetic examples, which follow. This list is not meant to be an all-inclusive list of abbreviations used in the application as additional standard abbreviations, which are readily understood by those skilled in the art of organic synthesis, can also be used in the synthetic schemes and examples Abbreviations:
- ACN Acetonitrile
- Alloc Allyloxycarbonyl
- AcOH Acetic acid
- BOC tert-butyloxycarbonyl
- CDI Bis(1H-imidazol-1-yl)methanone
- EDTA Ethylenediaminetetraacetic acid
- DCM Dichloromethane
- DIEA N,N-Diisopropylethylamine
- DMAP N,N-Dimethylpyridin-4-amine
- DMF Dimethylformamide
- EDC.HCl 1-Ethyl-3-[3-dimethylaminopropyl]carbodiimide hydrochloride
- HATU 1-[bis(dimethylamino)methylene]-1H-1,2,3-triazolo[4,5-b]pyridinium 3-oxid hexafluorophosphate)
- HOAt 1-Hydroxy-7-azabenzotriazole
- HOBt Hydroxybenzotriazole
- NHS 1-Hydroxypyrrolidine-2,5-dione (i.e., N-hydroxysuccinimide)
- TEAA Triethylammonium acetate
- TCEP Tris[2-carboxyethyl] phosphine
- THF Tetrahydrofuran
- MI Maleimide or maleimido
- PDI Polydispersity index
- RP-HPLC Reverse-phase high performance liquid chromatography
- SEC Size exclusion chromatography
- WCX Weak cation exchange chromatography General Information 8,8-bis((2-carboxyethoxy)methyl)-3,6-dioxo-1-phenyl-2,10-dioxa-4,7-diazadodecane-12-carboxylic acid was purchased from eNovation Chemicals LLC, Bridgewater, NJ 2,5-dioxopyrrolidin-1-yl3-(2-(2-(3-(2,5-dioxo-2,5-dihydro-1H-pyrrol-1yl)propanamido)ethoxy)ethoxy)propanoate was purchased from QuantaBiodesign Ltd, Boc-Glu(OtBu)-OH, di-tert-butyl dicarbonate, (S)-benzyl 2-((tert-butoxycarbonyl)amino)-3-hydroxypropanoate, 3-methoxy-3-oxopropan-1-ammonium chloride, Boc-Asp (OAll)-OH were purchased from Sigma-Aldrich 2-(2-(2-(2-aminoacetamido)acetamido)acetamido)acetic acid was purchased from Bachem Americas Inc. Torrance, CA $H_2N$-$PEG_{12}$-OMe was purchased from Quanta Biodesign, Ltd.

$H_2N$-$PEG_8$-OMe was purchased from ChemPep Inc., Wellington, FL $H_2N$-$PEG_6$-OMe was purchased from BroadPharm, San Diego, CA Glucamine was purchased from TCI America.

tert-butyl (2-(2-(2-aminoethoxy)ethoxy)ethyl)carbamate was purchased from A1 BioChem Labs, Wilmington, NC XMT-1535 is disclosed in co-pending application U.S. Ser. No. 15/457,574 filed Mar. 13, 2017.

Tumor growth inhibition (% TGI) was defined as the percent difference in median tumor volumes (MTVs) between treated and control groups.

Treatment efficacy was determined from the incidence and magnitude of regression responses of the tumor size observed during the study. Treatment may cause partial regression (PR) or complete regression (CR) of the tumor in an animal. In a PR response, the tumor volume was 50% or less of its Day 1 volume for three consecutive measurements during the course of the study, and equal to or greater than 13.5 mm³ for one or more of these three measurements. In a CR response, the tumor volume was less than 13.5 mm3 for three consecutive measurements during the course of the study. An animal with a CR response at the termination of a study was additionally classified as a tumor-free survivor (TFS). Animals were monitored for regression responses.

HPLC purification was performed on a Phenomenex Gemini 5 μm 110 Å, 250×10 mm, 5 micron, semi-preparation column.

Whenever possible the drug content of the conjugates was determined quantitatively by chromatography.

The protein content of the protein-polymer-drug conjugates was determined spectrophotometrically at 280 nm or by ELISA.

Antibody-polymer-drug conjugates, drug carrying-polymeric scaffolds, or antibody-carrying polymer scaffolds can be purified (i.e., removal of residual unreacted drug, antibody, or polymeric starting materials) by extensive diafiltration. If necessary, additional purification by size exclusion chromatography can be conducted to remove any aggregated antibody-polymer-drug conjugates. In general, the antibody-polymer-drug conjugates as purified typically contain <5% (e.g., <2% w/w) aggregated antibody-polymer-drug conjugates as determined by SEC; <0.5% (w/w) (e.g., <0.1% w/w) free (unconjugated) drug as determined by RP-HPLC or LC-MS/MS; <1% (w/w) of free polymer-drug conjugate as determined by SEC and/or RP-HPLC and <2% (w/w) (e.g., <1% w/w) unconjugated antibody or antibody fragment as determined by HIC-HPLC and/or WCX HPLC. Reduced or partially reduced antibodies were prepared using procedures described in the literature, see, for example, Francisco et al., Blood 102 (4): 1458-1465 (2003). The total drug (conjugated and unconjugated) concentration was determined by RP-HPLC or back-calculation from DAR measured by CE-SDS.

RP-HPLC, or CE-SDS were used to characterize the specificity and distribution of the cysteine bioconjugation sites in the PBRM-polymer-drug conjugates. The results gave the positional distribution of the drug-polymer conjugates on the heavy (H) and light (L) chains of the PBRM.

To determine the concentration of the free drug in a biological sample, an acidified sample was treated with acetonitrile. The free drug was extracted and the acetonitrile supernatant was analyzed. To determine the concentration of conjugated AF-HPA, the sample was subjected to exhaustive basic hydrolysis followed by immunocapture using anti-IgG1 antibody magnetic beads. The acetonitrile supernatant containing the released AF-HPA and AF was analyzed RP-HPLC. The total antibody was measured using the unique peptide after digestion.

Analysis of free AF and AF-HPA was conducted by RP-HPLC using a C-4 column, an acetonitrile gradient and UV detection. Peak areas are integrated and compared to AF and AF-HPA standards. The method is quantitive for AF-HPA and AF in plasma and tissue homogenates and linear over the concentration ranges of 0.1 to 150 ng/mL. The total drug (AF-HPA) released after hydrolysis with NaOH was measured under the same condition with the dynamic range from 1 ng/mL to 5000 ng/mL. The total antibody standards range from 0.1 μg/mL to 100 μg/mL.

Example 1: Synthesis of Monomeric PEG8 Scaffold (7)

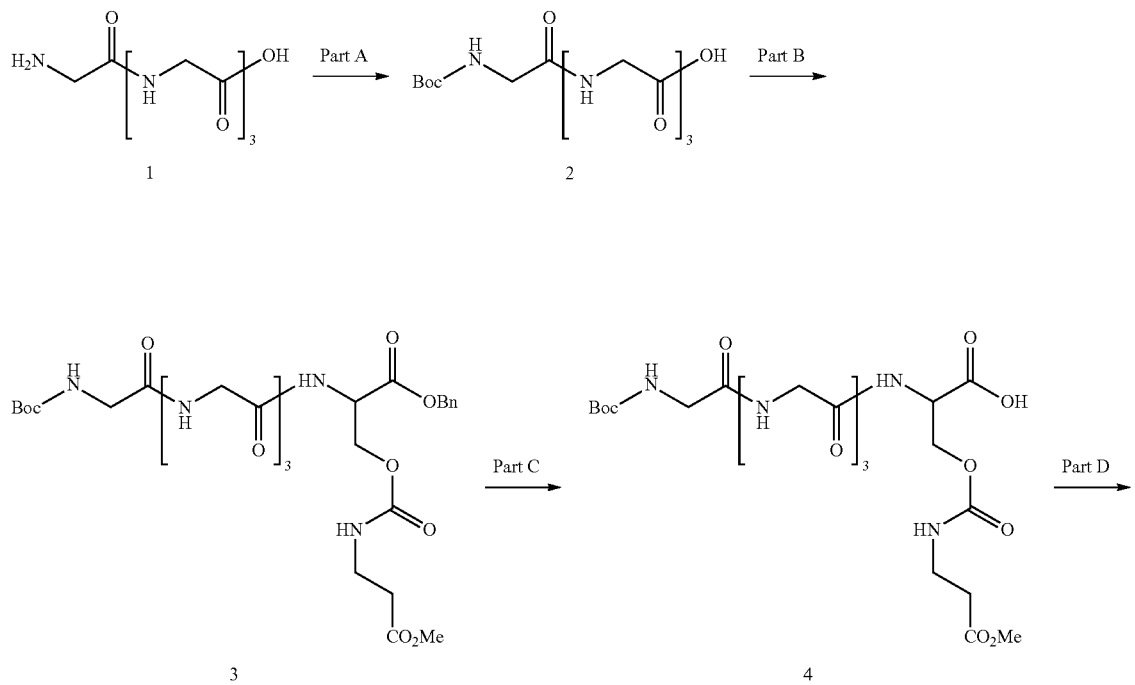

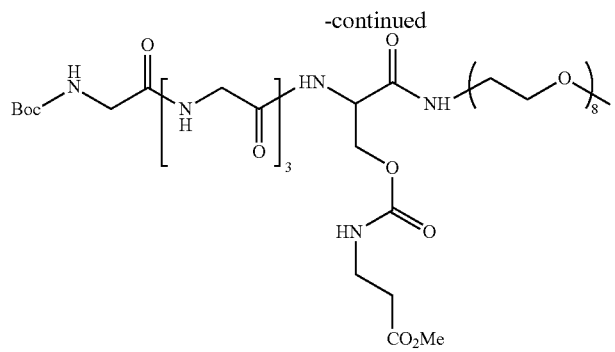

5

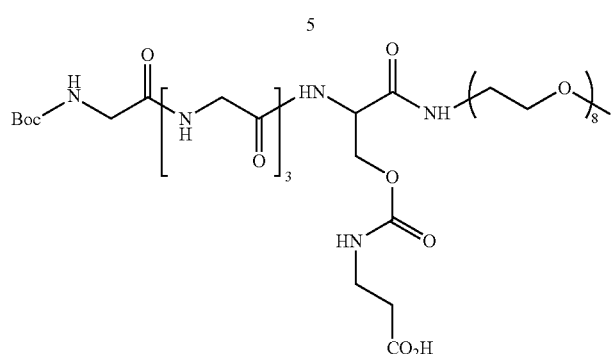

6

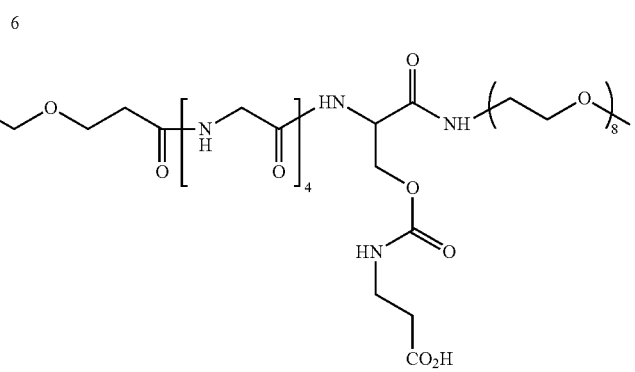

7

Part A:

Potassium carbonate (2.245 g, 16.25 mmol) was dissolved in dioxane/water (2:1, 120 mL) at room temperature, then 2-(2-(2-(2-aminoacetamido)acetamido)acetamido)acetic acid (compound 1, 2 g, 8.12 mmol) was added in one portion and the mixture was stirred until the reagents dissolved. Then di-tert-butyl dicarbonate (3.55 g, 16.25 mmol) in 1,4-dioxane (5 ml) was added dropwise and the reaction mixture was stirred at room temperature for 25 hours at which point LC-MS analysis indicated the reaction was complete. The crude mixture was neutralized to ~pH 7 with 1 M HCl, then adjusted to pH 2 with citric acid (0.9 equivalents), then concentrated by rotary evaporation and purified by RP C18 column CombiFlash chromatography to give compound 2 (2.57 g, 91% yield). $^1$H-NMR (400 MHz, DMSO-$d_6$): δ 8.06-8.20 ppm (m, 2H, 2NH), 8.01 (bs, 1H, NH), 6.98 (bs, 1H, NH), 3.73 (s, 6H, 3CH$_2$), 3.5-3.6 (d, 2H, CH$_2$), 1.37 (s, 9H, t-Bu). ESI MS: $C_{13}H_{22}N_4O_7$ [M+H]$^+$ 347.16 found 347.1.

Part B:

CDI (0.659 g, 4.06 mmol) was added in one portion to (S)-benzyl 2-((tert-butoxycarbonyl)amino)-3-hydroxypropanoate (1 g, 3.39 mmol) in THF (5 mL) at 0° C. The reaction mixture was stirred at room temperature for 1 hour at which point LC-MS analysis indicated the reaction was complete. Then 3-methoxy-3-oxopropan-1-ammonium chloride (1.182 g, 8.47 mmol) and DIEA (1.774 ml, 10.16 mmol) in DMF (3 mL) was added and the stirring continued at room temperature for 3.5 hours at which point LC-MS indicated the reaction was complete. The crude mixture was concentrated, neutralized, purified by RP C18 column CombiFlash chromatography to give Boc-Ser(O-β-Ala-OMe)-OBenzyl (1.085 g, 75% yield). $^1$H-NMR (400 MHz, CDCl$_3$): δ 5.3-5.42 (bs, 1H, NH), 5.1-5.28 (m, 3H, OCH$_2$—Ar), 4.5-4.6 (bs, 1H, CHN), 4.25-4.38 (dd, 2H, CH$_2$O), 3.71 (s, 3H, OMe), 3.35-3.50 (m, CH$_2$N), 2.53 (t, 2H, CH$_2$CO), 1.45 (s, 9H, t-Bu). ESI MS: $C_{20}H_{28}N_2O_8$ [M+Na]$^+$ 447.17; found 447.1.

Boc-Ser(β-Ala-OMe)-OBenzyl (1.085 g, 2.56 mmol) was dissolved in DCM (3.3 mL) containing TFA (1.1 mL) at 0° C. for 1 hour and then stirred at room temperature for 30 minutes until LC-MS indicated the reaction was complete. The TFA salt of benzyl 2-amino-3-(((3-methoxy-3-oxopropyl)carbamoyl)oxy)propanoate was concentrated by rotary evaporation.

Compound 2 (805 mg, 2.324 mmol) was dissolved in DMF (17 mL), cooled to 0° C. and NHS (401 mg, 3.49 mmol) was added followed by EDC (668 mg, 3.49 mmol) in DMF (6 mL). Separately the TFA salt of benzyl 2-amino-3-(((3-methoxy-3-oxopropyl)carbamoyl)oxy)propanoate (829 mg, 2.56 mmol) was dissolved in DMF (10 mL), stirred at 0° C. for 10 min and then DIEA (0.812 ml, 4.65 mmol), was added. This homogeneous mixture was added to the reaction mixture containing compound 2. The resulting mixture was stirred at 0° C. for about 1 hour and then at room temperature overnight. The reaction mixture was concentrated by rotary evaporation, pH 5-7, followed by purification by RP HPLC, to give compound 3 (149 mg, 80% yield). ESI MS: $C_{28}H_{40}N_6O_{12}$ [M+H]$^+$ 653.28, found 653.2.

Part C:

Compound 3 (1.213 g, 1.859 mmol) was dissolved in ethanol (80 mL) with heating and stirring, then cooled to room temperature and 10% Pd/C (198 mg) was added under H2. After 2 hours at room temperature LC-MS indicated the reaction was complete. The crude product was filtered and concentrated by rotary evaporation to give compound 4 (1.103 g, ~99% yield). ESI MS: $C_{21}H_{34}N_6O_{12}$ [M+H]$^+$ 563.23, found 563.1.

Part D:

Compound 4 (1.05 g, 1.86 mmol) was dissolved in a mixture of toluene/DMF and concentrated by rotary evaporation multiple times to remove the residual ethanol, then H$_2$N-PEGs-OMe (856 mg, 2.231 mmol) in DMF (15 mL) was added. The reaction mixture was cooled to 0° C., then HOAt (380 mg, 2.79 mmol), HATU (848 mg, 2.231 mmol), DMF (5 mL) and DIEA (0.812 ml, 4.65 mmol) were added. LC-MS showed the reaction was incomplete. Additional HOAt (253 mg) and HATU (353 mg) were added and the mixture warmed to room temperature. After 5 hours at room temperature the reaction mixture was warmed to 35° C. for ~45 minutes when LC-MS showed completion of the reaction. The crude reaction mixture was concentrated by rotary evaporation and purified by RP C18 column CombiFlash chromatography using ACN/water containing HOAc (0.1%) gradient as eluant, to give compound 5 (1.26 g, 73% yield).
$^1$H-NMR (400 MHz, DMSO-d$_6$) δ 8.00-8.25 (m, 5H, NH), 7.20 (t, 1H, NH), 7.00 (t, 1H, NH), 4.35-4.55 (m, 1H, CH), 3.93-4.20 (m, 2H, CH$_2$), 3.65-3.85 (m, 6H, CH$_2$), 3.58 (s, 3H, OMe), 3.55-3.63 (m, 2H, CH$_2$), 3.50 (bs, 26H, CH$_2$O), 3.35-3.45 (m, 4H, CH$_2$), 3.23 (s, 3H, OMe), 3.12-3.25 (m, 4H, CH$_2$N), 2.45 (t, 2H, CH$_2$CO), 1.37 (s, 9H, Ot-Bu). ESI MS: C38H$_{69}$N$_7$O$_{19}$ [M+H]$^+$ 928.47, found 928.3.

Part E:

Compound 5 (300 mg, 0.323 mmol) was dissolved in water (3.5 mL) and LiOH (77 μL of 4 M solution) at 0° C. was added. The reaction was monitored by LC-MS. After 1.5 hours additional aqueous LiOH (38 μL of 4 M solution) was added. After 20 minutes at 0° C., the reaction was neutralized with 1 M HCl, pH~5, followed by purification on C18 RP CombiFlash column using ACN/water containing HOAc (0.1%) gradient as eluant, to give compound 6 (253 mg, 86% yield). ESI MS: $C_{37}H_{67}N_7O_{19}$ [M+H]$^+$ 914.45, found 914.0.

Part F:

Compound 6 (117 mg, 0.128 mmol) was dissolved in DCM (3.75 mL) and treated at 0° C. with TFA (1.25 mL). After 45 min the reaction mixture was concentrated by rotary evaporation at 0° C. to give the TFA salt.

The TFA-salt of compound 6 (119 mg, 0.128 mmol) was dissolved in DMF (1.7 mL), then DIEA (5 equivalents) was added. The reaction mixture was cooled to 0° C., then 2,5-dioxopyrrolidin-1-yl3-(2-(2-(3-(2,5-dioxo-2,5-dihydro-1H-pyrrol-1yl)propanamido)ethoxy) ethoxy)propanoate (109 mg, 0.256 mmol) in DMF (0.5 mL) was added. Stirring was continued for 30 minutes at 0° C. and then at room temperature for 30 minutes, when LC-MS analysis indicated the reaction was complete. The reaction mixture was concentrated by rotary evaporation and purified by RP C18 column CombiFlash chromatography using ACN/water containing HOAc (0.1%) gradient as eluant, to give compound 7 (86 mg, 60% yield).
$^1$H NMR (400 MHz, DMSO-d$_6$+20 μL of D$_2$O) δ 12.07-12.25 (bs, 1H, CO$_2$H), 7.9-8.37 (m, 7H, NH), 7.11 (t, 1H, NH), 6.90-7.05 (s, 2H, CH=CH), 4.35-4.57 (m, 1H, CH), 3.95-4.20 (m, 2H, CH$_2$), 3.65-3.83 (m, 8H, CH$_2$), 3.25-3.65 (m, 40H, CH$_2$), 3.23 (s, 3H, OMe), 3.07-3.25 (m, 6H, CH$_2$), 2.20-2.43 (m, 6H, CH$_2$CO).

ESI MS: $C_{46}H_{77}N_9O_{23}$ [M+H]$^+$ 1124.52, found 1124.0.

Example 2: Synthesis of Trimeric PEG8 Scaffold (17)

Part A:

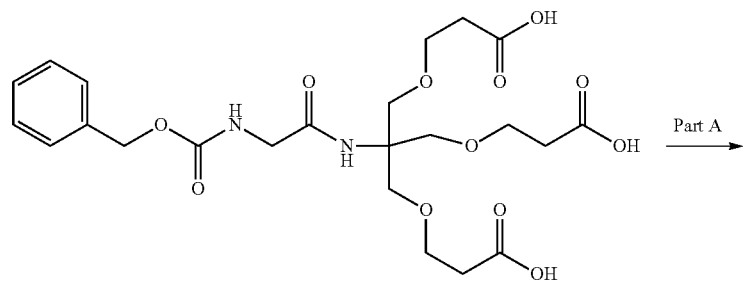

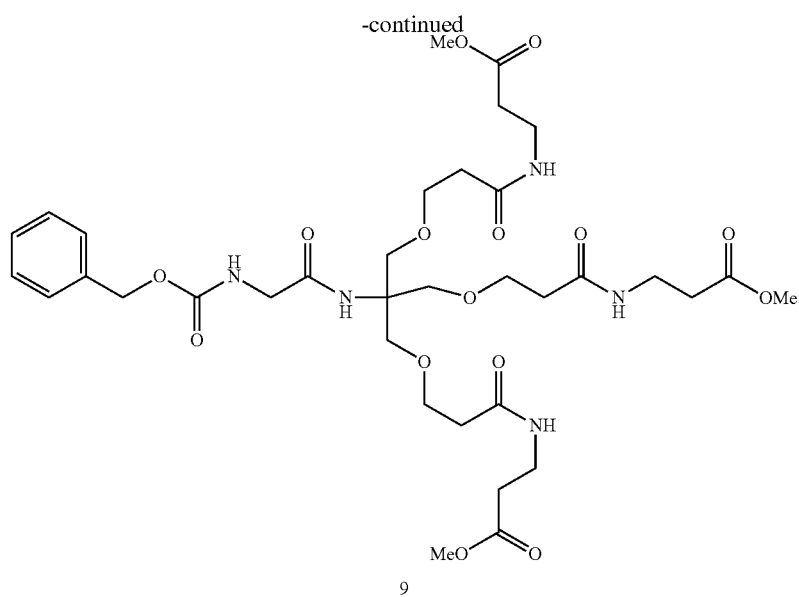

9

Compound 8 (0.5 g, 0.946 mmol) was dissolved in DCM/DMF (90:10, 25 mL), then HOAt (0.386 g, 2.84 mmol) and EDC (0.635 g, 3.31 mmol) were added and the resulting mixture was stirred at 0° C. for 15-20 minutes. Separately β-Ala-OMe hydrochloride (0.462 g, 3.31 mmol) in DCM/DMF (9:1, 5 mL) was treated with DIEA (0.578 ml, 3.31 mmol) and then added to the reaction mixture. Additional DIEA (0.578 ml) was added and the reaction mixture was allowed to warm up to room temperature and stirred overnight. LC-MS indicated the reaction was nearly complete. The crude reaction mixture was diluted with DCM and washed successively with HCl (0.2 M in brine), brine and aqueous NaOH (0.2M in brine) and brine. The organic phase was dried with MgSO$_4$, filtered and concentrated to give compound 9 that was used as is. ESI MS: $C_{35}H_{53}N_5O_{15}$ [M+H]$^+$ 784.35; found 784.0.

Part B:

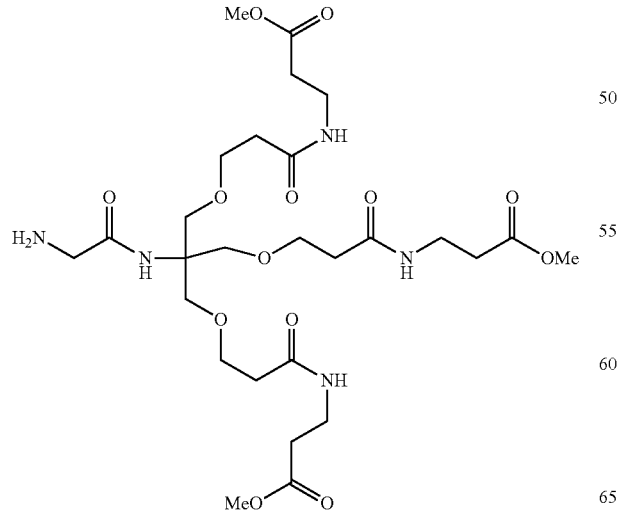

10

To compound 9 (735 mg, 0.938 mmol) in ethanol (50 mL) was added 10% Pd/C (100 mg, 0.094 mmol) under H$_2$. When LC-MS indicated the reaction was complete, the reaction mixture was filtered through Celite and concentrated to give compound 10 (0.565 g. 93% yield). ESI MS: $C_{27}H_{47}N_5O_{13}$ [M+H]$^+$ 650.32; found 650.0.

Part C:

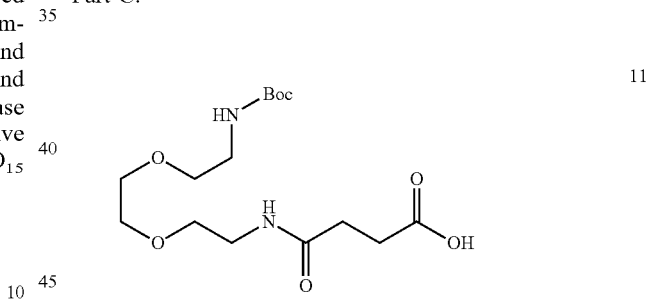

11

To tert-butyl (2-(2-(2-aminoethoxy)ethoxy)ethyl)carbamate (1 g, 4.03 mmol) in CHCl$_3$ (25 ml), at 0° C. was added dihydrofuran-2,5-dione (0.403 g, 4.03 mmol) and the reaction mixture was allowed to warm up to room temperature. After 20 hours, the reaction mixture was concentrated by rotary evaporation to give compound 11 (1.535 g). ESI MS: $C_{15}H_{28}N_2O_7$ [M−H]$^−$ 347.19; found 347.2.

Part D:

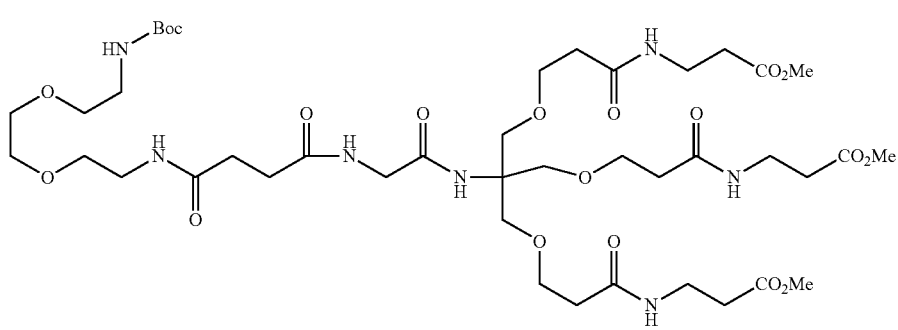

12

To compound 11 (201 mg, 0.576 mmol) in DMF (4.3 mL) at 0° C. was added HOAt) (115 mg, 0.847 mmol) and EDC (162 mg, 0.847 mmol). After 15 minutes, compound 10 (220 mg, 0.339 mmol) in DMF (0.7 mL) was added followed by DIEA (0.148 ml, 0.847 mmol). The reaction mixture was allowed to warm up slowly to room temperature and stirred overnight, then concentrated by rotary evaporation and purified by RP C18 column CombiFlash chromatography using ACN/water containing HOAc (0.1%) gradient as eluant, to give compound 12 (250 mg, 75% yield). ESI MS: $C_{42}H_{73}N_7O_{19}$ [M+H]$^+$ 979.5; found 980.0.

Part E:

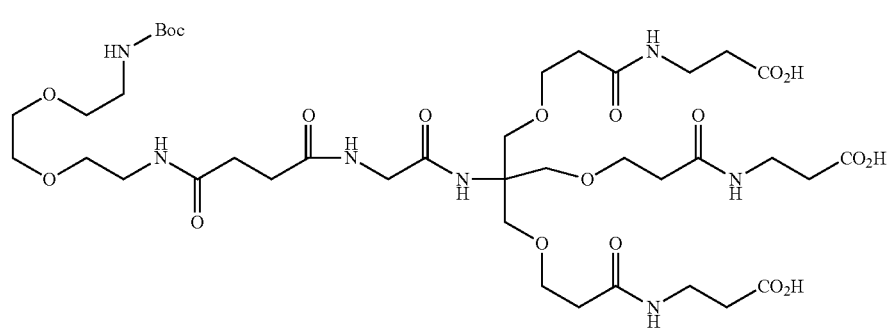

13

To compound 12 (250 mg, 0.255 mmol) in MeOH (4 ml) and water (0.5 mL) at 0° C. was added NaOH (51.0 mg, 1.275 mmol in water (0.5 mL)). After 45 minutes the reaction mixture was warmed to room temperature and stirred for 3 hours at room temperature, then neutralized with aqueous HCl (1M), concentrated and purified by C18 RP chromatography to give compound 13 (207 mg, 87% yield. ESI MS: $C_{39}H_{67}N_7O_{19}$ [M+H]$^+$ 938.45; found 938.0.

Part F:

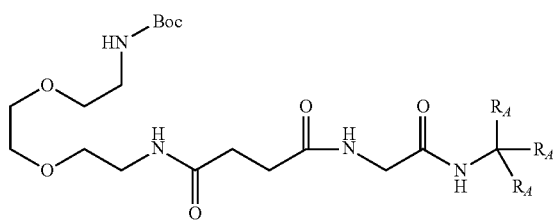

14

-continued

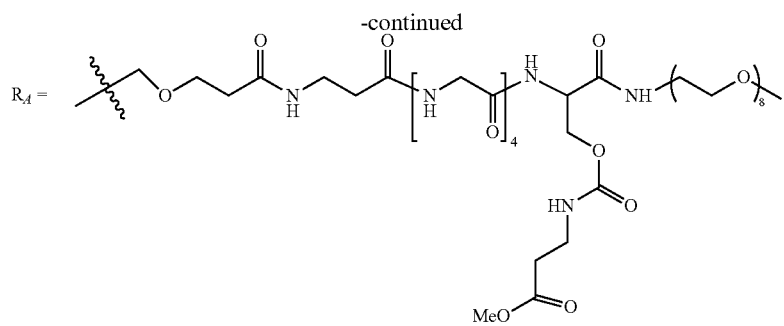

To compound 13 (90 mg, 0.096 mmol) in water (1.5 mL) at 0° C., was added HOAt (65.3 mg, 0.480 mmol) in NMP (350 μL) followed by EDC (92 mg, 0.480 mmol). The reaction mixture was stirred for 15 minutes. Separately compound 5 (294 mg, 0.355 mmol) was deprotected using TFA, neutralized and added to the reaction mixture. The pH of the resulting reaction mixture was adjusted to pH 7 and the reaction mixture was warmed slowly to room temperature and stirred overnight. The crude material was concentrated by rotary evaporation and purified by RP C18 column CombiFlash chromatography using ACN/water containing HOAc (0.1%) gradient as eluant, to give compound 14 (258 mg, 80% yield). ESI MS: $C_{138}H_{244}N_{28}O_{67}$ $[M+2H]^{2+}/2=1683.3$; found 1683.3.

Part G:

15

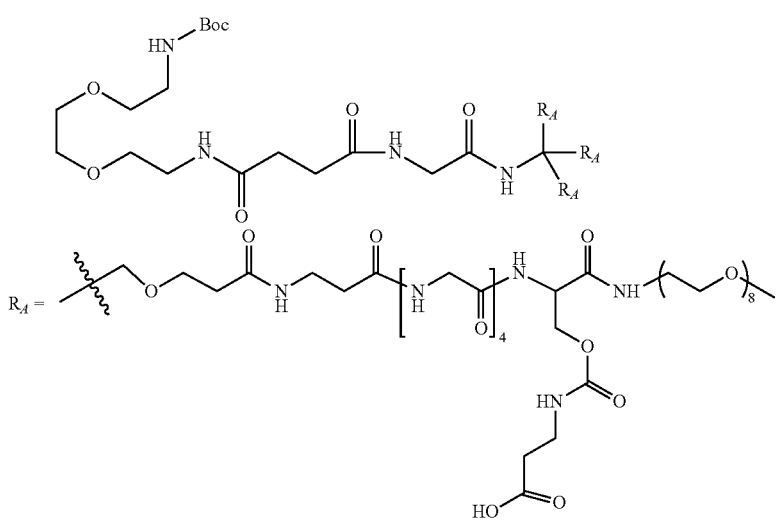

Compound 14 (222 mg, 0.066 mmol) in water (3 mL) was reacted with LiOH (16 mg) as described in Example 1, Part E, to give compound 15 (180 mg, 82% yield). ESI MS: $C_{135}H_{238}N_{28}O_{67}$ $[M+2H]^{2+}/2=1662.8$; found 1662.3.

Part H:

16

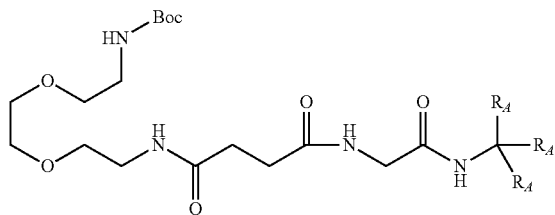

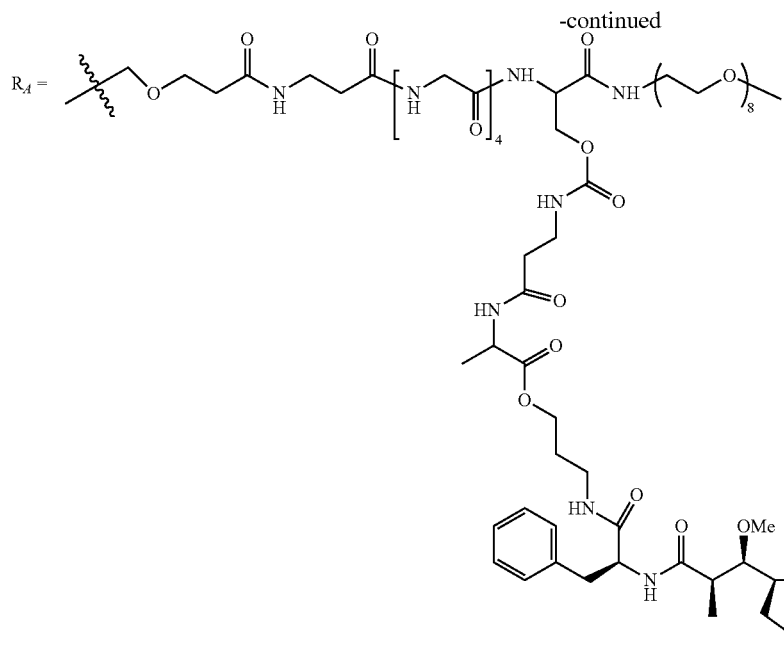

-continued

To compound 15 (157 mg, 0.047 mmol) in water (4.5 mL) at 0° C., was added HOAt (32.1 mg, 0.236 mmol) in NMP (500 μL) and EDC (27.2 mg, 0.142 mmol) and the resulting reaction mixture was stirred for 15 minutes. Separately a mixture of auristatin F-hydroxypropyl amide-alanine TFA-salt (182 mg, 0.165 mmol, prepared as described in U.S. Pat. No. 8,865,383) in water (1.5 mL) and NMP (250 μL) was neutralized, and then added to the reaction mixture at 0° C. The stirring was continued at 0° C. for 1.5 hours and then stirred at room temperature for 23 hours when LC-MS showed completion of the reaction. The crude reaction mixture was concentrated by rotary evaporation and purified by RP C18 column CombiFlash chromatography using ACN/water containing HOAc (0.1%) gradient as eluant, to give compound 16 (177 mg, 63% yield). ESI MS: [M+3H]$^{3+}$/3=1964.46; found 1964.5.

Part I:

17

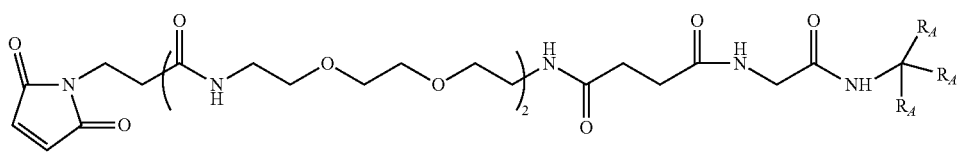

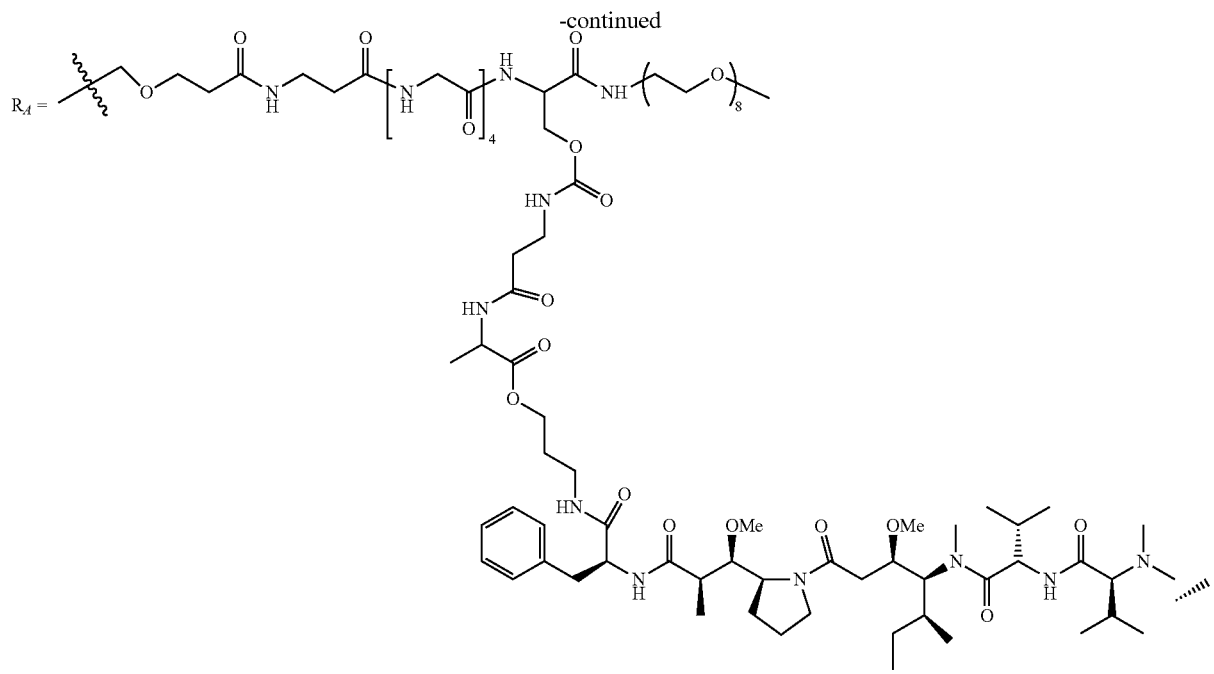

-continued

The TFA salt of compound 16 (40.3 mg, 6.96 μmol) in DCM was treated with DIEA until the reaction mixture was basic, then cooled to 0° C. before the addition of 2,5-dioxopyrrolidin-1-yl3-(2-(2-(3-(2,5-dioxo-2,5-dihydro-1H-pyrrol-1yl)propanamido)ethoxy) ethoxy)propanoate (14.80 mg, 34.8 μmol). After 45 minutes LC-MS analysis indicated the reaction was complete The crude reaction mixture was concentrated by rotary evaporation and purified by RP C18 column CombiFlash chromatography using ACN/water containing HOAc (0.1%) gradient as eluant, to give scaffold 17 (30 mg, 71% yield). ESI MS: $C_{282}H_{479}N_{51}O_{95}$ $[M+5H]^{5+}/5=1221.084$ found 1221.0; $[M+7H]^{7+}/7=872.49$ found 872.4.

Example 3: Synthesis of Compound 18

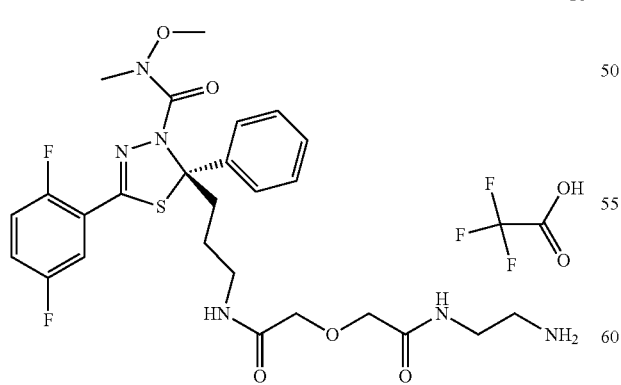

18

To 2,2-dimethyl-4,9-dioxo-3,11-dioxa-5,8-diazatridecan-13-oic acid (4.60 mg, 0.017 mmol, prepared as described in WO 2014/124317A1) and ARRY-520 (7 mg, 0.017 mmol) in DMF (150 μL) at 0° C. was added HOAt (3.40 mg, 0.025 mmol) and HATU (9.49 mg, 0.025 mmol), followed by DIEA (5.82 μL, 0.033 mmol) and stirring was continued for 95 minutes.

The reaction was quench by the addition of acetic acid and the crude mixture was purified by C18 RP HPLC to yield Boc protected compound 18 (7 mg, 62% yield). ESI MS: $C_{31}H_{40}F_2N_6O_7S$ [M+H] 679.26; found 678.9. The Boc protecting group was removed by treatment with TFA to give the compound 18.

Example 4: Synthesis of Compound 19

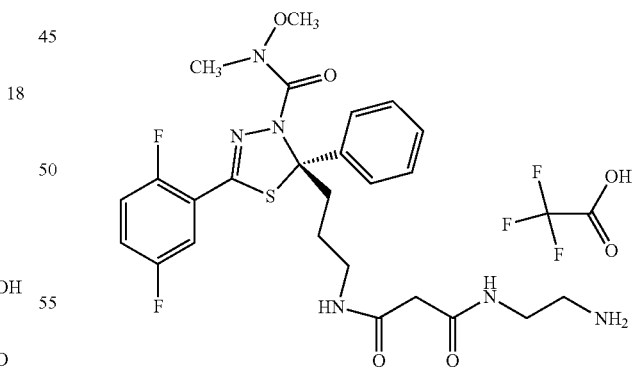

19

Compound 19 was prepared as described in Example 3 except 2,2-dimethyl-4,9-dioxo-3,1 1-dioxa-5,8-diazatridecan-13-oic acid (5.86 mg, 0.024 mmol) was used instead of 2,2-dimethyl-4,9-dioxo-3,11-dioxa-5,8-diazatridecan-13-oic acid. Boc protected compound 19: ESI MS: $C_{30}H_{38}F_2N_6O_6S$ $[M+H]^+$ 649.25; found 648.8.

Example 5: Synthesis of Compound 21

Part A:

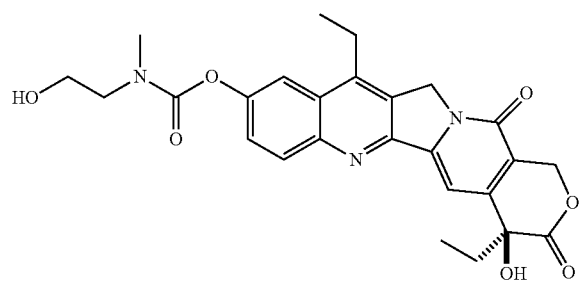

20

To SN38 (4.415 g, 11.25 mmol) in THF (380 mL) at 0° C. was slowly added HOBt hydrate (1.725 g, 11.25 mmol) in THF (65 mL) followed by the dropwise addition of 4-nitrophenyl carbonochloridate (4.54 g, 22.50 mmol) in THF (30 mL) and subsequent addition of DIEA (9.83 mL, 56.6 mmol). After 1 hour additional HOBt hydrate (1.725 g, 11.25 mmol) in THF (65 mL), DIEA (9.83 mL, 56.6 mmol) and 4-nitrophenyl carbonochloridate (1.135 g, 5.6 mmol) in THF (10 mL) were added. After 2.5 hours neat 2-(methylamino)ethanol (5.02 ml, 62.4 mmol) was added and the resulting reaction mixture was allowed to warm up to room temperature overnight. The crude reaction mixture was concentrated by rotary evaporation and purified by RP $C_{1-8}$ column CombiFlash chromatography using ACN/water containing HOAc (0.1%) gradient as eluant, to give compound 20 (3.695 g, 71.4% yield). ESI MS: $C_{26}H_{27}N_3O_7$ $[M+H]^+$ 494.18; found 494.0.

Part B:

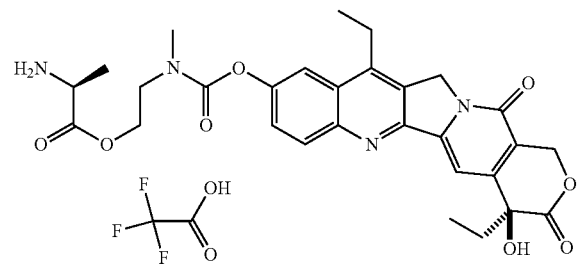

21

To Boc-Alanine (0.767 g, 4.05 mmol) in anhydrous DCM (170 mL) at 0° C., was added EDC (1.554 g, 8.11 mmol) followed by DMAP (0.495 g, 4.05 mmol). After 10 minutes compound 20 (2.0 g, 4.05 mmol) in anhydrous DCM (55) and added over 35 minutes. The reaction mixture was allowed to warm up to room temperature slowly over 1-1.5 hours. LC-MS analysis indicated the reaction was complete The crude reaction mixture was concentrated by rotary evaporation and purified by RP C18 column CombiFlash chromatography using ACN/water containing HOAc (0.1%) gradient as eluant, to give Boc protected compound 21 (1.70 g, 63% yield). The Boc protecting group was removed by treatment with TFA to give the compound 21 (1.97 g, 51% yield). ESI MS: $C_{29}H_{32}N_4O_8$ $[M+H]^+$ 565.2; found 565.4.

Example 6: Synthesis of Dimeric PEG8 Scaffold (24)

Part A:

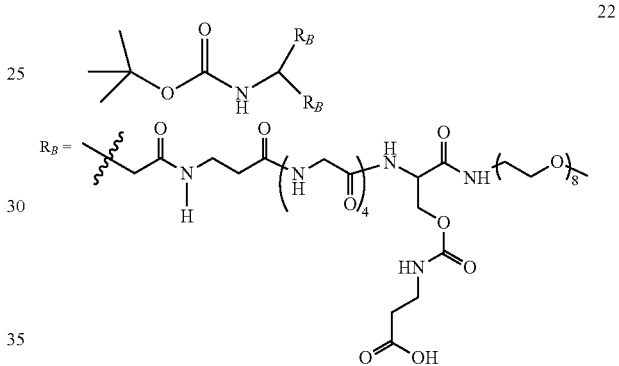

22

The methyl ester of compound 22 (0.495 g, 91% yield) was synthesized from 3,3'-((3-((tert-butoxycarbonyl)amino)pentanedioyl)bis(azanediyl))dipropionic acid (105 mg, 0.271 mmol, prepared from Boc protected homoaspartic acid using the procedures described in Atwell et al, Journal of Medicinal Chemistry, 29(1), 69-74; 1986 and WO2004089362) and compound 5 using the procedure described in Example 2, Part F. ESI MS: $C_{82}H_{145}N_{17}O_{40}$ m/z $[M+2H]^{2+}/2$ 1004.99 found 1004.5. The methyl ester of compound 22 was removed by treatment with LiOH using the procedure described in Example 1, Part E to give compound 22 (456 mg, 93% yield). ESI MS: $C_{80}H_{141}N_{17}O_{40}$: [M+H] 1980.95; found 1980.9.

Part B:

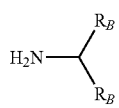

23

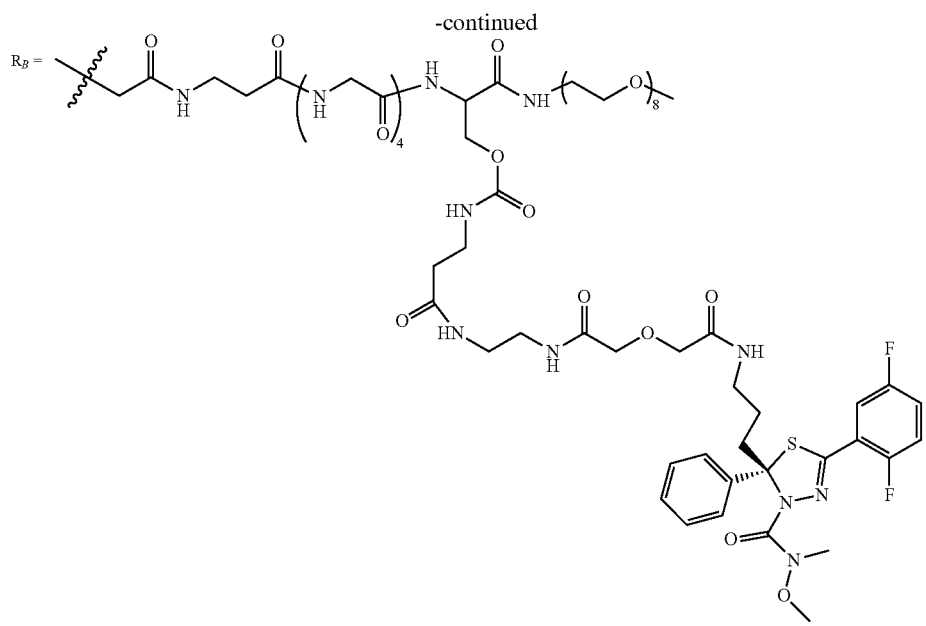
25
Boc protected compound 23 was prepared from compound 22 (5.14 mg, 2.59 μmol) and compound 18 (3 mg, 5.18 μmol) using the procedure described in Example 2, Part H. ESI MS: $C_{132}H_{201}F_4N_{29}O_{48}S_2$: $[M+2H]^{2+}/2$ 1551.18; found 1550.7. Boc protecting group was removed by treatment with TFA to give the compound 23.
Part C
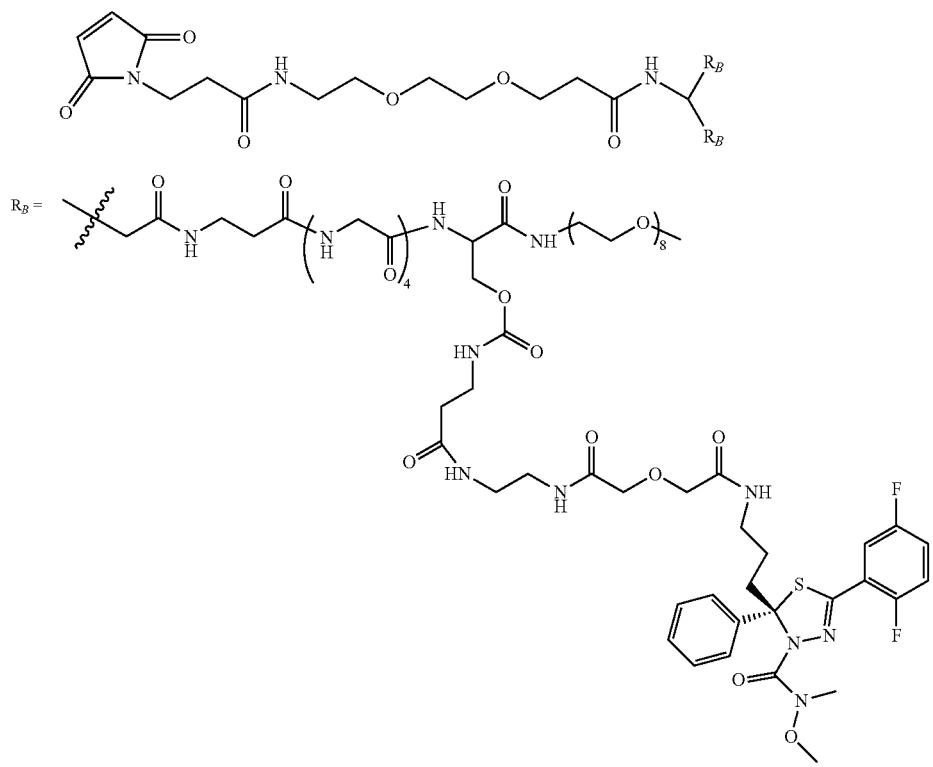
24
Scaffold 24 (3.05 mg) was prepared from compound 23 using the procedure described in Example 2, Part I. ESI MS: $C_{141}H_{211}F_4O_{52}S_2$: $[M+3H]^{3+}/3$ 1105.17; found 1105.15.

Example 7: Synthesis of Trastuzumab Conjugate of Scaffold 24 (Conjugate 25)

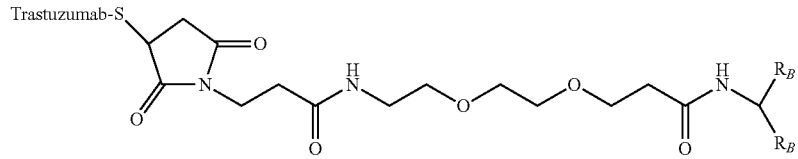

25

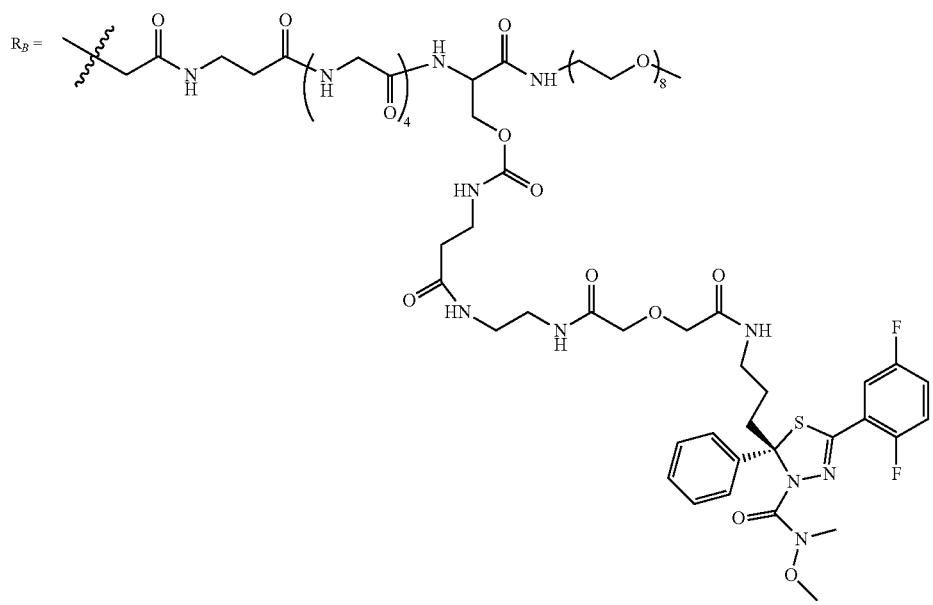

To a solution of Trastuzumab (10 mg, 0.067 μmol), in TEAA buffer (50 mM), 1 mM EDTA, pH 7, 1.03 mL) was added a solution of TCEP (0.077 mg, 0.270 μmol) and the resulting mixture was incubated for 1 h at 37° C. The reaction mixture was allowed to cool to room temperature and then diluted with TEAA buffer (2.9 mL). A solution of scaffold 24 (2.24 mg, 0.676 umol) (prepared as described in Example 6) in DMSO (0.5 mL) was then slowly added while vigorously stirring the reaction mixture. The reaction mixture was stirred at room temperature for ~1 h before quenching with cysteine (0.82 mg, 6.77 μmol). The crude product was purified by SEC (Biosep SEC 3000, pH 5.5, 50 mM sodium phosphate, 300 mM NaCl) followed by buffer exchange into formulation buffer (25 mM citrate, 75 mM NaCl, 50 mg/mL trehalose, pH 5.5) to give the conjugate 25 (3.85 mg, 38.5% yield). Purified conjugate had a drug to trastuzumab ratio of about 12.5 as determined by UV-Vis.

Example 8: Synthesis of Dimeric PEG8 Scaffold (27)

Part A:

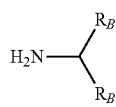

26

-continued

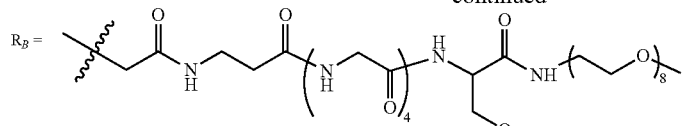

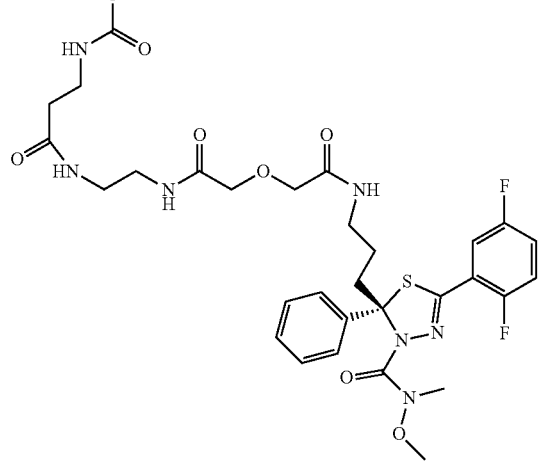

25

Boc protected compound 26 was prepared from compound 22 (8.76 mg, 4.42 µmol) and compound 19 (4.85 mg, 8.84 µmol) using the procedure described in Example 2, Part H. ESI MS: $C_{130}H_{197}F_4N_{29}O_{46}S_2$ $[M+2H]^{2+}/2$ 1521.16 found 1521.2. Boc protecting group was removed by treatment with TFA to give the compound 26.

Part B:

27

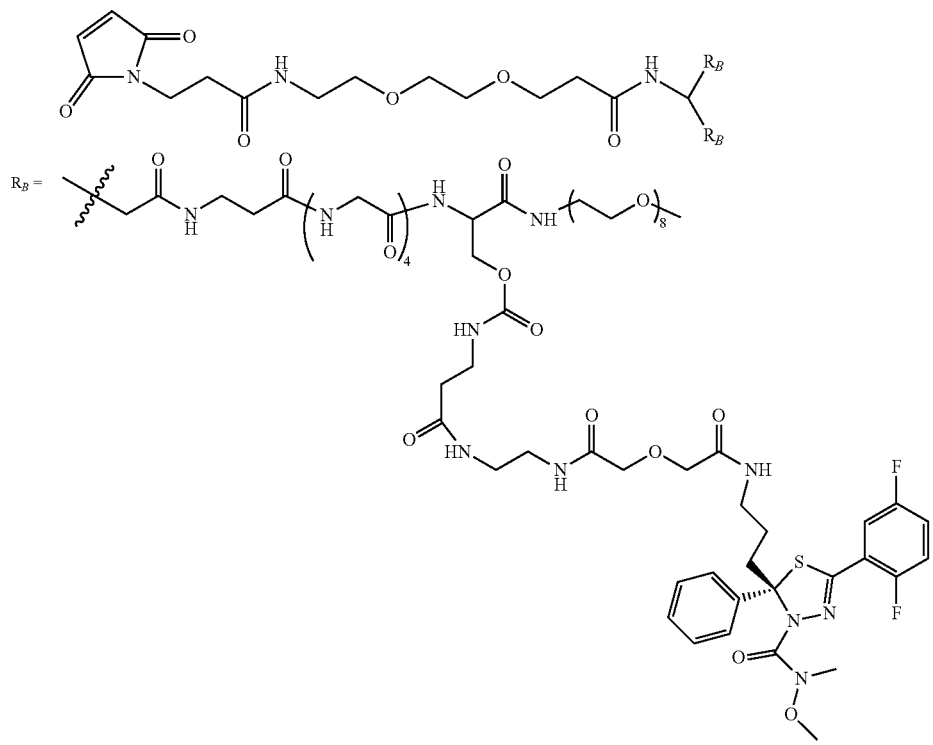

Scaffold 27 (4.05 mg) was prepared from compound 26 using the procedure described in Example 2, Part I. ESI MS: $C_{139}H_{207}F_4N_{31}O_{50}S_2$ m/z $[MH+2H]^{2+}/2=1626.7$ found 1626.70; $[MH+3H]^{3+}/3=1084.80$ found 1084.81.

Example 9: Synthesis of Trastuzumab Conjugate of Scaffold 27 (Conjugate 28)

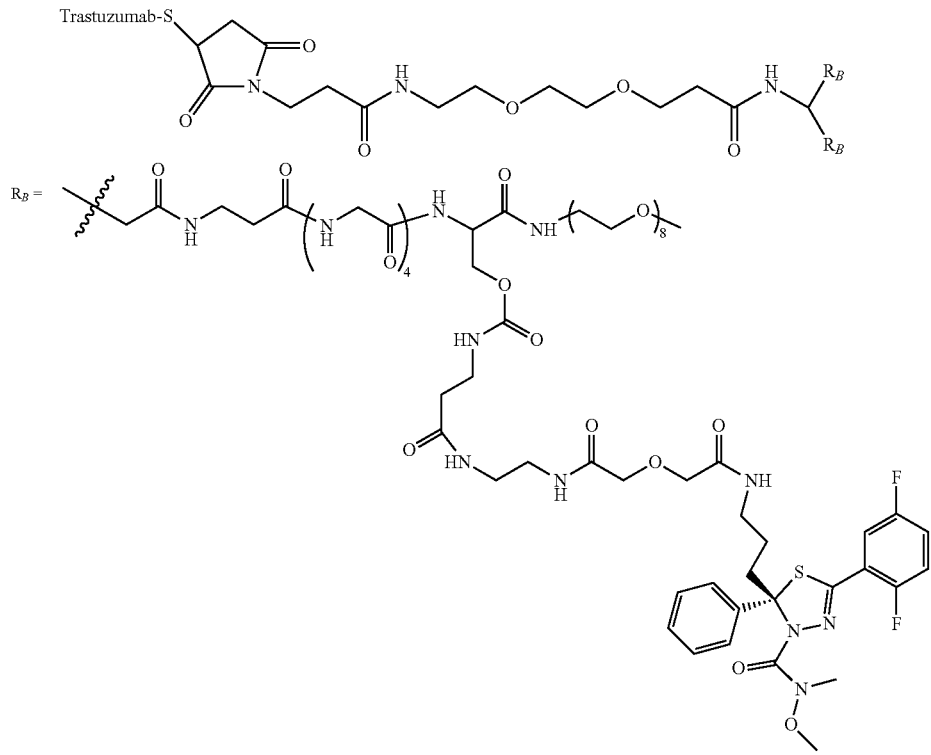

Conjugate 28 was prepared from scaffold 27 using the procedure described in Example 7. The purified conjugate had a drug to trastuzumab ratio of 2.8.

Example 10: Synthesis of Dimeric PEG8 Scaffold (30)

Part A:

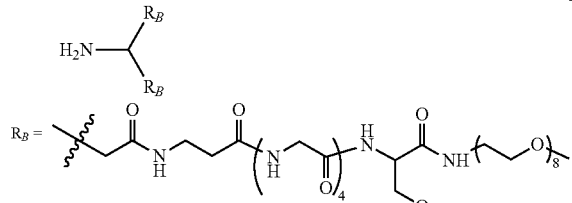

Boc protected compound 29 was prepared from compound 22 (7.5 mg, 3.79 µmol)) and ARRY-520 (1.910 mg, 4.54 µmol) using the procedure described in Example 2, Part H except HATU (7.20 mg, 0.019 mmol) was used instead of EDC. ESI MS: $C_{120}H_{181}F_4N_{25}O_{42}S_2$: $[M+2H]^{2+}/2$ 1393.11; found 1392.8. Boc protecting group was removed by treatment with TFA to give the compound 29.

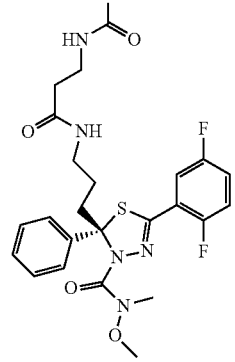

Part B:

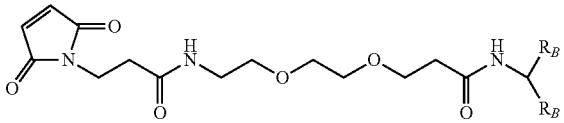

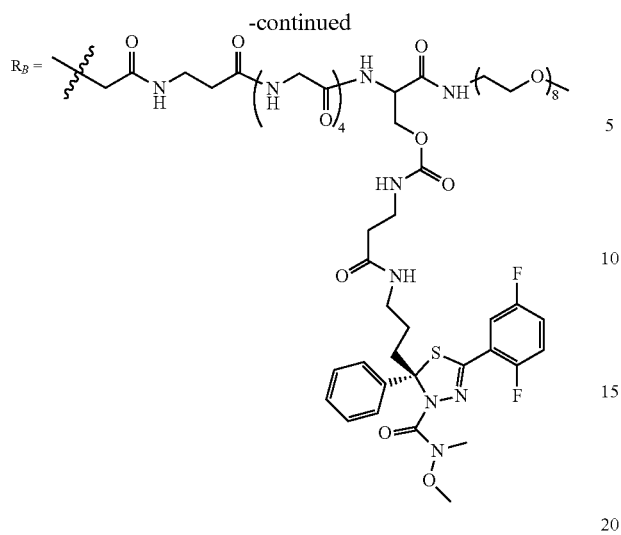

Scaffold 30 (5 mg, 75% yield) was prepared from compound 29 using the procedure described in Example 2, Part I. ESI MS: $C_{129}H_{191}F_4N_{27}O_{46}S_2$ m/z $[M+2H]^{2+}/2$ 1498.14; found 1497.8.

Example 11: Synthesis of Trastuzumab Conjugate of Scaffold 30 (Conjugates 31A and 31B)

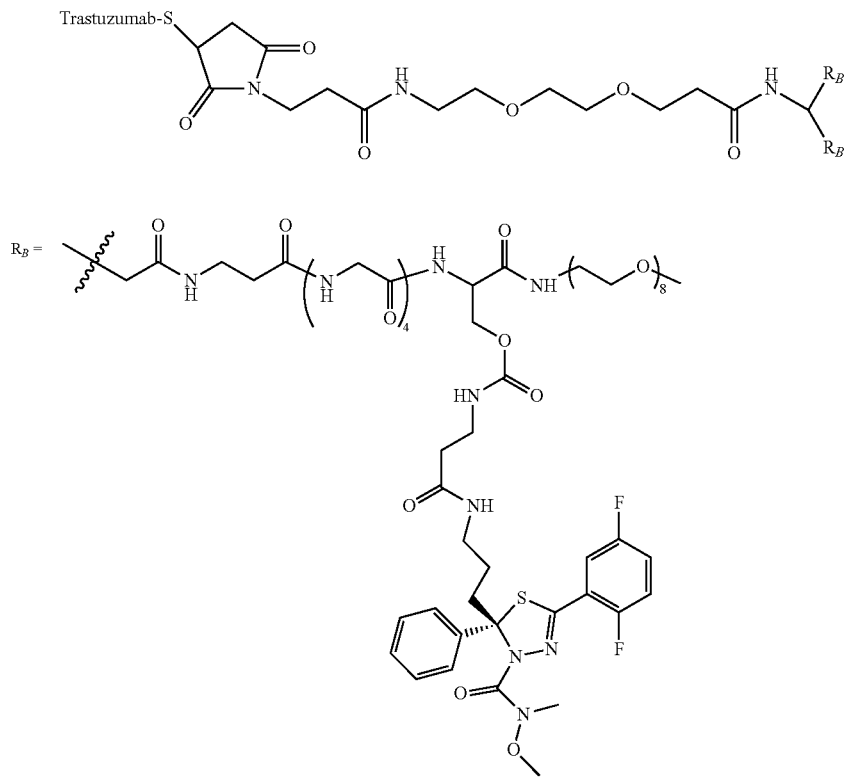

Conjugates 31A and 31B was prepared from scaffold 30 using the procedure described in Example 7. Purified conjugate 30A had a drug to trastuzumab ratio of 7.8 and conjugate 30B a drug to trastuzumab ratio of 7.6.

Example 12: Synthesis of Dimeric PEG8 Scaffold (33)

Part A:

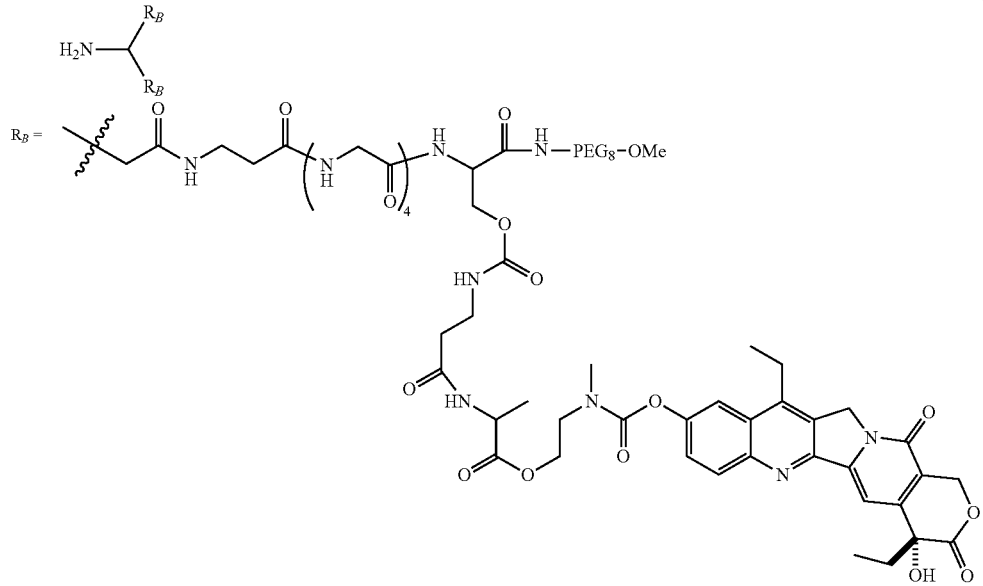

32

Boc protected compound 32 was prepared from compound 22 (12 mg, 6.06 μmol)) and compound 21 (13.32 mg, 18 μmol) using the procedure described in Example 2, Part H. ESI MS: $C_{138}H_{201}N_{25}O_{54}$: $[M+2H]^{2+}/2$ 1537.19; found 1537.3. Boc protecting group was removed by treatment with TFA to give the compound 32.

Part B:

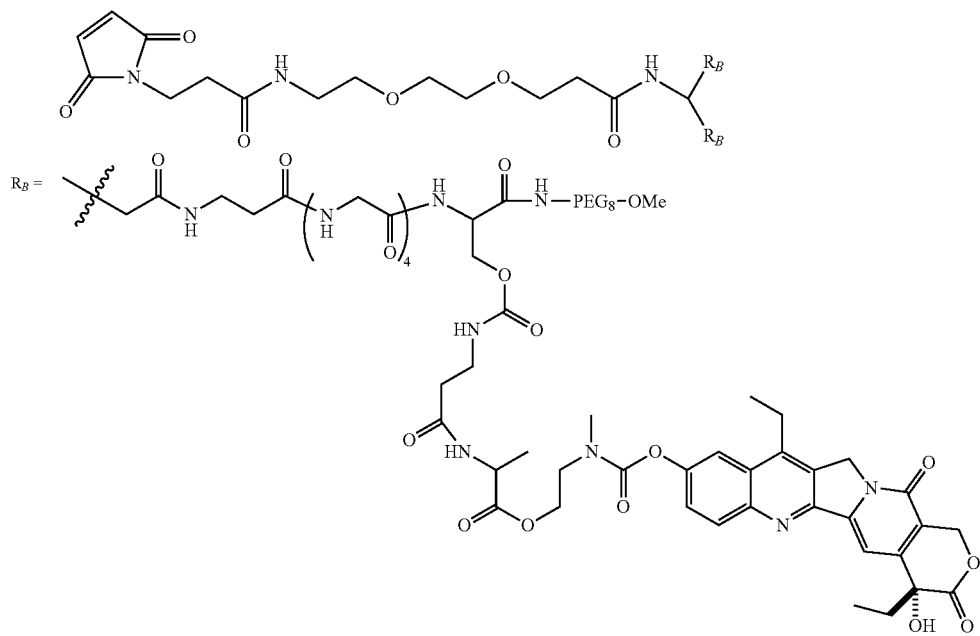

33

Scaffold 33 (4.5 mg) was prepared from compound 32 using the procedure described in Example 2, Part I. ESI MS: $C_{147}H_{211}N_{27}O_{58}$ $[M+2H]^{2+}/2$ 1642.22; found 1641.8; $[M+3H]^{3+}/3$ 1095.17 found 1095.0.

Example 13: Synthesis of Trastuzumab Conjugate of Scaffold 33 (Conjugates 34A and 34B)

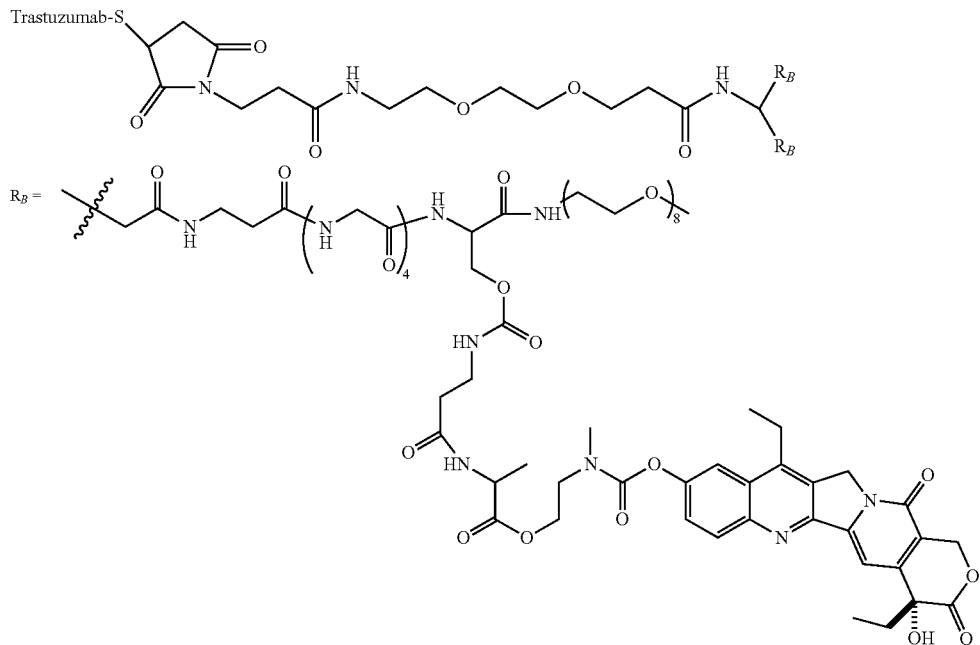

34

Conjugates 34A and 34B was prepared from scaffold 33 using the procedure described in Example 7. Purified conjugate 34A had a drug to trastuzumab ratio of 6.4 and conjugate 34B a drug to trastuzumab ratio of 6.3.

Example 14: Synthesis of Compound 35

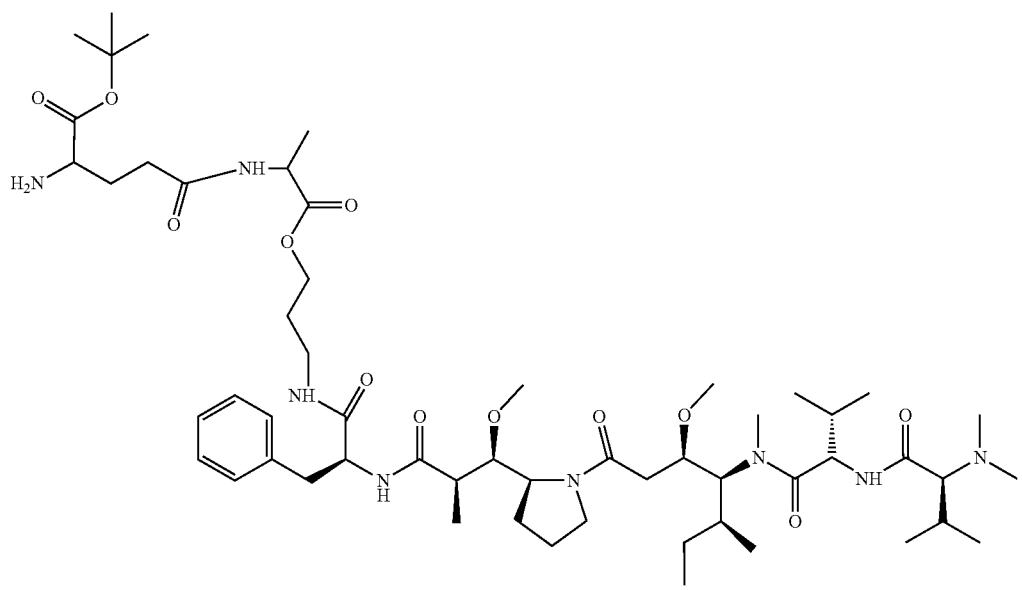

35

Boc protected compound 35 was prepared by treating Boc-Glu(OtBu)-OH (128 mg, 0.422 mmol) in DMF (1.5 mL) at 0° C., with NHS (81 mg, 0.704 mmol) followed by EDC (135 mg, 0.704 mmol). Separately auristatin F-hydroxypropyl amide-alanine TFA-salt (400 mg, 0.352 mmol, prepared as described in U.S. Pat. No. 8,865,383) and DIEA (0.184 mL, 1.056 mmol) in DMF (1 mL) were stirred at 0° C. for 10 min was added. This homogeneous mixture was added to the reaction mixture. The resulting mixture was stirred at 0° C. for about 1 hour and then at room temperature overnight. The reaction mixture was concentrated by rotary evaporation, followed by purification by RP HPLC (297 mg, 73% yield). The Boc protecting group was removed by treatment with TFA to give compound 35 (114 mg, 75% yield). ESI MS: $C_{55}H_{99}N_8O_{12}$ $[M+H]^+$ 1059.70 found 1059.4.

Example 15: Synthesis of Compound 36

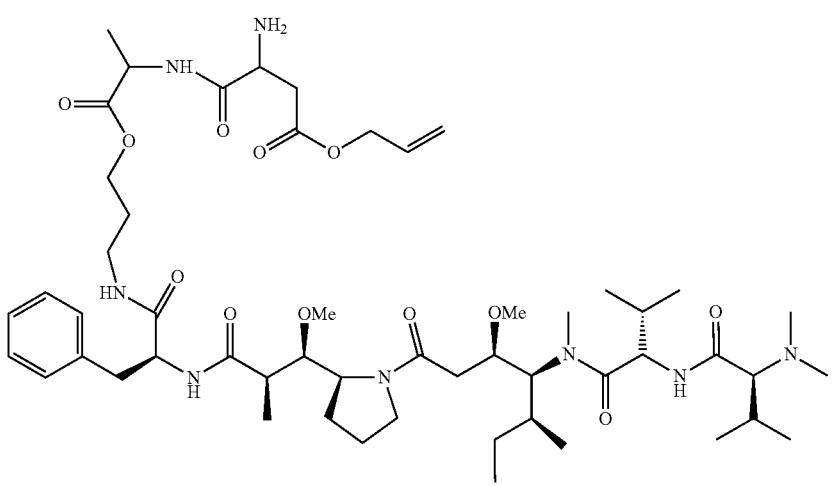

36

Compound 36 was prepared as described in Example 14 except Boc-Asp(OAll)-OH (80 mg, 0.292 mmol) was used instead of Boc-Glu(OtBu)-OH. ESI MS (Boc protected compound 36): $C_{58}H_{96}N_8O_{14}$ $[M+H]^+$ 1129.70; found 1129.6.

Example 16: Synthesis of Compound 37

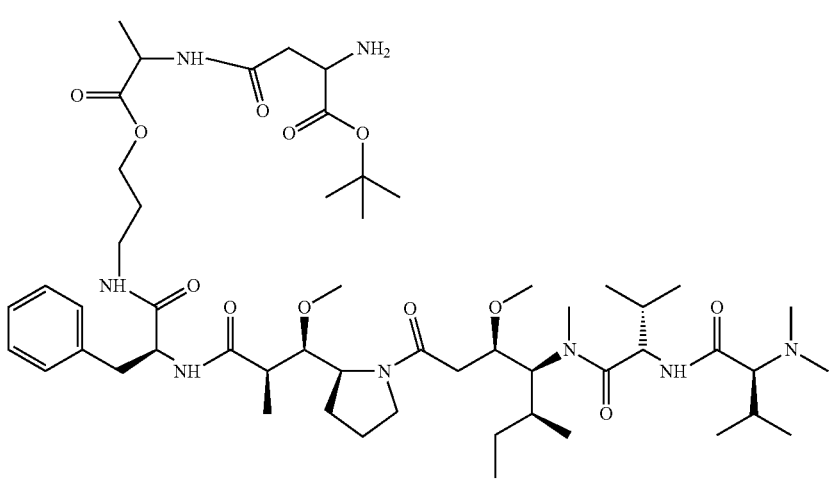

37

Compound 37 was prepared as described in Example 14 except Boc-Asp(OtBu)-OH (1 g, 0.857 mmol) was used instead of Boc-Glu(OtBu)-OH. ESI MS: $C_{58}H_{96}N_8O_{14}$ [M+H]$^+$ 1129.70; found 1129.6.
Example 17: Synthesis of Glucamine Scaffold 42
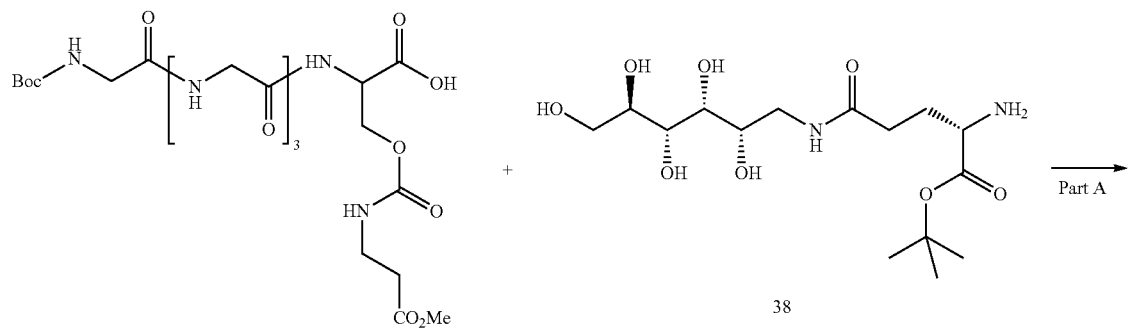
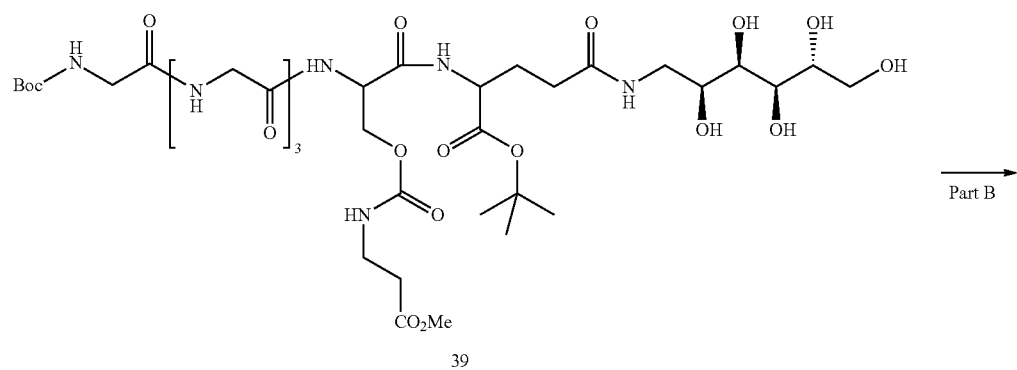
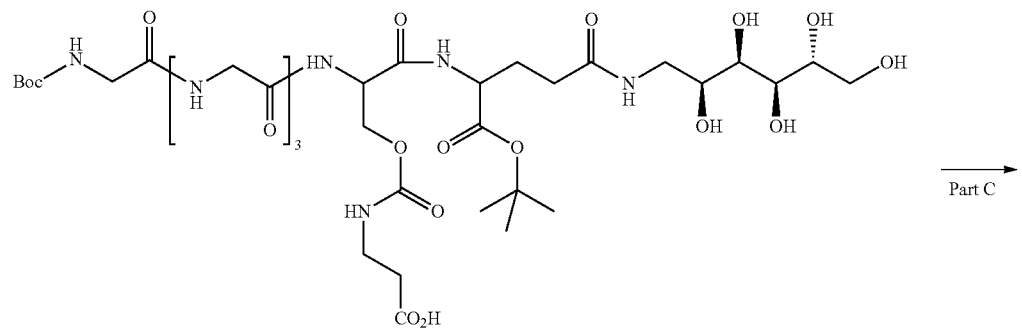

-continued

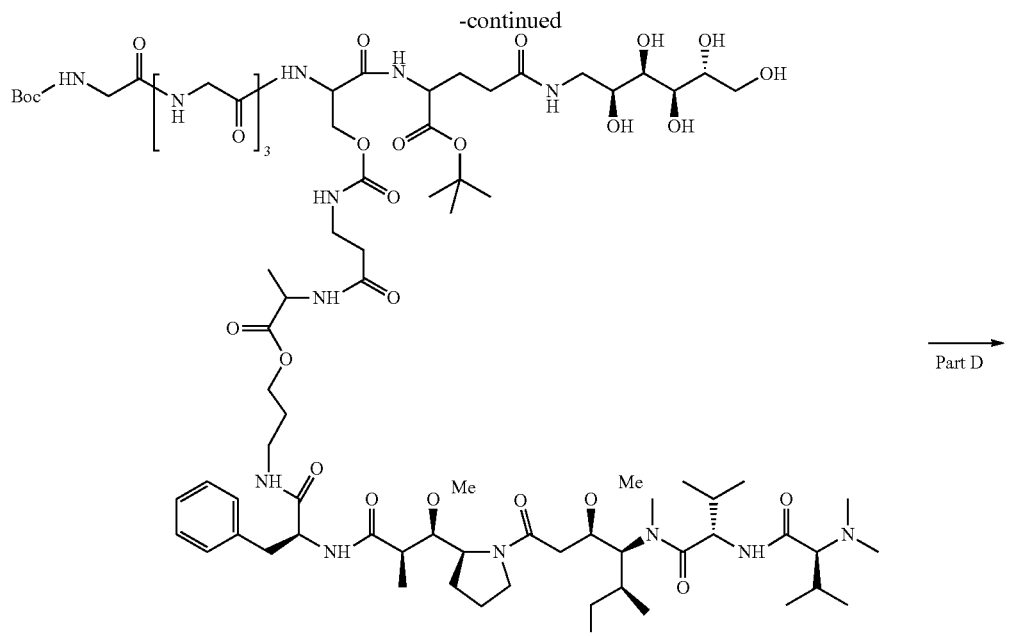

41

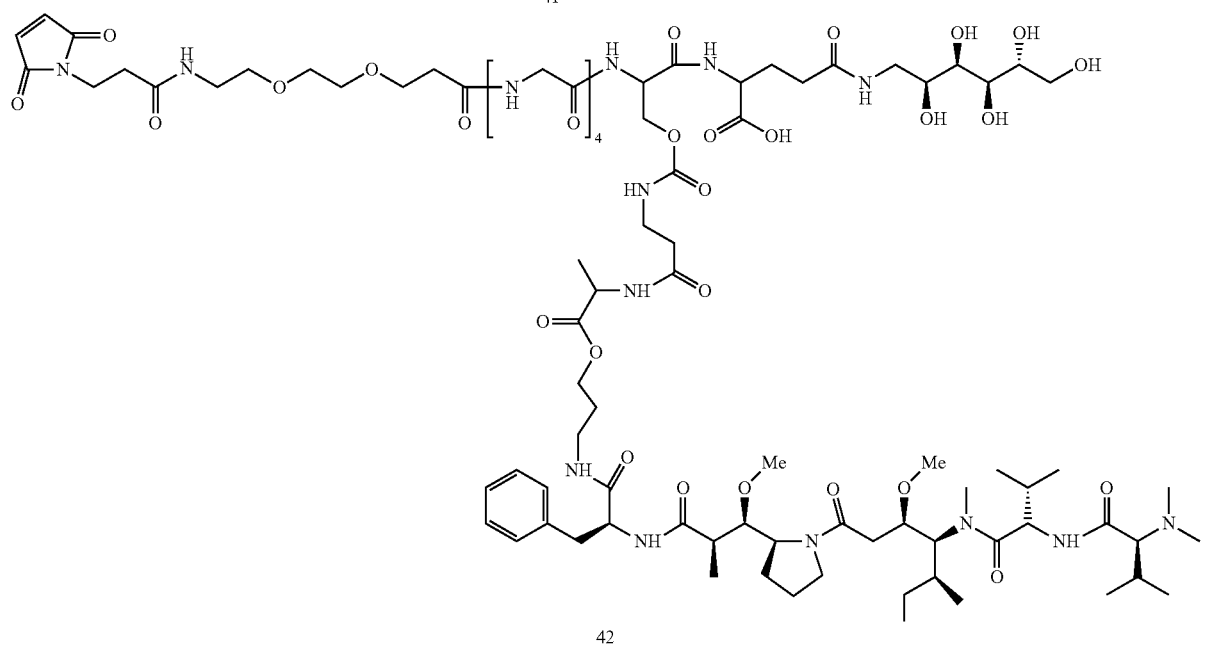

42

Part D →

Part A:

Boc protected compound 38 was prepared by reacting Boc-Glu-OH (837 mg, 2.76 mmol) in DMF (5 mL) at 0° C. with NHS (476 mg, 4.14 mmol) and EDC (794 mg, 4.14 mmol) followed by the addition of D-glucamine (500 mg, 2.76 mmol) in 8 mL of DMF (8 mL) and water (2.5 mL) according to the procedure described in Example 1, Part B. The product was purified by RP $C_{1-8}$ column CombiFlash chromatography using ACN/water containing HOAc (0.1%) gradient as eluant (737 mg, 57% yield). ESI MS: $C_{20}H_{38}N_2O_{10}$ [M+H]$^+$ 467.25; found 467.3. The Boc protecting group was removed by treatment with TFA to give compound 38. ESI MS: $C_{15}H_{30}N_2O_8$ [M+H]$^+$ 367.2; found 367.1.

Compound 39 was synthesized from compound 4 (80 mg, 0.143 mmol) and compound 38 (80 mg, 0.218 mmol) using the procedure described in Example 1, Part D (72 mg, 55% yield). ESI MS: $C_{36}H_{62}N_8O_{19}$ [M+H]$^+$ 911.4; found 911.3.

Part B:

Compound 40 was synthesized from compound 39 (21 mg, 0.023 mmol) and trimethylstannanol (29.2 mg, 0.161 mmol) using the procedure described in Nicolaou, K. C. et al. Angew. Chem. Int. Ed. 44, 1378-1382, 2005, followed by purification by RP C18 column CombiFlash chromatography using ACN/water containing HOAc (0.1%) gradient as eluant (15 mg, 72.5% yield). ESI MS: $C_{35}H_{60}N_8O_{19}$ [M+H]$^+$ 897.4; found 897.3.

Part C:

Compound 41 was synthesized from compound 40 (15.0 mg, 0.017 mmol) and auristatin F-hydroxypropyl amide-alanine TFA-salt (19.52 mg, 0.017 mmol, prepared as described in U.S. Pat. No. 8,865,383) using the procedure described in Example 2, Part H (18 mg, 61% yield). ESI MS: $C_{81}H_{137}N_{15}O_{27}$ m/z: $[M+2H]^{2+}/2$ 877.5; found 877.5. Part D:

Scaffold 42 was synthesized from compound 41 (18 mg, 10.27 µmol) and 2,5-dioxopyrrolidin-1-yl3-(2-(2-(3-(2,5-dioxo-2,5-dihydro-1H-pyrrol-1yl)propanamido)ethoxy) ethoxy propanoate (6.39 mg, 0.015 mmol) using the procedure described in Example 2, Part I (7 mg, 53% yield). ESI MS: $C_{86}H_{139}N_{17}O_{31}$ m/z: $[M+2H]^{2+}/2$ 953.99; found 953.9.

Example 18: Synthesis of Trastuzumab Conjugate of Scaffold 42 (Conjugates 43A and 43B)

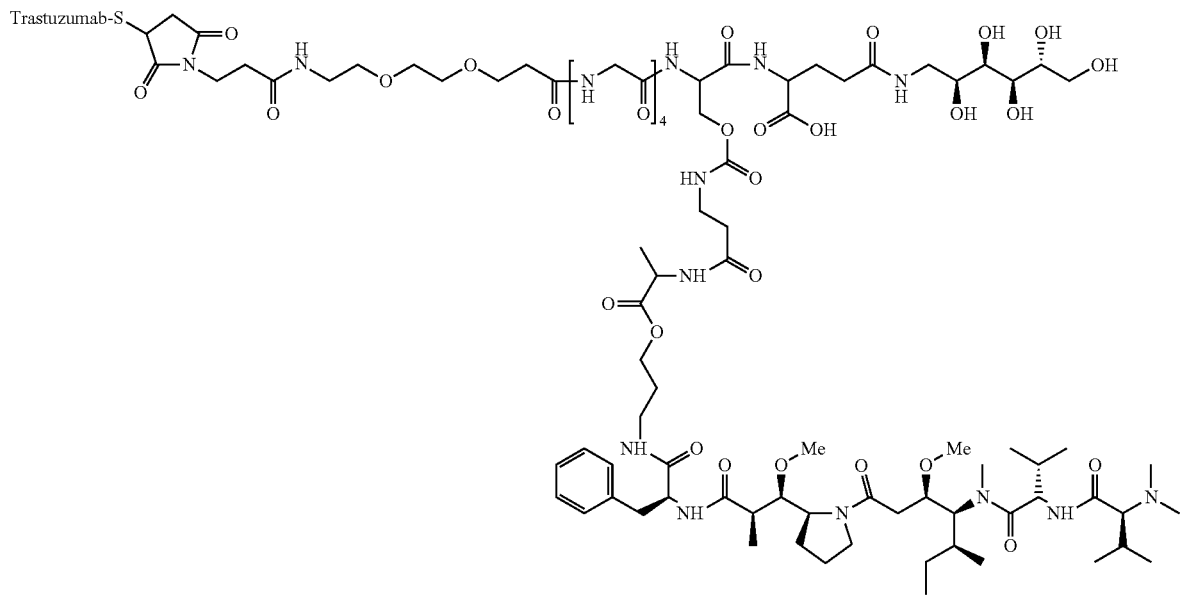

43

Conjugates 43A and 43B were prepared from scaffold 42 using the procedure described in Example 7. Purified conjugate 43A had a drug to trastuzumab ratio of 6.6 and conjugate 43B a drug to trastuzumab ratio of 6.5.

Example 19: Synthesis of Monomeric PEG8 Scaffold (45)
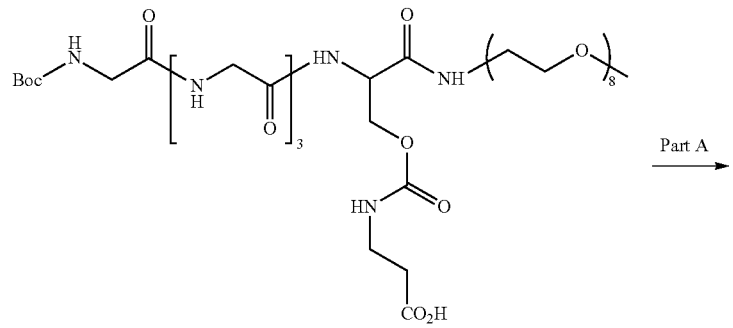
6
Part A →
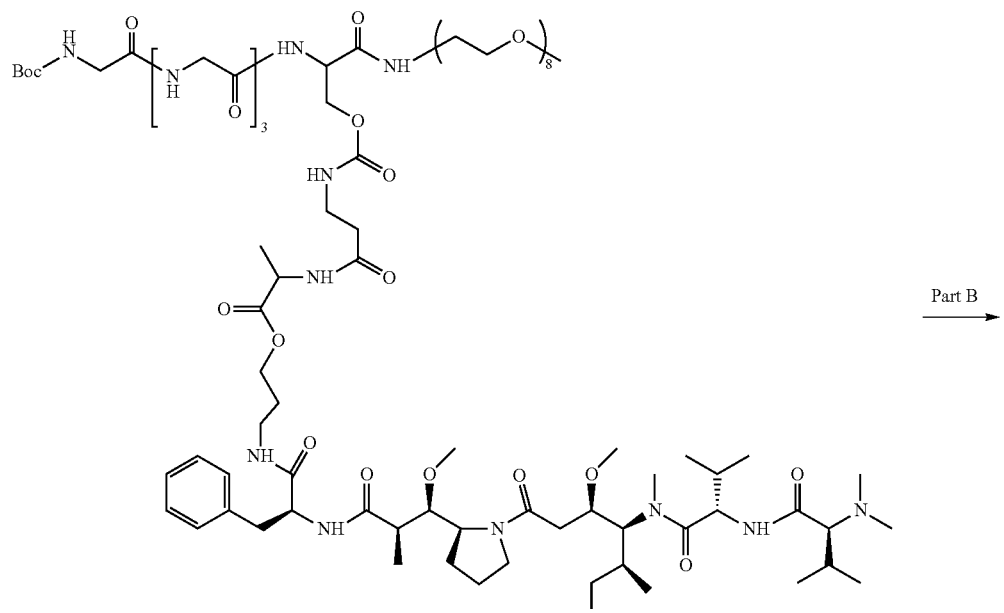
44
Part B →

-continued

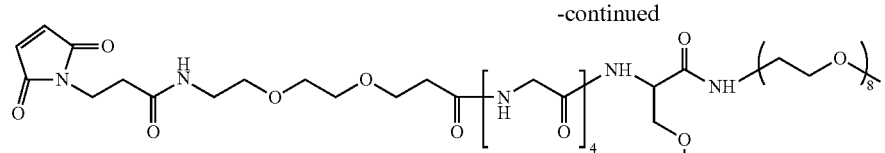
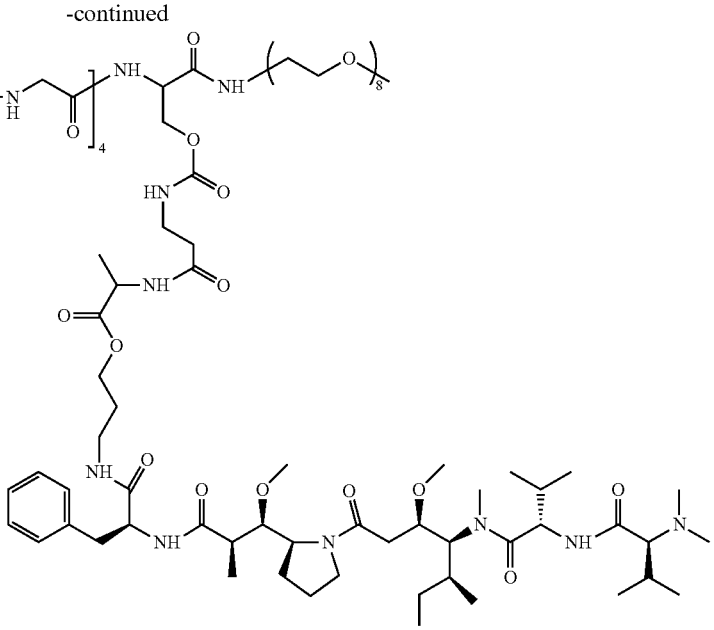

45

Part A:

Compound 44 was synthesized from compound 6 (20 mg, 0.022 mmol) and auristatin F-hydroxypropyl amide-alanine TFA-salt (25.5 mg, 0.022 mmol, prepared as described in U.S. Pat. No. 8,865,383) using the procedure described in Example 2, part H (10 mg, 25% yield). ESI MS: $C_{83}H_{144}N_{14}O_{27}$ m/z: $[M+2H]^{2+}/2$ 885.5 found 885.6.

Part B:

Scaffold 45 was synthesized from compound 44 (9.5 mg, 5.65 μmol) and 2,5-dioxopyrrolidin-1-yl3-(2-(2-(3-(2,5-dioxo-2,5-dihydro-1H-pyrrol-1yl)propanamido)ethoxy)ethoxy propanoate (4.84 mg, 0.011 μmol) using the procedure described in Example 2, Part I (8 mg, 71% yield). ESI MS: $C_{92}H_{154}N_{16}O_{31}$ $[M+H]^{2+}/2$ 990.55 found 990.6.

Example 20: Synthesis of Trastuzumab Conjugate of Scaffold 45 (Conjugates 46A and 46B)

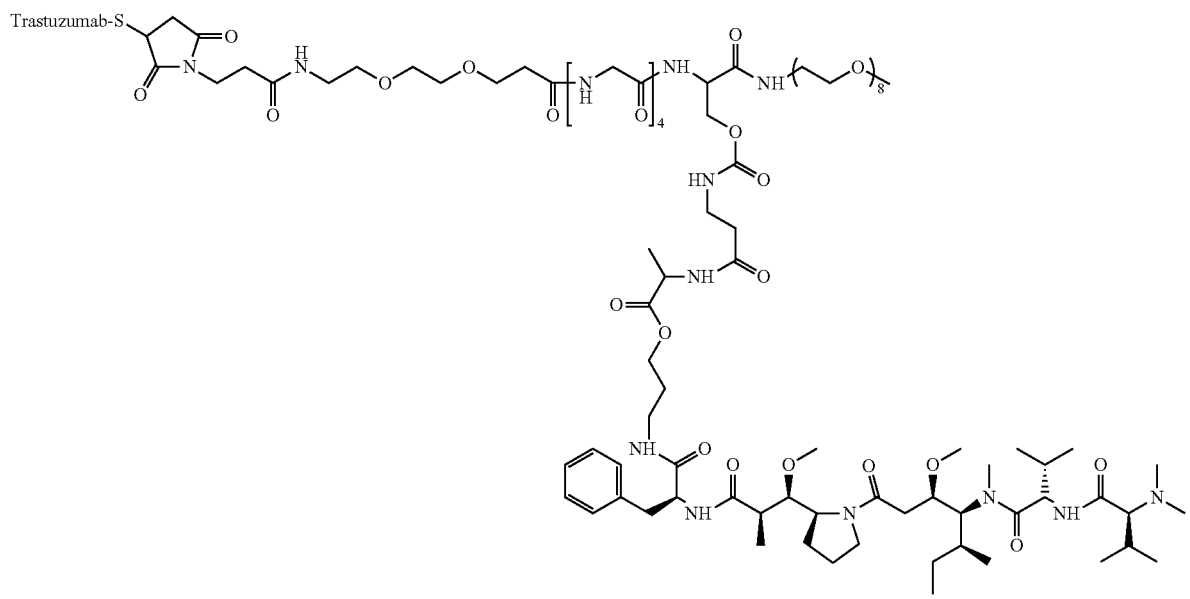

46

Conjugates 46A and 46B were prepared from scaffold 45 using the procedure described in Example 7. Purified conjugate 46A had a drug to trastuzumab ratio of 6.8 and conjugate 46B a drug to trastuzumab ratio of 6.5.

Example 21: Synthesis of Trastuzumab Conjugate of Scaffold 47 (Conjugate 48)

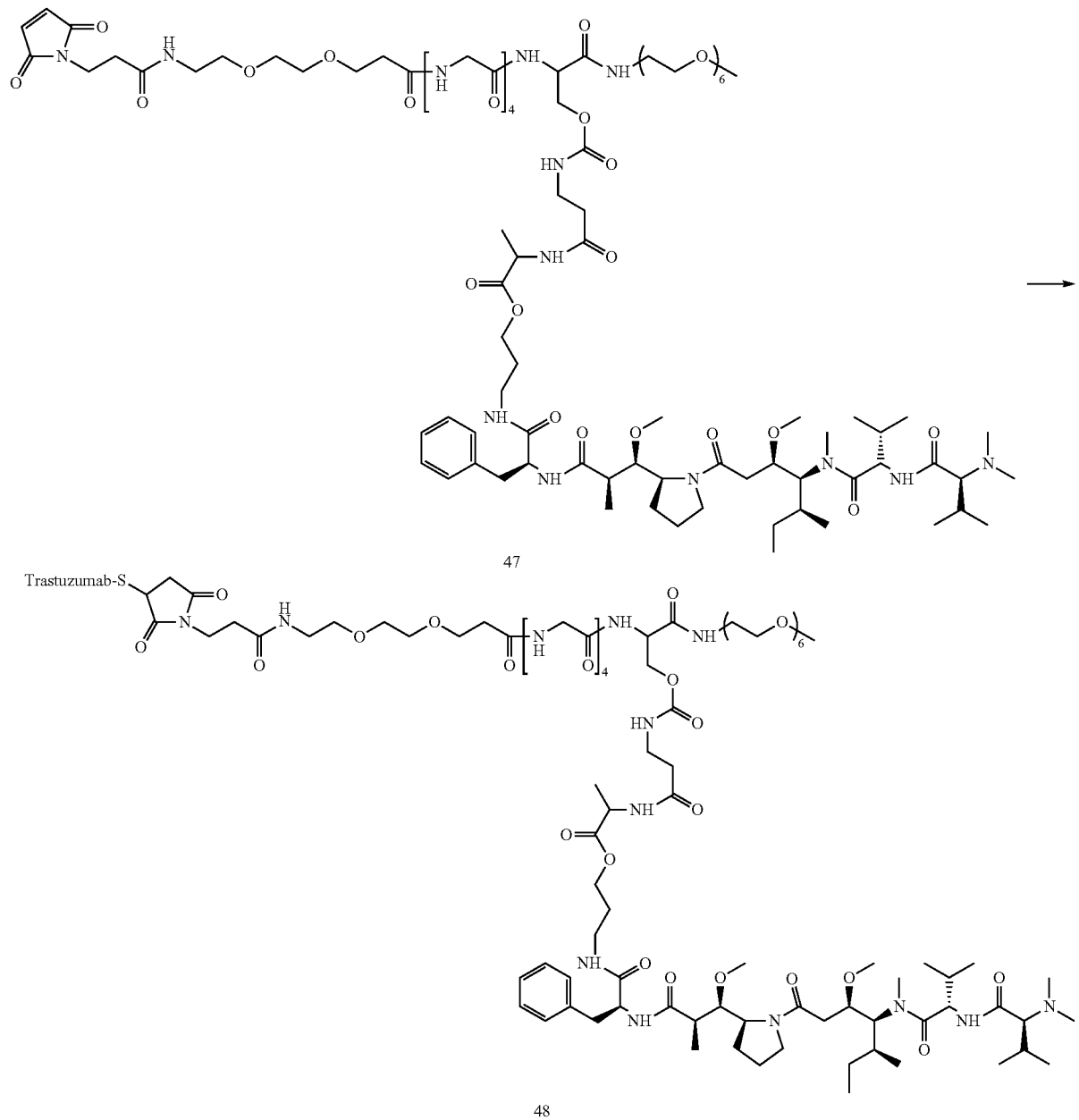

Scaffold 47 was synthesized as described in Example 19 except that the PEG6 analogue of compound 6 (20 mg, 0.024 mmol) and auristatin F-hydroxypropyl amide-alanine TFA-salt (29.7 mg, 0.025 mmol, prepared as described in U.S. Pat. No. 8,865,383) were used in Example 19, Part A. ESI MS (Compound 47): $C_{88}H_{146}N_{16}O_{29}$ [M+2H]$^{2+}$/2 946.52; found 946.5.

Conjugate 48 was prepared from scaffold 47 using the procedure described in Example 7. Purified conjugate 48 had a drug to trastuzumab ratio of 5.5.

Example 22: Synthesis of Trastuzumab Conjugate of Scaffold 49 (Conjugate 50)

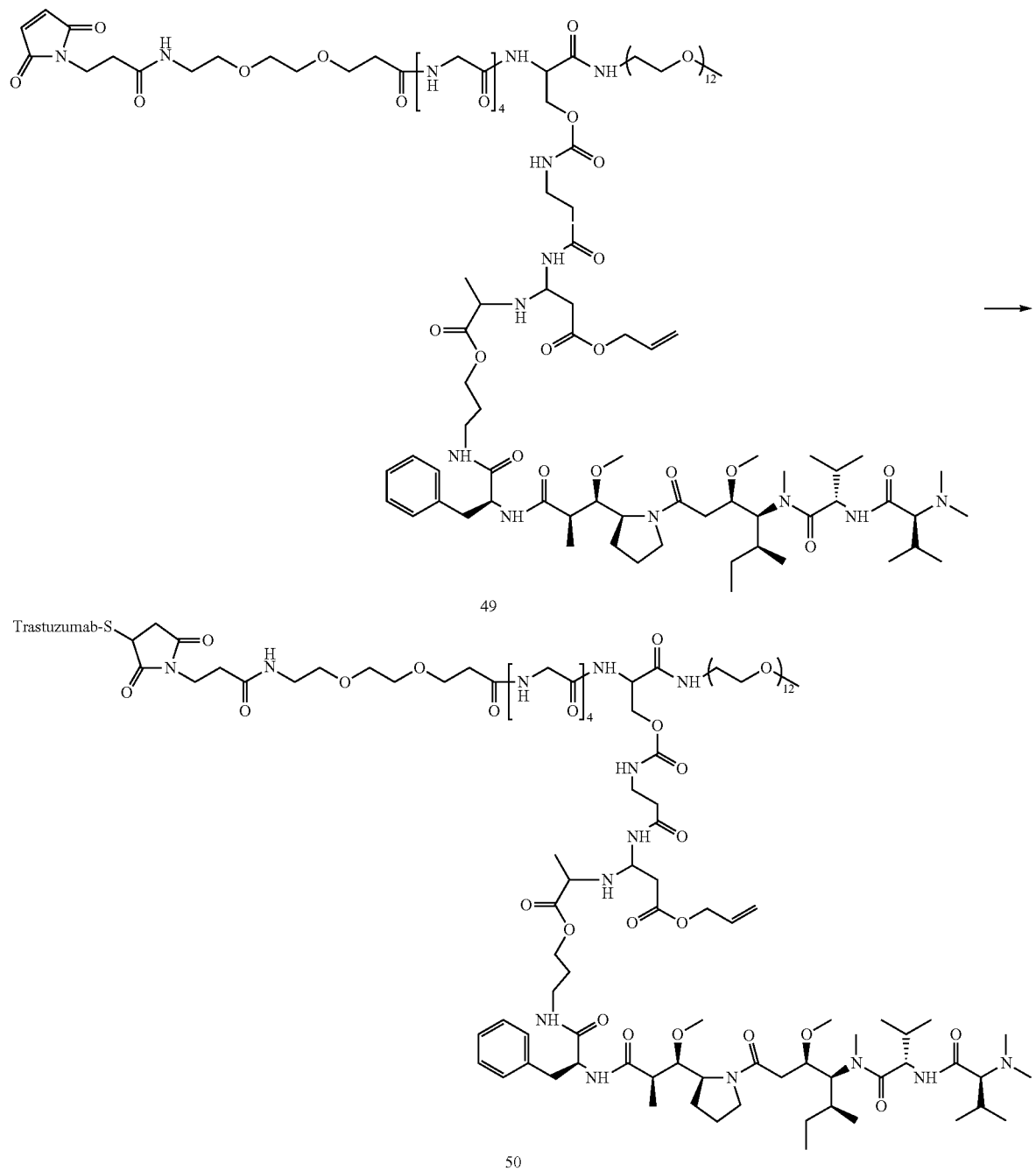

Scaffold 49 was synthesized as described in Example 19 except that the PEG12 analogue of compound 6 (101 mg, 0.092 mmol) and compound 36 (95 mg, 0.092 mmol) were used in Example 19, Part A. ESI MS (Compound 49): $C_{103}H_{172}N_{16}O_{35}$: $[M+2H]^{2+}/2$ 1097.6 found 1098.0; $[M+Na+H]^{2+}/2$ 1108.6; found 1108.5.

Conjugate 50 was prepared from scaffold 49 using the procedure described in Example 7.

Example 23: Synthesis of Trastuzumab Conjugate of Scaffold 51 (Conjugate 52)

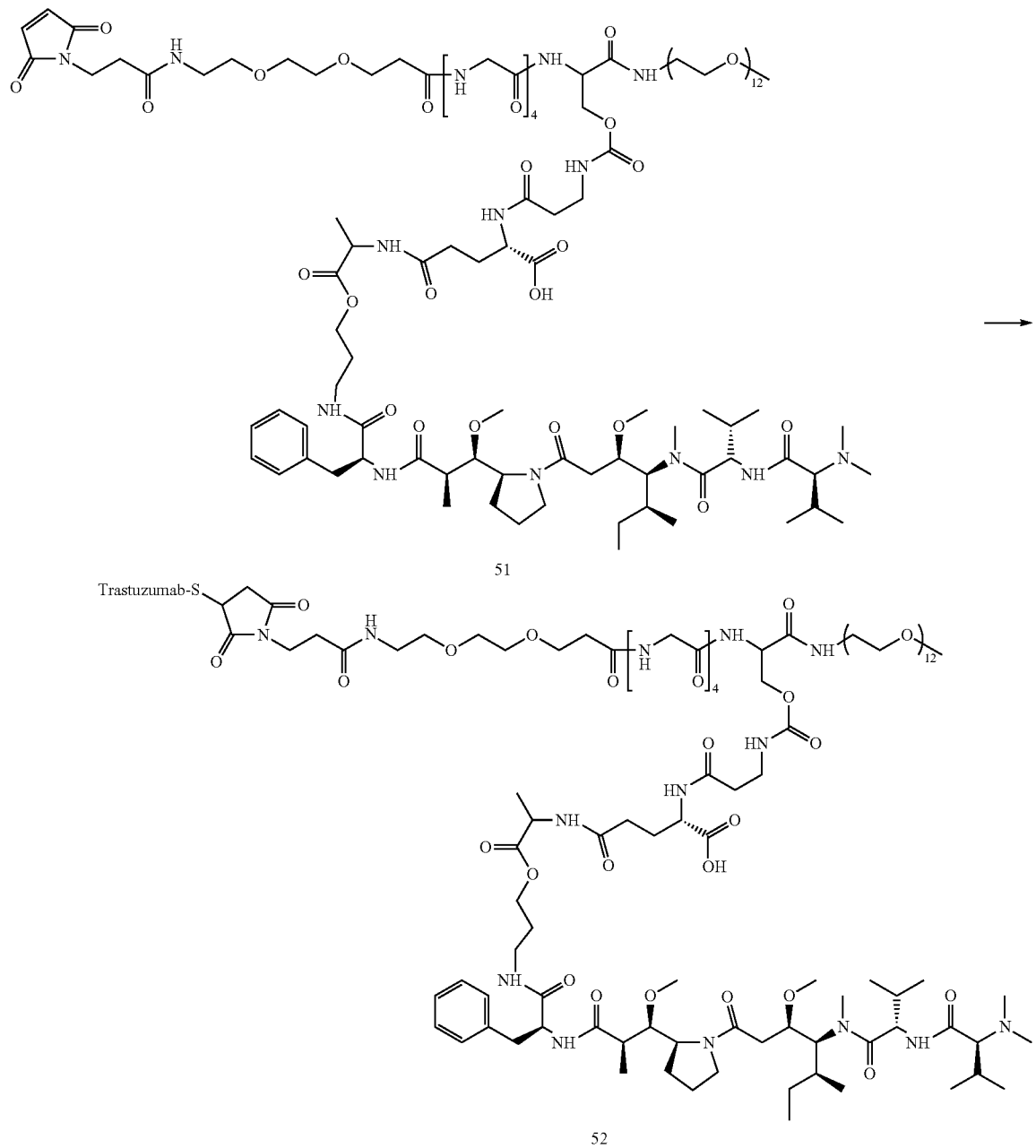

Scaffold 51 was synthesized as described in Example 19 except that the PEG12 analogue of compound 6 (100 mg, 0.092 mmol) and compound 35 (102 mg, 0.096 mmol) were used in Example 19, Part A. ESI MS (Compound 51): $C_{105}H_{177}N_{17}O_{38}$ $[M+2H]^+/2$ 1143.8 found 1143.6.

Conjugate 52 was prepared from scaffold 51 using the procedure described in Example 7. Purified Conjugate 52 had a drug to trastuzumab ratio of 12.6.

Example 24: Synthesis of XMT-1535 Conjugates of Scaffold 17 (Conjugates 53A, 53B, 53C 53D, 53E)

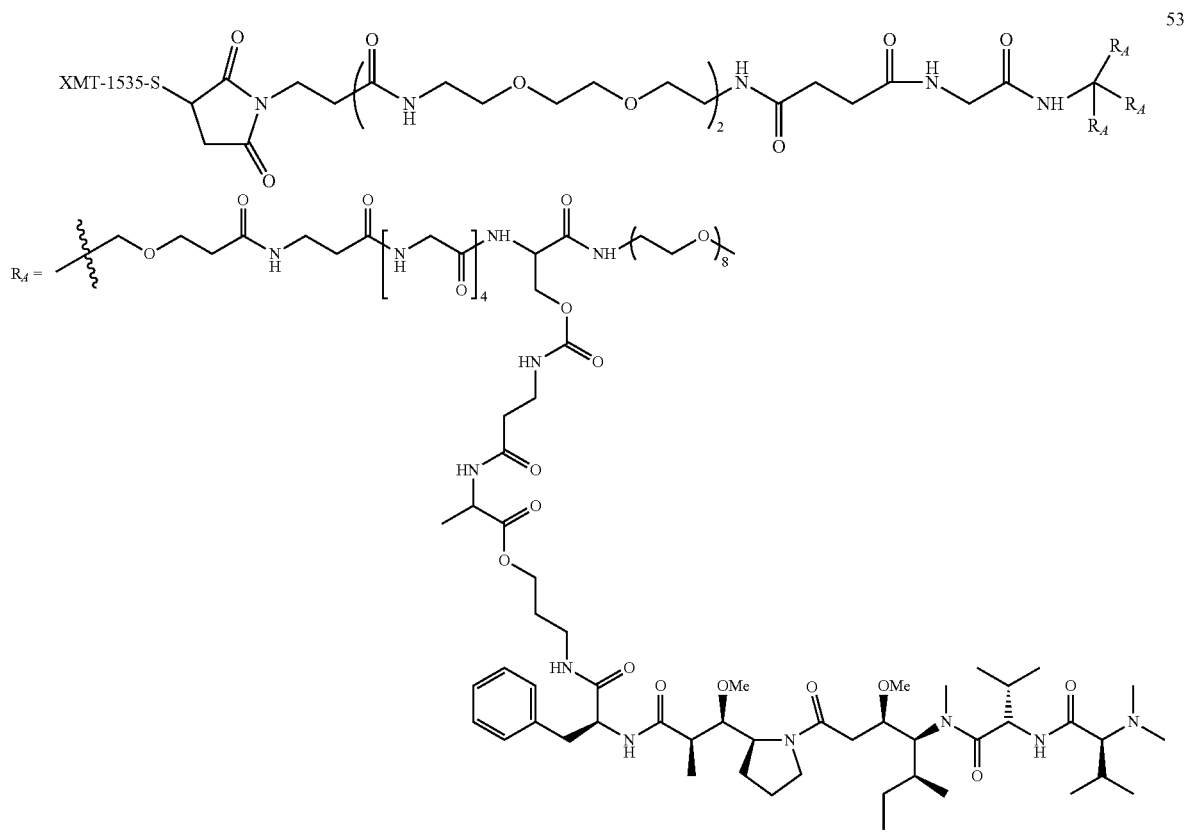

Conjugates 53A to 53E were prepared from scaffold 17 using the procedure described in Example 7 except that XMT-1535 was used instead of Trastuzumab and the amount of TCEP used in the reduction of XMT-1535 was varied as indicated in Table 1.

TABLE 1

| Conjugate # | TCEP equivalents | Drug to XMT-1535 ratio |
|---|---|---|
| 53A | 2 | 10.3 |
| 53B | 3 | 16.4 |

TABLE 1-continued

| Conjugate # | TCEP equivalents | Drug to XMT-1535 ratio |
|---|---|---|
| 53C | 3 | 16.9 |
| 53D | 3 | 15.2 |
| 53E | 4 | 21.8 |

Example 25—Synthesis of XMT-1535 Conjugates of Scaffold 54 (Conjugates 55A, 55B, 55C)

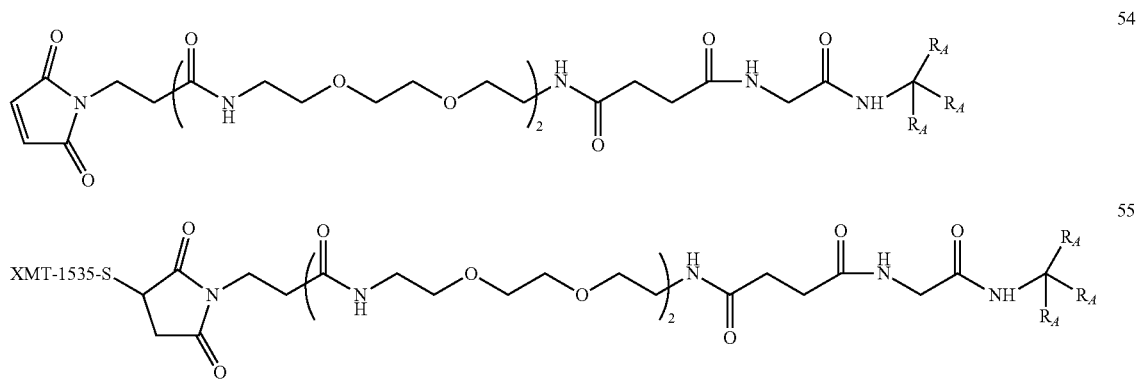

-continued

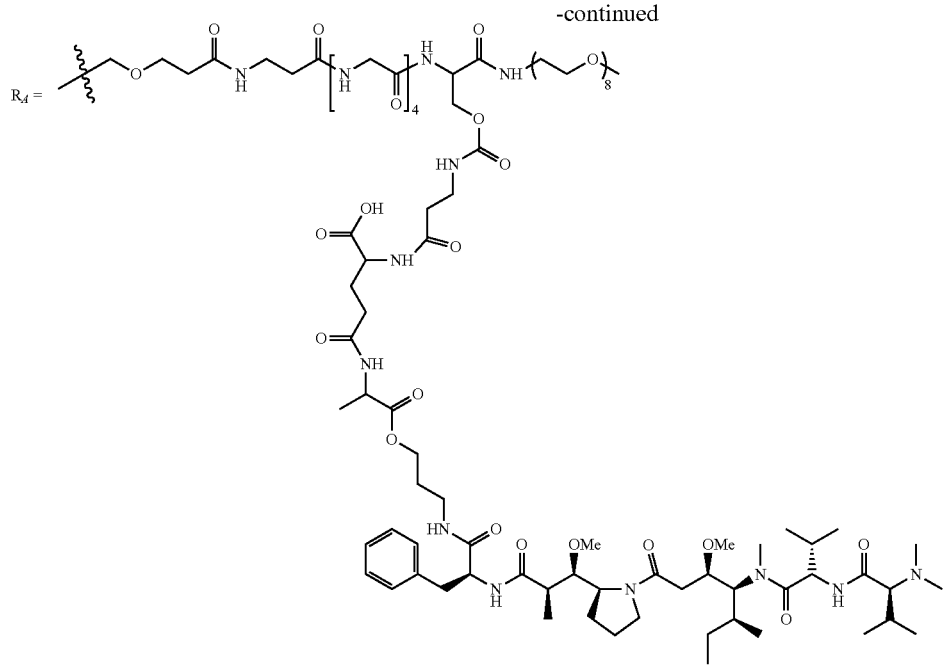

Scaffold 54 was synthesized as described in Example 2 except compound 35 (104 mg, 0.068 mmol) were used in Example 2, Part H. ESI MS: $C_{297}H_{500}N_{54}O_{104}$ m/z: $[M+5H]^{5+}/5=1298.51$; found 1298.4; $[M+6H]^{6+}/6=1082.258$; found 1082.2; $[M+7H]^{7+}/7=927.793$; found 927.8.

Conjugate 55 was prepared from scaffold 54 and XMT-1535 using the procedure described in Example 7. Purified conjugate 55A had a drug to XMT-1535 ratio of 24.7, conjugate 55B a drug to XMT-1535 ratio of 19.7 and conjugate 55C a drug to XMT-1535 ratio of 14.5.

Example 26: Synthesis of XMT-1535 Conjugates of Scaffold 56 (Conjugates 57)

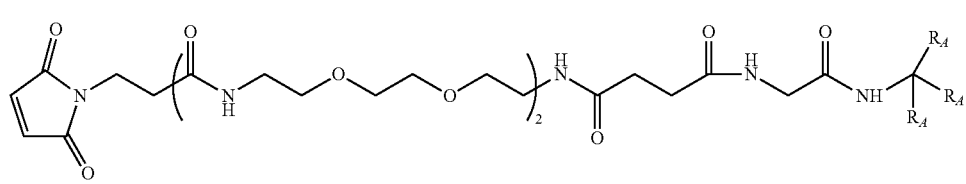

56

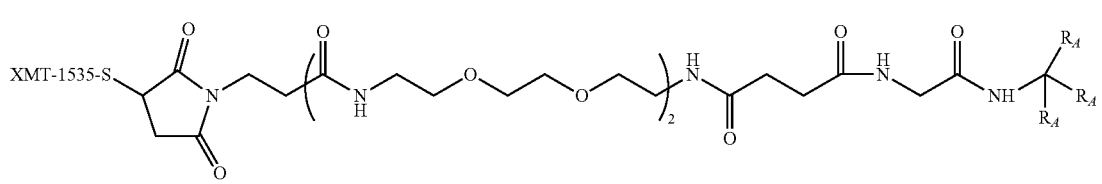

57

-continued
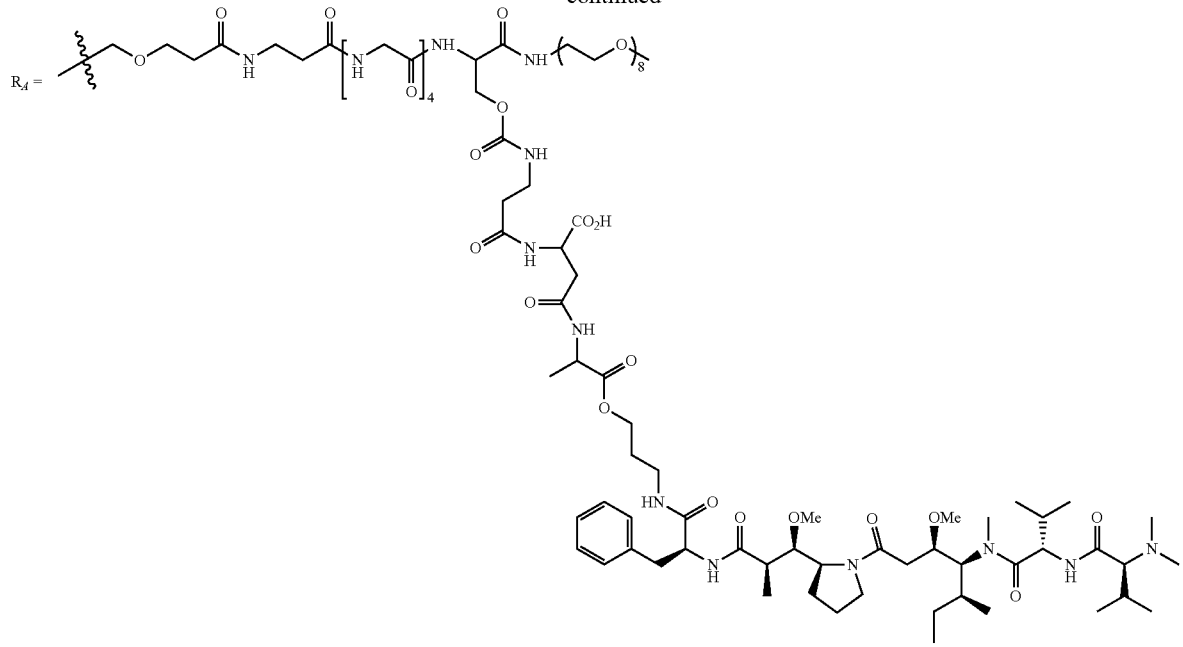
Scaffold 56 was synthesized as described in Example 2 except compound 37 (138 mg, 0.116 mmol) were used in Example 2, Part H. ESI MS: $C_{294}H_{494}N_{54}O_{104}$: $[M+5H]^{5+}/5=1290.10$ found 1289.7; $[M+7H]^{7+}/7=921.78$ found 921.8.
Conjugate 57 was prepared from scaffold 56 and XMT-1535 using the procedure described in Example 7. Purified conjugate 57 had a drug to XMT-1535 ratio of 16.5.
Example 27: Synthesis of XMT-1535 Conjugates of Scaffold 58 (Conjugates 59)
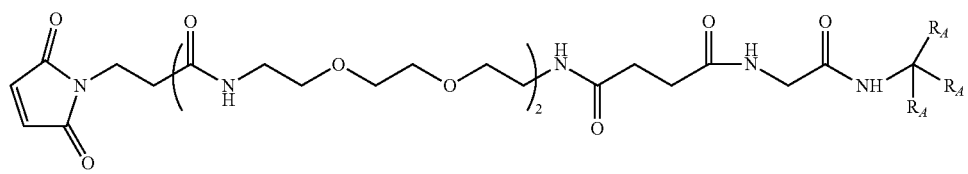
58
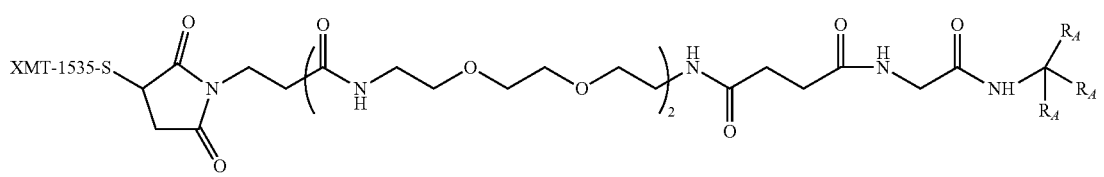
59

-continued

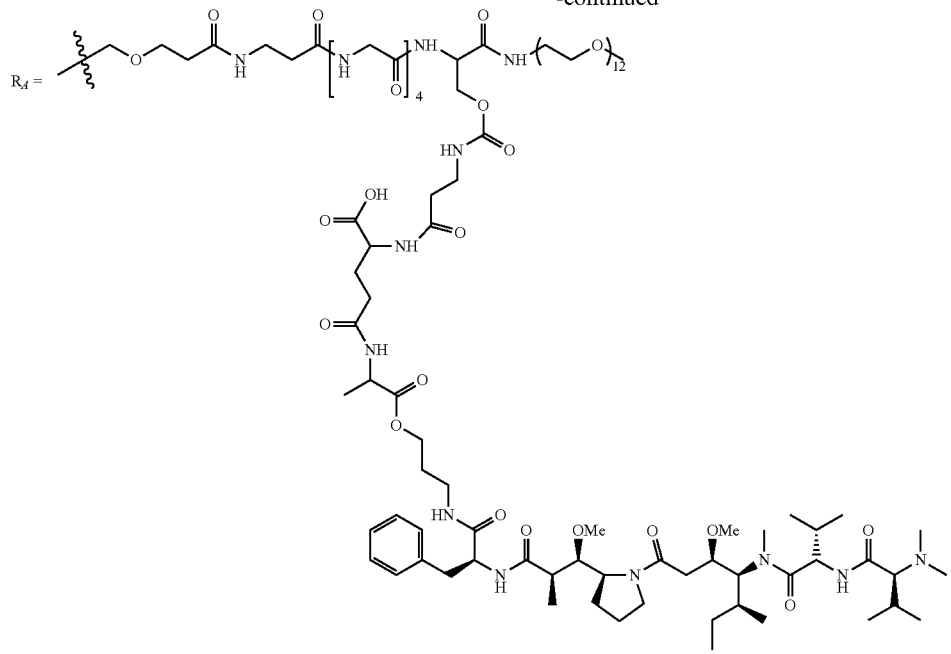

Scaffold 58 was synthesized as described in Example 2 except that the PEG12 analogue of compound 15 (152 mg, 0.039 mmol) and compound 35 (176 mg, 0.146 mmol) were used in Example 2, Part H. ESI MS (Compound 58): $C_{321}H_{548}N_{54}O_{116}$ [M] 7015.86; found 7015.86.

Conjugate 59 was prepared from scaffold 58 and XMT-1535 using the procedure described in Example 7. Purified conjugate 59 had a drug to XMT-1535 ratio of 15.9.

Example 28: Synthesis of XMT-1535 Conjugates of Scaffold 60 (Conjugate 61)

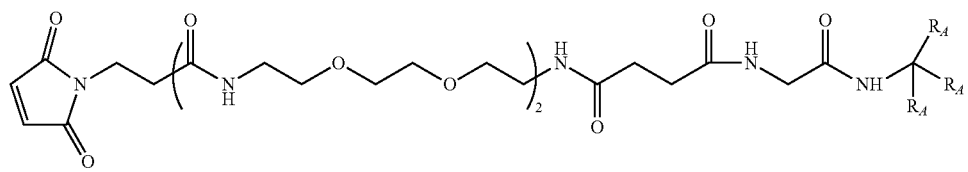

60

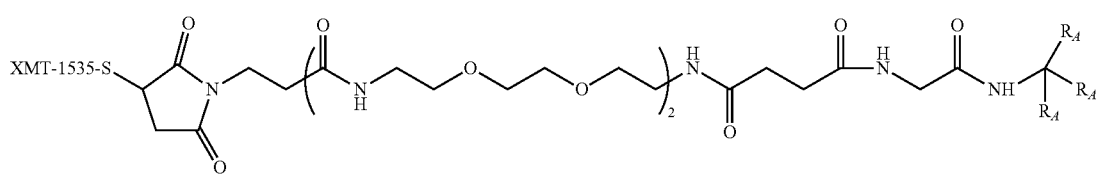

61

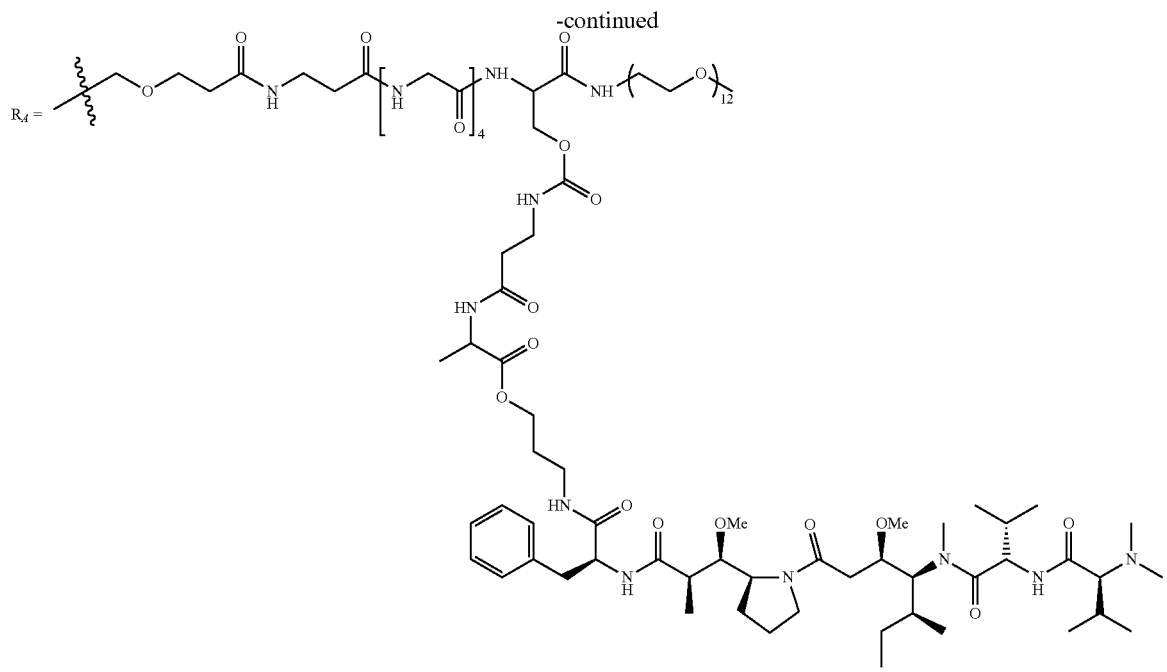

-continued

Scaffold 60 was synthesized as described in Example 2 except that the PEG12 analogue of compound 15 (170 mg, 0.044 mmol) and auristatin F-hydroxypropyl amide-alanine TFA-salt (179 mg, 0.163 mmol, prepared as described in U.S. Pat. No. 8,865,383) were used in Example 2, Part H. ESI MS: $C_{306}H_{527}N_{51}O_{107}$ [M] 6628.74; found 6628.75.

Conjugate 61 was prepared from scaffold 60 and XMT-1535 using the procedure described in Example 7. Purified conjugate 61 had a drug to XMT-1535 ratio of 16.3.

Example 29: Synthesis of XMT-1535 Conjugates of Scaffold 65 (Conjugate 66)

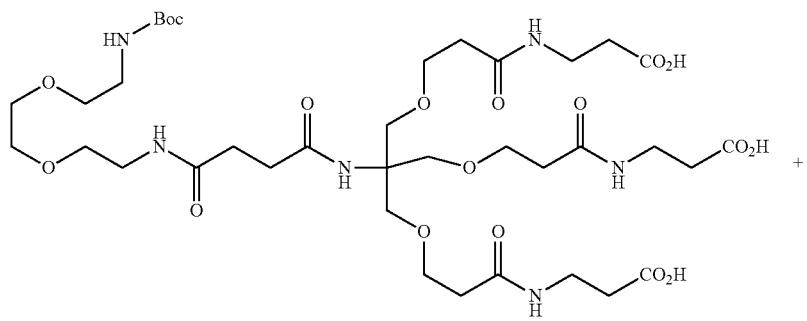

62

-continued
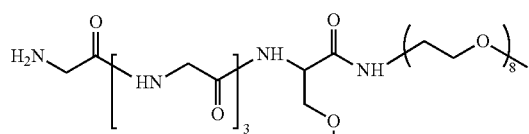
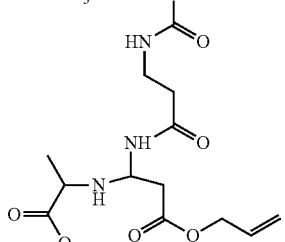
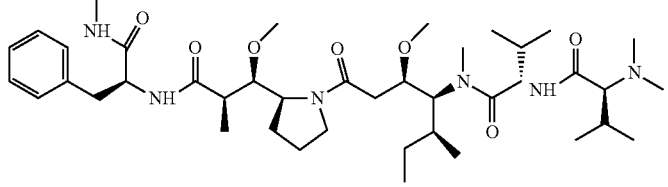
63
Part A →
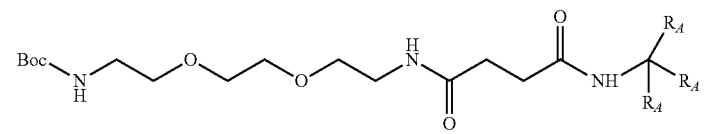
64
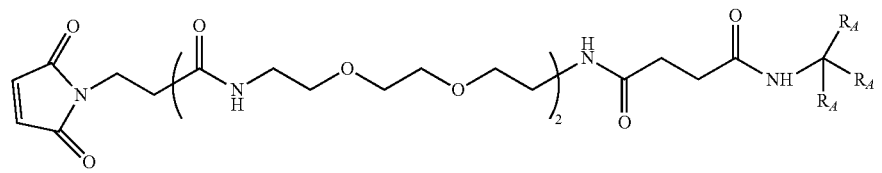
65
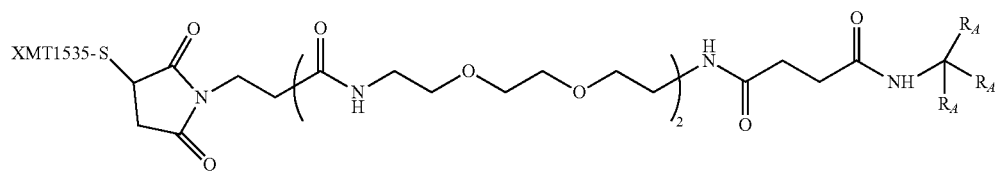
66

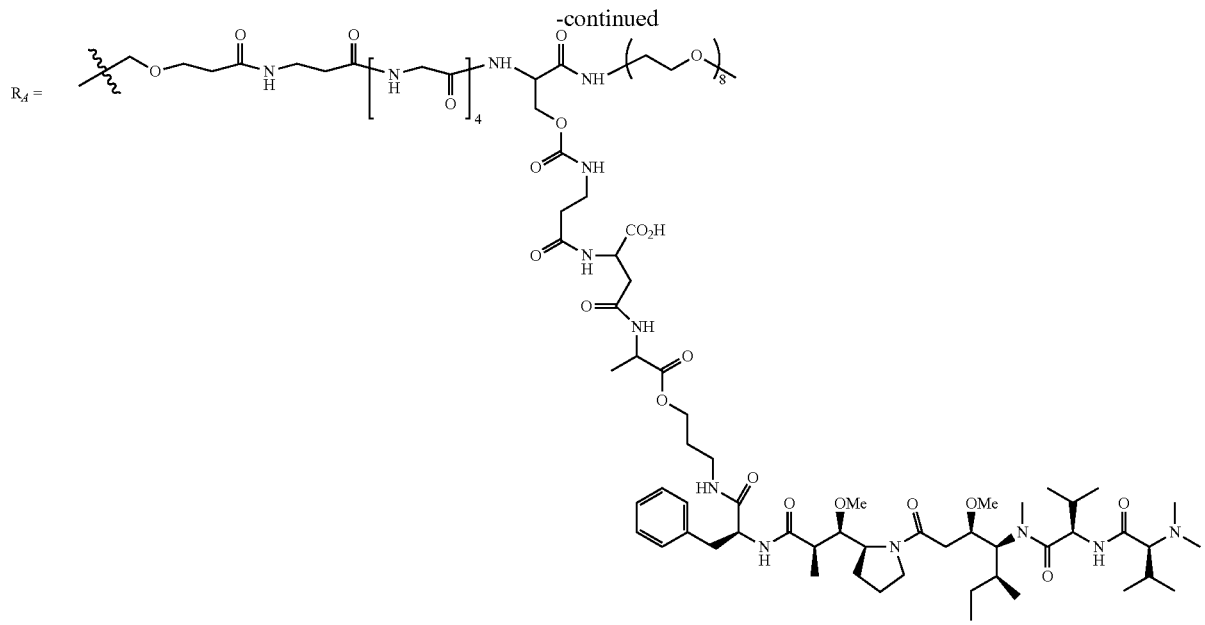

Part A:

Compound 64 was prepared by reacting compound 62 (5.03 mg, 5.71 μmol, prepared as described in Example 2, Part E, except dimethyl 3,3'-(2-amino-2-((3-methoxy-3-oxopropoxy)methyl)propane-1,3-diyl)bis(oxy)dipropanoate was used instead of compound 10) with compound 63 (40 mg, 0.019 mmol, prepared by reaction compound 6 (100 mg, 0.092 mmol) with compound 36 (153 mg, 0.135 mmol) using the procedure described in Example 2, Part H. ESI MS (Compound 64): $C_{316}H_{541}N_{51}O_{111}$ [M] 6826.83; found 6826.842.

Scaffold 65 was synthesized as described in Example 2, Part I. ESI MS (scaffold 65): $C_{316}H_{539}N_{53}O_{115}$ [M] 6916.795; found 6916.752.

Conjugate 66 was prepared from scaffold 58 and XMT-1535 using the procedure described in Example 7. Purified conjugate 66 had a drug to XMT-1535 ratio of 15.

Example 30: Synthesis of Trastuzumab Conjugate of Scaffold 54 (Conjugate 67)

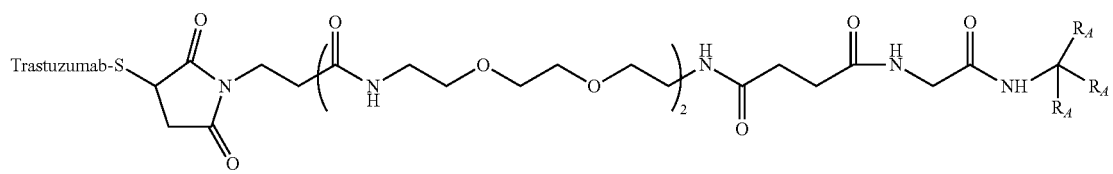

67

-continued
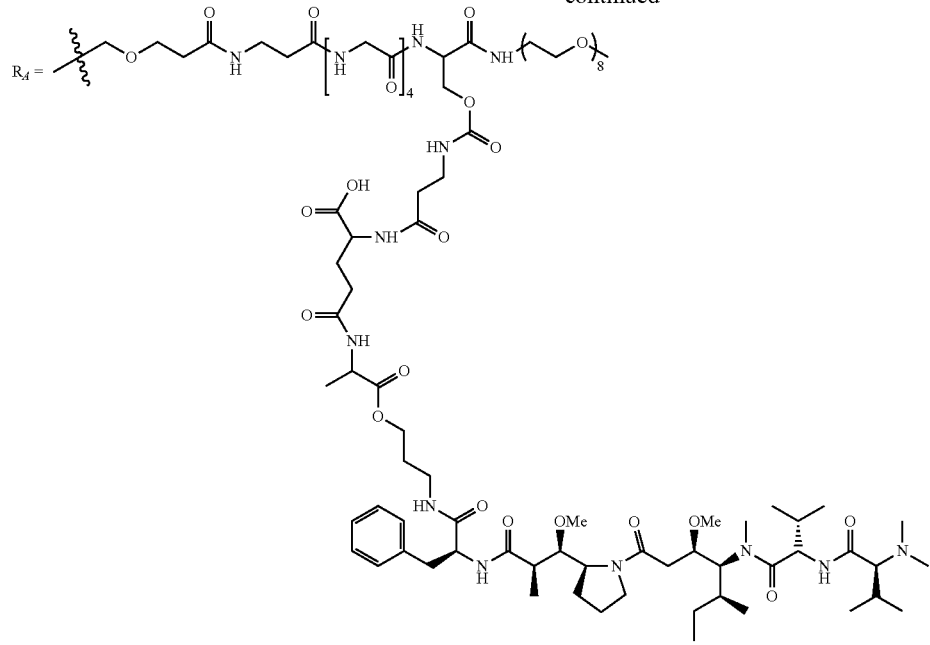
Conjugate 67 was prepared from scaffold 54 and Trastuzumab using the procedure described in Example 7. Purified conjugate 61 had a drug to XMT-1535 ratio of 13.0.
Example 31: Synthesis of Trastuzumab Conjugate of Scaffold 58 (Conjugate 68)
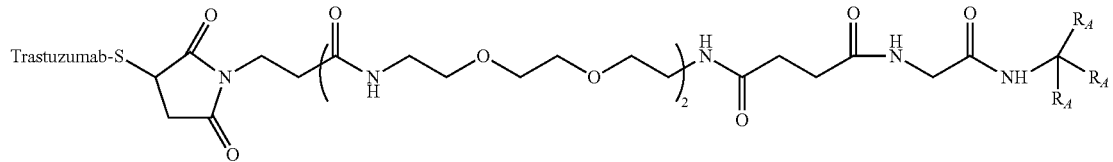

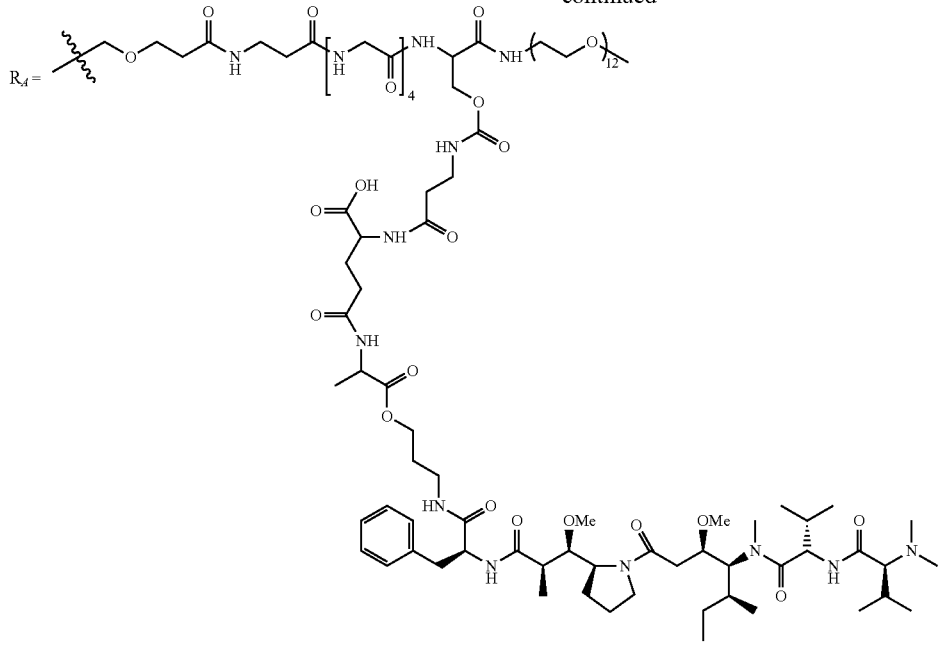

Conjugate 68 was prepared from scaffold 58 and Trastuzumab using the procedure described in Example 7. Purified conjugate 68 had a drug to XMT-1535 ratio of 12.1

Example 32: Synthesis of Bis-Glucamine Scaffold 75

Part A:

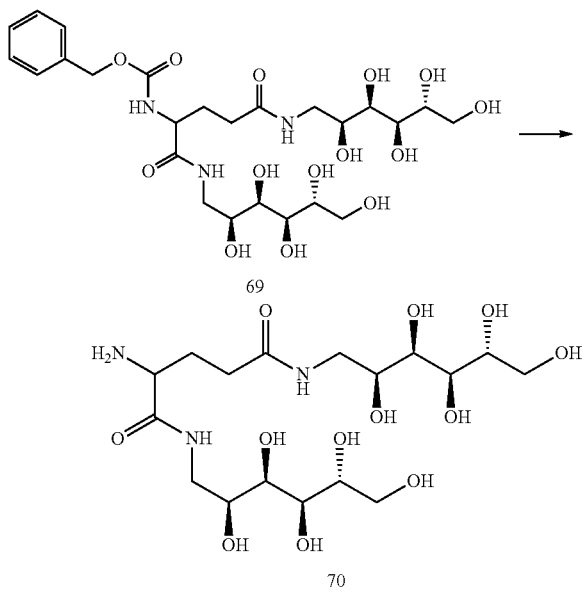

To 2-(((benzyloxy)carbonyl)amino)pentanedioic acid (2 g, 7.11 mmol) in water (75 mL) was added potassium carbonate (0.491 g, 3.56 mmol). To the resulting mixture at 0° C. was added HOAt (2.420 g, 17.78 mmol) and EDC (4.09 g, 21.33 mmol). After 10-15 min. D-glucamine (2.96 g, 16.35 mmol) in water (20 mL) was added followed by additional potassium carbonate (0.491 g, 3.56 mmol) in water (1 mL) until pH~7. After 24 hours, LC-MS indicated the reaction was incomplete. Additional HOAt (500 mg), D-glucamine (0.9 g) in water (3 mL) and EDC (1.5 g) were added and pH of the resulting mixture adjusted to 7-8 with $K_2CO_3$ (250 mg). The reaction mixture concentrated to dryness, dissolved in 10% MeOH in DCM was first purified by $SiO_2$ column chromatograph using EtOAc/DCM 10-50% as eluant followed by further purification to give compound 69 (2.02 g, 47% yield). ESI MS: $C_{25}H_{42}N_3O_{14}$ [M+H]: =608.27; found 608.3.

Compound 69 (2.015 g, 3.32 mmol) was treated with 10% Pd/C (0.35 g, 0.332 mmol) under $H_2$ as described in Example 1, Part C to give crude compound 70 quantitatively. ESI MS: $C_{17}H_{36}N_3O_{12}$ [M+H]: =474.2; found 474.3.

Part B:

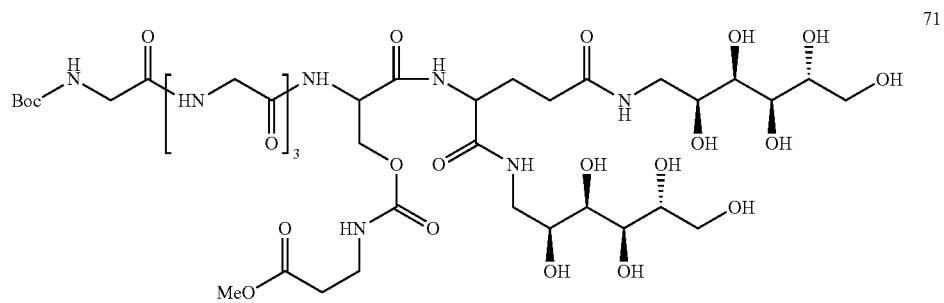

71

Compound 4 (750 mg, 1.333 mmol) in DMF was reacted with compound 70 (574 mg, 1.212 mmol) at 0° C. using the procedure described in Example 1, Part D to give compound 71 (559 mg, 45% yield). ESI MS: $C_{38}H_{68}N_9O_{23}$ $[M+H]^+$ 1018.4, found 1018.3.

Part C:

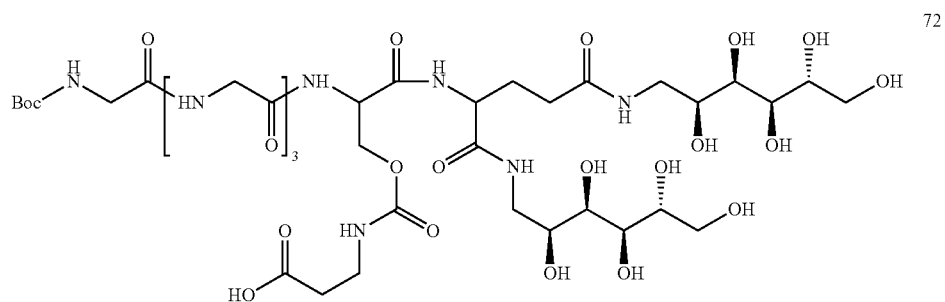

72

Compound 71 (555 mg, 0.545 mmol) in water at 0° C. and treated with a total of LiOH (408 μL of 2 M solution) over 2 hrs. followed by quenching the reaction with HOAc (35 μL). The crude product was purified by RP C18 column CombiFlash chromatography using ACN/water containing HOAc (0.1%) gradient as eluant, to give compound 72 (333 mg, 61% yield). ESI MS: $C_{37}H_{66}N_9O_{23}$ $[M+H]^+$ 1004.4, found 1004.4.

Part D:

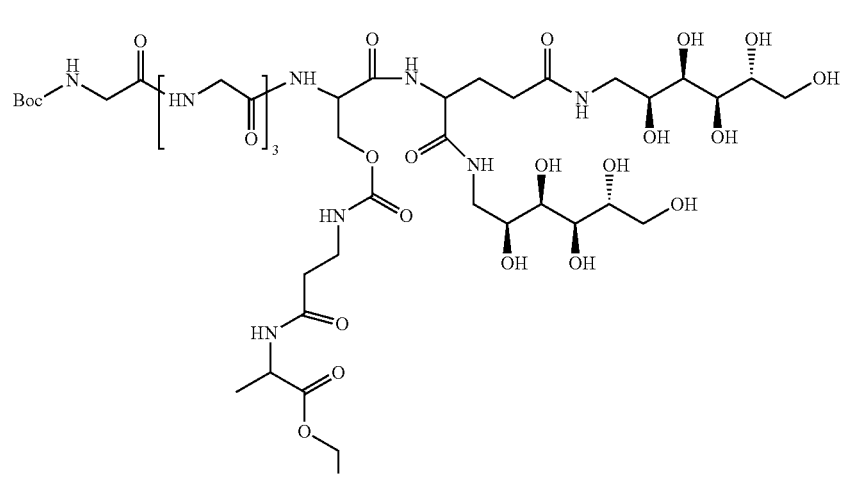

73

-continued
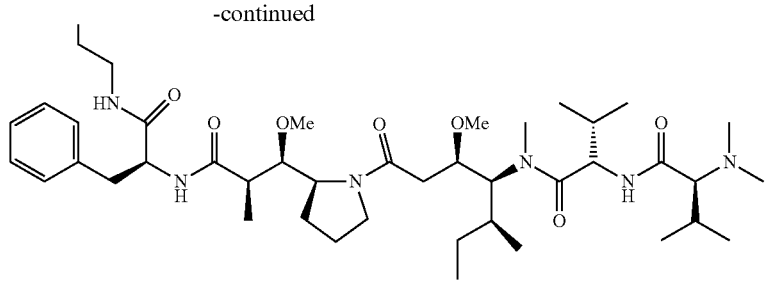
73
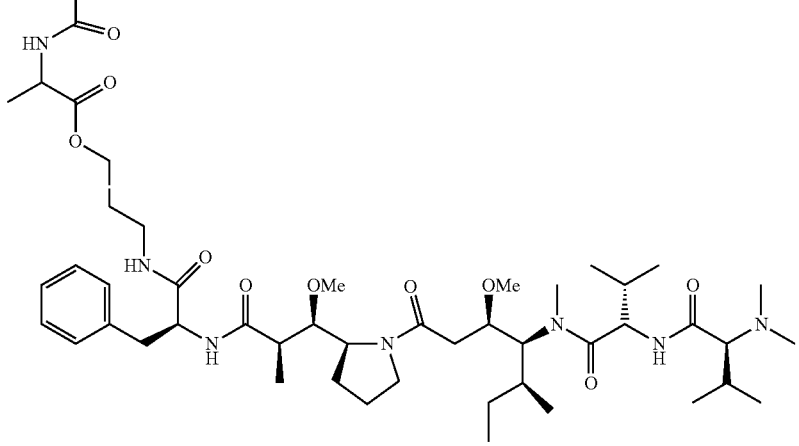
Compound 73 was synthesized from compound 72 (175.0 mg, 0.174 mmol) and auristatin F-hydroxypropyl amide-alanine TFA-salt (168 mg, 0.192 mmol, using the procedure described in Example 2, Part H (67 mg, 21% yield). ESI MS: $C_{83}H_{142}N_{16}O_{31}$ m/z: $[M+2H]^{2+}/2$ 930.5; found 930.5.
Part E:
74
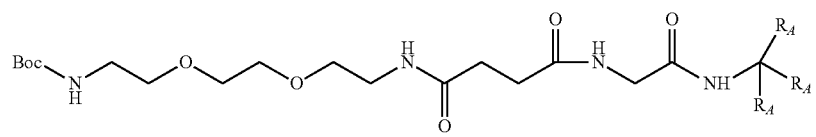
75
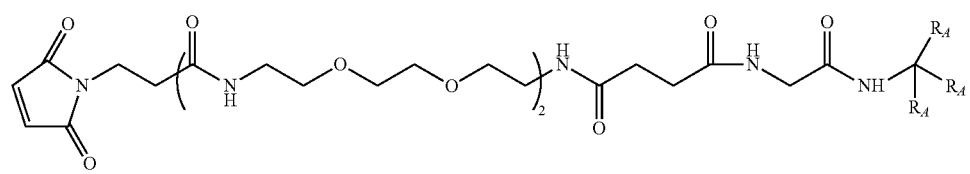

-continued
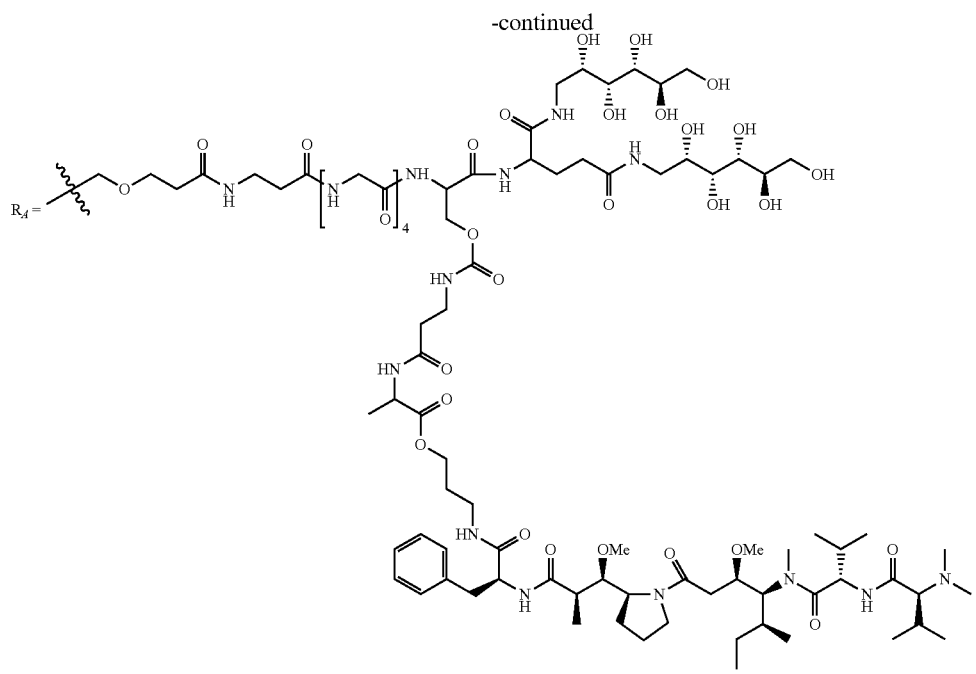
Compound 74 was prepared by reacting compound 13 (5.72 mg, 6.10 μmol 5.72 mg, 6.10 μmol), with deprotected compound 73 (40 mg, 0.021 mmol) using the procedure described in Example 2, Part H. ESI HRMS (Compound 74): $C_{273}H_{463}N_{55}O_{103}$ [M] 6160.3; found 6160.3.
Scaffold 75 was synthesized from compound 74 as described in Example 2, Part I. ESI MS (scaffold 75): $C_{282}H_{473}N_{57}O_{107}$ [M] 6370.33; found 6370.35.
Example 33: Synthesis of XMT-1535 Conjugate of Scaffold 75 (Conjugate 76)
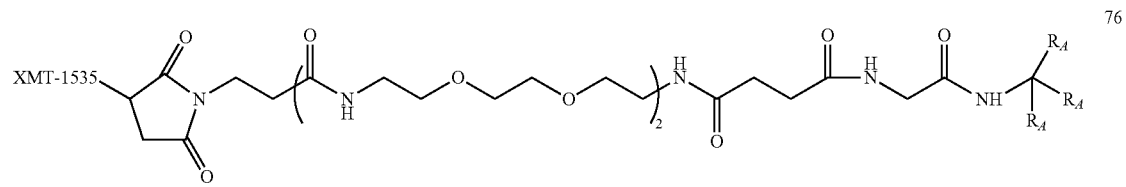

-continued
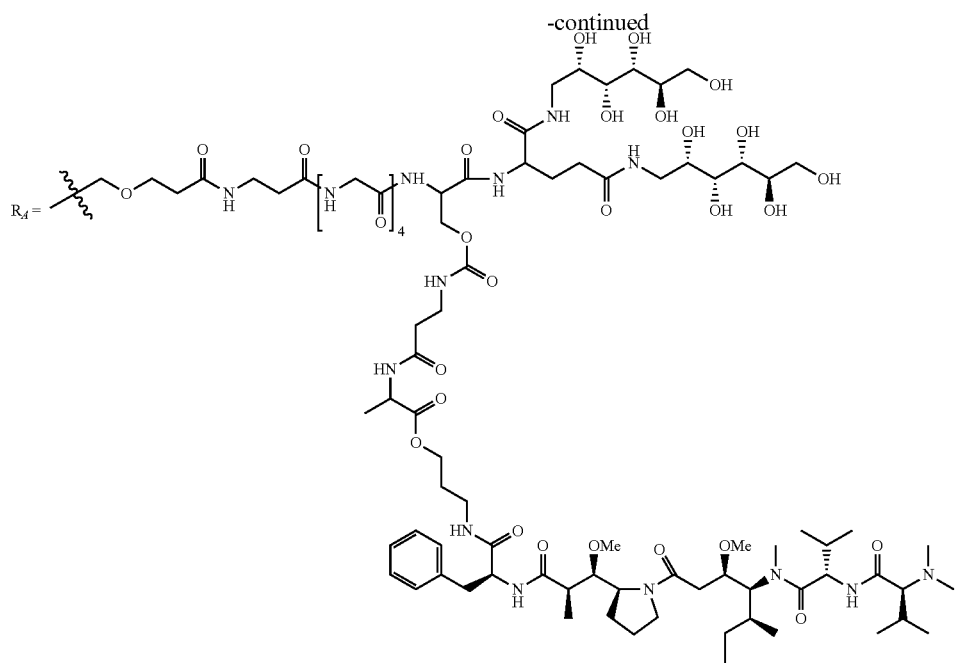
Conjugate 76 was prepared from scaffold 75 and XMT-1535 using the procedure described in Example 7 except the TCEP to antibody ratio was 3.25. Purified conjugate 76 had a drug to XMT-1535 ratio of 9.3.
Example 34: Synthesis of XMT-1535 Conjugates of Scaffold 77 (Conjugates 78)
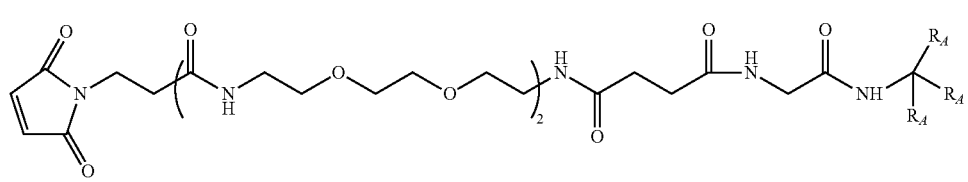
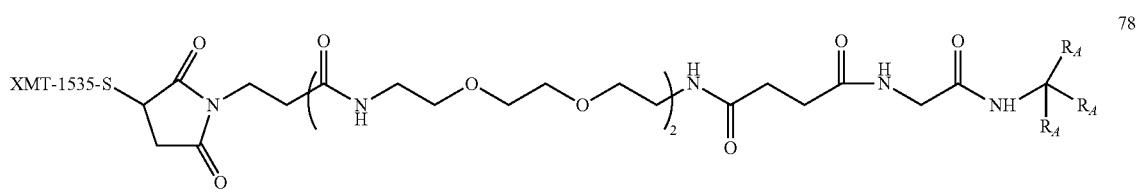

-continued

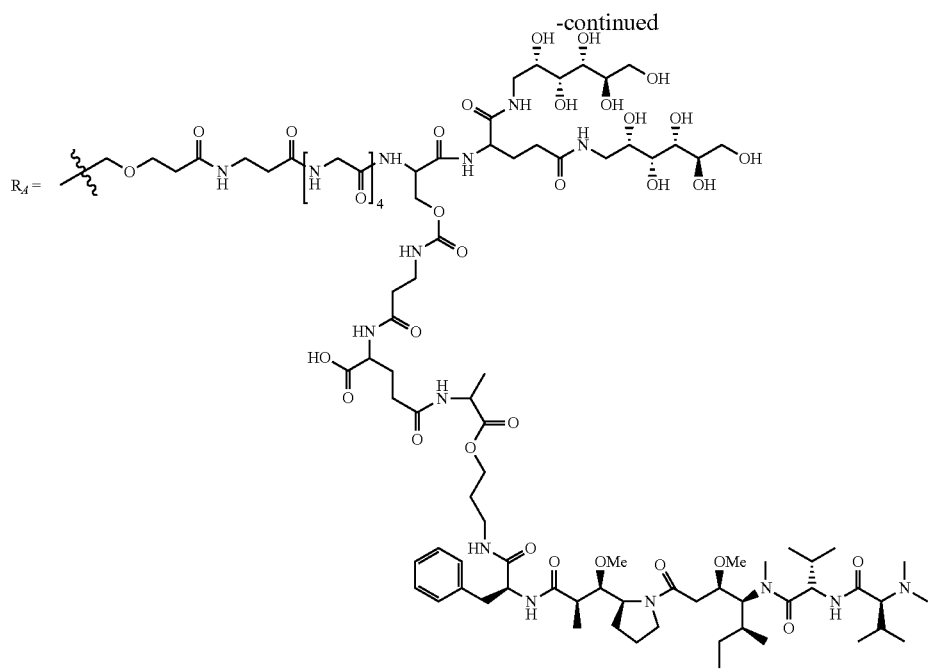

Scaffold 77 was synthesized as described in Example 32 except that benzyl protected compound 35 (259 mg, 0.214 mmol) was used in Example 32, Part D. ESI MS (Scaffold 77 MK2-079): $C_{297}H_{494}N_{60}O_{116}$ m/z: $[M+6H]^{6+}/6$ 1127.20 found 1127.24.

Conjugate 78 was prepared from scaffold 75 and XMT-1535 using the procedure described in Example 7 except the TCEP to antibody ratio was 3.25. Purified conjugate 78 had a drug to XMT-1535 ratio of 16.3.

Example 35: Synthesis of XMT-1535 Conjugates 79A and Conjugate 79B

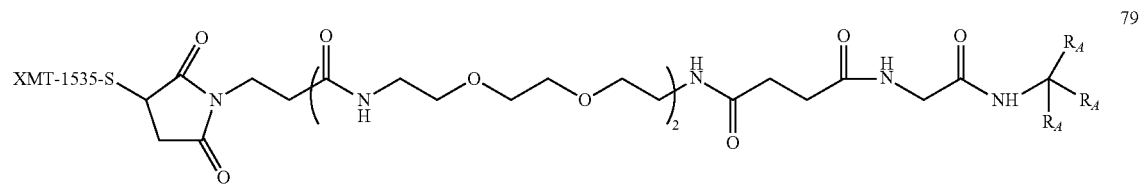

-continued

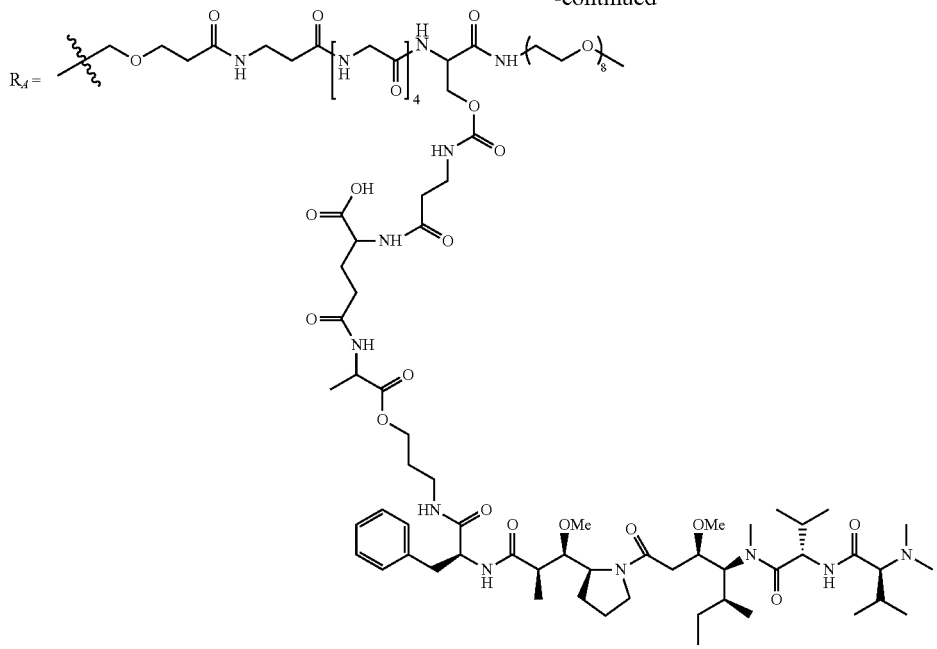

Conjugates 79A and 79B were prepared as described in Example 25 except the TCEP to antibody ratio was 4.0. Purified conjugate 79A had a drug to XMT-1535 ratio of 15.5 and purified conjugate 79B had a drug to XMT-1535 ratio of 13.7.

Example 36: Synthesis of Bis-Glucamine Scaffold 75

Part A:

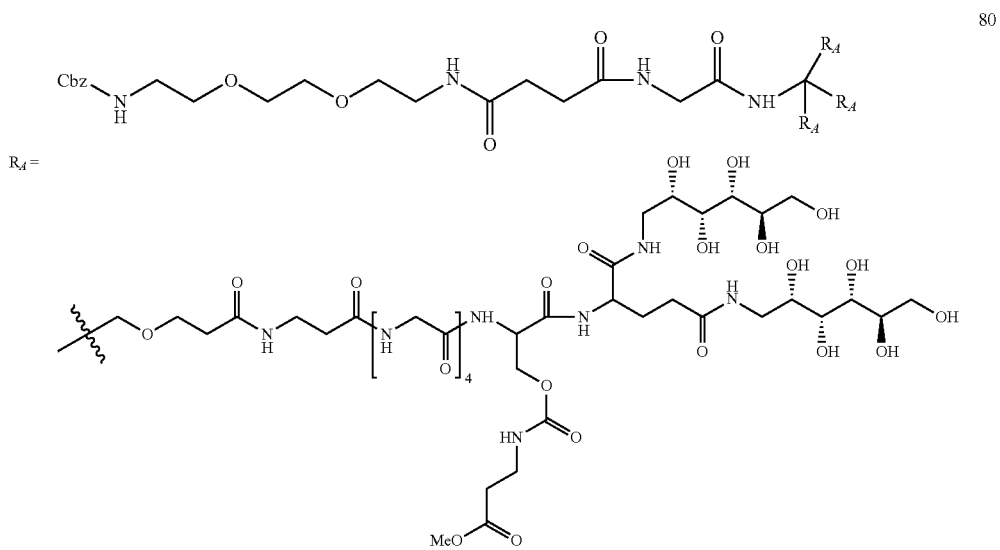

The Cbz-protected analogue of compound 13 (93 mg, 0.096 mmol)) in NMP/water (1:2) 2.0 mL was reacted with deprotected compound 71 in the form of its HCl-salt (291 mg, 0.317 mmol) as described in Example 2, Part F to give compound 80 (276 mg, 78% yield). ESI MS: $C_{141}H_{237}N_{34}O_{79}$ [M+H]$^+$ 3670.56; found 3670.25.

Part B:
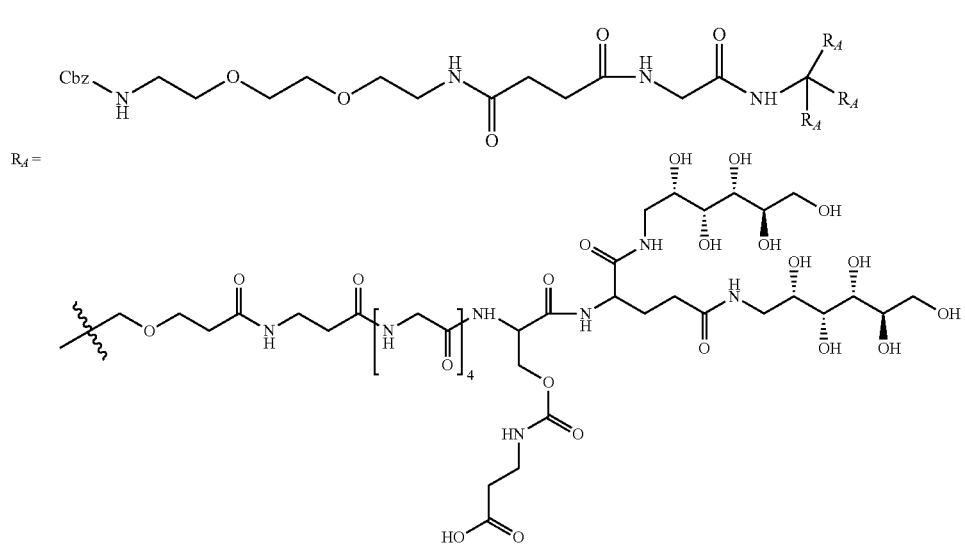
Compound 80 (175 mg, 0.048 mmol) in 4.9 mL of water (4.9 mL) at 0° C. was treated with aqueous LiOH (1 M solution, 6 equivalents total) to give the hydrolyzed acid compound. The crude product was purified by RP C18 column CombiFlash chromatography using ACN/water containing HOAc (0.1%) gradient as eluant, to give compound 81 (105 mg, 35% yield). ESI MS: $C_{138}H_{231}N_{34}O_{79}$ [M+H]$^+$ 3628.51; found 3628.57.
Part C:
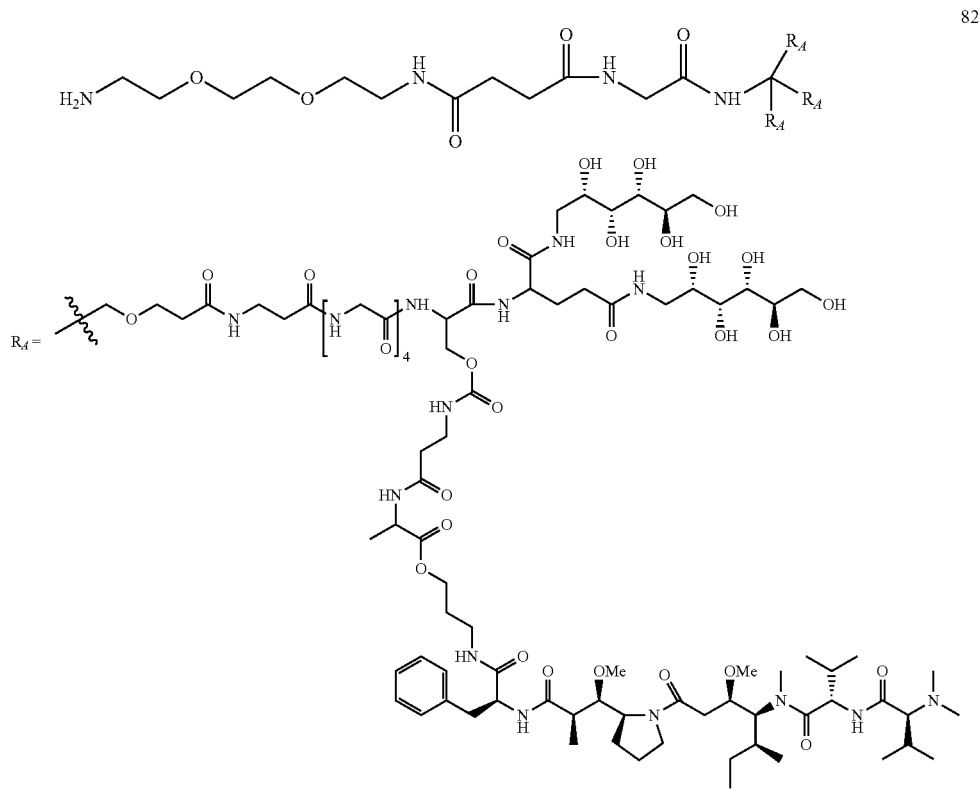

CBz protected compound 82 was synthesized from compound 81 (88 mg, 0.024 mmol) and auristatin F-hydroxypropyl amide-alanine TFA-salt (84 mg, 0.085 mmol, using the procedure described in Example 2, Part H (40.5 mg, 27% yield). ESI MS: $C_{276}H_{462}N_{55}O_{103}$ [M+H]$^+$: 6195.26; found 6195.37.

The protecting group was removed using 10% Pd/C (198 mg) in EtOH/water (1:1) under Eh as described in Example 2, Part B, to give compound 82 (10 mg, 43% yield). ESI MS: $C_{268}H_{456}N_{55}O_{101}$ [M+H]$^+$: 6061.23; found 6061.27.

Part D:

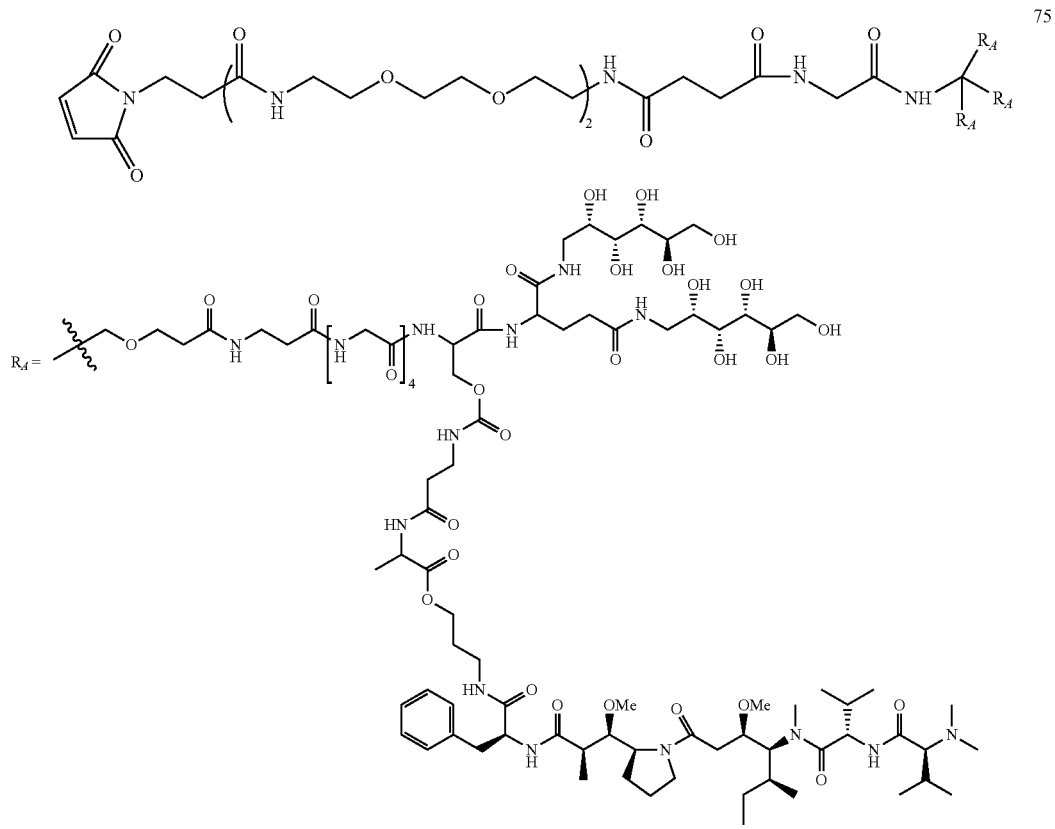

75

Scaffold 75 was synthesized from compound 82 and as described in Example 2, Part I and purified using a dialysis cell equipped with a 1 kDa membrane (yield 82%). ESI MS (scaffold 75): $C_{282}H_{473}N_{57}C_{107}$ [M] 6370.33; found 6370.50.

Example 37: Synthesis of XMT-1535 Conjugates of Scaffold 75 (Conjugate 83)

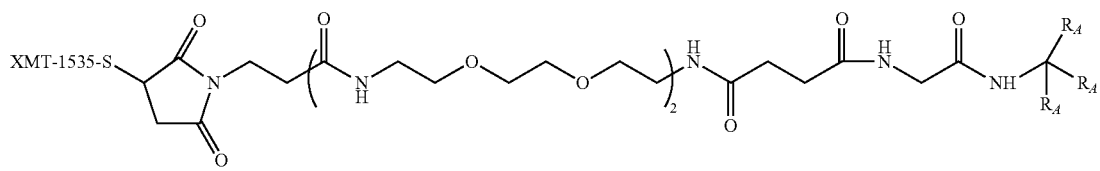

83

-continued
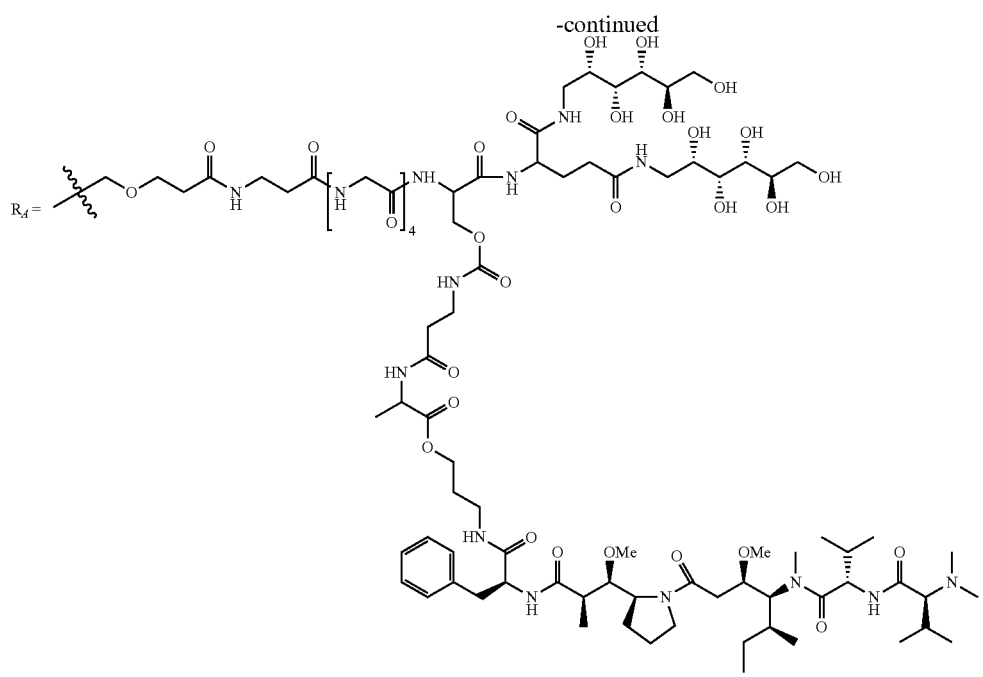
Conjugate 83 was prepared from scaffold 75 (as prepared in Example 36) and XMT-1535 using the procedure described in Example 7 except the TCEP to antibody ratio was 4.0. Purified conjugate 83 had a drug to XMT-1535 ratio of 15.7
Example 38: Synthesis of XMT-1535 Conjugates of Scaffold 84 (Conjugate 85)
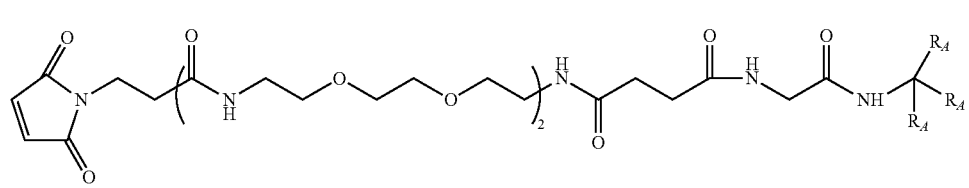
84
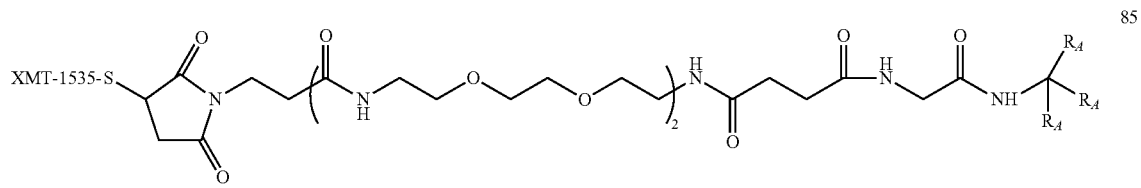
85

-continued

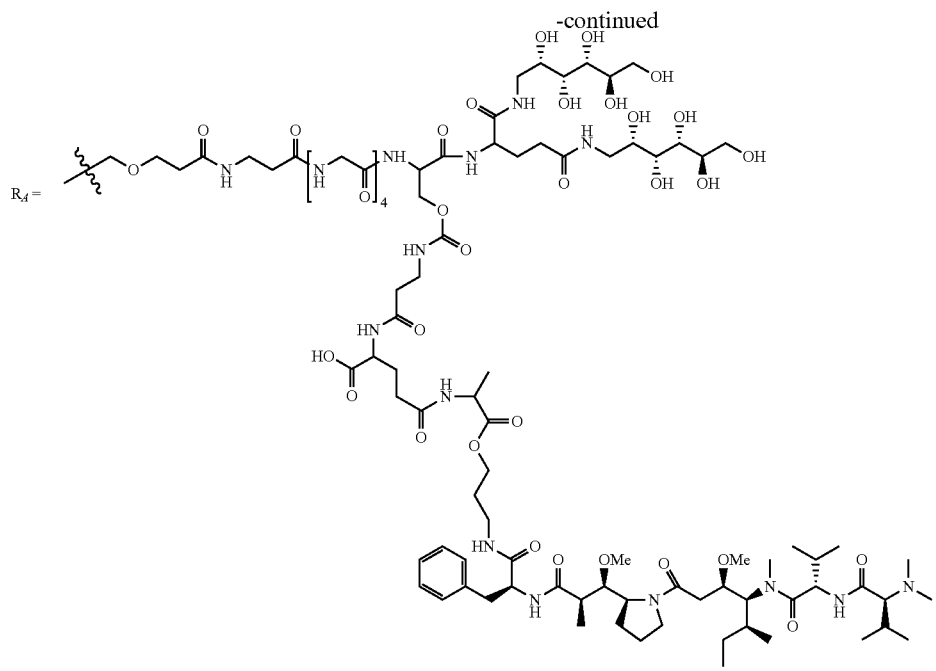

Scaffold 84 was prepared as described in Example 36, except the benzyl derivative of compound 35 (13.97 mg, 0.012 mmol) was used in Part C. ESI MS (scaffold 84): $C_{297}H_{494}N_{60}O_{116}$ m/z: $[M+6H]^{6+}$ 1127.25; found 1127.20.

Conjugate 85 was prepared from scaffold 84 and XMT-1535 using the procedure described in Example 7 except the TCEP to antibody ratio was 4.0. Purified conjugate 85 had a drug to XMT-1535 ratio of 13.1.

Example 39: Cell Viability Assay for the PBRM-Drug Conjugates

The conjugates were evaluated for their antiproliferation properties in tumor cell lines in vitro using CellTiter-Glo® (Promega Corp). Cells were plated at a density of 5,000 cells per well in black walled 96-well plate and allowed to adhere overnight at 37° C. in a humidified atmosphere of 5% $CO_2$. BT474, SKBR3, NCI-N87 cells (HER2 expressing cells), JIMT1 cells (HER2 medium expression level cells), MCF7 cells (HER2 low expressing levels cells), and OVCAR3 (ovarian adenocarcinoma cell line, not amplified) and were plated. CellTiter-Glo® reagent was added to the wells at room temperature and the luminescent signal was measured after 10 min using a SpectraMax M5 plate reader (Molecular Devices). Dose response curves were generated using Soft-Max Pro software. IC50 values were determined from four-parameter curve fitting.

Table I and Table II give illustrative results for the antiproliferation properties of the PBRM-drug conjugates.

TABLE I

| Conjugate No. | BT474 $IC_{50}$ (nmol/L) | SKBR3 $IC_{50}$ (nmol/L) | N87 $IC_{50}$ (nmol/L) | JIMT1 $IC_{50}$ (nmol/L) | MCF7 $IC_{50}$ (nmol/L) |
|---|---|---|---|---|---|
| 50 | 0.309 | 0.04 | 0.34 | 14.84 | 1.19 |
| 52 | 0.18 | 0.02 | 0.20 | 15.82 | 0.14 |
| 46A | 0.1 | 0.02 | 0.07 | 14.56 | 0.14 |
| 46B | 0.11 | 0.03 | 0.11 | 100 | 0.13 |

TABLE I-continued

| Conjugate No. | BT474 $IC_{50}$ (nmol/L) | SKBR3 $IC_{50}$ (nmol/L) | N87 $IC_{50}$ (nmol/L) | JIMT1 $IC_{50}$ (nmol/L) | MCF7 $IC_{50}$ (nmol/L) |
|---|---|---|---|---|---|
| 43A | 0.09 | 0.02 | 0.1 | 17.69 | 0.14 |
| 43B | 0.1 | 0.01 | 0.04 | 13.53 | 0.15 |
| 48 | 0.13 | 0.02 | 0.09 | 18.47 | 0.17 |
| 34A | 29.14 | 11.06 | 22.07 | 27.7 | 21.91 |
| 34B | 11.73 | 9.962 | 29.39 | 17.97 | 20.99 |
| 31A | <100 | <100 | <100 | <100 | <100 |
| 31B | <100 | <100 | <100 | <100 | <100 |
| 25 | <300 | <300 | <300 | <300 | <300 |
| 28 | <300 | <300 | <300 | <300 | <300 |

TABLE II

| Conjugate No. | OVCAR3 $IC_{50}$ (nmol/L) |
|---|---|
| 66 | 0.03 |
| 53A | 0.01 |
| 53B | 0.01 |
| 53E | 0.01 |
| 53C | 0.03 |
| 53D | 0.02 |
| 55A | 0.05 |
| 55C | 0.03 |
| 78 | 0.015 |
| 79A | 0.015 |
| 83 | 0.03 |

As shown in Tables I and II, the PBRM-drug conjugates show efficacy in the tested cell lines.

Example 40: Tumor Growth Response to Administration of PBRM-Drug Conjugates

Female CB-17 SCID mice were inoculated subcutaneously with NCI-N87 cells (n=10 for each group). Test compound or vehicle were dosed IV as a single dose on day 1. Tumor size was measured at the times indicated in FIG. 1 using digital calipers. Tumor volume was calculated and was used to determine the delay in tumor growth. Tumor volumes are reported as the mean±SEM for each group. FIG. 1 provides the results for the tumor response in mice inoculated subcutaneously with NCI-N87 cells (n=10 for each group) after IV administration as a single dose on day 1 of vehicle and Trastuzumab-drug conjugate, Conjugate 43B, Example 18, at 1.5 mg/kg. The results show that on day 70 Conjugate 43B resulted in 100% objective regressions consisting of 10 complete responses.

Female CB-17 SCID mice were subcutaneously implanted with OVCAR-3 (n=10 for each group). Test compounds or vehicle were dosed IV as a single dose on day 1. Tumor size was measured at the times indicated in FIGS. 2 and 3 using digital calipers. Tumor volume was calculated and was used to determine the delay in tumor growth. Mice were sacrificed when tumors reached a size of 1000 mm$^3$. Tumor volumes are reported as the mean±SEM for each group.

Figure 2:
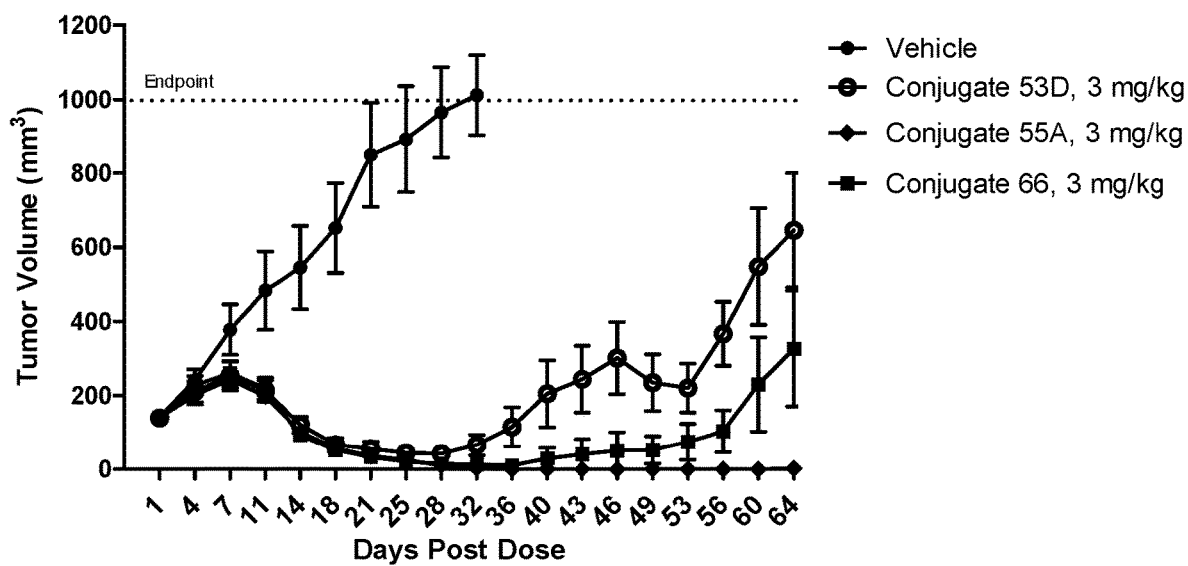
FIG. 2 illustrates the anti-tumor efficacy of the XMT-1535-drug conjugates: Example 24, Conjugate 53D; Example 25, Conjugate 55A; Example 29, Conjugate 66 as measured in an OVCAR3 mouse tumor xenograft model. XMT-1535 is an antibody disclosed in co-pending application U.S. Ser. No. 15/457,574 filed Mar. 13, 2017.

FIG. 2 provides the results for the tumor response in mice subcutaneously implanted with OVCAR-3 tumor fragments (n=10 for each group) after IV administration of vehicle; and the XMT-1535-drug conjugates: Example 24, Conjugate 53D; Example 25, Conjugate 55A; Example 29, Conjugate 66; each at 3 mg/kg as a single dose at day 1. At day 64, conjugates 53D had 6 partial response, 3 complete responses and 1 tumor free survivor; Conjugate 66 had 1 partial response, 9 complete responses and 5 tumor free survivors; and Conjugate 55A had 10 complete responses and 8 tumor free survivors.

Figure 3:
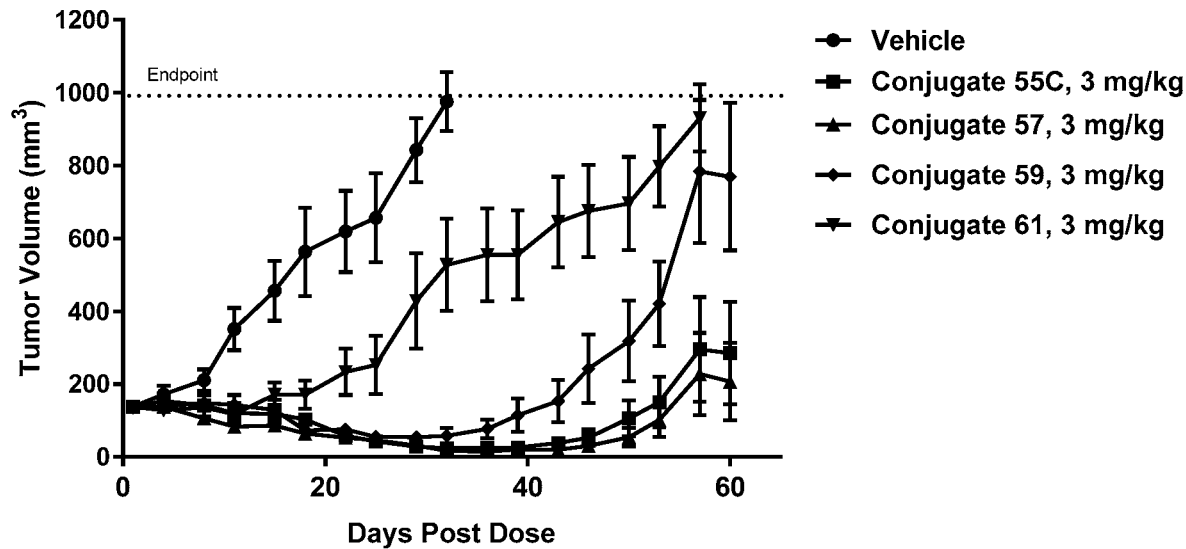
FIG. 3 illustrates the anti-tumor efficacy of the XMT-1535-drug conjugates: Example 25, Conjugate 55C; Example 26, Conjugate 57; Example 28, Conjugate 61; and Example 27, Conjugate 59; as measured in an OVCAR3 mouse tumor xenograft model.

FIG. 3 provides the results for the tumor response in mice subcutaneously implanted with OVCAR-3 tumor fragments (n=10 for each group) after IV administration of vehicle; and the XMT-1535-drug conjugates: Example 25, Conjugate 55C had 6 partial responses, 4 complete responses and 1 tumor free survivor; Example 26, Conjugate 57 had 4 partial responses, 6 complete responses and 5 tumor free survivors; Example 28, Conjugate 61 had 2 partial responses; and Example 27, Conjugate 59 had 7 partial responses and 1 complete response; each at 3 mg/kg as a single dose at day 1.

Figure 5:
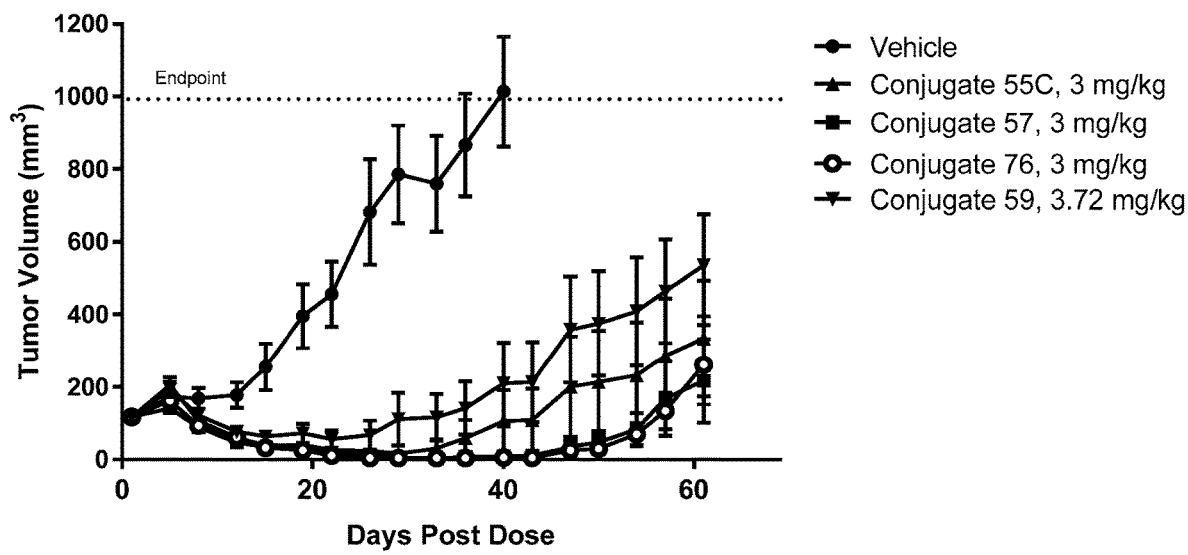
FIG. 5 illustrates the anti-tumor efficacy of the XMT-1535-drug conjugates: Example 33, Conjugate 76; Example 26, Conjugate 57; Example 25, Conjugate 55C; and Example 27, Conjugate 59; as measured in an OVCAR3 mouse tumor xenograft model.

FIG. 5 provides the results for the tumor response in mice subcutaneously implanted with OVCAR-3 tumor fragments (n=10 for each group) after IV administration of vehicle; and the XMT-1535-drug conjugates: Example 33, Conjugate 76 had 1 partial response, 9 complete responses and 4 tumor free survivors; Example 26, Conjugate 57 had 1 partial response, 8 complete responses and 7 tumor free survivors; Example 25, Conjugate 55C had 2 partial responses, 8 complete responses and 5 tumor free survivors; each at 3 mg/kg as a single dose at day 1 and Example 27, Conjugate 59 at 3.72 mg/kg as a single dose at day 1 had 1 partial response, 6 complete responses and 2 tumor free survivors.

Figure 6:
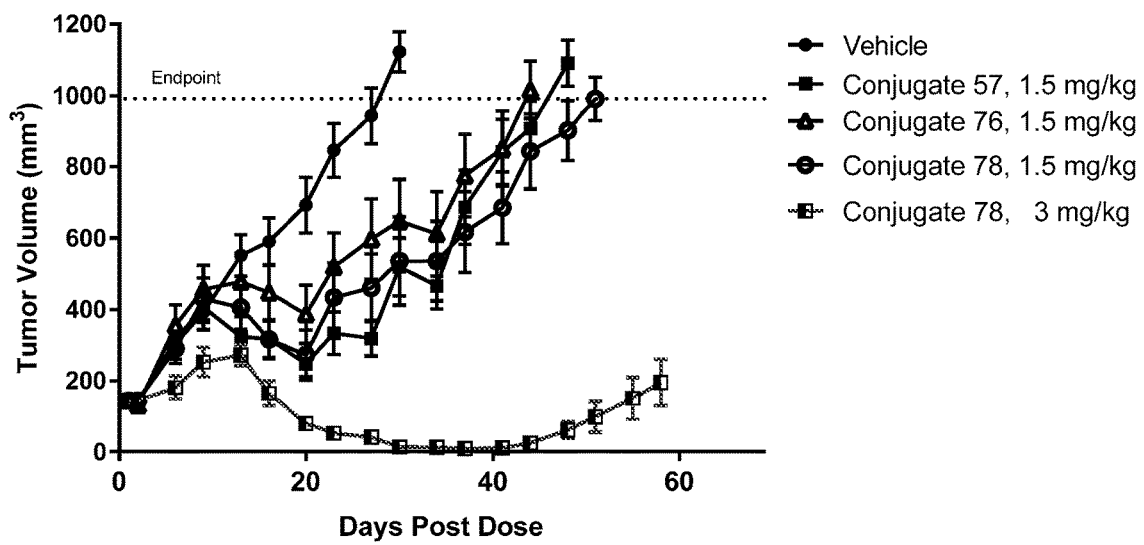
FIG. 6 illustrates the anti-tumor efficacy of the XMT-1535-drug conjugates: Example 26, Conjugate 57; Example 33, Conjugate 76; and Example 34, Conjugate 78; in an OVCAR3 mouse tumor xenograft model.

FIG. 6 provides the results for the tumor response in mice subcutaneously implanted with OVCAR-3 tumor fragments (n=10 for each group) after IV administration of vehicle; and the XMT-1535-drug conjugates: Example 26, Conjugate 57; Example 33, Conjugate 76; and Example 34, Conjugate 78; each at 1.5 mg/kg as a single dose at day 1 and Example 34, Conjugate 78; at 3.0 mg/kg as a single dose at day 1 had 4 partial responses, 6 complete responses and 3 tumor free survivors.

Female CB-17 SCID mice were subcutaneously implanted with Calu-3 cells (n=10 for each group). Test compounds or vehicle were dosed IV as a single dose on day 1. Tumor size was measured at the times indicated in FIG. 4 using digital calipers. Tumor volume was calculated and was used to determine the delay in tumor growth. Tumor volumes are reported as the mean±SEM for each group.

Figure 4:
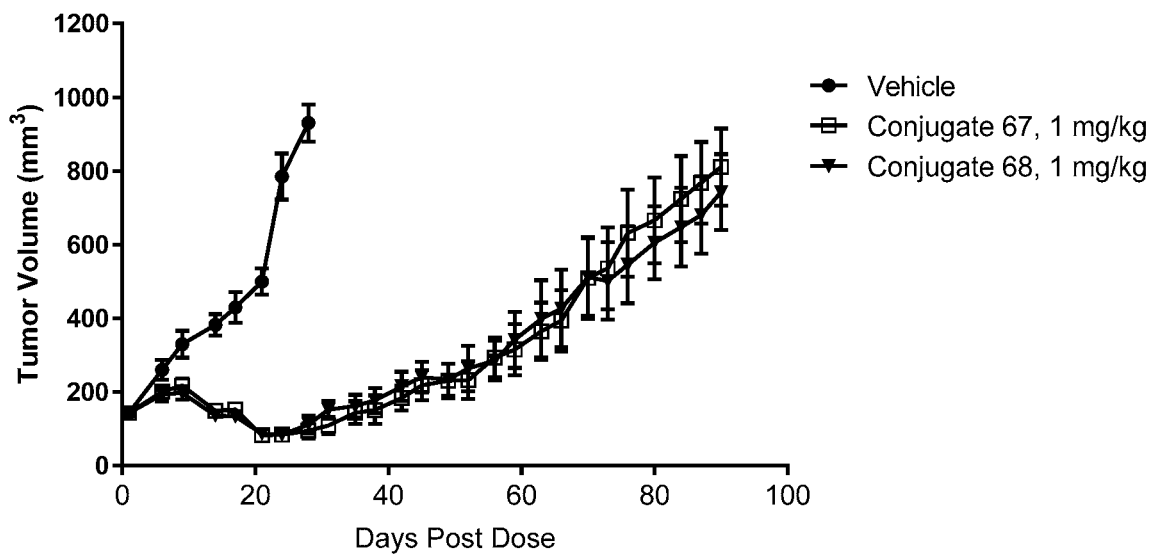
FIG. 4 illustrates the anti-tumor efficacy of the Trastuzumab-drug conjugates: Example 30, Conjugate 67; and Example 31, Conjugate 68 as measured in a Calu-3 mouse tumor xenograft model.

FIG. 4 provides the results for the tumor response in mice subcutaneously implanted with Calu-3 cells (n=10 for each group) after IV administration of vehicle; and the Trastuzumab-drug conjugates: Example 30, Conjugate 67; Example 31, Conjugate 68; each at 1 mg/kg as a single dose at day 1.

Example 41. Mouse Plasma PK after Administration of PBRM-Polymer-Drug Conjugates Female CD-1 mice were allowed to acclimate for at least 4 days prior to initial dosing. All mice were given regular chow and water ad libitum and were not fasted prior to compound administration. Test compounds or vehicle were dosed IV as a single dose on day 1.

The mice were injected intravenously with vehicle (n=3) or with PBRM-polymer-drug conjugate, Example 35, Conjugate 79A; Example 35, Conjugate 7B; Example 37, Conjugate 83; and Example 38, Conjugate 85, each at 3 mg/kg, n=27 for each group). Plasma was collected at 5 min, 1 h, 3 h, 6 h, 24 h, 48 h, 72 h, day 7 and day 14 post dosing. Body weight was measured prior to dosing on day 1 and on days 1, 7 and 14. All animals were observed throughout the fourteen day period for mortality or morbidity.

The total AF-HPA (conjugated AF-HPA and unconjugated (free) drug i.e. AF-HPA and AF) concentrations and conjugated AF-HPA concentrations were determined by LC-MS/MS analysis.

Figure 7A:
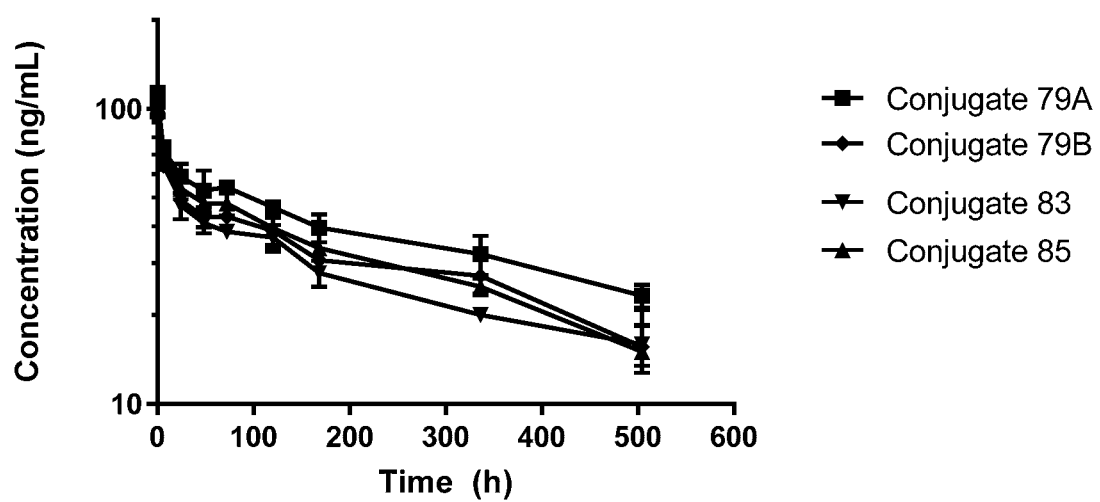
FIG. 7A, FIG. 7B and FIG. 7C shows the total antibody total AF-HPA and conjugated AF-HPA concentrations respectively for the PBRM-polymer-drug conjugate Example 35, Conjugate 79A; Example 35, Conjugate 7B; Example 37, Conjugate 83; and Example 38, Conjugate 85; as measured after administration of the conjugates to mice.
Figure 7B:
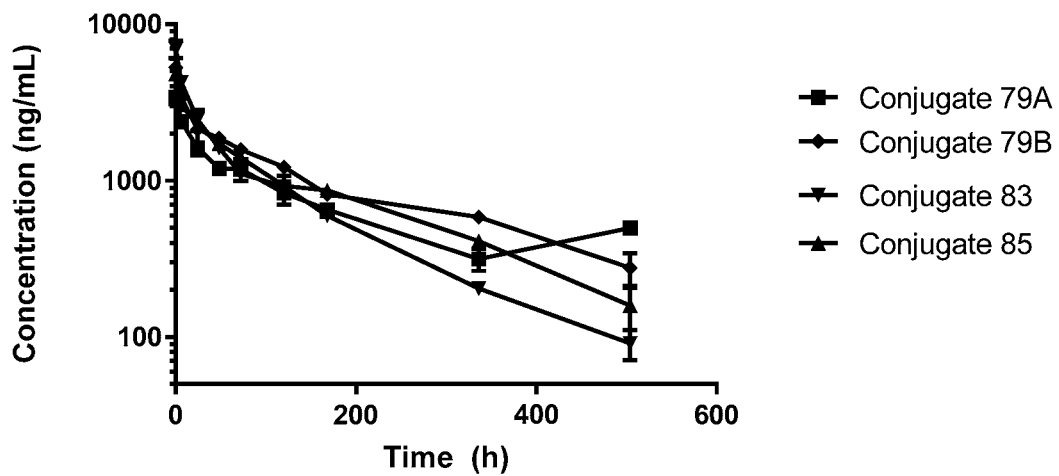
Figure 7C:
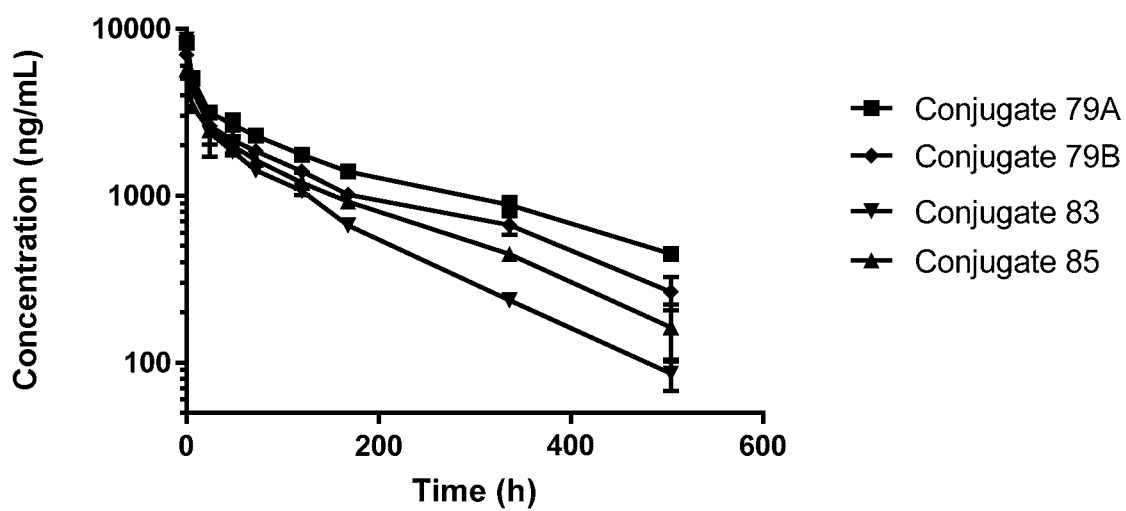

Table III gives the plasma pK. FIG. 7A shows the total antibody concentration; FIG. 7B shows the total AF-HPA concentration and FIG. 7C shows the conjugated AF-HPA concentration for the PBRM-polymer-drug conjugate.

TABLE III

| Plasma PK (PBRM-polymer-drug conjugates) | | | |
|---|---|---|---|
| Test Sample | AF-HPA to Antibody ratio | $T_{1/2}$ (hr) | $AUC_{0\ to\ 336}$ (μg · hr/mL) |
| C2344 Example 35, Conjugate 79B | 13.7 | 160 | 557 |
| C2345 Example 38, Conjugate 85 | 13.1 | 134 | 462 |
| C2262 Example 35, Conjugate 79A | 15.5 | 202 | 718 |
| C2269 Example 37, Conjugate 83 | 15.7 | 114 | 402 |

The results in Table III showed that the PBRM-polymer-drug conjugates had a half-life of ~114-202 hours (~4.75-8.42 days) with an $AUC_{0\ to\ 336}$ of ~402 to 718 μg·hr/mL and were independent of the AF-HPA to antibody ratio of the PBRM-polymer-drug conjugates.

All publications, including, e.g., non-patent literature, patent applications, and patents, cited in this specification are incorporated herein by reference for all purposes. The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A conjugate of Formula (I):

$$\text{PBRM} \left( L^{P'} \left( M^P \right)_{a_1} L^M \left( \left( L^3 \right)_{a_3} M^A \underset{L^D}{\overset{}{\underset{D}{\big|}}}_{a_4} (T^1)_{a_5} \right)_{a_2} \right)_{d_{13}}, \quad (I)$$

wherein
- $a_1$ is 1;
- $a_2$ is 3;
- $a_3$ is an integer from 0 to 1;
- $a_4$ is an integer from 1 to 5;
- $a_5$ is an integer from 1 to 3;
- $d_{13}$ is an integer from 1 to about 14;
- PBRM is an antibody or antibody fragment that binds to a target antigen;
- $L^{P'}$ is a divalent linker moiety connecting the PBRM to $M^P$, of which the corresponding monovalent moiety $L^P$, when not connected to PBRM, contains a functional group $W^P$, wherein each $W^P$ independently is:

[maleimide structure] or [ring A with alkyne], wherein
ring A is optionally substituted $C_{3-8}$ cycloalkyl or optionally substituted 5- to 12-membered heterocycloalkyl, wherein the cycloalkyl or heterocyloalkyl is monocyclic or bicyclic;

$MP^P$ is:

$$*\!-\!(\phantom{x})_{b_1}\!-\!C(O)\!-\!NH\!-\!(CH_2CH_2O)_{f_1}\!-\!R_3\!-\!(\phantom{x})_{b_1}\!-\!C(O)\!-\!R_4\!-\!**,$$

wherein * denotes attachment to $L^{P'}$ and ** denotes attachment to $L^M$;

$R_3$ is —C(O)—NR$_5$— or —NR$_5$—C(O)—;

$R_4$ is a bond or —NR$_5$—(CR$_{20}$R$_{21}$)—C(O)—;

each $R^5$ independently is hydrogen, $C_{1-6}$ alkyl, $C_{6-10}$ aryl, $C_{3-8}$ cycloalkyl, —COOH, or —COO—$C_{1-6}$ alkyl;

each $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5- to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

each $b_1$ independently is an integer from 0 to 6;
each $f_1$ independently is an integer from 1 to 6;
$g_2$ is an integer from 1 to 4;

$L_M$ is:

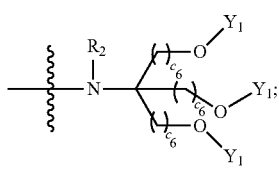

wherein:

} denotes attachment to $M^P$;

$Y_1$ denotes attachment to $L^3$ or attachment to $M^A$ when $L^3$ is absent;

$R_2$ is hydrogen, optionally substituted $C_{1-6}$ alkyl, optionally substituted $C_{1-6}$ heteroalkyl, —COOH, or —COO—$C_{1-6}$ alkyl;

each $c_6$ independently is an integer from 0 to 10;

$L^3$ is —X—$C_{1-10}$ alkylene—C(O)— or —CH$_2$—(CH$_2$)$_v$—C(O)—NR$_5$—(CH$_2$)$_v$—C(O)—, wherein each v independently is an integer from 1 to 10, from 1 to 6, or from 2 to 4, or v is 2, with X directly connected to $L^M$, wherein X is CH$_2$, O, or NR$_5$;

$MA^A$ is a peptide moiety that contains from two to ten amino acids selected from glycine, serine, glutamic acid, aspartic acid, lysine, cysteine and stereoisomers and combinations thereof;

$T^1$ is a hydrophilic group, wherein the hydrophilic is

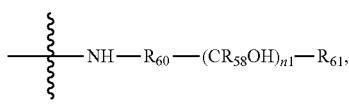

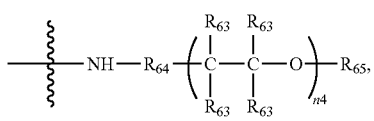

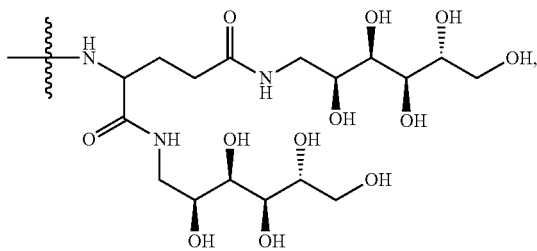 [SMILES: *NC(CCC(=O)NC[C@H](O)[C@@H](O)[C@H](O)[C@H](O)CO)C(=O)NC[C@H](O)[C@@H](O)[C@H](O)[C@H](O)CO]

or a combination thereof, and the

between $T^1$ and $M^A$ denotes direct or indirect attachment of $T^1$ and $M^A$;

wherein $n_1$ is an integer from 0 to about 6;

each $R_{58}$ independently is hydrogen or $C_{1-8}$ alkyl;

$R_{60}$ is a bond, a $C_{1-6}$ alkyl linker, or —CHR$_{59}$—, wherein $R_{59}$ is H, $C_{1-6}$ alkyl, $C_{3-8}$ cycloalkyl, or $C_{6-10}$ arylalkyl;

$R_{61}$ is —CH$_2$OR$_{62}$, —COOR$_{62}$, —(CH$_2$)$_{n2}$COOR$_{62}$, or $C_{3-8}$ heterocycloalkyl substituted with one or more hydroxyl, wherein the $C_{3-8}$ heterocycloalkyl comprises one to four heteroatom ring members independently selected from N, O, P, and S;

$R_{62}$ is H or $C_{1-8}$ alkyl;

$n_2$ is an integer from 1 to about 5;

$n_4$ is an integer from 1 to about 25;

each $R_{63}$ independently is hydrogen or $C_{1-8}$ alkyl;

$R_{64}$ is a bond or a $C_{1-8}$ alkyl linker;

$R_{65}$ is H, $C_{1-8}$ alkyl, or —(CH$_2$)$_{n2}$COOR$_{62}$;

each occurrence of D independently is a therapeutic agent having a molecular weight≤about 5 kDa; and each occurrence of $L^D$ independently comprises a peptide comprising an amino acid selected from alanine, β-alanine, arginine, aspartic acid, asparagine, histidine, glycine, glutamic acid, glutamine, leucine, serine, tyrosine, threonine, isoleucine, and tryptophan, connecting D to $M^A$, and $L^D$ comprises at least one cleavable bond such that when the bond is broken, D is released.

2. The conjugate of claim 1, wherein $L_3$ is —NR$_5$—(CH$_2$)$_v$—C(O)— or —CH$_2$—(CH$_2$)$_v$—C(O)—NR$_5$—(CH$_2$)$_v$—C(O), wherein each v independently is an integer from 1 to 10, from 1 to 6, or from 2 to 4, or v is 2.

3. The conjugate of claim 2, wherein $L_3$ is —NH—(CH$_2$)$_2$—C(O)— or —(CH$_2$)$_2$—C(O)—NH—(CH$_2$)$_2$—C(O)—.

4. The conjugate of claim 1, wherein $a_4$ is 1, 2, or 3.

5. The conjugate of claim 1, wherein $d_{13}$ is 4 or 5.

6. The conjugate of claim 1, wherein each $W^P$ independently is

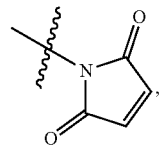 , 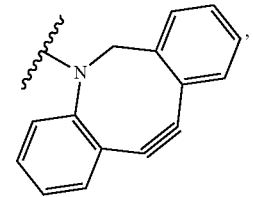 ,

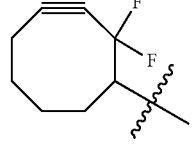 , or 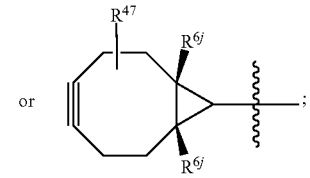 ;

wherein $R^{4j}$ is hydrogen, halogen, =OR, —NO$_2$, —CN, —S(O)$_2$R, $C_{1-24}$ alkyl (e.g., $C_{1-6}$ alkyl), or 6-24 membered aryl or heteroaryl, wherein the $C_{1-24}$ alkyl (e.g., $C_{1-6}$ alkyl), or 6-24 membered aryl or heteroaryl, is optionally substituted with one or more aryl or heteroaryl; or two $R_{4j}$ together form an annelated cycloalkyl, heterocycloalkyl, aryl, or heteroaryl; and $R^{6j}$ is hydrogen, halogen, $C_{1-24}$ alkyl (e.g., $C_{1-6}$ alkyl), or 6-24 membered aryl or heteroaryl, wherein the $C_{1-24}$ alkyl (e.g., $C_{1-6}$ alkyl), or 6-24 membered aryl or heteroaryl, is optionally substituted with one or more aryl or heteroaryl.

7. The conjugate of claim 1, wherein $M^P$ is

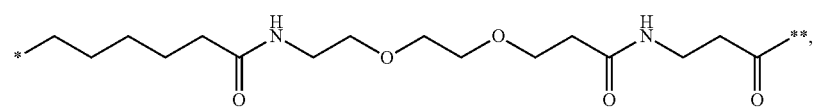 (4)

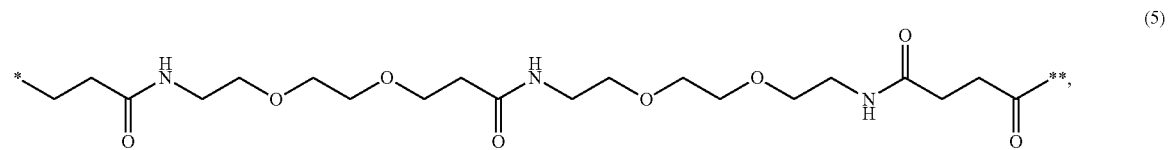 (5)

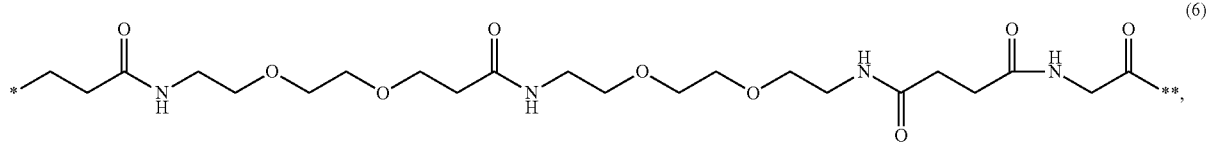 (6)

or wherein $b_1$ is 1, $f_1$ is 2, $g_2$ is 1, $R_3$ is —NH—C(O)—, and $R_4$ is —NH—(CH)$_2$—C(O)—; wherein * denotes attachment to $L^{P'}$ and ** denotes attachment to $L^M$.

8. The conjugate of claim 1, wherein $M^A$ is a peptide moiety that contains at least four glycines and at least one serine.

9. The conjugate of claim 1, wherein $M^A$ is a peptide moiety that contains at least four glycines and at least one glutamic acid.

10. The conjugate of claim 1, wherein $M^A$ is a peptide moiety that contains at least four glycines, at least one serine, and at least one glutamic acid.

11. The conjugate of claim 1, wherein the hydrophilic group is

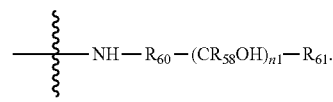

12. The conjugate of claim 11, wherein the hydrophilic group is glucamine.

13. The conjugate of claim 1, wherein the hydrophilic group is

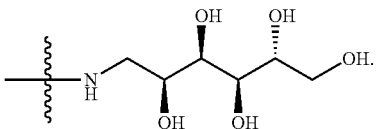

14. The conjugate of claim 1, wherein $n_4$ is an integer from about 2 to about 20.

15. The conjugate of claim 1, wherein $n_4$ is 8 or 12.

16. A pharmaceutical composition comprising the conjugate of claim 1 and a pharmaceutically acceptable carrier.

* * * * *

UNITED STATES PATENT AND TRADEMARK OFFICE
CERTIFICATE OF CORRECTION

PATENT NO. : 11,964,025 B2
APPLICATION NO. : 17/400387
DATED : April 23, 2024
INVENTOR(S) : Aleksandr V. Yurkovetskiy et al.

It is certified that error appears in the above-identified patent and that said Letters Patent is hereby corrected as shown below:

In the Claims

At Column 372, Claim number 1, Line number 35:
"$MP^P$ is:"
Should read:
--$M^P$ is:--

At Column 372, Claim number 1, Line number 62:
"droxylated $C_{3-8}$ cycloalkyl or a side chain of a natural"
Should read:
--droxylated $C_{3-8}$ cycloalkyl, or a side chain of a natural--

At Column 373, Claim number 1, Line number 1:
"$L_M$ is:"
Should read:
--$L^M$ is:--

At Column 373, Claim number 1, Line number 25:
"$MA^A$ is a peptide moiety that contains from two to ten"
Should read:
--$M^A$ is a peptide moiety that contains from two to ten--

At Column 373, Claim number 1, Line number 29:
"$T^1$ is a hydrophilic group, wherein the hydrophilic is"
Should read:
--$T^1$ is a hydrophilic group, wherein the hydrophilic group is--

At Column 374, Claim number 2, Line number 25:
"2. The conjugate of claim 1, wherein $L_3$ is -$NR_5$-"
Should read:

Signed and Sealed this
Fourth Day of June, 2024

Katherine Kelly Vidal
*Director of the United States Patent and Trademark Office*

--2. The conjugate of claim 1, wherein $L^3$ is -NR$_5$- --

At Column 374, Claim number 2, Line number 27:
"(CH$_2$)$_v$-C(O), wherein each v independently is an integer"
Should read:
--(CH2)$_v$-C(O)-, wherein each v independently is an integer--

At Column 374, Claim number 3, Line number 29:
"3. The conjugate of claim 2, wherein L$_3$ is -NH-"
Should read:
--3. The conjugate of claim 2, wherein $L^3$ is -NH- --

At Column 374, Claim number 6, Line number 54:

"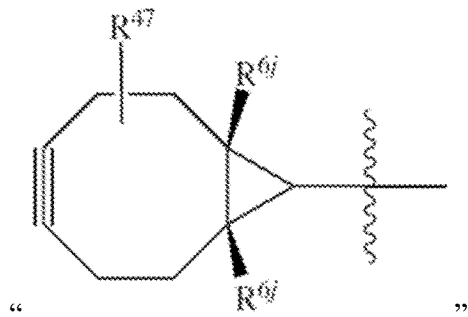"

Should read:

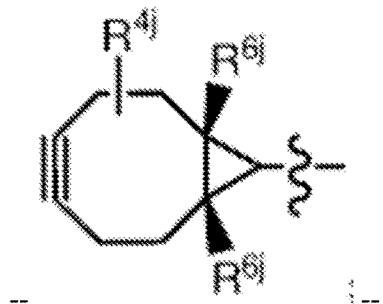
--                    --

At Column 374, Claim number 6, Line number 56:
"$R^{4j}$ is hydrogen, halogen, =OR, -NO$_2$, -CN, -S(O)$_2$R,"
Should read:
--$R^{4j}$ is hydrogen, halogen, -OR, -NO$_2$, -CN, -S(O)$_2$R,--

At Column 374, Claim number 6, Line number 60:
"tuted with one or more aryl or heteroaryl; or two R$_{4J}$"
Should read:
--tuted with one or more aryl or heteroaryl; or two $R^{4j}$--

At Column 375, Claim number 7, Line number 1:
"7. The conjugate of claim 1, wherein M$_P$ is"
Should read:
--7. The conjugate of claim 1, wherein $M^P$ is--

CERTIFICATE OF CORRECTION (continued)
U.S. Pat. No. 11,964,025 B2

At Columns 375 and 376, Claim number 7, Line number 10:

"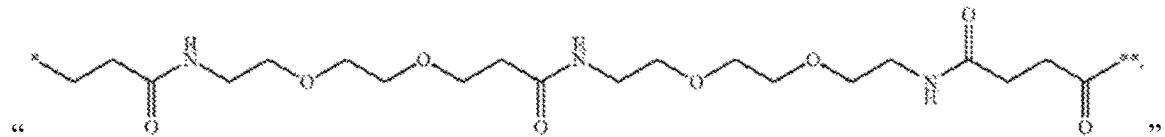"

Should read:

--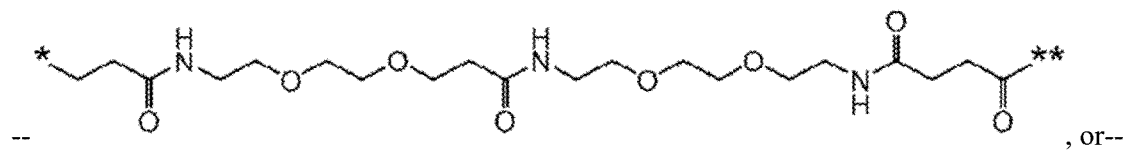, or--